US010881646B2

(12) United States Patent
Saha et al.

(10) Patent No.: US 10,881,646 B2
(45) Date of Patent: Jan. 5, 2021

(54) METHODS AND COMPOSITIONS FOR TREATING NON-ERK MAPK PATHWAY INHIBITOR-RESISTANT CANCERS

(71) Applicant: BIOMED VALLEY DISCOVERIES, INC., Kansas City, MO (US)

(72) Inventors: Saurabh Saha, Wellesley Hills, MA (US); Dean Welsch, Parkville, MO (US); Gary DeCrescenzo, Parkville, MO (US); Jeffrey James Roix, Boston, MA (US)

(73) Assignee: BIOMED VALLEY DISCOVERIES, INC., Kansas City, MO (US)

( * ) Notice: Subject to any disclaimer, the term of this patent is extended or adjusted under 35 U.S.C. 154(b) by 88 days.

(21) Appl. No.: 15/797,593

(22) Filed: Oct. 30, 2017

(65) Prior Publication Data
US 2018/0104228 A1 Apr. 19, 2018

Related U.S. Application Data

(63) Continuation of application No. 15/161,137, filed on May 20, 2016, now abandoned, which is a continuation-in-part of application No. PCT/US2014/071749, filed on Dec. 19, 2014.

(60) Provisional application No. 61/919,551, filed on Dec. 20, 2013.

(51) Int. Cl.
A61K 31/4439 (2006.01)
A61K 45/06 (2006.01)
A61K 31/506 (2006.01)
A61K 31/519 (2006.01)
G01N 33/574 (2006.01)
C12Q 1/6886 (2018.01)

(52) U.S. Cl.
CPC ........ *A61K 31/4439* (2013.01); *A61K 31/506* (2013.01); *A61K 31/519* (2013.01); *A61K 45/06* (2013.01); *C12Q 1/6886* (2013.01); *G01N 33/57484* (2013.01); *C12Q 2600/106* (2013.01); *C12Q 2600/156* (2013.01)

(58) Field of Classification Search
CPC .............. A61K 31/4439; A61K 31/506; A61K 31/519; A61K 45/06; C12Q 1/6886; C12Q 2600/106; C12Q 2600/156; G01N 33/57484
See application file for complete search history.

(56) References Cited

U.S. PATENT DOCUMENTS

2009/0306020 A1* 12/2009 Scheuring ............ A61K 31/585
514/121

OTHER PUBLICATIONS

Morris et al. (Cancer Discov., Jul. 2013, vol. 3, No. 7, pp. 742-750).*
Jin et al. (Bioorg Med Chem., Sep. 15, 2013, vol. 21, No. 18, pp. 5694-5706).*
Nazarian, R., et al. Melanomas acquire resistance to B-RAF (V600E) inhibition by RTK or N-RAS upregulation. Nature. 2010; 468(7326):973-977.
Nikolaev SI, et al. Exome sequencing identifies recurrent somatic MAP2K1 and MAP2K2 mutations in melanoma. Nat Genet 2012;44:133-9.
Nilsson, M., et al. Padlock probes: circularizing oligonucleotides for localized DNA detection. Science. 1994, No. 265, p. 2085-2088.
O'Hara AJ, et al. The genomics and genetics of endometrial cancer. Adv Genomics Genet 2012;2012:33-47.
Ojesina AI, et al. Landscape of genomic alterations in cervical carcinomas. Nature 2014;506:371-5.
Ota et al., Single nucleotide polymorphism detection by polymerase chain reaction-restriction fragment length polymorphism. Nat Protoc. 2007;2(11):2857-64.
Paraiso KHT, et al. Recovery of phospho-ERK activity allows melanoma cells to escape from BRAF inhibitor therapy. Br J Cancer 2010;102:1724-30.
Patgiri A, et al. An orthosteric inhibitor of the Ras-Sos interaction. Nat Chem Biol. 2011;7:585-587.
Pennycuick A, et al. Routine EGFR and KRAS mutation analysis using COLD-PCR in non-small cell lung cancer. Int J Clin Pract 2012;66:748-52.
Porter SB, et al. Inhibition of the CaaX proteases Rce1p and Ste24p by peptidyl (acyloxy)methyl ketones. Biochim Thophys Acta. 2007;1773(6):853-862.
Poulikakos PI, et al. RAF inhibitor resistance is mediated by dimerization of aberrantly spliced BRAF(V600E). Nature 2011;480:387-90.
Queirolo P, et al. Combined BRAF and MEK inhibition for the treatment of BRAF-mutated metastatic melanoma. Cancer Treat Rev 2015;41:519-26.
Rasola A, et al. Activation of mitochondria! ERK protects cancer cells from death through inhibition of the permeability transition. Proc Natl Acad Sci U S A 2010;107:726-31.

(Continued)

*Primary Examiner* — Robert H Havlin
(74) *Attorney, Agent, or Firm* — Bryan Cave Leighton Paisner LLP

(57) ABSTRACT

The present invention provides, inter alia, methods, pharmaceutical compositions, and kits for treating or ameliorating the effects of a cancer in a subject, which cancer is refractory or resistant to non-ERK MAPK pathway inhibitor therapy. Also provided are methods for identifying a subject having cancer who would benefit from therapy with an ERK inhibitor and methods for inhibiting phosphorylation of RSK in a cancer cell that is refractory or resistant to a non-ERK MAPK pathway inhibitor.

12 Claims, 145 Drawing Sheets
(113 of 145 Drawing Sheet(s) Filed in Color)
Specification includes a Sequence Listing.

(56) References Cited

OTHER PUBLICATIONS

Rizos H, et al. BRAF inhibitor resistance mechanisms in metastatic melanoma: spectrum and clinical impact. Clin Cancer Res 2014;20:1965-77.
Robert C, et al. Improved overall survival in melanoma with combined dabrafenib and trametinib. N Engl J Med 2015;372:30-9.
Romeo Y, et al. Regulation and function of the RSK family of protein kinases. Biochem J 2012;441:553-69.
Rudolph J, et al. Slow inhibition and conformation selective properties of extracellular signal-regulated kinase 1 and 2 inhibitors. Biochemistry 2015;54:22-31.
Shaul YD, et al. The MEL/ERK cascade: from signaling specificity to diverse functions. Biochim Biophys Acta 2007;1773:1213-26.
Shi H, et al. Acquired resistance and clonal evolution in melanoma during BRAF inhibitor therapy. Cancer Discov 2014;4:80-93.
Shima, F, et al. In silico discovery of small-molecule Ras inhibitors that display antitumor activity by blocking the Ras-effector interaction. PNAS. 2013;110(20):8182-7.
Schubert S, et al. Hyperactive Ras in developmental disorders and cancer. Nat Rev Cancer 2007;7:295-308.
Sun C, et al. Intrinsic resistance to MEK inhibition in KRAS mutant lung and colon cancer through transcriptional induction of ERBB3. Cell Rep 2014;7:86-93.
TAFLINAR [package insert]. Research Triangle Park, NC: GlaxoSmithKline; 2014.
Trunzer K, et al. Pharmacodynamic effects and mechanisms of resistance to vemurafenib in patients with metastatic melanoma. J Clin Oncol 2013;31:1767-74.
Villanueva, J., et al. Acquired resistance to BRAF inhibitors mediated by a RAF kinase switch in melanoma can be overcome by cotargeting MEK and IGF-1R/PI3K. Cancer Cell. 2010;18:683-695.
Wagle, N., et al. Dissecting therapeutic resistance to RAF inhibition in melanoma by tumor genomic profiling. Journal of Clinical Oncology 2011;29(22):3085-3096.
Wagle N, et al. MAP kinase pathway alterations in BRAF-mutant melanoma patients with acquired resistance to combined RAF/MEK inhibition. Cancer Discov 2014;4:61-8.
Wainstein E, et al. The dynamic subcellular localization of ERK: mechanisms of translocation and role in various organelles. Curr Opin Cell Biol 2016;39:15-20.
Wang, H., et al. Identification of the MEK1(F129L) activating mutation as a potential mechanism of acquired resistance to MEK inhibition in human cancers carrying the B-RAF V600E mutation. Cancer Res (2011);71(16):5535-45.
Yang W, et al. Genomics of Drug Sensitivity in Cancer (GDSC): a resource for therapeutic biomarker discovery in cancer cells. Nucleic Acids Res 2013;41:D955-D961.
MEKINIST [package insert]. Research Triangle Park, NC: GlaxoSmithKline; 2014.
Yao Z, et al. BRAF Mutants Evade ERK-Dependent Feedback by Different Mechanisms that Determine Their Sensitivity to Pharmacologic Inhibition. Cancer Cell 2015;28:370-83.
Yohe S. Molecular genetic markers in acute myeloid leukemia. J Clin Med 2015;4:460-78.
ZELBORAF [package insert]. South San Francisco, CA: Genentech USA, Inc.; 2015.
International Search Report and ISR Written Opinion for PCT/US2014/071749.
Morris et al., Discovery of a novel ERK inhibitor with activity in models of acquired resistance to BRAF and MEK inhibitors. Cancer Discov. Jul. 2013, vol. 3, No. 7, pp. 742-50.
Jin et al., Exploration of N-(2-aminoethyl)piperidine-4-carboxamide as a potential scaffold for development of VEGFR-2, ERK-2 and Abl-1 multikinase inhibitor. Bioorg Med Chem. Sep. 15, 2013, vol. 21, No. 18, pp. 5694-5706.
Absalan, F et al. (2008). Molecular Inversion Probe Assay. Methods in Molecular Biology 396. Humana Press. pp. 315-330.
Ahronian LG, et al. Clinical acquired resistance to RAF inhibitor combinations in BRAF-mutant colorectal cancer trough MAPK pathway alterations. Cancer Discov 2015;5:358-67.
Arcila ME, et al. MAP2K1 (MEK1) mutations define a distinct subset of lung adenocarcinoma associated with smoking. Clin Cancer Res 2015;21:1935-43.
Aronov AM, et al. Flipped out: structure-guided design of selective pyrazolylpyrrole ERK inhibitors. J Med Chem 2007;50:1280-7.
Aronov AM, et al. Structure-guided design of potent and selective pyrimidylpyrrole inhibitors of extracellular signal-regulated kinase (ERK) using conformational control. J Med Chem 2009;52:6362-8.
Arrington AK, et al. Prognostic and predictive roles of KRAS mutation in colorectal cancer. Int J Mol Sci 2012;13:12153-68.
Cargnello M, et al. Activation and function of the MAPKs and their substrates, the MAPK-activated protein kinases. Microbiol Mol Biol Rev 2011;75:50-83.
Carlino MS, et al. Preexisting MEK1P124 mutations diminish response to BRAF inhibitors in metastatic melanoma patients. Clin Cancer Res 2015;21:98-105.
Chapman PB, et al. Improved survival with vemurafenib in melanoma with BRAF V600E mutation. N Engl J Med 2011;364:2507-16.
Corcoran, R.B., et al. BRAF gene amplification can promote acquired resistance to MEK inhibitors in cancer cells harboring the BRAF V600E mutation. Sci Signal (2010);3(149): ra84.
Dai, B., et al. STAT3 mediates resistance to MEK inhibitor through microRNA miR-17. Cancer Res (2011);71:3658-3668.
Davies H, et al. Mutations of the BRAF gene in human cancer. Nature 2002;417:949-54.
Deschenes-Simard X, et al. ERKs in cancer: friends or foes? Cancer Res 2014;74:412-9.
Dobrzycka B, et al. Mutations in the KRAS gene in ovarian tumors. Folia Histochem Cytobiol 2009;47:221-4.
Emery, C.M., et al. MEK1 mutations confer resistance to MEK and B-RAF inhibition. PNAS (2009); 106(48):20411-6.
Fedorov O et al. Kinase inhibitor selectivity profiling using differential scanning fluorimetry. Methods Mol Biol 2012;795:109-18.
Fernandez-Medarde A, et al. Ras in cancer and developmental diseases. Genes Cancer 2011;2:344-58.
Flaherty KT, et al. Combined BRAF and MEK inhibition in melanoma with BRAF V600 mutations. N Engl J Med 2012;367:1694-703.
Goetz EM, et al. ERK mutations confer resistance to mitogen-activated protein kinase pathway inhibitors. Cancer Res 2014;74:7079-89.
Gollob JA, et al. Role of Raf kinase in cancer: therapeutic potential of targeting the Raf/MEK/ERK signal transduction pathway. Semin Oncol 2006;33:392-406.
Greger, J G., et al. Combinations of BRAF, MEK, and PI3K/mTOR inhibitors overcome acquired resistance to the BRAF inhibitor GSK2118436 dabrafenib, mediated by NRAS or MEK mutations. Molecular cancer therapeutics 11.4 (2012): 909-920.
Groenendijk FH, et al. Drug resistance to targeted therapies: deja vu all over again. Mol Oncol 2014;8:1067-83.
Hall RD, et al. BRAF mutations: signaling, epidemiology, and clinical experience in multiple malignancies. Cancer Control 2014;21:221-30.
Hardenbol, P., et al. Multiplexed genotyping with sequence-tagged molecular inversion probes. Nat. Biotechnol. 2003, No. 21 , p. 673-678.
Hatzivassiliou, G, et al. RAF inhibitors prime wild-type RAF to activate the MAPK pathway and enhance growth. Nature 464.7287 (2010): 431-435.
Hatzivassiliou G, et al. ERK inhibition overcomes acquired resistance to MEK inhibitors. Mol Cancer Ther 2012;11:1143-54.
Hauschild A, et al. Dabrafenib in BRAF-mutated metastatic melanoma: a multicentre, open-label, phase 3 randomised controlled trial. Lancet 2012;380:358-65.
Hayes TK, et al. Long-Term ERK Inhibition in KRAS-Mutant Pancreatic Cancer Is Associated with MYC Degradation and Senescence-like Growth Suppression. Cancer Cell 2016;29:75-89.
Hezel AF, et al. Phase II study of gemcitabine, oxaliplatin in combination with panitumumab in KRAS wild-type unresectable or metastatic biliary tract and gallbladder cancer. Br J Cancer 2014;111:430-6.

(56) References Cited

OTHER PUBLICATIONS

Jha S, et al. Dissecting therapeutic resistance to ERK inhibition. Mol Cancer Ther 2016;15:548-59.

Johannessen, C.M., et al. COT/MAP3K8 drives resistance to RAF inhibition through MAP kinase pathway reactivation. Nature (2010);468(7326):968-972.

Johnson DB, et al. Acquired BRAF inhibitor resistance: A multi-center meta-analysis of the spectrum and frequencies, clinical behaviour, and phenotypic associations of resistance mechanisms. Eur J Cancer 2015;51:2792-9.

Kanda M, et al. Presence of somatic Mutations in most early-stage pancreatic intraepithelial neoplasia. Gastroenterology 2012;142:730-733.

Khattak M, et al. Targeted therapy and immunotherapy in advanced melanoma: an evolving paradigm. Ther Adv Med Oncol 2013;5:105-18.

King, Alastair J., et al. Dabrafenib; preclinical characterization, increased efficacy when combined with trametinib, while BRAF/MEK tool combination reduced skin lesions. PloS one 8.7 (2013): e67583.

Larkin J, et al. Combined vemurafenib and cobimetinib in BRAF-mutated melanoma. N Engl J Med 2014;371:1867-76.

Little, A.S., et al. Amplification of the Driving Oncogene, KRAS or BRAF, Underpins Acquired Resistance to MEK1/2 Inhibitors in Colorectal Cancer Cells. Sci. Signal. 4, ra17 (2011).

Liu, Dingxie, et al. BRAF V600E maintains proliferation, transformation, and tumorigenicity of BRAF-mutant papillary thyroid cancer cells. Journal of Clinical Endocrinology & Metabolism 92.6 (2007): 2264-2271.

Liu B, et al. Computational design, chemical synthesis, and biological evaluation of a novel ERK inhibitor (BL-E1001) with apoptosis-inducing mechanisms in breast cancer. Oncotarget 2015;6:6762-75.

Long GV, et al. Increased MAPK reactivation in early resistance to dabrafenib/trametinib combination therapy of BRAF-mutant metastatic melanoma. Nat Commun 2014;5:5694.

Long GV, et al. Dabrafenib and trametinib versus dabrafenib and placebo for Val600 BRAF-mutant melanoma: a multicentre, double-blind, phase 3 randomised controlled trial. Lancet 2015;386:444-51.

Manandhar SP, et al. Small-molecule inhibitors of the Rce1p CaaX protease. J Biomol Screen. 2007;12(7):983-993.

Massey PR, et al. Multiplying therapies and reducing toxicity in metastatic melanoma. Cancer Biol Ther 2015;16:1014-8.

Maurer, T, et al. Small-molecule ligands bind to a distinct pocket in Ras and inhibit SOS-mediated nucleotide exchange activity. PNAS. 2012;109(14):5299-304.

McArthur GA, et al. Safety and efficacy of vemurafenib in BRAFv600E and BRAFv600K mutation-positive melanoma (BRIM-3): extended follow-up of a phase 3, randomised, open-label study. Lancet Oncol 2014;15:323-32.

Metzker, Emerging technologies in DNA sequencing Genome Res. 2005. 15: 1767-1776.

Mittal, Rohit et al. The acetyltransferase activity of the bacterial toxin YopJ of Yersinia is activated by eukaryotic host cell inositol hexakisphosphate. Journal of Biological Chemistry 285.26 (2010): 19927-19934.

* cited by examiner

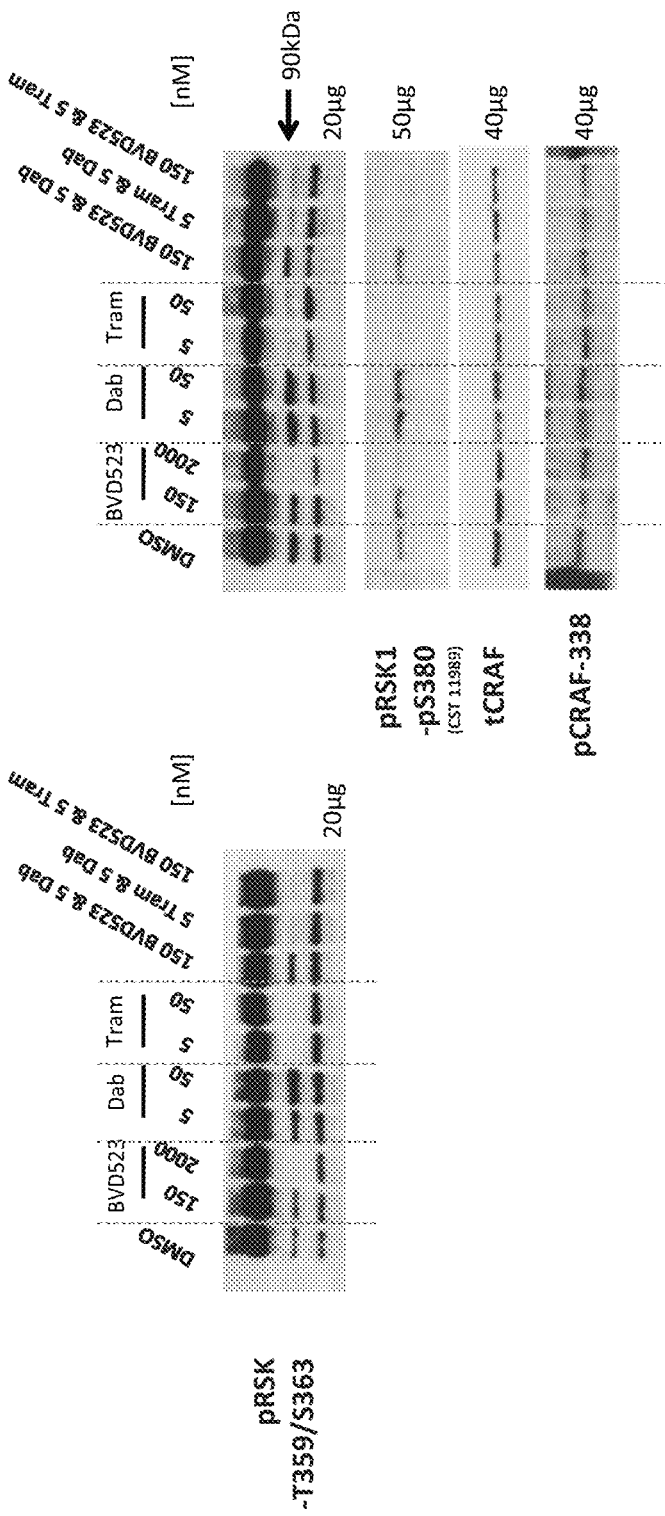

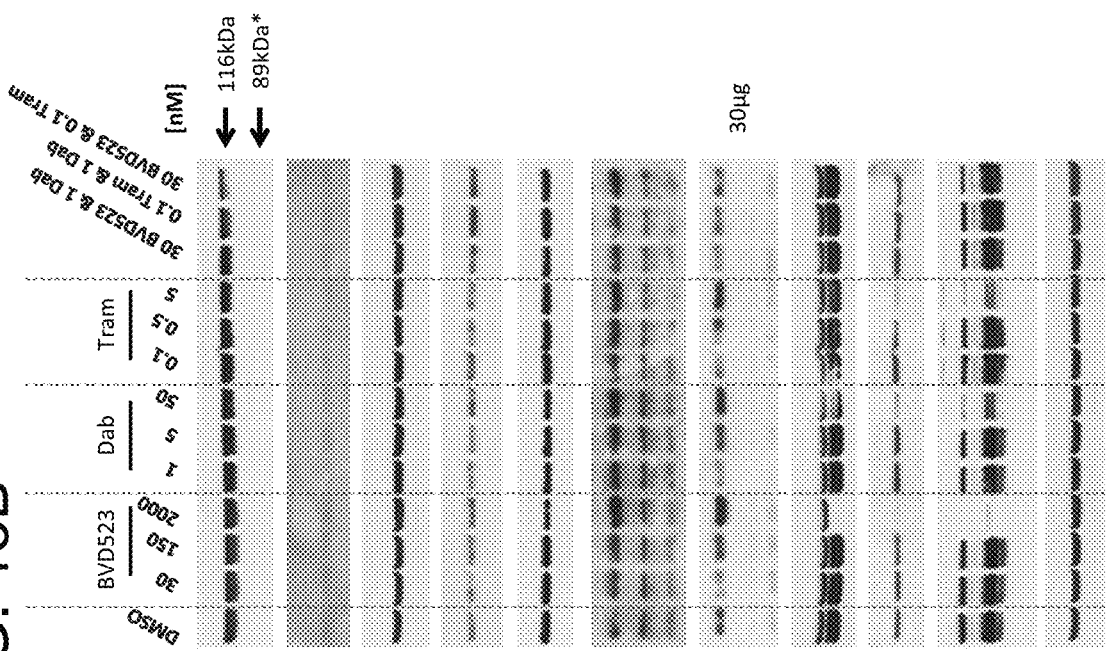
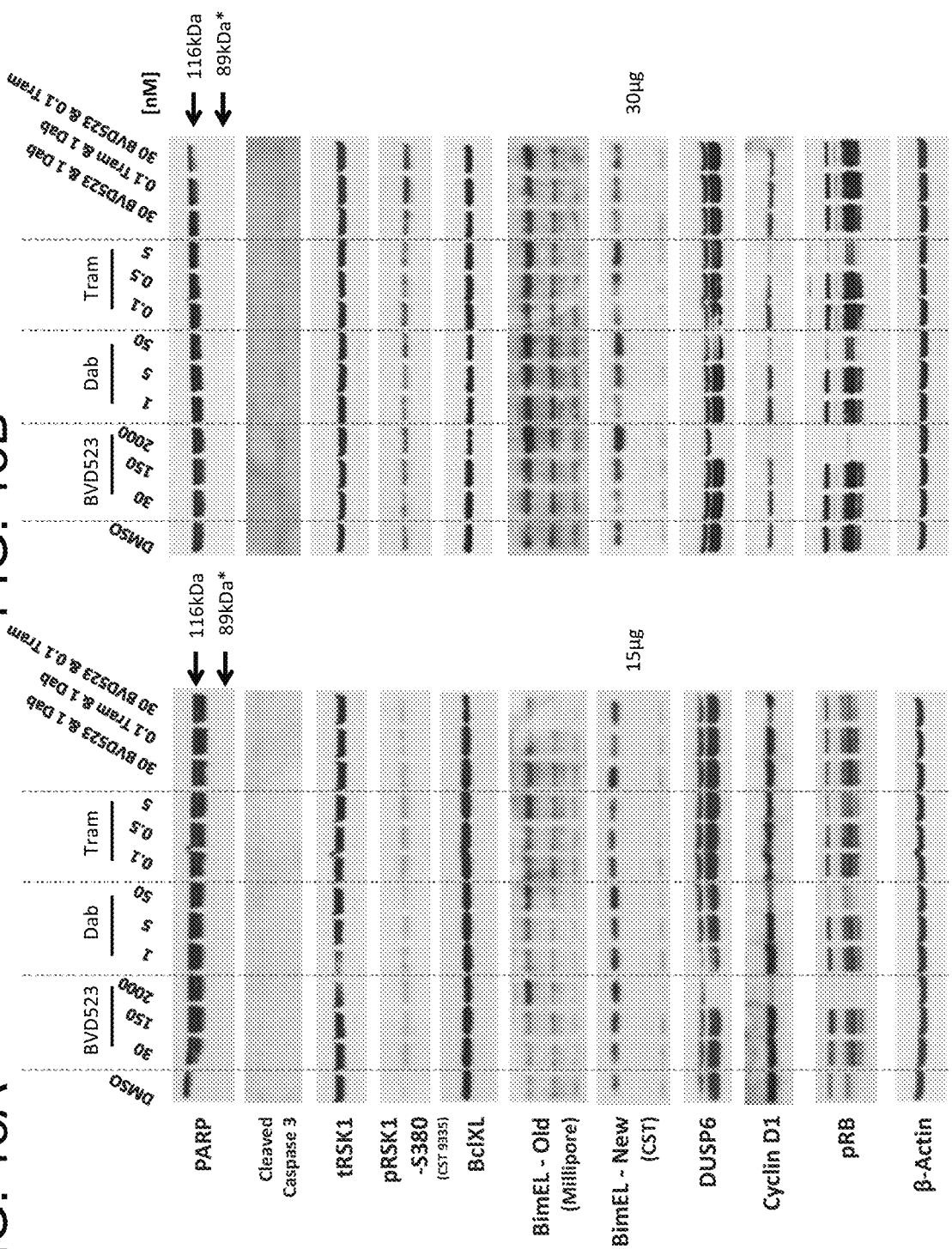
FIG. 18A
FIG. 18B

FIG. 19

| Resistance Condition | Starting Concentration (nM) | Maintenance Concentration (nM) | | |
|---|---|---|---|---|
| | | Month 1 | Month 2 | Month 3 |
| Dabrafenib_R | 5 | 25 | 400 | 3200 |
| Trametinib_R | 1 | 3 | 40 | 160 |
| BVD-523_R | 160 | 640 | 1800 | 1200 |
| Dabrafenib/Trametinib_R | 2.5/0.5 | 7.5/1.5 | 28/6 | 160/30 |
| Dabrafenib/BVD-523_R | 2.5/80 | 10/320 | 28/900 | 42/1500 |
| Trametinib/BVD-523_R | 0.5/80 | 2/320 | 2.5/400 | 4/600 |

| Resistance Condition | Multiple Above Starting Concentration | | |
|---|---|---|---|
| | Month 1 | Month 2 | Month 3 |
| Dabrafenib_R | 5X | 80X | 640X |
| Trametinib_R | 3X | 40X | 160X |
| BVD-523_R | 4X | 11.25X | 7.5X |
| Dabrafenib/Trametinib_R | 3X | 11.2X | 64X |
| Dabrafenib/BVD-523_R | 4X | 11.2X | 16.8X |
| Trametinib/BVD-523_R | 4X | 5X | 8X |

| Resistance Condition | IC50 Fold Change | | | |
|---|---|---|---|---|
| | Dabrafenib | Trametinib | BVD-523 | Paclitaxel |
| Parental | 1.00 | 1.00 | 1.00 | 1.00 |
| Trametinib_R | 2.51 | 2.60 | 1.78 | 2.53 |
| Dabrafenib_R | 3.79 | 3.28 | 1.84 | 0.82 |
| BVD-523_R | 238.11 | 105.20 | 16.84 | 2.97 |
| Trametinib + Dabrafenib_R | 103.17 | 38.60 | 4.22 | 1.66 |
| Dabrafenib + BVD-523_R | 71.87 | 18.04 | 4.32 | 1.35 |
| Trametinib + BVD-523_R | 27.51 | 26.69 | 3.81 | 3.96 |

| Resistance Condition | Percent Growth at ~10X Parental IC50 | | | |
|---|---|---|---|---|
| | Dabrafenib | Trametinib | BVD-523 | Paclitaxel |
| Parental | 13.30% | 6.80% | 0.00% | 1.95% |
| Trametinib_R | 33.53% | 30.15% | 20.02% | 13.52% |
| Dabrafenib_R | 36.45% | 25.96% | 8.21% | 9.36% |
| BVD-523_R | 301.02% | 172.91% | 57.49% | 34.02% |
| Trametinib + Dabrafenib_R | 131.10% | 125.01% | 12.65% | 15.44% |
| Dabrafenib + BVD-523_R | 93.55% | 71.37% | 8.70% | 11.41% |
| Trametinib + BVD-523_R | 86.71% | 64.03% | 27.70% | 30.71% |

| | Dabrafenib | Trametinib | BVD-523 | Paclitaxel |
|---|---|---|---|---|
| IC50, Parental (nM) | 4.11 | 0.38 | 186.21 | 3.65 |
| ~10X Parental concentration | 30.20 | 3.00 | 3019.95 | 36.48 |

FIG. 34C
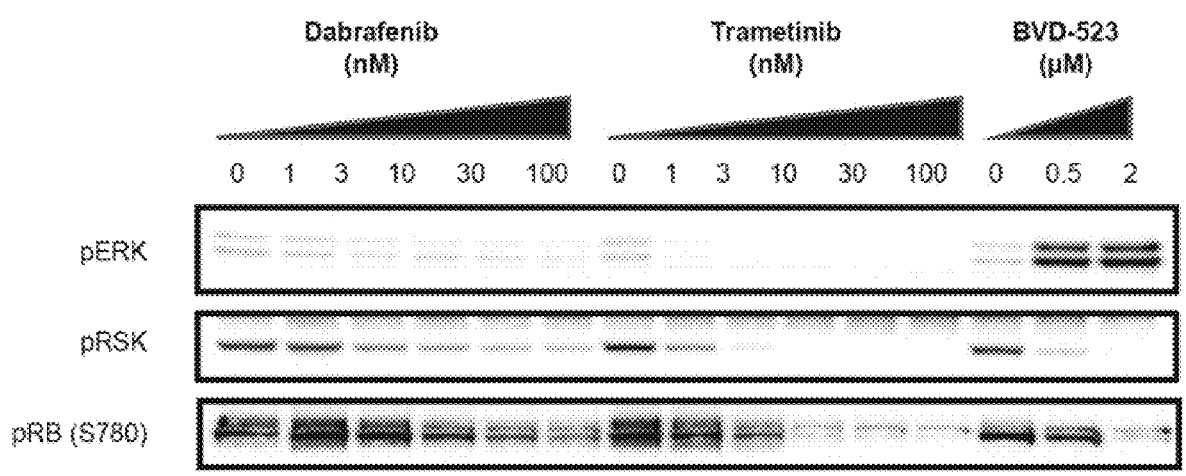
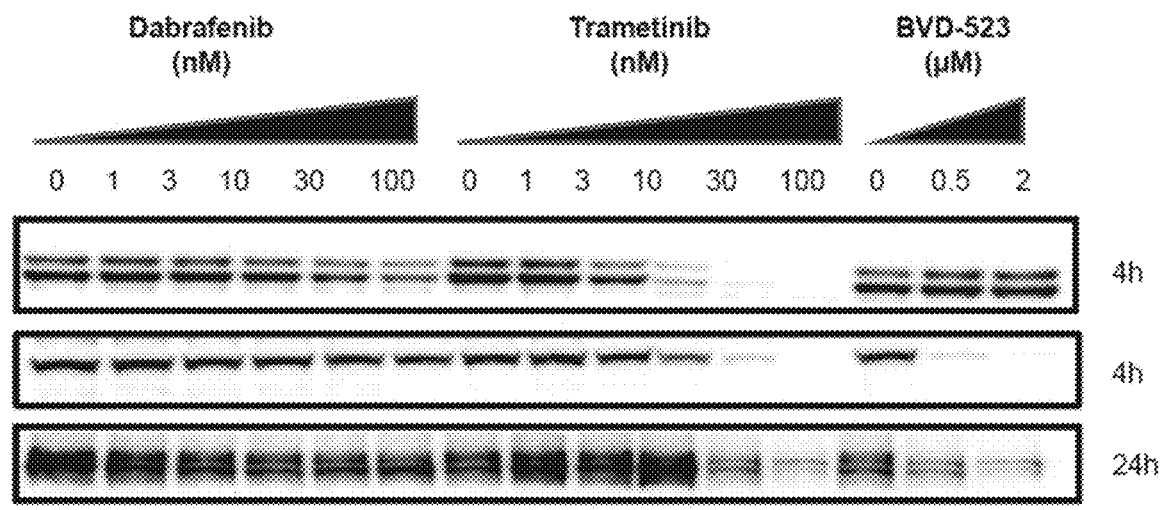

G1: Vehicle; po; BID to end
G2: BVD-523, 100 mg/kg orally; BID x 41
G3: Dabrafenib, 50 mg/kg orally; BID x 41
G4: Dabrafenib, 25 mg/kg + BVD-523, 50 mg/kg
G5: Dabrafenib, 50 mg/kg + BVD-523, 100 mg/kg

METHODS AND COMPOSITIONS FOR TREATING NON-ERK MAPK PATHWAY INHIBITOR-RESISTANT CANCERS

CROSS REFERENCE TO RELATED APPLICATIONS

This application claims benefit to and is a continuation application of U.S. patent application Ser. No. 15/161,137, filed May 20, 2016. The '137 application is a continuation in part of PCT international application no. PCT/US2014/071749, filed Dec. 19, 2014, which claims benefit of U.S. Patent Application Ser. No. 61/919,551, filed on Dec. 20, 2013 which, applications are incorporated by reference herein in their entireties.

FIELD OF INVENTION

The present invention provides, inter alia, methods, pharmaceutical compositions, and kits for treating or ameliorating the effects of a cancer in a subject, which cancer is refractory or resistant to non-ERK MAPK pathway inhibitor therapy.

INCORPORATION BY REFERENCE OF SEQUENCE LISTING

This application contains references to amino acids and/or nucleic acid sequences that have been filed concurrently herewith as sequence listing text file "0375608.txt", file size of 356 KB, created on Dec. 18, 2014. The aforementioned sequence listing is hereby incorporated by reference in its entirety pursuant to 37 C.F.R. § 1.52 (e)(5).

BACKGROUND OF THE INVENTION

Drug inhibitors that target components of the mitogen-activated protein kinases (MAPK) signaling pathway show clinical efficacy in a variety of cancers, particularly those bearing mutations in the BRAF protein kinase. Both RAF and MEK inhibitors are approved for single-agent use in advanced metastatic BRAF mutant melanoma. Either alone or in combination, BRAF and MEK inhibitor activity is unpredictable in other cancers, with promising efficacy in BRAF mutant thyroid and lung cancer, but only marginal activity in BRAF mutant colorectal cancer.

As with other targeted therapies, patterns of disease response to RAF and MEK inhibitors appear to be influenced by the intrinsic genetic heterogeneity present in the cancers where the drugs are used. For instance, it has been shown that certain genetic alterations, including PTEN and other changes that activate the PI3K cell growth signaling pathway, may predict a poor initial response, and/or relatively rapid progression, in BRAF mutant melanoma treated with the RAF inhibitor vemurafenib. Likewise, direct mutations in MEK gene loci appear to emerge in tumors that have progressed following either BRAF, MEK, or combined drug treatment. Several additional examples, from RAS and RAF gene amplification and splicing mutations, suggest that acquired drug resistance is produced when oncogenic pleiotropy encounters the selective pressure of targeted drug treatment.

In view of the foregoing, there is a need for novel targeted agents that would ideally inhibit diverse nodes of oncogenic pathways, and also be effective in combinations by inducing a burden of selective pressures that exceeds the adaptive capacity of diverse cancer genomes. The present application is directed to meeting these and other needs.

SUMMARY OF THE INVENTION

One embodiment of the present invention is a method for treating or ameliorating the effects of a cancer in a subject, which cancer is refractory or resistant to non-ERK MAPK pathway inhibitor therapy. The method comprises administering to the subject an effective amount of BVD-523 or a pharmaceutically acceptable salt thereof.

Another embodiment of the present invention is a method for treating or ameliorating the effects of a cancer in a subject. The method comprises:
 (a) identifying a subject with cancer that has become refractory or resistant to BRAF inhibitor therapy, MEK inhibitor therapy, or BRAF and MEK inhibitor therapy; and
 (b) administering to the subject with said refractory or resistant cancer an effective amount of an ERK inhibitor, which is BVD-523 or a pharmaceutically acceptable salt thereof.

A further embodiment of the present invention is a method for treating or ameliorating the effects of cancer in a subject, which cancer is refractory or resistant to BRAF inhibitor therapy, MEK inhibitor therapy, or both. The method comprises administering to the subject an effective amount of BVD-523 or a pharmaceutically acceptable salt thereof.

Another embodiment of the present invention is a method for identifying a subject having cancer who would benefit from therapy with an ERK inhibitor. The method comprises:
 (a) obtaining a biological sample from the subject; and
 (b) screening the sample to determine whether the subject has one or more of the following markers:
  (i) a switch between RAF isoforms,
  (ii) upregulation of receptor tyrosine kinase (RTK) or NRAS signaling,
  (iii) reactivation of mitogen activated protein kinase (MAPK) signaling,
  (iv) the presence of a MEK activating mutation,
  (v) amplification of mutant BRAF,
  (vi) STAT3 upregulation,
  (vii) mutations in the allosteric pocket of MEK that directly block binding of inhibitors to MEK or lead to constitutive MEK activity,
wherein the presence of one or more of the markers confirms that the subject's cancer is refractory or resistant to BRAF and/or MEK inhibitor therapy and that the subject would benefit from therapy with an ERK inhibitor, which is BVD-523 or a pharmaceutically acceptable salt thereof.

A further embodiment of the present invention is a pharmaceutical composition for treating or ameliorating the effects of a cancer in a subject, which cancer is refractory or resistant to non-ERK MAPK pathway therapy. The composition comprises a pharmaceutically acceptable carrier or diluent and an effective amount of BVD-523 or a pharmaceutically acceptable salt thereof.

Another embodiment of the present invention is a kit for treating or ameliorating the effects of a cancer in a subject, which cancer is refractory or resistant to non-ERK MAPK pathway therapy. The kit comprises any of the pharmaceutical compositions according to the present invention packaged together with instructions for its use.

Another embodiment of the present invention is a method for inhibiting phosphorylation of RSK in a cancer cell that is refractory or resistant to a non-ERK MAPK pathway inhibitor. The method comprises contacting the cancer cell with an effective amount of BVD-523 or a pharmaceutically acceptable salt thereof for a period of time sufficient for phosphorylation of RSK in the cancer cell to be inhibited.

Another embodiment of the present invention is a method of treating a subject having an unresectable or metastatic BRAF600 mutation-positive melanoma comprising administering to the subject 600 mg BID of BVD-523 or a pharmaceutically acceptable salt thereof.

Another embodiment of the present invention is a composition for treating a subject having an unresectable or metastatic BRAF600 mutation-positive melanoma, the composition comprising 600 mg of BVD-523 or a pharmaceutically acceptable salt thereof and optionally a pharmaceutically acceptable carrier, adjuvant, or vehicle.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A, FIG. 2C and FIG. 2G are normalized to control, whereas FIG. 2D, FIG. 2F and FIG. 2H show the raw data.

FIG. 4A, FIG. 4C and FIG. 4G are normalized to control, whereas FIG. 4D, FIG. 4F and FIG. 4H show the raw data.

FIG. 5A, FIG. 5C and FIG. 5G are normalized to control, whereas FIG. 5D, FIG. 5F and FIG. 5H show the raw data.

FIG. 16A and FIG. 16B show results from duplicate samples. Similarly, FIG. 16C and FIG. 16D also show results from duplicate samples. In FIG. 16A and FIG. 16B, pRSK1 had a relatively weak signal in A375 cells compared to other markers. A different pRSK1-S380 antibody from Cell Signaling (cat. #11989) was tested but did not give a detectable signal (data not shown). In FIG. 16C and FIG. 16D, pCRAF-338 gave a minimal signal.

FIG. 17A-FIG. 17D are a set of images showing Western blot analysis of MAPK signaling in a human colorectal carcinoma cell line (HCT116 cells) after a 4 hour treatment with various concentrations (in nM) of BVD-523, dabrafenib (Dab), and Trametinib (Tram). 40 μg of total protein was loaded in each lane except where indicated otherwise. In this experiment, duplicate samples were collected. FIG. 17A and FIG. 17B show results from duplicate samples. Similarly, FIG. 17C and FIG. 17D also show results from duplicate samples. In FIG. 17A and FIG. 17B, pRSK1 levels appear to be very low in HCT116 cells, and in FIG. 17C and FIG. 17D, pCRAF-338 signal was also very weak.

FIG. 18A-FIG. 18D are a set of images showing Western blot analysis of cell cycle and apoptosis signaling in A375 melanoma cells after a 24 hour treatment with various concentrations (in nM) of BVD-523 ("BVD523"), trametinib ("tram") and/or dabrafenib ("Dab") as labelled. 50 μg of total protein was loaded in each lane except where indicated otherwise. In this experiment, duplicate samples were collected. FIG. 18A and FIG. 18B show results from duplicate samples. Similarly, FIG. 18C and FIG. 18D also show results from duplicate samples. In FIG. 18A and FIG. 18B, no band of a size corresponding to cleaved PARP (89 kDa) was apparent.

FIG. 19 shows that BVD-523 can treat acquired resistance to targeted drugs in-vivo. A patient-derived line, ST052C, was isolated from a BRAFV600E melanoma patient that progressed following 10 months of therapy with MAPK-pathway directed therapies. Treated ex vivo, ST052C exhibited acquired cross-resistance to dabrafenib at 50 mg/kg BID. Meanwhile, BVD-523 was effective in ST052C as a single-agent at 100 mg/kg BID.

FIG. 23A shows a dose matrix showing inhibition (%) for the combination in RKO parental cells. FIG. 23O shows Bliss excess for the combination in FIG. 23K.

FIG. 24A shows a dose matrix showing inhibition (%) for the combination in RKO parental cells. FIG. 24O shows Bliss excess for the combination in FIG. 24K.

FIG. 25A shows a dose matrix showing inhibition (%) for the combination in RKO parental cells. FIG. 25O shows Bliss excess for the combination in FIG. 25K.

FIG. 27A shows increased signaling in RKO MEK1 (Q56P/+) cells. FIG. 27B-FIG. 27C show the results of a 4 hour treatment in Experiment 1 (See, Example 7) in RKO Parental (27B) and RKO MEK1 (Q56P/+) (27C) cells. FIG. 27D-FIG. 27E show the results of a 4 hour treatment in Experiment 2 (See, Example 7) in RKO Parental (27D) and RKO MEK1 (Q56P/+) (27E) cells. FIG. 27F-FIG. 27G show the results of a 4 hour treatment in Experiment 2 (See, Example 7) in RKO Parental (27F) and RKO MEK1 (Q56P/+) (27G) cells. FIG. 27H-FIG. 27I show a summary of results in RKO Parental (27H) and RKO MEK1 (Q56P/+) (27I) cells.

FIG. 28A shows a dose matrix showing inhibition (%) for the combination in A375 cells. FIG. 28B-FIG. 28C show the results of single agent proliferation assays for the combination in FIG. 28A. FIG. 28D shows Loewe excess for the combination in FIG. 28A and FIG. 28E shows Bliss excess for the combination in FIG. 28A.

FIG. 29A shows that BVD-523 demonstrates inhibition in a reversible ATP-competitive manner. This is demonstrated by a linear increase in $IC_{50}$ values for inhibition of ERK2 with increasing ATP concentration as shown in FIG. 29B. FIG. 29C shows a representative plot of the dose-response curve and FIG. 29D shows a plot of $IC_{50}$ over time. FIG. 29E shows BVD-523 binding to ERK2 and phospho-ERK2 (pERK2), compared with negative control protein p38. FIG. 29F shows BVD-523 binding to ERK2 compared with the ERK inhibitors SCH772984 and pyrazolylpyrrole.

FIG. 30A shows that BVD-523 demonstrates preferential activity in cells with MAPK pathway mutations, as defined by the presence of mutations in RAS family members and RAF. In addition, as shown in FIG. 30B, BVD-523 blocks sensitive cell lines in the G1 phase of the cell cycle. FIG. 30C shows that BVD-523 induced a concentration- and time-dependent increase in caspase activity in the A375, WM266, and LS411N cancer cell lines after 72 hours of exposure. FIG. 30D shows that the MAPK pathway and effector proteins are modulated by acute (4-hour) and prolonged (24-hour) BVD-523 treatment in $BRAF^{V600E}$-mutant A375 cells.

FIG. 31C shows that in Colo205 xenografts, increased ERK1/2 phosphorylation correlates with BVD-523 concentration.

FIG. 34A-FIG. 34D show that BVD-523 demonstrates activity in models of resistance to BRAF/MEK inhibition. The appearance of resistance to BVD-523, dabrafenib, or trametinib in $BRAF^{V600E}$ A375 cells following exposure to increasing concentrations of drug is indicated. A strict set of "criteria" was applied to determine when the dose could be increased in order to ensure that the kinetics of the acquisition of resistance between treatments was comparable. See, Example 1. Time is shown against multipliers of $IC_{50}$; each point on the plotted line represents a change of medium or cell split. FIG. 34A shows that adapting cells to growth in the presence of BVD-523 was more challenging than with either dabrafenib or trametinib. FIG. 34B shows that BVD-523 sensitivity is retained in A375 cells cultured to acquire resistance to combined BRAF (dabrafenib)+MEK (trametinib) inhibition. In FIG. 34C, cells were treated with compound for 96 h and viability was assessed using CellTiter-Glo®. BVD-523 activity is retained in $BRAF^{V600E}$ RKO cells cross-resistant to BRAF (dabrafenib) and MEK (trametinib) inhibitors due to endogenous heterozygous knock-in of MEK1$^{Q56P}$. FIG. 34D shows that BVD-523 inhibition of pRSK in $BRAF^{V600E}$-mutant cell line RKO is maintained in the presence of MEK1$^{Q56P}$, which confers resistance to MEK and BRAF inhibition. Knock-in of KRAS mutant alleles into SW48 cell lines significantly diminishes sensitivity to the MEK inhibitors trametinib and selumetinib, while comparatively sensitivity to BVD-523 is retained.

FIG. 36A-FIG. 36B show that the combination of BVD-523 plus dabrafenib exhibited superior antitumor activity compared with treatment with either agent alone in a A375 $BRAF^{V600E}$-melanoma cell line xenograft model with a tumor start volume of 75-144 mm³. FIG. 36C-FIG. 36D show similar data from the same model with an enlarged tumor volume (700-800 mm³) at the start of dosing. Plots of mean tumor growth (left panels) and Kaplan-Meier survival (right panels) are presented for each study. Abbreviations: BID, twice daily; QD, once daily.

DETAILED DESCRIPTION OF THE INVENTION

One embodiment of the present invention is a method for treating or ameliorating the effects of a cancer in a subject, which cancer is refractory or resistant to non-ERK MAPK pathway inhibitor therapy. The method comprises administering to the subject an effective amount of BVD-523 or a pharmaceutically acceptable salt thereof.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc.

Figure 18C:
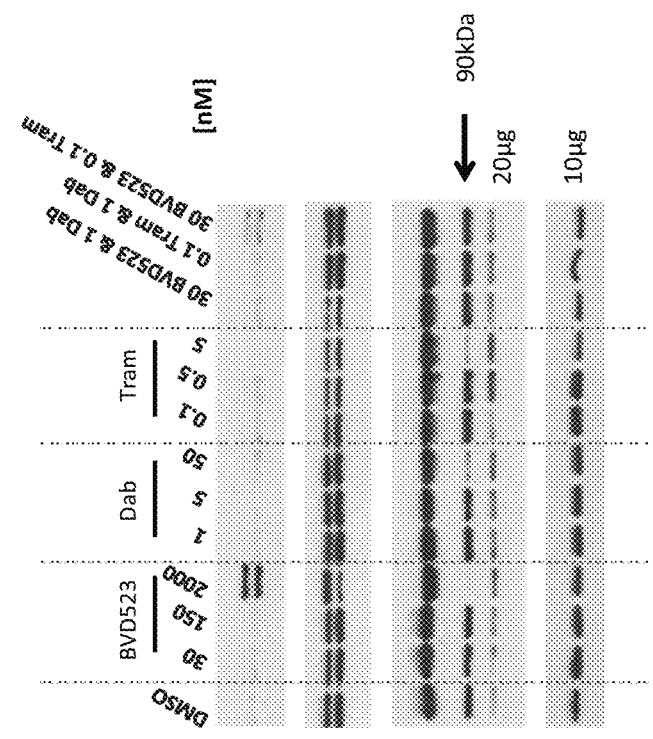
Figure 18D:
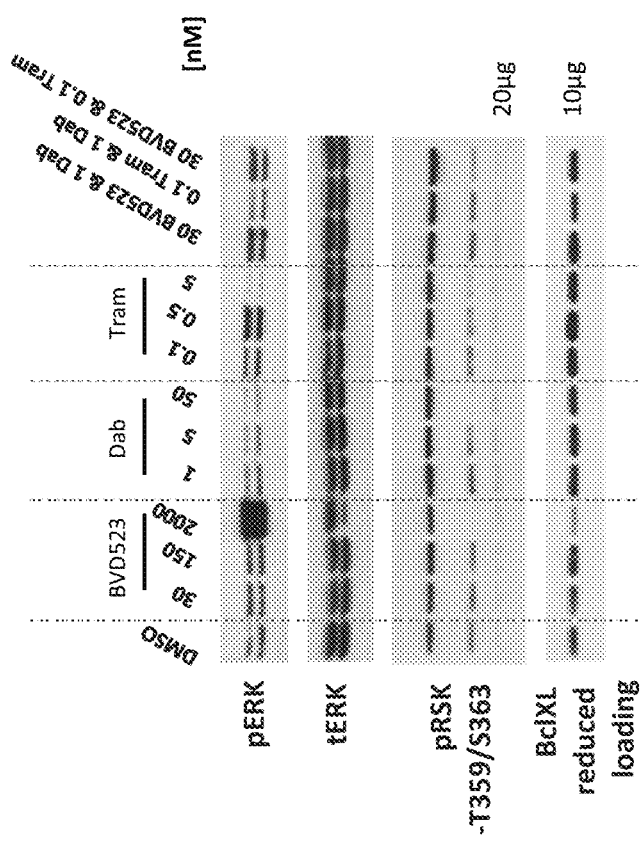

In the present invention, BVD-523 corresponds to a compound according to formula (I):

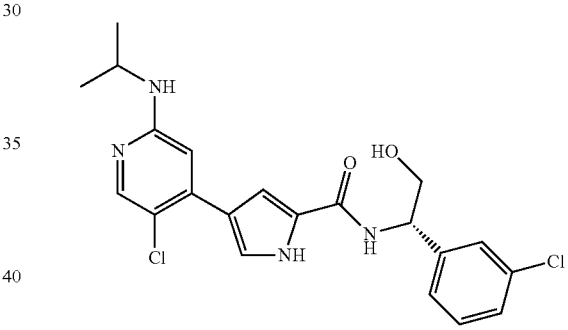

and pharmaceutically acceptable salts thereof. BVD-523 may be synthesized according to the methods disclosed, e.g., in U.S. Pat. No. 7,354,939. Enantiomers and racemic mixtures of both enantiomers of BVD-523 are also contemplated within the scope of the present invention. BVD-523 is an ERK1/2 inhibitor with a mechanism of action that is believed to be, e.g., unique and distinct from certain other ERK1/2 inhibitors, such as SCH772984 and the pyrimidinal structure used by Hatzivassiliou et al. (2012). For example, other ERK1/2 inhibitors, such as SCH772984, inhibit autophosphorylation of ERK (Morris et al., 2013), whereas BVD-523 allows for the autophosphorylation of ERK while still inhibiting ERK. (See, e.g., FIG. 18).

As used herein, the words "resistant" and "refractory" are used interchangeably. Being "resistant" to non-ERK MAPK pathway inhibitor therapy treatments means that non-ERK MAPK inhibitors have reduced efficacy in treating cancer.

As used herein, a "non-ERK MAPK inhibitor" means any substance that reduces the activity, expression or phosphorylation of proteins or other members of the MAPK pathway that results in a reduction of cell growth or an increase in cell death, with the exception of ERK1/2 inhibitors. As used herein, an "ERK1/2 inhibitor" means those substances that (i) directly interact with ERK1 and/or ERK2, e.g., by binding to ERK1/2 and (ii) decrease the expression or the activity of ERK1 and/or ERK2 protein kinases. Therefore, inhibitors that act upstream of ERK1/2, such as MEK inhibitors and RAF inhibitors, are not ERK1/2 inhibitors according to the present invention (but they are non-ERK MAPK inhibitors). Non-limiting examples of ERK1/2 inhibitors according to the present invention include AEZS-131 (Aeterna Zentaris), AEZS-136 (Aeterna Zentaris), BVD-523 (BioMed Valley Discoveries, Inc.), SCH-722984 (Merck & Co.), SCH-772984 (Merck & Co.), SCH-900353 (MK-8353) (Merck & Co.), pharmaceutically acceptable salts thereof, and combinations thereof.

Figure 21:
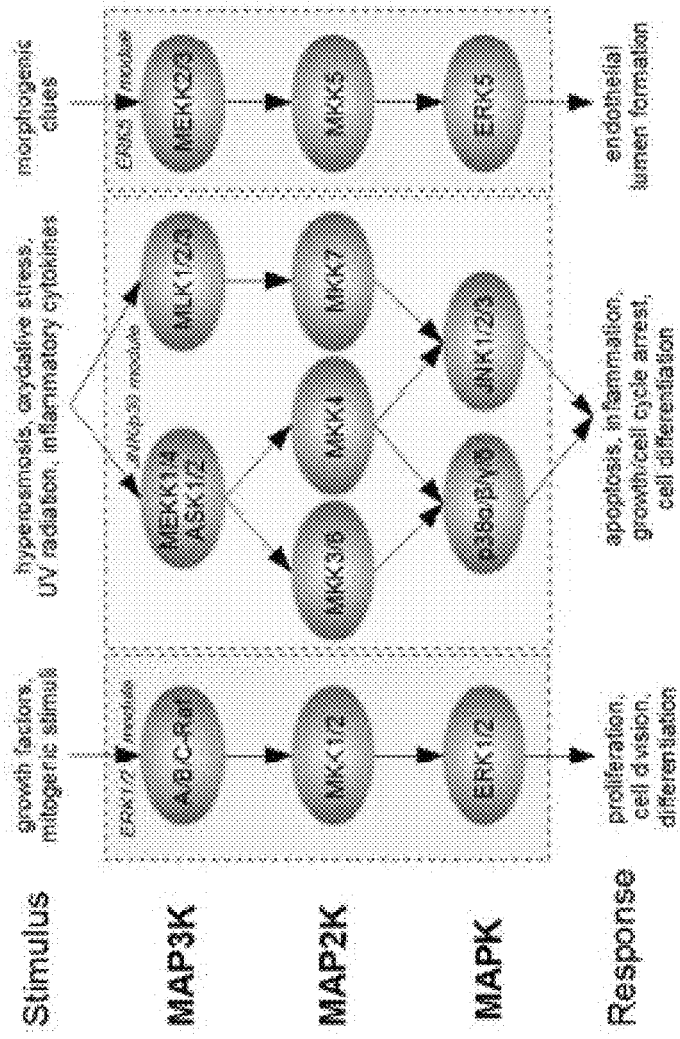
FIG. 21 shows a schematic of the mitogen-activated protein kinases (MAPK) pathway.
Figure 22A:
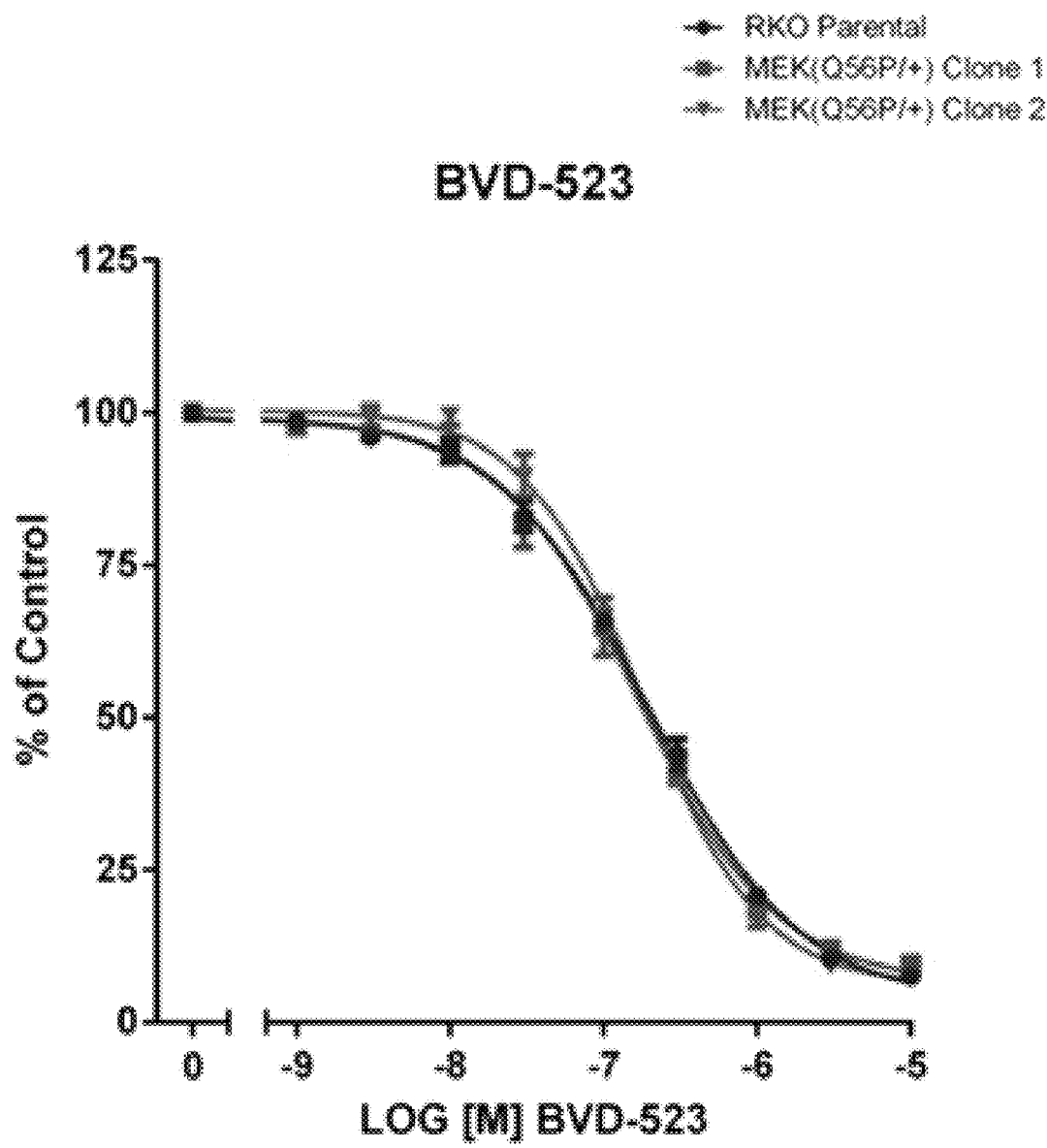
FIG. 22A-FIG. 22E show the results of single agent proliferation assays. Proliferation results are shown for treatment with BVD-523 (FIG. 22A), SCH772984 (FIG. 22B), Dabrafenib (FIG. 22C), Trametinib (FIG. 22D), and Paclitaxel (FIG. 22E).
Figure 22B:
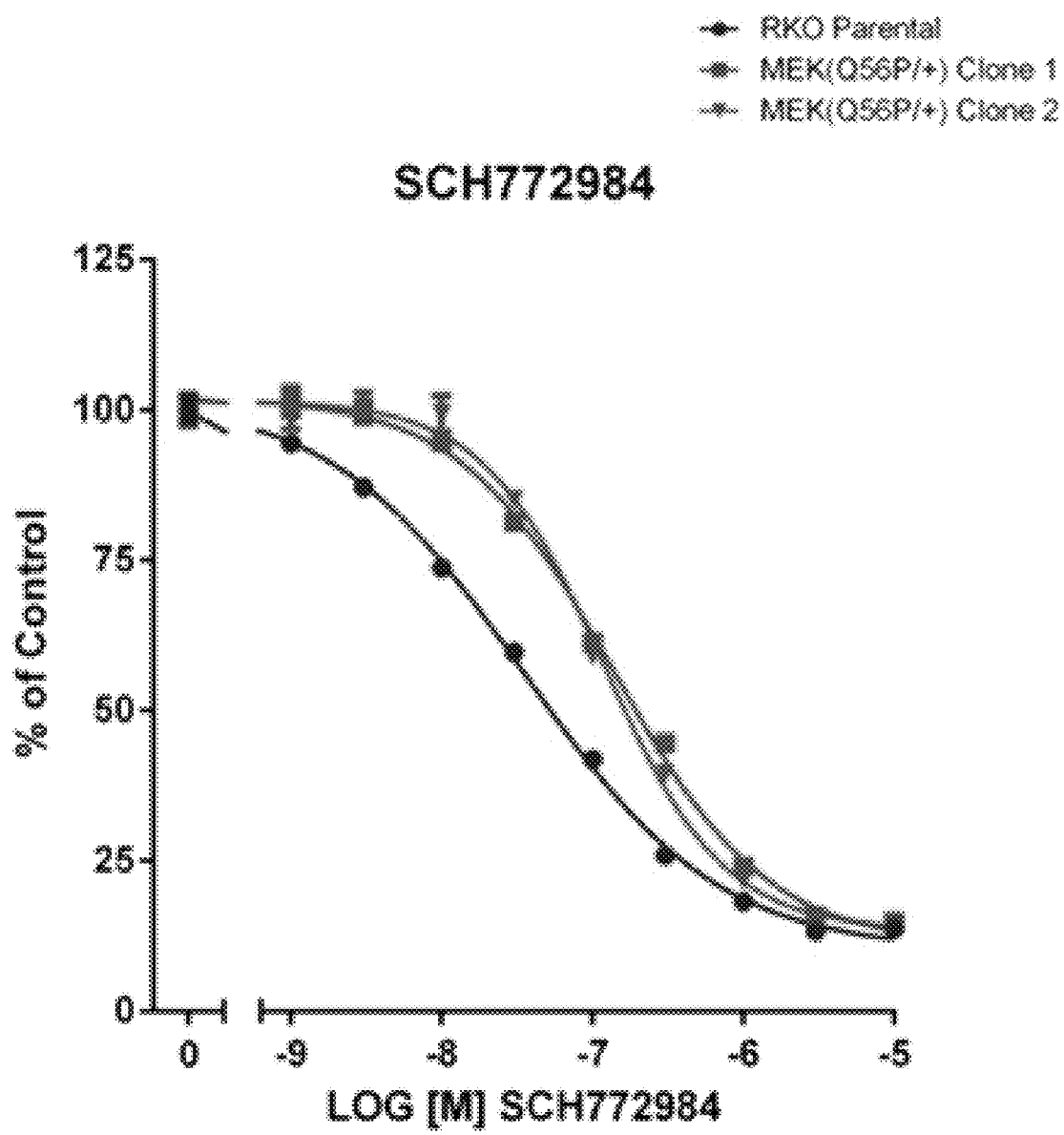
Figure 22C:
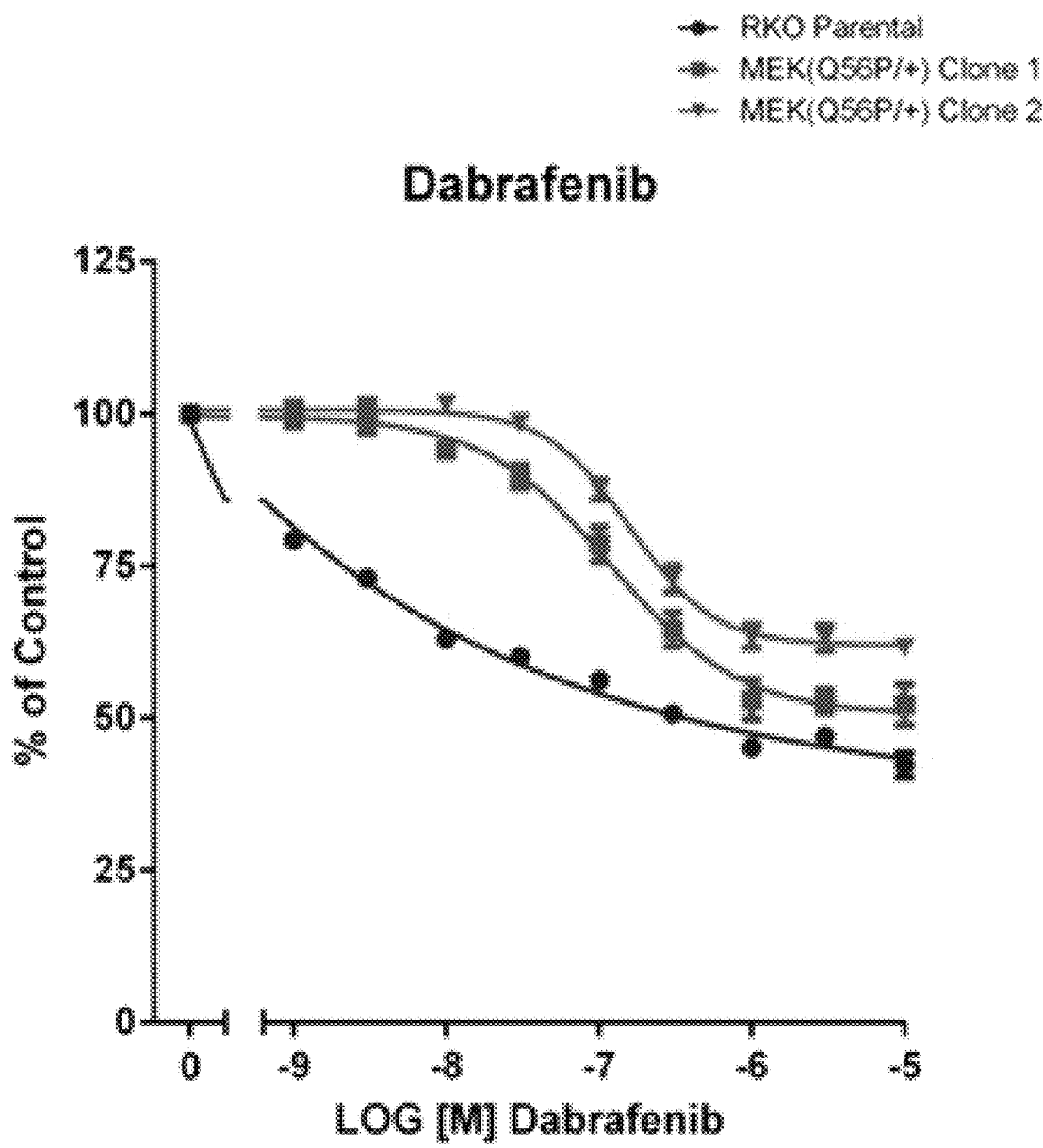
Figure 22D:
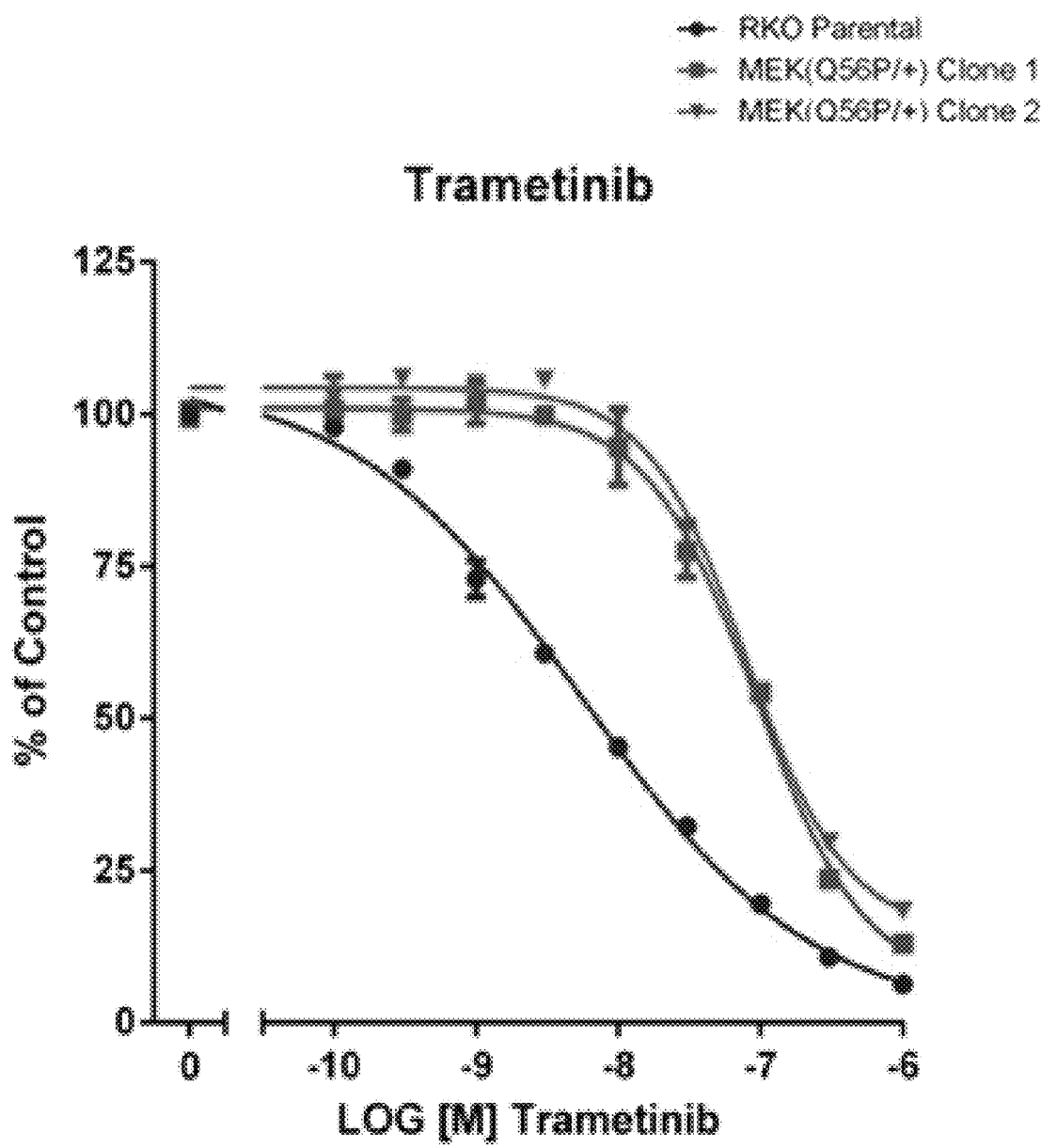
Figure 22E:
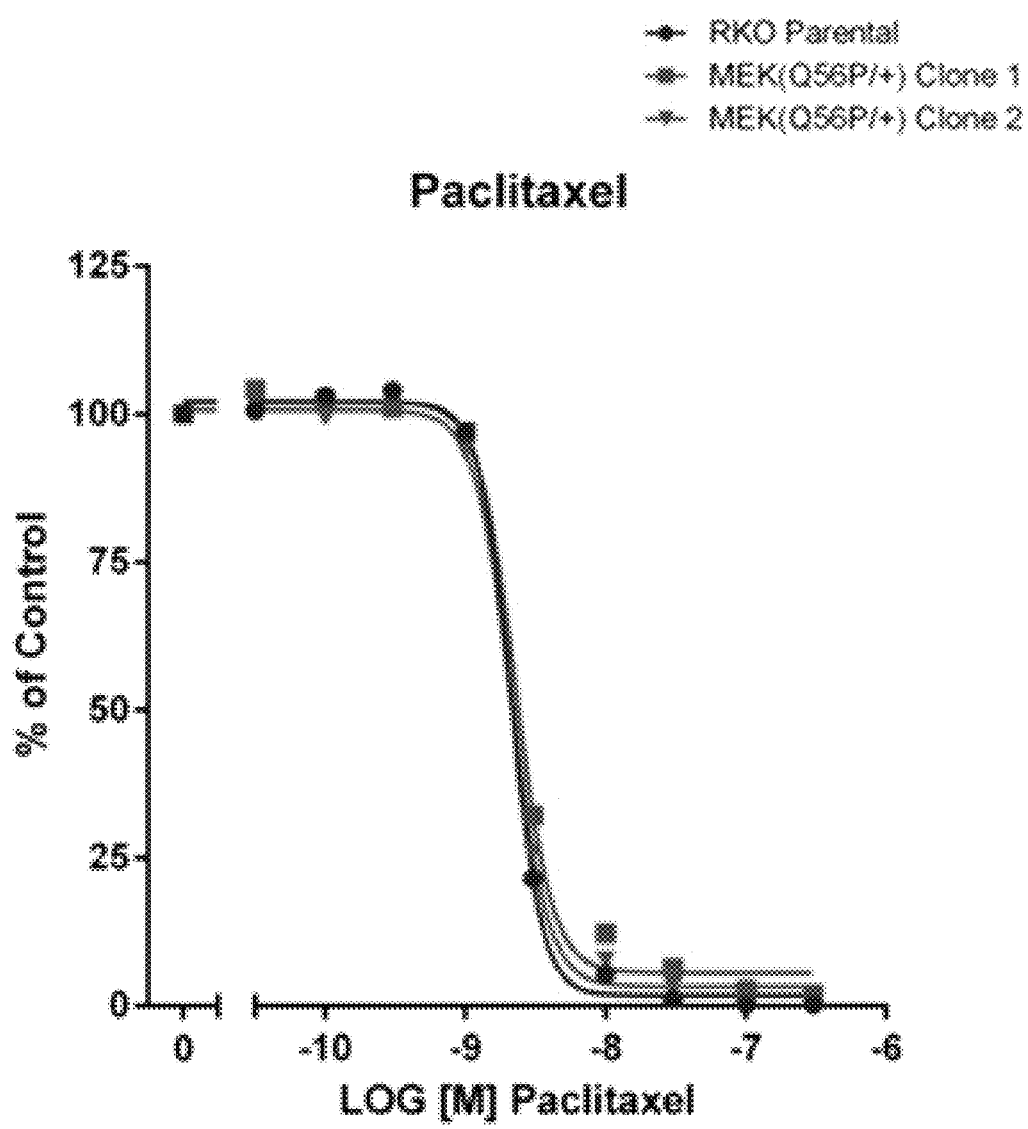
Figure 23A:
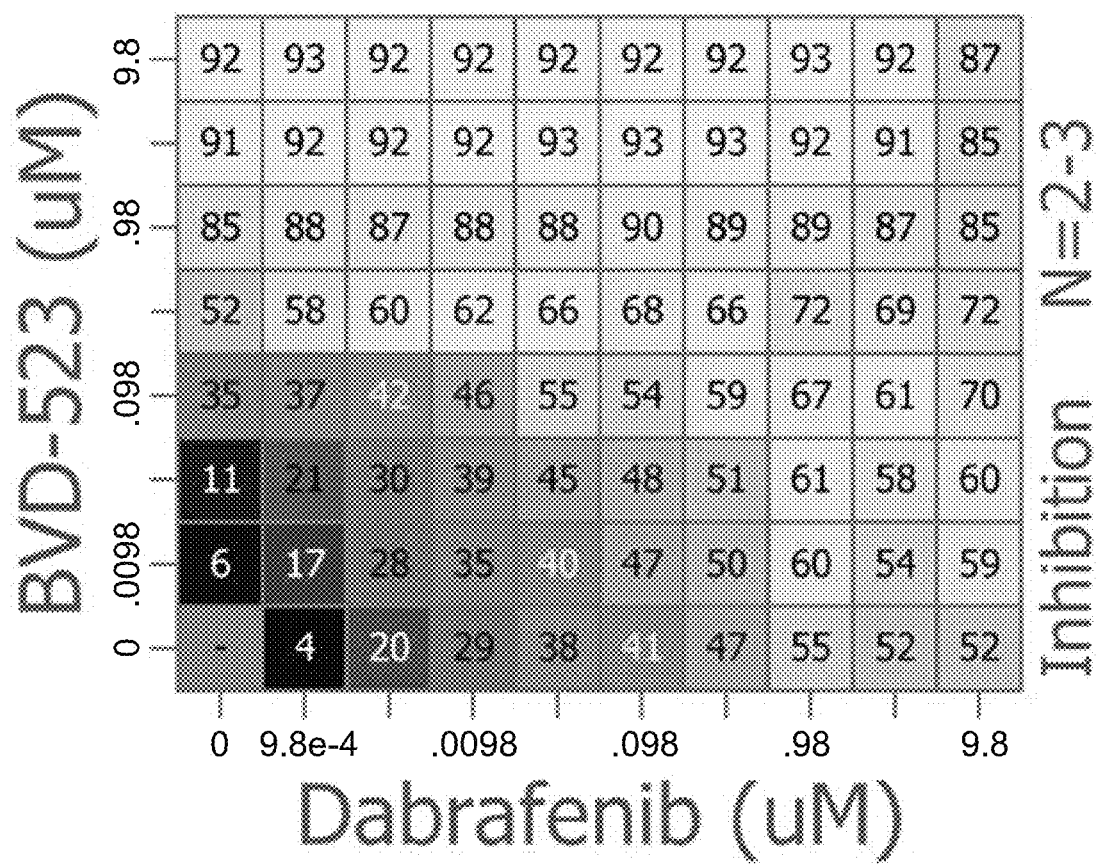
FIG. 23A-FIG. 23O show the results of the combination of BVD-523 and Dabrafenib.
Figure 23B:
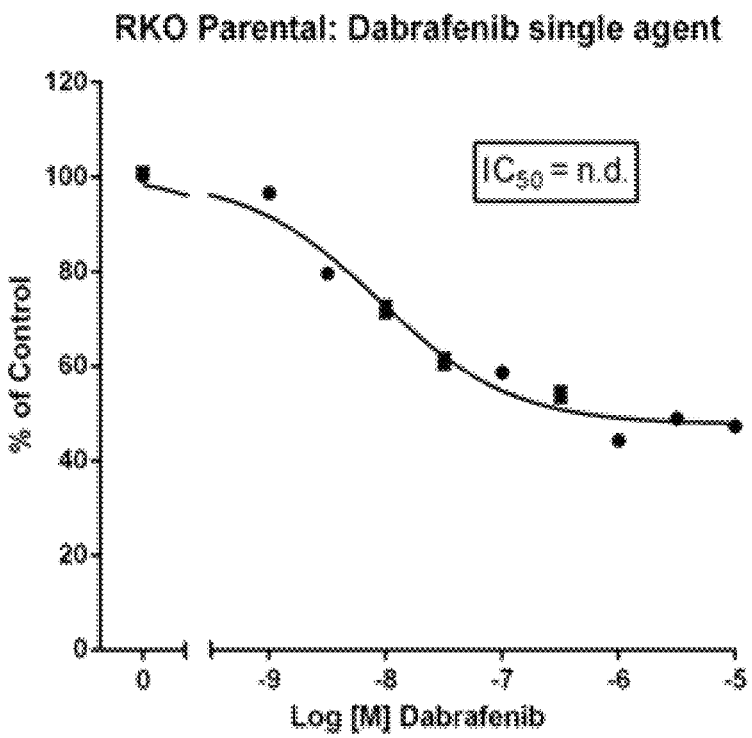
FIG. 23B-FIG. 23C show the results of single agent proliferation assays for the combination in FIG. 23A.
Figure 23C:
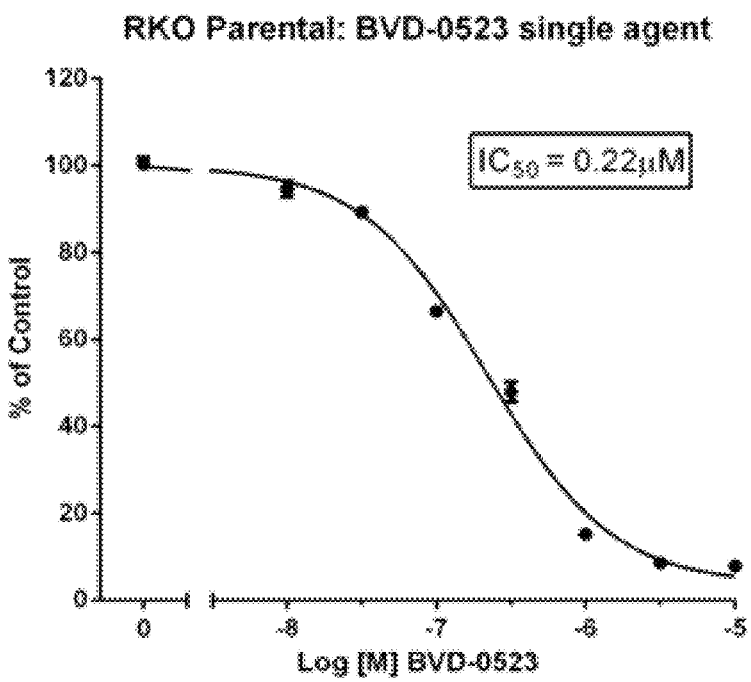
Figure 23D:
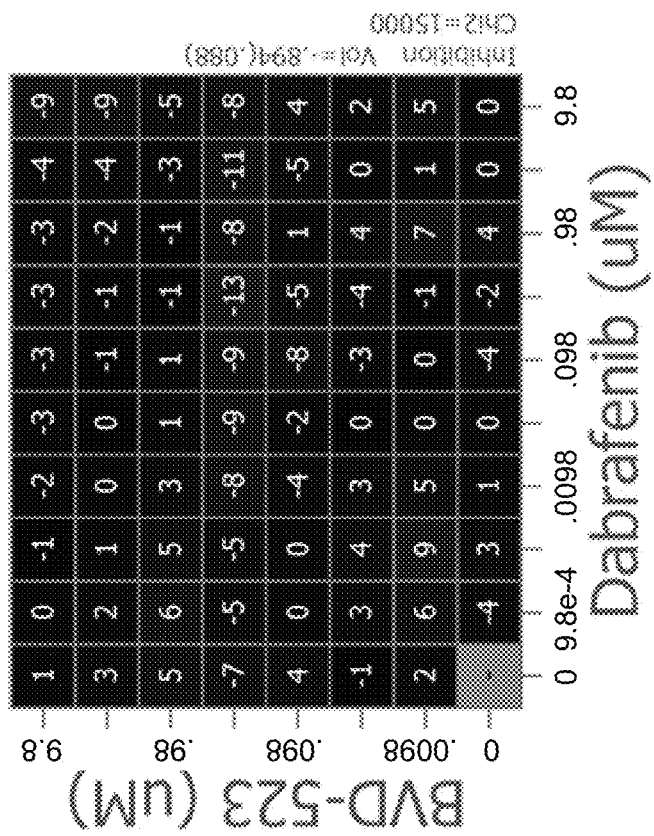
FIG. 23D shows Loewe excess for the combination in FIG. 23A
Figure 23E:
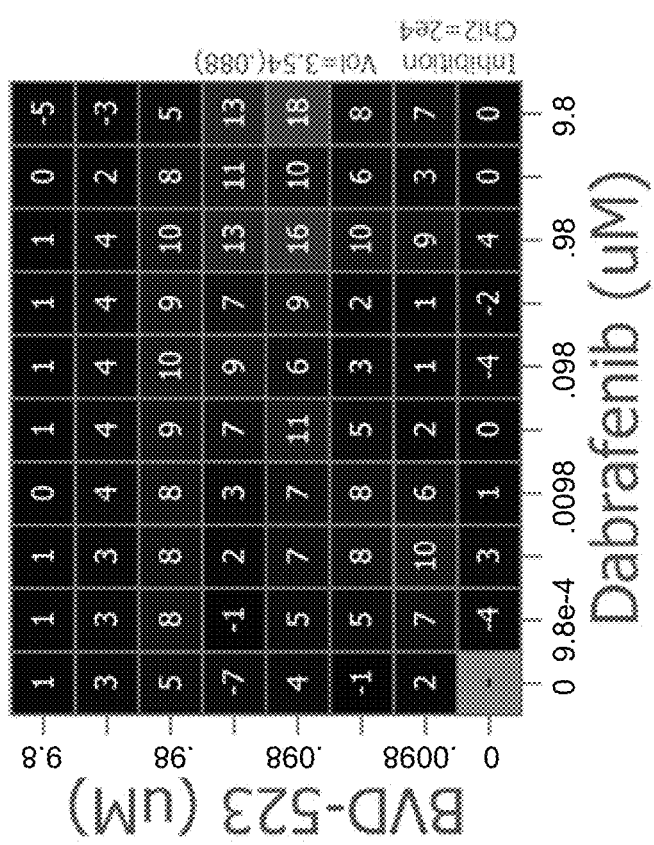
FIG. 23E shows Bliss excess for the combination in FIG. 23A.
Figure 23F:
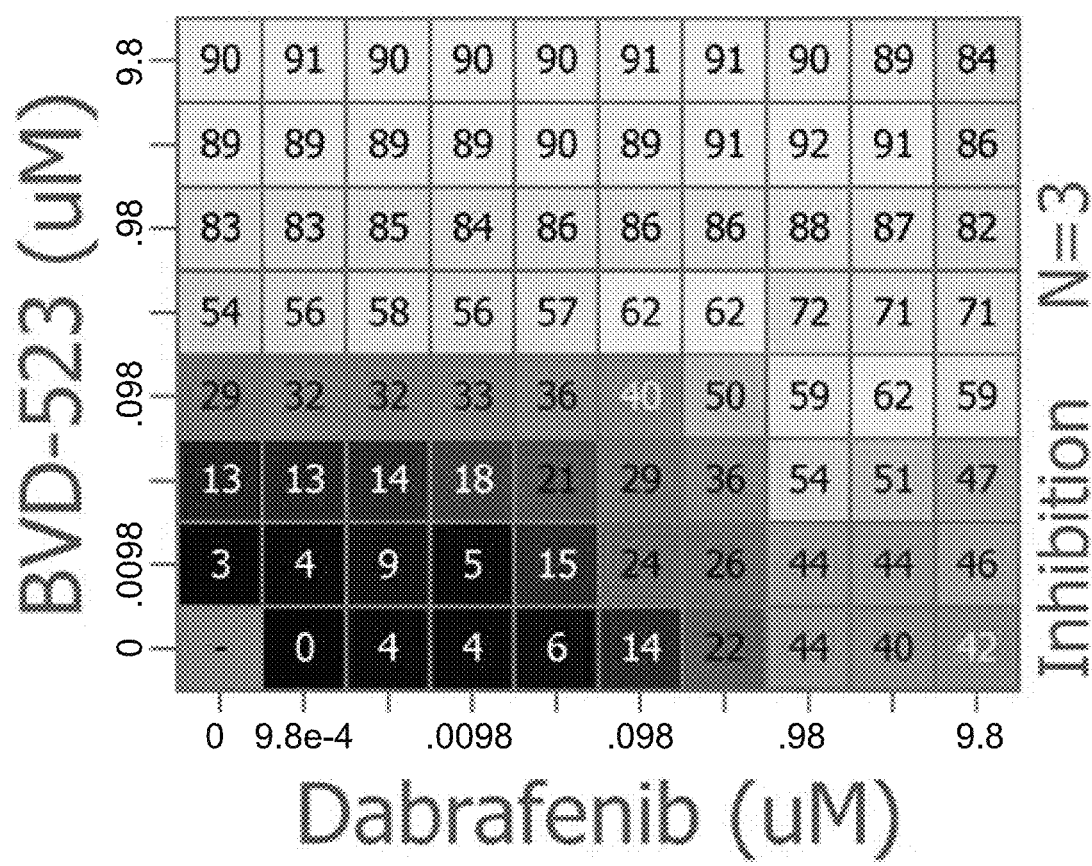
FIG. 23F shows a dose matrix showing inhibition (%) for the combination in RKO MEK1 (Q56P/+)-clone 1 cells.
Figure 23G:
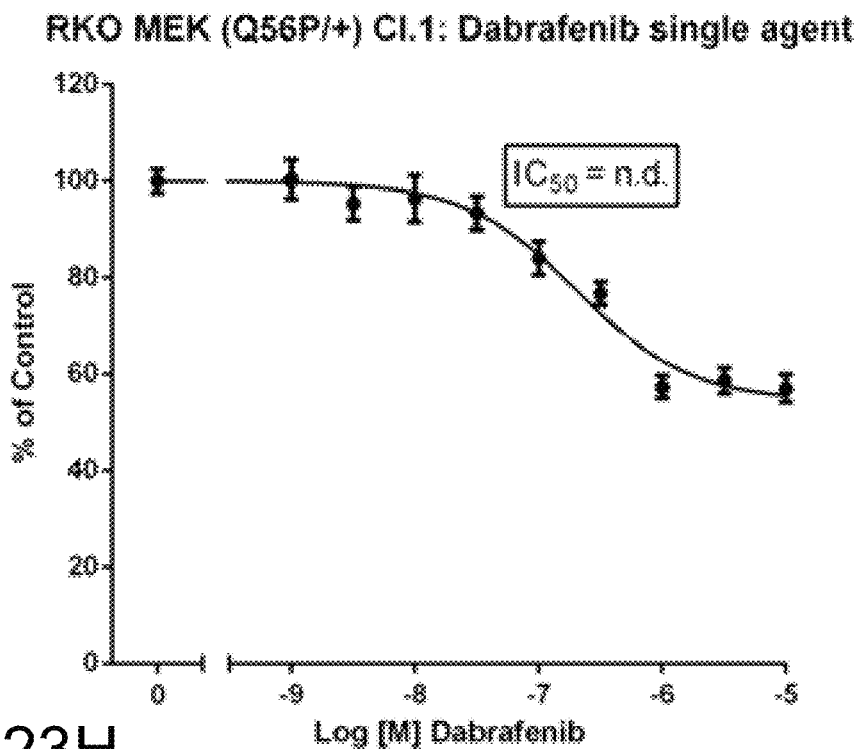
FIG. 23G-FIG. 23H show the results of single agent proliferation assays for the combination in FIG. 23F.
Figure 23H:
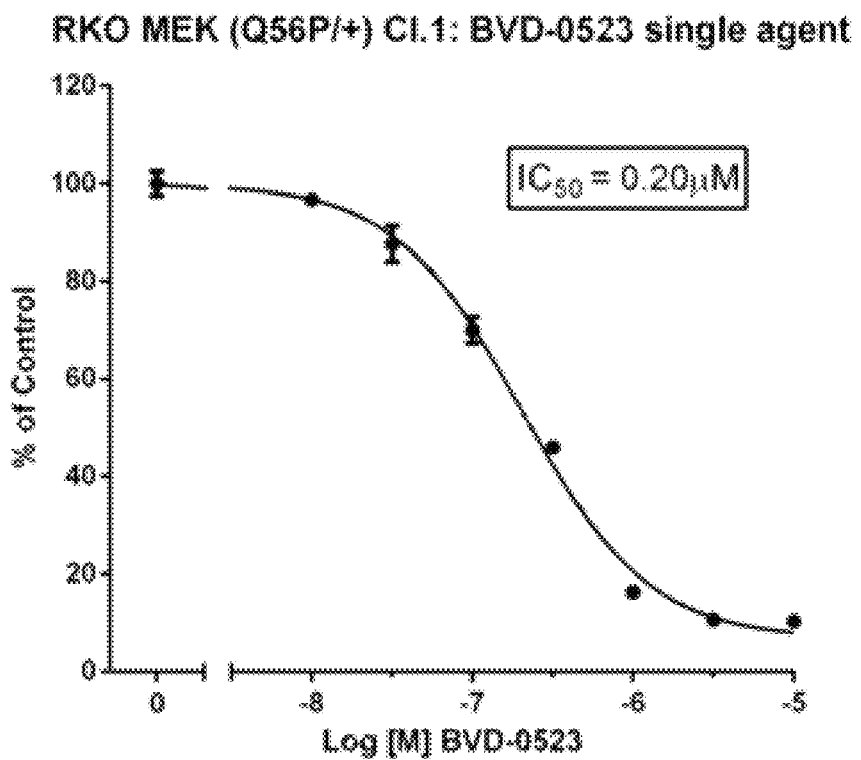
Figure 23I:
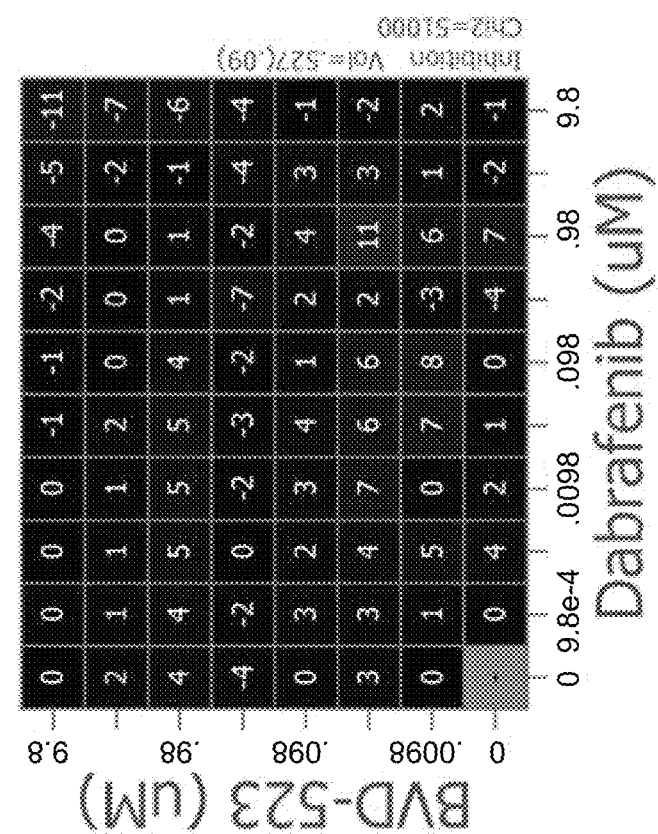
FIG. 23I shows Loewe excess for the combination in FIG. 23F
Figure 23J:
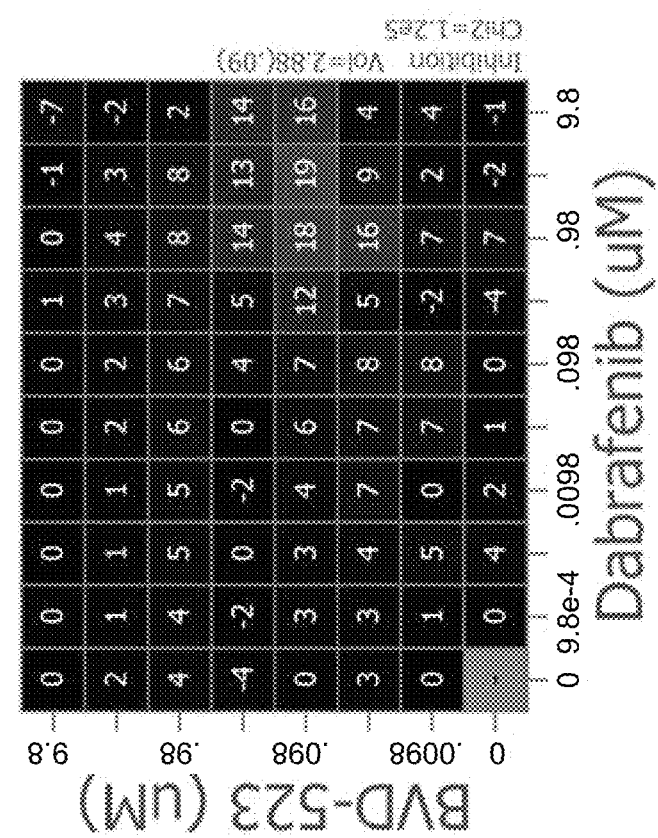
FIG. 23J shows Bliss excess for the combination in FIG. 23F.
Figure 23K:
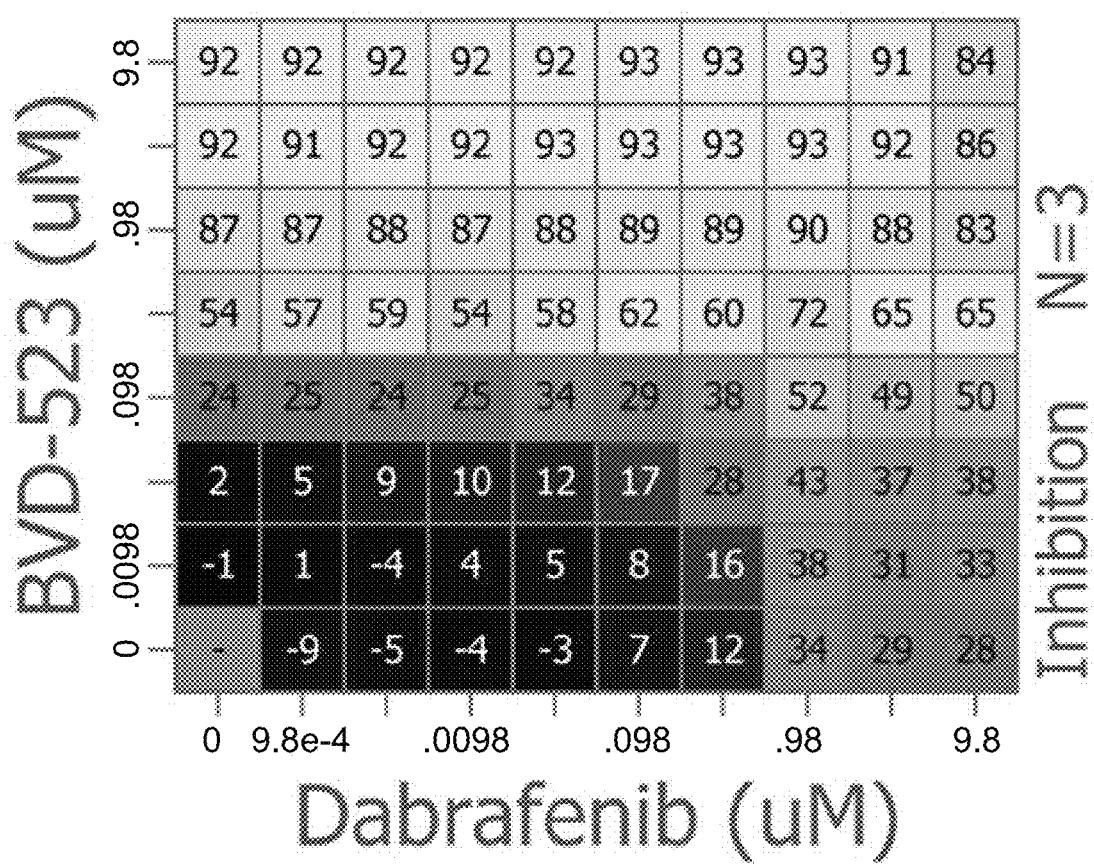
FIG. 23K shows a dose matrix showing inhibition (%) for the combination in RKO MEK1 (Q56P/+)-clone 2 cells.
Figure 23L:
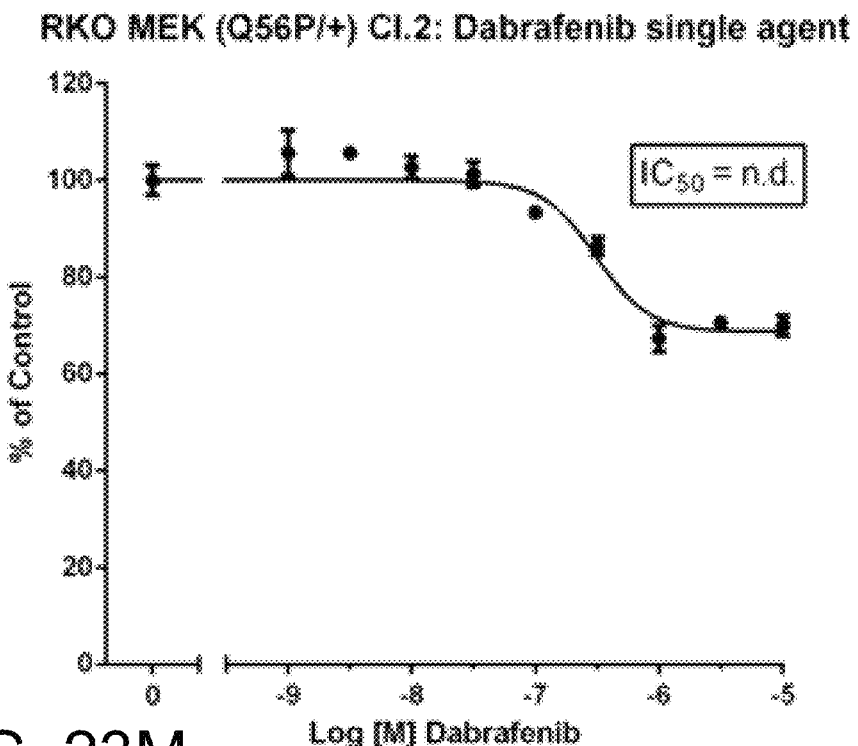
FIG. 23L-FIG. 23M show the results of single agent proliferation assays for the combination in FIG. 23K.
Figure 23M:
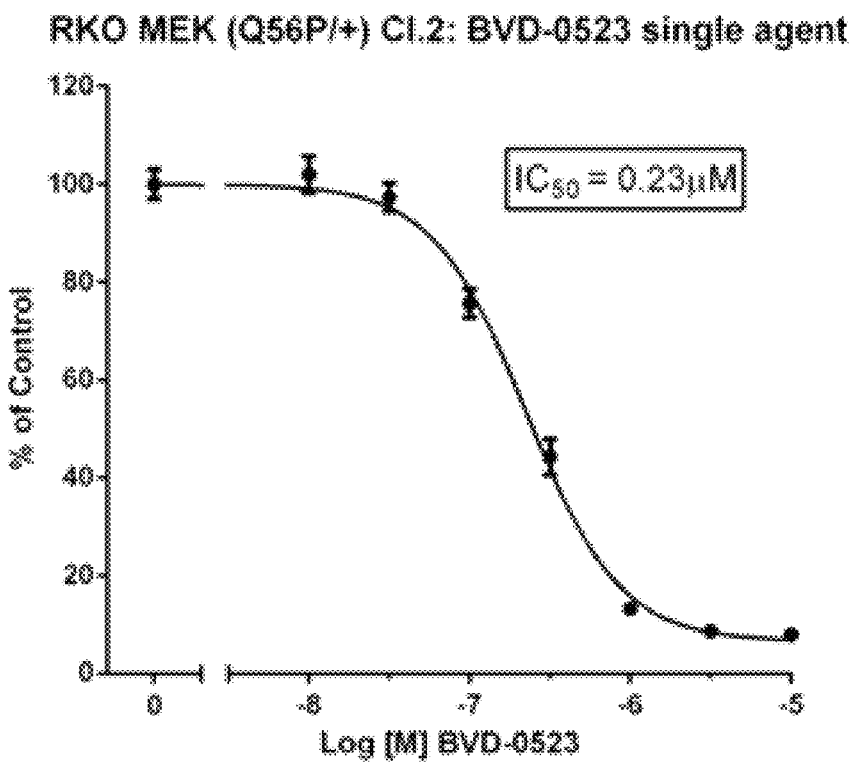
Figures 23N, 23O:
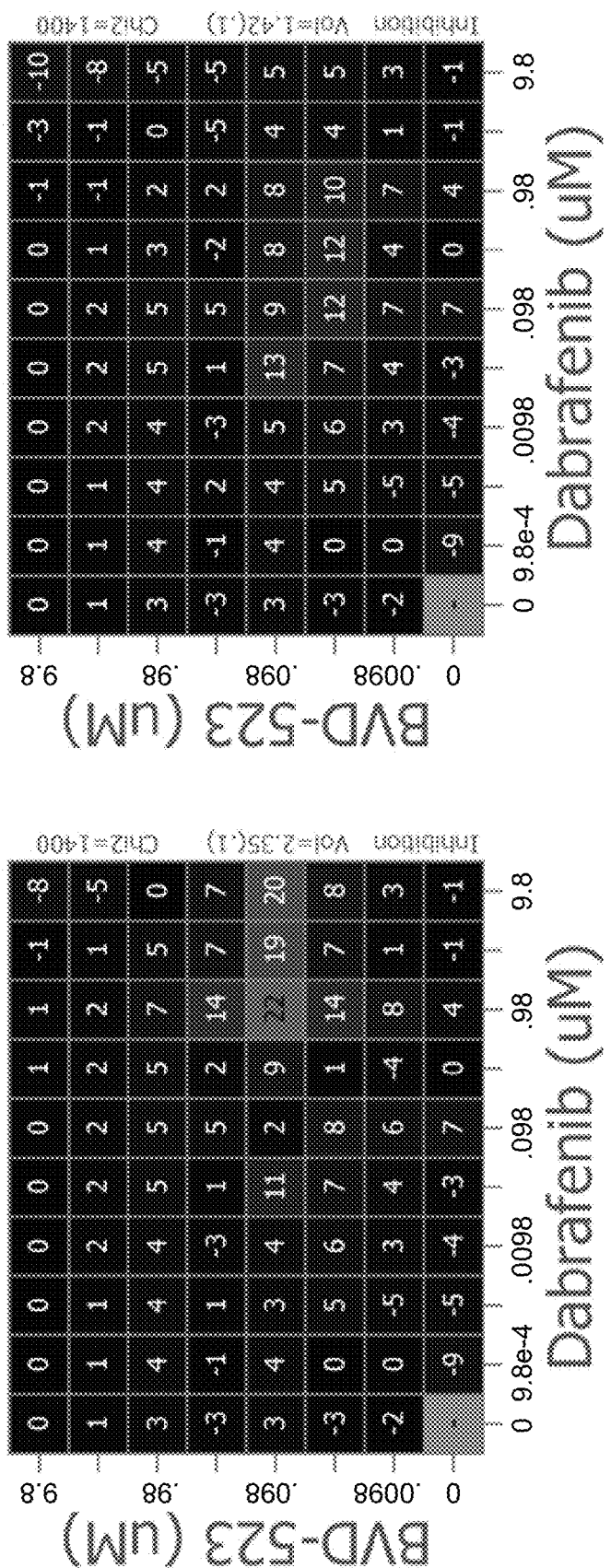
FIG. 23N shows Loewe excess for the combination in FIG. 23K
Figure 24A:
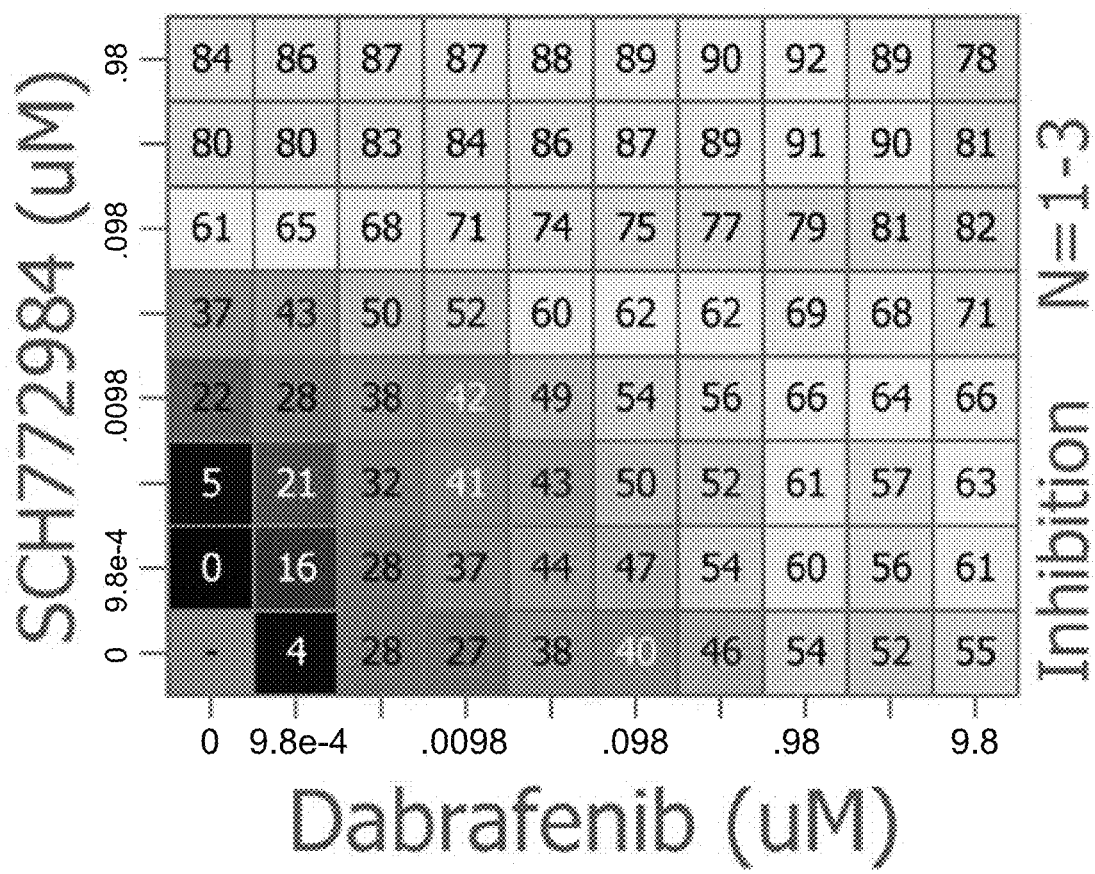
FIG. 24A-FIG. 24O show the results of the combination of SCH772984 and Dabrafenib.
Figure 24B:
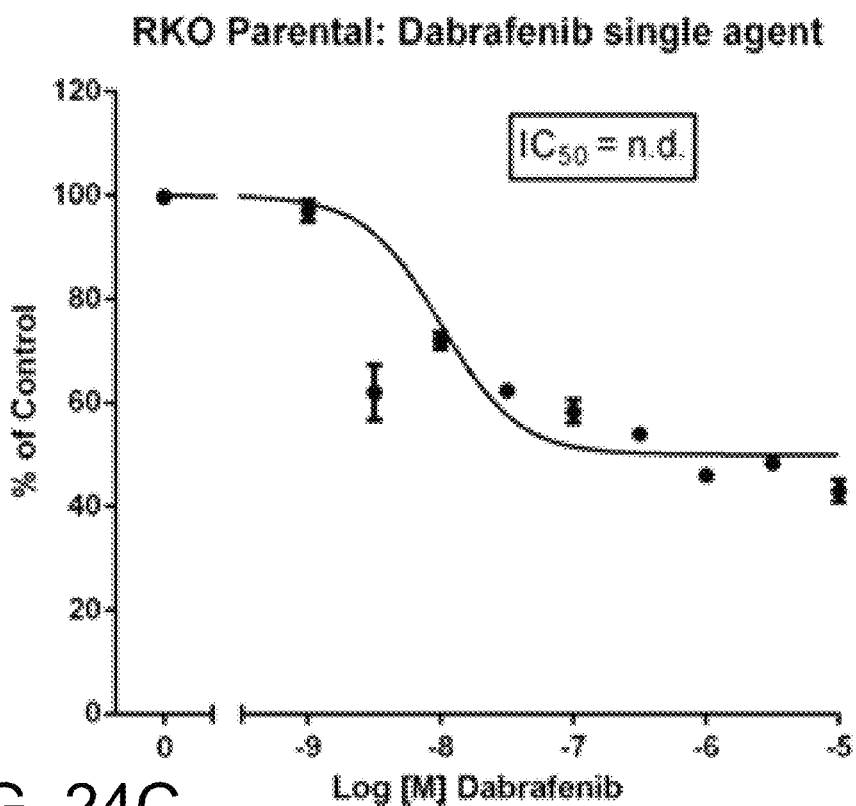
FIG. 24B-FIG. 24C show the results of single agent proliferation assays for the combination in FIG. 24A.
Figure 24C:
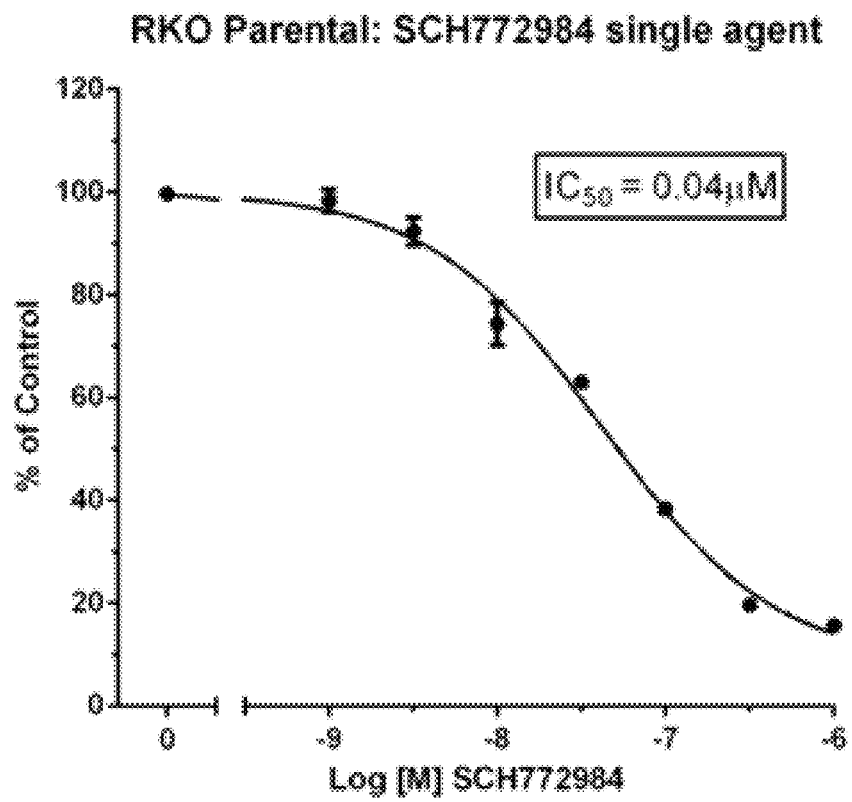
Figure 24E:
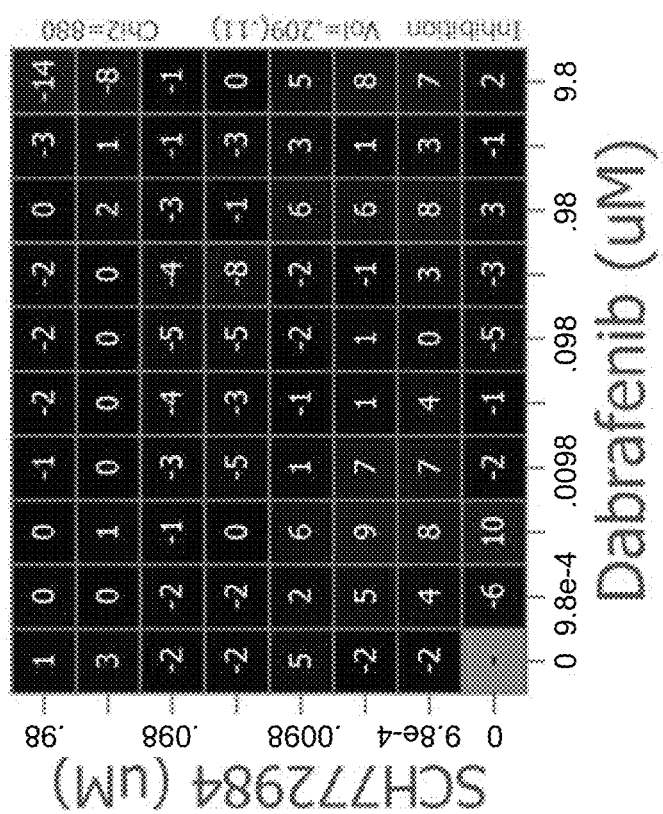
FIG. 24E shows Bliss excess for the combination in FIG. 24A.
Figure 24D:
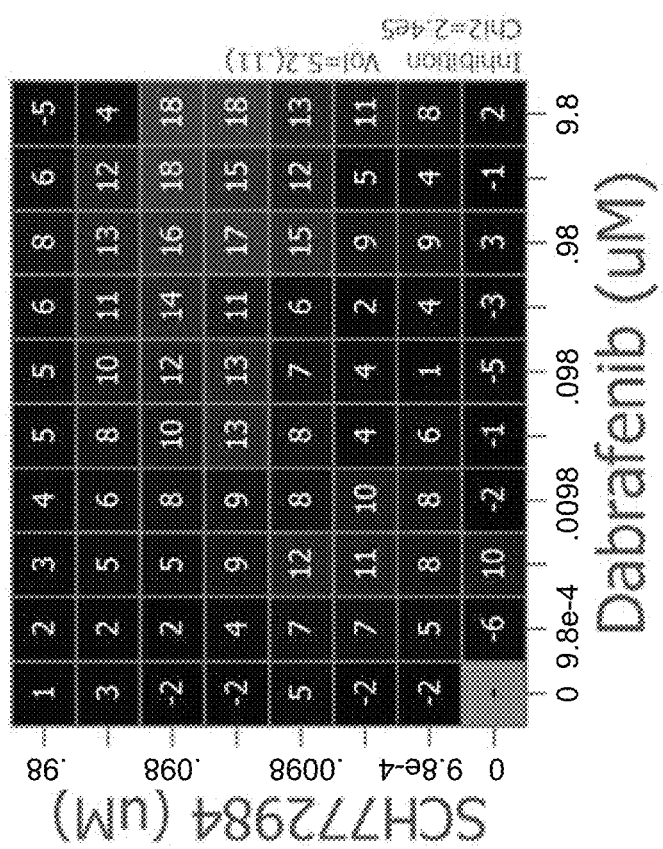
FIG. 24D shows Loewe excess for the combination in FIG. 24A
Figure 24F:
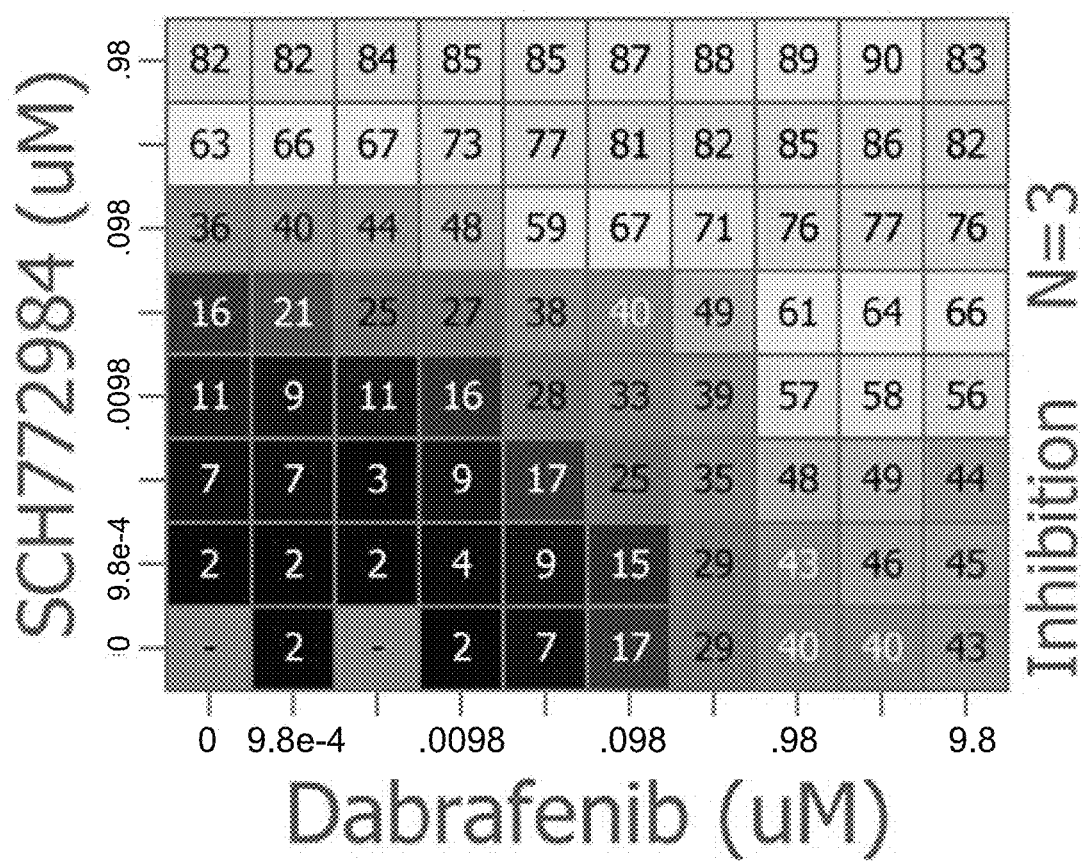
FIG. 24F shows a dose matrix showing inhibition (%) for the combination in RKO MEK1 (Q56P/+)-clone 1 cells.
Figure 24G:
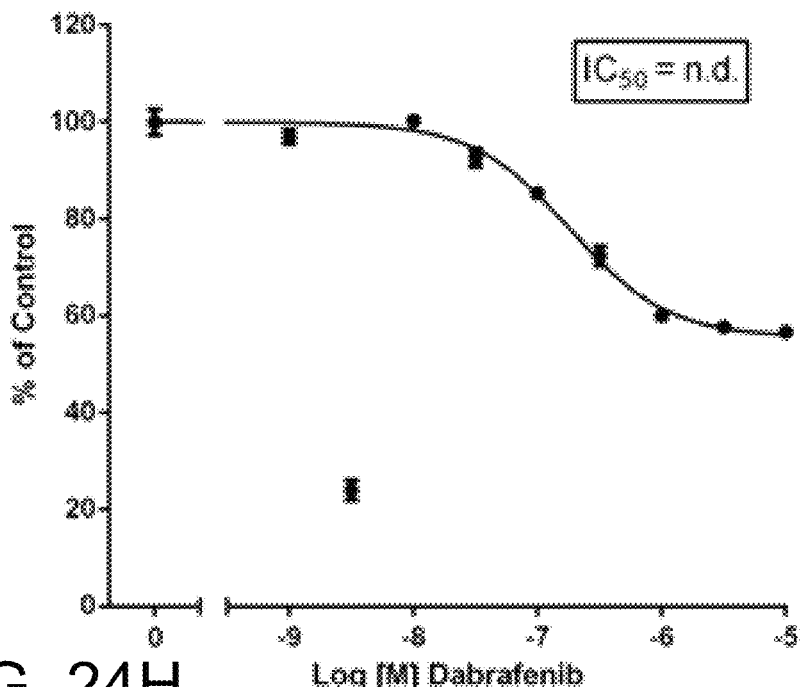
FIG. 24G-FIG. 24H show the results of single agent proliferation assays for the combination in FIG. 24F.
Figure 24H:
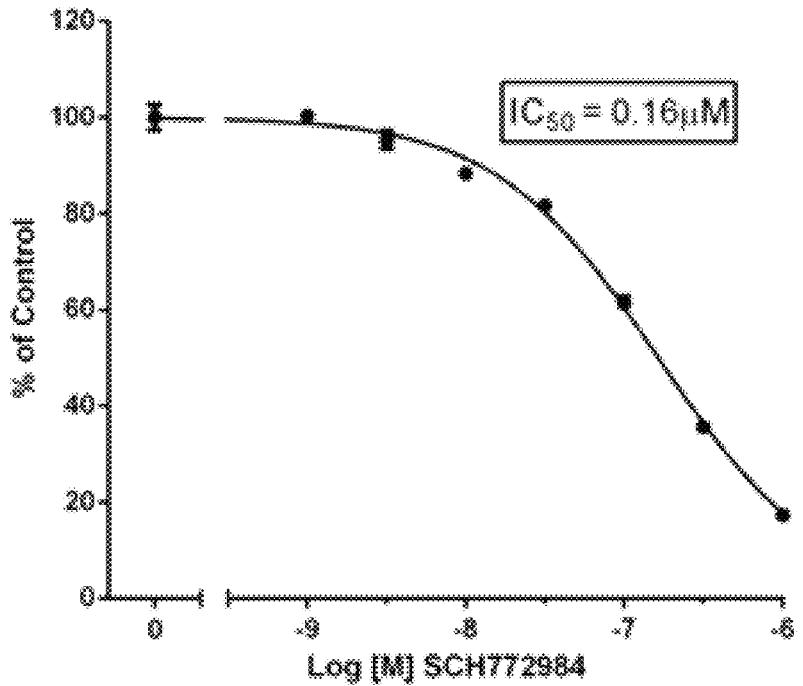
Figure 24J:
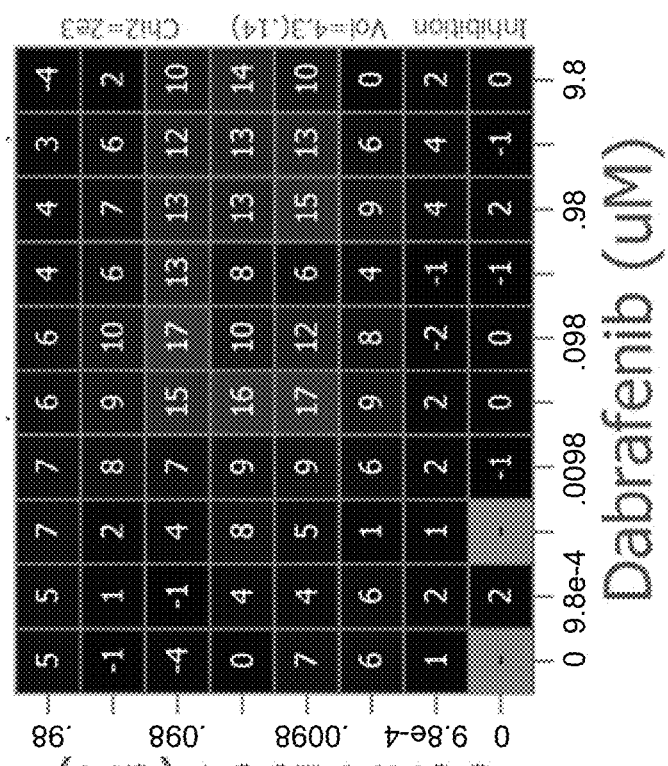
FIG. 24J shows Bliss excess for the combination in FIG. 24F.
Figure 24I:
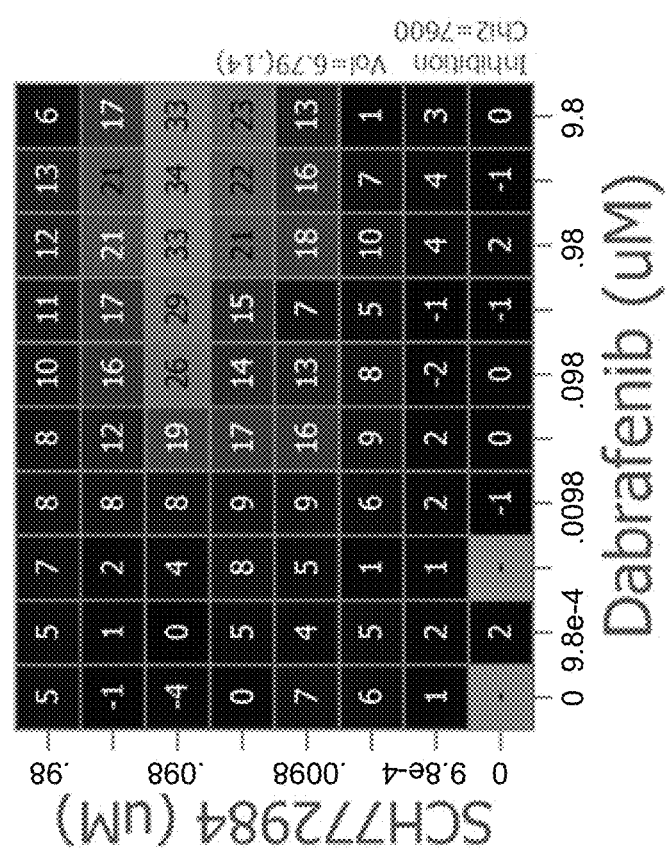
FIG. 24I shows Loewe excess for the combination in FIG. 24F
Figure 24K:
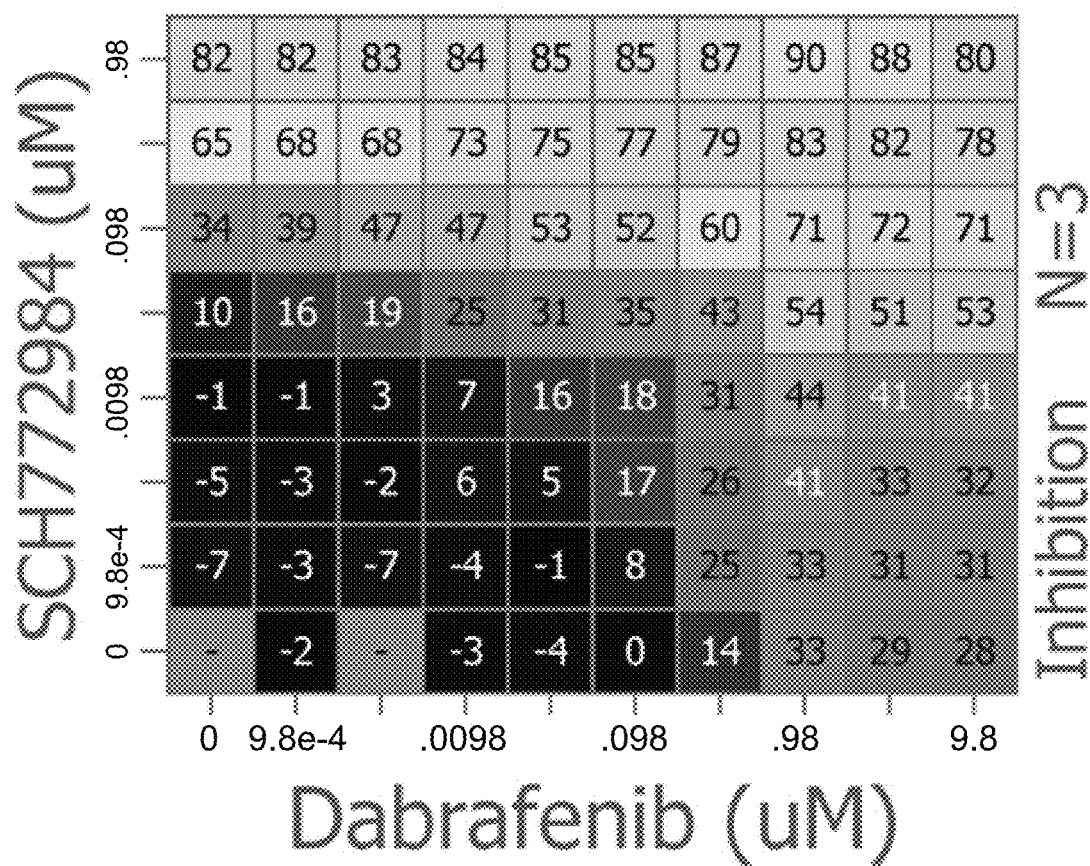
FIG. 24K shows a dose matrix showing inhibition (%) for the combination in RKO MEK1 (Q56P/+)-clone 2 cells.
Figure 24L:
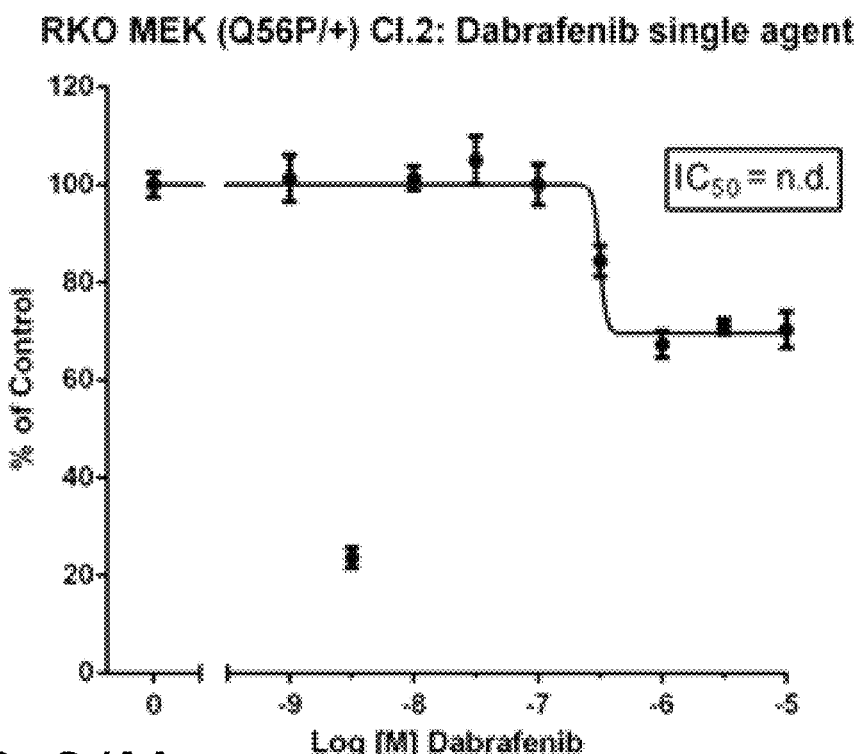
FIG. 24L-FIG. 24M show the results of single agent proliferation assays for the combination in FIG. 24K.
Figure 24M:
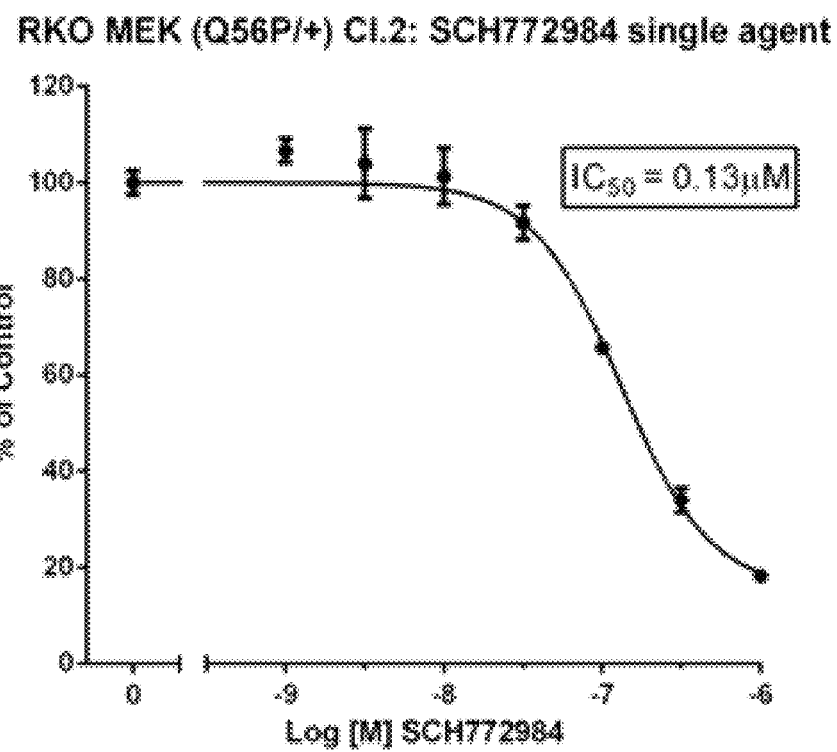
Figure 24N:
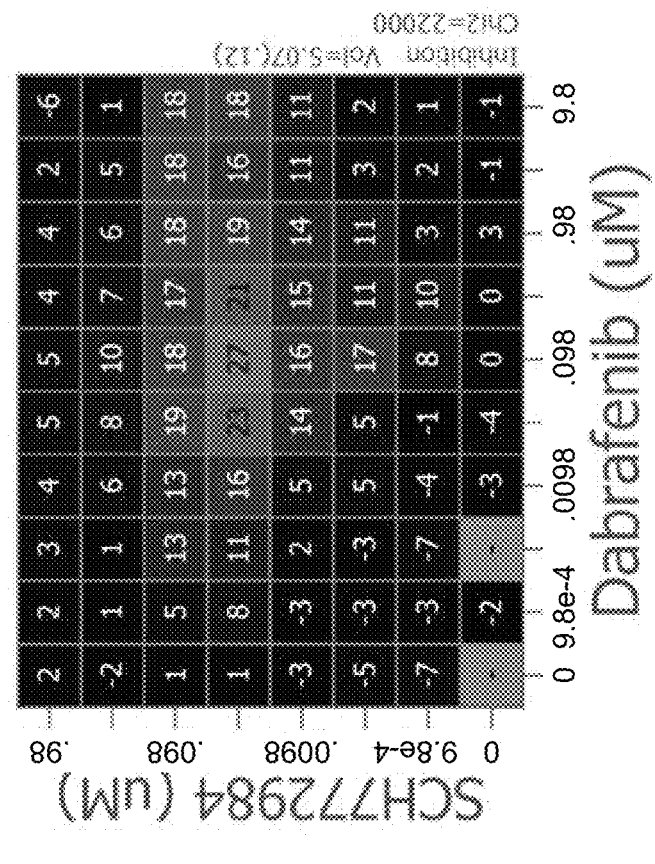
FIG. 24N shows Loewe excess for the combination in FIG. 24K
Figure 24O:
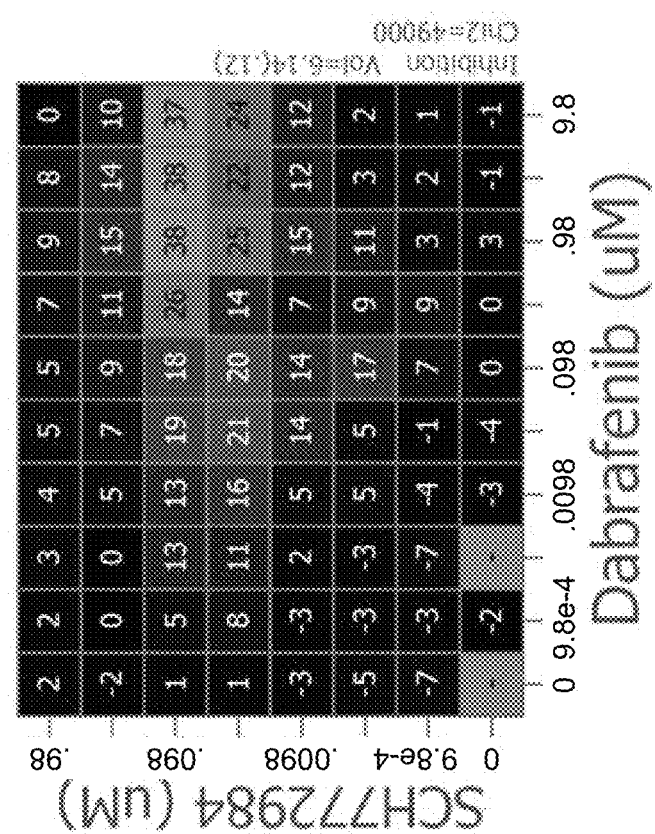

An overview of the mammalian MAPK cascades is shown in FIG. 21. The MAPK pathway is reviewed in e.g., Akinleye et al., 2013. Briefly, with respect to the ERK1/2 module in FIG. 21 (light purple box), the MAPK 1/2 signaling cascade is activated by ligand binding to receptor tyrosine kinases (RTK). The activated receptors recruit and phosphorylate adaptor proteins Grb2 and SOS, which then interact with membrane-bound GTPase Ras and cause its activation. In its activated GTP-bound form, Ras recruits and activates RAF kinases (A-RAF, B-RAF, and C-RAF/RAF-1). The activated RAF kinases activate MAPK 1/2 (MKK1/2), which in turn catalyzes the phosphorylation of threonine and tyrosine residues in the activation sequence Thr-Glu-Tyr of ERK1/2. With respect to the JNK/p38 module (yellow box in FIG. 21), upstream kinases, MAP3Ks, such as MEKK1/4, ASK1/2, and MLK1/2/3, activate MAP2K3/6 (MKK3/6), MAP2K4 (MKK4), and MAP2K7 (MKK7). These MAP2K's then activate JNK protein kinases, including JNK1, JNK2, and JNK3, as well as p38 α/β/γ/δ. To execute their functions, JNKs activate several transcription factors, including c-Jun, ATF-2, NF-ATc1, HSF-1 and STAT3. With respect to the ERK5 module (blue box in FIG. 21), the kinases upstream of MAP2K5 (MKK5) are MEKK2 and MEKK3. The best characterized downstream target of MEK5 is ERK5, also known as big MAP kinase 1 (BMK1) because it is twice the size of other MAPKs.

Non-limiting examples of non-ERK MAPK pathway inhibitors according to the present invention include RAS inhibitors, RAF inhibitors (such as, e.g., inhibitors of A-RAF, B-RAF, C-RAF (RAF-1)), MEK inhibitors, and combinations thereof. Preferably, the non-ERK MAPK pathway inhibitors are BRAF inhibitors, MEK inhibitors, and combinations thereof.

As used herein, a "RAS inhibitor" means those substances that (i) directly interact with RAS, e.g., by binding to RAS and (ii) decrease the expression or the activity of RAS. Non-limiting exemplary RAS inhibitors include, but are not limited to, farnesyl transferase inhibitors (such as, e.g., tipifarnib and lonafarnib), farnesyl group-containing small molecules (such as, e.g., salirasib and TLN-4601), DCAI, as disclosed by Maurer (Maurer et al., 2012), Kobe0065 and Kobe2602, as disclosed by Shima (Shima et al., 2013), HBS 3 (Patgiri et al., 2011), and AIK-4 (Allinky).

As used herein, a "RAF inhibitor" means those substances that (i) directly interact with RAF, e.g., by binding to RAF and (ii) decrease the expression or the activity of RAF, such as, e.g., A-RAF, B-RAF, and C-RAF (RAF-1). Non-limiting exemplary RAF inhibitors, including BRAF inhibitors, include:

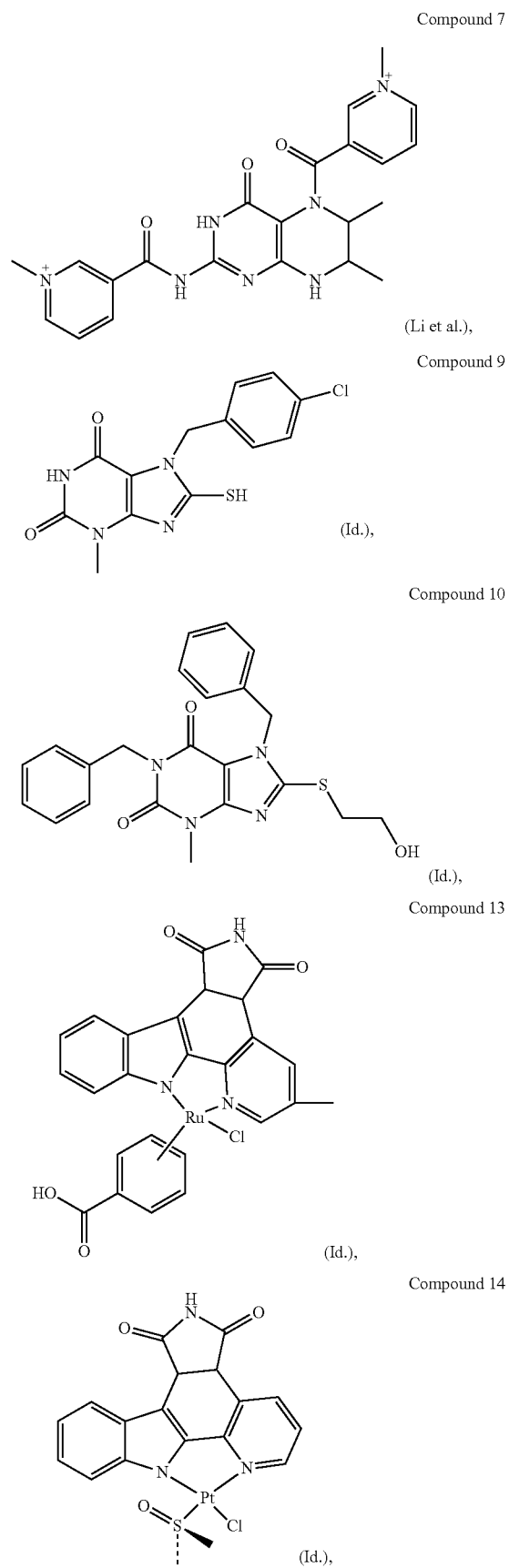

Compound 15
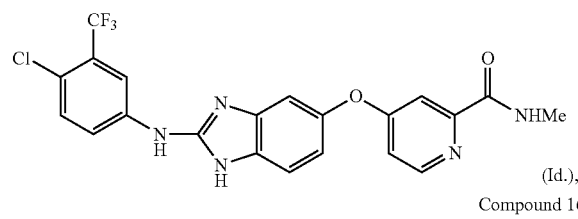
Compound 16
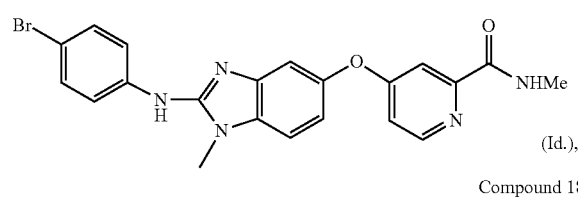
Compound 18
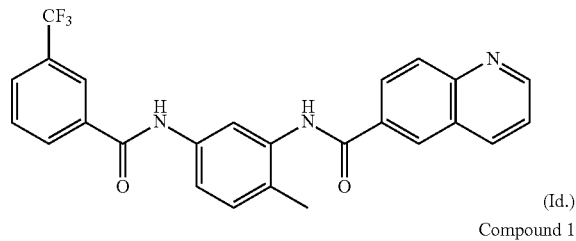
Compound 19
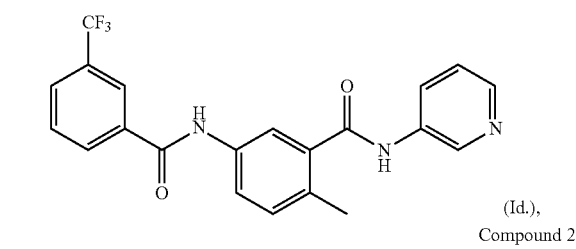
Compound 20
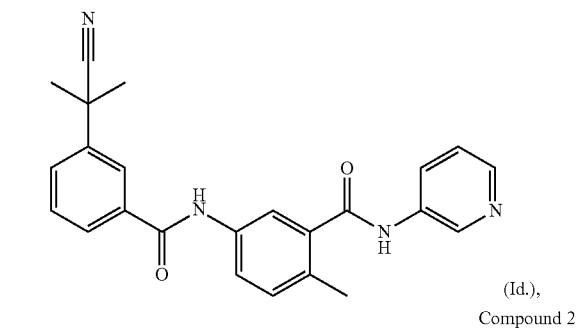
Compound 21
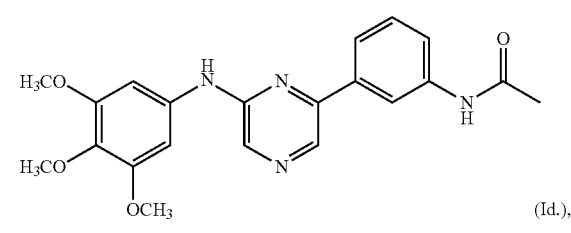
Compound 22
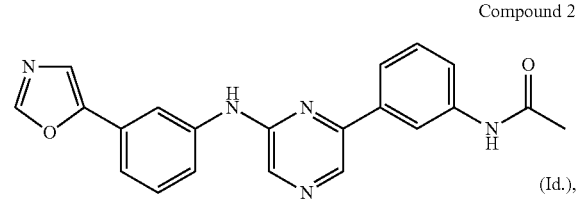
Compound 23
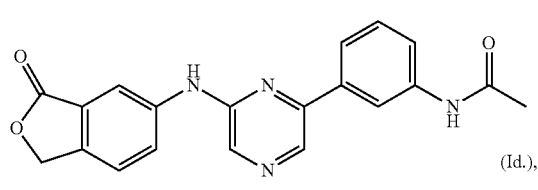
Compound 24
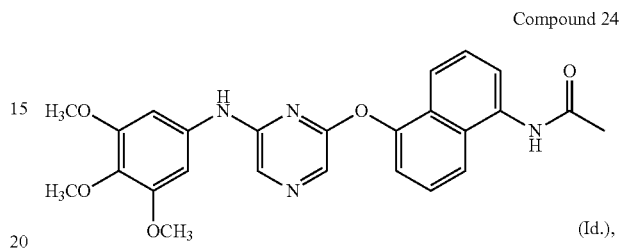
Compound 25
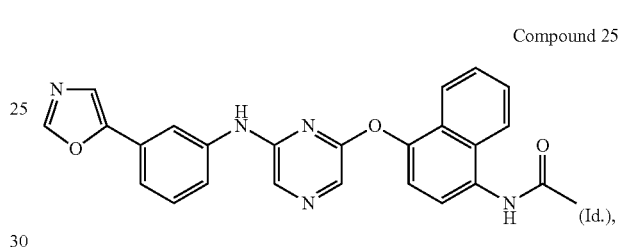
Compound 26
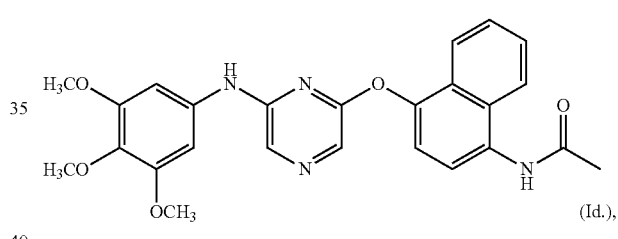
Compound 27
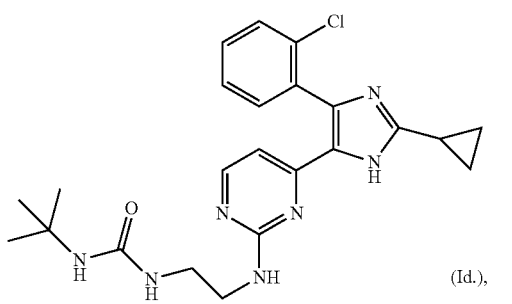
Compound 28
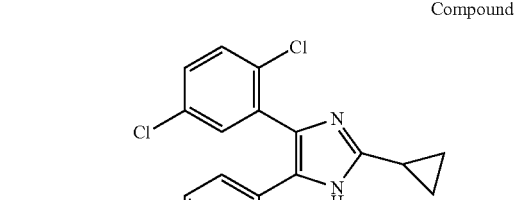
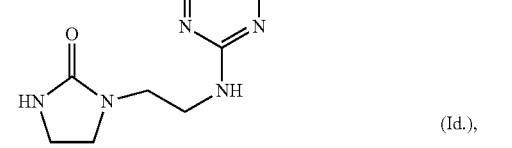

Compound 30
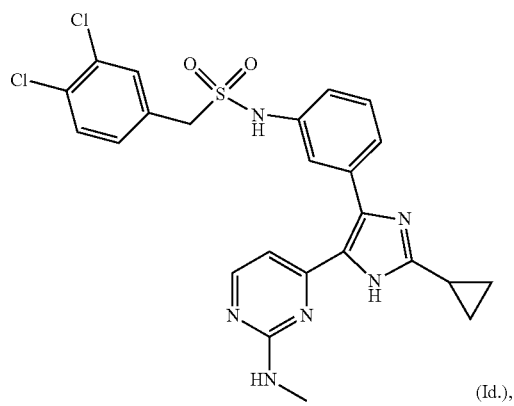
(Id.),
Compound 31
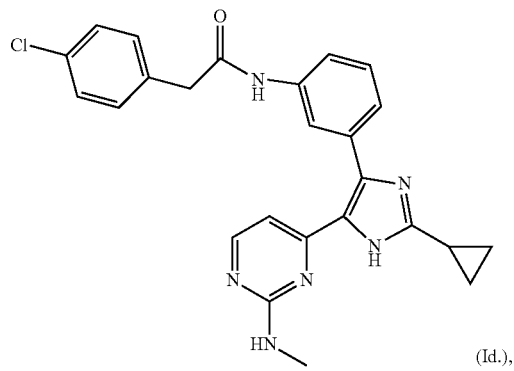
(Id.),
Compound 32
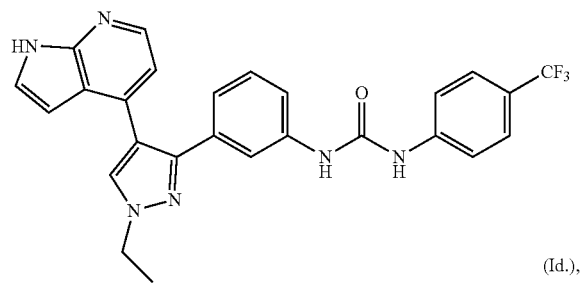
(Id.),
Compound 33
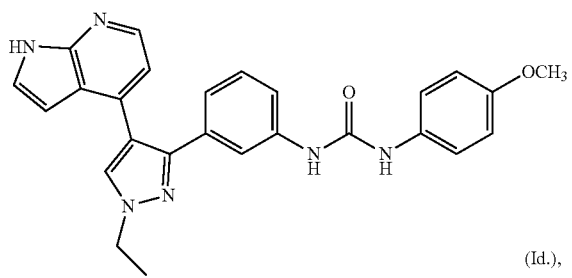
(Id.),
Compound 34
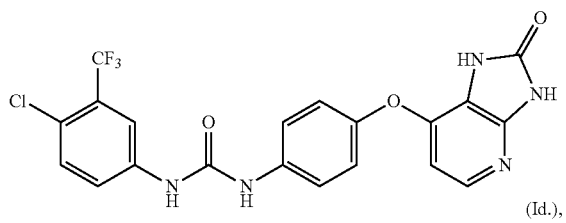
(Id.),
Compound 35
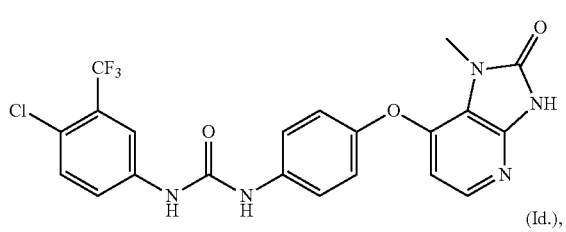
(Id.),
Compound 36
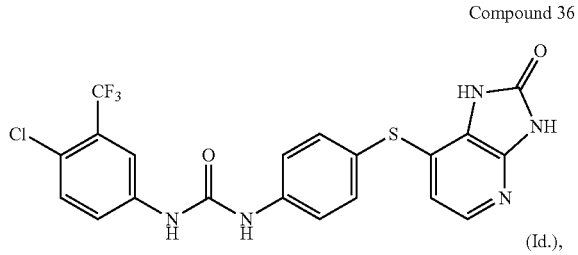
(Id.),
Compound 37
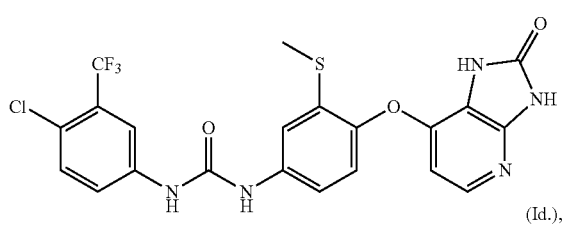
(Id.),
Compound 38
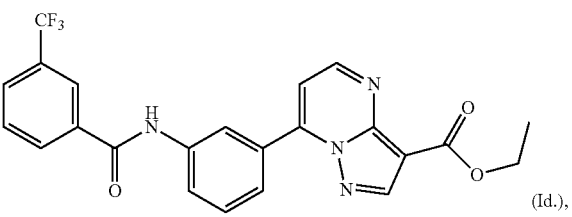
(Id.),
Compound 39
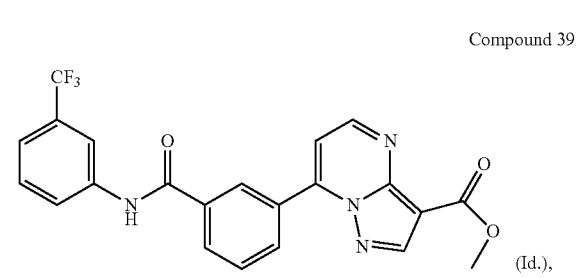
(Id.), -continued Compound 40

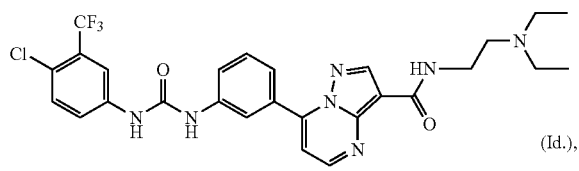

(Id.),

AAL881 (Novartis); AB-024 (Ambit Biosciences), ARQ-736 (ArQule), ARQ-761 (ArQule), AZ628 (Axon Medchem BV), BeiGene-283 (BeiGene), BUB-024 (MLN 2480) (Sunesis & Takeda), b-raf inhibitor (Sareum), BRAF kinase inhibitor (Selexagen Therapeutics), BRAF siRNA 313 (tacaccagcaagctagatgca) and 523 (cctatcgttagagtcttcctg) (Liu et al., 2007), CTT239065 (Institute of Cancer Research), dabrafenib (GSK2118436), DP-4978 (Deciphera Pharmaceuticals), HM-95573 (Hanmi), GDC-0879 (Genentech), GW-5074 (Sigma Aldrich), ISIS 5132 (Novartis), L779450 (Merck), LBT613 (Novartis), LErafAON (NeoPharm, Inc.), LGX-818 (Novartis), pazopanib (GlaxoSmithKline), PLX3202 (Plexxikon), PLX4720 (Plexxikon), PLX5568 (Plexxikon), RAF-265 (Novartis), RAF-365 (Novartis), regorafenib (Bayer Healthcare Pharmaceuticals, Inc.), RO 5126766 (Hoffmann-La Roche), SB-590885 (GlaxoSmithKline), SB699393 (GlaxoSmithKline), sorafenib (Onyx Pharmaceuticals), TAK 632 (Takeda), TL-241 (Teligene), vemurafenib (RG7204 or PLX4032) (Daiichi Sankyo), XL-281 (Exelixis), ZM-336372 (AstraZeneca), pharmaceutically acceptable salts thereof, and combinations thereof.

As used herein, a "MEK inhibitor" means those substances that (i) directly interact with MEK, e.g., by binding to MEK and (ii) decrease the expression or the activity of MEK. Thus, inhibitors that act upstream of MEK, such as RAS inhibitors and RAF inhibitors, are not MEF inhibitors according to the present invention. Non-limiting examples of MEK inhibitors include anthrax toxin, antroquinonol (Golden Biotechnology), ARRY-142886 (6-(4-bromo-2-chloro-phenylamino)-7-fluoro-3-methyl-3H-benzoimidazole-5-carboxylic acid (2-hydroxy-ethoxy)-amide) (Array BioPharma), ARRY-438162 (Array BioPharma), AS-1940477 (Astellas), AS-703988 (Merck KGaA), bentamapimod (Merck KGaA), BI-847325 (Boehringer Ingelheim), E-6201 (Eisai), GDC-0623 (Hoffmann-La Roche), GDC-0973 (cobimetinib) (Hoffmann-La Roche), L783277 (Merck), lethal factor portion of anthrax toxin, MEK162 (Array BioPharma), PD 098059 (2-(2'-amino-3'-methoxyphenyl)-oxanaphthalen-4-one) (Pfizer), PD 184352 (CI-1040) (Pfizer), PD-0325901 (Pfizer), pimasertib (Santhera Pharmaceuticals), RDEA119 (Ardea Biosciences/Bayer), refametinib (AstraZeneca), RG422 (Chugai Pharmaceutical Co.), RO092210 (Roche), RO4987655 (Hoffmann-La Roche), RO5126766 (Hoffmann-La Roche), selumetinib (AZD6244) (AstraZeneca), SL327 (Sigma), TAK-733 (Takeda), trametinib (Japan Tobacco), U0126 (1,4-diamino-2,3-dicyano-1,4-bis(2-aminophenylthio)butadiene) (Sigma), WX-554 (Wilex), YopJ polypeptide (Mittal et al., 2010), pharmaceutically acceptable salts thereof, and combinations thereof.

In one aspect of this embodiment, substantially all phosphorylation of ribosomal s6 kinase (RSK) is inhibited after administration of BVD-523 or a pharmaceutically acceptable salt thereof. As used herein in the context of RSK phosphorylation, "substantially all" means a reduction of greater than 50% reduction, preferably greater than 55%, 60%, 65%, 70%, 75%, 80%, 85%, 90%, 91%, 92%, 93%, 94%, 95%, 96%, 97%, 98%, or 99% A reduction.

In another aspect of this embodiment, the cancer has MAPK activity. As used herein, having "MAPK activity" means that proteins downstream of ERK are still active, even if proteins upstream of ERK may not be active. Such a cancer may be a solid tumor cancer or a hematologic cancer.

In the present invention, cancers include both solid and hemotologic cancers. Non-limiting examples of solid cancers include adrenocortical carcinoma, anal cancer, bladder cancer, bone cancer (such as osteosarcoma), brain cancer, breast cancer, carcinoid cancer, carcinoma, cervical cancer, colon cancer, endometrial cancer, esophageal cancer, extrahepatic bile duct cancer, Ewing family of cancers, extracranial germ cell cancer, eye cancer, gallbladder cancer, gastric cancer, germ cell tumor, gestational trophoblastic tumor, head and neck cancer, hypopharyngeal cancer, islet cell carcinoma, kidney cancer, large intestine cancer, laryngeal cancer, leukemia, lip and oral cavity cancer, liver tumor/cancer, lung tumor/cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell cancer, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancers (such as cutaneous t-cell lymphoma, Kaposi's sarcoma, mast cell tumor, and melanoma), small intestine cancer, soft tissue sarcoma, stomach cancer, testicular cancer, thymoma, thyroid cancer, urethral cancer, uterine cancer, vaginal cancer, vulvar cancer, and Wilms' tumor.

Examples of hematologic cancers include, but are not limited to, leukemias, such as adult/childhood acute lymphoblastic leukemia, adult/childhood acute myeloid leukemia, chronic lymphocytic leukemia, chronic myelogenous leukemia, and hairy cell leukemia, lymphomas, such as AIDS-related lymphoma, cutaneous T-cell lymphoma, adult/childhood Hodgkin lymphoma, mycosis fungoides, adult/childhood non-Hodgkin lymphoma, primary central nervous system lymphoma, Sezary syndrome, cutaneous T-cell lymphoma, and Waldenstrom macroglobulinemia, as well as other proliferative disorders such as chronic myeloproliferative disorders, Langerhans cell histiocytosis, multiple myeloma/plasma cell neoplasm, myelodysplastic syndromes, and myelodysplastic/myeloproliferative neoplasms.

Preferably, the cancer is selected from the group consisting of a cancer of the large intestine, breast cancer, pancreatic cancer, skin cancer, and endometrial cancers. More preferably, the cancer is melanoma.

In another aspect of this embodiment, the method further comprises administering to the subject at least one additional therapeutic agent effective for treating or ameliorating the effects of the cancer. The additional therapeutic agent may be selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

As used herein, an "antibody" encompasses naturally occurring immunoglobulins as well as non-naturally occurring immunoglobulins, including, for example, single chain antibodies, chimeric antibodies (e.g., humanized murine antibodies), and heteroconjugate antibodies (e.g., bispecific antibodies). Fragments of antibodies include those that bind antigen, (e.g., Fab', F(ab')$_2$, Fab, Fv, and rIgG). See also, e.g., Pierce Catalog and Handbook, 1994-1995 (Pierce Chemical Co., Rockford, Ill.); Kuby, J., Immunology, 3rd Ed., W.H. Freeman & Co., New York (1998). The term antibody also includes bivalent or bispecific molecules, diabodies, triabodies, and tetrabodies. The term "antibody" further includes both polyclonal and monoclonal antibodies.

Examples of therapeutic antibodies that may be used in the present invention include rituximab (Rituxan), Cetuximab (Erbitux), bevacizumab (Avastin), and Ibritumomab (Zevalin).

Cytotoxic agents according to the present invention include DNA damaging agents, antimetabolites, anti-microtubule agents, antibiotic agents, etc. DNA damaging agents include alkylating agents, platinum-based agents, intercalating agents, and inhibitors of DNA replication. Non-limiting examples of DNA alkylating agents include cyclophosphamide, mechlorethamine, uramustine, melphalan, chlorambucil, ifosfamide, carmustine, lomustine, streptozocin, busulfan, temozolomide, pharmaceutically acceptable salts thereof, prodrugs, and combinations thereof. Non-limiting examples of platinum-based agents include cisplatin, carboplatin, oxaliplatin, nedaplatin, satraplatin, triplatin tetranitrate, pharmaceutically acceptable salts thereof, prodrugs, and combinations thereof. Non-limiting examples of intercalating agents include doxorubicin, daunorubicin, idarubicin, mitoxantrone, pharmaceutically acceptable salts thereof, prodrugs, and combinations thereof. Non-limiting examples of inhibitors of DNA replication include irinotecan, topotecan, amsacrine, etoposide, etoposide phosphate, teniposide, pharmaceutically acceptable salts thereof, prodrugs, and combinations thereof. Antimetabolites include folate antagonists such as methotrexate and premetrexed, purine antagonists such as 6-mercaptopurine, dacarbazine, and fludarabine, and pyrimidine antagonists such as 5-fluorouracil, arabinosylcytosine, capecitabine, gemcitabine, decitabine, pharmaceutically acceptable salts thereof, prodrugs, and combinations thereof. Anti-microtubule agents include without limitation vinca alkaloids, paclitaxel (Taxol®), docetaxel (Taxotere®), and ixabepilone (Ixempra®). Antibiotic agents include without limitation actinomycin, anthracyclines, valrubicin, epirubicin, bleomycin, plicamycin, mitomycin, pharmaceutically acceptable salts thereof, prodrugs, and combinations thereof.

Cytotoxic agents according to the present invention also include an inhibitor of the PI3K/Akt pathway. Non-limiting examples of an inhibitor of the PI3K/Akt pathway include A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (5-(2,2-Difluoro-benzo[1,3]dioxol-5-ylmethylene)-thiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-115 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof.

In the present invention, the term "toxin" means an antigenic poison or venom of plant or animal origin. An example is diphtheria toxin or portions thereof.

In the present invention, the term "radionuclide" means a radioactive substance administered to the patient, e.g., intravenously or orally, after which it penetrates via the patient's normal metabolism into the target organ or tissue, where it delivers local radiation for a short time. Examples of radionuclides include, but are not limited to, 1-125, At-211, Lu-177, Cu-67, I-131, Sm-153, Re-186, P-32, Re-188, In-114m, and Y-90.

In the present invention, the term "immunomodulator" means a substance that alters the immune response by augmenting or reducing the ability of the immune system to produce antibodies or sensitized cells that recognize and react with the antigen that initiated their production. Immunomodulators may be recombinant, synthetic, or natural preparations and include cytokines, corticosteroids, cytotoxic agents, thymosin, and immunoglobulins. Some immunomodulators are naturally present in the body, and certain of these are available in pharmacologic preparations. Examples of immunomodulators include, but are not limited to, granulocyte colony-stimulating factor (G-CSF), interferons, imiquimod and cellular membrane fractions from bacteria, IL-2, IL-7, IL-12, CCL3, CCL26, CXCL7, and synthetic cytosine phosphate-guanosine (CpG).

In the present invention, the term "photoactive therapeutic agent" means compounds and compositions that become active upon exposure to light. Certain examples of photoactive therapeutic agents are disclosed, e.g., in U.S. Patent Application Serial No. 2011/0152230 A1, "Photoactive Metal Nitrosyls For Blood Pressure Regulation And Cancer Therapy."

In the present invention, the term "radiosensitizing agent" means a compound that makes tumor cells more sensitive to radiation therapy. Examples of radiosensitizing agents include misonidazole, metronidazole, tirapazamine, and trans sodium crocetinate.

In the present invention, the term "hormone" means a substance released by cells in one part of a body that affects cells in another part of the body. Examples of hormones include, but are not limited to, prostaglandins, leukotrienes, prostacyclin, thromboxane, amylin, antimullerian hormone, adiponectin, adrenocorticotropic hormone, angiotensinogen, angiotensin, vasopressin, atriopeptin, brain natriuretic peptide, calcitonin, cholecystokinin, corticotropin-releasing hormone, encephalin, endothelin, erythropoietin, follicle-stimulating hormone, galanin, gastrin, ghrelin, glucagon, gonadotropin-releasing hormone, growth hormone-releasing hormone, human chorionic gonadotropin, human placental lactogen, growth hormone, inhibin, insulin, somatomedin, leptin, liptropin, luteinizing hormone, melanocyte stimulating hormone, motilin, orexin, oxytocin, pancreatic polypeptide, parathyroid hormone, prolactin, prolactin releasing hormone, relaxin, renin, secretin, somatostain, thrombopoietin, thyroid-stimulating hormone, testosterone, dehydroepiandrosterone, androstenedione, dihydrotestosterone, aldosterone, estradiol, estrone, estriol, cortisol, progesterone, calcitriol, and calcidiol.

Some compounds interfere with the activity of certain hormones or stop the production of certain hormones. These hormone-interfering compounds include, but are not limited to, tamoxifen (Nolvadex®), anastrozole (Arimidex®), letrozole (Femara®), and fulvestrant (Faslodex®). Such compounds are also within the meaning of hormone in the present invention.

As used herein, an "anti-angiogenesis" agent means a substance that reduces or inhibits the growth of new blood vessels, such as, e.g., an inhibitor of vascular endothelial growth factor (VEGF) and an inhibitor of endothelial cell migration. Anti-angiogenesis agents include without limitation 2-methoxyestradiol, angiostatin, bevacizumab, cartilage-derived angiogenesis inhibitory factor, endostatin, IFN-α, IL-12, itraconazole, linomide, platelet factor-4, prolactin, SU5416, suramin, tasquinimod, tecogalan, tetrathiomolybdate, thalidomide, thrombospondin, thrombospondin, TNP-470, ziv-aflibercept, pharmaceutically acceptable salts thereof, prodrugs, and combinations thereof.

Another embodiment of the present invention is a method for treating or ameliorating the effects of a cancer in a subject. The method comprises:

(a) identifying a subject with cancer that has become refractory or resistant to BRAF inhibitor therapy, MEK inhibitor therapy, or BRAF and MEK inhibitor therapy; and (b) administering to the subject with said refractory or resistant cancer an effective amount of an ERK inhibitor, which is BVD-523 or a pharmaceutically acceptable salt thereof.

Suitable and preferred subjects are as disclosed herein. In this embodiment, the methods may be used to treat the cancers disclosed above. In accordance with the present invention, the cancer may have MAPK activity.

In one aspect of this embodiment, identifying a subject with cancer that is refractory or resistant to BRAF and/or MEK inhibitor therapy comprises:

(a) obtaining a biological sample from the subject; and (b) screening the sample to determine whether the subject has become resistant to an inhibitor therapy selected from the group consisting of BRAF inhibitor therapy, MEK inhibitor therapy, and combinations thereof.

In the present invention, biological samples include, but are not limited to, blood, plasma, urine, skin, saliva, and biopsies. Biological samples are obtained from a subject by routine procedures and methods which are known in the art.

Preferably, screening for a cancer that is refractory or resistant to BRAF inhibitor therapy may comprise, e.g., identifying (i) a switch between RAF isoforms, (ii) upregulation of RTK or NRAS signaling, (iii) reactivation of mitogen activated protein kinase (MAPK) signaling, (iv) the presence of a MEK activating mutation, and combinations thereof.

A switch between RAF isoforms may occur in subjects having acquired resistance to BRAF inhibitor therapy. To detect such a switch, BRAF inhibitor-resistant tumor cells may be retrieved from a patient and analyzed via Western blotting for ERK and phospho-ERK levels in the presence of a BRAF inhibitor. Comparison with BRAF inhibitor-sensitive cells treated with a BRAF inhibitor may reveal higher levels of phospho-ERK in BRAF inhibitor-resistant tumor cells, implying that a switch has taken place in which another RAF isoform phosphorylates ERK in place of BRAF. Confirmation of which RAF isoform has taken over may involve sh/siRNA-mediated knockdown of ARAF and CRAF individually in BRAF inhibitor-resistant cells exposed to a BRAF inhibitor, followed by subsequent Western blotting for ERK and phospho-ERK levels. If, for example, ARAF knockdown in BRAF inhibitor-resistant cells exposed to a BRAF inhibitor still results in high levels of phospho-ERK, it would indicate that CRAF has taken over phosphorylating ERK. Likewise, if CRAF was knocked down in BRAF inhibitor-resistant cells exposed to BRAF inhibitor and ERK was still highly phosphorylated, it would mean that ARAF has taken over ERK phosphorylation. RAF isoform switching may also involve simultaneous knockdown of ARAF and CRAF in BRAF inhibitor-resistant cells in the presence of BRAF inhibitor, effectively blocking all RAF-mediated phosphorylation. A resulting decrease in ERK phosphorylation would indicate that the BRAF inhibitor-resistant cells have the capacity to switch between RAF isoforms in order to phosphorylate ERK (Villanueva, et al., 2010).

Upregulation of RTK or NRAS signaling may also be a cause of BRAF inhibitor resistance. Detection may, e.g., first involve using Western blotting protocols with phospho-specific antibodies to analyze the activation of the downstream RAF effectors MEK1/2 and ERK1/2. If BRAF inhibitor-resistant cells show high activation levels of these proteins in the presence of a BRAF inhibitor, RTK or NRAS upregulation may be the cause. Gene expression profiling (or other related methods) of BRAF inhibitor-resistant cells in the presence of a BRAF inhibitor may reveal higher expression levels of KIT, MET, EGFR, and PDGFRβ RTKs as compared to BRAF inhibitor-sensitive cells. Real-time quantitative polymerase chain reaction experiments, or other similar procedures, focusing on any of these genes may confirm higher expression levels while phospho-RTK arrays (R&D Systems, Minneapolis, Minn.) may show elevated activation-associated tyrosine phosphorylation. Alternatively, NRAS activation may be detected by various gene sequencing protocols. Activating mutations in NRAS, particularly Q61K, may indicate that B-RAF signaling has been bypassed. In melanoma cells, activated NRAS uses C-RAF to signal to MEK-ERK. Thus, activated NRAS may enable a similar bypass pathway in BRAF inhibitor-resistant cells exposed to BRAF inhibitor. Further confirmation of these mechanisms in a given BRAF inhibitor-resistant sample may be accomplished, for example, using sh/siRNA-mediated knockdown of upregulated RTKs or activated NRAS in the presence of BRAF inhibitor. Any significant levels of growth inhibition may indicate that upregulation of RTK or NRAS signaling is the cause of BRAF inhibition in that particular sample (Nazarian, et al., 2010).

Detecting reactivation of MAPK signaling in BRAF inhibitor-resistant cells may indicate another bypass mechanism for BRAF inhibitor resistance. COT and C-RAF have been shown to be upregulated in a BRAF V600E background exposed to BRAF inhibitor. Quantiative real-time RT-PCR, e.g., may reveal increased COT expression in BRAF inhibitor-resistant cells in the presence of BRAF inhibitor. Furthermore, sh/siRNA-mediated knockdown of COT in BRAF inhibitor-resistant cells in the presence of BRAF inhibitor may reduce the viability of BRAF inhibitor-resistant cells, indicating that these particular cells may be sensitive to COT inhibition and/or combination BRAF inhibitor/MEK inhibitor treatments (Johannessen, et al., 2010).

Reactivation of MAPK signaling may also be accomplished in a BRAF inhibitor-resistant background by activating mutations in MEK1. Targeted, massively parallel sequencing of genomic DNA from a BRAF inhibitor-resistant tumor may reveal activating mutations in MEK1, such as C121S, G128D, N122D, and Y130, among others. Other, undocumented mutations in MEK1 may be analyzed by, for example, expressing the particular mutation in a BRAF inhibitor-sensitive cell line such as A375. Determining levels of growth inhibition in these cells upon exposure to BRAF inhibitor may indicate if the MEK1 mutation is causing resistance to BRAF inhibitory therapy. To confirm such a finding, Western blotting for elevated levels of phospho-ERK1/2 in cells ectopically expressing the MEK1 mutation may indicate that the MEK1 mutation is allowing the BRAF inhibitor-resistant tumor to bypass BRAF and promote phosphorylation of ERK through MEK1 (Wagle, et al., 2011).

In accordance with the present invention, screening for a cancer that is refractory or resistant to MEK inhibitor therapy may comprise, e.g., identifying (i) amplification of mutant BRAF, (ii) STAT3 upregulation, (iii) mutations in the allosteric pocket of MEK that directly block binding of inhibitors to MEK or lead to constitutive MEK activity, and combinations thereof.

Amplification of mutant BRAF may cause MEK inhibitor resistance. MEK inhibitor resistance is typically associated with high levels of phosphorylated ERK and MEK in the presence of a MEK inhibitor, which may be assessed via, for example, Western blotting. Amplification of mutant BRAF in MEK inhibitor-resistant cell lines may be detected by, for example, fluorescence in situ hybridization (FISH) or quantitative PCR from genomic DNA of the resistant cell lines. Confirmation that BRAF amplification is a primary cause of MEK inhibitor resistance may entail using BRAF-targeted sh/siRNAs in resistant cells. If a significant decrease in MEK or ERK phosphorylation is observed, BRAF amplification may be a suitable target for further therapeutic approaches. (Corcoran, et al., 2010).

Identifying STAT3 upregulation may indicate that a particular tumor sample is resistant to MEK inhibitor therapy. Genome-wide expression profiling may reveal the STAT3 pathway to be upregulated in a tumor. Other techniques, such as Western blotting for phospho-STAT3 and real-time qPCR for the STAT pathway-associated genes JAK1 and IL6ST may reveal upregulated STAT3. Further confirmation that STAT3 upregulation causes MEK inhibitor resistance in a particular sample may comprise the use of sh/siRNAs against STAT3 in the sample followed by appropriate Western blotting for MEK and ERK activation as well as phospho-STAT3 and total STAT3. Growth inhibition studies may show that STAT3 knockdown sensitizes previously MEK inhibitor-resistant cells to MEK inhibition. A similar effect may be seen if the sample were exposed to a STAT3 inhibitor such as JSI-124. Additional confirmation that STAT3 upregulation is the cause of MEK inhibitor resistance in a particular tumor could arise from Western blotting for BIM expression, including BIM-EL, BIM-L, and BIM-SL. BIM expression leads to MEK inhibitor-induced apoptosis, thus STAT3 upregulation may lower BIM levels. STAT3 is known to regulate the expression of miR 17-92, which suppresses BIM expression. Upregulated STAT3 may lead to higher levels of miR 17-92, which will lower BIM levels and promote resistance to MEK inhibition. Thus, real-time qPCR of miR 17-92 levels may also assist in assessing whether STAT3 upregulation is causing MEK inhibition resistance in a particular sample. (Dai, et al., 2011).

Mutations in the allosteric pocket of MEK that can directly block binding of inhibitors to MEK or lead to constitutive MEK activity may be detected by methods disclosed below. Such mutations have been identified previously by Emery and colleagues (Emery, et al., 2009) as well as Wang and colleagues (Wang et al., 2011). Other mutations may affect MEK1 codons located within or abutting the N-terminal negative regulatory helix, such as P124L and Q56P. (Id.).

Methods for identifying mutations in nucleic acids, such as the above identified MEK genes, are known in the art. Nucleic acids may be obtained from biological samples. In the present invention, biological samples include, but are not limited to, blood, plasma, urine, skin, saliva, and biopsies. Biological samples are obtained from a subject by routine procedures and methods which are known in the art.

Non-limiting examples of methods for identifying mutations include PCR, sequencing, hybrid capture, in-solution capture, molecular inversion probes, fluorescent in situ hybridization (FISH) assays, and combinations thereof.

Various sequencing methods are known in the art. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

PCR-based methods for detecting mutations are known in the art and employ PCR amplification, where each target sequence in the sample has a corresponding pair of unique, sequence-specific primers. For example, the polymerase chain reaction-restriction fragment length polymorphism (PCR-RFLP) method allows for rapid detection of mutations after the genomic sequences are amplified by PCR. The mutation is discriminated by digestion with specific restriction endonucleases and is identified by electrophoresis. See, e.g., Ota et al., 2007. Mutations may also be detected using real time PCR. See, e.g., International Application publication No. WO2012046981.

Hybrid capture methods are known in the art and are disclosed in e.g., U.S. Patent Publication No. 20130203632 and U.S. Pat. Nos. 8,389,219 and 8,288,520. These methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g. biotin) which can subsequently be immobilized to a solid surface, such as a bead (in-solution capture).

Molecular Inversion Probe (MIP) techniques are known in the art and are disclosed in e.g., Absalan et al., 2008. This method uses MIP molecules, which are special "padlock" probes (Nilsson et al, 1994) for genotyping. A MIP molecule is a linear oligonucleotide that contains specific regions, universal sequences, restriction sites and a Tag (index) sequence (16-22 bp). A MIP hybridizes directly around the genetic marker/SNP of interest. The MIP method may also use a number of "padlock" probe sets that hybridize to genomic DNA in parallel (Hardenbol et al., 2003). In case of a perfect match, genomic homology regions are ligated by undergoing an inversion in configuration (as suggested by the name of the technique) and creating a circular molecule. After the first restriction, all molecules are amplified with universal primers. Amplicons are restricted again to ensure short fragments for hybridization on a microarray. Generated short fragments are labeled and, through a Tag sequence, hybridized to a cTag (complementary strand for index) on an array. After the formation of Tag-cTag duplex, a signal is detected.

The following Tables 1, 2, and 3 show the SEQ ID Nos. of representative nucleic acid and amino acid sequences of wild type BRAF, N-RAS, and MEK1 from various animals in the sequence listing. These sequences may be used in methods for identifying subjects with mutant BRAF, N-RAS, and MEK1 genotypes.

TABLE 1

BRAF sequences

| SEQ ID NO. | polypeptide or nucleic acid sequence | Organism | Other information |
|---|---|---|---|
| 1 | nucleic acid | human | |
| 2 | polypeptide | human | |
| 3 | nucleic acid | rat (*Rattus norvegicus*) | |
| 4 | polypeptide | rat (*Rattus norvegicus*) | |
| 5 | nucleic acid | mouse, *Mus musculus* | |
| 6 | polypeptide | mouse, *Mus musculus* | |
| 7 | nucleic acid | rabbit, *Oryctolagus cuniculus* | |
| 8 | polypeptide | rabbit, *Oryctolagus cuniculus* | |
| 9 | nucleic acid | guinea pig, *Cavia porcellus* | |

TABLE 1-continued

BRAF sequences

| SEQ ID NO. | polypeptide or nucleic acid sequence | Organism | Other information |
|---|---|---|---|
| 10 | polypeptide | guinea pig, *Cavia porcellus* | |
| 11 | nucleic acid | dog, *Canis lupus familiaris* | variant x1 |
| 12 | polypeptide | dog, *Canis lupus familiaris* | variant x1 |
| 13 | nucleic acid | dog, *Canis lupus familiaris* | variant x2 |
| 14 | polypeptide | dog, *Canis lupus familiaris* | variant x2 |
| 15 | nucleic acid | cat, *Felis catus* | |
| 16 | polypeptide | cat, *Felis catus* | |
| 17 | nucleic acid | cow, *Bos taurus* | variant X1 |
| 18 | polypeptide | cow, *Bos taurus* | variant X1 |
| 19 | nucleic acid | cow, *Bos taurus* | variant X2 |
| 20 | polypeptide | cow, *Bos taurus* | variant X2 |
| 21 | nucleic acid | cow, *Bos taurus* | variant X3 |
| 22 | polypeptide | cow, *Bos taurus* | variant X3 |
| 23 | nucleic acid | cow, *Bos taurus* | variant X4 |
| 24 | polypeptide | cow, *Bos taurus* | variant X4 |
| 25 | nucleic acid | cow, *Bos taurus* | variant X5 |
| 26 | polypeptide | cow, *Bos taurus* | variant X5 |
| 27 | nucleic acid | cow, *Bos taurus* | variant X6 |
| 28 | polypeptide | cow, *Bos taurus* | variant X6 |
| 29 | nucleic acid | cow, *Bos taurus* | variant X7 |
| 30 | polypeptide | cow, *Bos taurus* | variant X7 |
| 31 | nucleic acid | cow, *Bos taurus* | variant X8 |
| 32 | polypeptide | cow, *Bos taurus* | variant X8 |
| 33 | nucleic acid | cow, *Bos taurus* | variant X9 |
| 34 | polypeptide | cow, *Bos taurus* | variant X9 |
| 35 | nucleic acid | cow, *Bos taurus* | variant X10 |
| 36 | polypeptide | cow, *Bos taurus* | variant X10 |
| 37 | nucleic acid | cow, *Bos taurus* | variant X11 |
| 38 | polypeptide | cow, *Bos taurus* | variant X11 |
| 39 | nucleic acid | cow, *Bos taurus* | variant 2 |
| 40 | polypeptide | cow, *Bos taurus* | variant 2 |
| 41 | nucleic acid | horse, *Equus caballus* | |
| 42 | polypeptide | horse, *Equus caballus* | |
| 43 | nucleic acid | chicken, *Gallus gallus* | |
| 44 | polypeptide | chicken, *Gallus gallus* | |

TABLE 2

N-RAS sequences

| SEQ ID NO. | polypeptide or nucleic acid sequence | Organism | Other information |
|---|---|---|---|
| 45 | nucleic acid | human | |
| 46 | polypeptide | human | |
| 47 | nucleic acid | rat (*Rattus norvegicus*) | |
| 48 | polypeptide | rat (*Rattus norvegicus*) | |
| 49 | nucleic acid | mouse, *Mus musculus* | |
| 50 | polypeptide | mouse, *Mus musculus* | |
| 51 | nucleic acid | guinea pig, *Cavia porcellus* | |
| 52 | polypeptide | guinea pig, *Cavia porcellus* | |
| 53 | nucleic acid | guinea pig, *Cavia porcellus* | variant X1 |
| 54 | polypeptide | guinea pig, *Cavia porcellus* | variant X1 |
| 55 | nucleic acid | dog, *Canis lupus familiaris* | |
| 56 | polypeptide | dog, *Canis lupus familiaris* | |
| 57 | nucleic acid | cat, *Felis catus* | |
| 58 | polypeptide | cat, *Felis catus* | |
| 59 | nucleic acid | cow, *Bos taurus* | |
| 60 | polypeptide | cow, *Bos taurus* | |
| 61 | nucleic acid | chicken, *Gallus gallus* | |
| 62 | polypeptide | chicken, *Gallus gallus* | |

TABLE 3

MEK1 sequences

| SEQ ID NO. | polypeptide or nucleic acid sequence | Organism |
| --- | --- | --- |
| 63 | nucleic acid | human |
| 64 | polypeptide | human |
| 65 | nucleic acid | rat (*Rattus norvegicus*) |
| 66 | polypeptide | rat (*Rattus norvegicus*) |
| 67 | nucleic acid | mouse, *Mus musculus* |
| 68 | polypeptide | mouse, *Mus musculus* |
| 69 | nucleic acid | rabbit, *Oryctolagus cuniculus* |
| 70 | polypeptide | rabbit, *Oryctolagus cuniculus* |
| 71 | nucleic acid | guinea pig, *Cavia porcellus* |
| 72 | polypeptide | guinea pig, *Cavia porcellus* |
| 73 | nucleic acid | dog, *Canis lupus familiaris* |
| 74 | polypeptide | dog, *Canis lupus familiaris* |
| 75 | nucleic acid | cat, *Felis catus* |
| 76 | polypeptide | cat, *Felis catus* |
| 77 | nucleic acid | cow, *Bos taurus* |
| 78 | polypeptide | cow, *Bos taurus* |
| 79 | nucleic acid | horse, *Equus caballus* |
| 80 | polypeptide | horse, *Equus caballus* |
| 81 | nucleic acid | chicken, *Gallus gallus* |
| 82 | polypeptide | chicken, *Gallus gallus* |

In another aspect of this embodiment, the method further comprises administering at least one additional therapeutic agent, preferably an inhibitor of the PI3K/Akt pathway, as disclosed herein.

A further embodiment of the present invention is a method for treating or ameliorating the effects of cancer in a subject, which cancer is refractory or resistant to BRAF inhibitor therapy, MEK inhibitor therapy, or both. The method comprises administering to the subject an effective amount of BVD-523 or a pharmaceutically acceptable salt thereof.

Suitable and preferred subjects are as disclosed herein. In this embodiment, the methods may be used to treat the cancers disclosed above, including those cancers with the mutational backgrounds, resistance profiles, and MAPK activity identified above. Methods of identifying such mutations are also as set forth above.

In a further aspect of this embodiment, the method further comprises administering to the subject at least one additional therapeutic agent, preferably an inhibitor of the PI3K/Akt pathway, as disclosed herein.

Another embodiment of the present invention is a method for identifying a subject having cancer who would benefit from therapy with an ERK inhibitor. The method comprises:
 (a) obtaining a biological sample from the subject; and
 (b) screening the sample to determine whether the subject has one or more of the following markers:
  (i) a switch between RAF isoforms,
  (ii) upregulation of RTK or NRAS signaling,
  (iii) reactivation of mitogen activated protein kinase (MAPK) signaling,
  (iv) the presence of a MEK activating mutation,
  (v) amplification of mutant BRAF,
  (vi) STAT3 upregulation,
  (vii) mutations in the allosteric pocket of MEK that directly block binding of inhibitors to MEK or lead to constitutive MEK activity,
wherein the presence of one or more of the markers confirms that the subject's cancer is refractory or resistant to BRAF and/or MEK inhibitor therapy and that the subject would benefit from therapy with an ERK inhibitor, which is BVD-523 or a pharmaceutically acceptable salt thereof.

Suitable and preferred subjects are as disclosed herein. In this embodiment, the methods may be used to identify a subject having cancers disclosed above, including those cancers with the mutational backgrounds, resistance profiles, and MAPK activity identified above. Methods of identifying such mutations are also as set forth above.

In one aspect of this embodiment, the method further comprises administering BVD-523 or a pharmaceutically acceptable salt thereof to a subject having one or more of the markers. Preferably, the method additionally comprises administering to the subject having one or more of the markers at least one additional therapeutic agent, preferably an inhibitor of the PI3K/Akt pathway, as disclosed herein.

An additional embodiment of the present invention is a pharmaceutical composition for treating or ameliorating the effects of a cancer in a subject, which cancer is refractory or resistant to non-ERK MAPK pathway therapy. The composition comprises a pharmaceutically acceptable carrier or diluent and an effective amount of BVD-523 or a pharmaceutically acceptable salt thereof.

Suitable and preferred subjects and types of non-ERK MAPK pathway inhibitor therapy are as disclosed herein. In this embodiment, the pharmaceutical composition may be used to treat the cancers disclosed above, including those cancers with the mutational backgrounds, resistance profiles, and MAPK activity identified above. Methods of identifying such mutations are also as set forth above.

In one aspect of this embodiment, the pharmaceutical composition further comprises at least one additional therapeutic agent, preferably an inhibitor of the PI3K/Akt pathway, as disclosed herein.

Another embodiment of the present invention is a kit for treating or ameliorating the effects of a cancer in a subject, which cancer is refractory or resistant to non-ERK MAPK pathway therapy. This kit comprises any pharmaceutical composition according to the present invention packaged together with instructions for its use.

The kits may also include suitable storage containers, e.g., ampules, vials, tubes, etc., for each pharmaceutical composition and other reagents, e.g., buffers, balanced salt solutions, etc., for use in administering the pharmaceutical compositions to subjects. The pharmaceutical compositions and other reagents may be present in the kits in any convenient form, such as, e.g., in a solution or in a powder form. The kits may further include a packaging container, optionally having one or more partitions for housing the pharmaceutical composition and other optional reagents.

Suitable and preferred subjects and types of non-ERK MAPK pathway inhibitor therapy are as disclosed herein. In this embodiment, the kit may be used to treat the cancers disclosed above, including those cancers with the mutational backgrounds, resistance profiles, and MAPK activity identified herein. Methods of identifying such mutations are as set forth above.

In one aspect of this embodiment, the kit further comprises at least one additional therapeutic agent, preferably an inhibitor of the PI3K/Akt pathway, as disclosed herein.

Another embodiment of the present invention is a method for inhibiting phosphorylation of RSK in a cancer cell that is refractory or resistant to a non-ERK MAPK pathway inhibitor. The method comprises contacting the cancer cell with an effective amount of BVD-523 or a pharmaceutically acceptable salt thereof for a period of time sufficient for phosphorylation of RSK in the cancer cell to be inhibited. In this embodiment, "contacting" means bringing BVD-523 or a pharmaceutically acceptable salt thereof and optionally one or more additional therapeutic agents into close proximity to the cancer cells. This may be accomplished using conventional techniques of drug delivery to mammals, or in the in vitro situation by, e.g., providing BVD-523 or a pharmaceutically acceptable salt thereof and optionally other therapeutic agents to a culture media in which the cancer cells are located. In the ex vivo situation, contacting may be carried out by, e.g., providing BVD-523 or a pharmaceutically acceptable salt thereof and optionally other therapeutic agents to a cancerous tissue.

Suitable and preferred types of non-ERK MAPK pathway inhibitors are as disclosed herein. In this embodiment, effecting cancer cell death may be accomplished in cancer cells having various mutational backgrounds, resistance profiles, and MAPK activity as disclosed above. Methods of identifying such mutations are also as set forth above.

The methods of this embodiment, which may be carried out in vitro, ex vivo, or in vivo, may be used to effect cancer cell death, by e.g., killing cancer cells, in cells of the types of cancer disclosed herein.

In one aspect of this embodiment, greater than 50% of RSK phosphorylation is inhibited. In another aspect of this embodiment, greater than 75% of RSK phosphorylation is inhibited. In an additional aspect of this embodiment, greater than 90% of RSK phosphorylation is inhibited. In a further aspect of this embodiment, greater than 95% of RSK phosphorylation is inhibited. In another aspect of this embodiment, greater than 99% of RSK phosphorylation is inhibited. In an additional aspect of this embodiment, 100% of RSK phosphorylation is inhibited.

In a further aspect of this embodiment, the cancer cell is a mammalian cancer cell. Preferably, the mammalian cancer cell is obtained from a mammal selected from the group consisting of humans, primates, farm animals, and domestic animals. More preferably, the mammalian cancer cell is a human cancer cell.

In a further aspect of this embodiment, the contacting step comprises administering BVD-523 or a pharmaceutically acceptable salt to a subject from whom the cancer cell was obtained.

In the present invention, an "effective amount" or a "therapeutically effective amount" of a compound or composition disclosed herein is an amount of such compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of a compound or composition according to the invention will be that amount of the composition, which is the lowest dose effective to produce the desired effect. The effective dose of a compound or composition of the present invention may be administered as two, three, four, five, six or more sub-doses, administered separately at appropriate intervals throughout the day.

A suitable, non-limiting example of a dosage of a BVD-523 and other anti-cancer agents disclosed herein is from about 1 mg/kg to about 2400 mg/kg per day, such as from about 1 mg/kg to about 1200 mg/kg per day, 75 mg/kg per day to about 300 mg/kg per day, including from about 1 mg/kg to about 100 mg/kg per day. Other representative dosages of such agents include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg, 2100 mg/kg, 2200 mg/kg, and 2300 mg/kg per day. The effective dose of BVD-523 and other anti-cancer agents disclosed herein, may be administered as two, three, four, five, six or more sub-doses, administered separately at appropriate intervals throughout the day.

The BVD-523, other inhibitors, and various other anti-cancer agents disclosed herein, or a pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, BVD-523, other inhibitors, and various other anti-cancer agents disclosed herein, or a pharmaceutical composition of the present invention may be administered in conjunction with other treatments. BVD-523, other inhibitors, and various other anti-cancer agents disclosed herein, or a pharmaceutical composition of the present invention may be encapsulated or otherwise protected against gastric or other secretions, if desired.

The pharmaceutical compositions of the invention comprise one or more active ingredients in admixture with one or more pharmaceutically-acceptable diluents or carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.).

Pharmaceutically acceptable diluents or carriers are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable diluent or carrier used in a pharmaceutical composition of the invention must be "acceptable" in the sense of being compatible with the other ingredients of the formulation and not injurious to the subject. Diluents or carriers suitable for a selected dosage form and intended route of administration are well known in the art, and acceptable diluents or carriers for a chosen dosage form and method of administration can be determined using ordinary skill in the art.

The pharmaceutical compositions of the invention may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The pharmaceutical compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable diluents or carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

The pharmaceutical compositions of the present invention for rectal or vaginal administration may be presented as a suppository, which may be prepared by mixing one or more active ingredient(s) with one or more suitable nonirritating diluents or carriers which are solid at room temperature, but liquid at body temperature and, therefore, will melt in the rectum or vaginal cavity and release the active compound. The pharmaceutical compositions of the present invention which are suitable for vaginal administration also include pessaries, tampons, creams, gels, pastes, foams or spray formulations containing such pharmaceutically-acceptable diluents or carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable diluent or carrier. The ointments, pastes, creams and gels may contain excipients. Powders and sprays may contain excipients and propellants.

The pharmaceutical compositions of the present invention suitable for parenteral administrations may comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These pharmaceutical compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid diluent or carrier, for example water for injection, immediately prior to use. Extemporaneous injection solutions and suspensions may be prepared from sterile powders, granules and tablets of the type described above.

The present invention provides treatment of cancer which is refractory or resistant to non-ERK MAPK pathway inhibitor therapy and discloses combinations shown to enhance the effects of ERK inhibitors. Herein, applicants have also shown that the combination of different ERK inhibitors is likewise synergistic. Therefore, it is contemplated that the effects of the combinations described herein can be further improved by the use of one or more additional ERK inhibitors. Accordingly, some embodiments of the present invention include one or more additional ERK inhibitors.

The present invention also provides a method of treating a subject having an unresectable or metastatic BRAF600 mutation-positive melanoma comprising administering to the subject 600 mg BID of BVD-523 or a pharmaceutically acceptable salt thereof.

In some embodiments of the invention, the mutation is a BRAFV600E mutation.

The present invention also provides a composition for treating a subject having an unresectable or metastatic BRAF600 mutation-positive melanoma, the composition comprising 600 mg of BVD-523 or a pharmaceutically acceptable salt thereof and optionally a pharmaceutically acceptable carrier, adjuvant, or vehicle.

The following examples are provided to further illustrate the methods of the present invention. These examples are illustrative only and are not intended to limit the scope of the invention in any way.

EXAMPLES

Example 1

Materials and Methods

Cancer cell lines were maintained in cell culture under standard media and serum conditions. For dose escalation studies, A375 cells were split, grown to about 40-60% confluence, and then treated with the initial dose of the specified drug. Table 4 shows a summary of drug treatments that were escalated.

TABLE 4

Summary of Treatments Being Escalated

| Treatment | Inhibitor |
|---|---|
| 1 | Trametinib (MEKi) |
| 2 | Dabrafenib (BRAFi) |
| 3 | BVD-523 (ERKi) |
| 4 | Dabrafenib (BRAFi) + Trametinib (MEKi) |
| 5 | Dabrafenib (BRAFi) + BVD-523 (ERKi) |
| 6 | Trametinib (MEKi) + BVD-523 (ERKi) |

Figure 20:
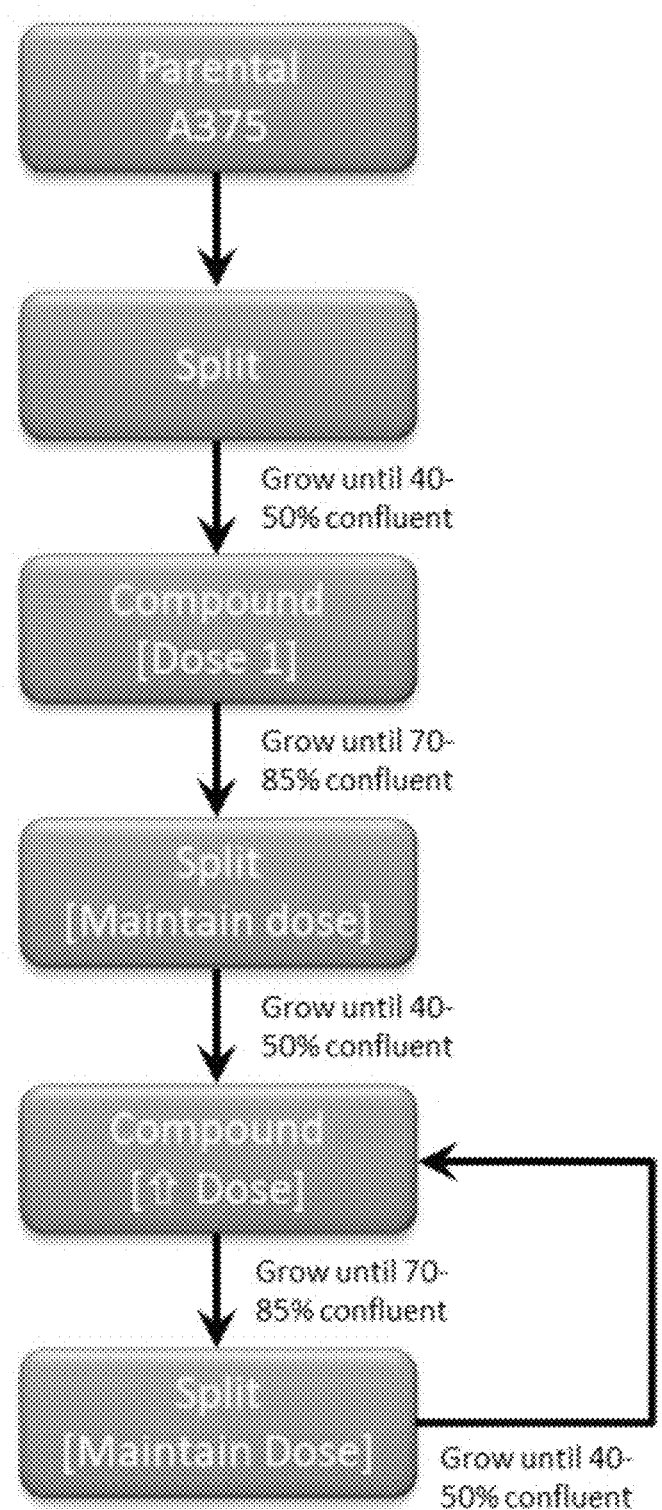
FIG. 20 is a flowchart showing the dose escalation protocol used herein.

Single agent dose escalations were performed based on Little et al., 2011 and are outlined in FIG. 20. Cells were then allowed to grow until 70-90% confluence and split. Split ratios were kept as "normal" as possible and reasonably consistent between treatments (e.g. a minimum of 50% of the normal split ratio of the parentals). Medium was refreshed every 3-4 days. When cells again reached about 40-60% confluence, the dose was escalated. In the event that the 40-60% window was missed, the cells were split again and dosed once they reached 40-60% confluence. Again, medium was refreshed every 3-4 days. The process was repeated as required (FIG. 20).

For single agent treatments, starting concentrations and dose increases were conducted by starting with the approximate $IC_{50}$, escalating in small increments or, gently, for the initial 4-5 doses, doubling the dose, increasing by the same increment for the next 4 doses, then moving to 1.5-fold increases in concentration for subsequent doses.

For combination treatments, starting concentrations and dose increases were conducted by starting with half of the approximate $IC_{50}$ of each compound (combination assay suggests this will result in about 40-70% inhibition range), escalating as per single agents (i.e. doing an initial doubling and then increasing by the same increment for the next 4 doses, then moving to 1.5-fold increases in concentration). Table 5 shows the projected dose increases using these schemes.

TABLE 5

Projected Dose Increases-Month 1

| Dose | Tram (nM) | Dab (nM) | BVD-523 (µM) | Dab/Tram Dab (nM) | Dab/Tram Tram (nM) | Dab/523 Dab (nM) | Dab/523 523 (µM) | Tram/523 Tram (nM) | Tram/523 523 (µM) |
|---|---|---|---|---|---|---|---|---|---|
| 1 | 1 | 5 | 0.16 | 2.5 | 0.5 | 2.5 | 0.08 | 0.5 | 0.08 |
| 2 | 2 | 10 | 0.32 | 5 | 1 | 5 | 0.16 | 1 | 0.16 |
| 3 | 3 | 15 | 0.48 | 7.5 | 1.5 | 7.5 | 0.24 | 1.5 | 0.24 |
| 4 | 4 | 20 | 0.64 | 10 | 2 | 10 | 0.32 | 2 | 0.32 |
| 5 | 5 | 25 | 0.80 | 12.5 | 2.5 | 12.5 | 0.40 | 2.5 | 0.40 |
| 6 | 8 | 38 | 1.2 | 19 | 4 | 19 | 0.6 | 4 | 0.6 |
| 7 | 11 | 56 | 1.8 | 28 | 6 | 28 | 0.9 | 6 | 0.9 |
| 8 | 17 | 84 | 2.7 | 42 | 8 | 42 | 1.4 | 8 | 1.4 |

TABLE 5-continued

Projected Dose Increases-Month 1

| | | | | Dab/Tram | | Dab/523 | | Tram/523 | |
|------|------------|-----------|----------------|-------------|-------------|-------------|-------------|-------------|-------------|
| Dose | Tram (nM) | Dab (nM) | BVD-523 (μM) | Dab (nM) | Tram (nM) | Dab (nM) | 523 (μM) | Tram (nM) | 523 (μM) |
| 9  | 25   | 127   | 4.1   | 63   | 13   | 63   | 2.0   | 13   | 2.0 |
| 10 | 38   | 190   | 6.1   | 95   | 19   | 95   | 3.0   | 19   | 3.0 |
| 11 | 57   | 285   | 9.1   | 142  | 28   | 142  | 4.6   | 28   | 4.6 |
| 12 | 85   | 427   | 13.7  | 214  | 43   | 214  | 6.8   | 43   | 6.8 |
| 13 | 128  | 641   | 20.5  | 320  | 64   | 320  | 10.3  | 64   | 10.3 |
| 14 | 192  | 961   | 30.8  | 481  | 96   | 481  | 15.4  | 96   | 15.4 |
| 15 | 288  | 1442  | 46.1  | 721  | 144  | 721  | 23.1  | 144  | 23.1 |
| 16 | 432  | 2162  | 69.2  | 1081 | 216  | 1081 | 34.6  | 216  | 34.6 |
| 17 | 649  | 3244  | 103.8 | 1622 | 324  | 1622 | 51.9  | 324  | 51.9 |
| 18 | 973  | 4865  | 155.7 | 2433 | 487  | 2433 | 77.8  | 487  | 77.8 |
| 19 | 1460 | 7298  | 233.5 | 3649 | 730  | 3649 | 116.8 | 730  | 116.8 |
| 20 | 2189 | 10947 | 350.3 | 5474 | 1095 | 5474 | 175.2 | 1095 | 175.2 |

Clonal resistant cell populations were derived from resistant cell pools by limiting dilution.

Proliferation assays were used to track changes in sensitivity to the escalated agent(s) at appropriate time intervals (e.g. each month, although the timing is dependent on adequate cell numbers being available). For proliferation assays, cells were seeded in 96-well plates at 3000 cells per well in drug-free DMEM medium containing 10% FBS and allowed to adhere overnight prior to addition of compound or vehicle control. Compounds were prepared from DMSO stocks to give a final concentration range as shown in FIG. 2A-FIG. 2H. The final DMSO concentration was constant at 0.1%. Test compounds were incubated with the cells for 96 hours at 37° C. and 5% $CO_2$ in a humidified atmosphere. Alamar Blue 10% (v/v) was then added and incubated for 4 hours and fluorescent product was detected using a BMG FLUOstar plate reader. The average media only background value was deducted and the data analyzed using a 4-parameter logistic equation in GraphPad Prism. Paclitaxel was used as a positive control.

Proliferation assays for month 1 were initiated at day 28 using cells growing in the concentrations of each agent indicated in Table 6.

TABLE 6

Initial Concentrations of Drugs Used in Proliferation Assays - Month 1

| Line | Dab | Tram | BVD-523 |
|------|-----|------|---------|
| Parental | — | — | — |
| Tram | — | 2 nM | — |
| Dab | 15 nM | — | — |
| BVD-523 | — | — | 0.48 μM |
| Tram + Dab | 5 nM | 1 nM | — |
| Dab + BVD-523 | 7.5 nM | — | 0.24 μM |
| Tram + BVD-523 | — | 1 nM | 0.16 μM |

Proliferation assays for month 2 were initiated at day 56 using cells growing in the concentrations of each agent indicated in Table 7.

TABLE 7

Initial Concentrations of Drugs Used in Proliferation Assays - Month 2

| Line | Dab | Tram | BVD-523 |
|------|-----|------|---------|
| Parental | — | — | — |
| Tram | — | 8 nM | — |
| Dab | 127 nM | — | — |

TABLE 7-continued

Initial Concentrations of Drugs Used in Proliferation Assays - Month 2

| Line | Dab | Tram | BVD-523 |
|------|-----|------|---------|
| BVD-523 | — | — | 0.8 μM |
| Tram + Dab | 10 nM | 2 nM | — |
| Dab + BVD-523 | 12.5 nM | — | 0.4 μM |
| Tram + BVD-523 | — | 2 nM | 0.32 μM |

At the end of the 3 month escalation period, cultures were maintained at the top concentration for 2 weeks prior to the final round of proliferation assays and potential single cell cloning. As the proliferation assays/single cell cloning required actively proliferating cells, for treatments where cells were proliferating very slowly at the top concentration or that were only recently escalated, a backup culture was also maintained at a lower concentration (Table 8). For the BVD-523 treatment, where cells appeared to have almost completely stopped growing and looked particularly fragile at the top concentration (1.8 μM), cultures were maintained at a lower concentration for the 2 week period.

TABLE 8

Details of Treatments Being Cultured at a Fixed Concentration for 2 Weeks

| Treatment | Inhibitor | Culture 1 | Backup Culture |
|-----------|-----------|-----------|----------------|
| 1 | Tram | 160 nM | 80 nM |
| 2 | Dab | 3.2 μM | — |
| 3 | BVD-523 | 1.2 μM | 0.8 μM |
| 4 | Dab + Tram | D: 160 nM<br>T: 30 nM | D: 80 nM<br>T: 16 nM |
| 5 | Dab + BVD-523 | D: 42 nM<br>523: 1.4 μM | D: 28 nM<br>523: 0.9 μM |
| 6 | Tram + BVD-523 | T: 4 nM<br>523: 0.6 μM | T: 2.5 nM<br>523: 0.4 μM |

Proliferation assays for month 3 used cells growing in the concentrations of each agent indicated in Table 9.

TABLE 9

Initial Concentrations of Drugs Used in Proliferation Assays - Month 3

| Line | Dab | Tram | BVD-523 |
|------|-----|------|---------|
| Parental | — | — | — |
| Tram | — | 160 nM | — |
| Dab | 3.2 μM | — | — |
| BVD-523 | — | — | 1.2 μM |
| Tram + Dab | 80 nM | 16 nM | — |
| Dab + BVD-523 | 28 nM | — | 0.9 μM |
| Tram + BVD-523 | — | 2.5 nM | 0.4 μM |

For combination studies, A375 cells (ATCC) were seeded into triplicate 96-well plates at a cell density of 3000 cells/well in DMEM plus 10% FBS and allowed to adhere overnight prior to addition of test compound or vehicle control. Combinations were tested using a 10×8 dose matrix with a final DMSO concentration of 0.2%. A 96 hour assay incubation period followed, with subsequent addition of Alamar Blue 10% (v/v) and 4 hours incubation prior to reading on a fluorescent plate reader. After reading Alamar Blue, the medium/Alamar Blue mix was flicked off and 100 μl of CellTiter-Glo/PBS (1:1) added and the plates processed as per the manufacturers instructions (Promega). Media only background values were subtracted before the data was analysed. The Bliss additivity model was then applied.

In brief, predicted fractional inhibition values for combined inhibition were calculated using the equation $C_{bliss}=A+B-(A\times B)$ where A and B are the fractional inhibitions obtained by drug A alone or drug B alone at specific concentrations. $C_{bliss}$ is the fractional inhibition that would be expected if the combination of the two drugs were exactly additive. $C_{bliss}$ values are subtracted from the experimentally observed fractional inhibition values to give an 'excess over Bliss' value. Excess over Bliss values greater than 0 indicate synergy, whereas values less than 0 indicate antagonism. Excess over Bliss values are plotted as heat maps±SD.

The single and combination data are also presented as dose-response curves generated in GraphPad Prism (plotted using % viability relative to DMSO only treated controls).

For focused combination studies, the Alamar Blue viability assays were performed as described above for combination studies. Additionally, Caspase-Glo 3/7 assays were performed. In brief, HCT116 cells were seeded in triplicate in white 96-well plates at a cell density of 5000 cells/well in McCoy's 5A plus 10% FBS. A375 cells were seeded at a density of 5000 cells/well in DMEM plus 10% FBS. Cells were allowed to adhere overnight prior to addition of test compound or vehicle control. The final concentration of DMSO was 0.2%, and 800 nM staurosporine was included as a positive control. 24 and 48 hour assay incubation periods were used. Then, Caspase-Glo® 3/7 50% (v/v) was added, plates were mixed for 5 minutes on an orbital shaker and incubated for 1 hour at room temperature prior to reading on a luminescent plate reader. Media only background values were subtracted before the data was analysed.

For Differential Scanning Fluorimetry, SYPRO orange (5,000× solution, Invitrogen) was diluted (1:1,000) in buffer solution (10 mM HEPES, 150 mM NaCl, pH 7.5). HisX6 tagged proteins included inactive ERK2, active ERK2 (ppERK2), or p38a at a final concentration of 1 µM. The protein/dye solution and compounds in 100% DMSO were added to wells (2% v/v final DMSO concentration) to achieve the desired final concentrations, mixed, and placed into an RT-PCR instrument. Next, a melting curve was run from 25-95° C. at a rate of 1° C. per minute and the melting temperature (Tm) was determined for each protein in the absence or presence of compounds. The change in Tm (ΔTm) in the presence of various drug concentrations is presented.

For Ki determination of ERK1, activated ERK1 (10 nM) was incubated with various concentrations of the compounds in 2.5% (v/v) DMSO for 10 minutes at 30° C. in 0.1 M HEPES buffer (pH 7.5), 10 mM MgCl$_2$, 2.5 mM phosphoenolpyruvate, 200 µM nicotinamide adenine dinucleotide (NADH), 150 µg/mL pyruvate kinase, 50 µg/mL lactate dehydrogenase, and 200 µM Erktide peptide. The reaction was initiated by the addition of 65 µM of ATP. Decreased absorbance rate (340 nm) was monitored and the IC$_{50}$ was determined as a function of inhibitor concentration.

For Ki determination of ERK2, the inhibitory activity of BVD-523 against ERK2 was determined using a radiometric assay, with final concentration of the components being 100 mM HEPES (pH 7.5), 10 mM MgCl$_2$, 1 mM dithiothreitol (DTT), 0.12 nM ERK2, 10 µM myelin basic protein (MBP), and 50 µM $^{33}$P-γ-ATP. All reaction components, with the exception of ATP and MBP, were premixed and aliquoted (33 µL) into a 96-well plate. A stock solution of compound in DMSO was used to make up to 500-fold dilutions; a 1.5-µL aliquot of DMSO or inhibitor in DMSO was added to each well. The reaction was initiated by adding the substrates $^{33}$P-γ-ATP and MBP (33 µL). After 20 minutes the reaction was quenched with 20% (w/v) tricholoracetic acid (TCA) (55 µL) containing 4 mM ATP, transferred to the GF/B filter plates, and washed 3 times with 5% (w/v) TCA). Following the addition of Ultimate Gold™ scintillant (50 µL), the samples were counted in a Packard TopCount. From the activity versus concentration titration curve, the Ki value was determined by fitting the data to an equation for competitive tight binding inhibition kinetics using Prism software, version 3.0.

For IC$_{50}$ determination of ERK2, activity was assayed by a standard coupled-enzyme assay. The final concentrations were as follows: 0.1 M HEPES (pH 7.5), 10 mM MgCl$_2$, 1 mM DTT, 2.5 mM phosphoenolpyruvate, 200 µM NADH, 50 µg/mL pyruvate kinase, 10 µg/mL lactate dehydrogenase, 65 µM ATP, and 800 µM peptide (ATGPLSPGPFGRR). All of the reaction components except ATP were premixed with ERK and aliquoted into assay-plate wells. BVD-523 in DMSO was introduced into each well, keeping the concentration of DMSO per well constant. BVD-523 concentrations spanned a 500-fold range for each titration. The assay-plate was incubated at 30° C. for 10 minutes in the plate reader compartment of the spectrophotometer (molecular devices) before initiating the reaction by adding ATP. The absorbance change at 340 nm was monitored as a function of time; the initial slope corresponds to the rate of the reaction. The rate versus concentration of the BVD-523 titration curve was fitted either to an equation for competitive tight-binding inhibition kinetics to determine a value for Ki or to a 3-parameter fit to determine the IC$_{50}$ using Prism software, version 3.0.

For apoptosis assays, cells were plated at $2\times10^4$ cells per well in a 96-well plate and allowed to attach overnight or grow to 50% confluency. Cells were treated with a serial dilution of BVD-523 in media (final volume 200 µL, concentration ranges 4-0.25 µM) and incubated for 48 hours in a 37° C. CO$_2$ incubator. Cells were washed with 100 µL of PBS, and 60 µL of radioimmunoprecipitation assay buffer was added (50 mM Tris-HCl, pH 8.0, 150 mM NaCl, 1.0% [w/v] NP-40, 0.5% [w/v] sodium deoxycholate, 1% [w/v] SDS), then incubated for 10 minutes at 4° C. to lyse the cells. A 30-µL lysate aliquot was added to 100 µL of caspase assay buffer (120 mM HEPES, 12 mM EDTA, 20 mM dithiothreitol, 12.5 µg/mL AC-DEVD-AMC caspase substrate) and incubated at RT from 4 hours to overnight. The plate was read in a fluorimeter (excitation wavelength 360 nm, emission wavelength 460 mm). The remaining 30 µL of lysate was analyzed for total protein content using the BioRad Protein Assay Kit (sample-to-working reagent ratio of 1:8). Final normalized caspase activity was derived as fluorescence units per µg protein and converted to a fold increase in caspase activity when compared with DMSO controls.

For measurement of antitumor activity in A375 xenografts, xenografts were initiated with A375 cells maintained by serial subcutaneous transplantation in female athymic nude mice. Each test mouse received an A375 tumor fragment (1 mm$^3$) implanted subcutaneously in the right flank. Once tumors reached target size (80-120 mm$^3$), animals were randomized into treatment and control groups, and drug treatment was initiated.

To evaluate BVD-523 monotherapy, BVD-523 in 1% (w/v) carboxymethylcellulose (CMC) was administered orally, per os (p.o.), BID at doses of 5, 25, 50, 100, or 150 mg/kg. Oral temozolomide was administered as a positive reference compound at 75 or 175 mg/kg once daily (QD) for a total of five treatments (QD×5).

The efficacy of BVD-523 in combination with dabrafenib was evaluated in mice randomized into 9 groups of 15 and 1 group of 10 (Group 10). Dabrafenib was administered p.o.

at 50 or 100 mg/kg QD and BVD-523 was administered p.o. at 50 or 100 mg/kg BID, alone and in combination, until study end; vehicle-treated and temozolomide-treated (150 mg/kg QD×5) control groups were also included. Combination dosing was stopped on Day 20 to monitor for tumor regrowth. Animals were monitored individually and euthanized when each tumor reached an endpoint volume of 2000 mm$^3$, or the final day (Day 45), whichever came first, and median time to endpoint (TTE) calculated. The combination was also evaluated in an upstaged A375 model where larger tumors in the range 228-1008 mm$^3$ were evaluated. Here, mice were randomized into 1 group (Group 1) of 14 and 4 groups (Groups 2-5) of 20. Dosing was initiated on Day 1 with dabrafenib plus BVD-523 (25 mg/kg dabrafenib+50 mg/kg BVD-523 or 50 mg/kg dabrafenib+100 mg/kg BVD-523), with each agent given p.o. BID until study end. The study included 50-mg/kg dabrafenib and 100-mg/kg BVD-523 monotherapy groups as well as a vehicle-treated control group. Tumors were measured twice weekly. Combination dosing was stopped on Day 42 to monitor for tumor regrowth through study end (Day 60). Treatment outcome was determined from % TGD, defined as the percent increase in median TTE for treated versus control mice, with differences between groups analyzed via log rank survival analysis. For TGI analysis, % TGI values were calculated and reported for each treatment (T) group versus the control (C) using the initial (i) and final (f) tumor measurements based on the following formula: % TGI=1−Tf−Ti/Cf−C. Mice were also monitored for CR and PR responses. Animals with a CR at the end of the study were additionally classified as TFS.

For measurement of BVD-523 activity in Colo205 xenografts, human Colo205 cells were cultured in RPMI 1640 supplemented with 10% (v/v) fetal bovine serum (FBS), 100 units/mL penicillin, 100 µg/mL streptomycin (Invitrogen), and 2 mM L-glutamine. Cells were cultured for fewer than four passages prior to implantation. Female athymic nude mice (19-23 g) were injected subcutaneously with 2×10$^6$ Colo205 cells into the right dorsal axillary region on Day 0.

Mice with an approximate tumor volume of 200 mm$^3$ were randomized into 6 experimental groups. Vehicle control, 1% CMC (w/v), was prepared weekly. BVD-523 was suspended in 1% (w/v) CMC at the desired concentration and homogenized on ice at 6,500 rpm for 50 minutes. BVD-523 suspensions were prepared weekly and administered p.o. BID at total daily doses of 50, 100, 150, and 200 mg/kg (n=12/group) on an 8- or 16-hour dosing schedule for 13 days. The vehicle control (n=12) was administered using the same dosing regimen. CPT-11 was administered as a positive reference compound (n=12). Each 1 mL of CPT-11 injection contained 20 mg irinotecan, 45 mg sorbitol, and 0.9 mg lactic acid. CPT-11 was administered at 100 mg/kg/day intraperitoneally every 4 days for 2 consecutive doses.

For measurement of ERK1/2 Isotope-Tagged Internal Standard (ITIS) Mass Spectrometry in Colo205 Xenografts, frozen tumors were lysed in 10 volumes of ice cold lysis buffer (10 mM TRIS-HCl, pH 8.0, 10 mM MgCl$_2$, 1% (v/v) Triton X-100, Complete™ Protease Inhibitor Cocktail [Roche, cat. No. 1836170], Phosphatase Inhibitor Cocktail I [Sigma, cat. No. P-2850], Phosphatase Inhibitor Cocktail II [Sigma cat. No. 5726], and benzonase [Novagen cat. No. 70664]). Lysates were clarified by centrifugation (100,000×g for 60 minutes at 4° C.) and the supernatants adjusted to 2 mg/mL with lysis buffer. ERK1 was immunoprecipitated using agarose-coupled and pan-anti-ERK1 (Santa Cruz Biotechnology cat. No. sc-93ac) antibodies. Immunoprecipitated proteins were resolved by SDS-PAGE and stained with SYPRO Ruby (Invitrogen), and the ERK bands excised via razor. Gel slices were washed in 300 µL of 20 mM NH$_4$HCO$_3$, diced into small pieces, and placed in Page Eraser Tip (The Nest Group cat no. SEM0007). Gel fragments were reduced and alkylated prior to trypsin digestion. Tryptic fragments were isolated in 75 µL of 50% (v/v) Acetonitrile, 0.2% (v/v) trifluoroacetic acid and the resulting sample concentrated to 0-10 µL in a SpeedVac.

For ITIS analysis, digested samples were spiked with heavy-atom labeled peptide standards and fractional phosphorylation was quantified by coupled liquid chromatography-tandem mass spectrometry (MS). Nanocapillary chromatography was performed using a Rheos 2000 binary pump from Flux Instruments delivering nanoscale flow after 1:750 splitting, an LC Packings Inertsil nano-precolumn (C18, 5 mm, 100 Å, 30 mm ID×1 mm), and a New Objective PicoFrit AQUASIL resolving column (C18, 5 mm, 75/15 mm ID×10 cm), which also served as an electrospray ionization (ESI) emitter. An Applied Biosystem API 3000 mass spectrometer coupled with a nano-ESI source was used for MS analysis. An in-house-made gas nozzle connected to a nebulizing gas source was used to help steady nano-flow spray. Data were acquired in a multiple reaction monitoring (MRM) mode: nebulizing gas at 3; curtain gas at 7; collision gas at 5; ion spray voltage at 2150 volts, exit potential at 10 volts; Q1/Q3 resolution Low/Unit; and dwell time of 65 msec for all MRM channels. All raw MS data were processed using a combination of the Analyst software suite from Applied Biosystem and custom tools.

For assessment of drug sensitivity in cell-line models of acquired resistance, drug sensitivity of dose-escalated A375 cells and isogenic RKO cells was assessed in 96-hour proliferation assays. RKO isogenic cells (McCoy's 5A containing 10% [v/v] FBS) or dose-escalated A375 cells (DMEM containing 10% FBS were seeded into 96-well plates and allowed to adhere overnight prior to addition of compound or vehicle control. Note that the dose-escalated A375 cells were seeded in the absence of inhibitor. Compounds were prepared from 0.1% (v/v) DMSO stocks to give a final concentration as indicated. Test compounds were incubated with the cells for 96 hours at 37° C. in a 5% CO$_2$ humidified atmosphere. For the RKO cells, CellTiter-Glo® reagent (Promega) was added according to manufacturer's instructions and luminescence detected using a BMG FLUOstar plate reader. For the A375 assays Alamar blue (ThermoFisher) 10% (v/v) was added and incubated for 4 h, and fluorescent product was then detected using a BMG FLUOstar. The average media only background value was deducted and the data analyzed using a 4-parameter logistic equation in GraphPad Prism.

IC$_{50}$ Determination of ERK1 was measured in a final reaction volume of 25 µL. ERK1 (human) (5-10 mU) was incubated with 25 mM Tris (pH 7.5), 0.02 mM ethyleneglycoltetracetic acid, 250 µM peptide, 10 mM Mg acetate, and γ-$^{33}$P-ATP (specific activity approximately 500 cpm/pmol, concentration as required). Adding Mg ATP initiated the reaction. After incubation for 40 minutes at room temperature (RT), the reaction was stopped by adding 5 µL of a 3% (w/v) phosphoric acid solution. Then, 10 µL of the reaction was spotted onto a P30 filtermat, and washed 3 times for 5 minutes in 75 mM of phosphoric acid then once in methanol before drying and scintillation counting.

RKO MEK1 Q56P Isogenic cells were produced by Horizon Discovery (Cambridge, UK; #HD 106-019) using a recombinant AAV-mediated gene targeting strategy. Briefly, rAAV virus was generated following transfection of the appropriate targeting vector and helper vectors in HEK293T cells, purified using an AAV purification kit (Virapur, San Diego, USA) and titrated using qPCR. Parental homozygous RKO cells (homozygous wild type for MEK1) were then infected with rAAV virus and clones that had integrated the selection cassette were identified by G418 selection and expanded. Correctly targeted clones that were heterozygous for knock-in of the MEK1 Q56P point mutation into a single allele were identified by PCR and sequencing.

Isogenic SW48 cell lines heterozygous for knock-in of mutant KRAS (De Roock et al 2010, JAMA, 304, 1812-1820) were obtained from Horizon Discovery (Catalogue numbers; HD 103-002, HD 103-006 HD 103-007, HD 103-009, HD 103-010, HD 103-011, HD 103-013). For proliferation assay, cells were seeded into 96-well plates in McCoy's 5A medium supplemented with 10% FBS and allowed to adhere overnight prior to addition of compound or vehicle control. Test compounds were incubated with the cells for 96 hours at 37° C. in a 5% $CO_2$ atmosphere. Viability was then assessed using Alamar blue.

The proprietary KinaseProfiler assay was conducted at Upstate Discovery and employed radiometric detection similar to that employed by Davies et al, was used to profile the selectivity of BVD-523 against a panel of 70 kinases.

A drug sensitivity analysis was carried out as part of The Genomics of Drug Sensitivity in Cancer Project using high-throughput screening, as previously described (Yang et al. 2013).

For Western blot analysis, A375 cells were seeded onto 10 cm dishes in Dulbecco's Modified Eagle's Medium plus 10% (v/v) FBS. Cells were allowed to adhere overnight prior to the addition of test compound or vehicle. For experiments with RKO cells, these cells were seeded in 6-well plates or 10 cm dishes with McCoy's 5A+10% (v/v) FBS. Cells were then treated at the desired concentration and duration. Cells were harvested by trypsinization, pelleted, and snap frozen. Lysates were prepared with RIPA buffer supplemented with protease and phosphatase inhibitor cocktails (Roche), clarified by centrifugation at 11,000 rpm for 10 minutes, and quantitated by bicinchoninic acid assay. Samples were resolved by SDS-PAGE, blotted onto polyvinylidene difluoride membranes, and probed using antibodies (i.e., pRB [Ser780], cat. no. 9307; CCND1, cat. no. ab6152; BCL-xL, cat. no. 2762; PARP, cat. no. 9542; DUSP6, cat. no. 3058S) directed to the indicated targets.

For Reverse Phase Protein Analysis (RPPA), A375, MIAPaCa-2, HCT116, Colo205, HT-29, and AN3Ca cells (ATCC) were plated at 80% confluence, allowed to recover overnight (MIAPaCa-2 cells were plated at 30% confluence and allowed to recover for 3 days), then treated with 10 μM of each compound (i.e., BVD-523, SCH722984, GDC-0994, or Vx-11e) for 6 hours at 37° C. Control wells were treated with DMSO at 0.1% (v/v) for 6 hours prior to cell lysate generation. Samples were then analyzed using reverse-phase protein microarray technology (Theranostics Health).

For analysis of pERK IHC in Colo205 xenografts, xenograft tumors were processed overnight in 70% through 100% graded ethanols, cleared in two changes of xylene, infiltrated with paraffin, and embedded into paraffin blocks. Then, 5-μm sections were cut and placed onto positively charged glass slides and baked for at least 30 minutes, but not longer than 1 hour, at 60° C. A single section from each animal and dose group was probed with anti-phospho p42/p44 MAPK antibody (pERK [1:100], CST; Cat no. 9101; Lot no. 16), counterstained with hematoxylin, and then analyzed microscopically using a Zeiss Axioplan 2 microscope. An isotype control (rabbit, Zymed laboratories, catalog no. 08-6199, lot no. 40186458) was run as a negative control.

For FACS analysis, cells were scraped and pelleted at 1,500 rpm for 5 minutes, then re-suspended in 1 mL of buffer and frozen at −70° C. The frozen cells were thawed and centrifuged again, followed by 10 minutes of re-suspension in 0.25 mL of Buffer A (trypsin in spermine tetrahydrochloride detergent buffer) to disaggregate cell clumps and digest cell membranes and cytoskeletons. Buffer B (trypsin inhibitor and Ribonuclease I in buffer, 0.2 mL) was added for 10 minutes in the dark. The resulting DNA-stained nuclei were filtered and analyzed by FACS. The histograms were analyzed to establish the proportion of cells in the G1, S, and G2/M phases of the cell cycle based on the presence of n and 2n DNA (or higher) content.

For measurement of in vitro combination activity, five thousand G-361 cells were seeded into triplicate 96-well plates containing McCoy's 5A with 10% (v/v) FBS and allowed to adhere overnight. The vemurafenib/BVD-523 combination was tested using a 10×8 dose matrix. Compounds were incubated with the cells for 72 hours at 37° C. in a 5% $CO_2$ humidified atmosphere. CellTiter-Glo reagent was added according to manufacturer's instructions and luminescence detected using a MBG FLUOstar plate reader. The interactions across the dose matrix were determined by the Loewe Additivity and Bliss independence models using Horizon's Chalice Combination Analysis Software.

For generating compound resistance in vitro by dose escalation, A375 parental cells (ATCC CRL-1619) were grown to ~40-60% confluence in Dulbecco's Modified Eagle's Medium (DMEM) supplemented with 10% heat-inactivated FBS and penicillin/streptomycin, then treated with initial doses of BVD-523, trametinib, or dabrafenib either alone or in combination at or slightly below each compound's $IC_{50}$; for combination studies, initial dosing was half of each compound's $IC_{50}$. Cells were allowed to grow until ~70-90% confluence and split; medium was refreshed every 3-4 days. When cells again reached ~40-60% confluence, the dose was escalated by the same increment (equivalent to the starting concentration) then moved to 1.5-fold increases in concentration followed by a further move to 2-fold increases if the cells continued to adapt rapidly (e.g., the first six doses of the dabrafenib escalation were: 5, 10, 15, 20, 25, and 37.5 nM). This process was repeated as required.

Figure 30A:
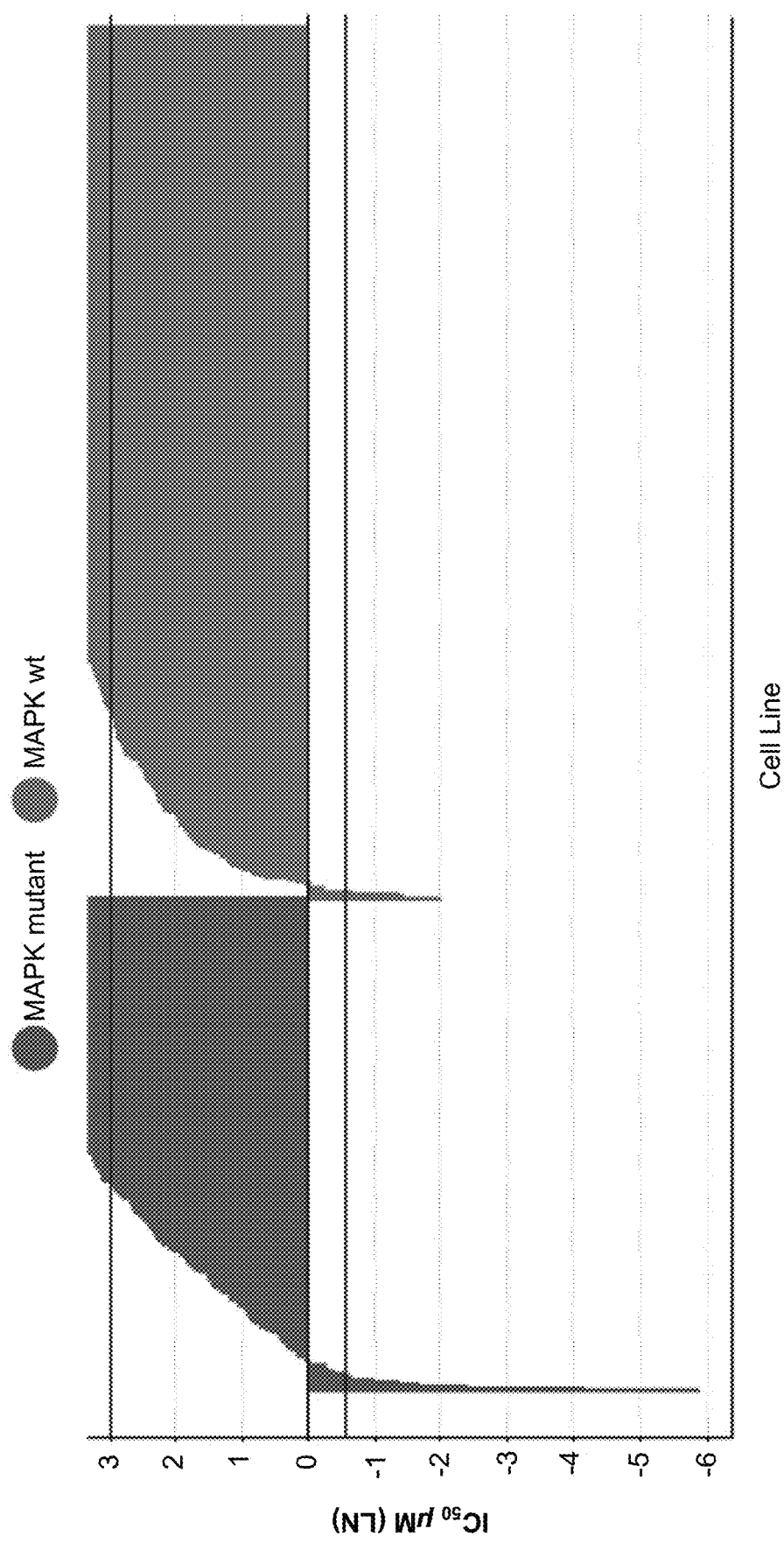
FIG. 30A-FIG. 30D show that BVD 523 inhibits cellular proliferation and enhances caspase 3 and caspase 7 activity in vitro.

Cell viability assays for FIG. 30A were performed by a Resazurin (Alamar Blue) metabolic assay after 5 days in drug in full serum under high glucose conditions. Cells were seeded in 384-well microplates at ~15%-50% confluence in medium with 10% FBS and penicillin/streptavidin plus high glucose (18-25 mM). The optimal cell number for each cell line was determined to optimize growth during drugging. For adherent cell lines, after overnight incubation cells were treated with 9 concentrations of each compound (2-fold dilutions series) using liquid handling robotics, and returned to the incubator for assay at a 96-h time point. For suspension cell lines, cells were treated with compound immediately after plating and returned to the incubator for a 96-h time point. Cells were then stained with 55 μg/ml Resazurin (Sigma) prepared in glutathione-free media for 4 hours. Quantitation of fluorescent signal intensity was performed using a fluorescent plate reader at excitation and emission wavelengths of 535/595 nm for Resazurin. All screening plates were subjected to stringent quality control measures. Effects on cell viability were measured and a curve-fitting algorithm was applied to the raw dataset to derive a multiparameter description of drug response, including the half maximal inhibitory concentration ($IC_{50}$). $IC_{50}$ is expressed in natural log of the $IC_{50}$ in μM (LN_$IC_{50}$; EXP returns $IC_{50}$ in μM). Extrapolation of the $IC_{50}$ was allowed for where it yielded very high values. If desired the data was restricted to the tested concentration range by capping $IC_{50}$ values at the maximum tested concentration (and the minimum tested concentration for low values).

For efficacy testing of BVD-523 in a patient-derived xenograft (AT052C) representing melanoma from a $BRAF^{V600E}$ patient that had become clinically refractory to vemurafenib. Tumor fragments were harvested from host animals and implanted into immune-deficient mice. The study was initiated at a mean tumor volume of approximately 170 mm³, at which point the animals were randomized into four groups including a control (1% [v/v] CMC p.o., BID×31) and three treatment groups (BVD-523 [100 mg/kg], dabrafenib [50 mg/kg], or BVD-523/dabrafenib [100/50 mg/kg], n=10/group); All treatment drugs were administered p.o. on a BID×31 schedule.

For $IC_{50}$ determination for the inhibition of PMA-stimulated RSK1 phosphorylation by BVD-523 in human whole blood samples, $IC_{50}$ values for the inhibition of PMA stimulated RSK1 phosphorylation by BVD-523 were determined for 10 healthy donors (aged 22-61 years) using an 8-point concentration curve ranging from 10 μM to 5 nM of BVD-523. Controls consisted of 3 unstimulated samples and 3 PMA-stimulated samples for each donor. Both phosphor-RSK (pRSK) and total RSK levels were determined and data were calculated using pRSK/RSK levels for each sample.

Thirty milliliters of blood was drawn from each donor into sodium heparin vacutainers. One mL of whole blood was added to each of twenty-two 2-mL microtubes per donor. The microtubes tubes were labeled with the donor number (1 through 10) and the subsequent treatment designation: "A" for PMA stimulation only (maximum), "B" for BVD-523-containing samples that received PMA stimulation; and "C" for the unstimulated samples (minimum). Dimethyl sulfoxide (DMSO) was added to all tubes in groups A and C to a final concentration of 0.1%. Samples were then rocked gently at room temperature.

BVD-523 (10 mM in 100% DMSO) was serially diluted with 3-fold dilutions into 100% DMSO. These serially diluted BVD-523 samples in 100% DMSO were then diluted 10-fold in Dulbecco's Modified Eagle Medium containing 10% fetal bovine serum and penicillin/streptomycin/glutamine, and 10 μL of each of these working solutions was added per mL of blood for each designated BVD-523 concentration. Each concentration of BVD-523 was run in duplicate, two 1-mL blood samples each, yielding 16 total samples for the full 8-point concentration curve. Samples were then rocked gently at room temperature for a minimum of 2 hours but not longer than 3 hours.

Human whole blood samples in groups A and B for all donors were stimulated with PMA at a final concentration of 100 nM for 20 minutes at room temperature. Samples in group C were not treated with PMA but were rocked and handled as all other samples.

Upon completion of PMA treatment for each sample, peripheral blood mononuclear cells were isolated from the human whole blood. One mL of blood from each sample was gently layered onto 0.75 mL of room-temperature Histopaque 1077 in a 2-mL microcentrifuge tube. The samples were centrifuged for 2 minutes at 16,000×g in an Eppendorf microcentrifuge. The interface and upper layers were removed and added to tubes containing 1 mL of cold Dulbecco's phosphate-buffered saline (DPBS). These samples were then centrifuged for 30 seconds at 16,000×g to pellet the cells. The buffer supernatant was removed by aspiration and the pellets were re-suspended in 1 mL of cold DPBS. The pellets from each sample were then re-pelleted as above. The buffer was removed by aspiration and the pellets were lysed as indicated below.

Complete lysis buffer consisted of Meso Scale Discovery Tris lysis buffer, 1× Halt Protease inhibitor cocktail, 1× Phosphatase inhibitor cocktail 2, 1× Phosphatase inhibitor cocktail 3, 2 mM phenylmethanesulfonyl fluoride, and 0.1% sodium dodecyl sulfate. Lysis buffer was kept on ice and made fresh for each sample group. Final cell pellets were lysed by the addition of 120 μL of complete lysis buffer. Samples were vortexed until the cell pellet disappeared and then flash frozen on dry ice. Samples were stored at −20° C. prior to measurement of pRSK and total RSK by ELISA.

For the pRSK ELISA (PathScan), thawed lysates were combined 1:1 with sample diluent (provided in ELISA kit): 120 μL of lysate added to 120 μL of sample diluent in a round bottom 96-well plate. This combination was then transferred to the pRSK microwells at 100 μL per well. For the total RSK ELISA (PathScan), 20 μL of the lysate already diluted 1:1 in sample diluent was further diluted in 200 μL of sample diluent in a round bottom 96-well plate. This combination was then transferred to the total RSK microwells at 100 μL per well. The plates were sealed with a plate seal and incubated 16 to 18 hours at 4° C., a time that was shown to yield the best detection of the target protein. Both ELISAs were developed according to the kit instructions.

Patients aged ≥18 years were eligible for participation if they had noncurable, histologically confirmed metastatic or advanced stage malignant tumors; an ECOG performance status of 0 or 1; adequate renal, hepatic, bone marrow, and cardiac function; and a life expectancy ≥3 months. Patients may have received up to 2 prior lines of chemotherapy for their metastatic disease. Exclusion criteria were known uncontrolled brain metastases; gastrointestinal conditions which could impair absorption of study medication; history or current evidence/risk of retinal vein occlusion or central serous retinopathy; and concurrent therapy with drugs known to be strong inhibitors of CYP1A2, CYP2D6, and CYP3A4 or strong inducers of CYP3A4. All participants provided informed consent prior to initiation of any study procedures.

Patients that received at least one dose of BVD-523 were included in the analysis useing SAS (version 9.3) software. The data cutoff was Dec. 1, 2016. This study is registered with ClinicalTrials.gov, number NCT01781429.

The present invention presents data from an open-label, multicenter phase I study to assess the safety, pharmacokinetics, and pharmacodynamics of escalating doses of BVD-523 in patients with advanced malignancies. The dosing regimen combined both accelerated titration and standard cohort 3+3 dose escalation schema, which were used jointly to identify the MTD and RP2D of BVD-523 in patients with advanced solid tumors. One to 6 patients per treatment cohort were assigned to receive sequentially higher oral doses of BVD-523 on a BID schedule (12-hour intervals) in 21-day cycles, starting at a dose of 10 mg BID. BVD-523 was administered BID continuously in 21-day cycles at the following doses: 10 mg (n=1); 20 mg (n=1); 40 mg (n=1); 75 mg (n=1); 150 mg (n=1); 300 mg (n=4); 600 mg (n=7); 750 mg (n=4); and 900 mg (n=7).

Patients received BID oral doses until disease progression, unacceptable toxicity, or a clinical observation satisfying another withdrawal criterion. Dose escalations occurred in up to 100% increments in single-patient cohorts until 1 patient experienced a ≥Grade 2 toxicity (excluding alopecia or diarrhea). Cohorts were then expanded to at least 3 patients each and subsequent dose-escalation increments were reduced from up to 100% to a maximum of 50%. When at least 1 patient in a 3-patient cohort experienced a DLT, up to 3 additional patients were treated at this dose level. When more than 1 DLT occurred in patients, this dose level was defined as the nontolerated dose and dose escalation was stopped. Intrapatient dose escalation was allowed, provided the patients receiving the highest current dose had been observed for at least 3 weeks and dose-limiting side effects were reported in fewer than 2 of 6 patients assigned to a given dose. Patients experiencing DLTs or unacceptable toxicity had their treatment interrupted until the toxicity returned to ≤Grade 1. Resumption of BVD-523 treatment was then initiated at the next lower dose level tested or at a 20% to 30% dose decrease, aligning with capsule dosage.

The primary objective of the phase I study was to define the safety and tolerability of BVD-523 by determining the dose-limiting toxicities, the MTD, and the RP2D. The secondary objectives included the determination of the pharmacokinetic profile of BVD-523 in patients with advanced malignancies and the investigation of any preliminary clinical effects on tumor response, as assessed by physical or radiologic exam using RECIST v1.1. The exploratory objectives included evaluation of pharmacodynamic marker (biomarker) measures and investigation of preliminary clinical effects on tumor response assessed by $^{18}$F-FDG-PET as indicated.

For determination of MTD, DLT, and RP2D, MTD was defined as the highest dose cohort at which ≤33% of patients experienced BVD-523-related DLTs in the first 21 days of treatment. DLT was defined as a BVD-related toxicity in the first 21 days of treatment that resulted in ≥Grade 4 hematologic toxicity for >1 day; Grade 3 hematologic toxicity with complications (e.g., thrombocytopenia with bleeding); ≥Grade 3 nonhematologic toxicity, except untreated nausea, vomiting, constipation, pain, and rash (these become DLTs if the AE persisted despite adequate treatment); or a treatment interruption exceeding 3 days in Cycle 1 (or the inability to being in Cycle 2 for >7 days) due to BVD-523-related toxicity.

The RP2D could be as high as the MTD and was determined in discussion with the clinical investigators, the medical monitor, and the sponsor. Observations related to pharmacokinetics, pharmacodynamics, and any cumulative toxicity observed after multiple cycles were included in the rationale supporting the RP2D.

With regard to safety assessments, AEs were defined as any untoward medical occurrence in a patient who was administered a medicinal product that does not necessarily have a causal relationship with BVD-523, and was coded using the MedDRA coding dictionary. An SAE was any untoward medical occurrence that occurred at any dose that resulted in death, was life-threatening, required inpatient hospitalization or prolongation of existing hospitalization, or resulted in persistent or significant disability/incapacity or a congenital anomaly/birth defect. The severity of AEs were graded according to the National Cancer Institute Common Terminology Criteria for Adverse Events, Grading Scale, version 4.

Safety evaluations were conducted at baseline, on Days 8, 15, 22, 29, 36, and 43, and, in patients who continued treatment, every 3 weeks or if clinically indicated thereafter. Each evaluation included a physical examination and clinical laboratory studies. Electrocardiograms were repeated if clinically significant and at the discretion of the investigator. The investigators made judgments regarding whether or not AEs were related to study drug and followed up until resolution or stabilization, or the AE was judged to be no longer clinically significant.

For pharmacokinetic analysis, the pharmacokinetic population consisted of patients who received at least one dose of BVD-523 and had evaluable pharmacokinetic data for plasma and/or urine. Blood samples were collected prior to dosing, and then at 0.5 (±5 min), 1 (±5 min), 2 (±10 min), 4 (±10 min), 6 (±10 min), 8 (±10 min), and 12 (±2 hr) hours on Day 1 (Visit 2; baseline/initiation of treatment) and Day 15 (Visit 4; at steady state) after the morning dose. On Day 22, prior to dose administration, a final blood sample was collected for pharmacokinetic analyses. Urine samples were collected predose and at the 1- to 6-hour and 6- to 12-±2-hour intervals postdose on Days 1 and 15. Plasma and urine samples were analyzed for BVD-523 and metabolites using validated LC/MS/MS methods. Standard pharmacokinetic parameters were obtained using Phoenix WinNonlin (Pharsight) with a noncompartmental method. Relationship between dose and exposure was calculated using standard least-squares regression analysis.

For pharmacodynamic confirmation of target inhibition by BVD-523, targeted ERK inhibition by BVD-523 was determined by examining pRSK as a target biomarker in human whole blood samples obtained from patients with advanced solid tumors (N=27) who had received different doses of BVD-523 (10-900 mg BID) during the phase I study. The activity of BVD-523 from 4 timepoints (baseline predose, baseline 4 hours postdose, Day 15 predose, and Day 15 4 hours postdose) was expressed as a percent activity (pRSK) of PMA-stimulated blood incubated with BVD-523.

For measurement of antitumor response, tumor measurements based on physical examination occurred at baseline and on the first day of each treatment cycle. CT and other assessments were made every 2 to 3 cycles. Findings were assessed in accordance with RECIST v1.1: CR was defined as disappearance of all target lesions; PR was defined as a ≥30% decrease in the sum of the longest diameters of target lesions, taking baseline measurements as reference; stable disease was defined as being of neither sufficient shrinkage to qualify for PR nor sufficient increase to qualify for progressive disease, taking as reference the baseline measurement. Metabolic response was assessed by visualizing tumor uptake of $^{18}$F-glucose via $^{18}$F-FDG-PET scanning prior to receiving the first dose of BVD-523 and at Day 15 (Visit 4).

Example 2

Dose Escalation and Proliferation Assays—Month 1

Dose Escalation Progress—Month 1

Figure 1A:
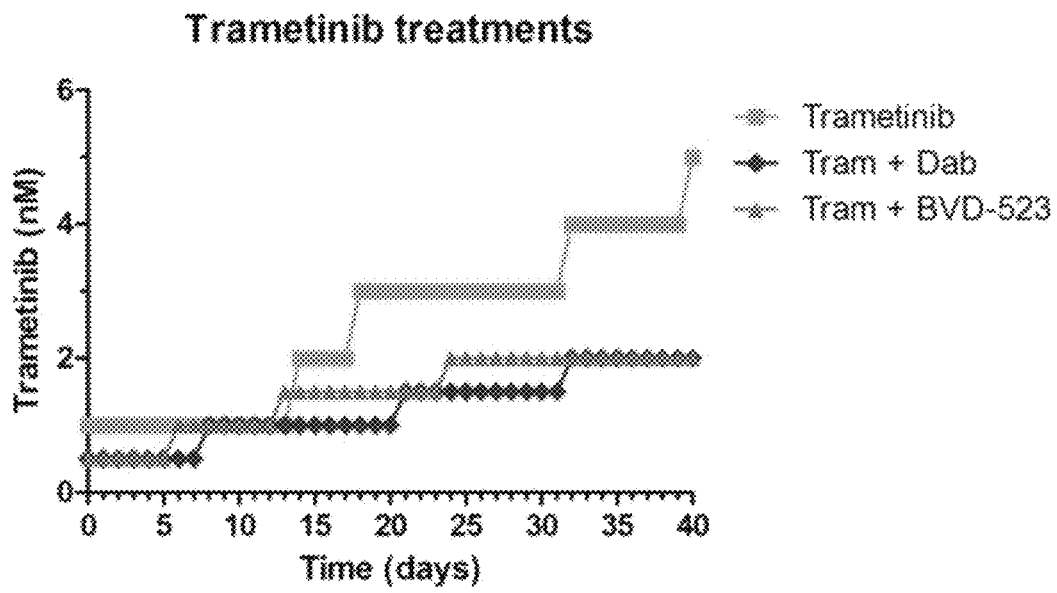
FIG. 1A-FIG. 1C show the progress of a dose escalation study in a human malignant melanoma cell line (A375 cells) for month 1. Various treatments (trametinib (a type 2 MEK inhibitor), dabrafenib (a BRAF inhibitor), and BVD-523 (an ERK1/2 inhibitor)) are as labeled.
Figure 1B:
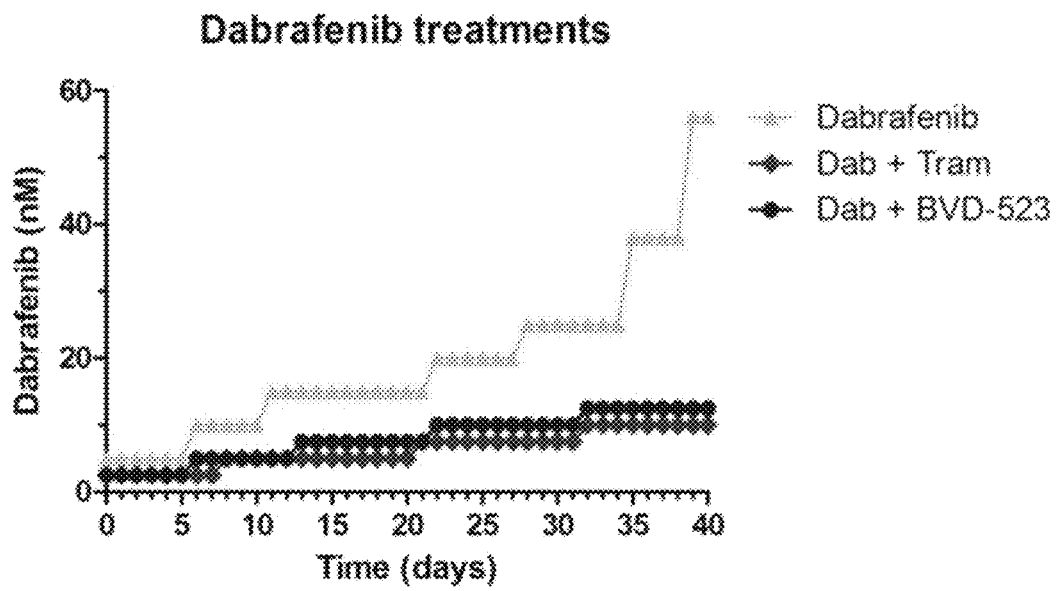
Figure 1C:
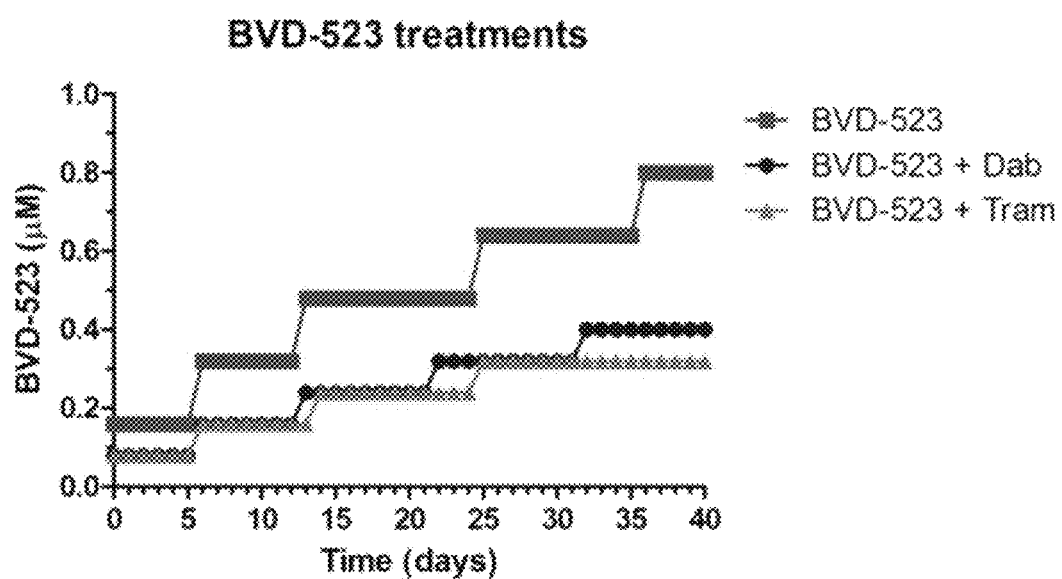
Figure 2A:
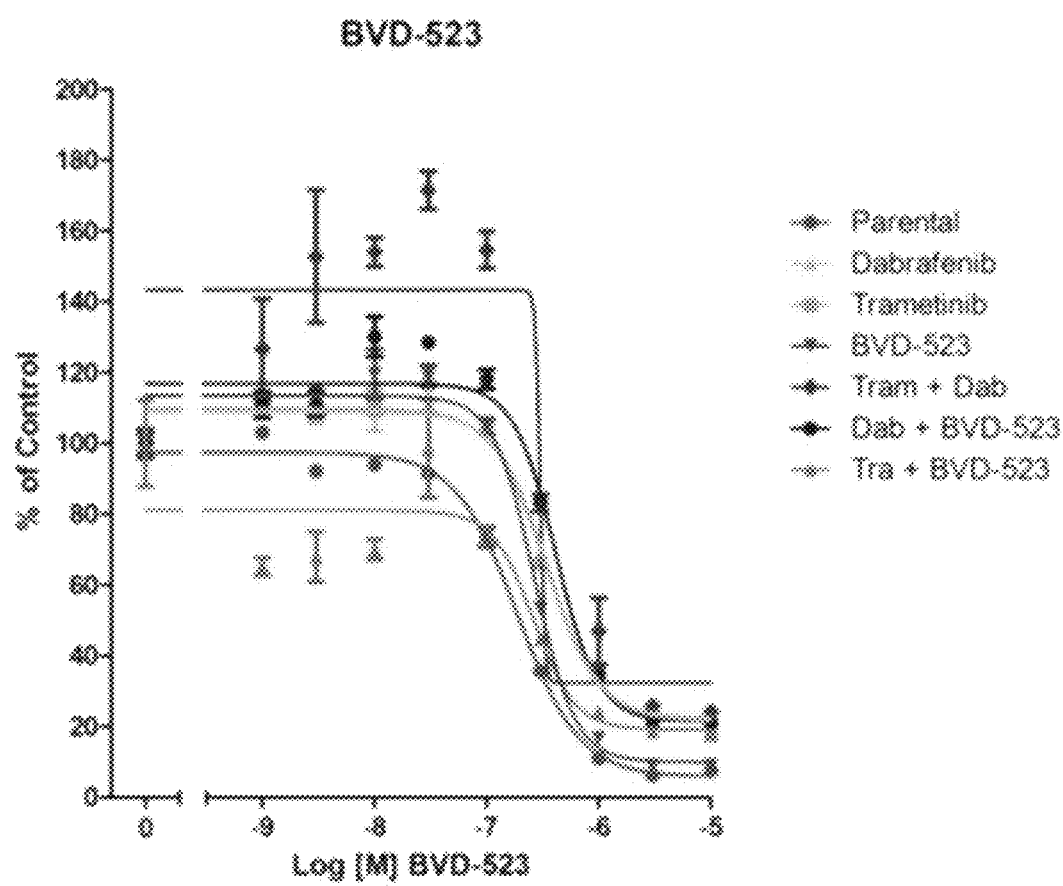
FIG. 2A-FIG. 2H show the results of a proliferation assay that tracks changes in sensitivity to the escalated agent(s) at month 1. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 1 of the dose escalation study. Parental refers to the control cells that have not been treated with drugs.
Figure 2B:
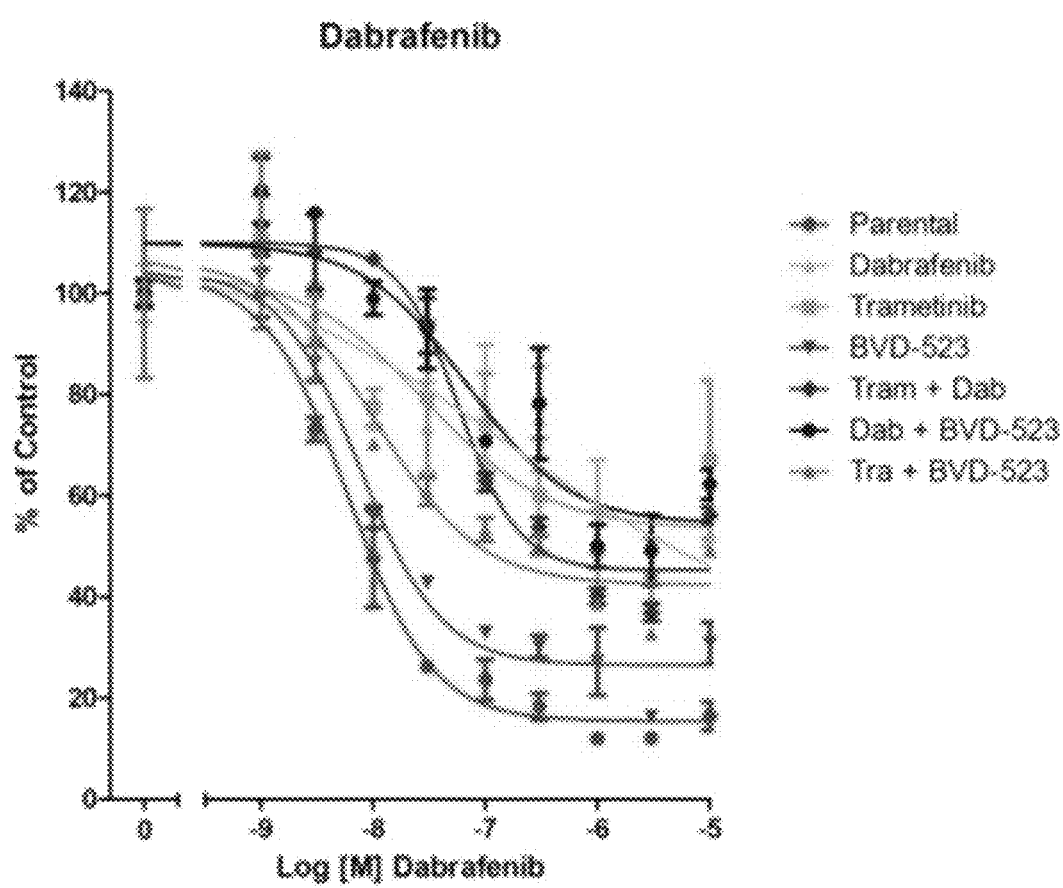
Figure 2C:
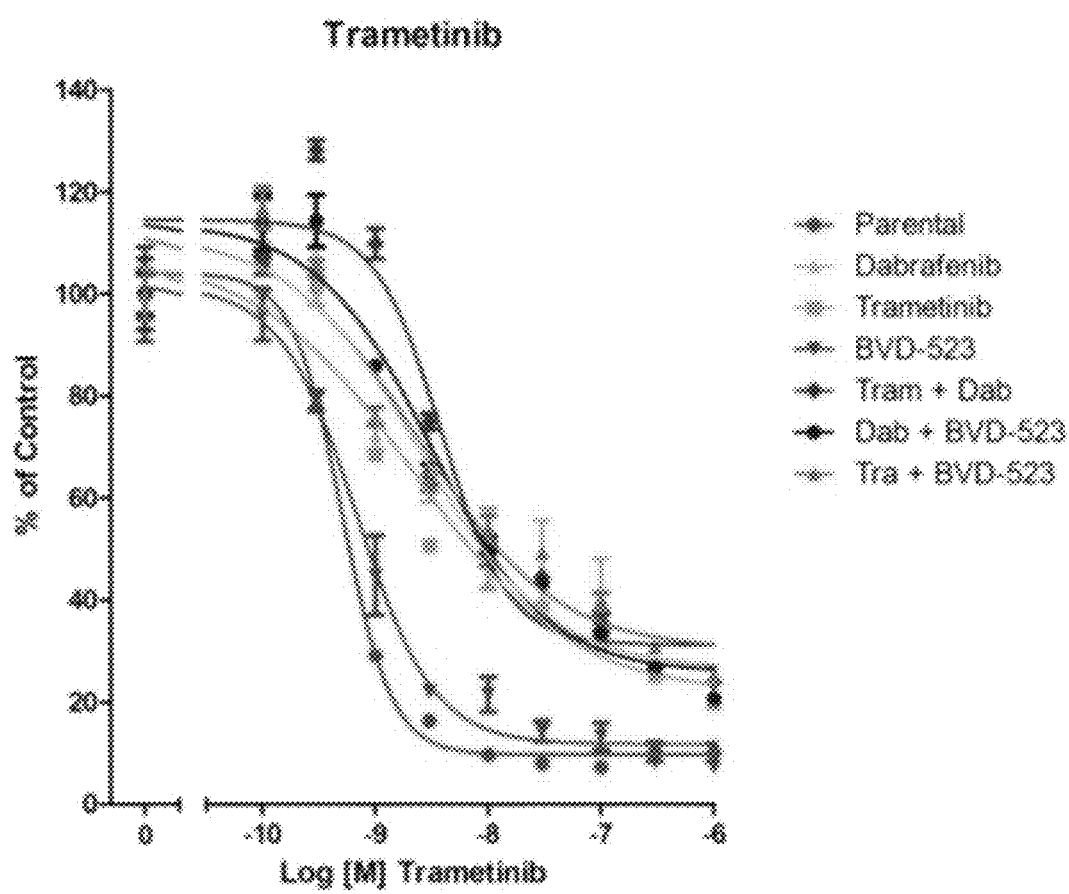
Figure 2D:
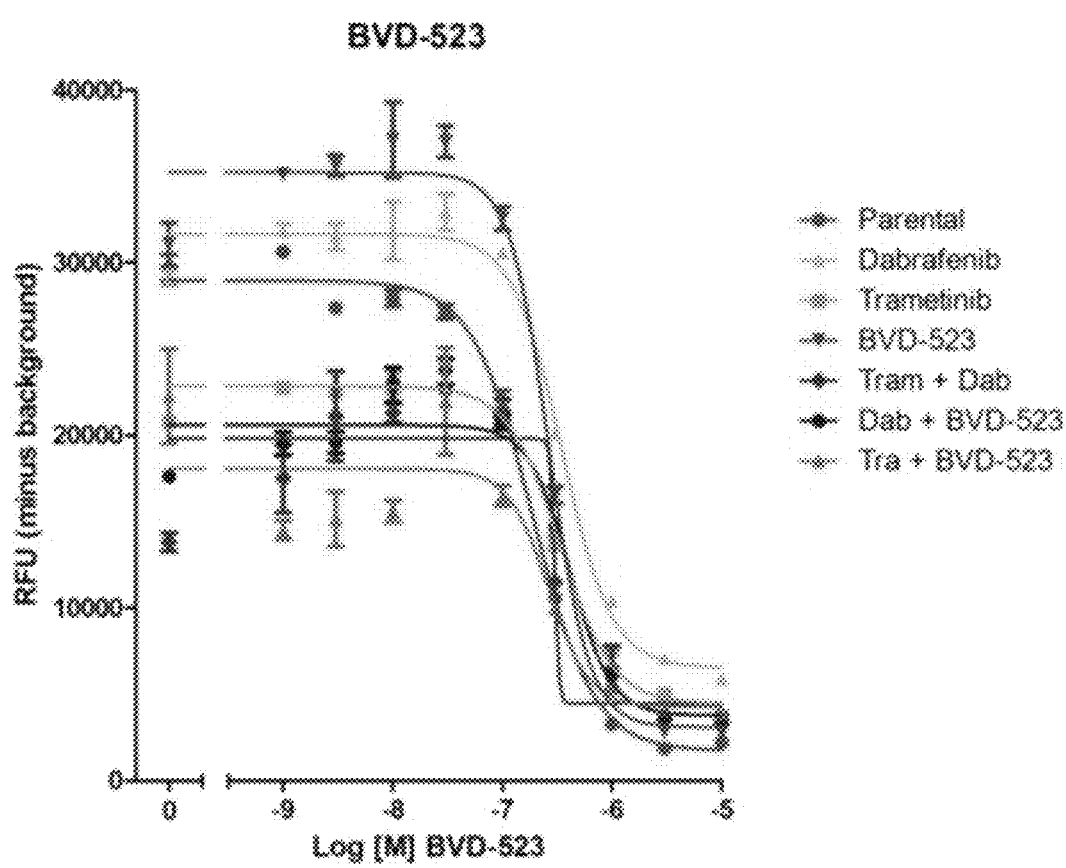
Figure 2E:
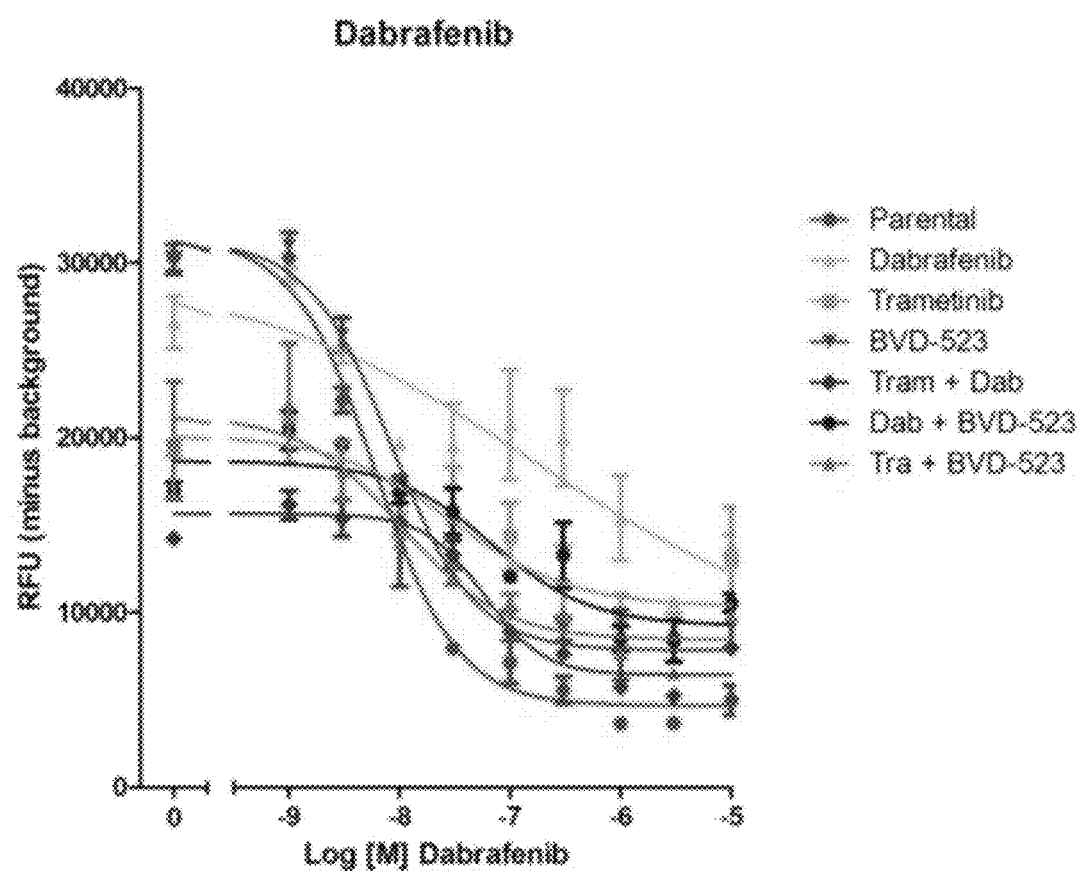
Figure 2F:
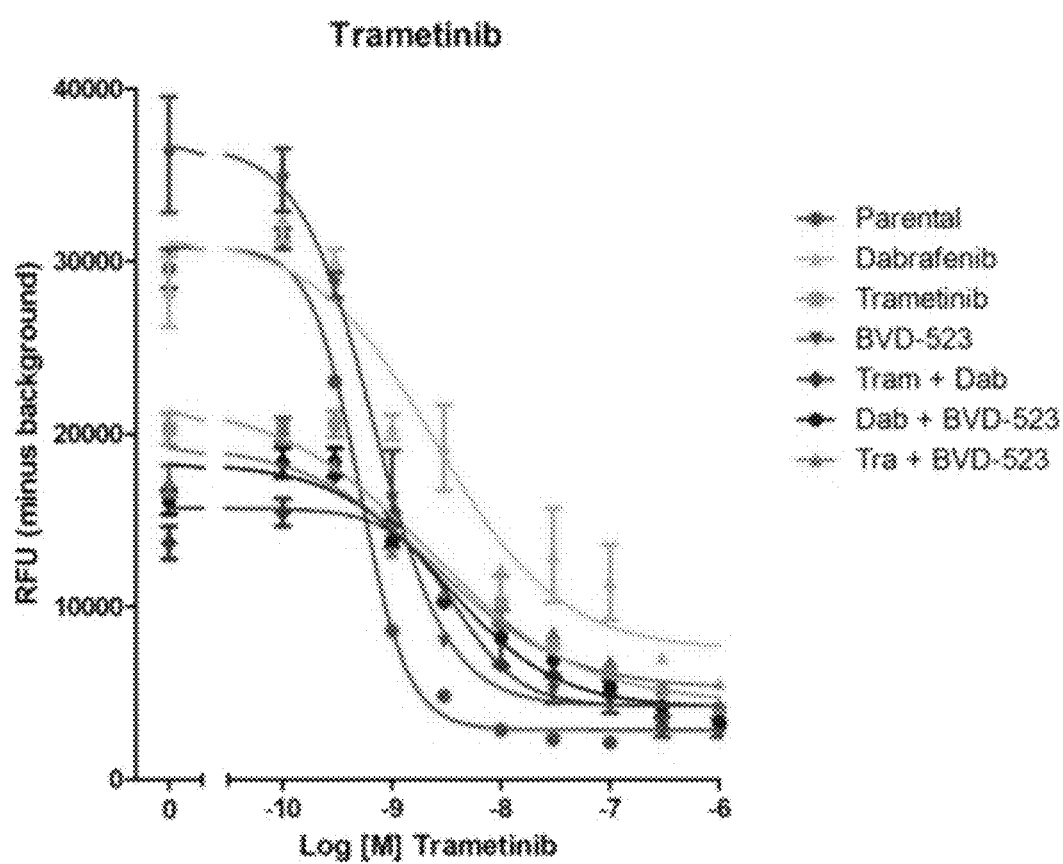
Figure 2G:
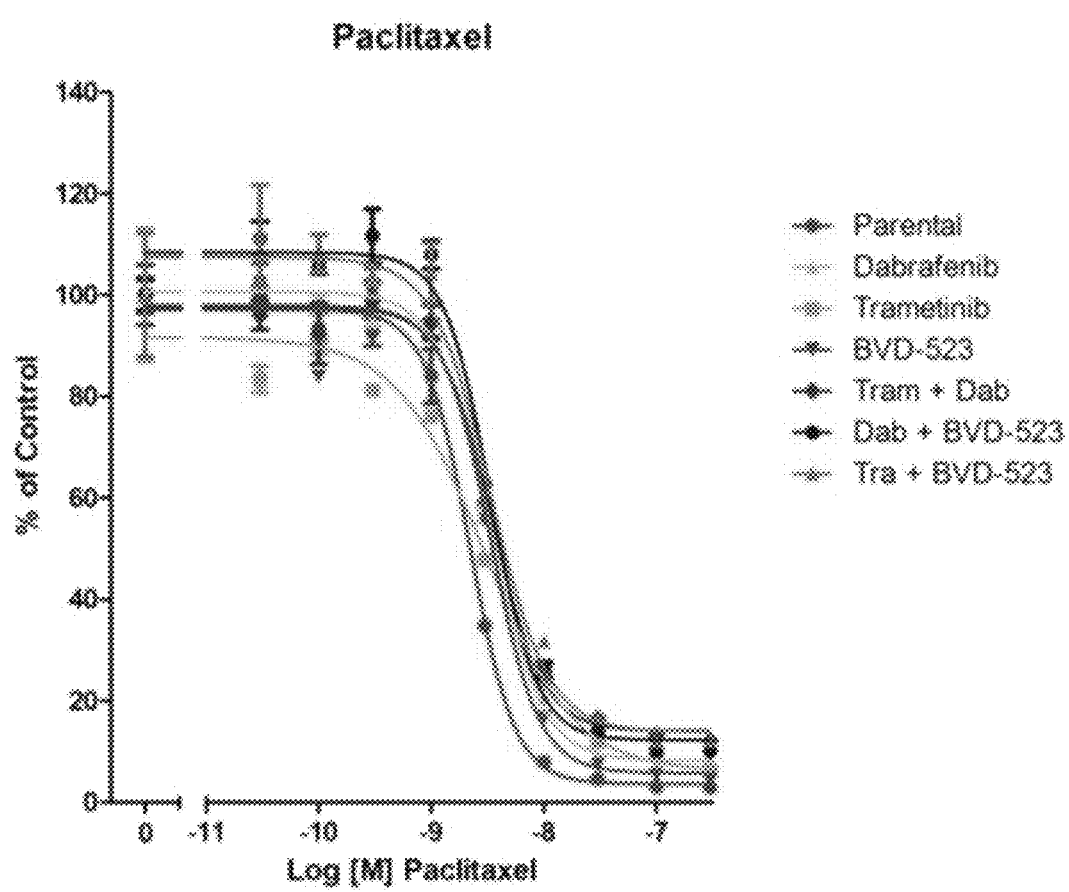
Figure 2H:
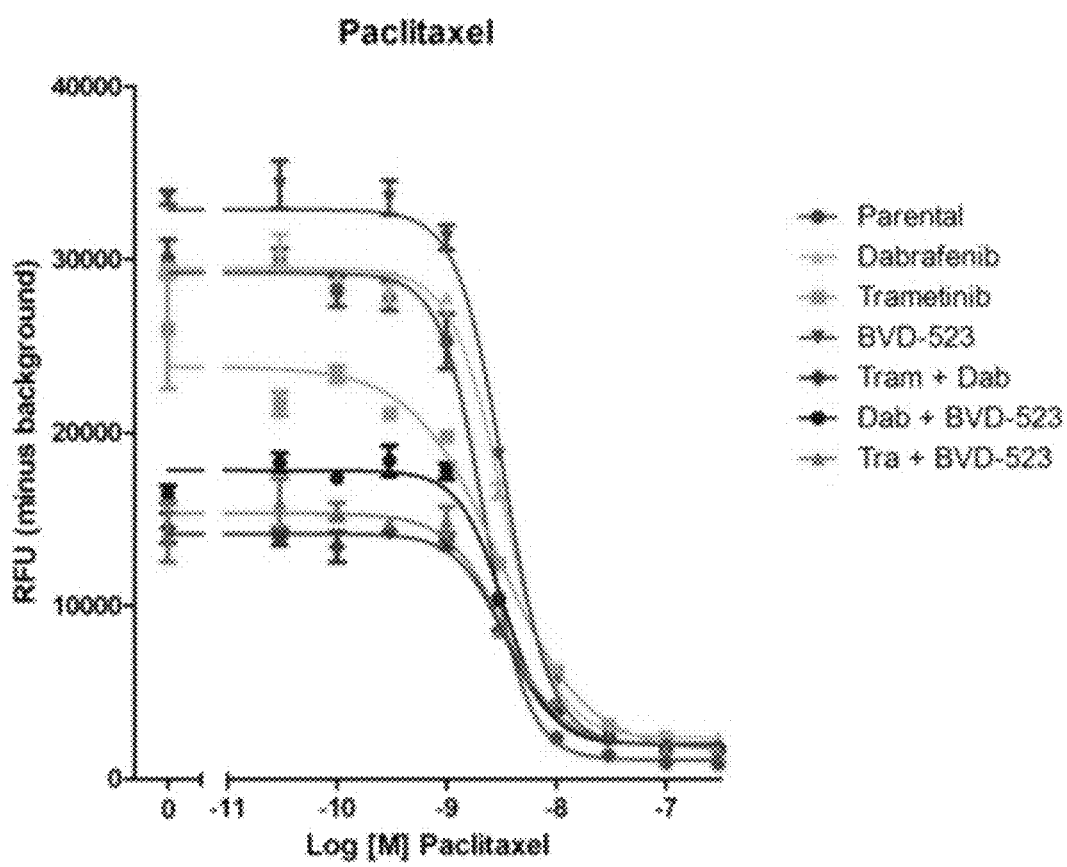

A375 cells were dose escalated using BVD-523, dabrafenib, and trametinib either as single agents or in combination. Doses were increased in small increments during the first month. Other than a marked reduction in growth rate, cells generally tolerated the escalations well and the doses were planned to be more aggressively escalated using larger increments in month 2. FIG. 1A-FIG. 1C show month 1 progress for the dose escalation studies.

Proliferation Assay Results—Month 1

Proliferation assays were performed to assess the response of the escalated cells lines vs. parental cell line, to BVD-523, dabrafenib, and trametinib treatments.

FIG. 2A-FIG. 2H show normalized and raw proliferation assay results from month 1 of the studies. Note that differences in max signals in DMSO controls between different treatments (FIG. 2D, FIG. 2F, and FIG. 2H) suggest differential growth rates between treatments. These differences may influence the responses of lines to inhibitors in the proliferation assays.

Table 10 shows $IC_{50}$ data for month 1 of the studies.

TABLE 10

$IC_{50}$ Data-Month 1

| | Cell Line, Relative $IC_{50}$ (nM) | | | | | | |
|---|---|---|---|---|---|---|---|
| Compound | Par* | Tram | Dab | BVD-523 | Dab/Tram | Dab/523 | Tram/523 |
| Dabrafenib | 6 | 29 | about 161 | 8 | 58 | 68 | 11 |
| Trametinib | 0.5 | 2.2 | 2.5 | 0.7 | 3.9 | 3.1 | 2.5 |
| BVD-523 | 189 | 335 | 350 | 268 | 300 | 412 | 263 |
| Paclitaxel | 2.2 | 3.0 | 3.3 | 3.4 | 3.5 | 3.4 | 3.4 |

*Par = Parental cell line

There were early hints that cells grown in the presence of escalating doses of dabrafenib or trametinib, either as single agents or in combinations, were exhibiting decreased responses to these two agents in proliferation assays.

In the early stages of month 2, the growth rate of cells in the dabrafenib only treatment notably increased relative to the early stages of month 1. This enabled an increased rate of progression and suggested that resistance was becoming apparent.

Example 3

Dose Escalation and Proliferation Assays—Month 2

Dose Escalation Progress—Month 2

Figure 3A:
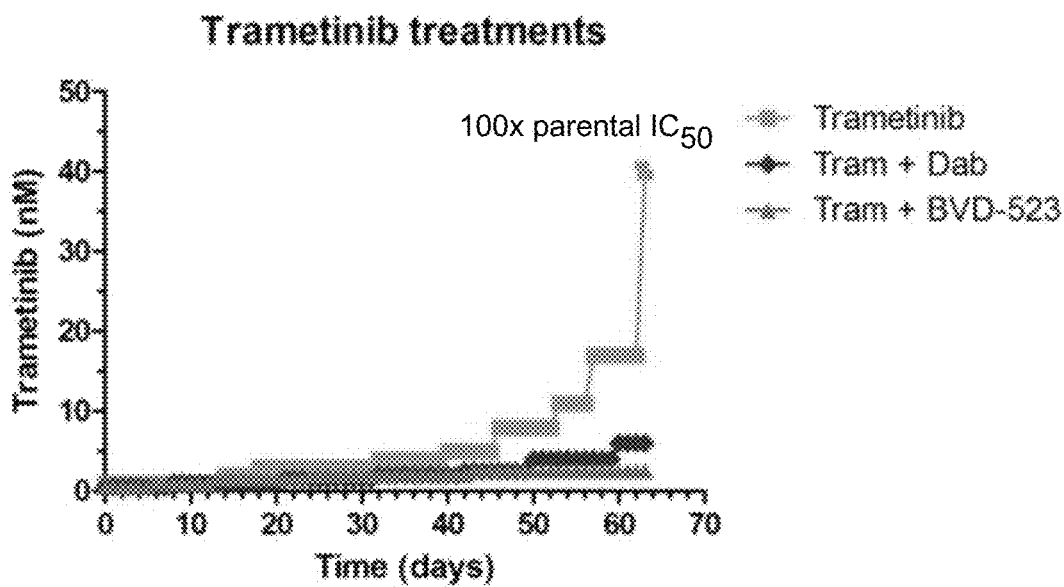
FIG. 3A-FIG. 3D show the progress of a dose escalation study in A375 cells for month 2. Various treatments (trametinib, dabrafenib, and BVD-523) are as labeled.
Figure 3B:
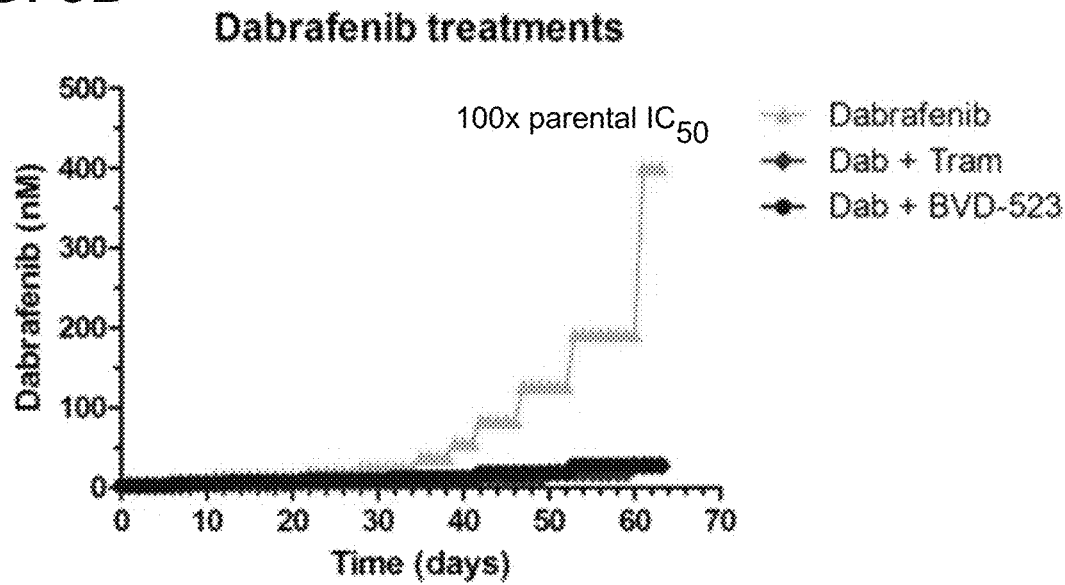
Figure 3C:
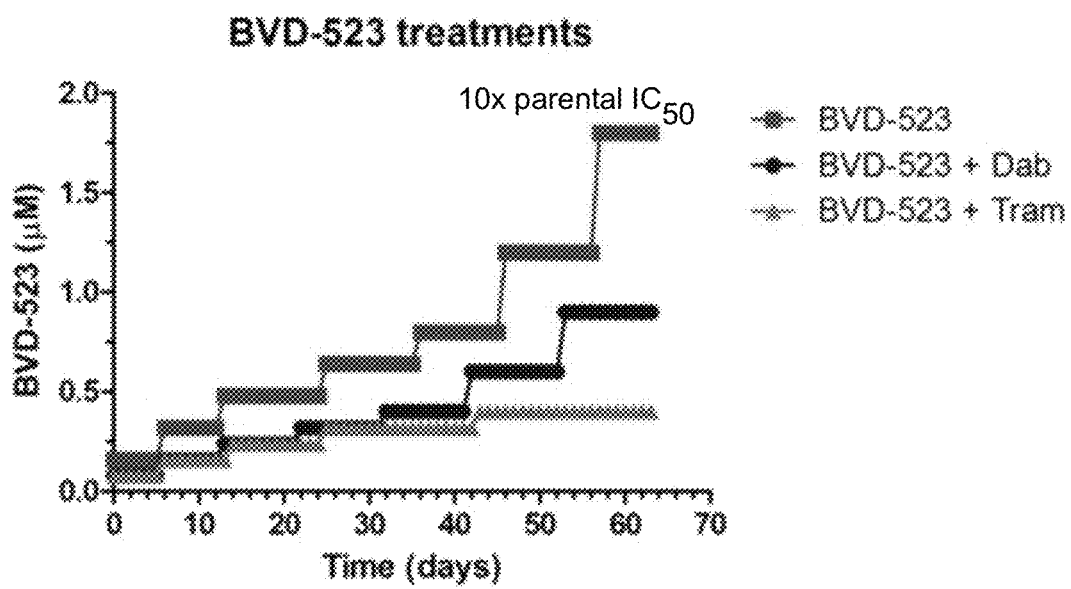
Figure 3D:
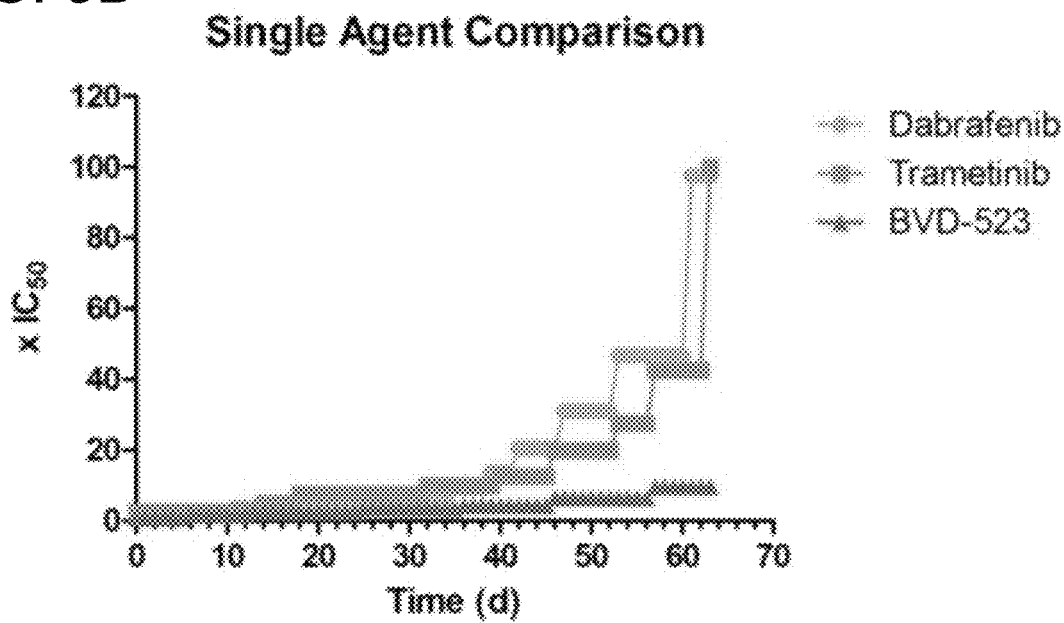
Figure 4A:
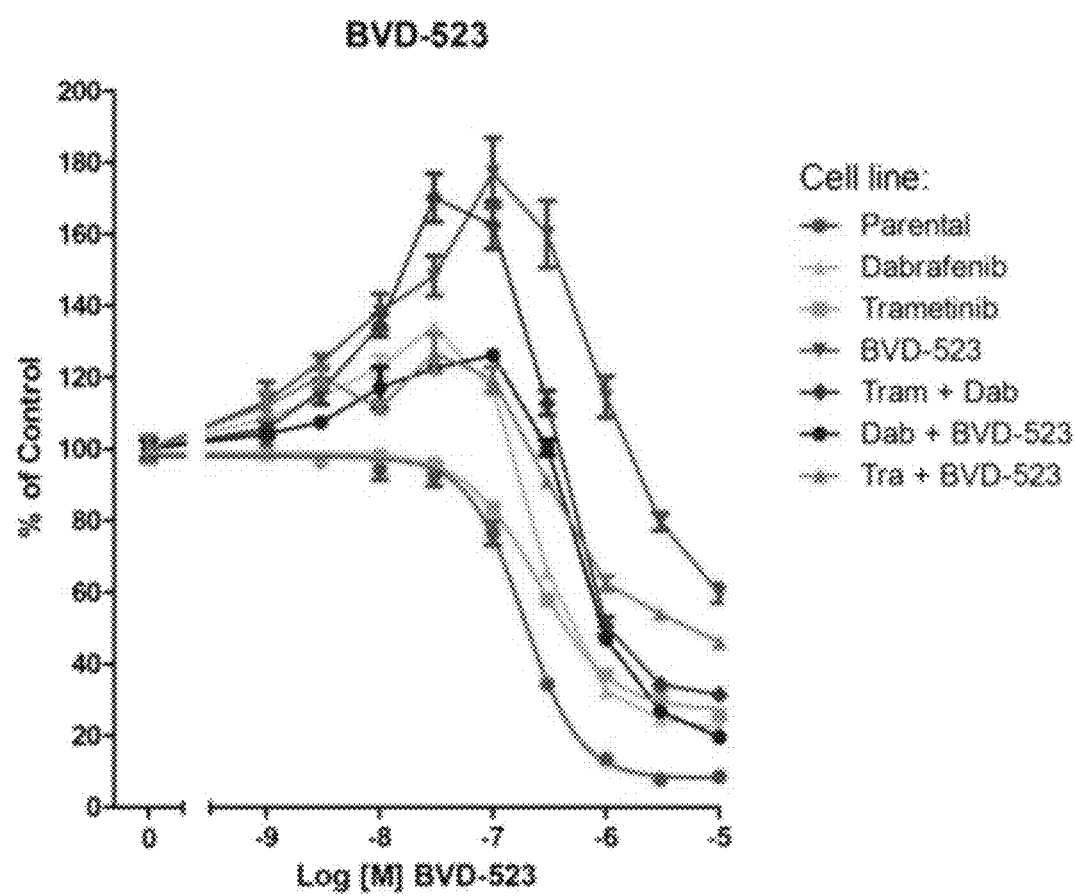
FIG. 4A-FIG. 4H show the results of a proliferation assay that tracks changes in sensitivity to the escalated agent(s) at month 2. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 2 of the dose escalation study. Parental refers to the control cells that have not been treated with drugs.
Figure 4B:
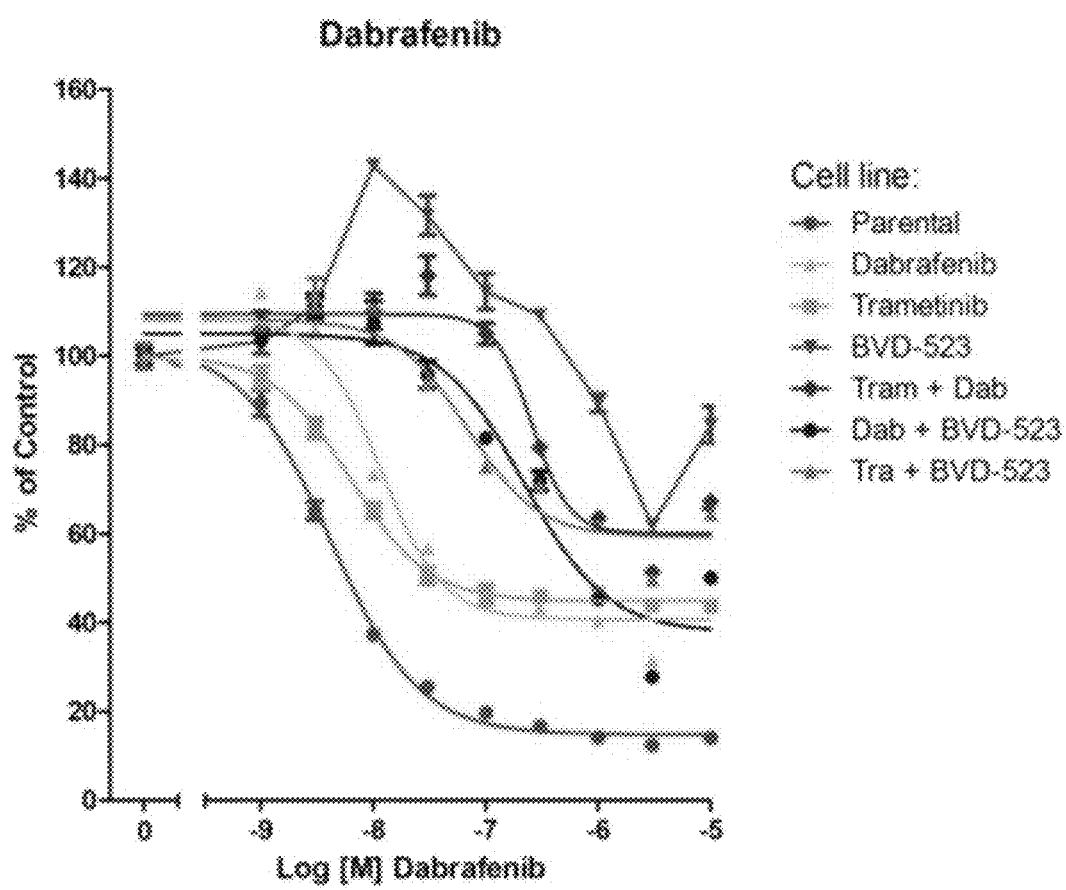
Figure 4C:
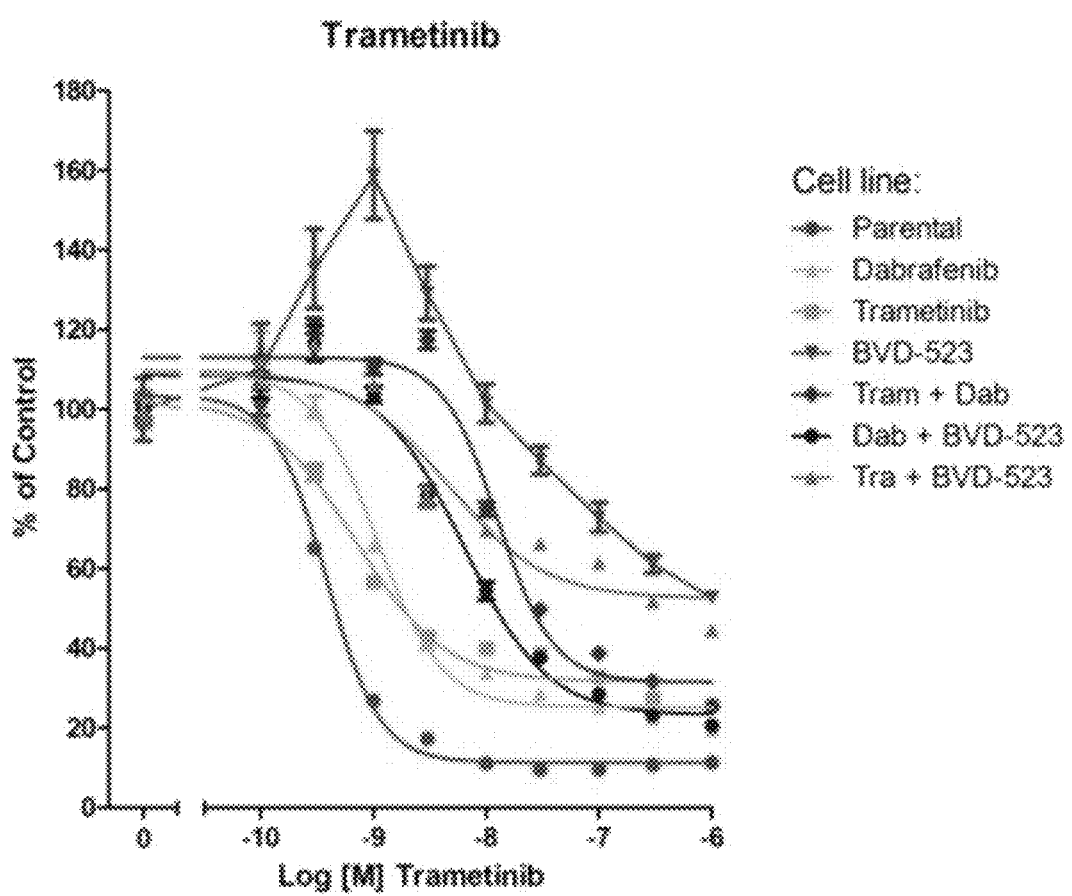
Figure 4D:
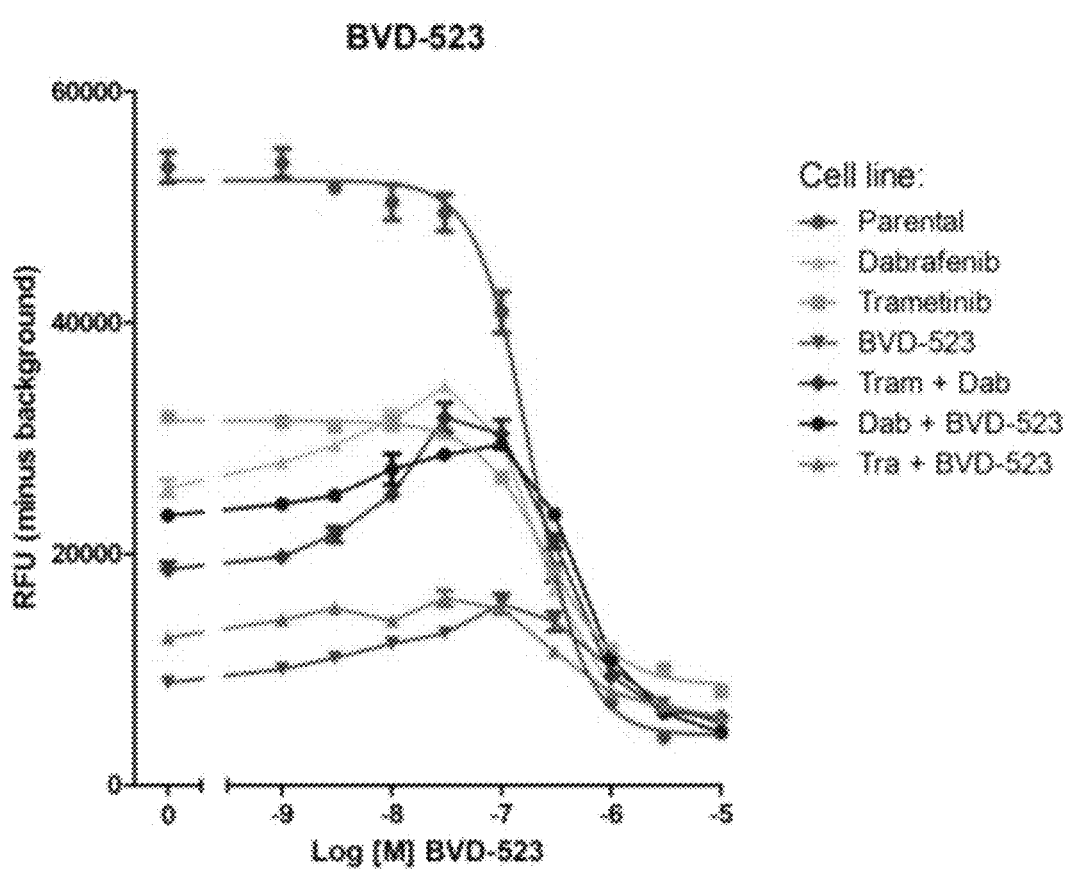
Figure 4E:
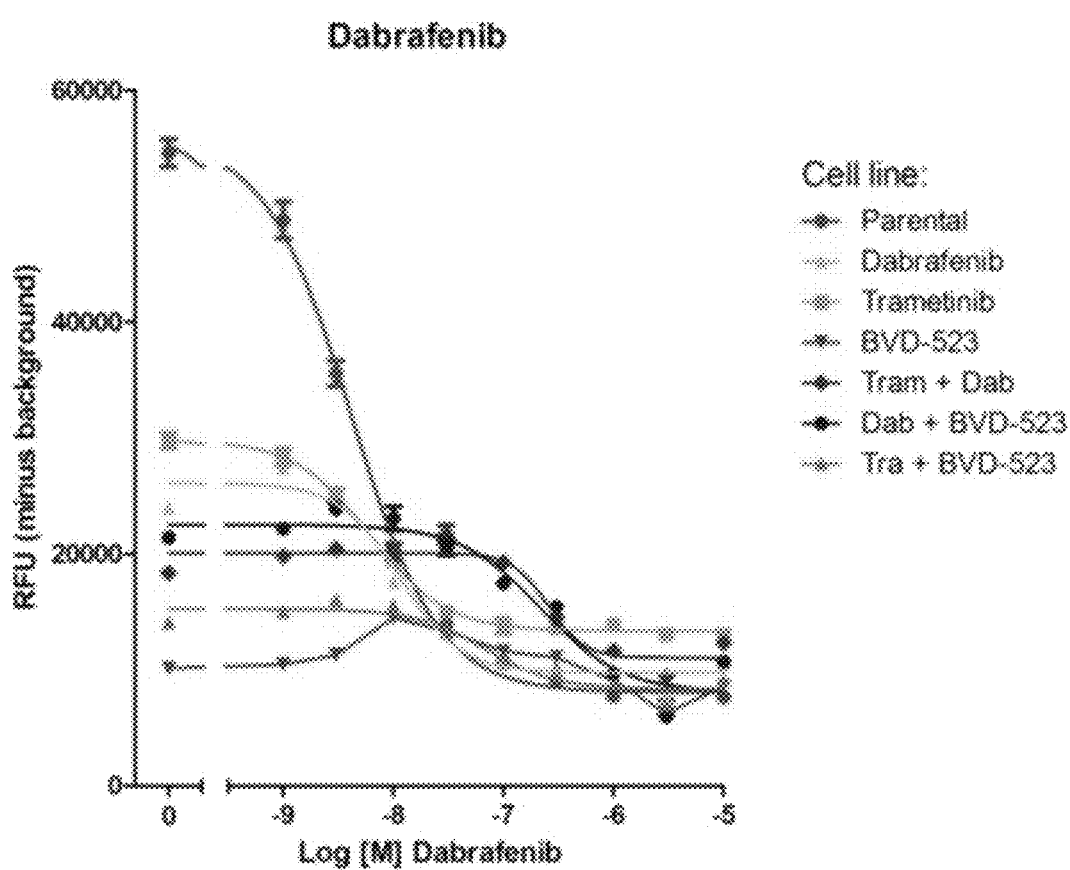
Figure 4F:
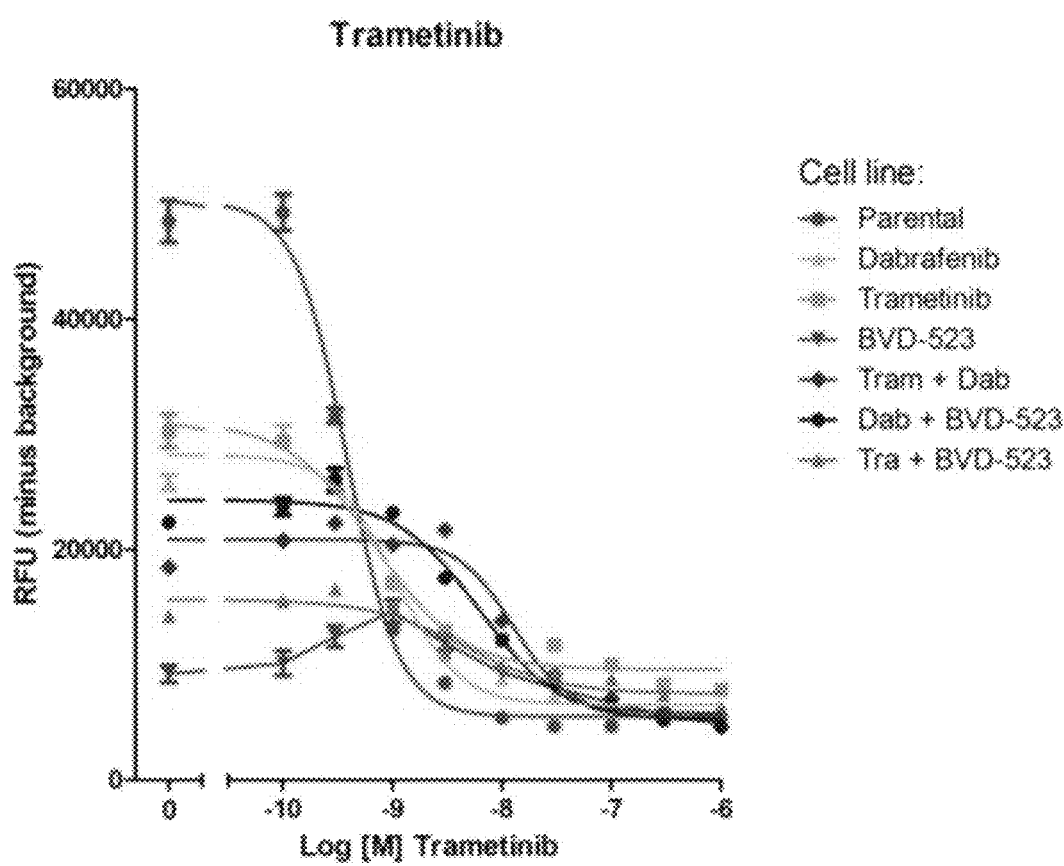
Figure 4G:
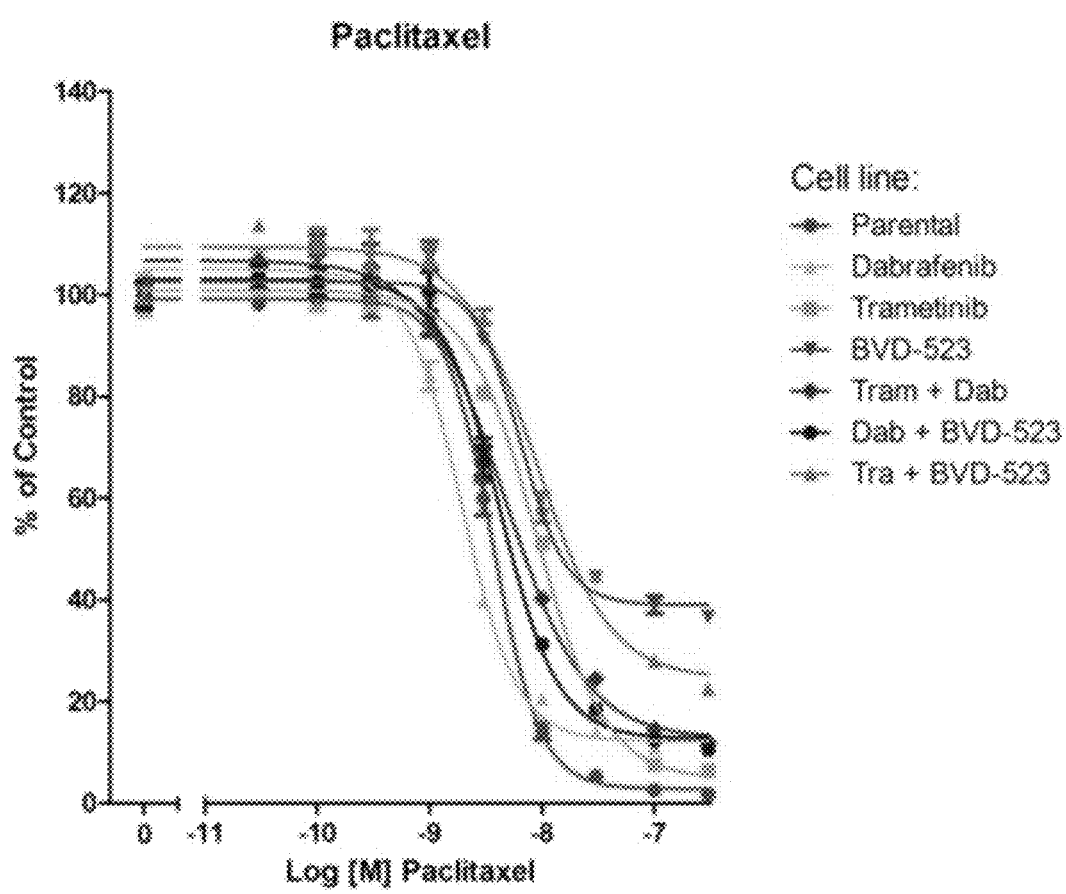
Figure 4H:
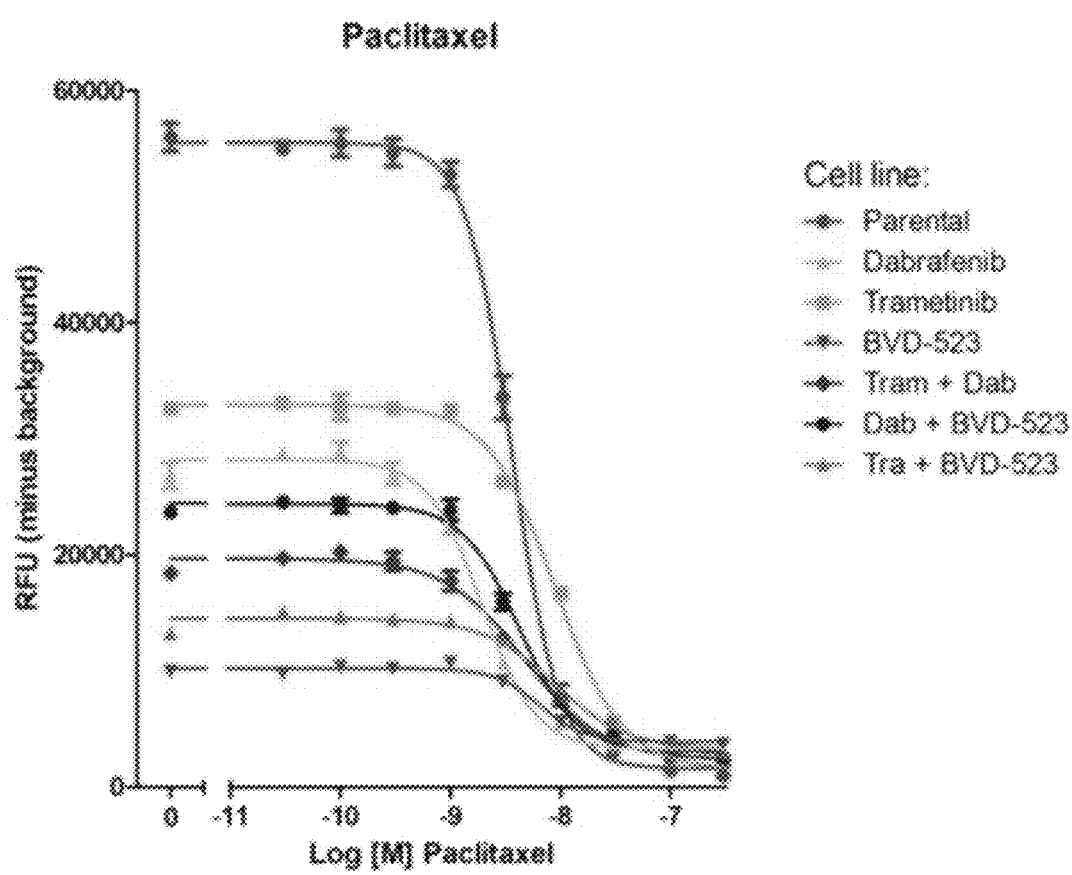
Figure 5A:
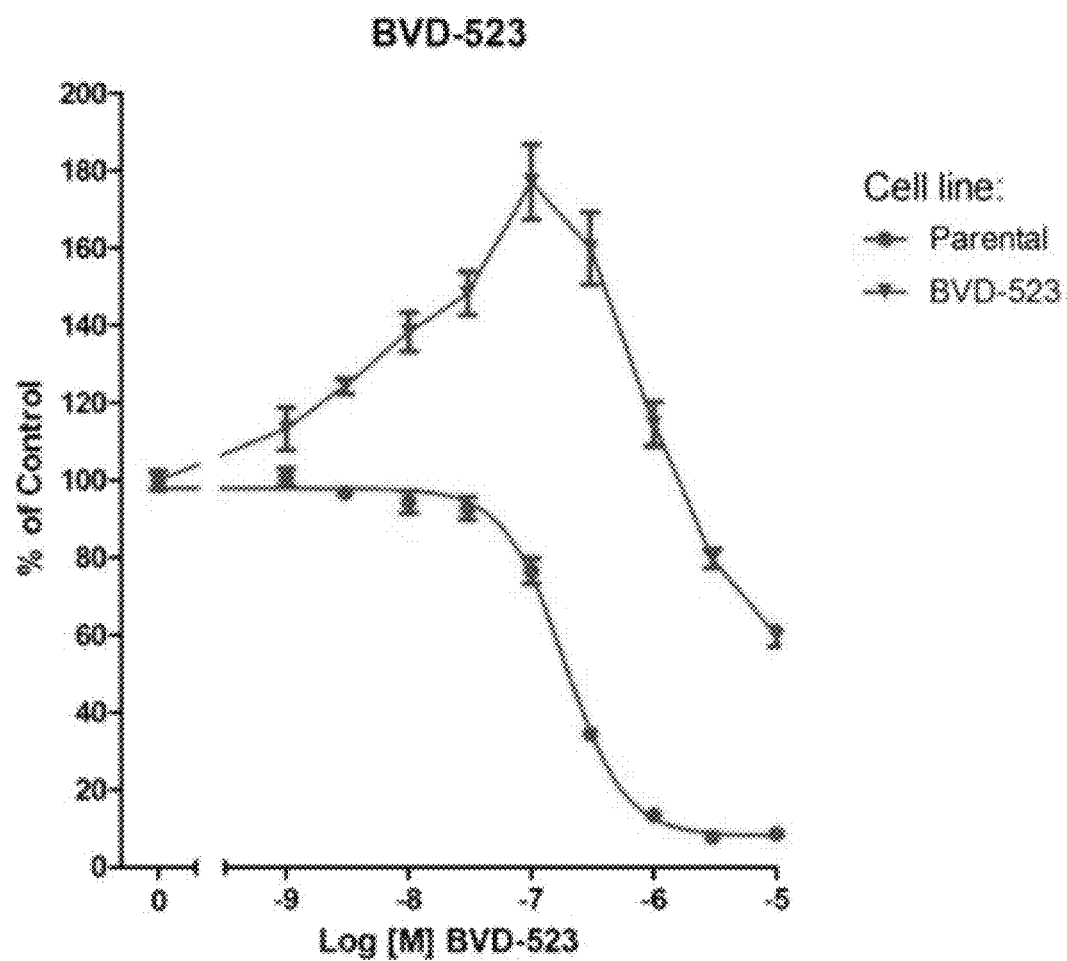
FIG. 5A-FIG. 5H show only the parental and BVD-523 cell line data from FIG. 4A-FIG. 4H. Various treatments (trametinib, dabrafenib, BVD-523, and pacitaxel) are as labeled.
Figure 5B:
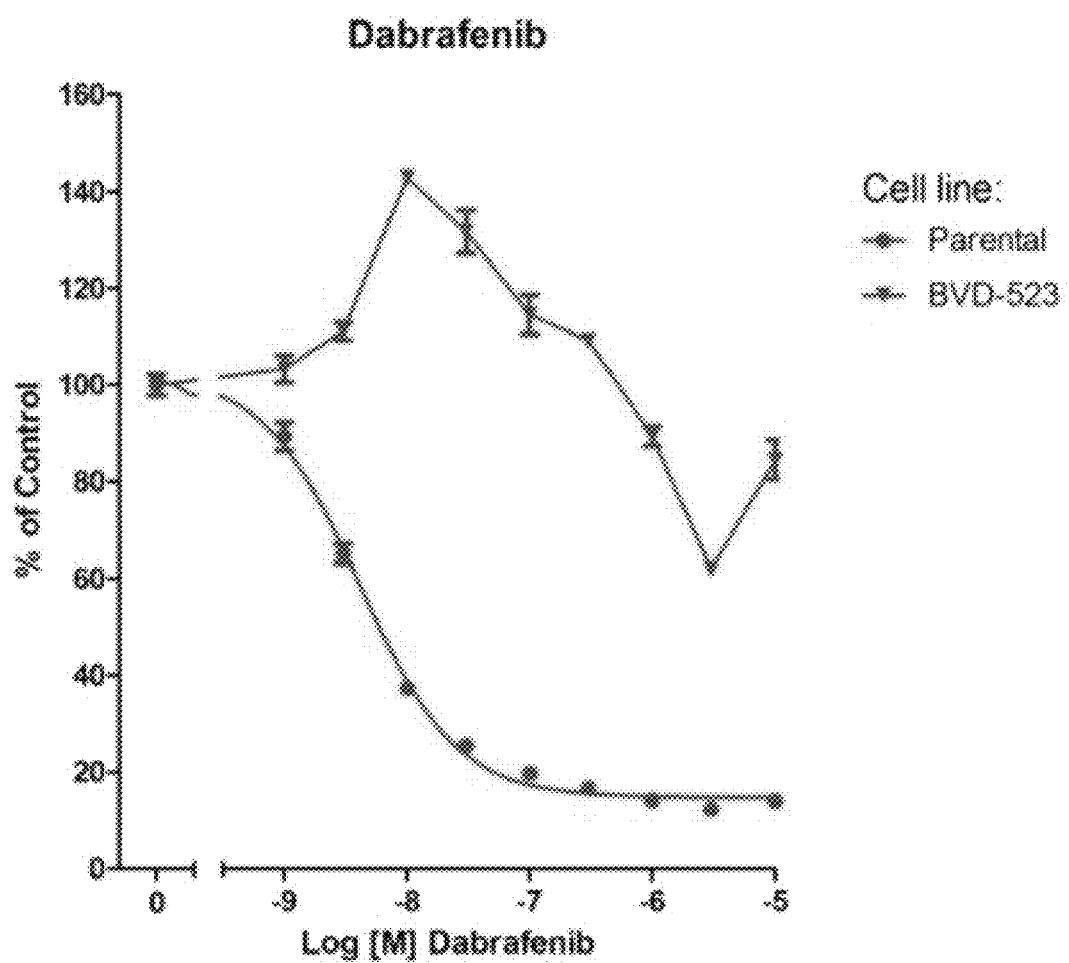
Figure 5C:
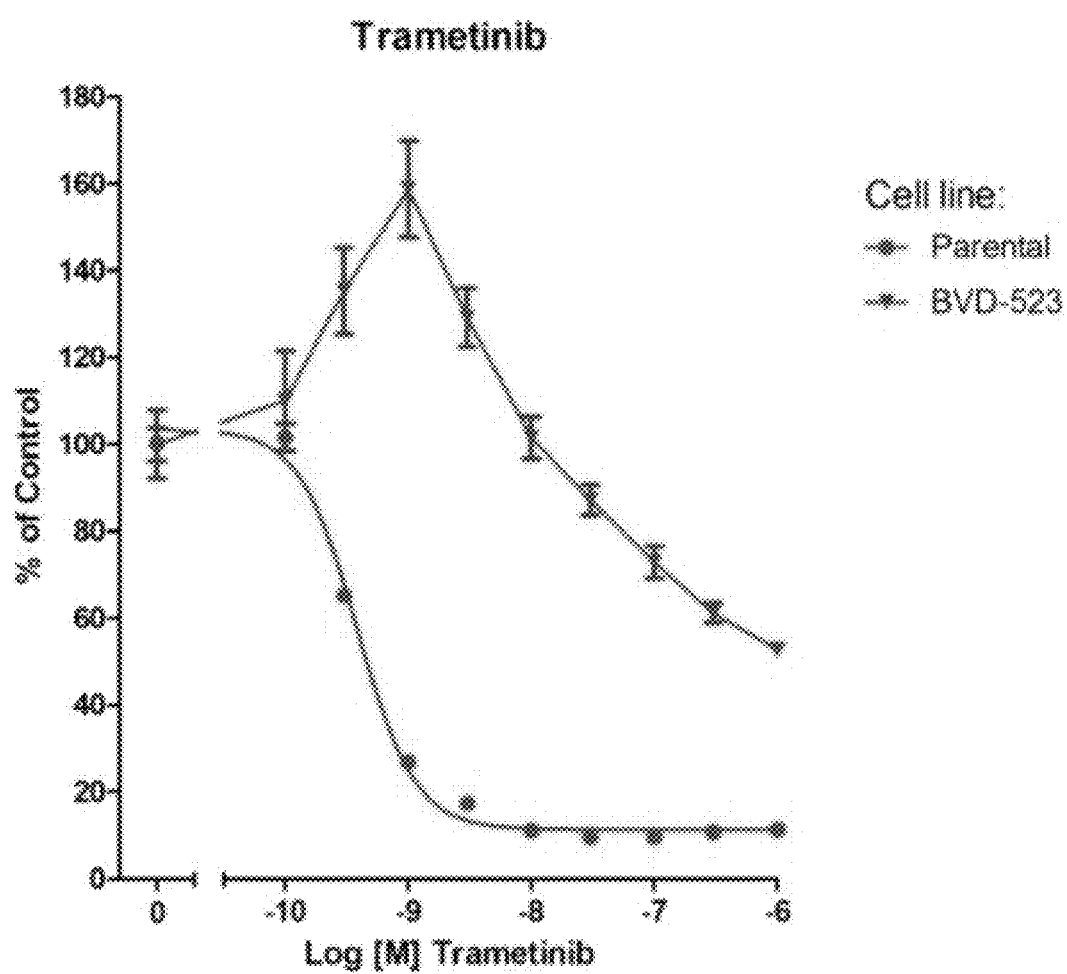
Figure 5D:
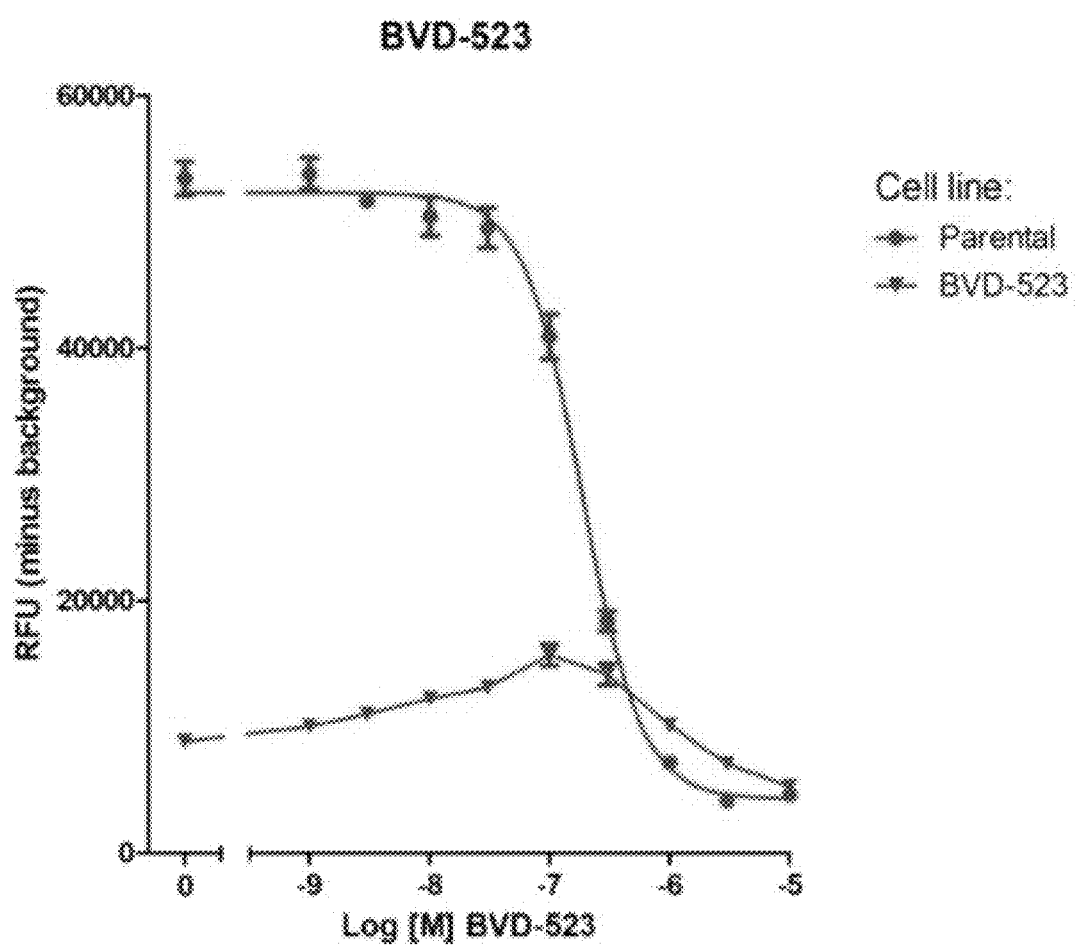
Figure 5E:
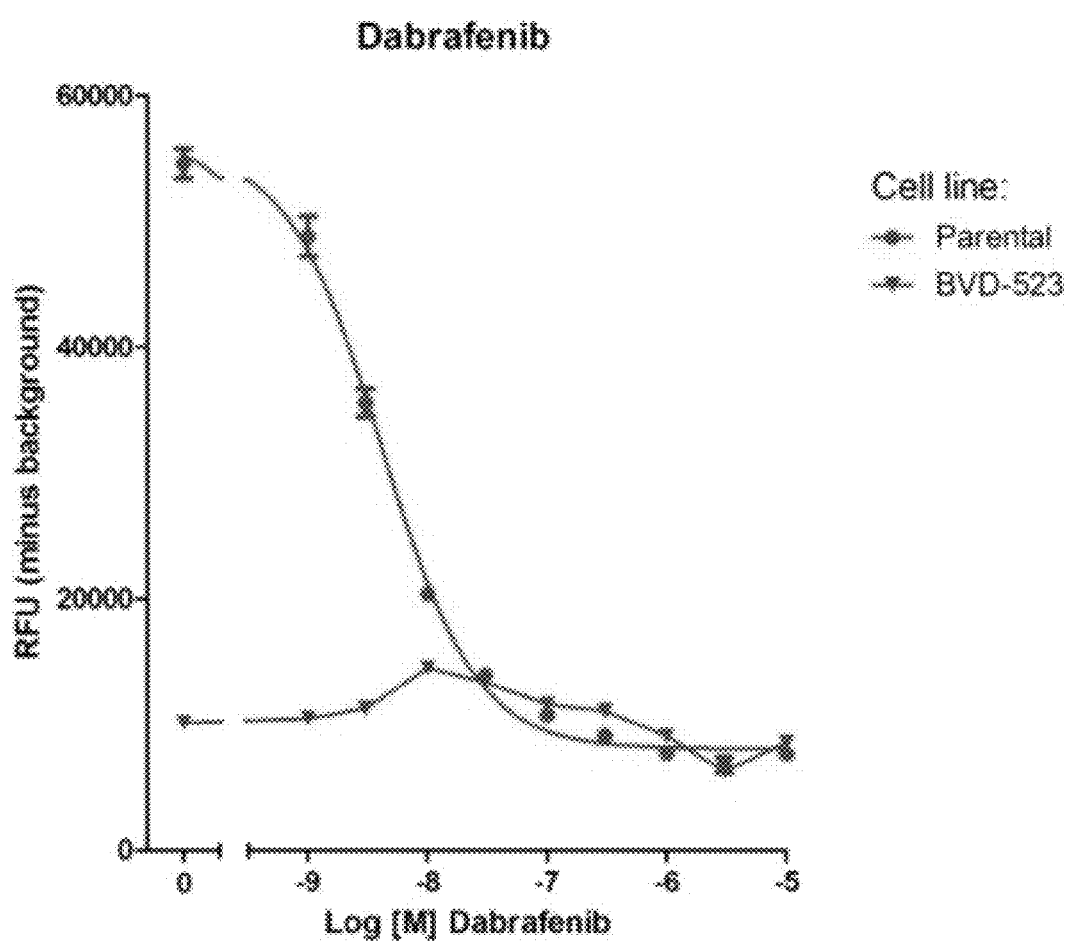
Figure 5F:
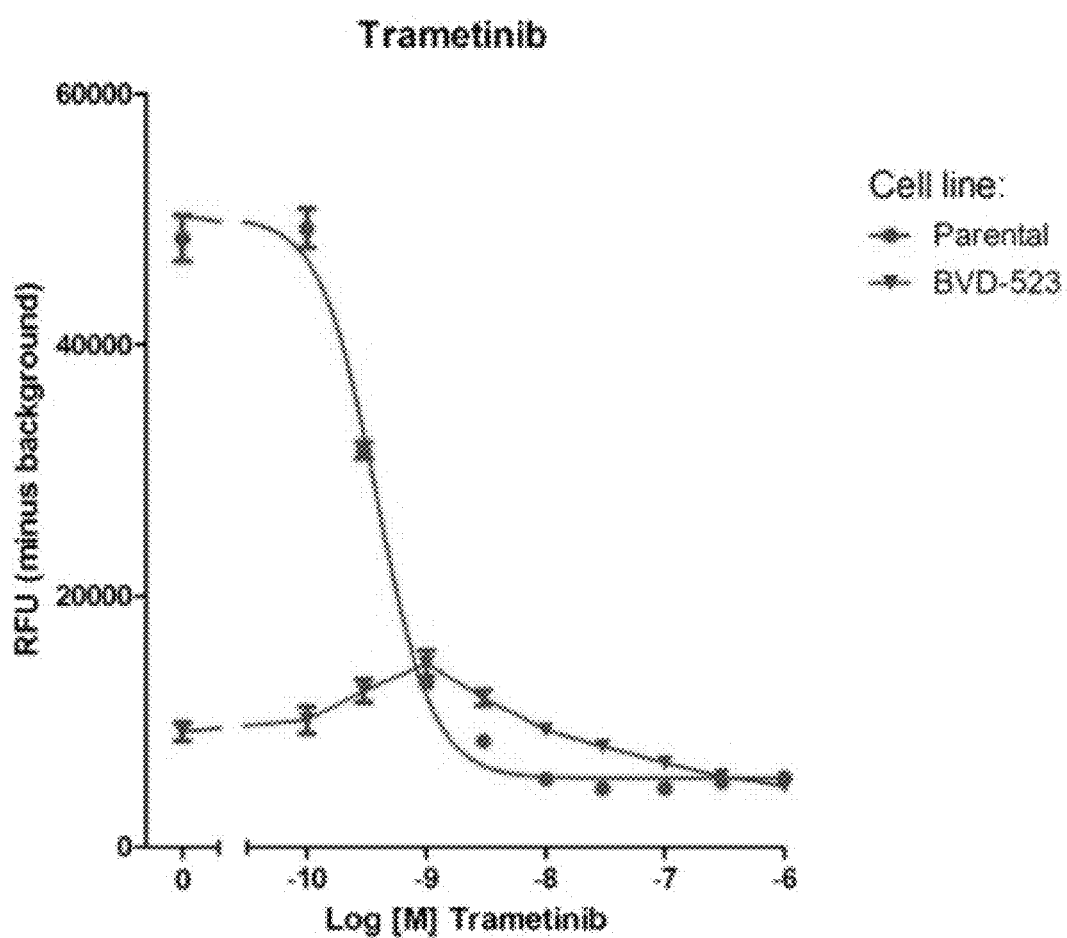
Figure 5G:
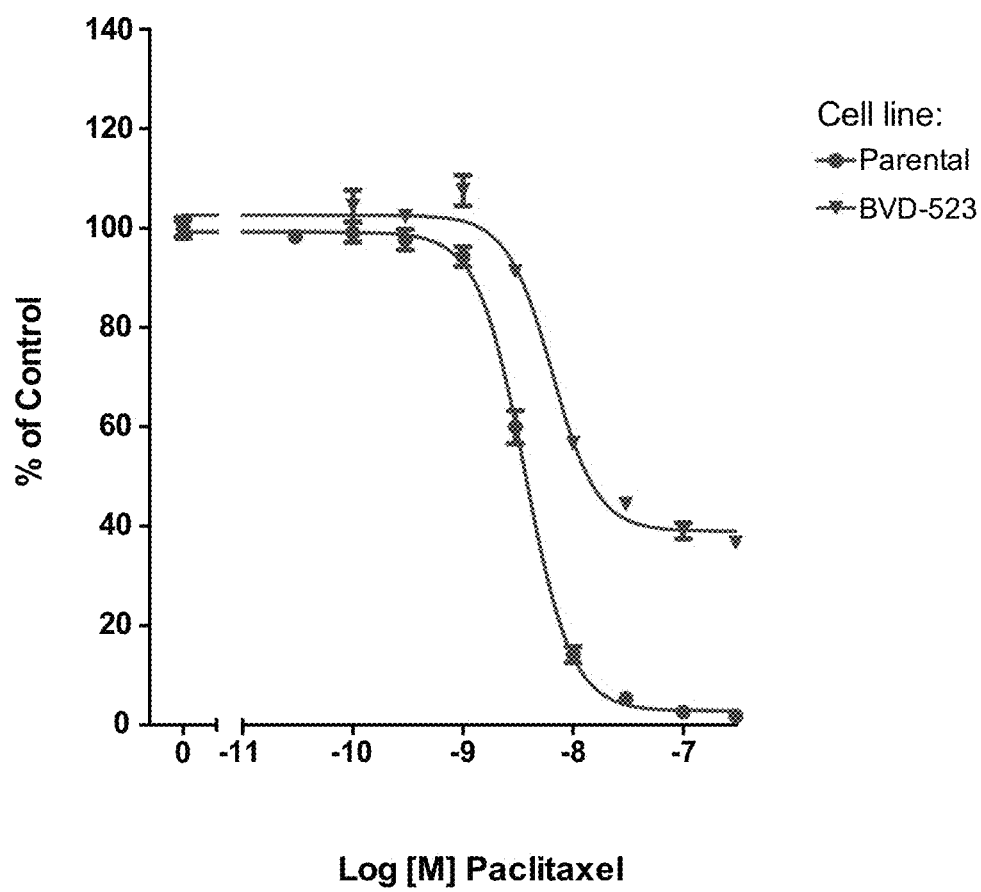
Figure 5H:
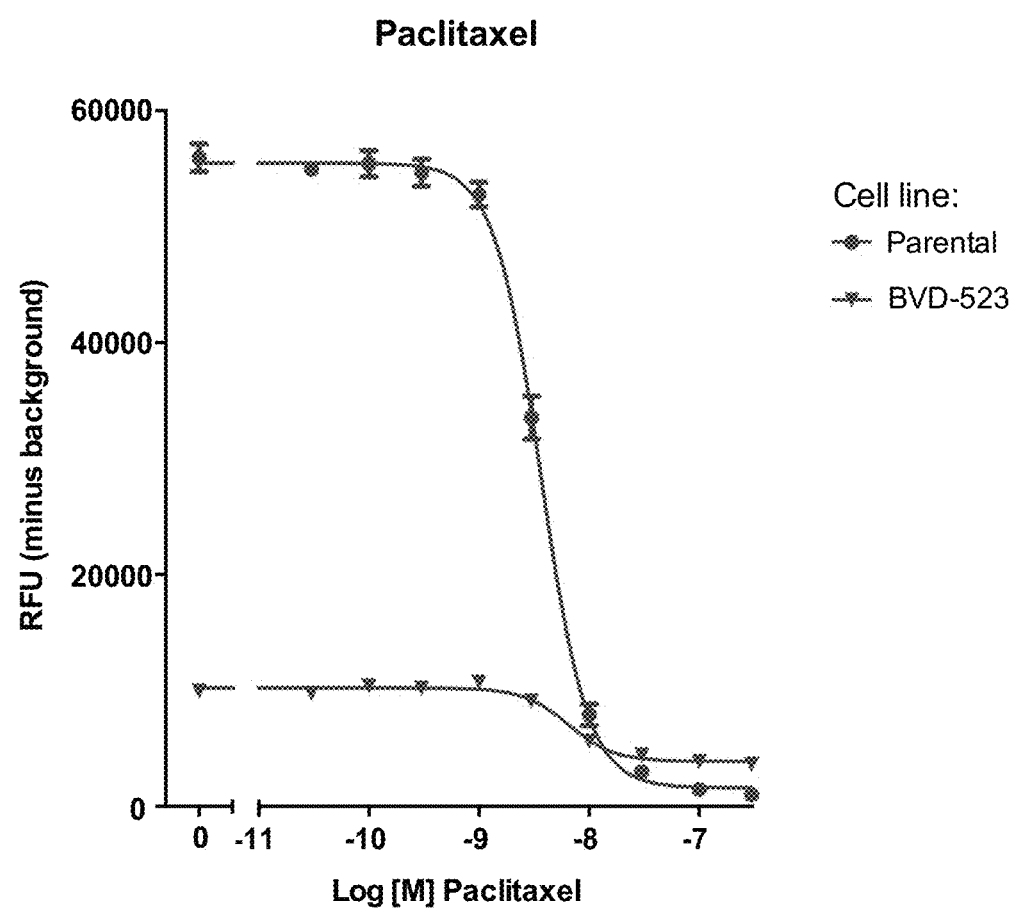

The second month of studies saw most treatments move into a phase where doses were increased in greater increments (1.5-fold) compared to the initial gentle escalation phase. The single agent escalation of dabrafenib and trametinib was quickest, with cells growing in concentrations equivalent to 100× parental cell $IC_{50}$ (FIG. 3A and FIG. 3B). The single agent escalation of BVD-523 progressed more slowly compared to dabrafenib and trametinib (FIG. 3C). See FIG. 3D for a comparison of the single agent escalations. BVD-523 escalated cells had a more "fragile" appearance and there was a greater number of floating cells compared to the dabrafenib and trametinib escalated populations.

The combined agent escalations progressed more slowly than the single agent treatments. The BVD-523/trametinib combination was particularly effective in preventing cells from progressing.

Proliferation Assay Results—Month 2

Proliferation assays on single agent escalated dabrafenib and trametinib cell populations revealed modest shifts in the dose response curves, suggesting that an additional period of escalation would be beneficial to further enrich for resistant cells. Interestingly, in the proliferations assay, there was evidence to suggest that cells exposed to BVD-523 grew less well upon inhibitor withdrawal, perhaps indicating a level of addiction.

FIG. 4A-FIG. 4H show normalized and raw proliferation assay results from month 2 of the studies. Note that differences in max signals in DMSO controls between different treatments (FIG. 4D, FIG. 4F, and FIG. 4H) suggest differential growth rates between treatments. These differences may influence the responses of lines to inhibitors in the proliferation assays.

FIG. 5A-FIG. 5H show normalized and raw proliferation assay results from month 2 of the studies with a focus on parental and BVD-523 line data only.

Table 11 shows $IC_{50}$ data for month 2 of the studies. Relative $IC_{50}$s were determined from 4-parameter curve fits in Prism.

TABLE 11

$IC_{50}$ Data-Month 2

| | Cell Line, Relative $IC_{50}$ (nM) | | | | | | |
|---|---|---|---|---|---|---|---|
| Compound | Par* | Tram | Dab | BVD-523 | Dab/Tram | Dab/523 | Tram/523 |
| Dabrafenib | 4.1 | 6.2 | 11.5 | 697 | 256 | 218 | 68 |
| Trametinib | 0.4 | 0.7 | 1.1 | 24.3 | 12.6 | 6.2 | 4.6 |
| BVD-523 | 187 | 252 | 284 | 1706 | 561 | 678 | 435 |
| Paclitaxel | 3.7 | 8.9 | 1.9 | 6.5 | 4.7 | 4.2 | 8.9 |

*Par = Parental cell line

Example 4

Dose Escalation and Proliferation Assays—Month 3

Dose Escalation Progress—Month 3

Figure 6A:
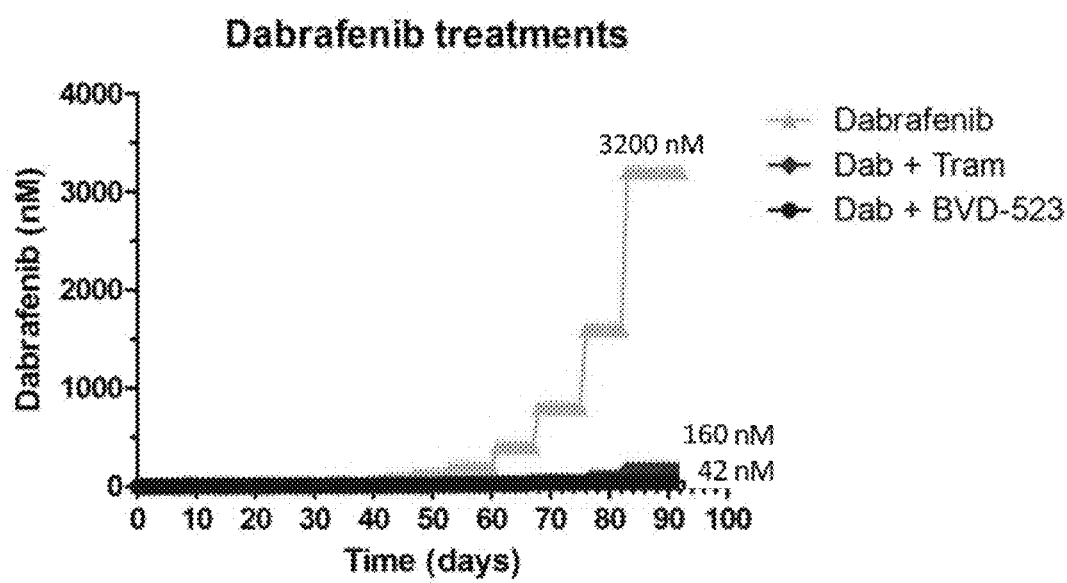
FIG. 6A-FIG. 6D show the progress of the dose escalation study in a human malignant cell line (A375 cells) for month 3. Various treatments (trametinib, dabrafenib, and BVD-523) are as labeled.
Figure 6B:
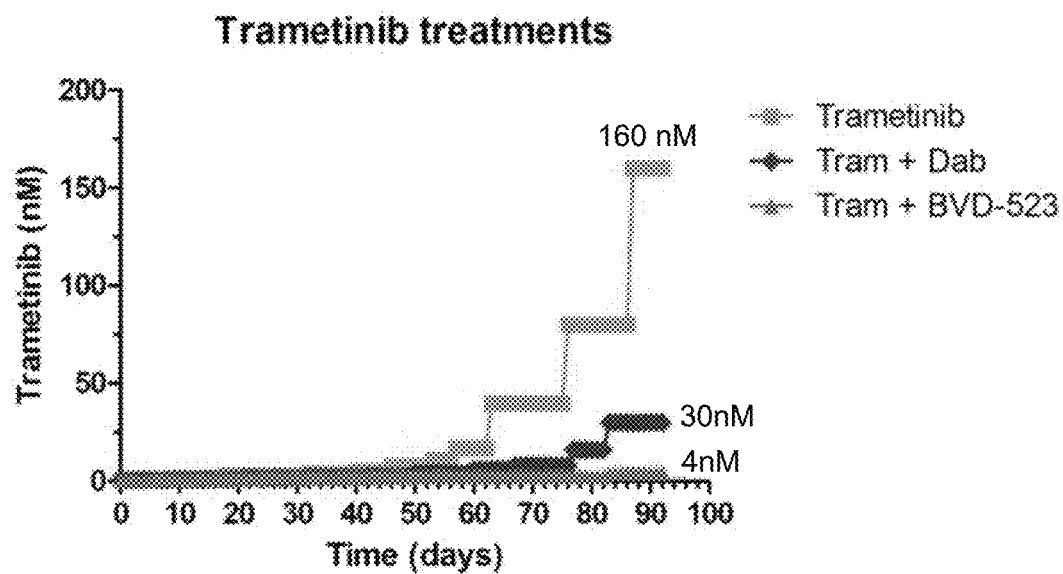
Figure 6C:
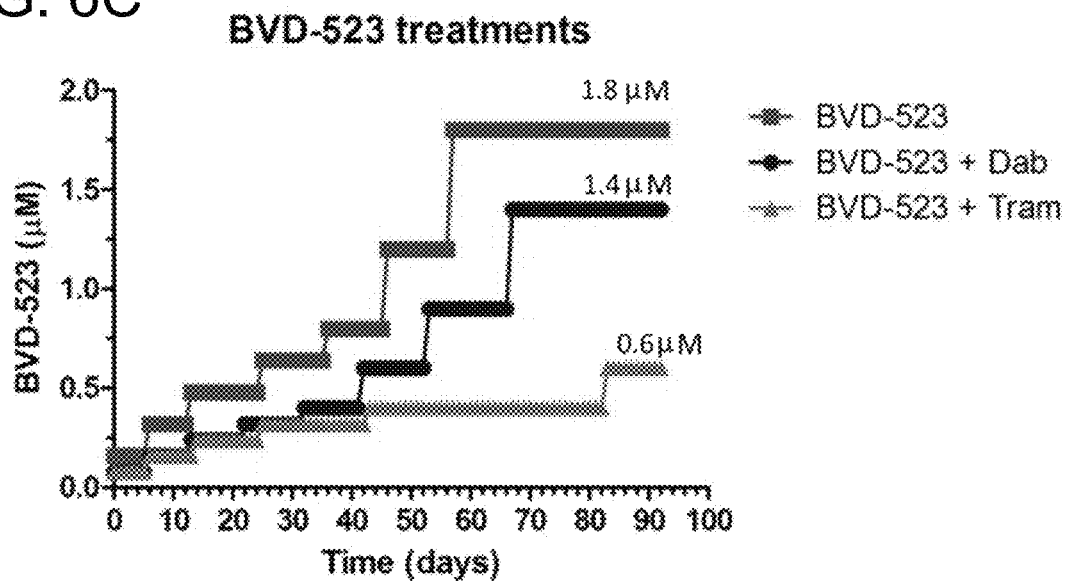
Figure 6D:
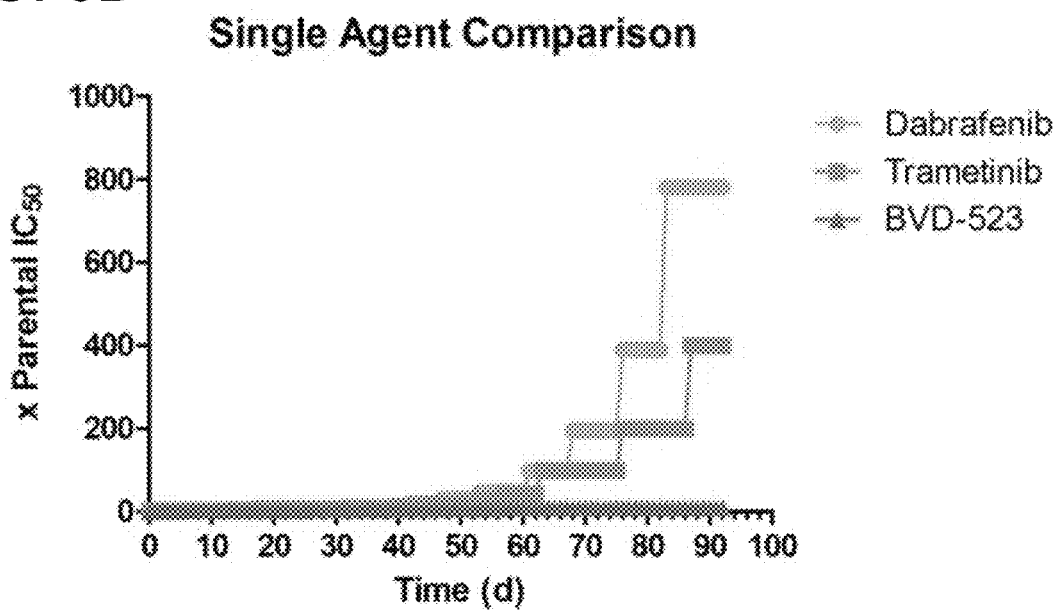

FIG. 6A-FIG. 6C show single and combination agent escalation for month 3 of the studies. FIG. 6D shows a comparison of single agent escalations.

Proliferation Assay Results—Month 3

Figure 7:
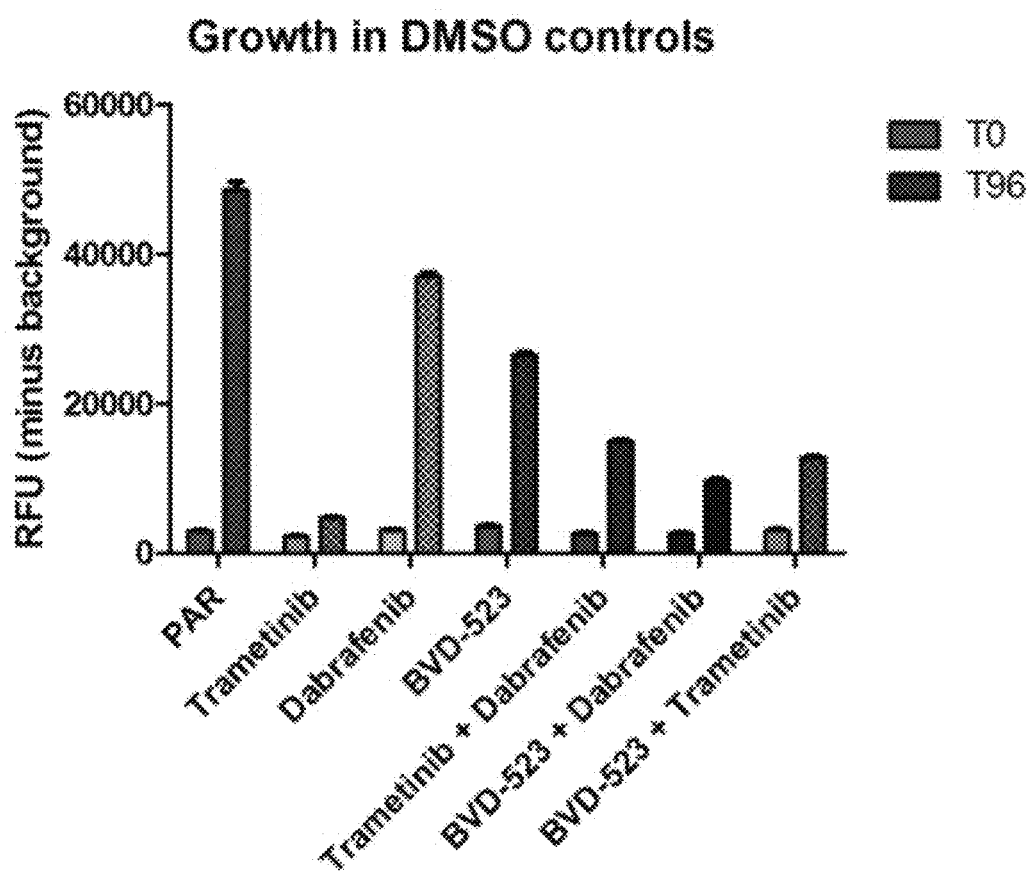
FIG. 7 is a histogram showing the results of a proliferation assay as applied to cells grown in the DMSO control wells from the dose escalation assay.
Figure 8A:
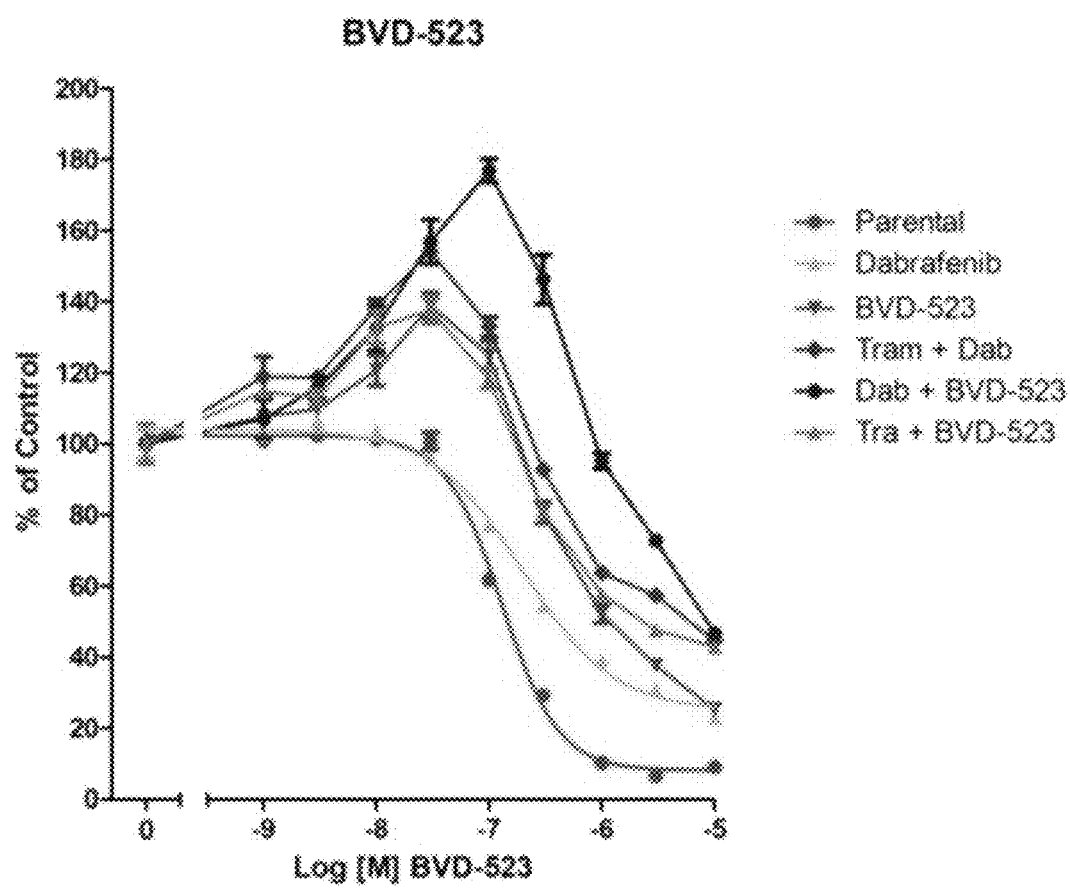
FIG. 8A-FIG. 8D are a set of line graphs showing proliferation assays for month 3 of the study. Various treatments (trametinib, dabrafenib, BVD-523, and pacitaxel) are as labeled on the top of the graph. The caption to the right of the graph shows the various types of cells generated from the dose escalation study. For example, "dabrafenib" refers to the cells that have been treated with the highest dose of dabrafenib from month 3 of the dose escalation study. Parental refers to the control cells that have not been treated with drugs.
Figure 8B:
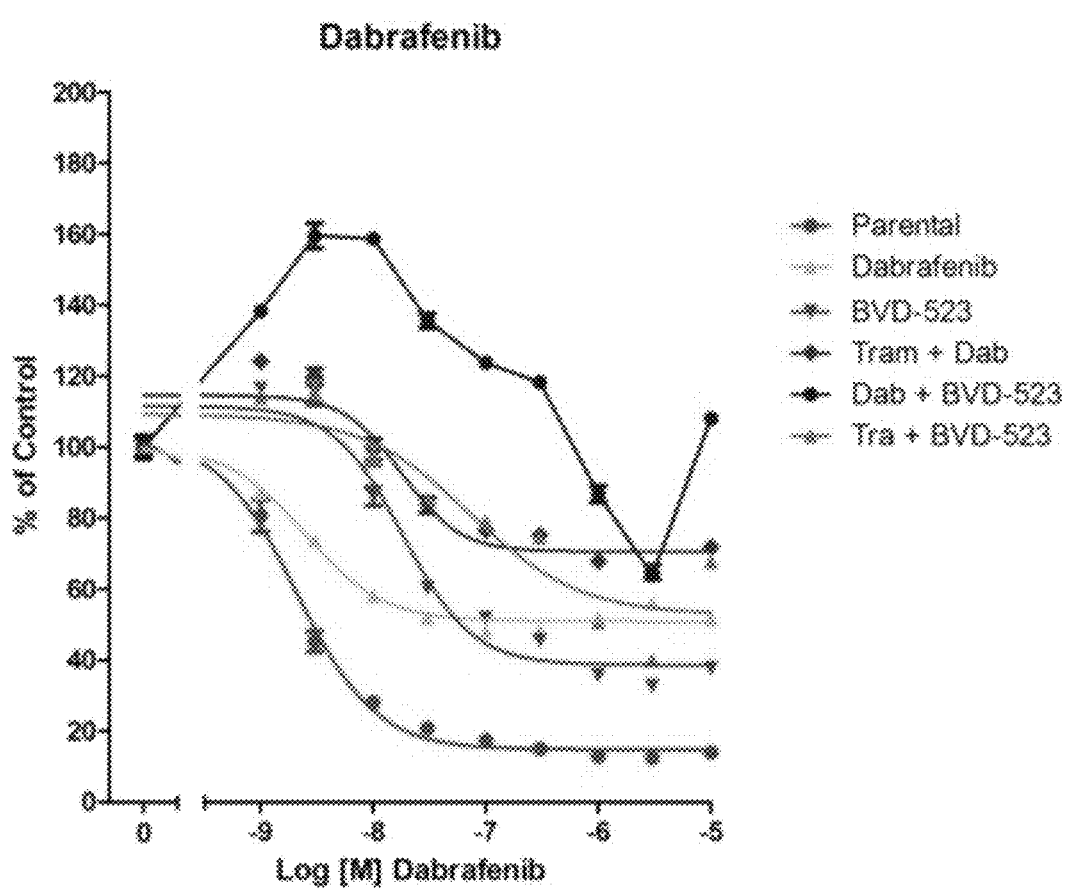
Figure 8C:
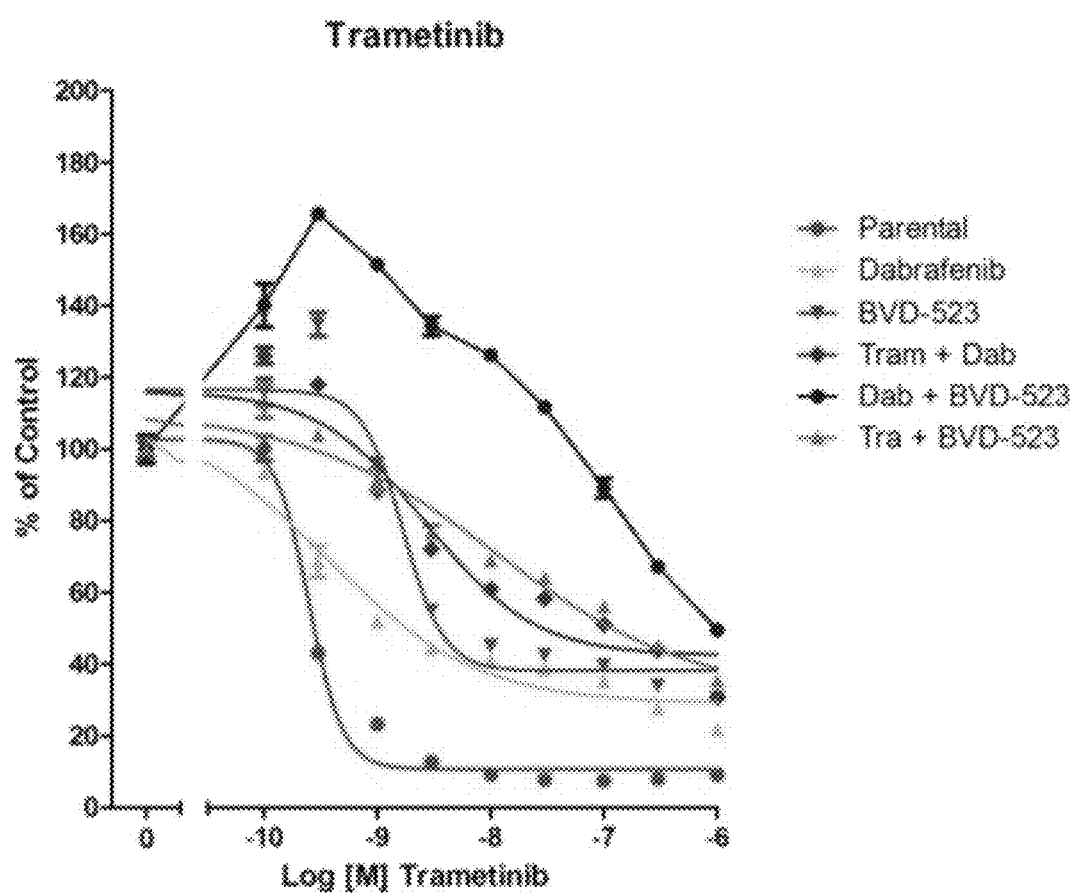
Figure 8D:
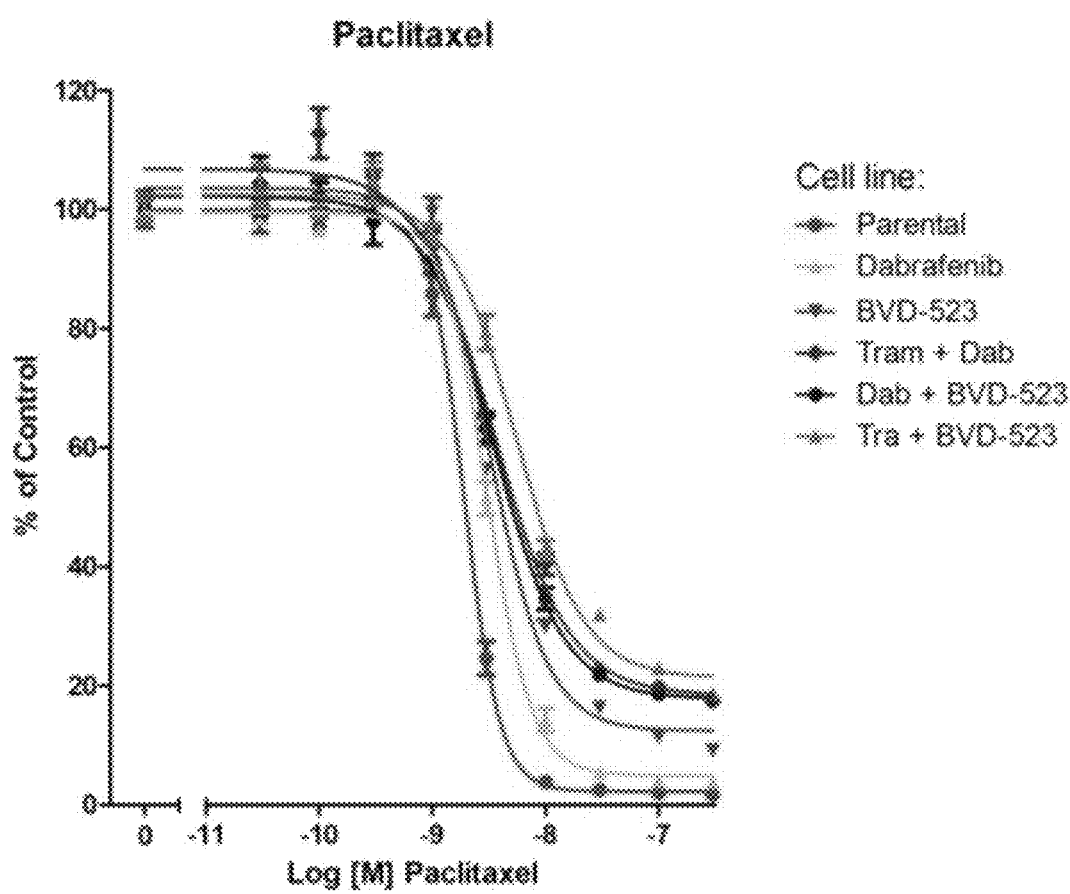
Figure 9A:
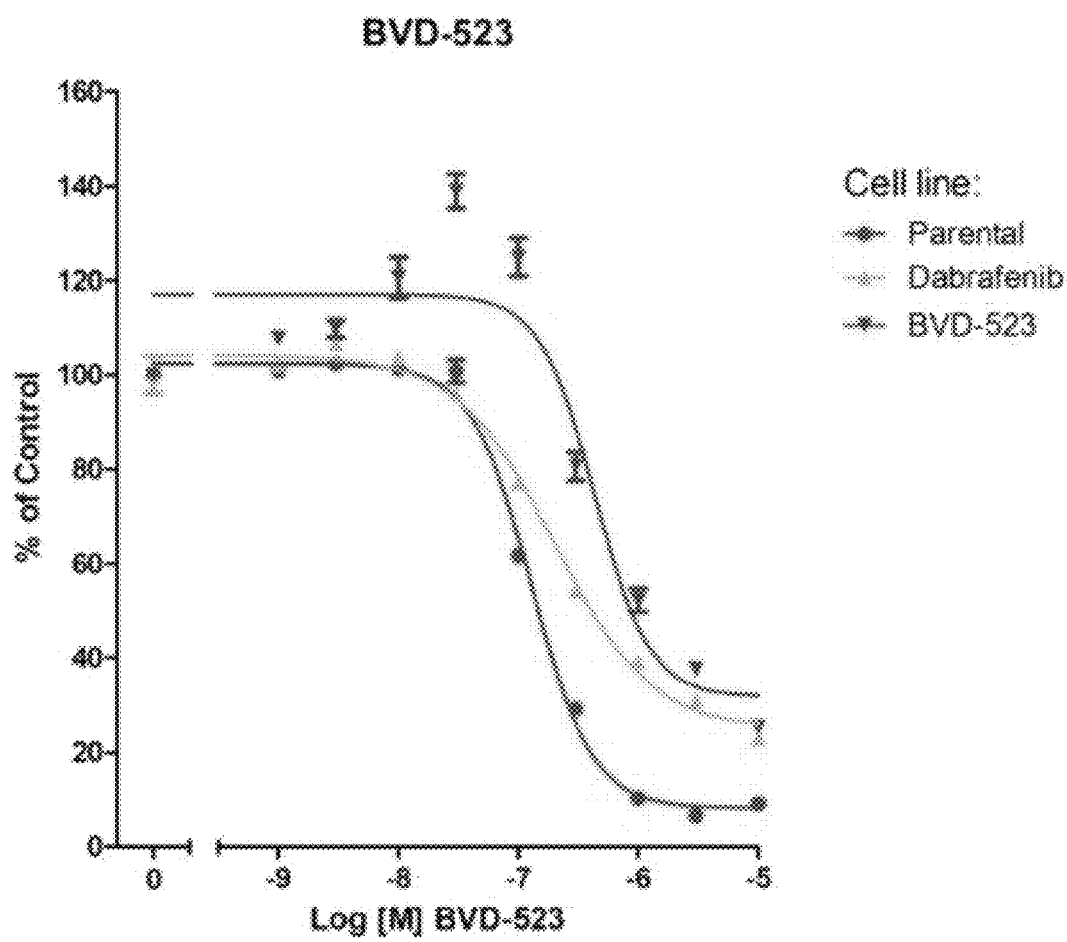
FIG. 9A-FIG. 9D show only the parental, dabrafenib, and BVD-523 cell line data from FIG. 8A-FIG. 8D.
Figure 9B:
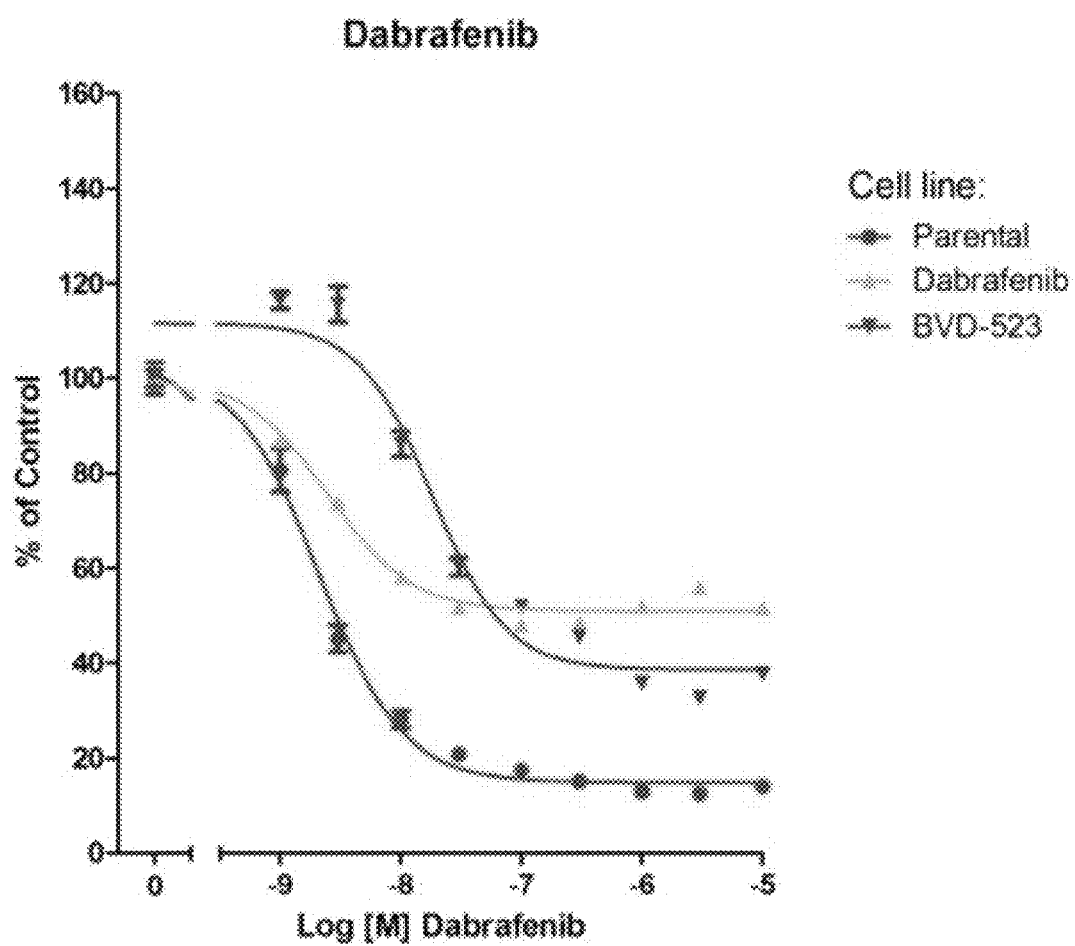
Figure 9C:
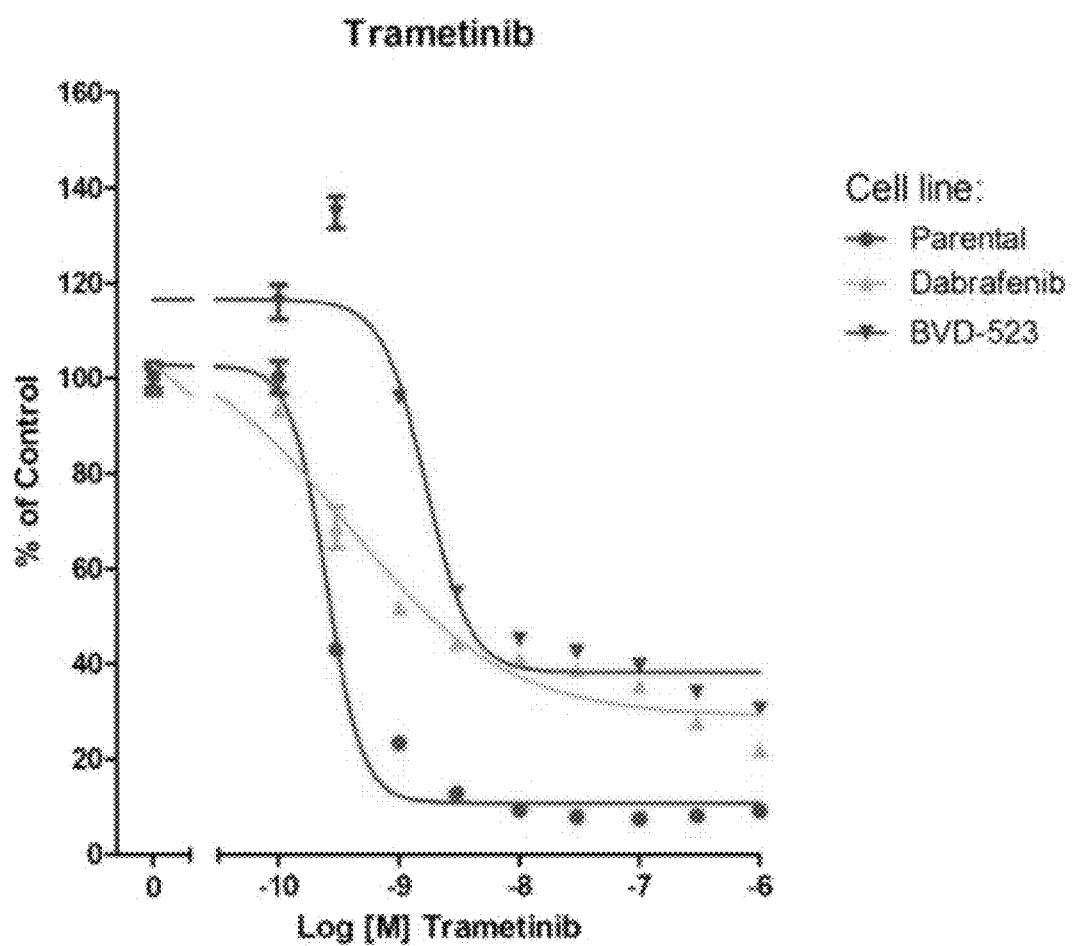
Figure 9D:
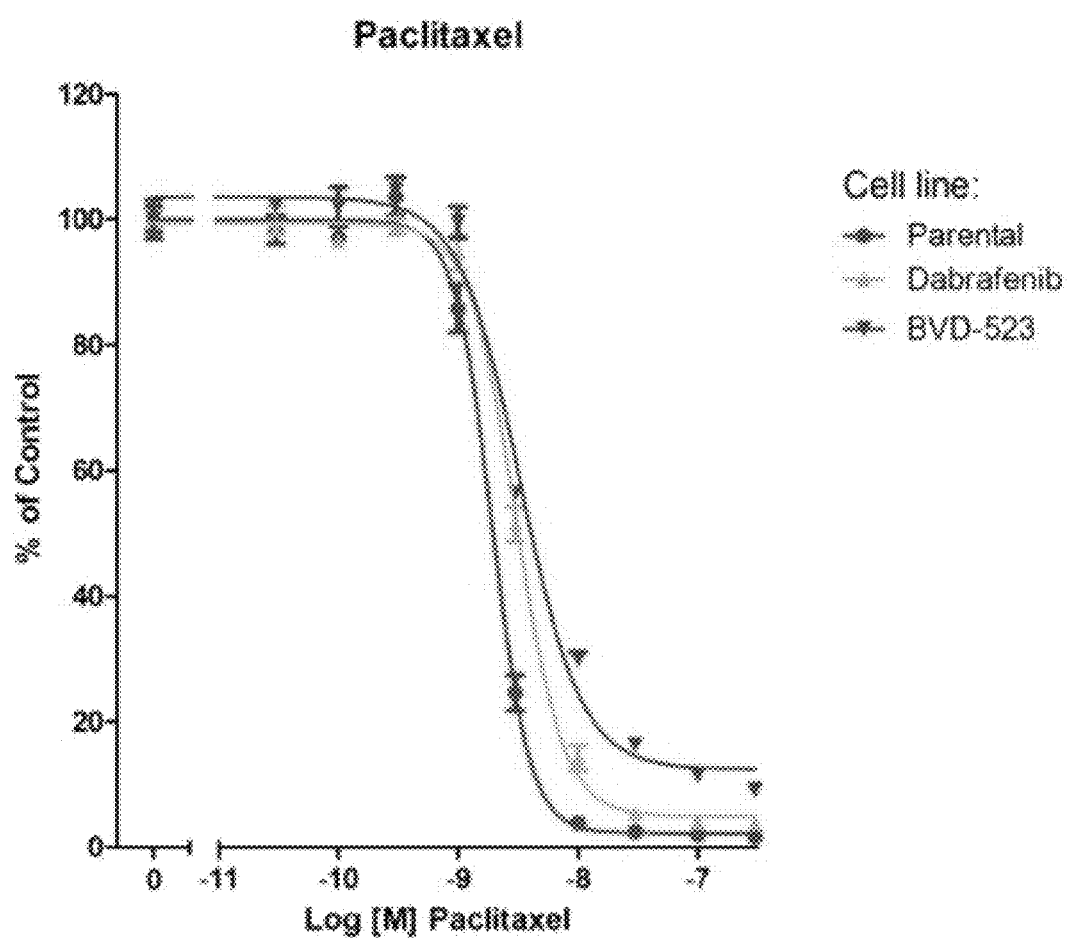
Figure 10A:
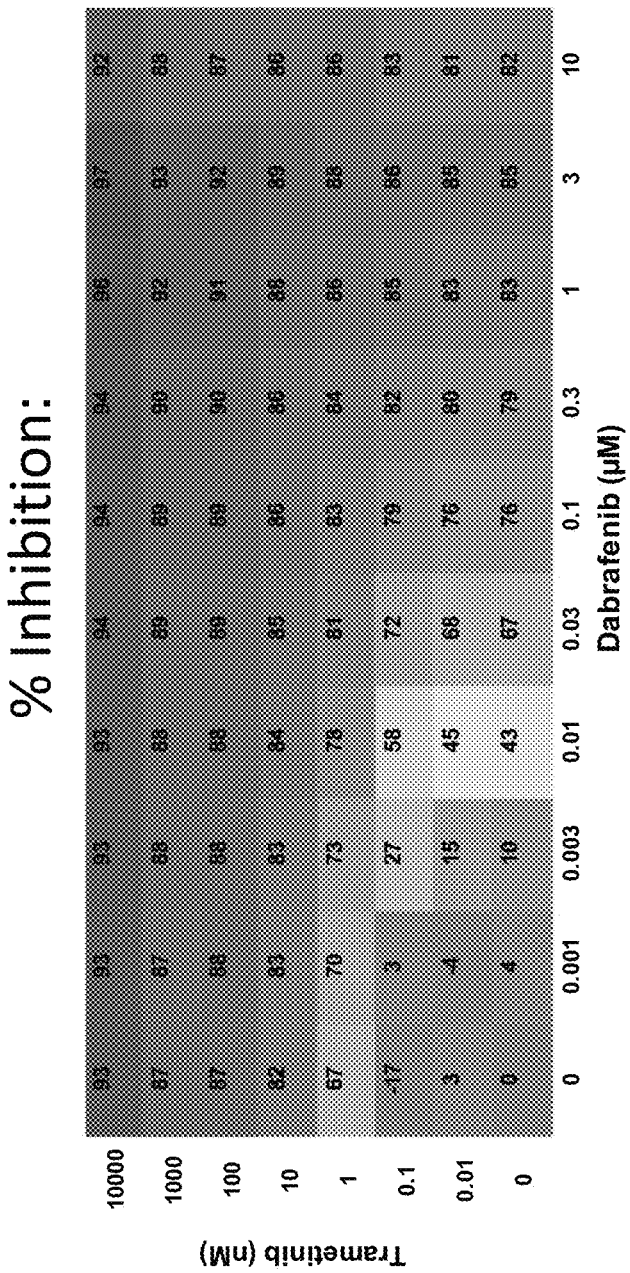
FIG. 10A is a dose matrix showing % inhibition of the trametinib/dabrafenib combination in A375 cells using the Alamar Blue cell viability assay.
Figure 10B:
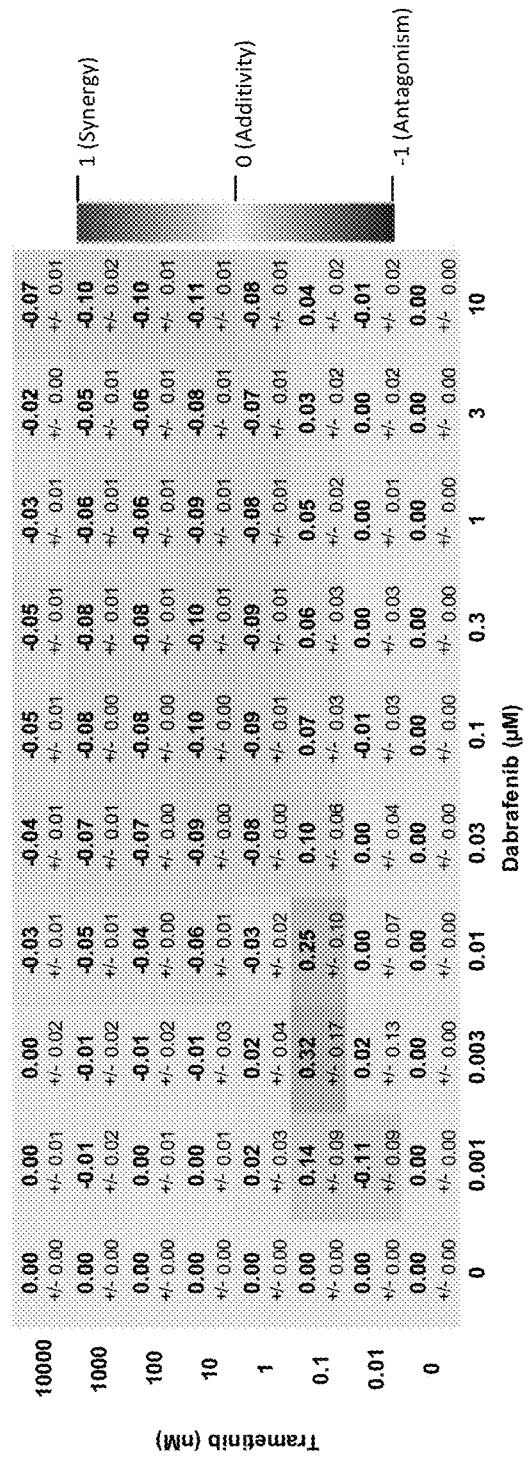
FIG. 10B is a dose matrix showing excess over Bliss for the trametinib/dabrafenib combination.
Figure 10D:
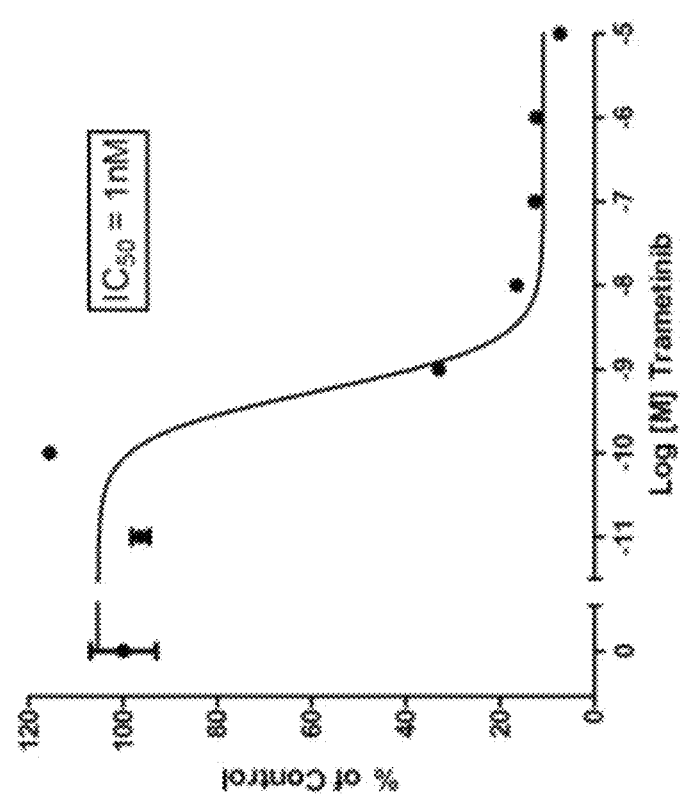
FIG. 10C and FIG. 10D show % viability relative to DMSO only treated controls for dabrafenib and trametinib single agent treatments in A375 cells using the Alamar Blue cell viability assay.
Figure 10C:
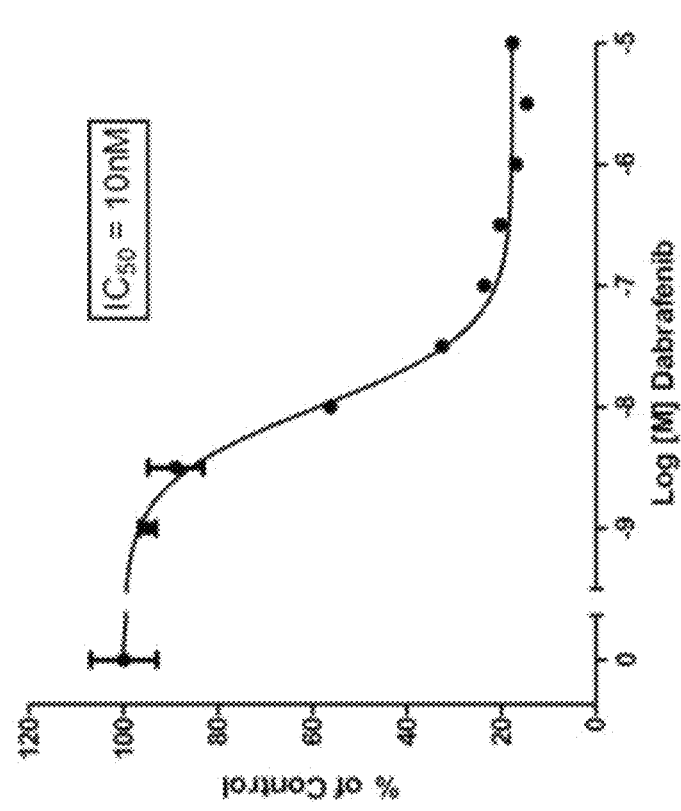
Figure 10E:
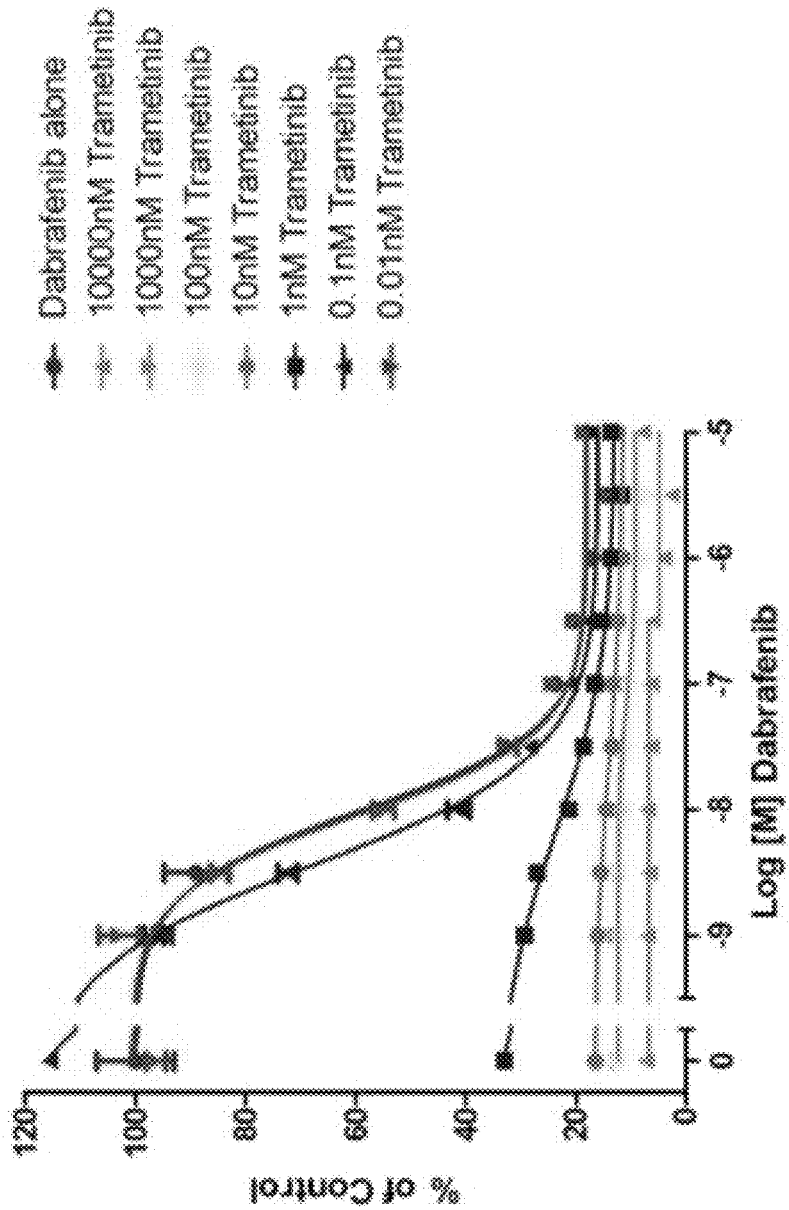
FIG. 10E shows % viability relative to DMSO only treated controls for dabrafenib and trametinib combination treatments in A375 cells using the Alamar Blue cell viability assay.
Figure 11A:
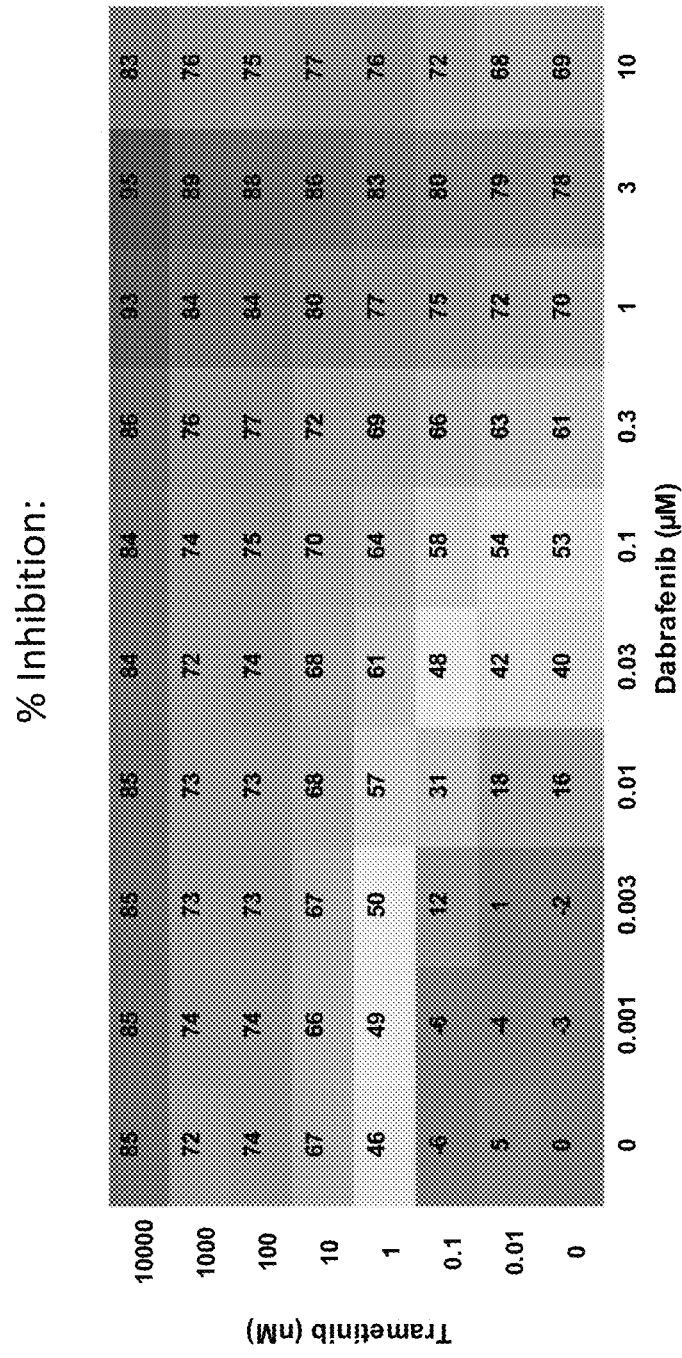
FIG. 11A is a dose matrix showing % inhibition of the trametinib/dabrafenib combination in A375 cells using the CellTiter-Glo cell viability assay.
Figure 11B:
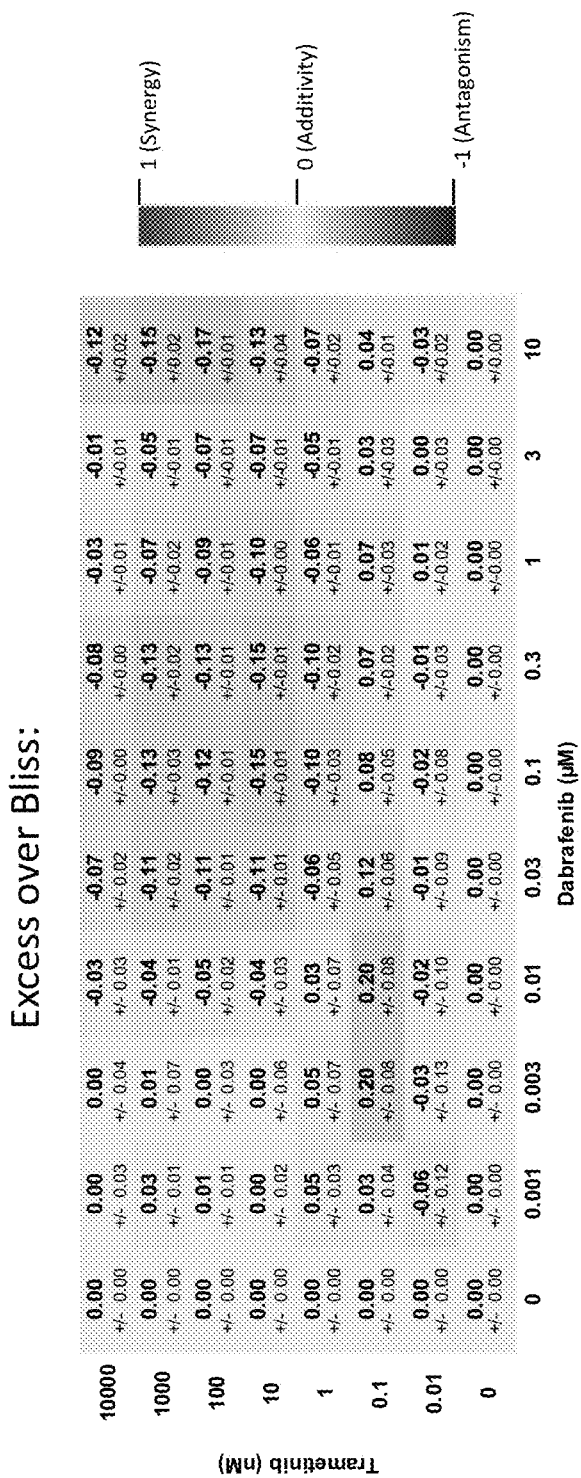
FIG. 11B is a dose matrix showing excess over Bliss for the trametinib/dabrafenib combination.
Figures 11C, 11D:
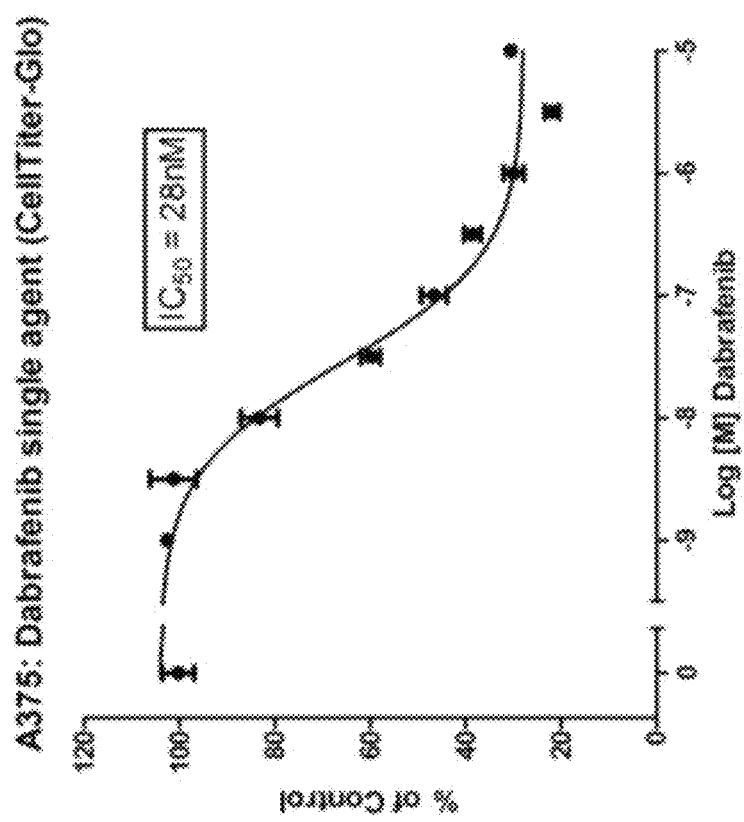
FIG. 11C and FIG. 11D show % viability relative to DMSO only treated controls for dabrafenib and trametinib single agent treatments in A375 cells using the CellTiter-Glo cell viability assay.
Figure 11E:
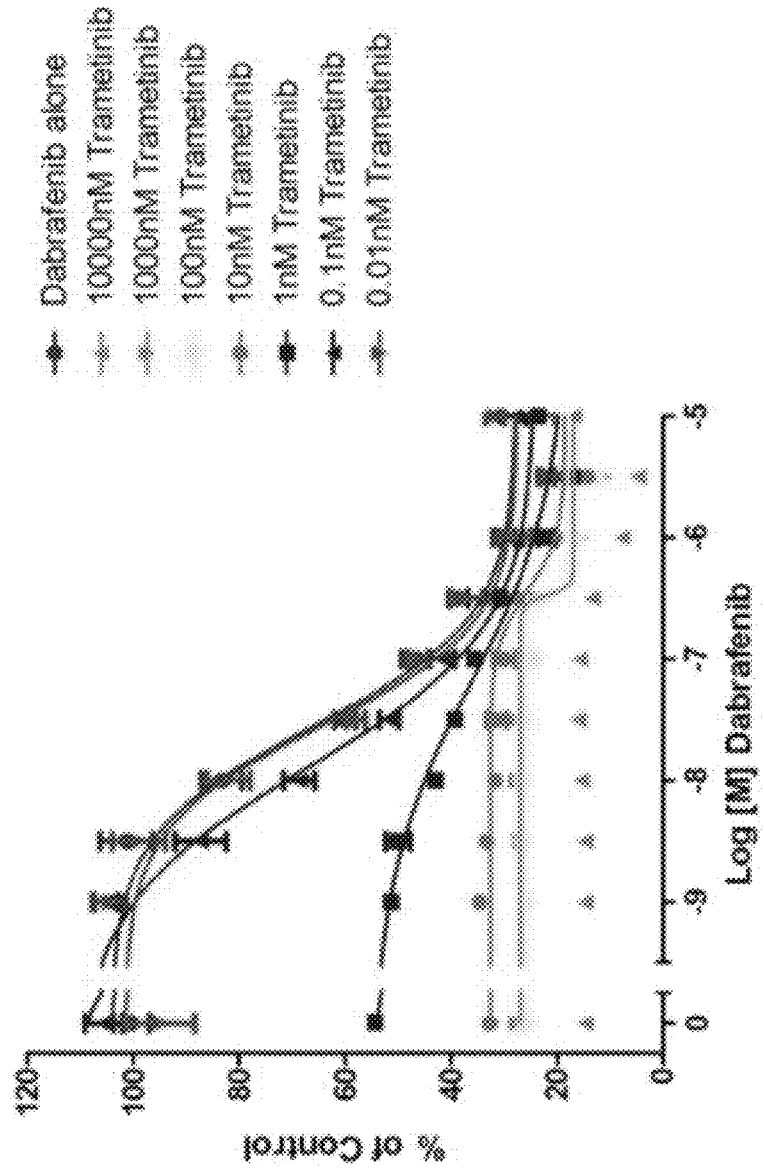
FIG. 11E shows % viability relative to DMSO only treated controls for dabrafenib and trametinib combination treatments in A375 cells using the CellTiter-Glo cell viability assay.
Figure 12A:
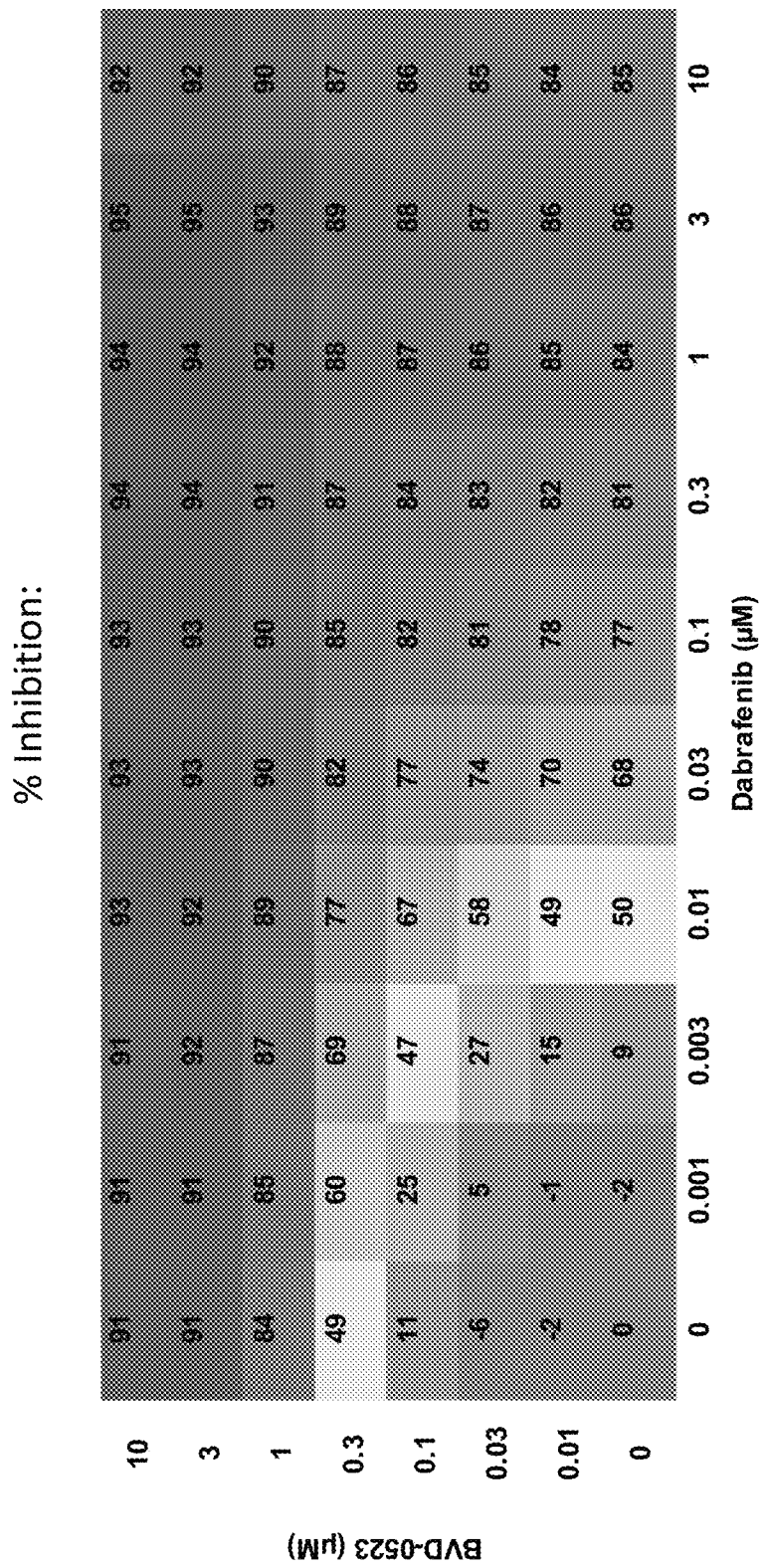
FIG. 12A is a dose matrix showing % inhibition of the BVD-523/dabrafenib combination in A375 cells using the Alamar Blue cell viability assay.
Figure 12B:
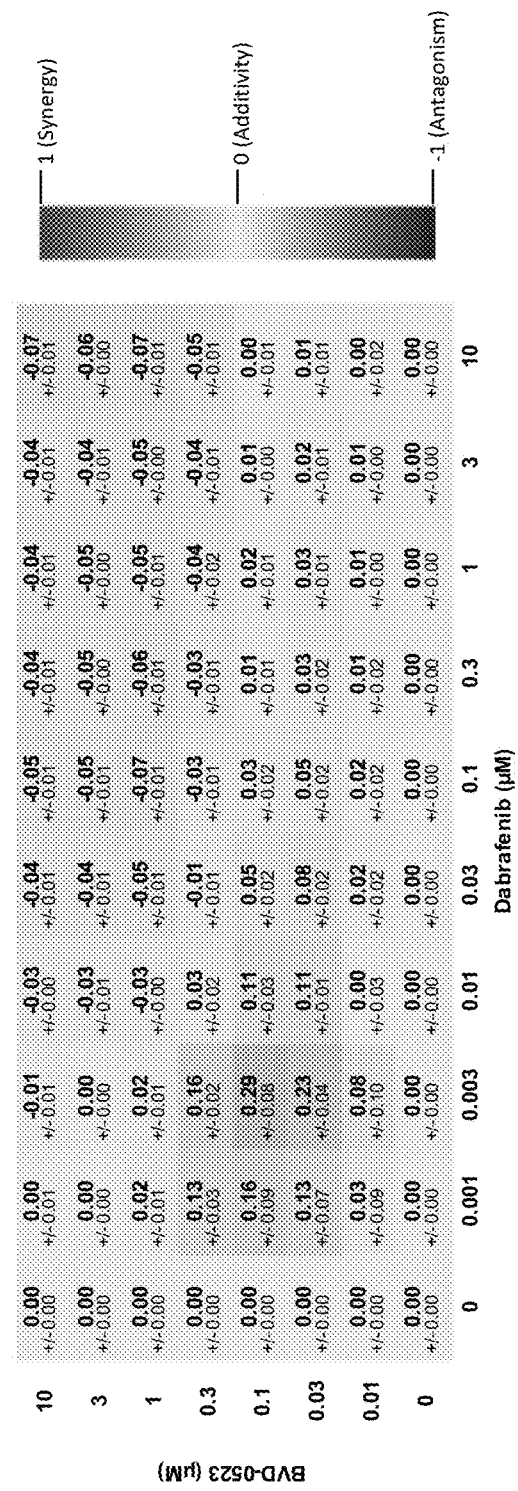
FIG. 12B is a dose matrix showing excess over Bliss for the BVD-523/dabrafenib combination.
Figure 12D:
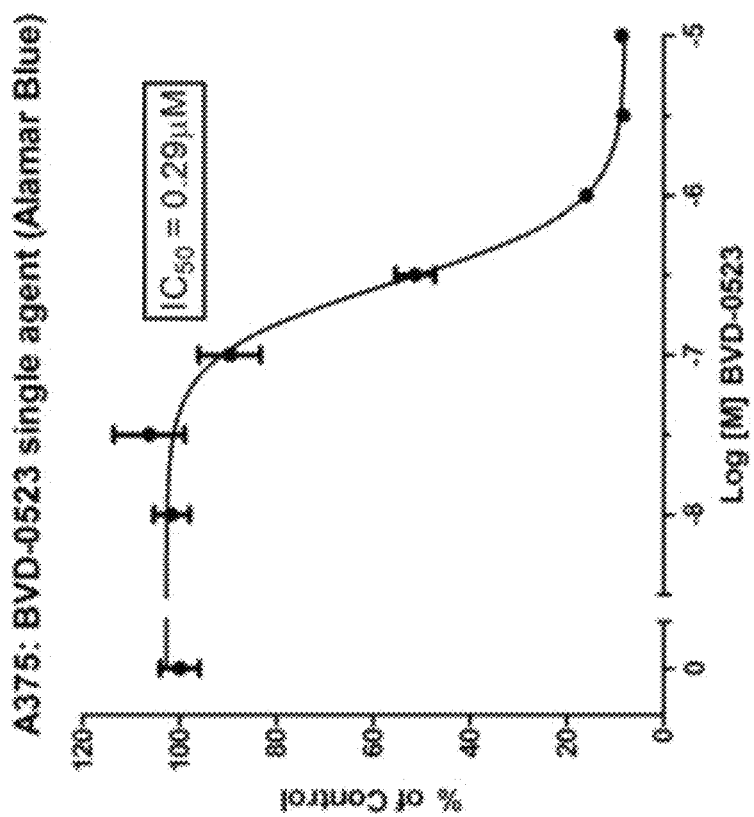
FIG. 12C and FIG. 12D show % viability relative to DMSO only treated controls for dabrafenib and BVD-523 single agent treatments in A375 cells using the Alamar Blue cell viability assay.
Figure 12C:
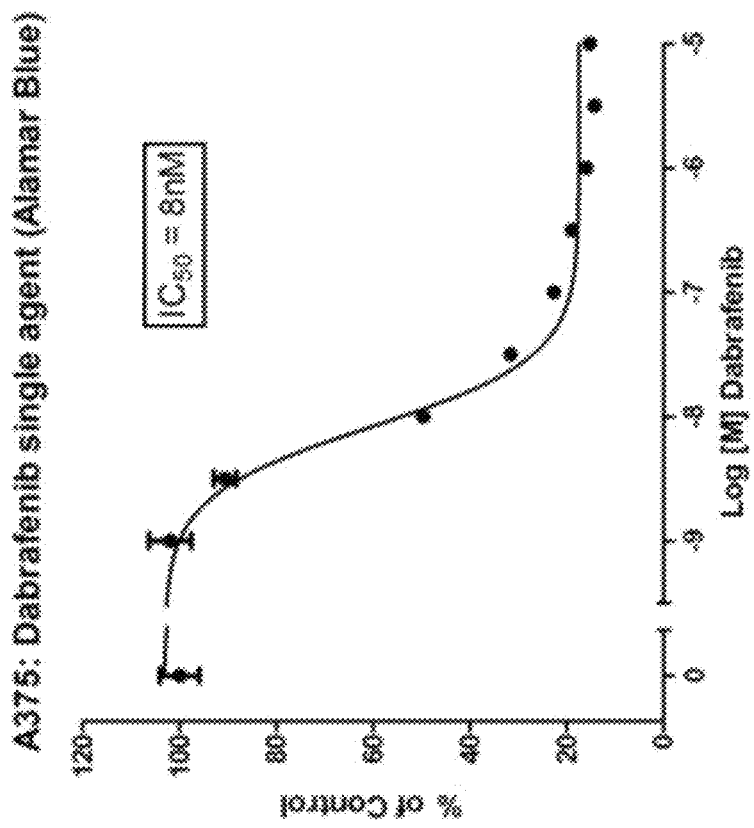
Figure 12E:
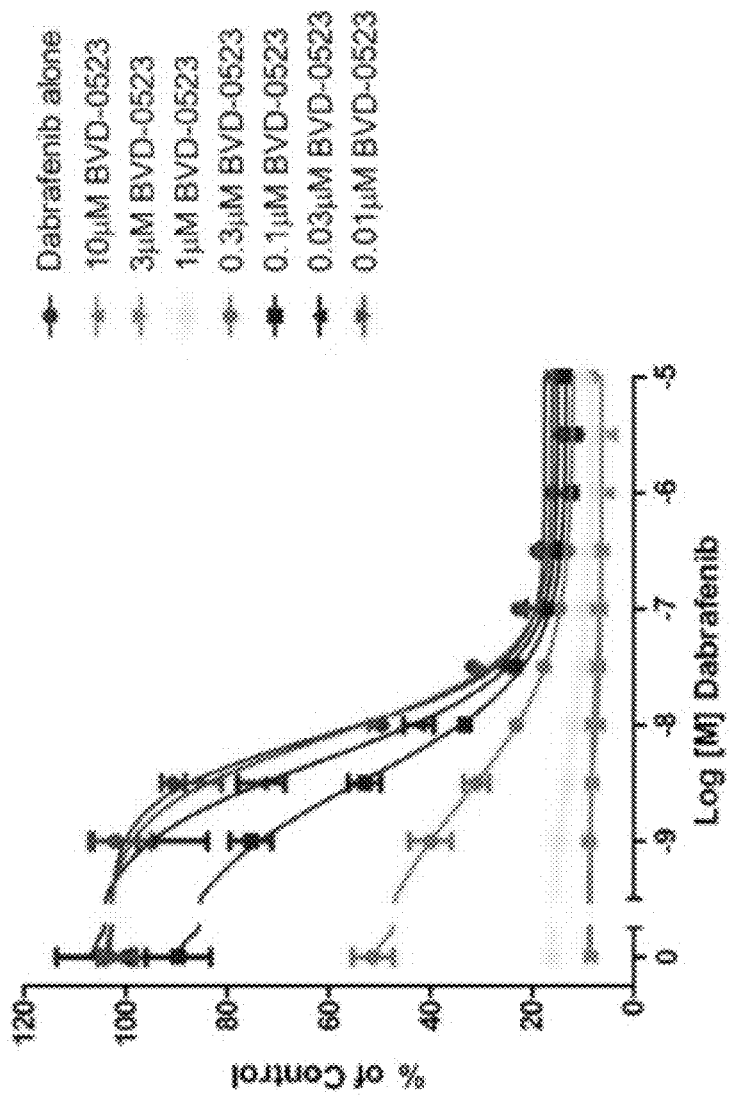
FIG. 12E shows % viability relative to DMSO only treated controls for dabrafenib and BVD-523 combination treatments in A375 cells using the Alamar Blue cell viability assay.
Figure 13A:
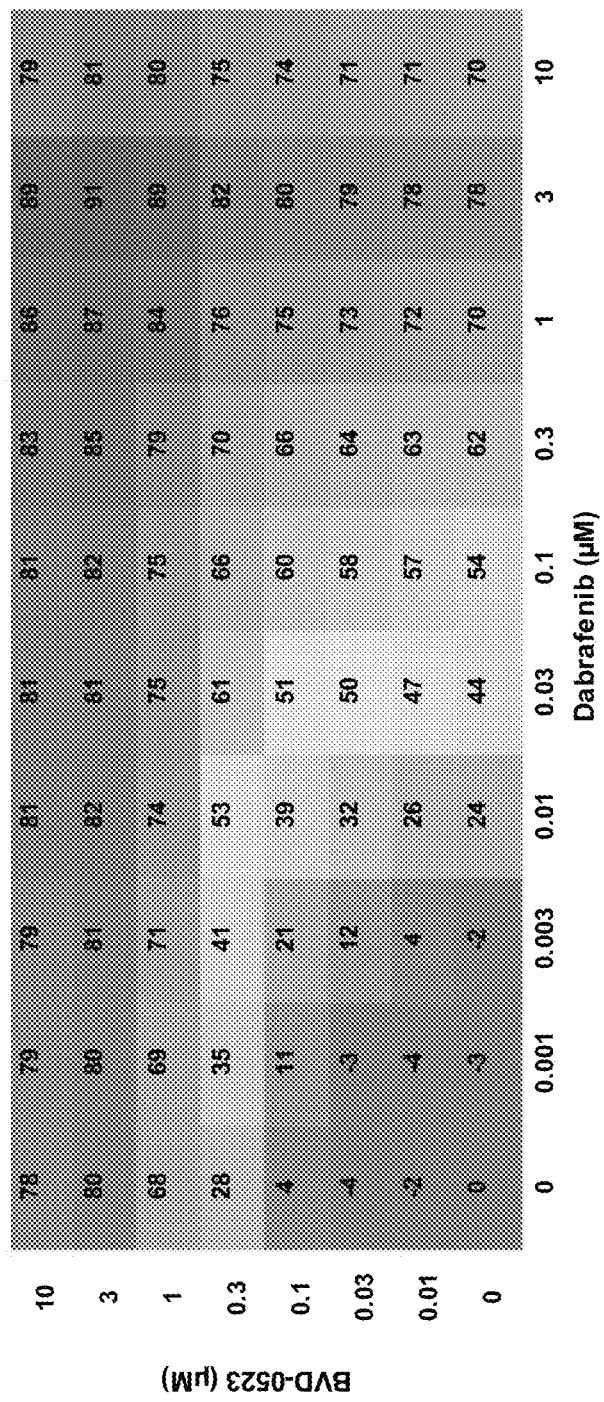
FIG. 13A is a dose matrix showing % inhibition of the BVD-523/dabrafenib combination in A375 cells using the CellTiter-Glo cell viability assay.
Figure 13B:
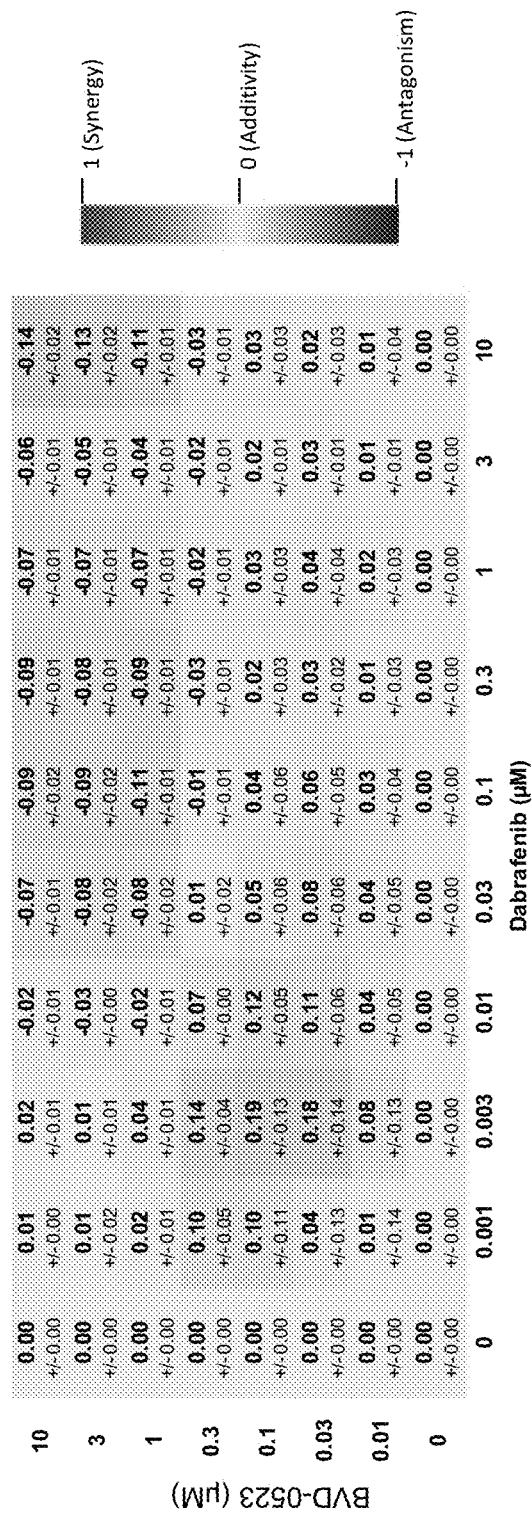
FIG. 13B is a dose matrix showing excess over Bliss for the BVD-523/dabrafenib combination.
Figure 13C:
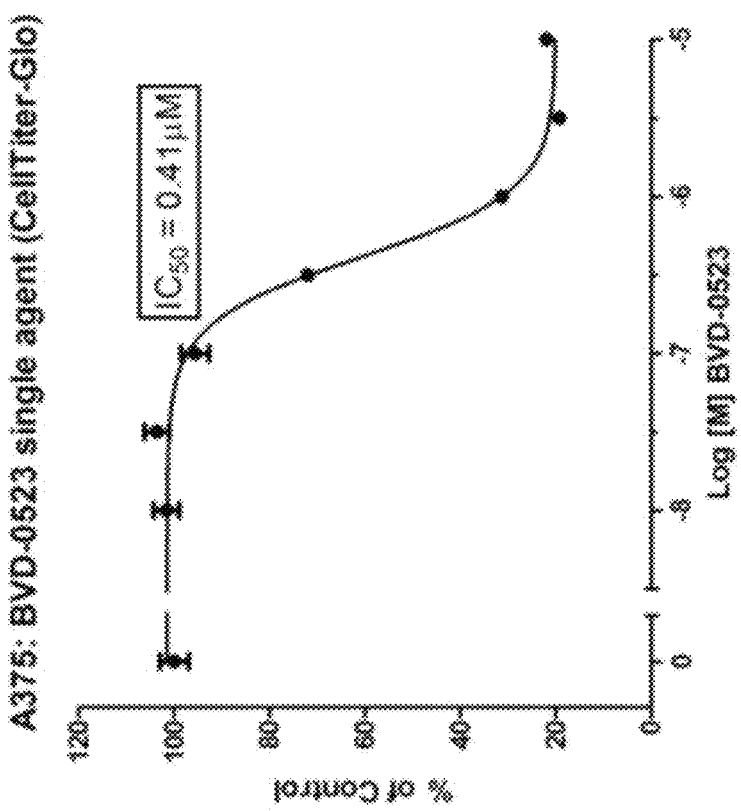
FIG. 13C and FIG. 13D show % viability relative to DMSO only treated controls for dabrafenib and BVD-523 single agent treatments in A375 cells using the CellTiter-Glo cell viability assay.
Figure 13D:
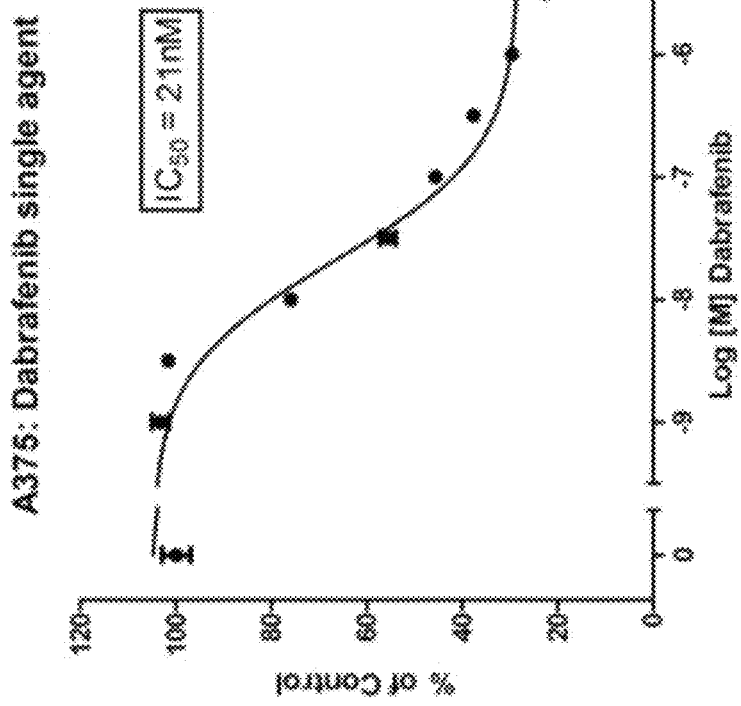
Figure 13E:
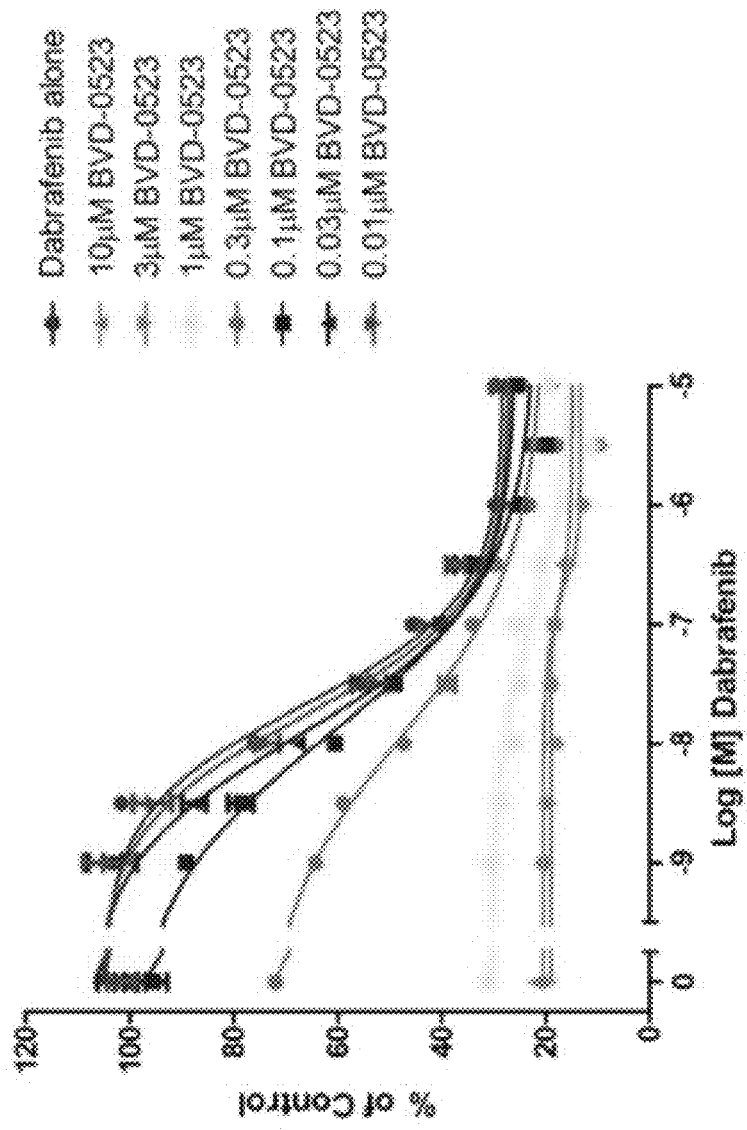
FIG. 13E shows % viability relative to DMSO only treated controls for dabrafenib and BVD-523 combination treatments in A375 cells using the CellTiter-Glo cell viability assay.
Figure 14A:
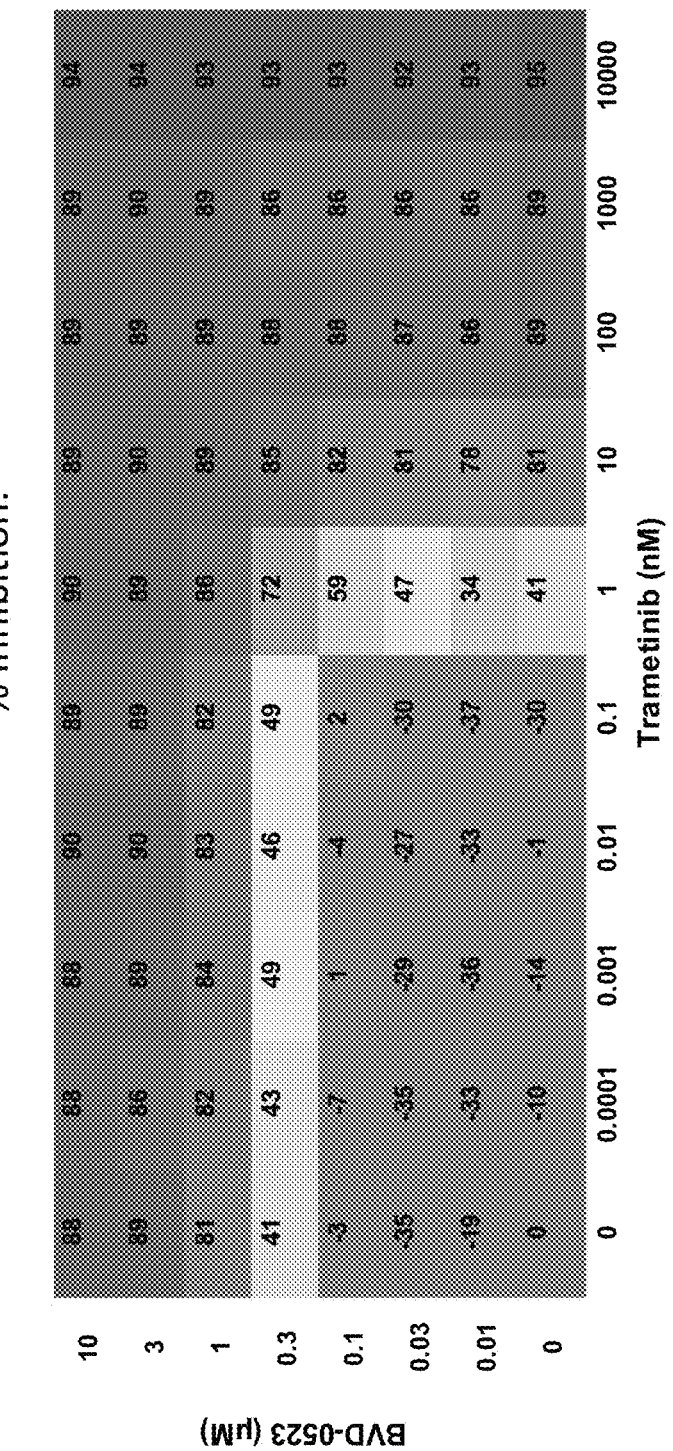
FIG. 14A is a dose matrix showing % inhibition of the trametinib/BVD-523 combination in A375 cells using the Alamar Blue cell viability assay.
Figure 14B:
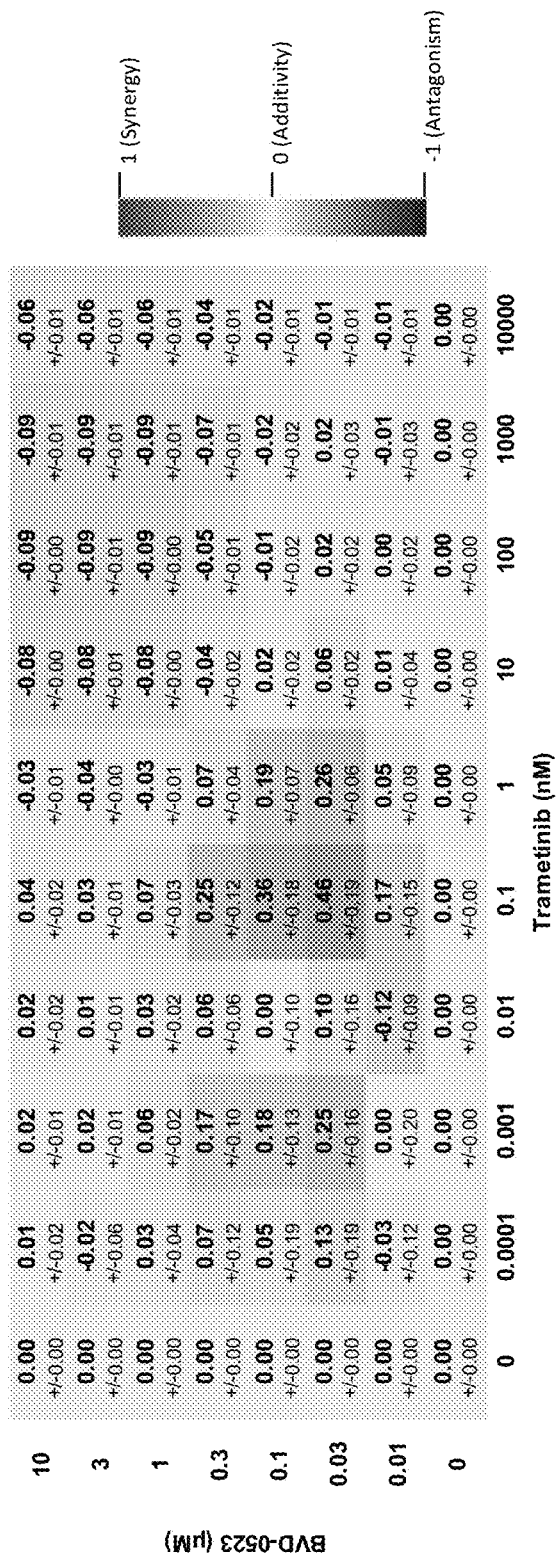
FIG. 14B is a dose matrix showing excess over Bliss for the trametinib/BVD-523 combination.
Figure 14D:
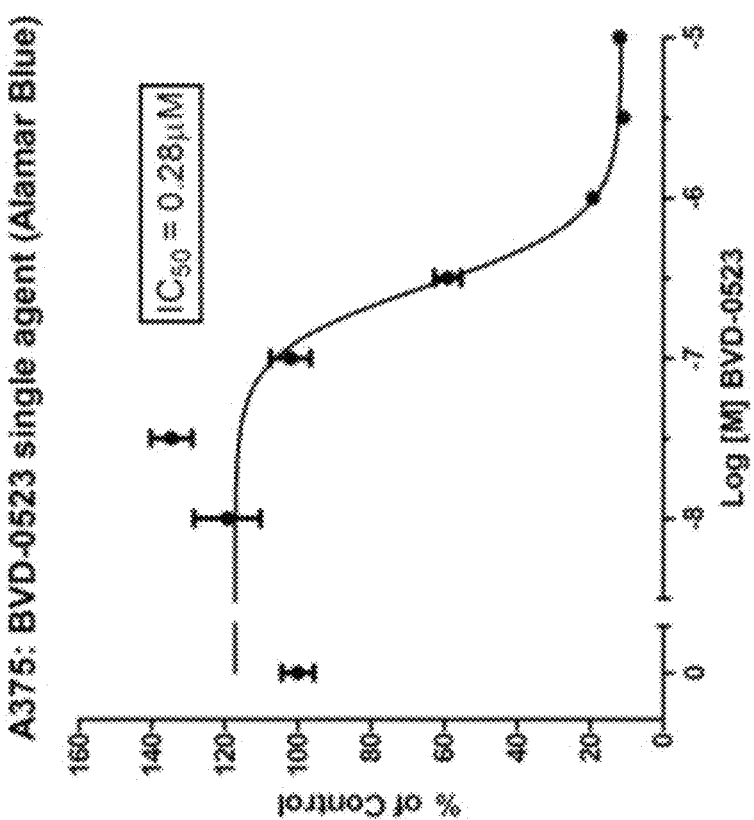
FIG. 14C and FIG. 14D show % viability relative to DMSO only treated controls for BVD-523 and trametinib single agent treatments in A375 cells using the Alamar Blue cell viability assay.
Figure 14C:
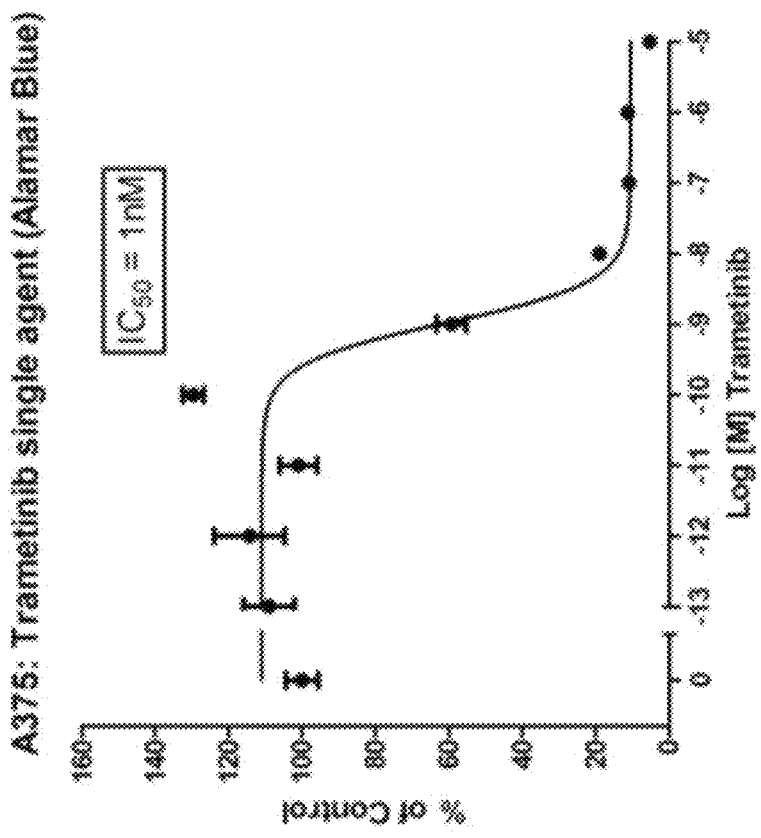
Figure 14E:
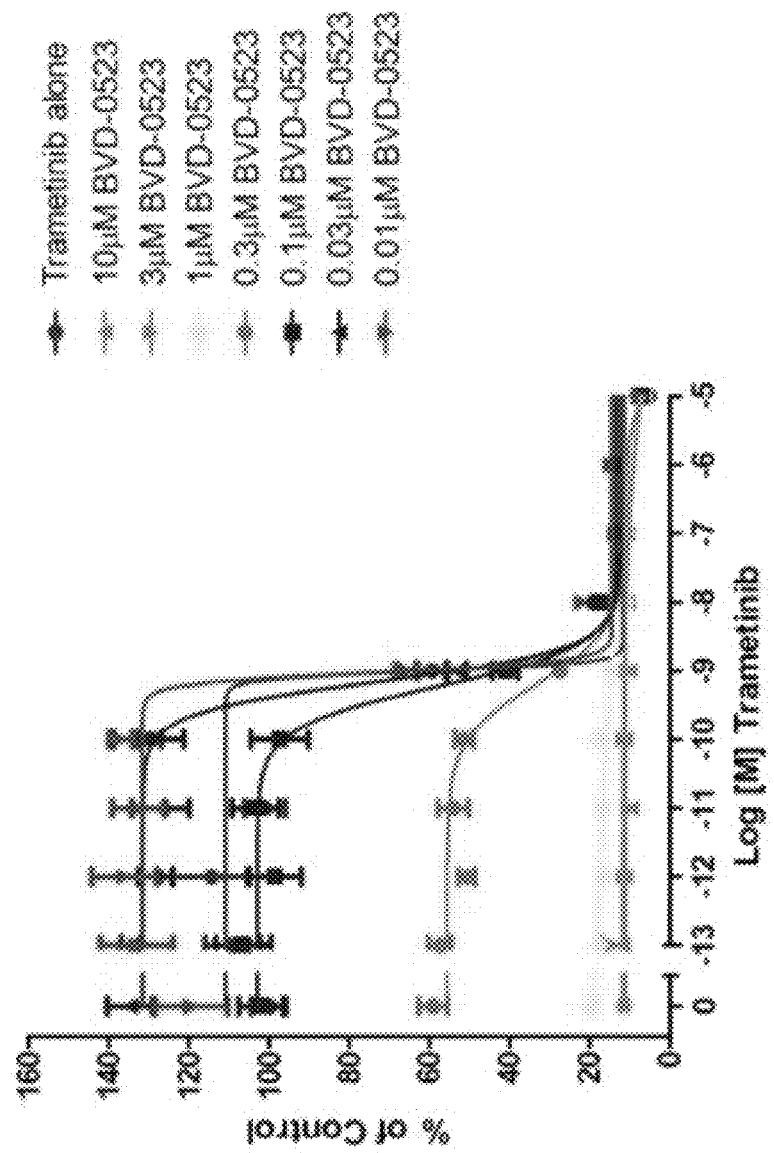
FIG. 14E shows % viability relative to DMSO only treated controls for BVD-523 and trametinib combination treatments in A375 cells using the Alamar Blue cell viability assay.
Figure 15A:
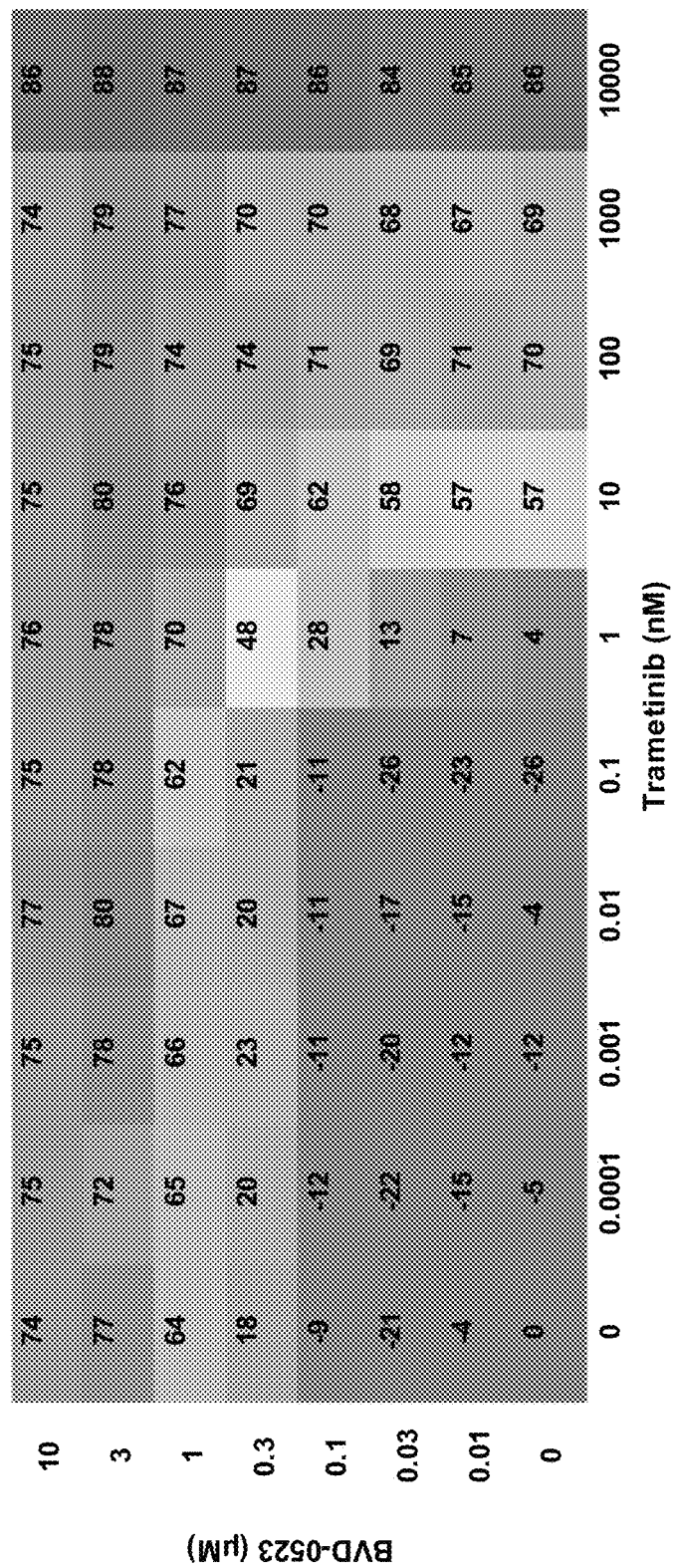
FIG. 15A is a dose matrix showing % inhibition of the trametinib/BVD-523 combination in A375 cells using the CellTiter-Glo cell viability assay.
Figure 15B:
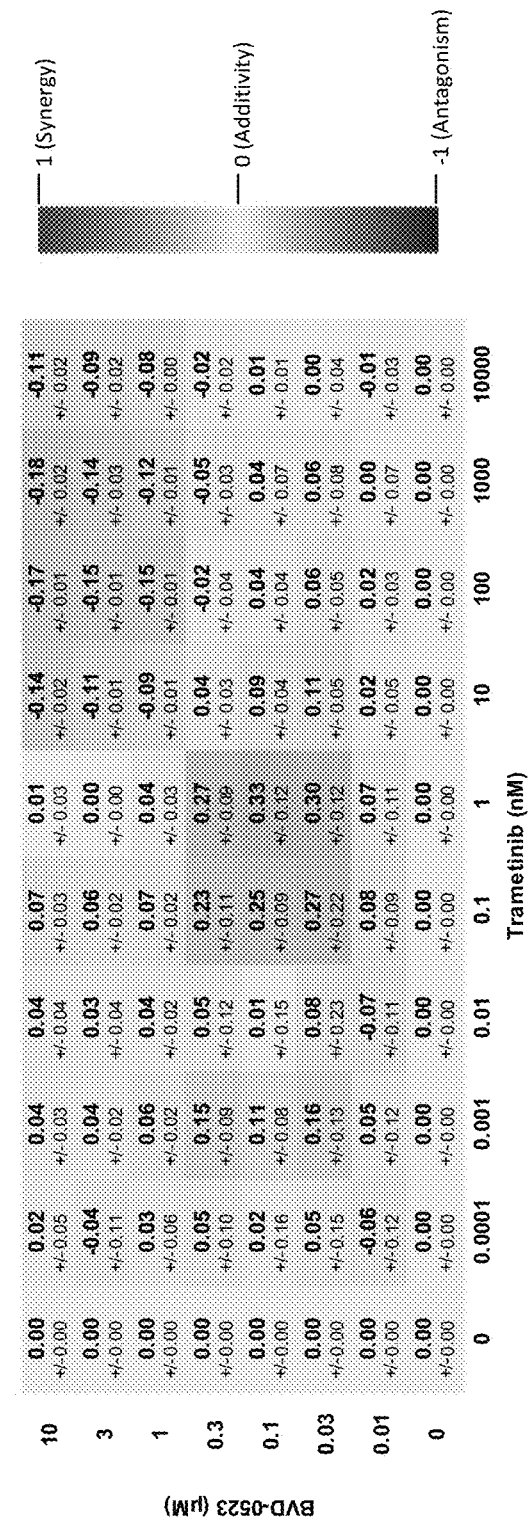
FIG. 15B is a dose matrix showing excess over Bliss for the trametinib/BVD-523 combination.
Figure 15D:
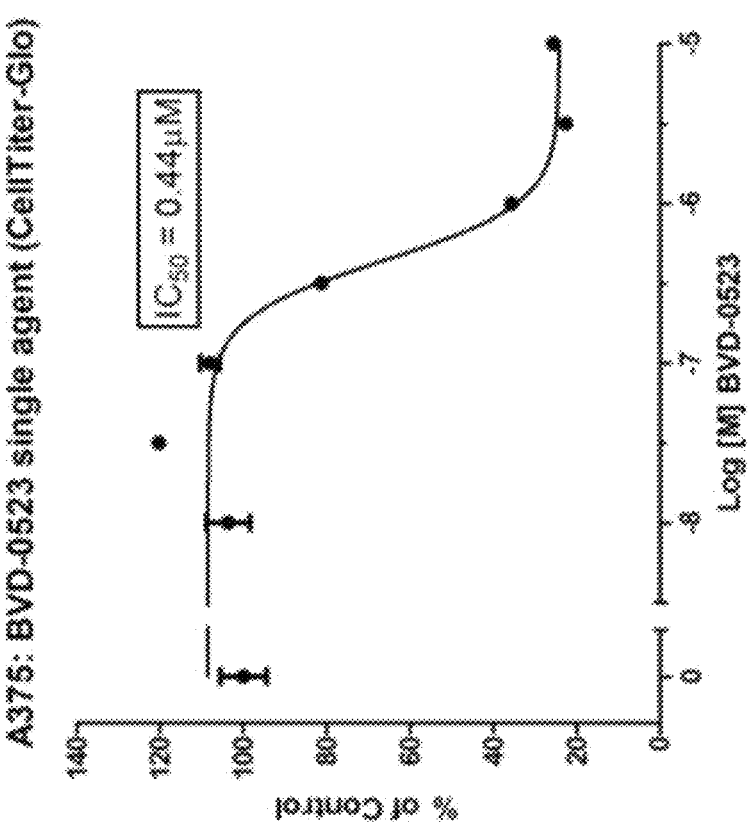
FIG. 15C and FIG. 15D show % viability relative to DMSO only treated controls for BVD-523 and trametinib single agent treatments in A375 cells using the CellTiter-Glo cell viability assay.
Figure 15C:
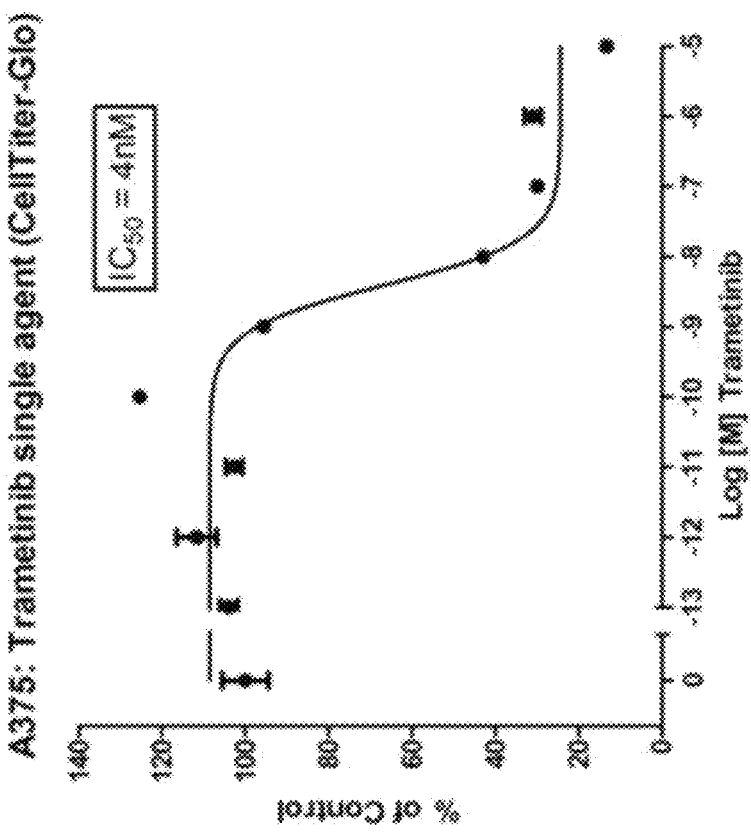
Figure 15E:
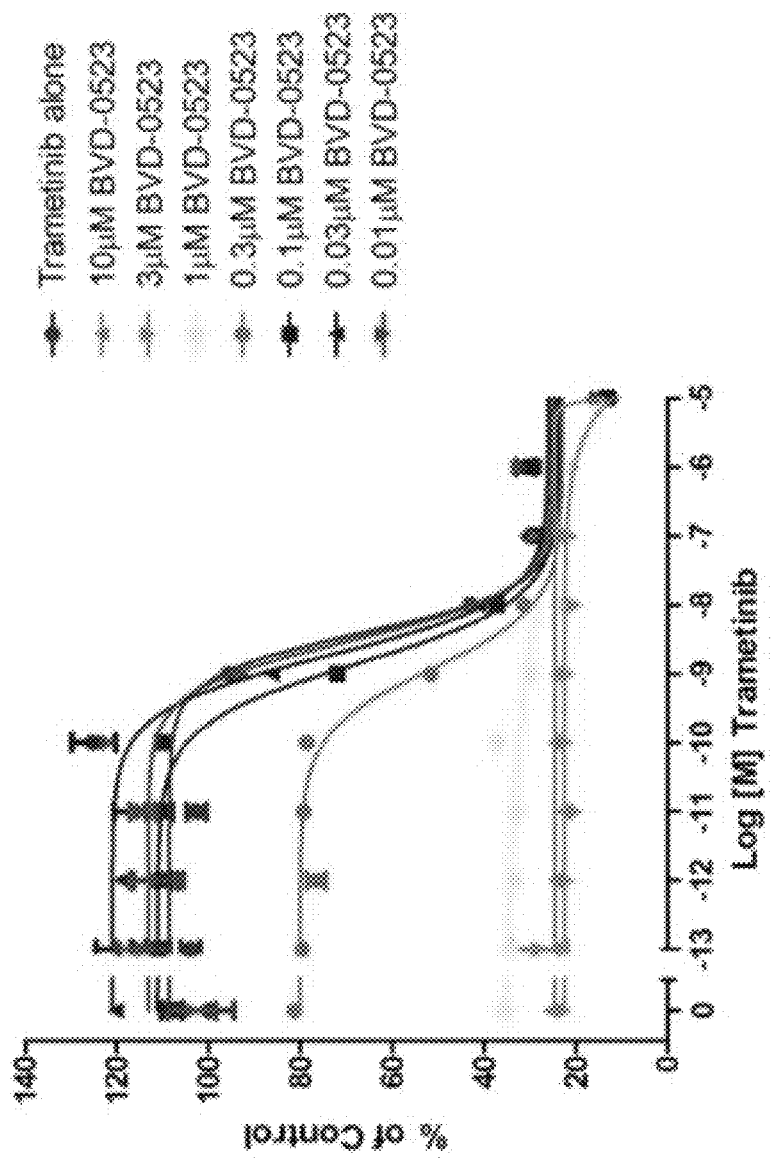
FIG. 15E shows % viability relative to DMSO only treated controls for BVD-523 and trametinib combination treatments in A375 cells using the CellTiter-Glo cell viability assay.
Figure 16A:
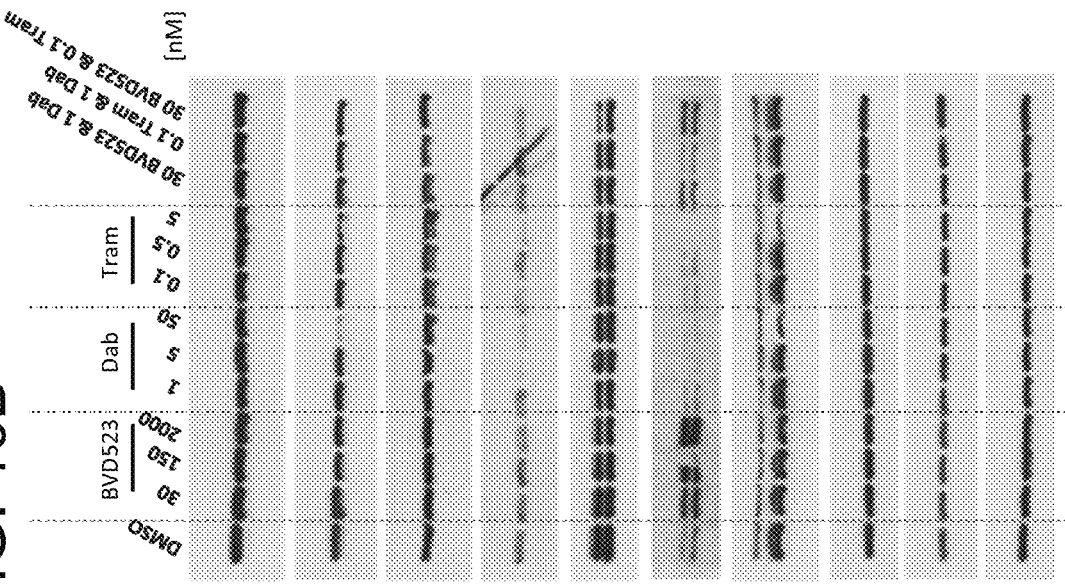
FIG. 16A-FIG. 16D are a set of images showing Western blot analysis of MAPK signaling in A375 cells after a 4 hour treatment with various concentrations (in nM) of BVD-523, dabrafenib (Dab), and Trametinib (Tram). 40 μg of total protein was loaded in each lane except where indicated otherwise. In this experiment, duplicate samples were collected.
Figure 16B:
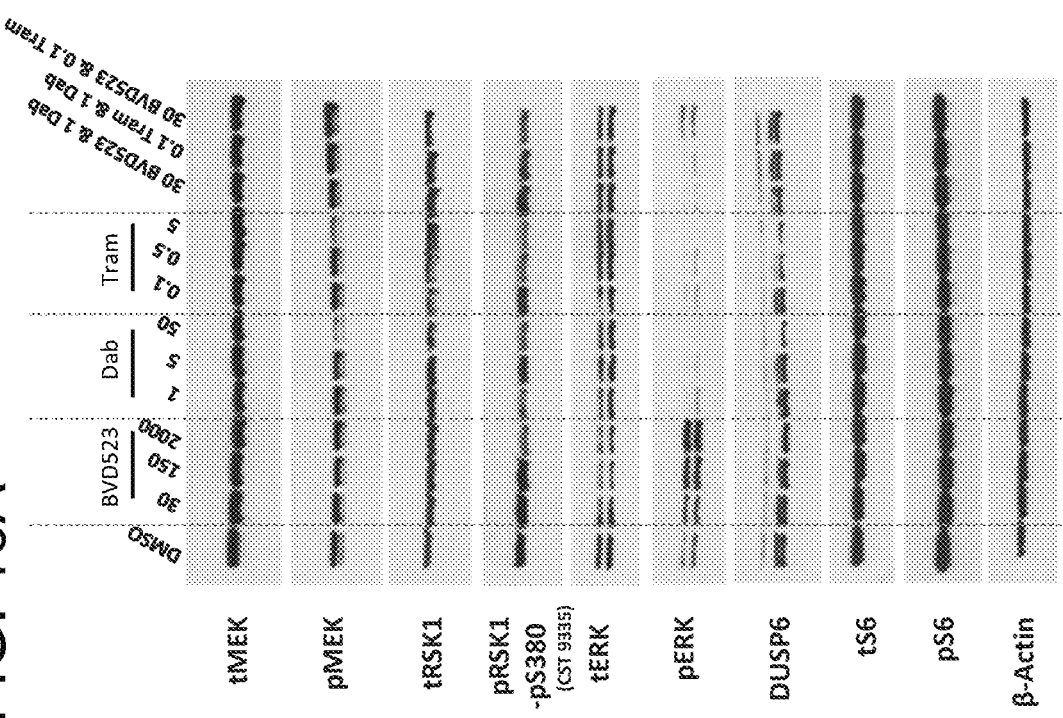
Figure 16D:
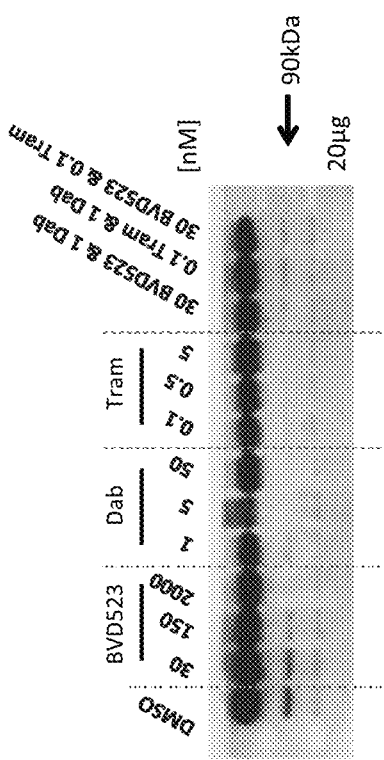
Figure 16C:
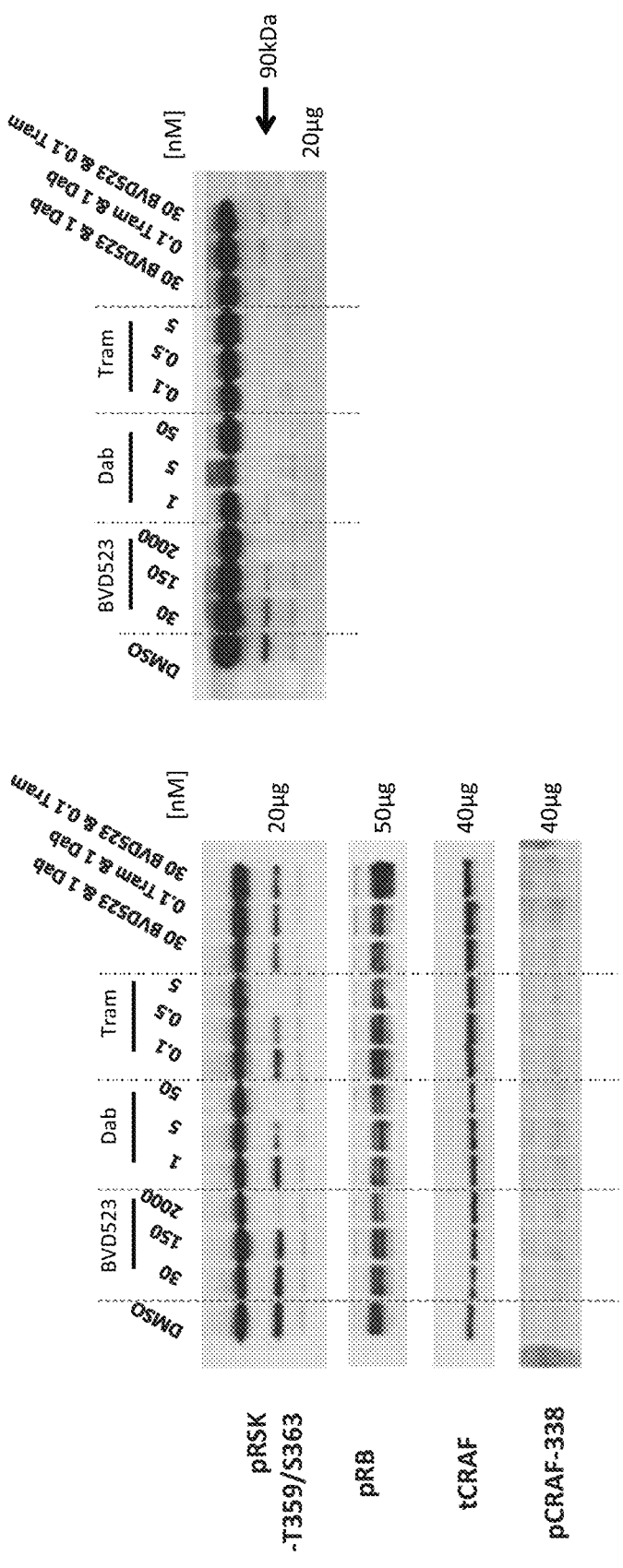
Figure 17A:
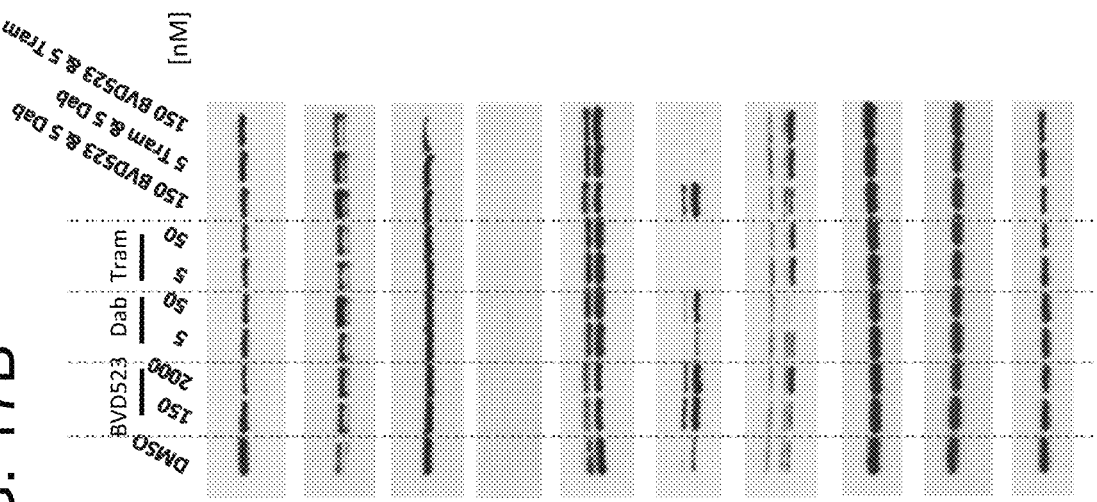
Figure 17B:
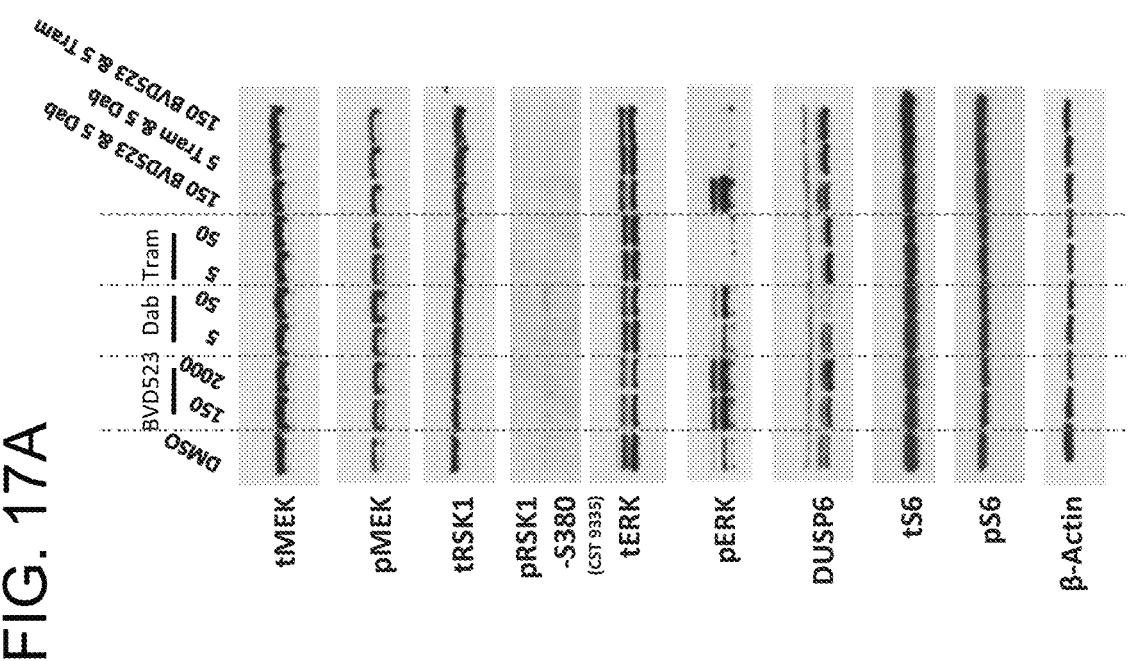

FIG. 7 shows an assessment of growth during the proliferation assay in DMSO control wells. FIG. 8A-FIG. 8D show results from month 3 of the studies. FIG. 9A-FIG. 9D show results from month 3 of the studies with a focus on single treatment cell lines.

Table 12 shows $IC_{50}$ data for month 3 of the studies. Relative $IC_{50}$s were determined from 4-parameter curve fits in Prism. $IC_{50}$ values were not determined for the cell line escalated with trametinib due to a lack of growth during the assay (ND: not done).

TABLE 12

$IC_{50}$ Data-Month 3

| | Cell Line, Relative $IC_{50}$ (nM) | | | | | | |
|---|---|---|---|---|---|---|---|
| Compound | Par* | Tram | Dab | BVD-523 | Dab/Tram | Dab/523 | Tram/523 |
| Dabrafenib | 2.1 | ND | 2.5 | 18.4 | 17.9 | 337 | 73 |
| Trametinib | 0.2 | ND | 0.4 | 1.7 | 2.7 | 90 | 11.2 |
| BVD-523 | 129 | ND | 198 | 433 | 323 | 1151 | 296 |
| Paclitaxel | 1.9 | ND | 1.9 | 6.5 | 4.7 | 4.2 | 8.9 |

*Par = Parental cell line

FIG. 19 shows single and combination agent escalation for month 3 of the studies. Cell line variants were obtained that could grow in the presence of dabrafenib or trametinib at concentrations greater than 100 times the $IC_{50}$ of these agents in parental A375 cell. In comparison, cell lines resistant to BVD-523 could only be maintained in less than 10× of parental $IC_{50}$ concentration. Sensitivity testing suggested dabrafenib and trametinib-resistant cell lines remained relatively sensitive to BVD-523; the increased $IC_{50}$ "shift" for BVD-523 in resistant cell lines was more modest than those corresponding $IC_{50}$ increases following dabrafenib or trametinib treatment. Likewise, compared to dabrafenib or trametinib treatment, more complete inhibition of cell growth was observed when resistant cell lines were treated with BVD-523 at concentrations 10-fold above its $IC_{50}$ in the parental A375 line. In total, patterns of resistance and cross-sensitivity suggest BVD-523 may remain effective in settings of acquired resistance.

Example 5

Combination Study Results

As expected, A375 cells, which carry a BRAF (V600E) mutation, were sensitive to dabrafenib. Single agent $IC_{50}$ values calculated using Alamar Blue (FIG. 10A-FIG. 10E, FIG. 12A-FIG. 12E, and FIG. 14A-FIG. 14E) were generally slightly lower for Dabrafenib and BVD-523 compared to those derived using CellTiter-Glo (FIG. 11A-FIG. 11E, FIG. 13A-FIG. 13E, and FIG. 15A-FIG. 15E). Published $IC_{50}$ values for Dabrafenib and Trametinib in a 72 hour CellTiter-Glo assay were 28±16 nM and 5±3 nM respectively (Greger et al., 2012; King et al., 2013)—the single agent results reported here are consistent with these values. There was some evidence for a window of synergy in all treatments. Variation between triplicates was low, however, there was some evidence of edge effects that likely explains the apparent enhanced growth observed in some treatments versus the no drug control (e.g. particularly apparent in the Trametinib/BVD-523 combination). This makes the interpretation of the Bliss analysis more challenging as in some treatments it may have resulted in the artefactual enhancement in the level of synergy.

The combination assays were repeated for A375 cells. Single agent BVD-523, Trametinib and Dabrafenib potencies were consistent with those reported in the previous studies disclosed herein.

In sum, taken together the data show that MEK and BRAF resistant cells could be overcome by treatment with the ERK inhibitor, BVD-523.

Example 6

BVD-523 Altered Markers of MAPK Kinase Activity and Effector Function

For Western blot studies, HCT116 cells (5×10$^6$) were seeded into 10 cm dishes in McCoy's 5A plus 10% FBS. A375 cells (2.5×10$^6$) were seeded into 10 cm dishes in DMEM plus 10% FBS. Cells were allowed to adhere overnight prior to addition of the indicated amount of test compound (BVD-523) or vehicle control. Cells were treated for either 4 or 24 hours before isolation of whole-cell protein lysates, as specified below. Cells were harvested by trypsinisation, pelleted and snap frozen. Lysates were prepared with RIPA (Radio-Immunoprecipitation Assay) buffer, clarified by centrifugation and quantitated by bicinchoninic acid assay (BCA) assay. 20-50 μg of protein was resolved by SDS-PAGE electrophoresis, blotted onto PVDF membrane and probed using the antibodies detailed in Table 13 (for the 4-hour treatment) and Table 14 (for the 24-hour treatment) below.

TABLE 13

Antibody Details

| Antigen | Size (kDa) | Supplier | Cat No | Dilution | Incubation/ Block Conditions | Secondary |
|---|---|---|---|---|---|---|
| pRSK1/2 p5380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/5363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| pMEK1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| pS6-pS235 | 32 | Cell Signaling | 2211S | 1:3000 | o/n 4° C. 5% milk | anti-rabbit |
| Total S6 | 32 | Cell Signaling | 2217 | 1:2000 | o/n 4° C. 5% milk | anti-rabbit |
| DUSP6 | 48 | Cell Signaling | 3058S | 1:1000 | o/n 4° C. 5% BSA | anti-rabbit |
| Total CRAF | 73 | BD Biosciences | 610152 | 1:2000 | o/n 4° C. 5% milk | anti-mouse |
| pCRAF-Ser338 | 73 | Cell Signaling | 9427 | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| β-Actin | 42 | Sigma | A5441 | 1:500,000 | o/n 4° C. 5% milk | anti-mouse |

TABLE 14

Antibody details

| Antigen | Size (kDa) | Supplier | Cat No | Dilution | Incubation/ Block Conditions | Secondary |
|---|---|---|---|---|---|---|
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| Bim-EL | 23 | Millipore | AB17003 | 1:1000 | o/n 4° C. 5% BSA | anti-rabbit |
| Bim-EL | 23 | Cell Signaling | 2933 | 1:1000 | o/n 4° C. 5% BSA | anti-rabbit |
| BCL-xL | 30 | Cell Signaling | 2762 | 1:2000 | o/n 4° C. 5% BSA | anti-rabbit |
| PARP | 116/89 | Cell Signaling | 9542 | 1:1000 | o/n 4° C. 5% milk | anti-rabbit |
| Cleaved Caspase 3 | 17,19 | Cell Signaling | 9664X | 1:1000 | o/n 4° C. 5% milk | anti-rabbit |
| DUSP6 | 48 | Cell Signaling | 3058S | 1:1000 | o/n 4° C. 5% BSA | anti-rabbit |
| pRSK1/2 pS380 | 90 | Cell Signaling | 9335 | 1:1000 | o/n 4° C. 5% BSA | anti-rabbit |
| pRSK1/2 pS380 | 90 | Cell Signaling | 11989 | 1:2000 | o/n 4° C. 5% BSA | anti-rabbit |
| pRSK-T359/5363 | 90 | Millipore | 04-419 | 1:40000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |
| B-Actin | 42 | Sigma | A5441 | 1:500,000 | o/n 4° C. 5% milk | anti-mouse |

FIG. 16A-FIG. 16D, FIG. 17A-FIG. 17D, and FIG. 18A-FIG. 18D show Western blot analyses of cells treated with BVD-523 at various concentrations for the following: 1) MAPK signaling components in A375 cells after 4 hours; 2) cell cycle and apoptosis signaling in A375 24 hours treatment with various amounts of BVD-523; and 3) MAPK signaling in HCT-116 cells treated for 4 hours. The results show that acute and prolonged treatment with BVD-523 in RAF and RAS mutant cancer cells in-vitro affects both substrate phosphorylation and effector targets of ERK kinases. The concentrations of BVD-523 required to induce these changes is typically in the low micromolar range.

Changes in several specific activity markers are noteworthy. First, the abundance of slowly migrating isoforms of ERK kinase increase following BVD-523 treatment; modest changes can be observed acutely, and increase following prolonged treatment. While this could indicate an increase in enzymatically active, phosphorylated forms of ERK, it remains noteworthy that multiple proteins subject to both direct and indirect regulation by ERK remain "off" following BVD-523 treatment. First, RSK1/2 proteins exhibit reduced phosphorylation at residues that are strictly dependent on ERK for protein modification (T359/5363). Second, BVD-523 treatment induces complex changes in the MAPK feedback phosphatase, DUSP6: slowly migrating protein isoforms are reduced following acute treatment, while total protein levels are greatly reduced following prolonged BVD-523 treatment. Both of these findings are consistent with reduced activity of ERK kinases, which control DUSP6 function through both post-translational and transcriptional mechanisms. Overall, despite increases in cellular forms of ERK that are typically thought to be active, it appears likely that cellular ERK enzyme activity is fully inhibited following either acute or prolonged treatment with BVD-523.

Consistent with these observations, effector genes that require MAPK pathway signaling are altered following treatment with BVD-523. The G1/S cell-cycle apparatus is regulated at both post-translational and transcriptional levels by MAPK signaling, and cyclin-D1 protein levels are greatly reduced following prolonged BVD-523 treatment. Similarly, gene expression and protein abundance of apoptosis effectors often require intact MAPK signaling, and total levels of Bim-EL increase following prolonged BVD-523 treatment. As noted above, however, PARP protein cleavage and increased apoptosis were not noted in the A375 cell background; this suggests that additional factors may influence whether changes in BVD-523/ERK-dependent effector signaling are translated into definitive events such as cell death and cell cycle arrest.

Consistent with the cellular activity of BVD-523, marker analysis suggests that ERK inhibition alters a variety of molecular signaling events in cancer cells, making them susceptible to both decreased cell proliferation and survival.

In sum, FIG. 16A-FIG. 16D, FIG. 17A-FIG. 17D, and FIG. 18A-FIG. 18D show that BVD-523 inhibits the MAPK signaling pathway and may be more favorable compared to RAF or MEK inhibition in this setting.

Finally, properties of BVD-523 may make this a preferred agent for use as an ERK inhibitor, compared to other agents with a similar activity. It is known that kinase inhibitor drugs display unique and specific interactions with their enzyme targets, and that drug efficacy is strongly influenced by both the mode of direct inhibition, as well as susceptibility to adaptive changes that occur following treatment. For example, inhibitors of ABL, KIT, EGFR and ALK kinases are effective only when their cognate target is found in active or inactive configurations. Likewise, certain of these inhibitors are uniquely sensitive to either secondary genetic mutation, or post-translational adaptive changes, of the protein target. Finally, RAF inhibitors show differential potency to RAF kinases present in certain protein complexes and/or subcellular localizations. In summary, as ERK kinases are similarly known to exist in diverse, variable, and complex biochemical states, it appears likely that BVD-523 may interact with and inhibit these targets in a fashion that is distinct and highly preferable to other agents.

Example 7

Effects of BVD-523 and Benchmark ERK BRAF and MEK Inhibitors on Viability and MAPK Signalling Single Agent Proliferation Assay Cells were seeded in 96-well plates at the densities indicated in Table 15 in McCoy's 5A containing 10% FBS and allowed to adhere overnight prior to addition of compound or vehicle control. Compounds were prepared from DMSO stocks to give the desired final concentrations. The final DMSO concentration was constant at 0.1%. Test compounds were incubated with the cells for 96 h at 37° C., 5% $CO_2$ in a humidified atmosphere. CellTiter-Glo® reagent (Promega, Madison, Wis.) was added according to manufacturer's instructions and luminescence detected using the BMG FLUOstar plate reader (BMG Labtech, Ortenberg, Germany). The average media only background value was deducted and the data analysed using a 4-parameter logistic equation in GraphPad Prism (GraphPad Software, La Jolla, Calif.).

Combination Proliferation Assay

Cells were seeded into triplicate 96-well plates at the densities indicated in Table 15 in McCoy's 5A containing 10% FBS and allowed to adhere overnight prior to addition of test compound or vehicle control. Combinations were tested using a 10×8 dose matrix. The final DMSO concentration was constant at 0.2%.

Test compounds were incubated with the cells for 96 h at 37° C., 5% $CO_2$ in a humidified atmosphere. Cells were stained with Hoechst stain and fluorescence detected as described above. The average media only background value was deducted and the data analysed.

Combination interactions across the dose matrix were determined by the Loewe Additivity and Bliss independence models using Chalice™ Combination Analysis Software (Horizon Discovery Group, Cambridge, Mass.) as outlined in the user manual (available at chalice.horizondiscovery.com/chalice-portal/documentation/analyzer/home.jsp). Synergy is determined by comparing the experimentally observed level of inhibition at each combination point with the value expected for additivity, which is derived from the single-agent responses along the edges of the matrix. Potential synergistic interactions were identified by displaying the calculated excess inhibition over that predicted as being additive across the dose matrix as a heat map, and by reporting a quantitative 'Synergy Score' based on the Loewe model. The single agent data derived from the combination assay plates were presented as dose-response curves generated in Chalice™.

TABLE 15

Cell Line Seeding Density

| Cell Line | Seeding density (cells/well) | | |
|---|---|---|---|
| | 96-well Proliferation | 6-Well Western | 10 cm dish Westerns |
| RKO Parental | 1000 | $1 \times 10^6$ | $2.9 \times 10^6$ |
| RKO MEK1 (Q56P/+) Clone 1 | 1250 | Not tested | Not tested |
| RKO MEK1 (Q56P/+) Clone 2 | 1000 | $7.5 \times 10^5$ | $2 \times 10^6$ |

Western Blotting

Cells were seeded into 6-well plates (Experiment 1) or 10 cm dishes (Experiment 2) at the densities indicated in Table 15 in McCoy's 5A containing 10% FBS and allowed to adhere overnight prior to addition of compound or vehicle control. Test compounds were added and incubated with the cells for 4 or 24 h at 37° C., 5% $CO_2$ in a humidified atmosphere. Cells were harvested by trypsinisation, pelleted by centrifugation and snap frozen on dry ice.

Lysates were prepared using RIPA buffer (50 mM Tris-hydrochloride, pH 8.0; 150 mM sodium chloride; 1.0% Igepal CA-630 (NP-40); 0.5% sodium deoxycholate; 0.1% sodium dodecyl sulphate; 1× complete EDTA-free protease inhibitor cocktail (Roche, Nutley, N.J.; cat 05 892 791 001); 1× phosSTOP phosphatase inhibitor cocktail (Roche Nutley, N.J.; cat. 04 906 837 001)) and clarified by centrifugation at 11,000 rpm for 10 min in a bench-top centrifuge.

Total protein in the lysates was quantitated by BCA assay according to the manufacturer's instructions (Pierce™ BCA Protein Assay Kit; Thermo Scientific, Waltham, Mass.; cat. 23225), boiled in sample buffer (NuPAGE LDS Sample Buffer; (Invitrogen, Carlsbad, Calif.; cat. NP0007)) and stored at −80° C.

Equal amounts of protein (40 μg) were resolved on NuPAGE 4-12% Bis-Tris gels (Invitrogen, Carlsbad, Calif.; cat. WG1402BOX) and blotted onto PVDF membranes using iBlot gel transfer stacks (Invitrogen, Carlsbad, Calif.; cat. IB4010-01) on an iBlot gel transfer device (Invitrogen Carlsbad, Calif.) according to the manufacturer's instructions.

Blots were probed using the antibodies and block conditions detailed in Table 16. Western blots were developed using Pierce™ ECL2 Western blotting substrate (Thermo Scientific, Waltham, Mass.; cat. 80196) and imaged using a FluorChem M Western blot imager (ProteinSimple, San Jose, Calif.).

TABLE 16

Antibodies and Western Blotting Conditions

| Antigen | Size (kDa) | Supplier | Cat No | Dilution | Incubation/block Conditions | Secondary |
|---|---|---|---|---|---|---|
| pRSK-T359/S363 | 90 | Millipore | 04-419 | 1:20000 | o/n 4° C. 5% BSA | anti-rabbit |
| Total RSK | 90 | Cell Signaling | 9333 | 1:1000 | o/n 4° C. 5% BSA | anti-rabbit |
| pErk 1/2 | 42/44 | Cell Signaling | 9106S | 1:500 | o/n 4° C. 5% milk | anti-mouse |
| Total ERK | 42/44 | Cell Signaling | 9102 | 1:2000 | o/n 4° C. 5% milk | anti-rabbit |

TABLE 16-continued

Antibodies and Western Blotting Conditions

| Antigen | Size (kDa) | Supplier | Cat No | Dilution | Incubation/block Conditions | Secondary |
|---|---|---|---|---|---|---|
| pMEK 1/2 | 45 | Cell Signaling | 9154 | 1:1000 | o/n 4° C. 5% BSA | anti-rabbit |
| Total MEK | 45 | Cell Signaling | 9126 | 1:1000 | o/n 4° C. 5% BSA | anti-rabbit |
| DUSP6 | 48 | Cell Signaling | 3058S | 1:1000 | o/n 4° C. 5% BSA | anti-rabbit |
| pRB (Ser780) | 105 | Cell Signaling | 9307 | 1:2000 | o/n 4° C. 5% BSA | anti-rabbit |
| CCND1 | 34 | Abcam | ab6152 | 1:500 | o/n 4° C. 5% milk | anti-mouse |
| B-Actin | 42 | Sigma | A5441 | 1:100,000 | o/n 4° C. 5% milk | anti-mouse |
| Anti-rabbit HRP-conjugated secondary | — | Cell Signaling | 7074S | 1:2000 | 1 h room temp; Block matched to primary Antibody | — |
| Anti-mouse HRP-conjugated secondary | — | Cell Signaling | 7076 | 1:5000 | 1 h room temp; Block matched to primary Antibody | — |

The MEK1 (Q56P) mutation exemplifies a class of clinically relevant MEK1/2 activating mutations known to upregulate the MAPK pathway and drive acquired resistance to BRAF or MEK inhibitors.

This study used a pair of RKO BRAF(V600E) cell lines that are isogenic for the presence or absence of a MEK1 (Q56P) activating mutation, to assess the effect that activating MEK mutations have in response to the novel ERK inhibitor BVD-523 versus other benchmark MAPK inhibitors.

Effects of on cell viability were assessed by quantitating cellular ATP levels using CellTiter-Glo® after 96 h. Single agent assays demonstrated that the double mutant BRAF (V600E)::MEK1(Q56P) cells displayed a markedly reduced sensitivity to inhibition with benchmark clinical BRAF (exemplified by Dabrafenib) or MEK (exemplified by Trametinib) inhibitors relative to the parental BRAF(V600E) cells, which demonstrates the suitability of this isogenic model for recapitulating the acquired resistance known to be associated with this class of mutation in the clinic (Table 17).

TABLE 17

Single Agent $IC_{50}$ Values

| Compound | RKO Parental | RKO MEK1 Q56P/+ Cl.1 | RKO MEK1 Q56P/+ Cl.2 |
|---|---|---|---|
| BVD-523 | 0.20 | 0.17 | 0.18 |
| SCH772984 | 0.04 | 0.14 | 0.12 |
| Dabrafenib | n.d. | n.d. | n.d. |
| Trametinib | 0.006 | 0.093 | 0.080 |
| Paclitaxel | 0.002 | 0.002 | 0.002 | n.d.—not determined, only a partial dose response achieved

In contrast, response to BVD-523 was identical in both the parental and double mutant cells, indicating that BVD-523 is not susceptible to this mechanism of acquired resistance.

These results were identical in two independently derived double mutant BRAF(V600E)::MEK1(Q56P) cell line clones confirming that these differences in response versus the parental cells were specifically related to the presence of the MEK1 mutation rather than an unrelated clonal artifact (FIG. 22A-FIG. 22E). Similar results were also observed with a second mechanistically distinct benchmark ERK inhibitor (SCH772984), which supports the notion that these observations are specifically related to inhibition of ERK and not due to an off-target effect.

The effect of combining BVD-523 with a BRAF inhibitor (exemplified by Dabrafenib) was also assessed in these cell lines across a matrix of concentrations using the Loewe Addivity or Bliss Independence models with Horizon's Chalice™ combination analysis software (FIG. 23-FIG. 23O and FIG. 24A-FIG. 24O). The presence of potentially synergistic interactions was then assessed by displaying the calculated excess inhibition over that predicted as being additive across the dose matrix as a heat map, and by calculating a 'Volume Score' that shows whether the overall response to a combination is synergistic (positive values), antagonistic (negative values) or additive (~0).

Figure 25A:
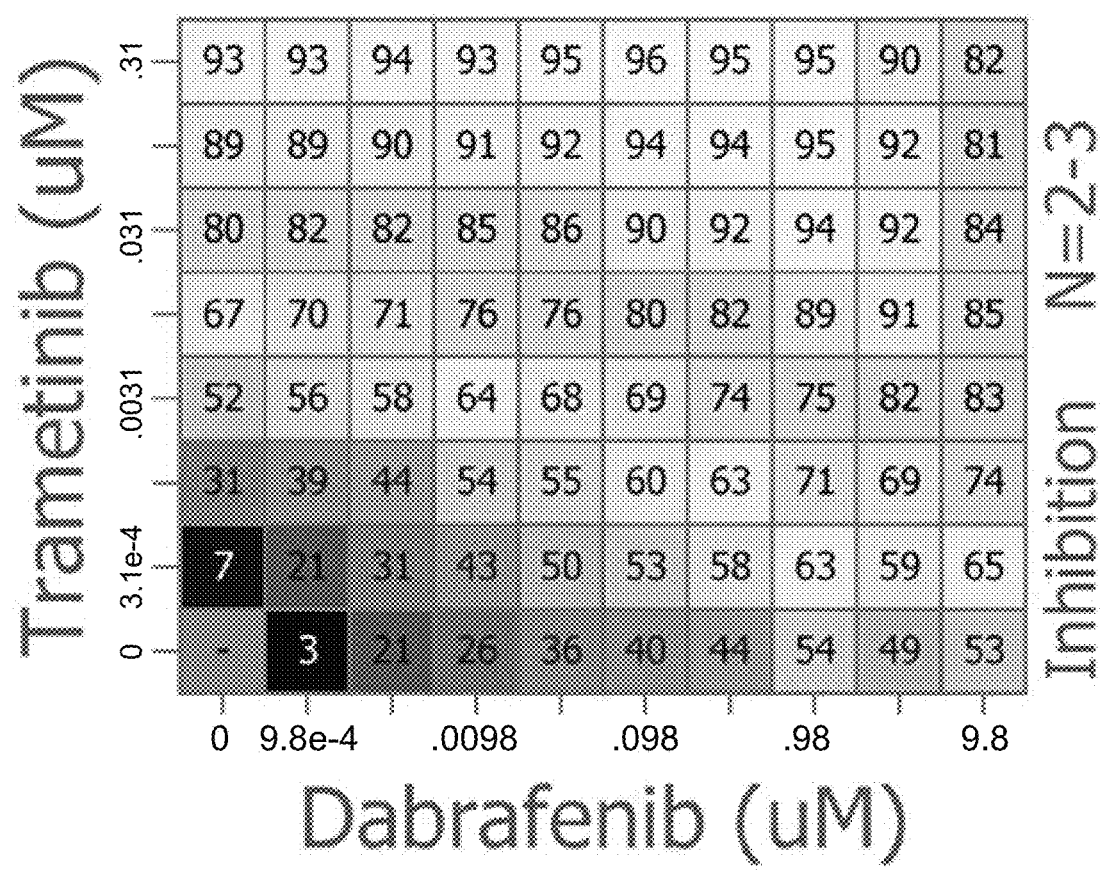
FIG. 25A-FIG. 25O show the results of the combination of Trametinib and Dabrafenib.
Figure 25B:
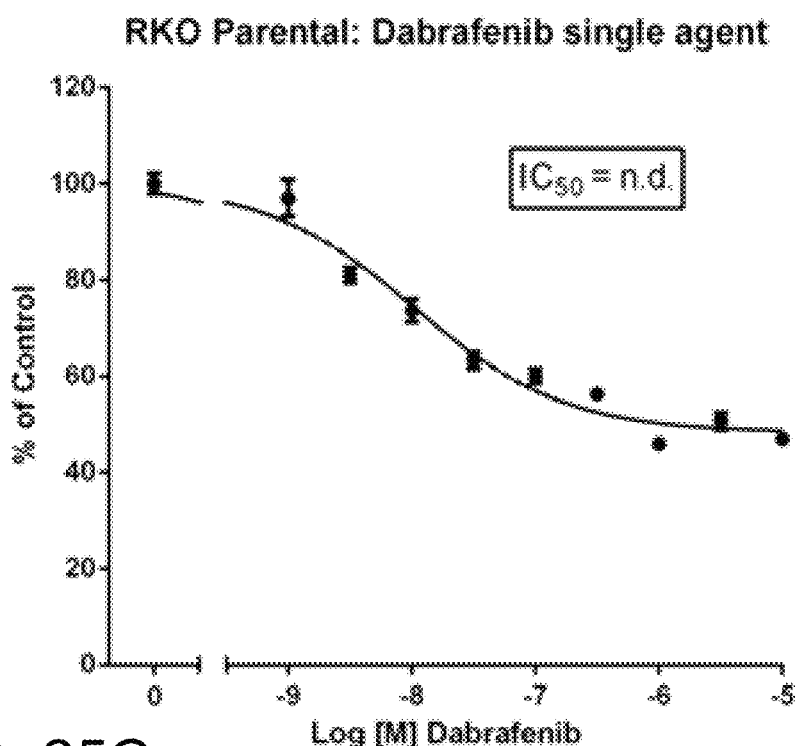
FIG. 25B-FIG. 25C show the results of single agent proliferation assays for the combination in FIG. 25A.
Figure 25C:
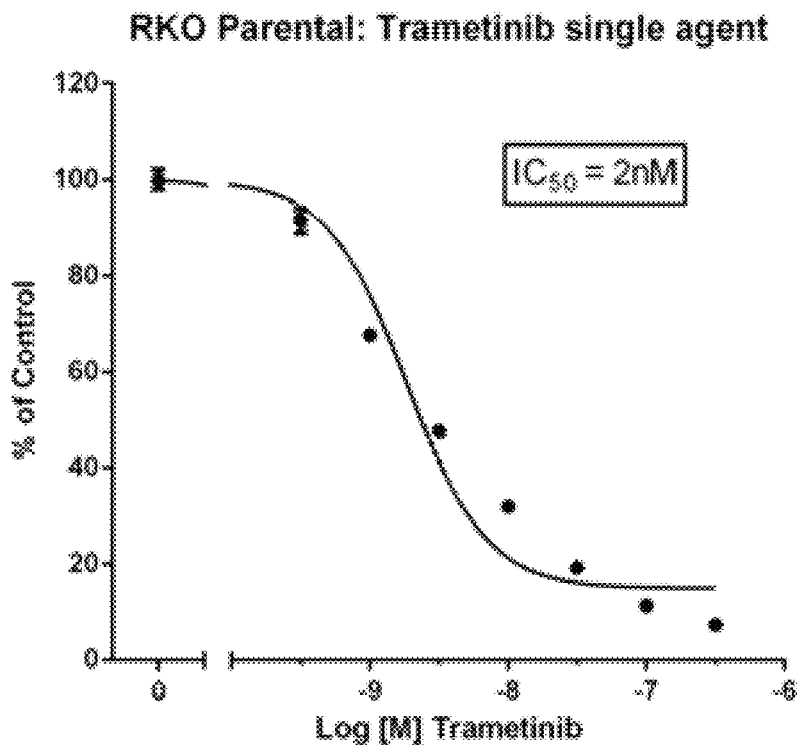
Figure 25D:
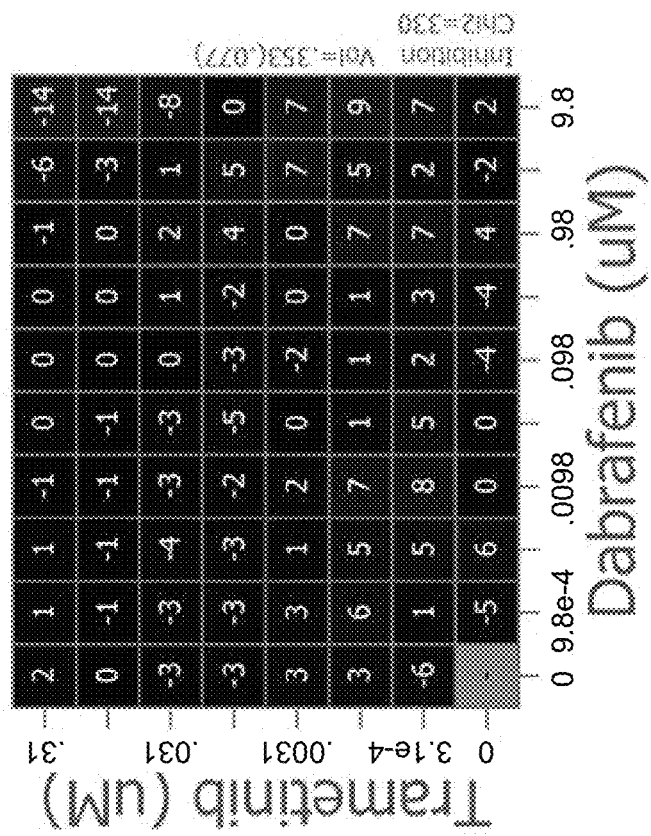
FIG. 25D shows Loewe excess for the combination in FIG. 25A
Figure 25E:
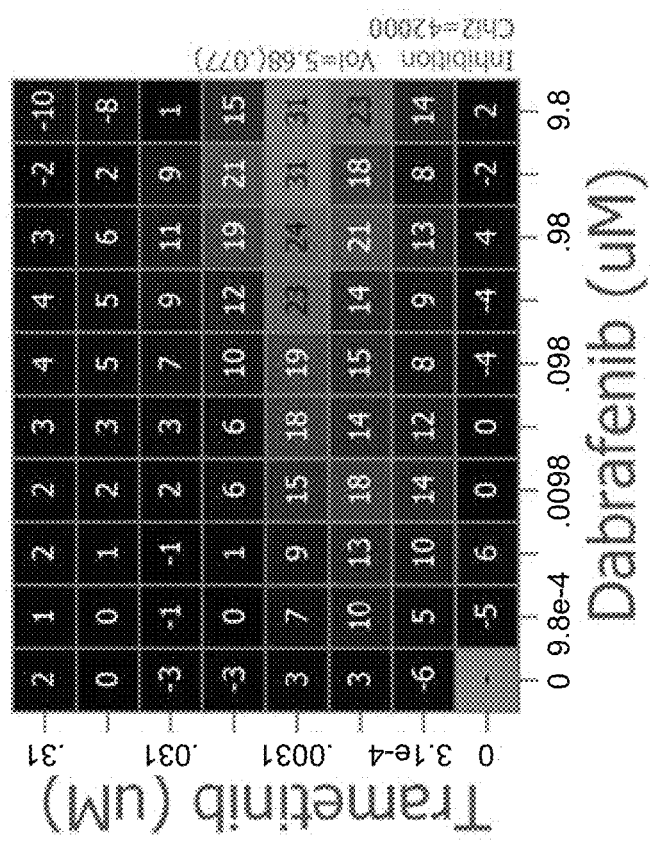
FIG. 25E shows Bliss excess for the combination in FIG. 25A.
Figure 25F:
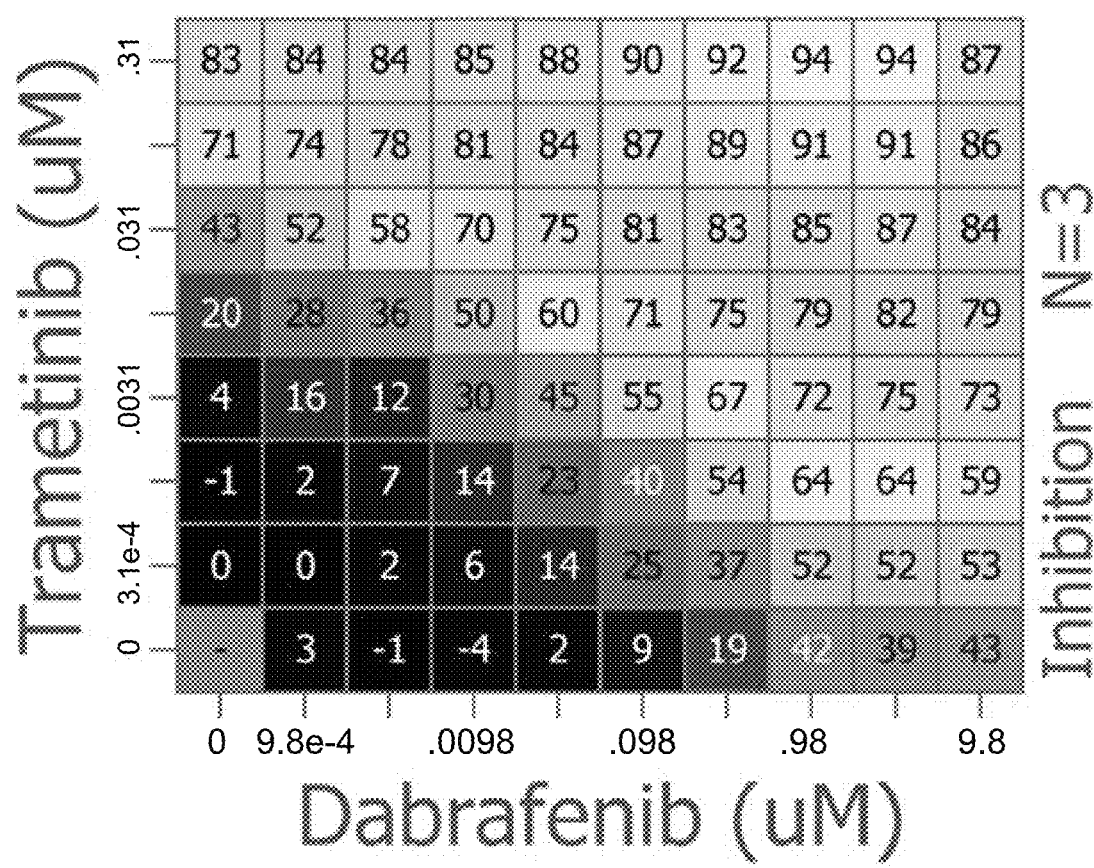
FIG. 25F shows a dose matrix showing inhibition (%) for the combination in RKO MEK1 (Q56P/+)-clone 1 cells.
Figure 25G:
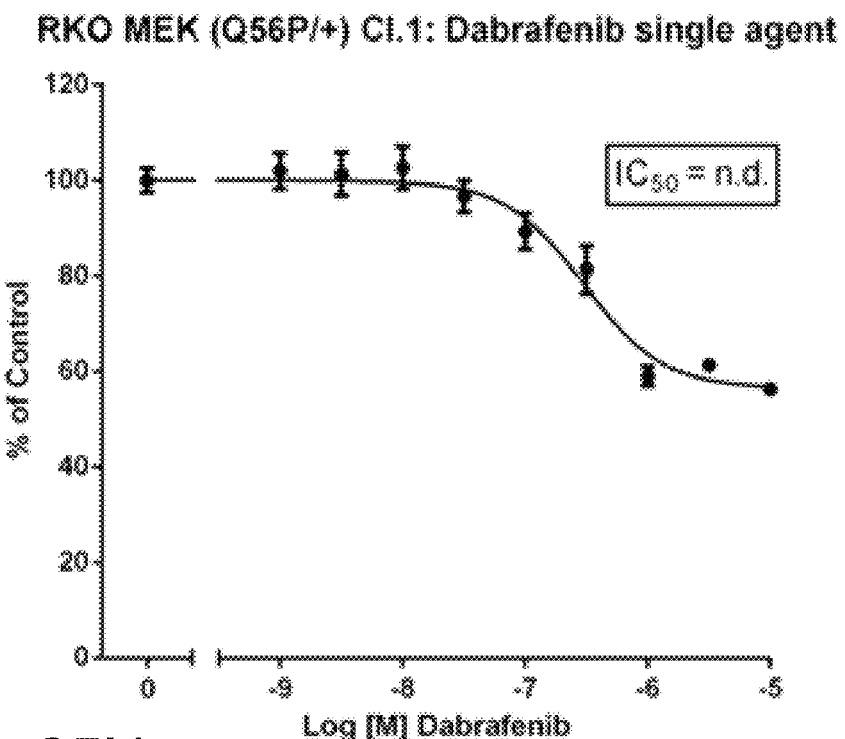
FIG. 25G-FIG. 25H show the results of single agent proliferation assays for the combination in FIG. 25F.
Figure 25H:
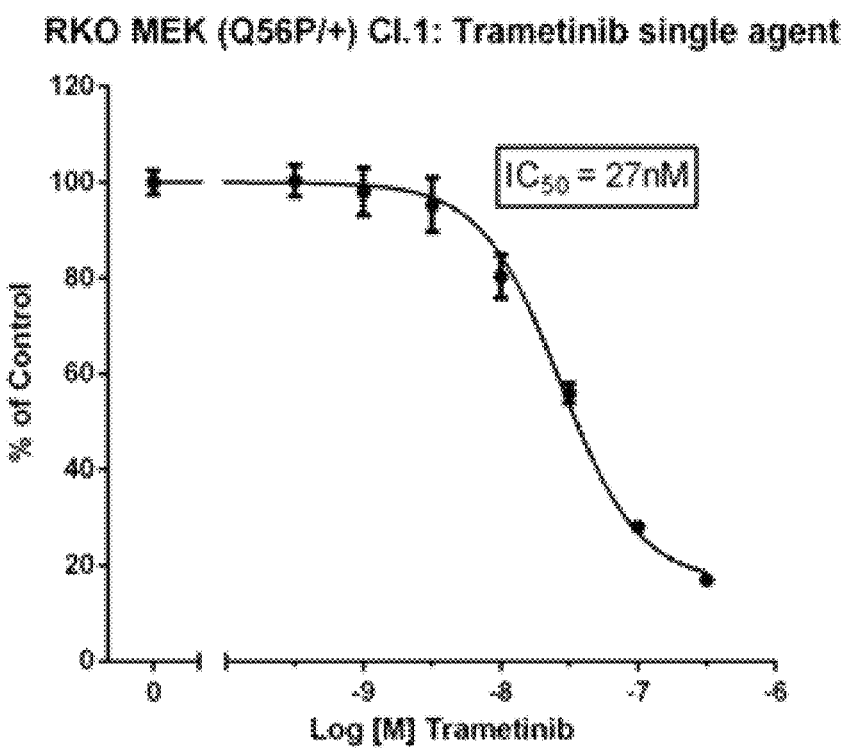
Figures 25I, 25J:
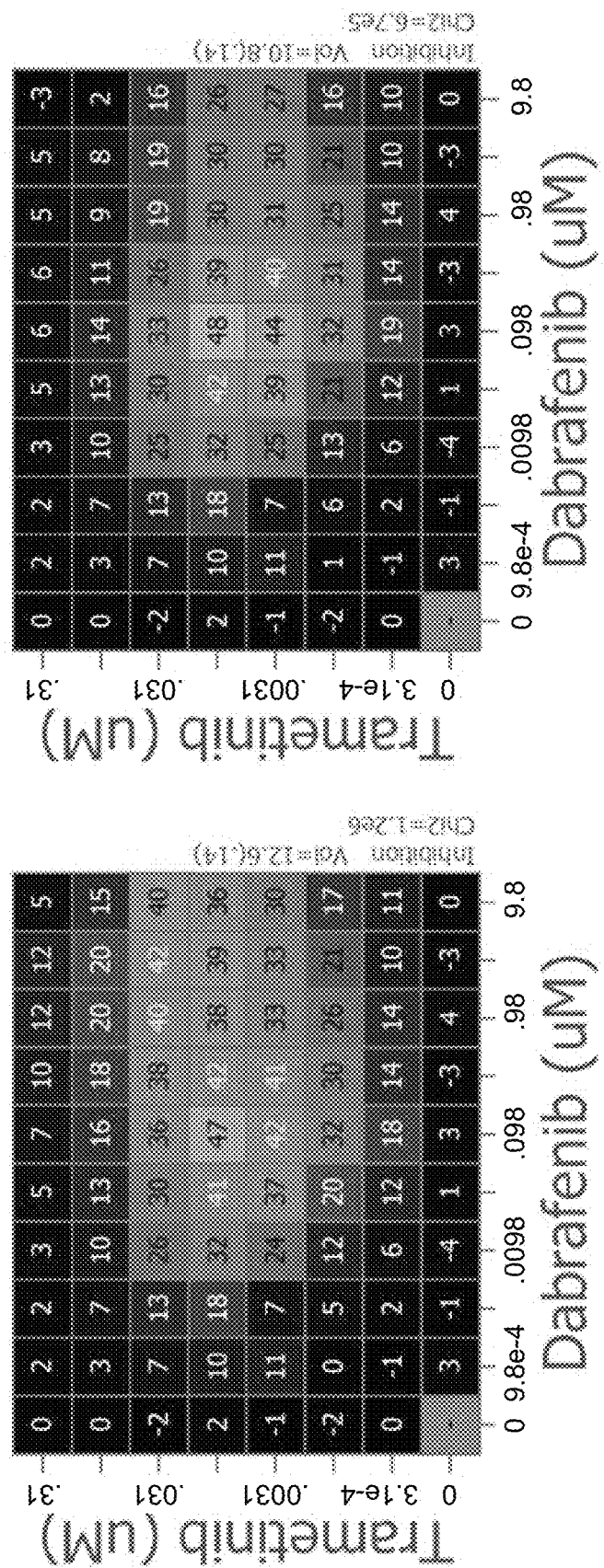
FIG. 25I shows Loewe excess for the combination in FIG. 25F
FIG. 25J shows Bliss excess for the combination in FIG. 25F.
Figure 25K:
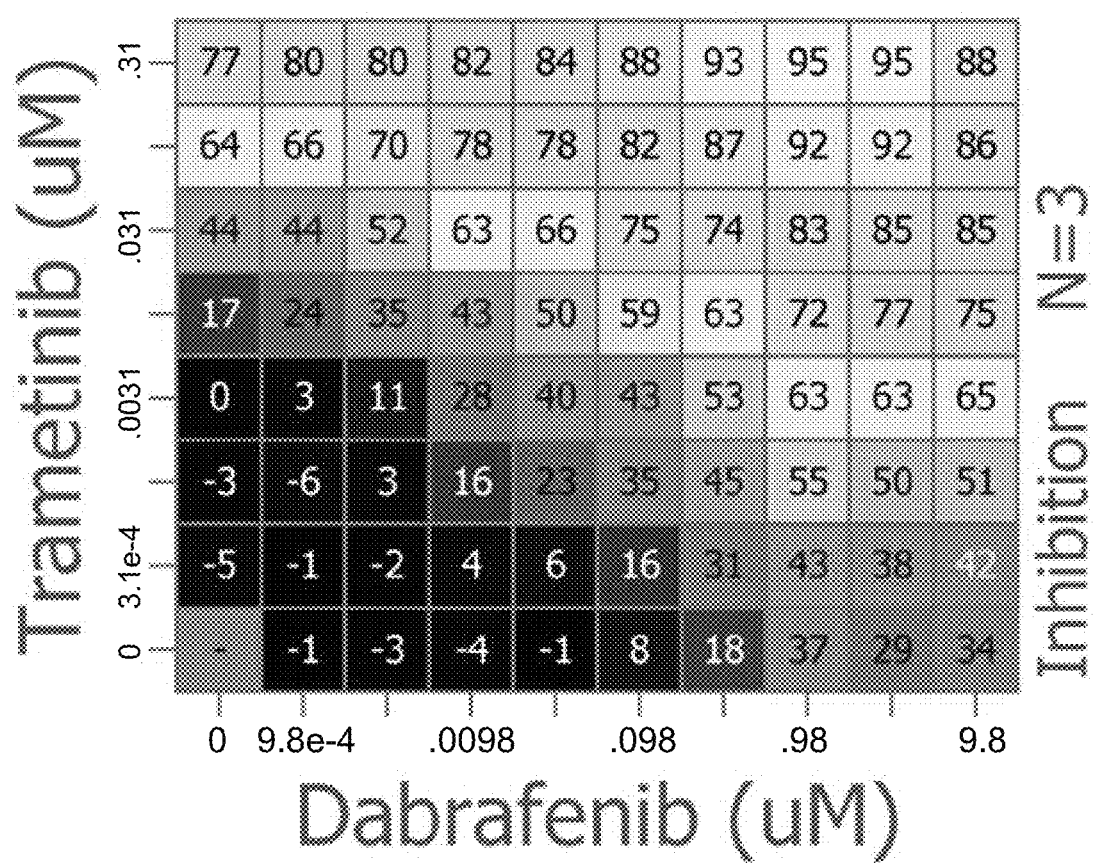
FIG. 25K shows a dose matrix showing inhibition (%) for the combination in RKO MEK1 (Q56P/+)-clone 2 cells.
Figure 25L:
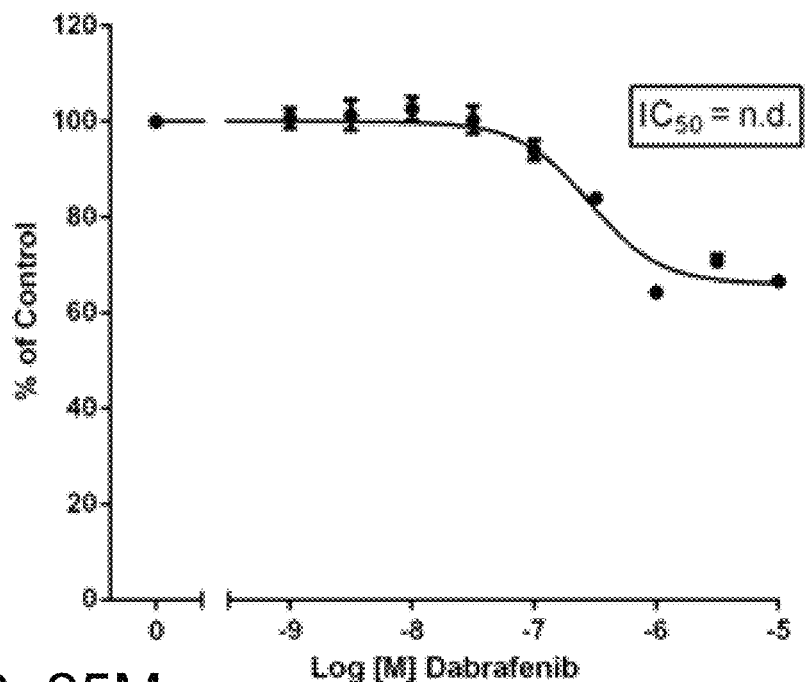
FIG. 25L-FIG. 25M show the results of single agent proliferation assays for the combination in FIG. 25K.
Figure 25M:
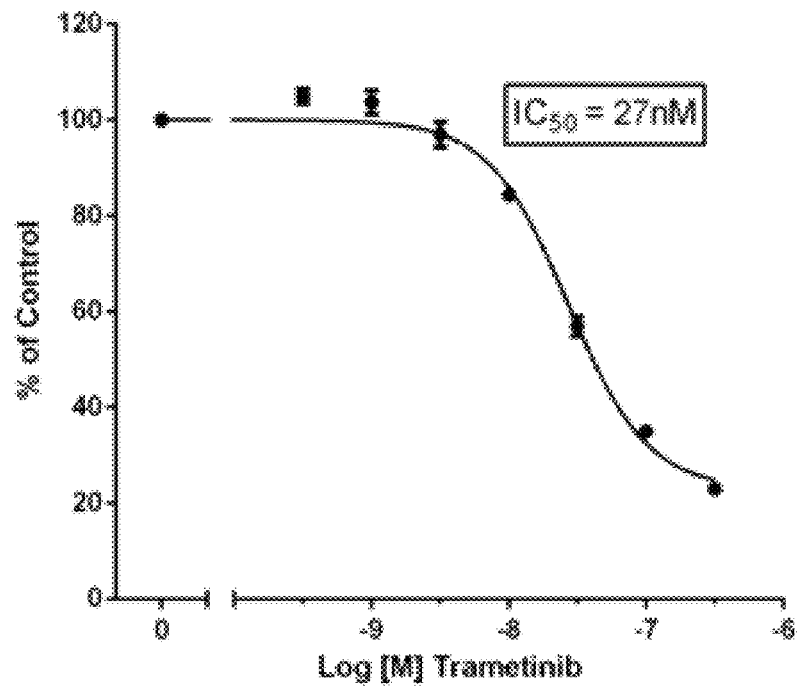
Figure 25N:
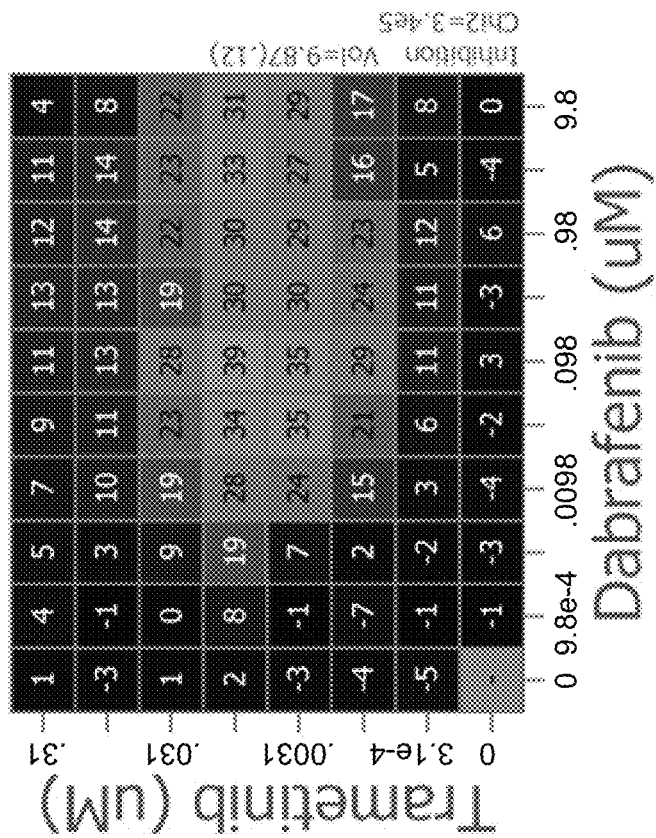
FIG. 25N shows Loewe excess for the combination in FIG. 25K
Figure 25O:
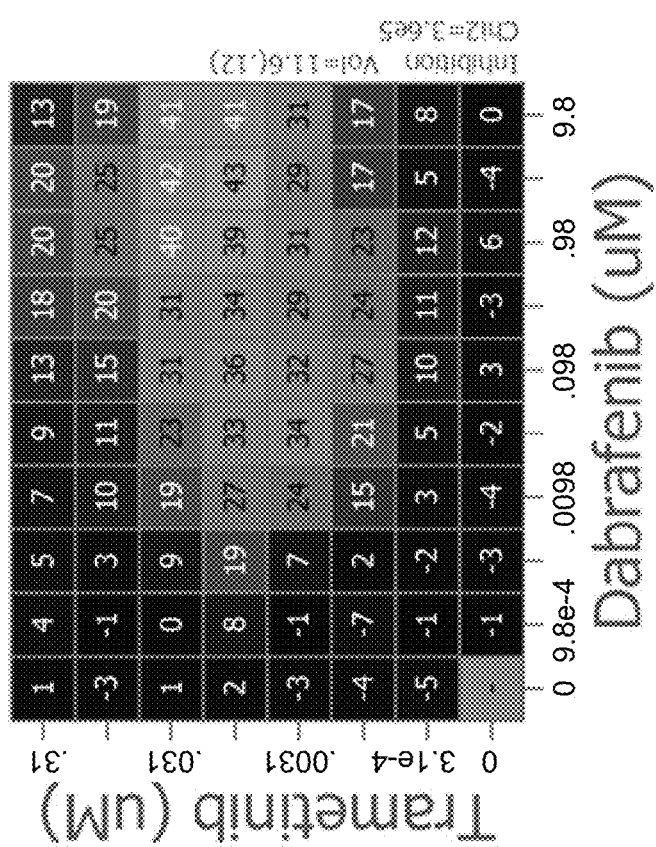
Figure 26A:
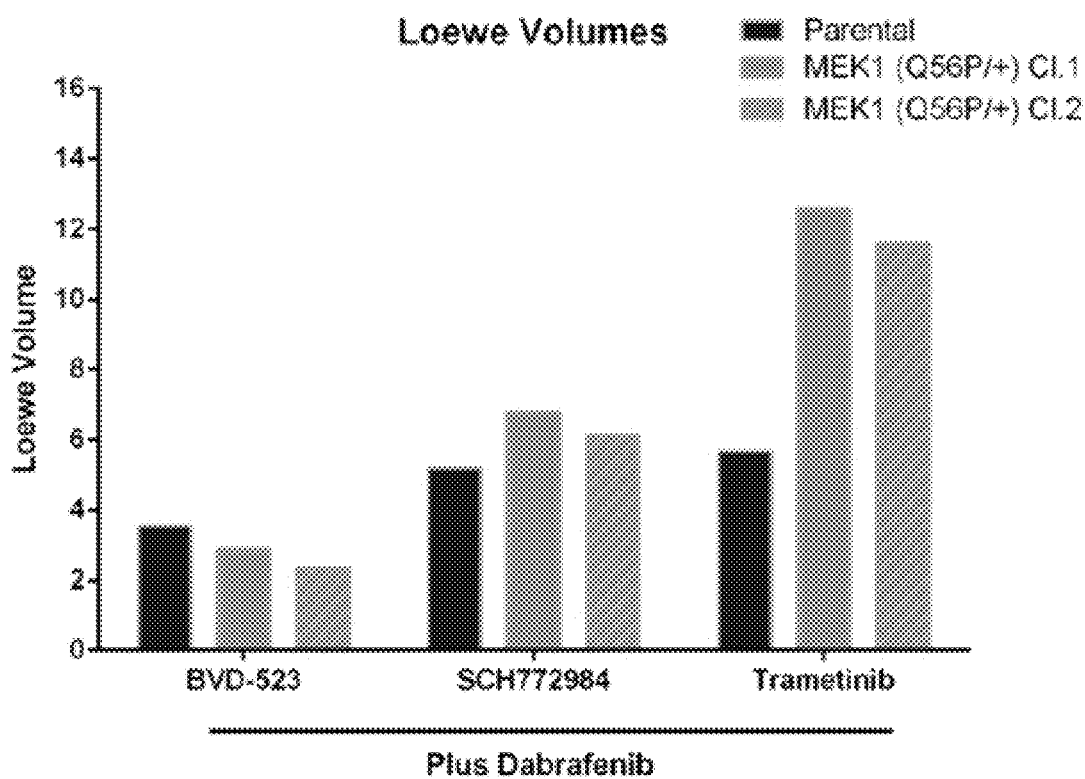
FIG. 26A shows Lowe Volumes for the combinations tested.
Figure 26B:
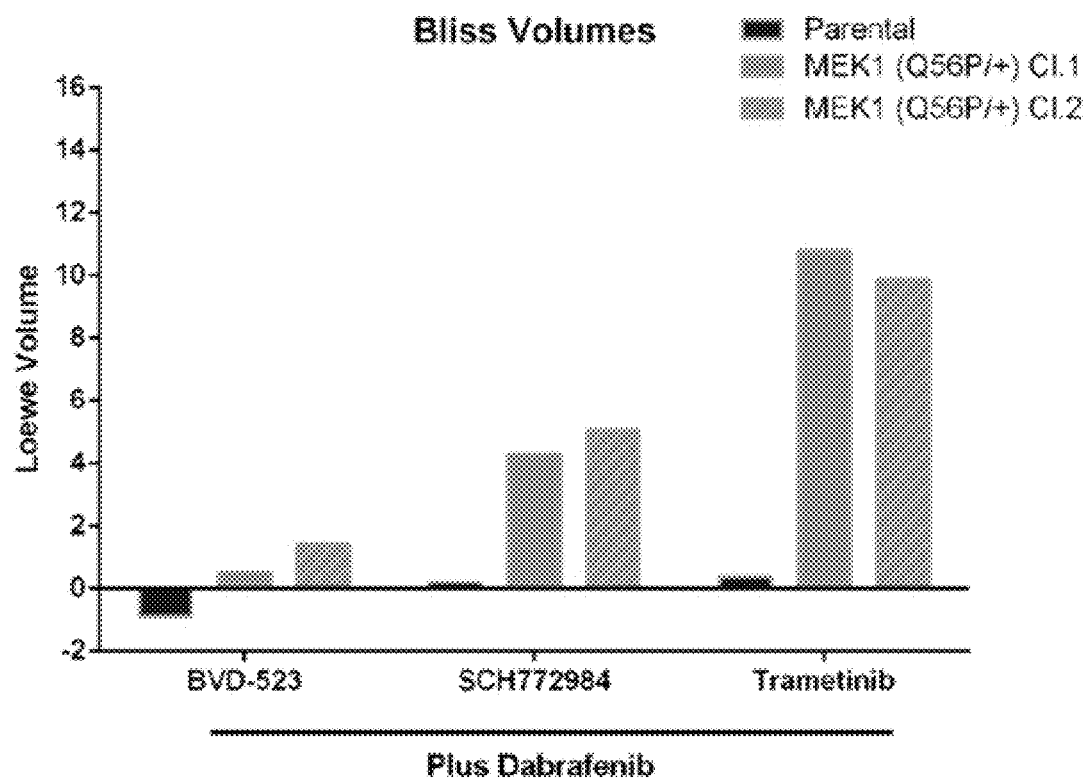
FIG. 26B shows Bliss Volumes for the combinations tested.
Figure 26C:
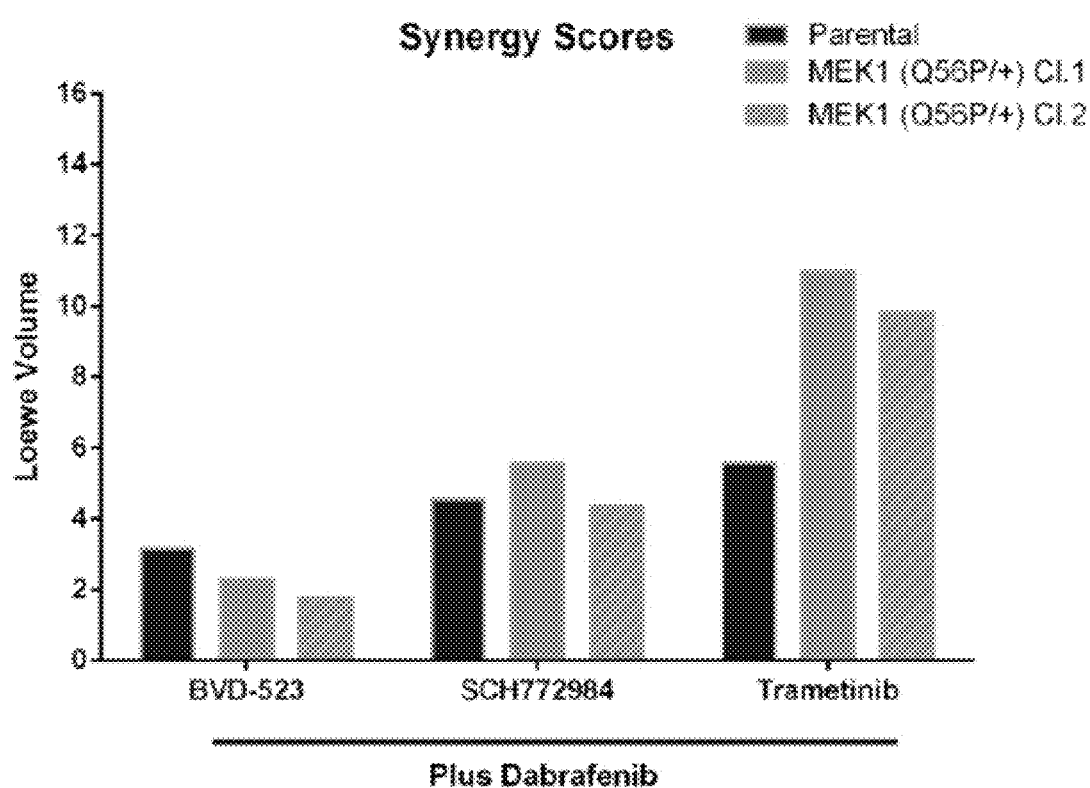
FIG. 26C shows Synergy Scores for the combinations tested.
Figure 27A:
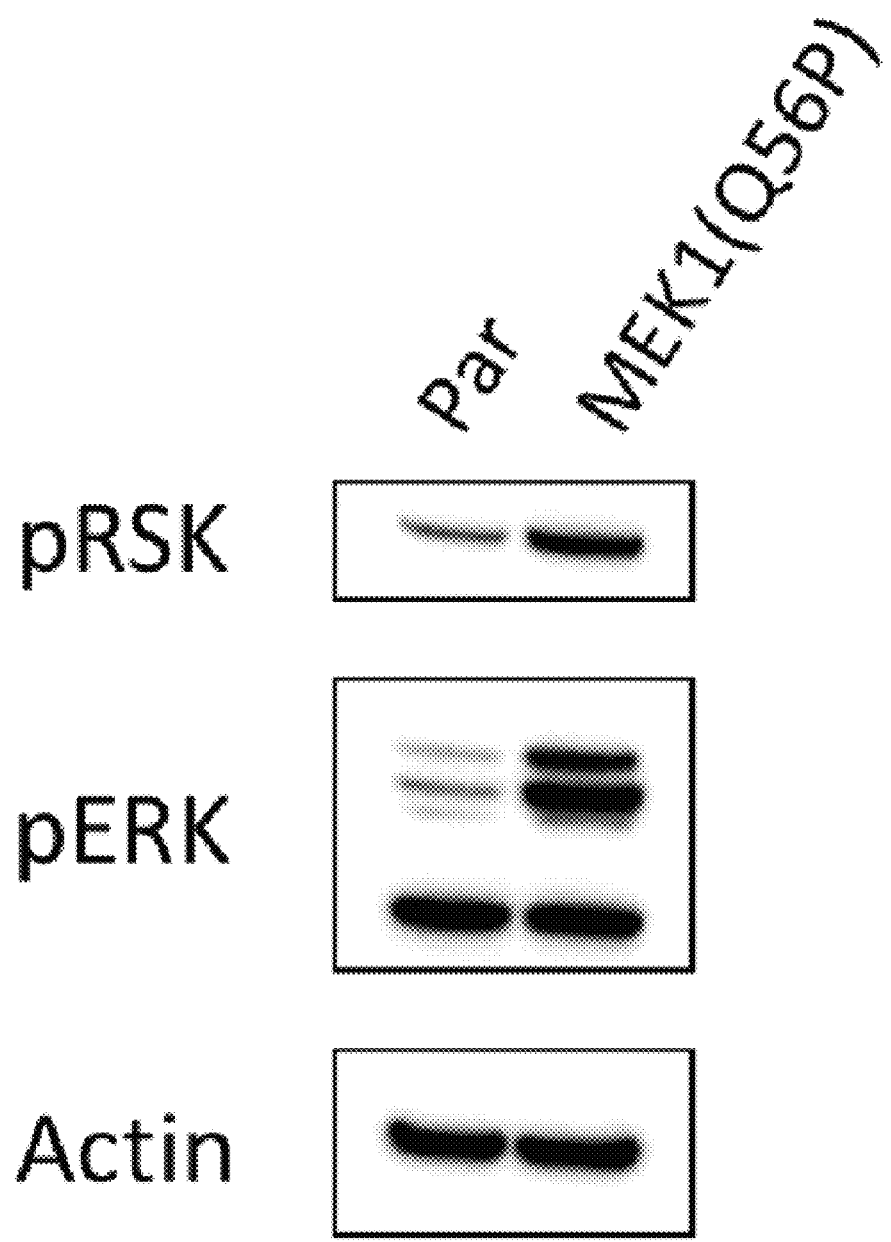
FIG. 27A-FIG. 27I show the changes in MAPK and Effector Pathway Signaling in MEK acquired resistance. Isogenic RKO parental and MEK1 (Q56P/+) cells were treated with compound for 4 or 24 h and then immunoblotted with the indicated antibodies. Dabrafenib was the BRAF inhibitor and trametinib was the MEK inhibitor.
Figure 27B:
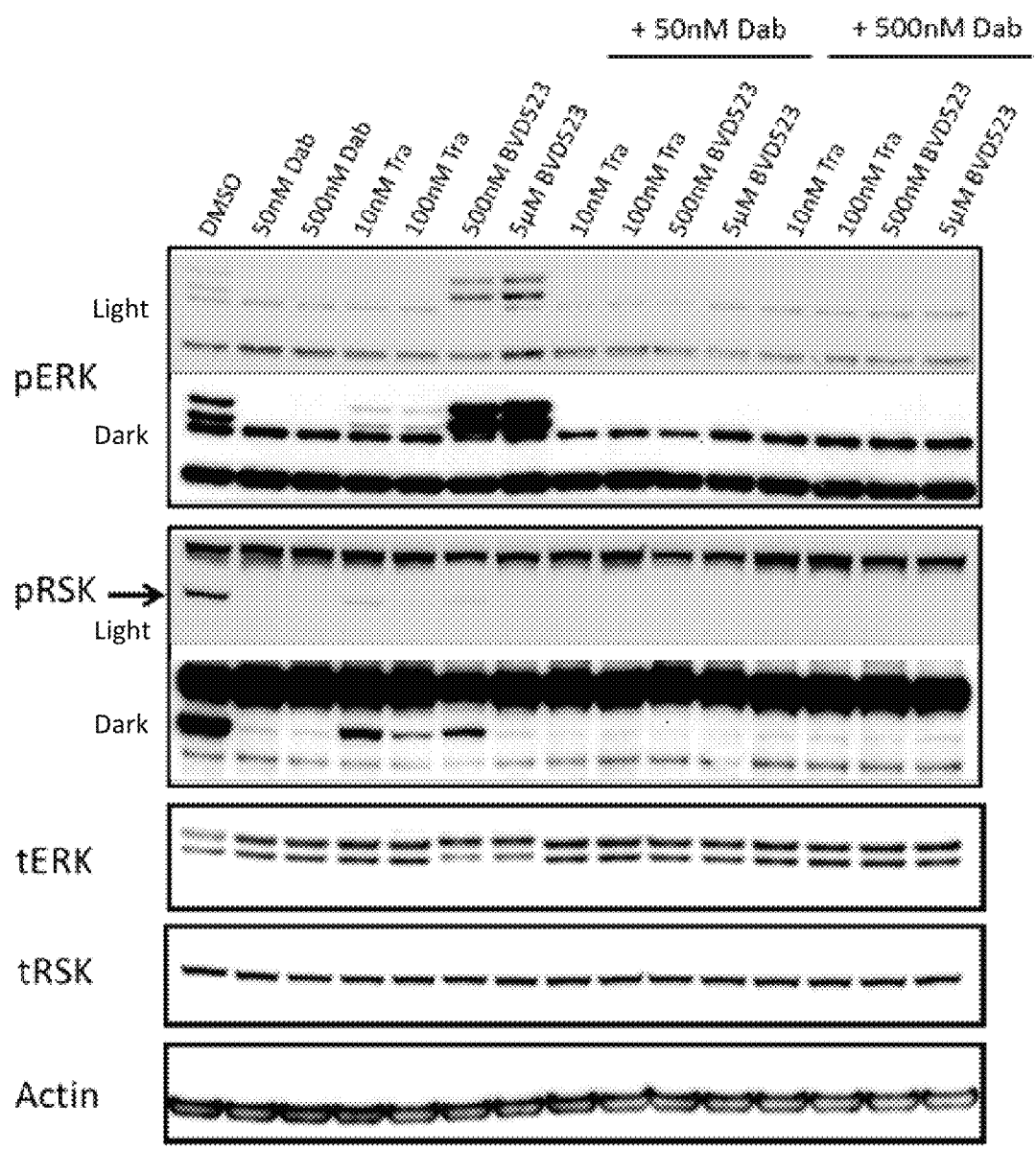
Figure 27C:
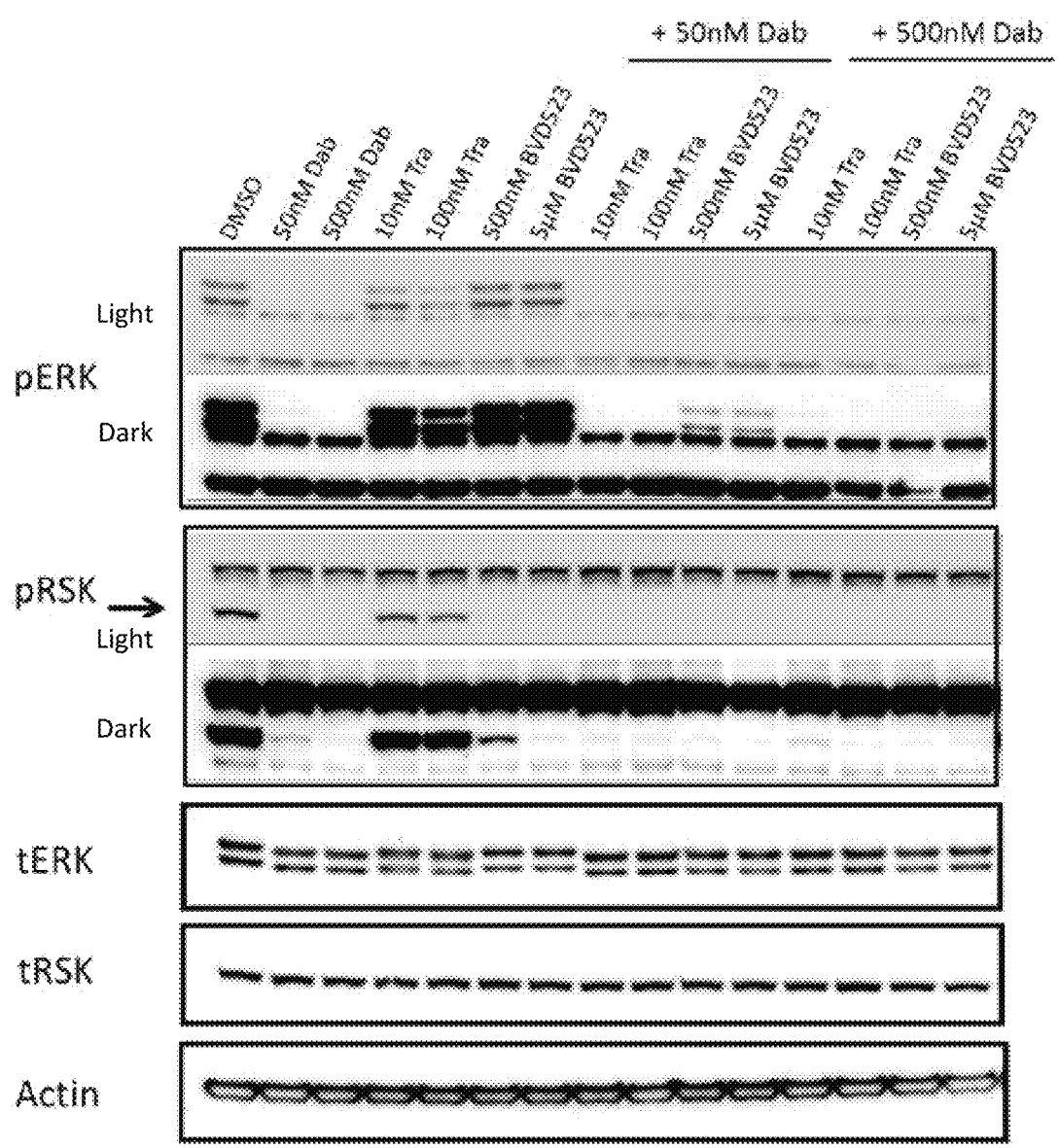
Figure 27D:
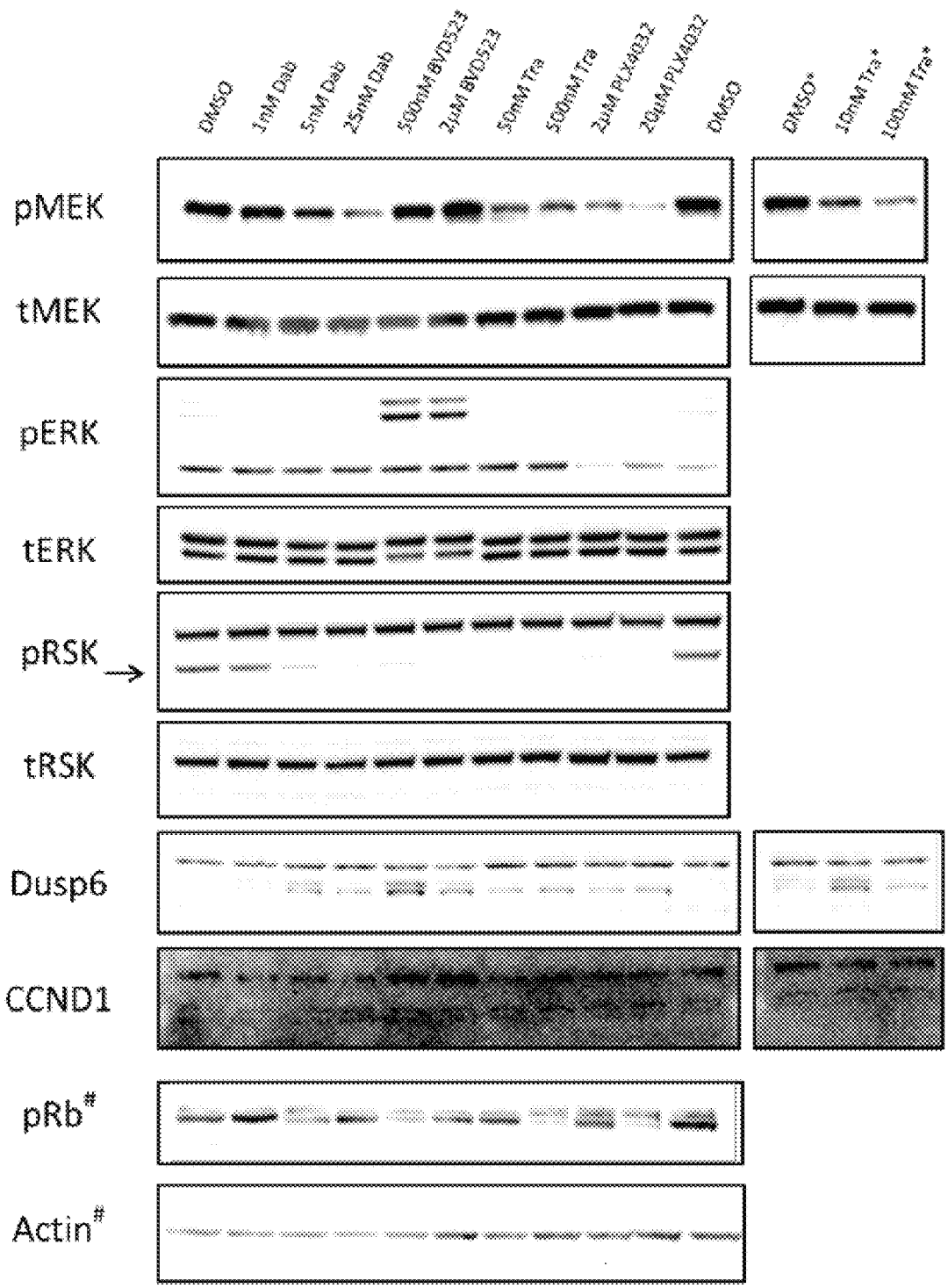
Figure 27E:
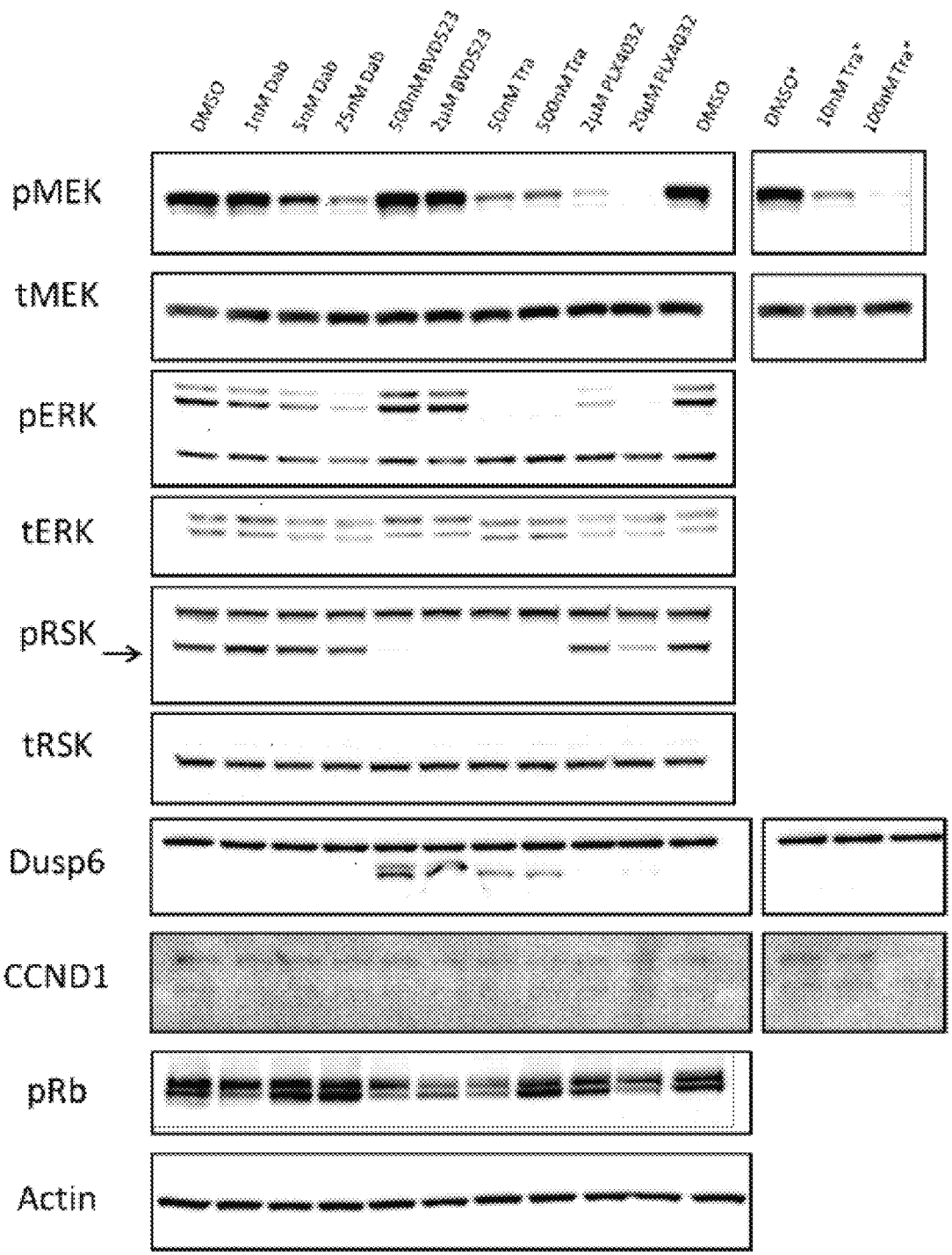
Figure 27F:
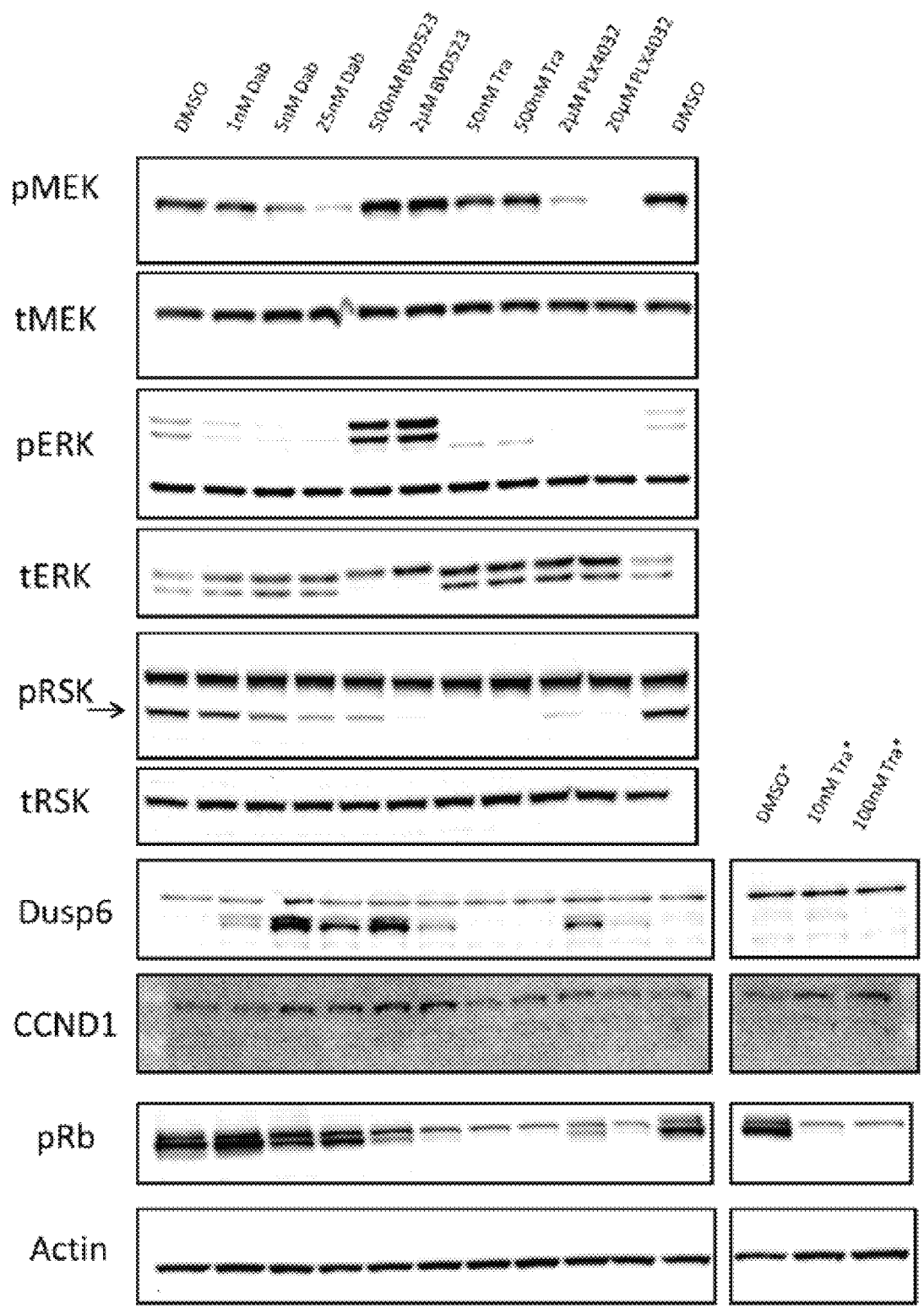
Figure 27G:
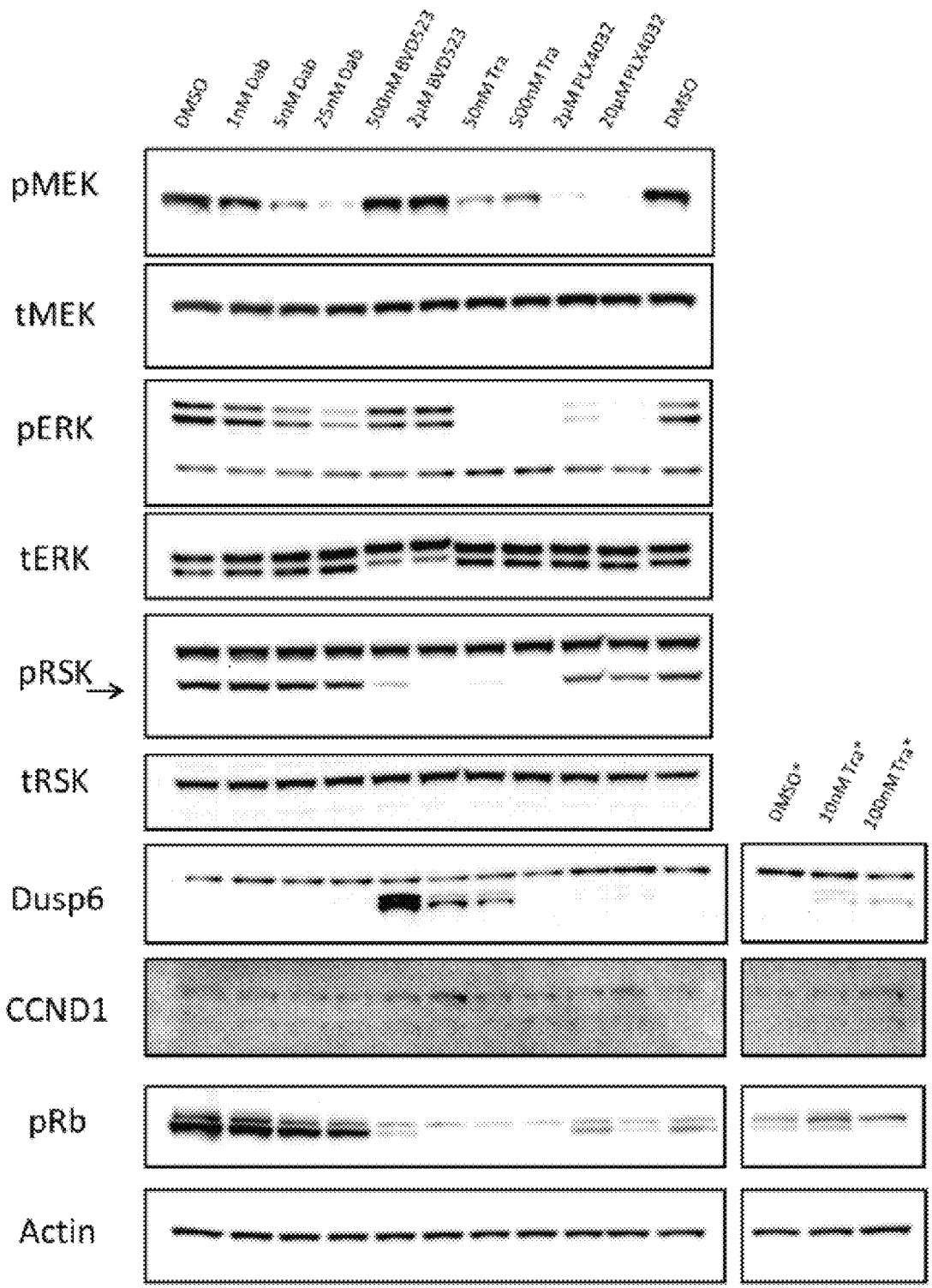
Figure 27H:
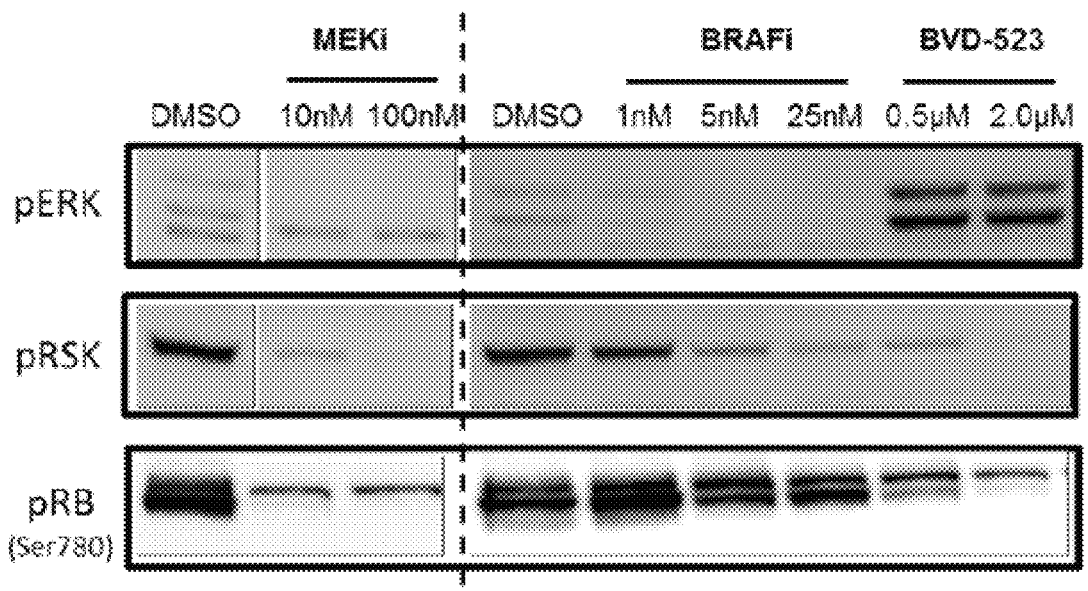
Figure 27I:
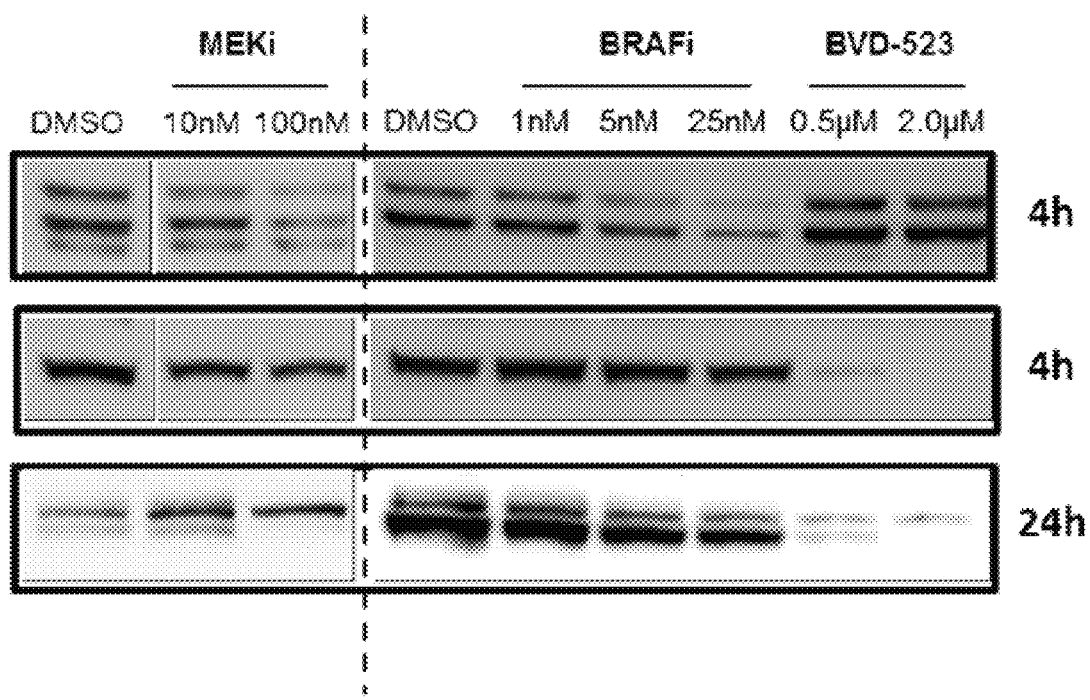
Figure 28A:
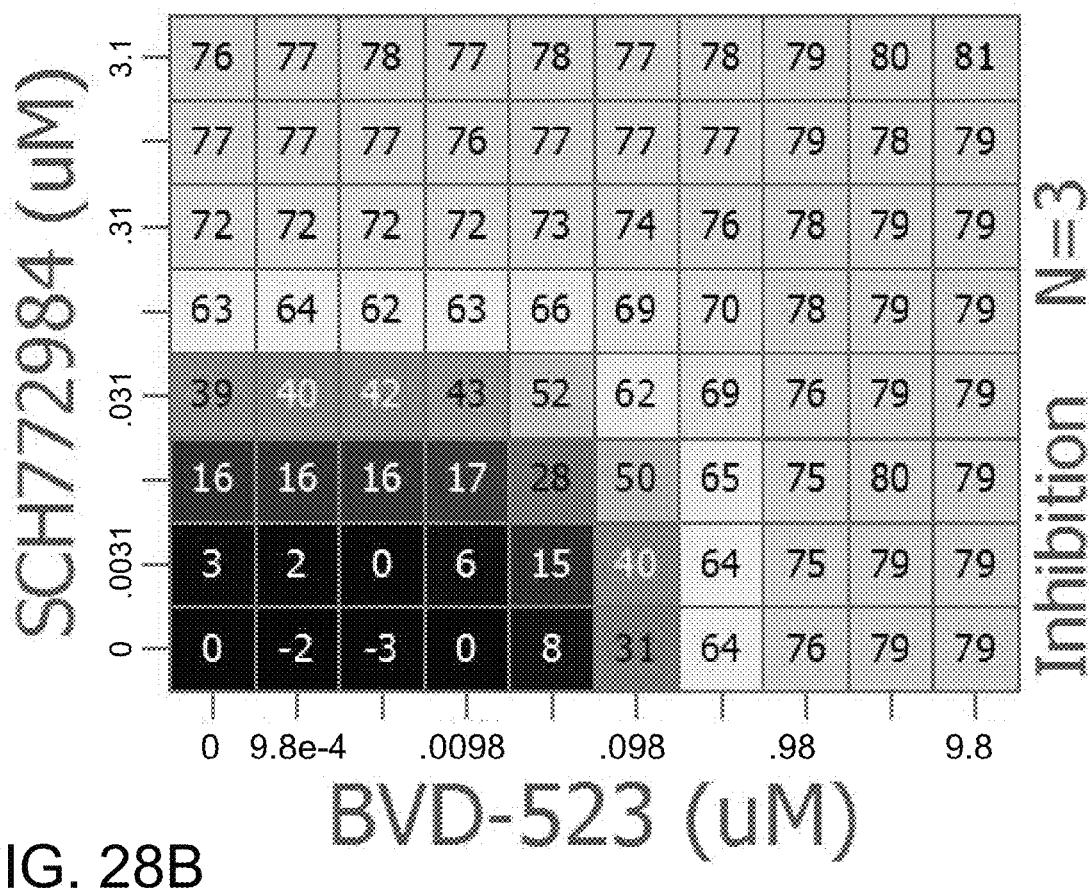
FIG. 28A-FIG. 28E show the results of the combination of BVD-523 and SCH772984.
Figure 28B:
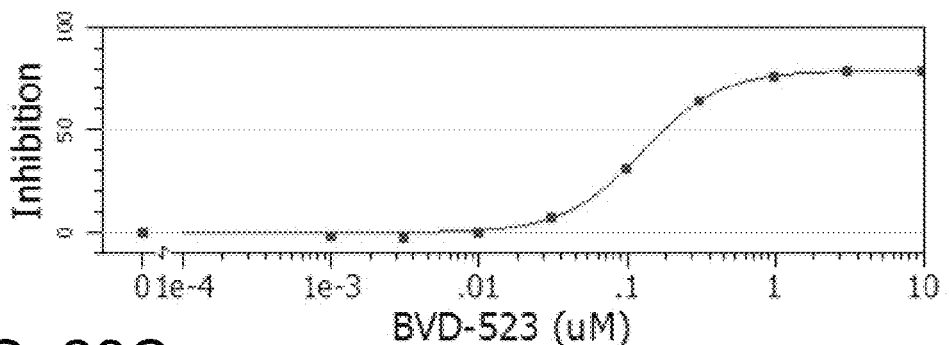
Figure 28C:
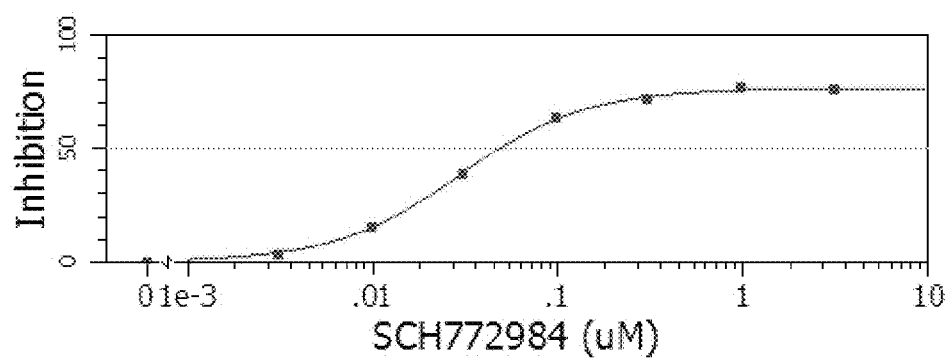
Figure 28D:
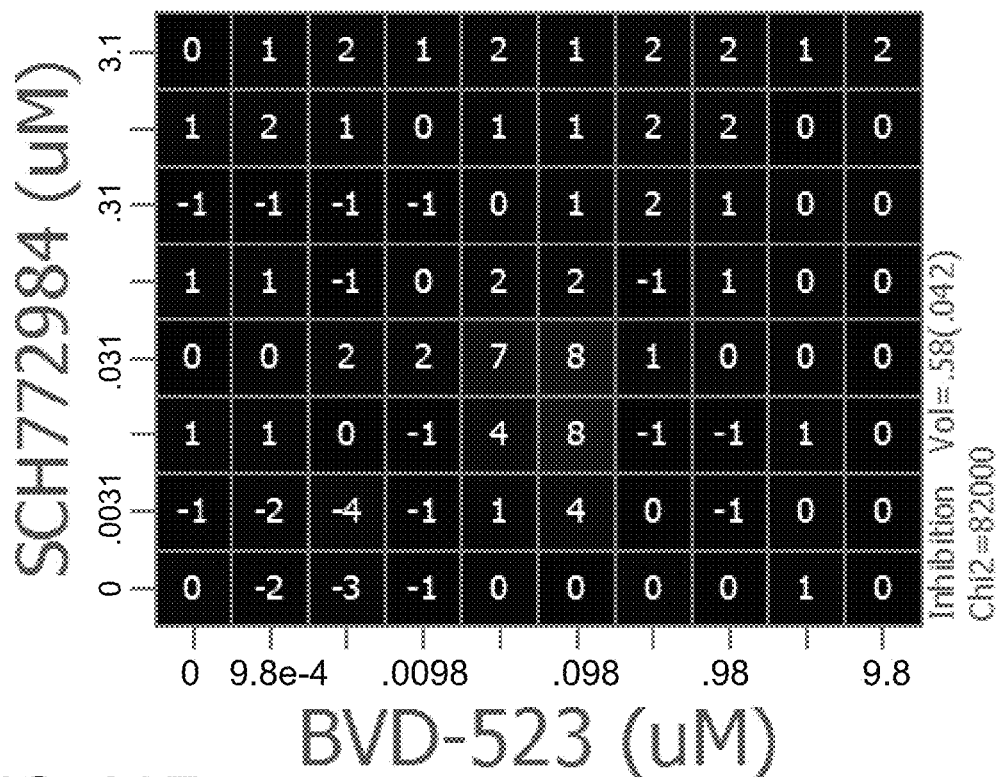
Figure 28E:
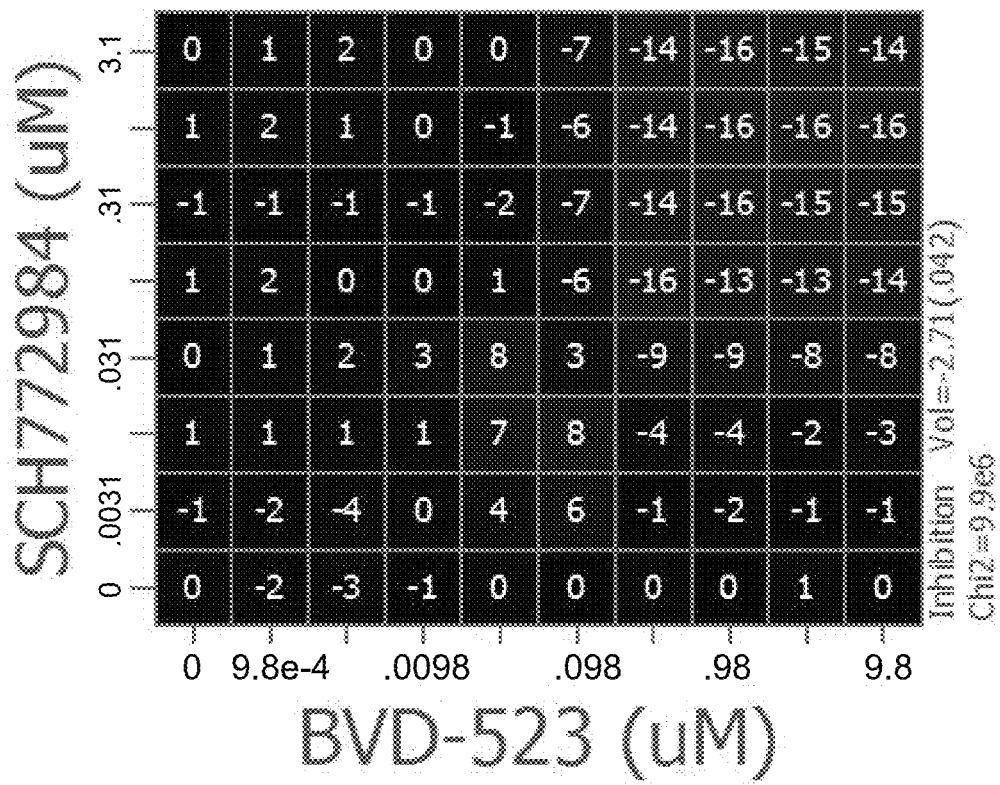

The results suggest that the BVD-523::Dabrafenib combination was mainly additive in the parental and mutant cell line. In contrast, the combination of a MEK inhibitor (trametinib) plus Dabrafenib, while being mostly additive in the parental cell line, showed strong synergy in the double mutant BRAF(V600E)::MEK1(Q56P) cell line (FIG. 25A-FIG. 25O). Loewe Volumes, Bliss Volumes and Synergy scores for the combinations tested are shown in Tables 18-20, respectively and are shown graphed in FIG. 26A-FIG. 26C.

TABLE 18

Loewe Volumes

| | RKO Parental | RKO MEK1 (Q56P) - Clone 1 | RKO MEK1 (Q56P) - Clone 2 |
|---|---|---|---|
| BVD-523 × Dabrafenib | 3.54 | 2.88 | 2.35 |
| Dabrafenib × SCH772984 | 5.7 | 6.79 | 6.14 |
| Dabrafenib × Trametinib | 5.68 | 12.6 | 11.6 |

TABLE 19

Bliss Volumes

| | RKO Parental | RKO MEK1 (Q56P) - Clone 1 | RKO MEK1 (Q56P) - Clone 2 |
|---|---|---|---|
| BVD-523 × Dabrafenib | −0.894 | 0.527 | 1.42 |
| Dabrafenib × SCH772984 | 0.209 | 4.3 | 5.07 |
| Dabrafenib × Trametinib | 0.353 | 10.8 | 9.87 |

TABLE 20

Synergy Scores

|  | RKO Parental | RKO MEK1 (Q56P) - Clone 1 | RKO MEK1 (Q56P) - Clone 2 |
|---|---|---|---|
| BVD-523 × Dabrafenib | 3.18 | 2.31 | 1.77 |
| Dabrafenib × SCH772984 | 4.56 | 5.57 | 4.36 |
| Dabrafenib × Trametinib | 5.58 | 11 | 9.83 |

Effects on MAPK pathway signally was assessed by Western blotting. The levels of basal ERK phosphorylation (DMSO samples) was markedly up-regulated in the MEK1 (Q56P)-expressing line relative to parental further confirming that this isogenic model faithfully recapitulates the expected phenotype for the expression of MEK activating acquired resistance mutations.

In the parental BRAF(V600E) RKO cells, a reduced level of RSK1/2 phosphorylation is observed following acute treatment with RAF, MEK and ERK kinase inhibitors at pharmacologically active concentrations. In contrast, isogenic, double mutant BRAFV600E::MEK1Q56P cells do not exhibit reduced RSK phosphorylation following BRAF or MEK inhibitor treatment, while BVD-523 remains effective at similar concentrations (FIG. 27A-FIG. 27I). The dotted lines indicate that the trametinib-treated samples (plus matched DMSO control) and blots are derived from a separate experiment to the BRAFi and BVD-523 treated samples.

Changes in effector gene signaling consistent with cell growth inhibition patterns are observed following prolonged inhibitor treatment. In parental RKO lines, a reduced level of phosphorylated pRB is observed following prolonged MEK and ERK inhibitor treatment. At the level of pRB modulation, MEK1 mutant lines appear insensitive to low concentration MEK inhibitor treatment, while higher concentrations remain effective. Critically, BVD-523 potency against pRB activity does not appear to be strongly affected by MEK mutation. Surprisingly, RAF inhibitor treatment does not affect pRB status, despite potent inhibition of upstream signaling, in both parental and MEK mutant backgrounds.

In summary, these results show that BVD-523 is not susceptible to acquired resistance driven by MEK activating mutations such as MEK1 (Q56P). In addition they suggest that in combination the interactions between BVD-523 and BRAFi (exemplified by Dabrafenib) are additive irrespective of the presence of a MEK activating mutation.

Example 8

Combination Interactions Between ERK Inhibitors

RAF mutant melanoma cell line A375 cells were cultured in DMEM with 10% FBS and seeded into triplicate 96-well plates at an initial density of 2000 cells per well. Combination interactions between ERK inhibitors BVD-523 and SCH772984 were analized after 72 hours as described above in Example 4. Viability was determined using CellTiter-Glo® reagent (Promega, Madison, Wis.) according to manufacturer's instructions and luminescence was detected using the BMG FLUOstar plate reader (BMG Labtech, Ortenberg, Germany).

Visualization of the Loewe and Bliss 'excess inhibition' heat maps suggested that the combination of BVD-523 and SCH772984 was mainly additive with windows of potential synergy in mid-range doses (FIG. 28A-FIG. 28E).

In summary, these results suggest that interactions between BVD-523 and SCH772984 are at least additive, and in some cases synergistic.

Example 9

Targeting the MAPK Signaling Pathway in Cancer: Promising Activity with the Novel Selective ERK1/2 Inhibitor BVD-523 (Ulixertinib)

Treatment strategies for cancer have evolved from classic cytotoxic-based approaches to agents that counteract the effects of genetic lesions that drive aberrant signaling essential to tumor proliferation and survival. For example, the ERK module of the mitogen-activated protein kinase (MAPK) signaling cascade (RAS-RAF-MEK-ERK) (Cargnello and Rouxx 2011) can be engaged by several receptor tyrosine kinases (e.g., EGFR and ErbB-2) in addition to constitutively activated mutations of pathway components such as RAS and BRAF (Gollob et al. 2006). Through aberrant activation of ERK signaling, genetic alterations in RAS or BRAF result in rapid tumor growth, increased cell survival, and resistance to apoptosis (Poulikakos et al. 2011, Corcoran et al. 2010, Nazarian et al. 2010, Shi et al. 2014, Wagle et al. 2011). Activating mutations of RAS family members KRAS and NRAS are found in ~30% of all human cancers, with particularly high incidence in pancreatic (Kanda et al. 2012) and colorectal cancer (Arrington et al. 2014). Constitutively activating mutations in the BRAF gene that normally encodes for valine at amino acid 600 have been observed in melanoma, thyroid carcinoma, colorectal cancer, and non-small cell lung cancer (Hall et al. 2014). Cancers bearing genetic mutations that result in changes of the downstream components ERK and MEK have also been reported (Ojesina et al. 2014, Arcila et al. 2015). Alterations that activate the MAPK pathway are also common in the setting of resistance to targeted therapies (Groenendijk et al. 2014). Thus, targeting the MAPK pathway terminal master kinases (ERK1/2) is a promising strategy for tumors harboring such pathway activating alterations (e.g., BRAF, NRAS, and KRAS).

Three MAPK pathway-targeting drugs have been approved by the US Food and Drug Administration (FDA) for single-agent treatment of nonresectable or metastatic cutaneous melanoma with $BRAF^{V600}$ mutations: the BRAF inhibitors vemurafenib and dabrafenib and the MEK inhibitor trametinib. Furthermore, the combination of dabrafenib and trametinib is also approved in this indication (Queirolo et al. 2015 and Massey et al. 2015). An additional MEK inhibitor, cobimetinib, is approved in this indication as part of a combination regimen with BRAF inhibitors. Clinical experience with these drugs validates the MAPK pathway as a therapeutic target. In phase III trials of patients with $BRAF^{V600}$-mutant melanoma, the single agents vemurafenib and dabrafenib demonstrated superior response rates (approximately 50% vs. 5-19%) and median progression-free survival (PFS, 5.1-5.3 months vs. 1.6-2.7 months) over cytotoxic chemotherapy (dacarbazine) (Chapman et al. 2011 and Hauschild et al. 2012). Furthermore, clinical use of concomitant BRAF-plus MEK-targeted therapies has demonstrated that simultaneous targeting of different nodes in the MAPK pathway can enhance the magnitude and duration of response. First-line use of BRAF plus MEK-targeted agents (dabrafenib/trametinib or cobimetinib/vemurafenib) further improved median overall survival compared with single-agent BRAF inhibition (Robert et al. 2015, Long et al. 2015, Larkin et al. 2014). Thus, combined BRAF-/MEK-targeted therapy is a valuable treatment option for patients with metastatic melanoma with BRAF$^{V600}$ mutations.

Despite improvements in clinical outcomes seen with BRAF-/MEK-inhibitor combination therapies, durable benefit is limited by the eventual development of acquired resistance and subsequent disease progression, with median PFS ranging from approximately 9 to 11 months. (Robert et al. 2015, Long et al. 2015, Larkin et al. 2014, and Flaherty et al. 2012). Genetic mechanisms of acquired resistance to single-agent BRAF inhibition have been intensely studied, and identification of resistance mechanisms include splice variants of BRAF (Poulikakos et al. 2011), BRAF$^{V600E}$ amplification (Corcoran et al. 2010), MEK mutations (Wagle et al. 2014), NRAS mutations, and RTK activation (Nazarian et al. 2010 and Shi et al. 2014). Resistance mechanisms in the setting of BRAF-/MEK-inhibitor combination therapy are beginning to emerge and mirror that of BRAF single-agent resistance (Wagle et al. 2014 and Long et al. 2014). These genetic events all share in common the ability to reactivate ERK signaling. Indeed, reactivated MAPK pathway signaling as measured by ERK transcriptional targets is common in tumor biopsies from BRAF inhibitor-resistant patients (Rizos et al. 2014). Furthermore, ERK1/2 reactivation has been observed in the absence of a genetic mechanism of resistance (Carlino et al. 2015). Therefore, the quest to achieve durable clinical benefit has led researchers to focus on evaluating additional agents that target the downstream MAPK components ERK1/2. Inhibiting ERK may provide important clinical benefit to patients with acquired resistance to BRAF/MEK inhibition. ERK family kinases have shown promise as therapeutic targets in preclinical cancer models, including those cancers resistant to BRAF or MEK inhibitors (Morris et al. 2013 and Hatzivassiliou et al. 2012). However, the potential use of such ERK1/2 inhibitors expands beyond acquired-resistance in melanoma.

Targeting ERK1/2 is a rational strategy in any tumor type harboring known drivers of MAPK, not only BRAF/MEK therapy-relapsed patients. As ERK1 and ERK2 reside downstream in the pathway, they represent a particularly attractive treatment strategy within the MAPK cascade that may avoid upstream resistance mechanisms. Here, preclinical characterization of BVD-523 (ulixertinib) in models of MAPK pathway-dependent cancers is reported, including drug-naïve and BRAF/MEK therapy acquired-resistant models. Results of a phase I dose-finding study of BVD-523 are included as a companion publication in this journal. See, Examples 17-24.

In the present invention, BVD-523 was shown to be a potent, highly selective, reversible, small molecule ATP-competitive inhibitor of ERK1/2 with in vitro and in vivo anticancer activity.

BVD-523 (ulixertinib) was identified and characterized as a novel, reversible, ATP-competitive ERK1/2 inhibitor with high potency and ERK1/2 selectivity. BVD-523 caused reduced proliferation and enhanced caspase activity, most notably in cells harboring MAPK (RAS-RAF-MEK) pathway mutations. In in vivo BRAF$^{V600E}$ xenograft studies, BVD-523 showed dose-dependent growth inhibition and tumor regressions. Interestingly, BVD-523 inhibited phosphorylation of target substrates despite increased phosphorylation of ERK1/2. BVD-523 also demonstrated antitumor activity in models of acquired resistance to single-agent and combination BRAF/MEK targeted therapy. Synergistic antiproliferative effects in a BRAF$^{V600E}$-mutant melanoma cell line xenograph model were also demonstrated when BVD-523 was used in combination with BRAF inhibition. These studies suggest that BVD-523 holds promise as a treatment for ERK-dependent cancers, including those whose tumors have acquired resistance to other treatments targeting upstream nodes of the MAPK pathway.

Example 10

Discovery and Initial Characterization of a Novel ERK1/2 Inhibitor, BVD-523 (Ulixertinib)

Following extensive optimization of leads originally identified using a high-throughput, small-molecule screen (Aronov et al. 2009), a novel adenosine triphosphate (ATP)-competitive ERK1/2 inhibitor, BVD-523 (ulixertinib) was identified (FIG. 29 A). BVD-523 is a potent ERK inhibitor with a $K_i$ of 0.04±0.02 nM against ERK2. It was shown to be a reversible, competitive inhibitor of ATP, as the IC$_{50}$ values for ERK2 inhibition increased linearly with increasing ATP concentration (FIG. 29B and FIG. 29C). The IC$_{50}$ remained nearly constant for incubation times minutes, suggesting rapid equilibrium and binding of BVD-523 with ERK2 (FIG. 29D). BVD-523 is also a tight-binding inhibitor of recombinant ERK1 (Rudolph et al. 2015), exhibiting a $K_i$ of <0.3 nM.

Figure 29A:
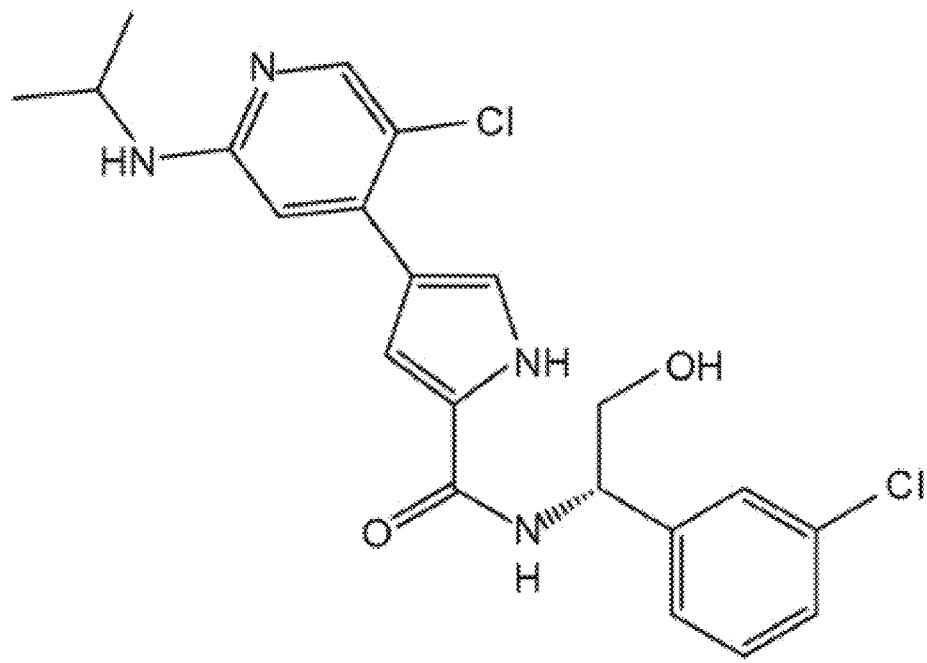
FIG. 29A-FIG. 29F show discovery and characterization of the novel ERK1/2 inhibitor BVD-523 (ulixertinib).
Figure 29B:
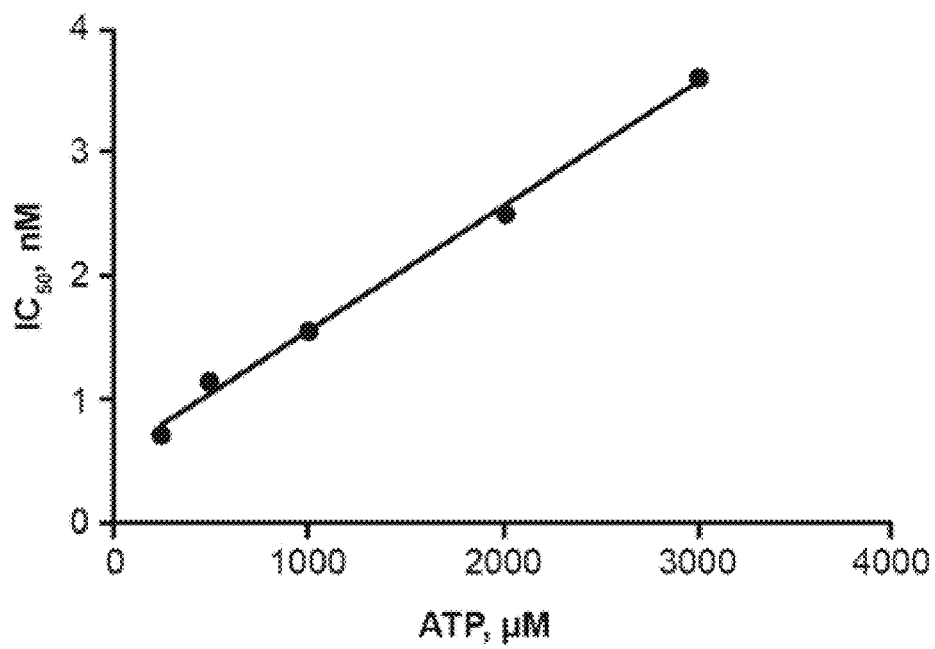
Figure 29C:
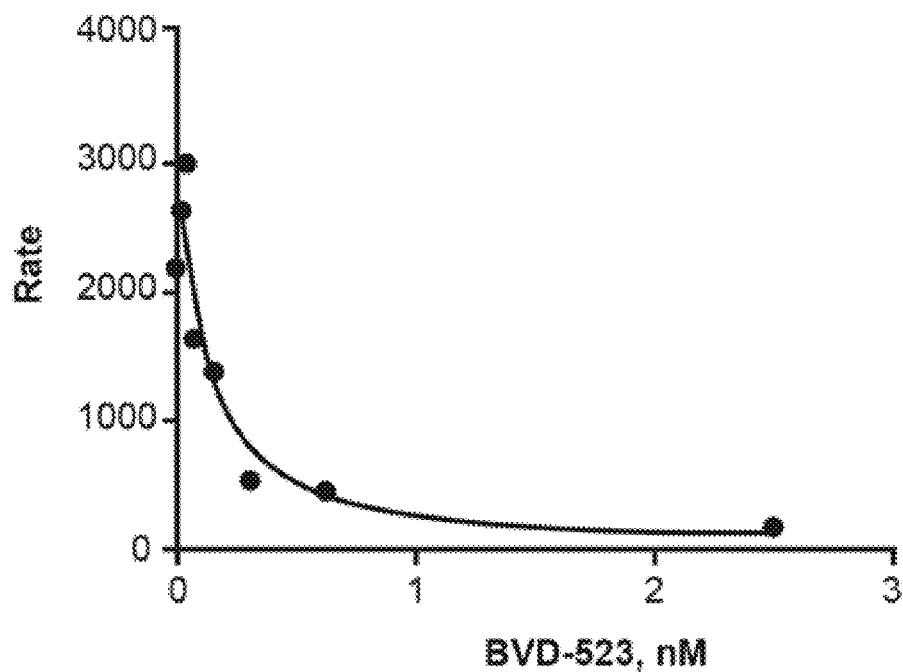
Figure 29D:
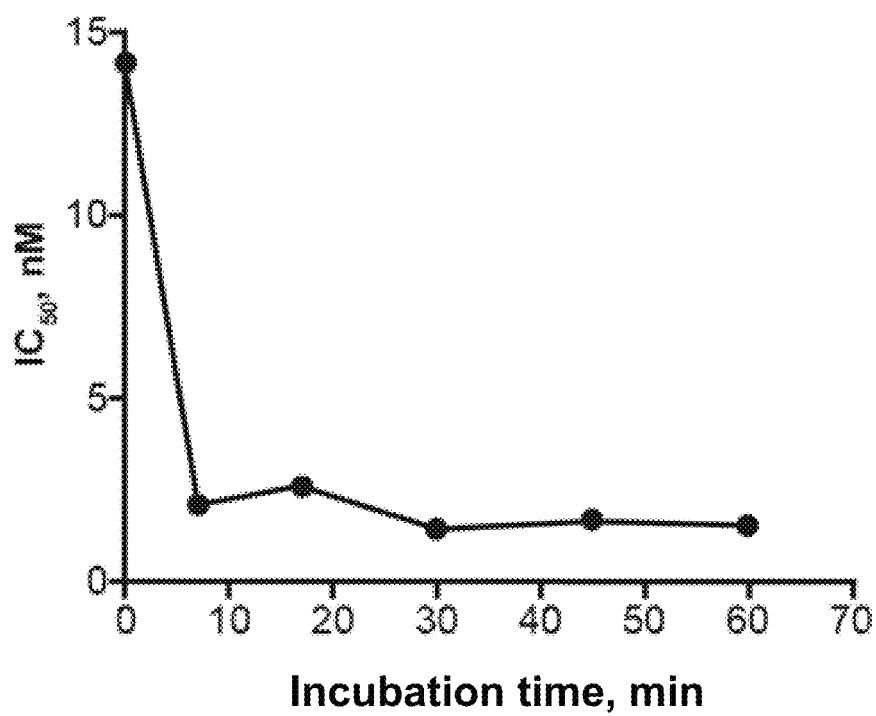
Figure 29E:
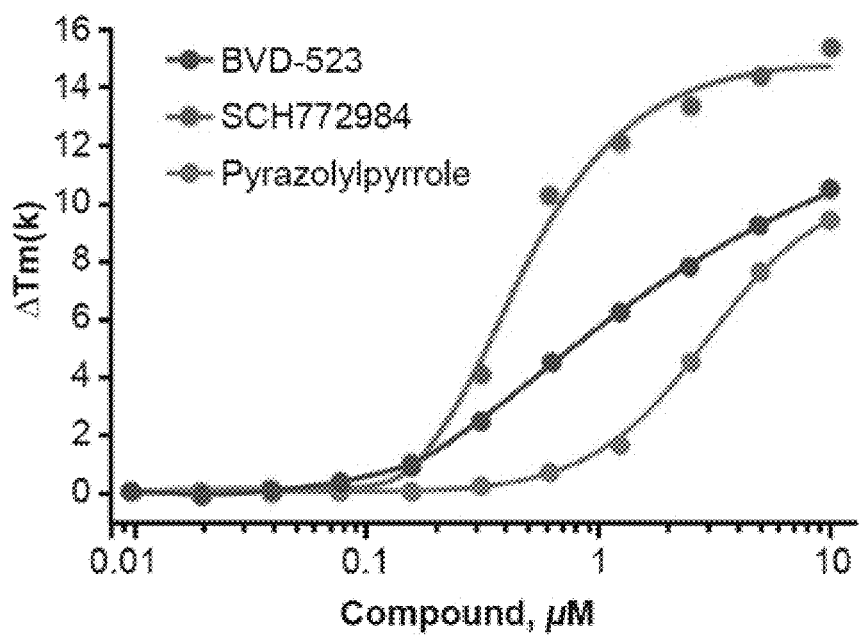
Figure 29F:
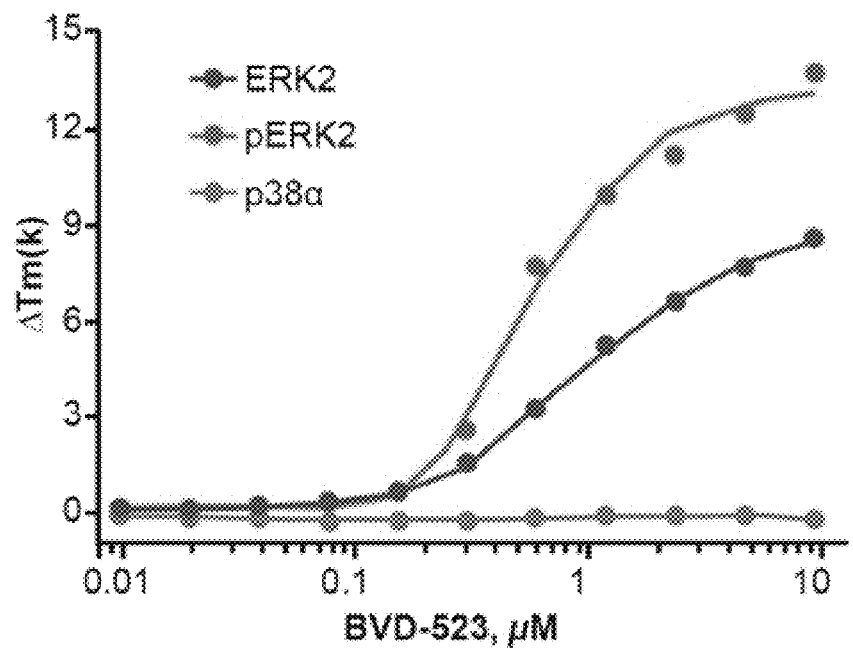

Binding of BVD-523 to ERK2 was demonstrated using calorimetric studies and compared to data generated using the ERK inhibitors SCH772984 and pyrazolylpyrrole (Arovov et al. 2007). All compounds bound and stabilized inactive ERK2 with increasing concentration, as indicated by positive ΔTm values (FIG. 29E). The 10- to 15-degree change in ΔTm observed with BVD-523 and SCH-772984 is consistent with compounds that have low-nanomolar binding affinities (Fedorov et al. 2012). BVD-523 demonstrated a strong binding affinity to both phosphorylated active ERK2 (pERK2) and inactive ERK2 (FIG. 29F). A stronger affinity to pERK2 compared with inactive ERK2 was observed. BVD-523 did not interact with the negative control protein p38a MAP kinase (FIG. 29F).

BVD-523 demonstrated excellent ERK1/2 kinase selectivity based on biochemical counter-screens against 75 kinases in addition to ERK1 and ERK2. The ATP concentrations were approximately equal to the $K_m$ in all assays. Kinases inhibited to greater than 50% by 2 µM BVD-523 were retested to generate $K_i$ values (or apparent Ki; Table 21). Twelve of the 14 kinases had a $K_i$ of <1 µM. The selectivity of BVD-523 for ERK2 was >7000-fold for all kinases tested except ERK1, which was inhibited with a Ki of <0.3 nM (10-fold). Therefore, BVD-523 is a highly potent and selective inhibitor of ERK1/2.

TABLE 21

BVD-523 displays selectivity for ERK1 and ERK2 kinases.

| Kinase | Ki (µM) |
|---|---|
| CDK1/cyclinB | 0.07$^a$ |
| CDK2/cyclinA | 0.36 |
| CDK5/p35 | 0.09$^a$ |
| CDK6/cycinD3 | 0.09$^a$ |
| ERK1 | 0.0003 |
| ERK2 | 0.00004 |
| GSK3b | 0.32 |
| JNK2α | 0.65$^a$ |
| JNK3 | 1.3 |
| P38γ | 0.45$^a$ |
| P38δ | 0.24$^a$ |
| ROCKI | 11.1 |

TABLE 21-continued

BVD-523 displays selectivity for ERK1 and ERK2 kinases.

| Kinase | Ki (µM) |
|---|---|
| ROCKII | 0.27[a] |
| RSK3 | 0.45 |

[a]Apparent.

<50% inhibition at 2 µM: ABL, AKT3, AMPK, AUR1, AUR2, AXL, BLK, CAMKII, CAMKIV, CHK1, CHK2, CK1, CK2, CSK, EGFR, EPHB4, FES, FGFR3, FLT3, FYN, IGF1R, IKKα, IKKβ, IKKi, IRAK4, IRTK, ITK, JAK3, JNK1α1, KDR, LCK, LYN, cMET, MKK4, MKK6, MKK7β, MLK2, MSK1, MST2, NAK, NEK2, p38α, p38β, p70S6K, PAK2, PDGFRα, PDK1, PKA, PKCα, PKCβII, PKCγ, PKCi, PKCθ, PRAK, PRK2, cRAF, SGK, SRC, SYK, TAK1, TIE2, ZAP70

Example 11

BVD-523 Preferentially Inhibits Cellular Proliferation and Enhances Caspase-3/7 Activity In Vitro in Cancer Cell Lines with MAPK Pathway-Activating Mutations BVD-523 cellular activity was assessed in a panel of approximately 1,000 cancer cell lines of various lineages and genetic backgrounds (FIG. 30A and Table 22). Cell lines were classified as MAPK wild type (wt) or mutant depending on the absence or presence of mutations in RAS family members and BRAF. Although some MAPK-wt cell lines were sensitive to BVD-523, generally BVD-523 inhibited proliferation preferentially in cells with MAPK pathway alterations.

Figure 30B:
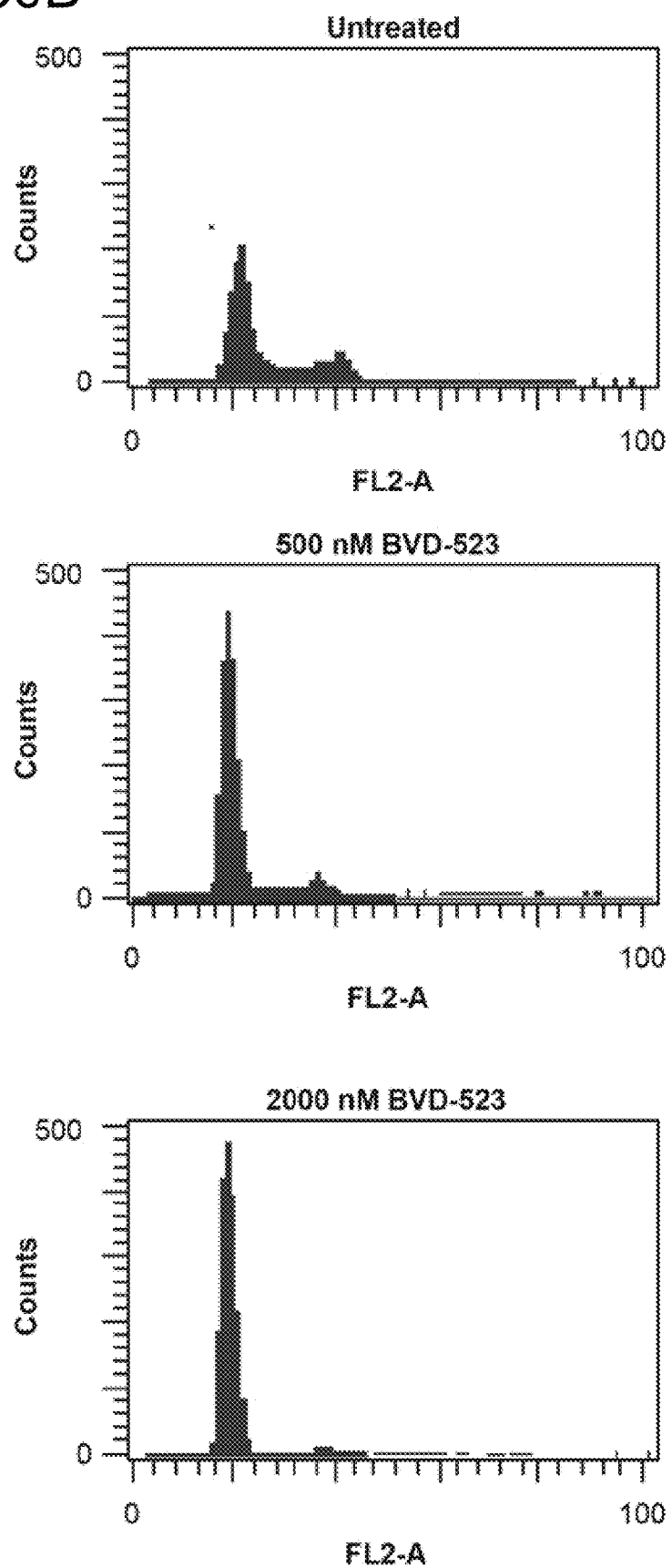

Next, the growth and survival impact of BVD-523 treatment on sensitive cells was characterized. Fluorescence activated cell sorting (FACS) analysis was performed on $BRAF^{V600E}$-mutant melanoma cell line UACC-62 following treatment with BVD-523 at 500 nM or 2000 nM for 24 hours. Treated cells were arrested in the G1 phase of the cell cycle in a concentration-dependent manner (FIG. 30B).

Figure 30C:
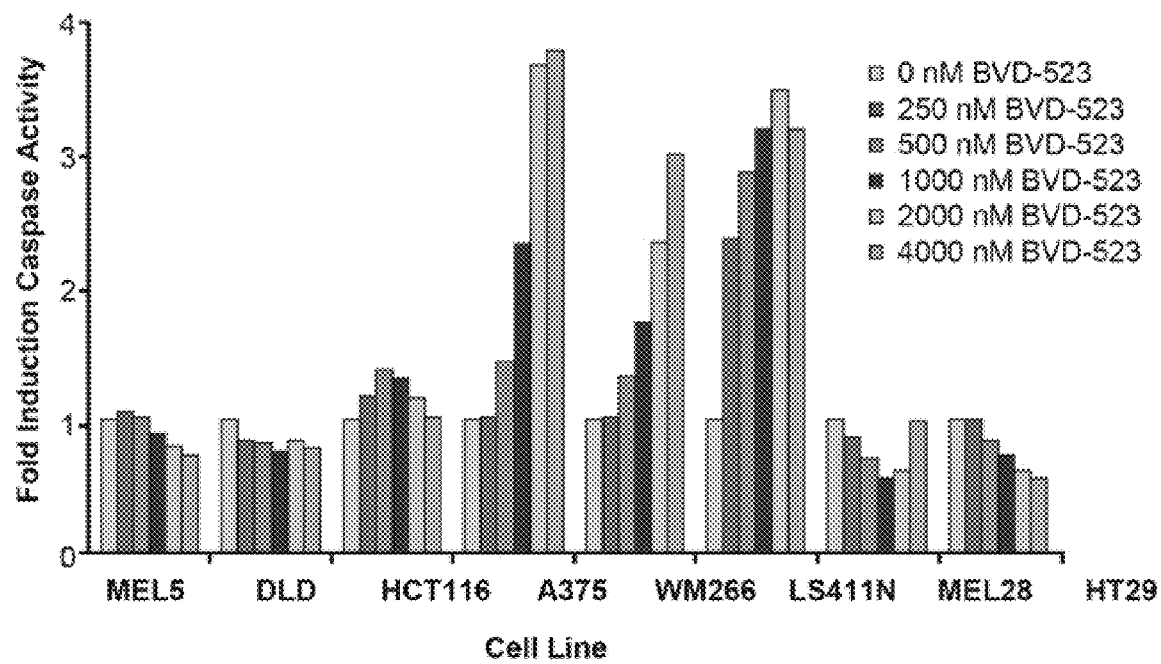

In addition, caspase-3/7 activity was analyzed as a measure of apoptosis in multiple human cancer cell lines. A concentration- and cell-line-dependent increase in caspase 3/7 was observed following treatment with BVD-523 for 72 hours (FIG. 30C). BVD-523 treatment resulted in pronounced caspase-3/7 induction in a subset of MAPK-activated cell lines harboring a $BRAF^{V600}$ mutation (A375, WM266, and LS411N). This is consistent with earlier observations for preferential inhibition of proliferation by BVD-523 in MAPK pathway-mutant cancer cell lines (FIG. 30A).

Figure 30D:
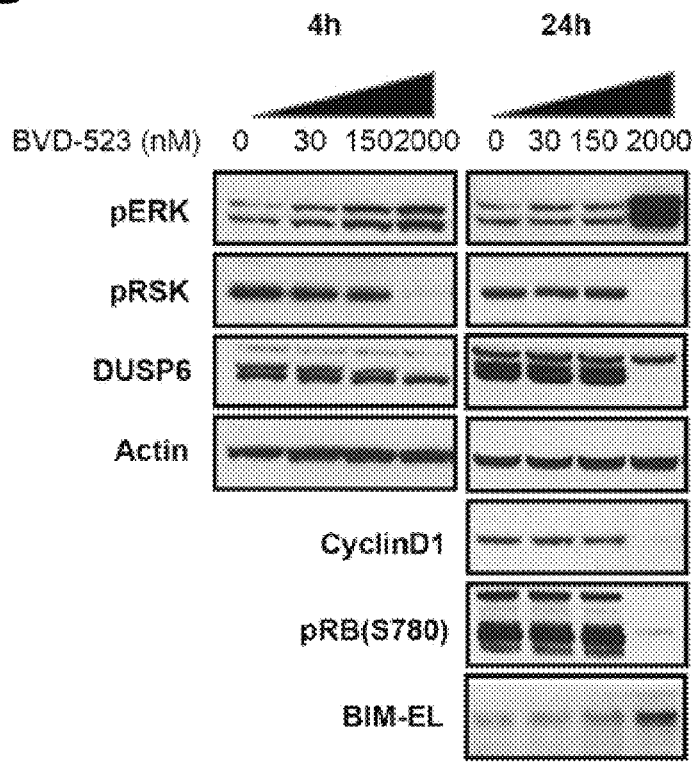

To further characterize the mechanism of action and effects on signaling elicited by BVD-523, the levels of various effector and MAPK-related proteins were assessed in BVD-523-treated $BRAF^{V600E}$-mutant A375 melanoma cells (FIG. 30D). Phospho-ERK1/2 levels increased in a concentration-dependent manner after 4 and 24 hours of BVD-523 treatment. Despite prominent concentration-dependent increases in pERK1/2 observed with 2 µM BVD-523 treatment, phosphorylation of the ERK1/2 target RSK1/2 was reduced at both 4 and 24 hours, which is consistent with sustained inhibition. Total protein levels of DUSP6, a distal marker of ERK1/2 activity, were also attenuated at 4 and 24 hours. Following 24 hours of treatment with BVD-523, the apoptotic marker BIM-EL increased in a dose-dependent manner, while cyclin D-1 and pRB was attenuated at 2 µM. All effects are consistent with on-target ERK1/2 inhibition.

TABLE 22

| Barcode | Organ | Cell ID | Cell Line | Compound No | Fitted MGH_IC50 | Viability ratio | | | | | | | | |
|---|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_8049_00277140 | Biliary Tract | 8049 | ETK-1 | 456 | 3.525905 | 0.587 | 0.805 | 0.874 | 0.9304 | 0.8796 | 0.954 | 1.0285 | 1.094 | 0.9918 |
| 026_664_00277150 | Biliary Tract | 664 | HuCCT1 | 456 | 3.600435 | 0.663 | 0.734 | 0.847 | 0.9661 | 0.9652 | 1.029 | 0.9656 | 1.0172 | 0.9981 |
| 026_653_00278500 | Biliary Tract | 653 | EGI-1 | 456 | 4.229085 | 0.693 | 0.686 | 0.74 | 0.7843 | 0.8546 | 0.889 | 0.967 | 0.9286 | 0.9525 |
| 026_8204_00278540 | Biliary Tract | 8204 | TGBC24TKB | 456 | 5.609877 | 0.768 | 0.875 | 0.826 | 0.8122 | 0.8629 | 0.862 | 0.8909 | 0.9353 | 0.9353 |
| 026_8188_00293390 | Biliary Tract | 8188 | TGBC1TKB | 456 | 6.179370 | 0.915 | 0.929 | 0.913 | 0.9808 | 0.9201 | 1.144 | 1.0128 | 0.9048 | 0.9496 |
| 026_330_00278580 | Bone | 330 | H-EMC-SS | 456 | 0.038629 | 0.36 | 0.392 | 0.383 | 0.4615 | 0.437 | 0.566 | 0.7772 | 0.9442 | 0.9662 |
| 026_8047_00283120 | Bone | 8047 | ES7 | 456 | 1.846677 | 0.515 | 0.521 | 0.539 | 0.5362 | 0.7569 | 0.769 | 0.8353 | 0.9371 | 0.9503 |
| 026_8053_00287650 | Bone | 8053 | EW-13 | 456 | 2.197657 | 0.333 | 0.545 | 0.665 | 0.8165 | 0.9099 | 0.962 | 0.9571 | 0.9945 | 1.0406 |
| 026_8227_00288230 | Bone | 8227 | CADO-ES1 | 456 | 2.294467 | 0.359 | 0.554 | 0.585 | 1.0384 | 0.9034 | 0.952 | 1.1264 | 1.2671 | 1.0023 |
| 026_8050_00279380 | Bone | 8050 | EW-1 | 456 | 2.409222 | 0.487 | 0.555 | 0.593 | 0.6879 | 0.6908 | 0.788 | 0.8057 | 0.892 | 0.9331 |
| 026_306_00278530 | Bone | 306 | SK-ES-1 | 456 | 2.4607 | 0.527 | 0.556 | 0.577 | 0.682 | 0.673 | 0.855 | 0.8706 | 0.8641 | 0.8867 |
| 026_305_00277180 | Bone | 305 | U-2 OS | 456 | 2.847932 | 0.145 | 0.599 | 0.657 | 0.7441 | 0.8231 | 0.793 | 0.8449 | 0.9969 | 0.8925 |
| 026_337_00283440 | Bone | 337 | HuO9 | 456 | 2.916396 | 0.448 | 0.696 | 0.939 | 0.8026 | 0.8478 | 0.903 | 0.9796 | 0.8682 | 1.0954 |
| 026_8227_00304340 | Bone | 8227 | CADO-ES1 | 456 | 2.975471 | 0.542 | 0.666 | 0.884 | 0.8917 | 0.9918 | 0.974 | 1.0247 | 1.0031 | 1.0728 |
| 026_8043_00283110 | Bone | 8043 | ES1 | 456 | 2.981717 | 0.543 | 0.663 | 0.705 | 0.7865 | 0.811 | 0.835 | 0.7995 | 0.9278 | 0.8292 |
| 026_8142_00282550 | Bone | 8142 | NOS-1 | 456 | 3.203574 | 0.547 | 0.775 | 0.825 | 0.892 | 0.7556 | 0.894 | 0.8477 | 1.1038 | 0.9881 |
| 026_8055_00290580 | Bone | 8055 | EW-18 | 456 | 3.311765 | 0.638 | 0.688 | 0.718 | 1.1012 | 0.9293 | 0.993 | 1.0646 | 1.1264 | 1.0895 |
| 026_8058_00293350 | Bone | 8058 | EW-3 | 456 | 3.363484 | 0.715 | 0.595 | 0.72 | 0.7195 | 0.8774 | 0.8 | 0.8628 | 0.9101 | 1.2148 |
| 026_339_00277160 | Bone | 339 | NY | 456 | 3.400937 | 0.59 | 0.789 | 0.875 | 0.9222 | 0.9594 | 0.975 | 0.933 | 1.1433 | 0.9637 |
| 026_8165_00287690 | Bone | 8165 | SK-PN-DW | 456 | 3.476926 | 0.621 | 0.812 | 0.933 | 0.9706 | 0.9188 | 0.991 | 1.0026 | 1.0012 | 1.0432 |
| 026_326_00282540 | Bone | 326 | MHH-ES-1 | 456 | 3.524605 | 0.618 | 0.719 | 0.824 | 0.8235 | 0.8745 | 0.966 | 1.1187 | 1.0416 | 0.913 |
| 026_8048_00279370 | Bone | 8048 | ES8 | 456 | 3.530755 | 0.572 | 0.698 | 0.765 | 0.8053 | 0.8255 | 0.912 | 0.931 | 0.9069 | 1.0095 |
| 026_331_00278590 | Bone | 331 | HOS | 456 | 3.602447 | 0.53 | 0.798 | 0.749 | 0.7609 | 0.8727 | 0.839 | 0.8786 | 0.8236 | 0.972 |
| 026_8045_00282660 | Bone | 8045 | ESS | 456 | 3.665641 | 0.704 | 0.653 | 0.874 | 0.8827 | 0.7407 | 0.913 | 0.8294 | 1.0585 | 1.162 |
| 026_8059_00282520 | Bone | 8059 | EW-7 | 456 | 3.827217 | 0.662 | 0.72 | 0.76 | 0.831 | 0.8857 | 0.95 | 0.9309 | 0.9266 | 0.9963 |
| 026_8201_00282520 | Bone | 8201 | ES3 | 456 | 3.982944 | 0.707 | 0.721 | 0.778 | 0.8414 | 0.8385 | 0.989 | 0.9588 | 1.0248 | 1.0261 |
| 026_8056_00314310 | Bone | 8056 | EW-22 | 456 | 4.196343 | 0.701 | 0.827 | 0.819 | 0.8824 | 0.9413 | 0.894 | 0.9848 | 1.0221 | 1.1139 |
| 026_329_00282700 | Bone | 329 | G-292 Clone A141B1 | 456 | 4.264519 | 0.705 | 0.918 | 0.893 | 0.949 | 1.0435 | 1.016 | 0.9814 | 0.9215 | 1.1209 |
| 026_324_00278550 | Bone | 324 | CAL-72 | 456 | 4.286956 | 0.731 | 0.942 | 0.942 | 0.9262 | 0.9863 | 0.966 | 0.9797 | 0.9547 | 1.0113 |
| 026_304_00283460 | Bone | 304 | Saos-2 | 456 | 4.597501 | 0.742 | 0.784 | 0.9 | 0.8765 | 0.9306 | 0.926 | 0.9516 | 0.95 | 1.0352 |
| 026_325_00283060 | Bone | 325 | CAL-78 | 456 | 4.650689 | 0.727 | 0.913 | 0.918 | 0.9149 | 0.8999 | 0.897 | 0.9065 | 1.0242 | 1.0181 |
| 026_1138_00278560 | Bone | 1138 | CS1 | 456 | 4.765346 | 0.744 | 0.848 | 0.864 | 0.8601 | 0.8818 | 1.016 | 1.0005 | 0.9749 | 0.977 |
| 026_8162_00282560 | Bone | 8162 | SJSA-1 | 456 | 4.867417 | 0.802 | 0.803 | 0.805 | 0.7765 | 0.762 | 0.974 | 1.0651 | 1.0412 | 1.0623 |
| 026_336_00283430 | Bone | 336 | HuO-3N1 | 456 | 4.900372 | 0.724 | 0.86 | 0.806 | 0.8427 | 0.8308 | 0.87 | 0.8972 | 0.9772 | 1.0073 |
| 026_328_00278600 | Bone | 328 | TC-71 | 456 | 5.117725 | 0.844 | 0.939 | 0.97 | 1.0221 | 0.9857 | 1.072 | 1.023 | 1.0842 | 1.0771 |
| 026_8054_00282530 | Bone | 8054 | EW-16 | 456 | 5.180986 | 0.835 | 0.775 | 0.925 | 0.8021 | 1.0185 | 0.934 | 0.9339 | 1.058 | 1.1414 |
| 026_335_00308220 | Bone | 335 | MG-63 | 456 | 5.257203 | 0.884 | 0.841 | 0.852 | 0.8745 | 1.0185 | 1.081 | 1.1007 | 1.0325 | 1.0709 |
| 026_1241_00283070 | Bone | 1241 | CHSA8926 | 456 | 5.394244 | 0.883 | 0.851 | 0.947 | 0.9788 | 0.9327 | 1.019 | 1.0879 | 1.0294 | 1.119 |
| 026_8044_00279340 | Bone | 8044 | ES4 | 456 | 6.158016 | 0.822 | 0.876 | 0.92 | 0.8612 | 0.8592 | 0.873 | 0.8969 | 0.9914 | 0.9632 |
| 026_8057_00283080 | Bone | 8057 | EW-24 | 456 | 6.273162 | 0.927 | 0.899 | 0.97 | 0.9817 | 0.9704 | 1.012 | 0.9822 | 0.9596 | 0.9793 |
| 026_8051_00285230 | Bone | 8051 | EW-11 | 456 | 6.340509 | 0.924 | 1.008 | 0.846 | 0.9309 | 1.047 | 0.868 | 0.9762 | 1.0834 | 1.048 |
| 026_8046_00279351 | Bone | 8046 | ES6 | 456 | 6.745328 | 0.882 | 1.065 | 1.046 | 1.0203 | 1.0617 | 0.85 | 0.8881 | 1.0547 | 0.9578 |
| 026_8146_00285140 | Brain | 8146 | ONS-76 | 456 | 1.017095 | 0.362 | 0.369 | 0.387 | 0.52 | 0.6146 | 0.733 | 0.8773 | 0.9176 | 1.1016 |
| 026_8009_00285111 | Brain | 8009 | AM-38 | 456 | 2.859683 | 0.545 | 0.617 | 0.664 | 0.5881 | 0.5592 | 0.692 | 0.826 | 0.9522 | 1.078 |
| 026_8091_00285281 | Brain | 8091 | KS-1 | 456 | 2.979142 | 0.617 | 0.59 | 0.62 | 0.7057 | 0.7844 | 0.875 | 0.9025 | 1.0584 | 1.1343 |

TABLE 22-continued

| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| | | | | | | | | | | Viability ratio | | | | |
| 026_388_00285240 | Brain | 388 | MOG-G-CCM | 456 | 3.029922 | 0.505 | 0.754 | 0.852 | 0.977 | 0.9597 | 0.989 | 1.1211 | 1.0361 | 1.0747 |
| 026_352_00283150 | Brain | 352 | LN-229 | 456 | 3.053877 | 0.552 | 0.647 | 0.662 | 0.7206 | 0.8119 | 0.932 | 0.9285 | 1.0381 | 1.0748 |
| 026_8214_00290680 | Brain | 8214 | YH-13 | 456 | 3.068585 | 0.558 | 0.628 | 0.773 | 1.0443 | 0.9614 | 1.113 | 1.1139 | 1.093 | 1.2619 |
| 026_8214_00288290 | Brain | 8214 | YH-13 | 456 | 3.531592 | 0.627 | 0.651 | 0.866 | 0.8387 | 0.8073 | 0.922 | 1.077 | 1.0619 | 1.1182 |
| 026_358_00293700 | Brain | 358 | D283 Med | 456 | 3.551231 | 0.64 | 0.743 | 0.916 | 0.9078 | 0.9464 | 0.928 | 0.871 | 0.9767 | 1.4204 |
| 026_8061_00290830 | Brain | 8061 | GB-1 | 456 | 3.686496 | 0.613 | 0.692 | 0.809 | 0.8255 | 0.8977 | 0.877 | 0.9922 | 0.9416 | 0.8923 |
| 026_374_00283180 | Brain | 374 | U-251 MG | 456 | 3.933399 | 0.654 | 0.733 | 0.861 | 0.8164 | 0.8981 | 0.891 | 0.9222 | 0.9976 | 1.1342 |
| 026_343_00283160 | Brain | 343 | PFSK-1 | 456 | 3.963833 | 0.626 | 0.904 | 1.007 | 1.0229 | 0.934 | 1.078 | 1.0411 | 1.0084 | 1.052 |
| 026_393_00283190 | Brain | 393 | YKG-1 | 456 | 3.987729 | 0.646 | 0.714 | 0.77 | 0.8178 | 0.8374 | 0.848 | 0.953 | 0.8805 | 1.0209 |
| 026_8028_00287650 | Brain | 8028 | D-263MG | 456 | 4.157483 | 0.662 | 0.709 | 0.734 | 0.7813 | 0.8341 | 0.839 | 0.9023 | 0.9333 | 1.0435 |
| 026_379_00283140 | Brain | 379 | GAMG | 456 | 4.214093 | 0.681 | 0.701 | 0.829 | 0.8043 | 0.8412 | 0.83 | 0.9322 | 0.8908 | 1.046 |
| 026_8019_00293320 | Brain | 8019 | CAS-1 | 456 | 4.309856 | 0.732 | 0.772 | 0.825 | 0.9222 | 0.9783 | 1.227 | 0.8865 | 0.8407 | 1.1628 |
| 026_8001_00285100 | Brain | 8001 | 8-MG-BA | 456 | 4.345495 | 0.688 | 0.845 | 0.88 | 0.8958 | 0.9285 | 0.912 | 0.9148 | 0.9398 | 1.07 |
| 026_351_00283450 | Brain | 351 | LN-18 | 456 | 4.481815 | 0.685 | 0.822 | 0.862 | 0.8746 | 0.8966 | 0.902 | 0.9022 | 0.9311 | 0.9325 |
| 026_357_00283410 | Brain | 357 | H4 | 456 | 4.481909 | 0.721 | 0.808 | 0.876 | 0.858 | 0.8822 | 0.94 | 1.0232 | 0.9287 | 1.0614 |
| 026_8085_00293731 | Brain | 8085 | KINGS-1 | 456 | 4.48888 | 0.797 | 0.781 | 0.82 | 0.9645 | 0.9641 | 1.015 | 0.9981 | 1.0442 | 0.974 |
| 026_350_00284910 | Brain | 350 | M059J | 456 | 4.537622 | 0.723 | 0.834 | 0.869 | 0.8888 | 0.9473 | 0.909 | 0.9144 | 1.0191 | 1.0818 |
| 026_8015_00308070 | Brain | 8015 | Becker | 456 | 4.548091 | 0.696 | 0.814 | 0.876 | 0.8121 | 0.825 | 0.889 | 0.917 | 0.9113 | 1.0138 |
| 026_8160_00287680 | Brain | 8160 | SF539 | 456 | 4.738405 | 0.726 | 0.89 | 0.827 | 0.8875 | 0.9392 | 0.934 | 0.952 | 1.0525 | 0.9285 |
| 026_8159_00287670 | Brain | 8159 | SF268 | 456 | 4.804304 | 0.786 | 0.825 | 0.923 | 0.9225 | 0.9772 | 0.99 | 0.978 | 0.9754 | 0.9699 |
| 026_359_00283100 | Brain | 359 | Daoy | 456 | 4.81575 | 0.683 | 0.74 | 0.796 | 0.8102 | 0.876 | 0.896 | 0.9135 | 0.9254 | 0.9257 |
| 026_8217_00284910 | Brain | 8217 | SK-MG-1 | 456 | 4.83361 | 0.725 | 0.784 | 0.83 | 0.844 | 0.8849 | 0.901 | 0.9119 | 0.9353 | 0.9859 |
| 026_342_00285160 | Brain | 342 | SW 1783 | 456 | 4.84471 | 0.796 | 0.905 | 0.896 | 0.9349 | 1.0662 | 0.935 | 1.0347 | 1.0148 | 1.08 |
| 026_8029_00288240 | Brain | 8029 | D-336MG | 456 | 4.925588 | 0.792 | 0.892 | 0.997 | 0.8872 | 0.9556 | 0.944 | 1.105 | 1.0724 | 1.1057 |
| 026_8030_00295500 | Brain | 8030 | D-392MG | 456 | 4.966575 | 0.791 | 0.866 | 0.824 | 0.9331 | 0.8638 | 1.022 | 0.9531 | 0.9688 | 1.0531 |
| 026_8089_00287440 | Brain | 8089 | KNS-81-FD | 456 | 5.077406 | 0.804 | 0.89 | 0.869 | 0.8138 | 0.8421 | 1.049 | 1.0747 | 0.9317 | 1.1222 |
| 026_8138_00285290 | Brain | 8138 | NMC-G1 | 456 | 5.086457 | 0.771 | 0.817 | 0.763 | 0.762 | 0.8138 | 0.887 | 0.968 | 1.0104 | 1.049 |
| 026_8139_00285130 | Brain | 8139 | no-10 | 456 | 5.147267 | 0.824 | 0.888 | 0.928 | 0.9069 | 0.9436 | 0.99 | 0.943 | 1.05 | 1.0543 |
| 026_8083_00293720 | Brain | 8083 | KALS-1 | 456 | 5.203248 | 0.817 | 0.765 | 0.902 | 0.9843 | 0.9376 | 0.896 | 0.9382 | 1.0116 | 0.9496 |
| 026_378_00284880 | Brain | 378 | DK-MG | 456 | 5.2953 | 0.789 | 0.757 | 0.713 | 0.7178 | 0.7297 | 0.901 | 0.8425 | 0.9101 | 1.0114 |
| 026_383_00284900 | Brain | 383 | LN-405 | 456 | 5.313289 | 0.839 | 0.886 | 0.901 | 0.937 | 0.8868 | 1.041 | 0.949 | 1.0816 | 1.0986 |
| 026_8032_00293340 | Brain | 8032 | D-542MG | 456 | 5.342096 | 0.822 | 0.856 | 0.927 | 0.9108 | 0.8977 | 0.934 | 0.9191 | 0.9743 | 0.9895 |
| 026_344_00282720 | Brain | 344 | LNZTA3WT4 | 456 | 5.43481 | 0.777 | 1.136 | 0.931 | 0.9386 | 0.9371 | 1.018 | 1.0441 | 1.0001 | 0.9944 |
| 026_8167_00290910 | Brain | 8167 | SNB75 | 456 | 5.474524 | 0.76 | 0.772 | 0.83 | 0.8023 | 0.8147 | 1.01 | 0.8804 | 0.1523 | 0.9382 |
| 026_8087_00285270 | Brain | 8087 | KNS-42 | 456 | 5.484622 | 0.862 | 0.858 | 0.846 | 0.8777 | 0.9301 | 0.972 | 0.9923 | 1.0701 | 1.0135 |
| 026_354_00287481 | Brain | 354 | U-87 MG | 456 | 5.588679 | 0.851 | 0.949 | 0.942 | 0.9605 | 0.9939 | 1.004 | 1.0222 | 0.9964 | 1.0855 |
| 026_8140_00285300 | Brain | 8140 | no-11 | 456 | 5.608459 | 0.844 | 0.885 | 0.896 | 0.959 | 0.9411 | 0.893 | 0.9627 | 0.1352 | 0.9432 |
| 026_8221_00284860 | Brain | 8221 | D-423MG | 456 | 5.731372 | 0.807 | 0.783 | 0.798 | 0.8469 | 0.8833 | 0.945 | 0.9877 | 0.9131 | 0.9215 |
| 026_348_00283400 | Brain | 348 | DBTRG-05MG | 456 | 5.749405 | 0.792 | 0.75 | 0.763 | 0.7919 | 0.7917 | 0.856 | 0.9393 | 0.9013 | 0.9922 |
| 026_341_00285310 | Brain | 341 | SW 1088 | 456 | 5.805148 | 0.869 | 0.907 | 0.895 | 0.8893 | 0.9105 | 0.919 | 0.966 | 0.8961 | 0.9922 |
| 026_356_00283420 | Brain | 356 | Hs 683 | 456 | 5.858982 | 0.841 | 0.993 | 0.888 | 0.8789 | 0.8908 | 1.04 | 0.8743 | 0.906 | 1.058 |
| 026_8031_00287640 | Brain | 8031 | D-502MG | 456 | 5.99897 | 0.825 | 0.819 | 0.771 | 0.7649 | 0.8658 | 0.834 | 0.9457 | 0.9922 | 0.9572 |
| 026_8224_00284870 | Brain | 8224 | D-566MG | 456 | 6.026403 | 0.839 | 0.84 | 0.858 | 0.8841 | 0.9252 | 0.941 | 0.968 | 0.9815 | 0.9816 |
| 026_389_00284920 | Brain | 389 | MOG-G-UVW | 456 | 6.074777 | 0.861 | 0.876 | 0.879 | 0.9129 | 0.9904 | 0.902 | 1.0597 | 0.9108 | 1.0304 |
| 026_341_00283470 | Brain | 341 | SW1088 | 456 | 6.105387 | 0.913 | 0.89 | 0.897 | 0.897 | 0.9463 | 0.931 | 0.9486 | 0.9506 | 1.1024 |
| 026_375_00283480 | Brain | 375 | 42-MG-BA | 456 | 6.106423 | 0.896 | 0.892 | 0.932 | 0.944 | 0.9633 | 0.976 | 0.9735 | 0.9871 | 1.0285 |
| 026_1122_00283170 | Brain | 1122 | SF-295 | 456 | 6.112956 | 0.879 | 0.909 | 0.909 | 0.9301 | 0.9215 | 0.946 | 0.9199 | 0.9433 | 1.0329 |
| 026_8158_00290650 | Brain | 8158 | SF126 | 456 | 6.158755 | 0.86 | 0.97 | 1 | 1.0676 | 1.0025 | 1.187 | 0.9851 | 0.9627 | 1.1324 |

TABLE 22-continued

| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_340_00285250 | Brain | 340 | CCF-STTG1 | 456 | 6.170298 | 0.851 | 0.911 | 0.916 | 0.9011 | 0.9748 | 0.919 | 0.9109 | 0.9323 | 0.9837 |
| 026_380_00284890 | Brain | 380 | GMS-10 | 456 | 6.23472 | 0.842 | 0.885 | 0.853 | 0.8466 | 0.8914 | 0.914 | 0.8882 | 1.0019 | 1.0545 |
| 026_354_00290361 | Brain | 354 | U-87 MG | 456 | 6.315816 | 0.93 | 0.874 | 0.977 | 0.9346 | 0.9336 | 1.084 | 0.9295 | 1.062 | 1.073 |
| 026_8063_00290841 | Brain | 8063 | GI-1 | 456 | 6.443002 | 0.809 | 0.877 | 0.913 | 0.9018 | 0.9184 | 0.86 | 0.9241 | 0.9072 | 0.9709 |
| 026_8027_00293330 | Brain | 8027 | D-247MG | 456 | 6.453915 | 0.928 | 0.905 | 0.908 | 0.8398 | 0.8592 | 0.911 | 0.9463 | 0.9529 | 0.9044 |
| 026_346_00283390 | Brain | 346 | A172 | 456 | 6.640511 | 0.941 | 0.953 | 0.995 | 1.0208 | 0.9242 | 1.026 | 1.0141 | 1.0236 | 1.0356 |
| 026_8089_00291170 | Brain | 8089 | KNS-81-FD | 456 | 7.067458 | 0.854 | 0.823 | 0.854 | 0.8437 | 0.8524 | 0.889 | 0.8917 | 0.9075 | 0.9111 |
| 026_355_00285180 | Brain | 355 | U-118 MG | 456 | 7.408088 | 0.965 | 1.005 | 0.945 | 0.9352 | 0.9307 | 0.932 | 0.9407 | 0.945 | 0.9851 |
| 026_347_00282740 | Brain | 347 | T98G | 456 | 7.802123 | 0.986 | 1.098 | 0.951 | 1.0602 | 0.9957 | 1.038 | 1.0462 | 0.9753 | 0.982 |
| 026_417_00271110 | Breast | 417 | DU4475 | 456 | -3.0044 | 0.119 | 0.118 | 0.124 | 0.1202 | 0.1235 | 0.121 | 0.164 | 0.4789 | 0.6922 |
| 26_465_00271670 | Breast | 465 | MRK-nu-1 | 456 | 1.744742 | 0.115 | 0.398 | 0.572 | 0.6893 | 0.7807 | 0.868 | 0.921 | 0.9463 | 1.1175 |
| 026_438_00273540 | Breast | 438 | HCC1599 | 456 | 1.968855 | 0.352 | 0.459 | 0.617 | 0.7517 | 0.8021 | 0.899 | 0.9102 | 0.9757 | 1.0216 |
| 026_435_00271290 | Breast | 435 | HCC1187 | 456 | 2.132259 | 0.375 | 0.482 | 0.801 | 0.7466 | 0.7917 | 0.794 | 0.9164 | 0.9352 | 0.9707 |
| 026_403_00271400 | Breast | 403 | MCF7 | 456 | 2.857648 | 0.493 | 0.634 | 0.765 | 0.8761 | 0.9706 | 0.973 | 0.9569 | 0.1047 | 1.0456 |
| 026_401_00273450 | Breast | 401 | MDA-MB-468 | 456 | 3.05753 | 0.415 | 0.718 | 0.931 | 0.9526 | 0.909 | 0.954 | 0.9512 | 1.0282 | 0.9601 |
| 26_451_00271640 | Breast | 451 | CAL-85-1 | 456 | 3.06898 | 0.489 | 0.695 | 0.808 | 0.7646 | 0.8147 | 0.885 | 0.8459 | 1.0885 | 0.9906 |
| 026_404_00273430 | Breast | 404 | MDA-MB-231 | 456 | 3.086092 | 0.483 | 0.731 | 0.783 | 0.824 | 0.8358 | 0.874 | 0.9446 | 0.9609 | 1.0599 |
| 026_418_00271550 | Breast | 418 | Hs 578T | 456 | 3.125956 | 0.071 | 0.614 | 0.832 | 0.7916 | 0.8611 | 0.836 | 0.9556 | 0.9556 | 1.0186 |
| 026_402_00272120 | Breast | 402 | CAMA-1 | 456 | 3.166443 | 0.55 | 0.636 | 0.773 | 0.8152 | 0.9017 | 0.886 | 0.906 | 0.9417 | 0.9695 |
| 026_426_00274200 | Breast | 426 | HCC1569 | 456 | 3.228782 | 0.571 | 0.713 | 0.945 | 0.9056 | 0.9414 | 0.938 | 0.9814 | 1.028 | 1.0046 |
| 026_431_00271130 | Breast | 431 | HCC1806 | 456 | 3.337319 | 0.566 | 0.672 | 0.68 | 0.6852 | 0.6987 | 0.765 | 0.8378 | 1.0081 | 1.1468 |
| 026_414_00271900 | Breast | 414 | AU565 | 456 | 3.409308 | 0.533 | 0.816 | 0.949 | 0.9831 | 0.7917 | 0.924 | 0.9729 | 0.9876 | 1.1475 |
| 026_452_00271130 | Breast | 452 | COLO-824 | 456 | 3.645131 | 0.358 | 0.743 | 0.843 | 0.9519 | 0.9643 | 0.904 | 0.9021 | 1.0288 | 0.9665 |
| 026_416_00271360 | Breast | 416 | BT-549 | 456 | 3.723874 | 0.659 | 0.818 | 0.911 | 0.9492 | 0.9446 | 0.965 | 0.9707 | 0.9785 | 1.0314 |
| 026_8144_00274240 | Breast | 8144 | OCUB-M | 456 | 3.727884 | 0.44 | 0.801 | 0.89 | 0.9127 | 1.0139 | 1.046 | 0.9729 | 0.96 | 1.0167 |
| 026_432_00271960 | Breast | 432 | HCC70 | 456 | 3.73179 | 0.605 | 0.733 | 0.855 | 0.8647 | 0.8214 | 0.887 | 0.9582 | 0.9394 | 1.1987 |
| 026_457_00273420 | Breast | 457 | EVSA-T | 456 | 3.968951 | 0.686 | 0.879 | 0.927 | 0.9385 | 0.9505 | 0.975 | 0.9713 | 0.9606 | 1.0214 |
| 026_466_00274370 | Breast | 466 | YMB-1-E | 456 | 3.997753 | 0.654 | 0.836 | 0.87 | 0.9113 | 0.9082 | 0.908 | 0.9623 | 1.0457 | 0.9738 |
| 026_441_00285120 | Breast | 441 | HCC2157 | 456 | 3.997874 | 0.474 | 1.044 | 0.849 | 0.8244 | 0.6122 | 0.948 | 1.0739 | 0.6695 | 1.0405 |
| 026_443_00271990 | Breast | 443 | MDA-MB-330 | 456 | 4.004084 | 0.601 | 0.92 | 0.94 | 0.9085 | 0.9663 | 0.971 | 0.9817 | 0.9257 | 1.0607 |
| 026_436_00271300 | Breast | 436 | HCC1395 | 456 | 4.036641 | 0.703 | 0.897 | 0.946 | 0.9395 | 1.0136 | 1.033 | 1.0207 | 1.0407 | 1.1296 |
| 026_412_00271190 | Breast | 412 | UACC-893 | 456 | 4.234383 | 0.421 | 0.859 | 0.854 | 0.8448 | 0.9188 | 0.999 | 0.9512 | 1.0422 | 0.9971 |
| 026_450_00271390 | Breast | 450 | CAL-51 | 456 | 4.319545 | 0.85 | 0.725 | 0.783 | 0.8043 | 0.8395 | 0.899 | 0.9313 | 0.9642 | 1.0975 |
| 026_449_00271380 | Breast | 449 | CAL-148 | 456 | 4.389344 | 0.678 | 0.676 | 1.08 | 0.9571 | 0.7093 | 0.888 | 0.981 | 0.8213 | 1.2196 |
| 026_434_00271920 | Breast | 434 | HCC143 | 456 | 4.464516 | 0.747 | 0.808 | 0.808 | 0.822 | 0.8893 | 0.923 | 0.919 | 0.949 | 1.1427 |
| 026_433_00276270 | Breast | 433 | HCC202 | 456 | 4.571252 | 0.726 | 0.9 | 0.944 | 0.8549 | 0.8115 | 0.943 | 0.972 | 0.9241 | 0.9618 |
| 026_422_00274230 | Breast | 422 | MDA-MB-175-VII | 456 | 4.594595 | 0.686 | 0.73 | 0.74 | 0.7666 | 0.8545 | 0.848 | 0.9155 | 0.9541 | 0.9487 |
| 026_461_00271330 | Breast | 461 | MFM-223 | 456 | 4.656681 | 0.7 | 0.875 | 0.908 | 0.9465 | 0.988 | 1.047 | 1.0015 | 1.1431 | 1.0159 |
| 026_427_00271330 | Breast | 427 | MDA-MB-453 | 456 | 4.669025 | 0.787 | 0.819 | 0.921 | 0.9998 | 0.9757 | 0.998 | 1.0349 | 1.0264 | 1.1651 |
| 026_448_00271370 | Breast | 448 | CAL-120 | 456 | 4.779687 | 0.795 | 0.746 | 0.796 | 0.8032 | 0.8728 | 0.85 | 0.9852 | 1.0071 | 1.0287 |
| 026_411_00271420 | Breast | 411 | UACC-812 | 456 | 5.072094 | 0.744 | 0.894 | 0.873 | 0.9564 | 0.9958 | 0.944 | 0.9931 | 1.0326 | 0.9659 |
| 026_442_00273480 | Breast | 442 | HCC2218 | 456 | 5.225292 | 0.82 | 0.923 | 0.963 | 1.0597 | 1.042 | 1.043 | 1.0714 | 1.0498 | 1.0318 |
| 026_398_00271300 | Breast | 398 | HCC1428 | 456 | 5.256241 | 0.614 | 0.899 | 1.013 | 0.8915 | 0.9851 | 0.983 | 0.9959 | 0.9937 | 1.0331 |
| 026_464_00308490 | Breast | 464 | T47D | 456 | 5.26439 | 0.85 | 0.853 | 0.869 | 0.8588 | 0.823 | 0.978 | 0.9397 | 0.9562 | 0.968 |
| 026_400_00273440 | Breast | 400 | MDA-MB-436 | 456 | 5.286367 | 0.825 | 0.844 | 0.848 | 0.8326 | 0.8721 | 0.851 | 0.8881 | 0.9805 | 0.933 |
| 026_437_00280161 | Breast | 437 | HCC1500 | 456 | 5.288806 | 0.725 | 0.982 | 0.913 | 0.8847 | 0.9397 | 1.088 | 0.8523 | 0.9109 | 0.9883 |
| 026_440_00271950 | Breast | 440 | HCC1954 | 456 | 5.303093 | 0.796 | 0.813 | 0.885 | 0.8155 | 0.8463 | 0.861 | 0.0199 | 1.0209 | 0.9481 |
| 026_413_00271930 | Breast | 413 | HCC1419 | 456 | 5.337084 | 0.807 | 0.807 | 0.932 | 0.9634 | 0.9633 | 0.941 | 0.9595 | 0.9516 | 1.1518 |

TABLE 22-continued

| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| | | | | | | | | | | Viability ratio | | | | |
| 026_410_00272180 | Breast | 410 | ZR-75-30 | 456 | 5.373081 | 0.83 | 0.857 | 0.88 | 0.8529 | 0.9183 | 0.913 | 0.911 | 1.03 | 0.9685 |
| 026_439_00271940 | Breast | 439 | HCC1937 | 456 | 5.44243 | 0.841 | 0.952 | 0.975 | 1.0253 | 0.9632 | 0.953 | 1.0302 | 1.0262 | 1.0774 |
| 026_408_00271350 | Breast | 408 | BT-20 | 456 | 5.735872 | 0.871 | 0.955 | 0.93 | 0.9913 | 0.9764 | 0.972 | 1.0674 | 0.9818 | 1.1818 |
| 026_399_00272160 | Breast | 399 | MDA-MB-415 | 456 | 5.879088 | 0.884 | 0.875 | 0.885 | 0.8851 | 0.9175 | 0.914 | 0.9179 | 0.9049 | 0.9735 |
| 026_458_00274220 | Breast | 458 | HDQ-P1 | 456 | 6.259493 | 0.84 | 1.072 | 1.136 | 1.0763 | 1.0797 | 1.042 | 1.0437 | 1.0231 | 1.0073 |
| 026_397_00274350 | Breast | 397 | HCC38 | 456 | 6.744219 | 0.874 | 1.053 | 1.023 | 1.0222 | 0.9856 | 0.93 | 0.9274 | 0.9402 | 0.9941 |
| 026_405_00274360 | Breast | 405 | MDA-MB-361 | 456 | 6.792889 | 0.935 | 0.959 | 0.987 | 0.9819 | 0.9119 | 0.921 | 0.9597 | 0.998 | 0.9922 |
| 026_425_00280231 | Breast | 425 | MDA-MB-157 | 456 | 7.000504 | 0.906 | 1.069 | 1.05 | 0.9597 | 0.9229 | 0.966 | 0.9422 | 0.9712 | 0.9545 |
| 026_454_00272140 | Breast | 454 | EFM-192A | 456 | 7.097342 | 0.942 | 1.032 | 1.041 | 1.0545 | 0.9812 | 0.979 | 1.0186 | 1.0191 | 0.9742 |
| 026_420_00271541 | Breast | 420 | BT-474 | 456 | 7.458914 | 0.191 | 1.089 | 1.053 | 1.0824 | 1.0008 | 0.955 | 0.9764 | 0.9678 | 1.0149 |
| 026_453_00273410 | Breast | 453 | EFM-19 | 456 | 8.207256 | 1.096 | 1.286 | 1.208 | 1.1112 | 1.0544 | 1.042 | 1.0064 | 1.0474 | 1.0572 |
| 026_415_00316440 | Breast | 415 | BT-483 | 456 | 8.21654 | 1.148 | 1.275 | 1.181 | 1.1462 | 1.089 | 1.147 | 1.0671 | 1.0911 | 1.1123 |
| 026_8176_00316650 | Cervix | 8176 | TC-YIK | 456 | 0.842618 | 0.29 | 0.416 | 0.488 | 0.5211 | 0.5993 | 0.669 | 0.7672 | 0.7877 | 1.0572 |
| 026_479_00264920 | Cervix | 479 | HT-3 | 456 | 1.420025 | 0.257 | 0.608 | 0.574 | 0.5844 | 0.5901 | 0.637 | 0.8649 | 0.8189 | 0.8617 |
| 026_478_00271910 | Cervix | 478 | C-33 A | 456 | 2.72591 | 0.472 | 0.615 | 0.658 | 0.6776 | 0.6753 | 0.734 | 0.7964 | 0.8383 | 0.9143 |
| 026_478_00269410 | Cervix | 478 | C-33 A | 456 | 2.976483 | 0.445 | 0.701 | 0.714 | 0.731 | 0.8172 | 0.771 | 0.9038 | 0.852 | 0.9634 |
| 026_493_00268830 | Cervix | 493 | ME-180 | 456 | 3.07379 | 0.509 | 0.667 | 0.695 | 0.7355 | 0.6828 | 0.732 | 0.7953 | 0.9097 | 1.0456 |
| 026_476_00269050 | Cervix | 476 | C-4 I | 456 | 3.232632 | 0.508 | 0.792 | 0.857 | 0.8645 | 0.8671 | 0.933 | 1.0078 | 1.0484 | 1.1636 |
| 026_8145_00271140 | Cervix | 8145 | OMC-1 | 456 | 3.295968 | 0.531 | 0.786 | 0.84 | 0.8546 | 0.9307 | 0.911 | 1.0261 | 1.0441 | 1.0392 |
| 026_484_00263710 | Cervix | 484 | Ca Ski | 456 | 3.639931 | 0.327 | 0.715 | 0.879 | 0.8811 | 0.8284 | 0.817 | 0.9599 | 1.0361 | 1.165 |
| 026_469_00264610 | Cervix | 469 | HeLa | 456 | 3.981495 | 0.311 | 0.783 | 0.933 | 0.9784 | 0.9807 | 0.982 | 0.9321 | 0.9429 | 0.9946 |
| 026_493_00264480 | Cervix | 493 | ME-180 | 456 | 4.007923 | 0.639 | 0.799 | 0.885 | 0.9474 | 0.9337 | 0.873 | 0.9457 | 0.8694 | 0.8949 |
| 026_474_00271150 | Cervix | 474 | SiHa | 456 | 4.596545 | 0.742 | 0.846 | 0.832 | 0.8807 | 0.9276 | 0.898 | 1.0004 | 0.9967 | 1.1646 |
| 026_482_00262520 | Cervix | 482 | SISO | 456 | 5.313141 | 0.851 | 0.946 | 0.96 | 0.9752 | 0.9888 | 0.276 | 0.975 | 0.947 | 0.9669 |
| 026_482_00274250 | Cervix | 482 | SISO | 456 | 5.375837 | 0.842 | 0.881 | 0.887 | 0.9541 | 0.9605 | 0.96 | 0.9679 | 1.044 | 1.0481 |
| 026_482_00264740 | Cervix | 482 | SISO | 456 | 5.709731 | 0.838 | 0.89 | 0.925 | 0.9202 | 0.9445 | 0.931 | 0.9609 | 0.9695 | 0.9938 |
| 026_468_00264600 | Cervix | 468 | DoTc2 4510 | 456 | 5.749229 | 0.363 | 0.92 | 0.961 | 0.9796 | 0.9907 | 0.984 | 1.01 | 0.9525 | 0.9858 |
| 026_473_00264650 | Cervix | 473 | SW756 | 456 | 5.953892 | 0.162 | 0.868 | 0.813 | 0.7938 | 0.8104 | 0.779 | 0.9163 | 0.8951 | 0.9568 |
| 026_491_00264830 | Cervix | 491 | SKG-IIIa | 456 | 6.261878 | 0.721 | 1.002 | 1.008 | 1.007 | 1.0125 | 0.97 | 1.0049 | 0.9721 | 0.9931 |
| 026_476_00264900 | Cervix | 476 | C-4 I | 456 | 6.792994 | 0.225 | 0.991 | 0.994 | 0.9083 | 0.8797 | 0.89 | 0.982 | 0.9123 | 0.9144 |
| 026_474_00264930 | Cervix | 474 | SiHa | 456 | 7.505839 | 0.532 | 0.824 | 0.865 | 0.9092 | 0.9029 | 0.879 | 0.8904 | 0.8746 | 0.8785 |
| 026_472_00264630 | Cervix | 472 | MS751 | 456 | 7.679336 | 1.023 | 0.945 | 0.949 | 0.9806 | 0.9744 | 0.979 | 0.9915 | 0.9775 | 0.9824 |
| 026_8180_00276230 | Esophagus | 8180 | TE-15 | 456 | 0.823778 | 0.313 | 0.365 | 0.448 | 0.4963 | 0.618 | 0.64 | 0.8902 | 0.6859 | 1.0361 |
| 026_502_00276550 | Esophagus | 502 | KYSE-450 | 456 | 1.219587 | 0.422 | 0.41 | 0.448 | 0.5484 | 0.5334 | 0.703 | 0.7332 | 0.8892 | 0.853 |
| 026_497_00276550 | Esophagus | 497 | KYSE-150 | 456 | 1.304746 | 0.328 | 0.402 | 0.467 | 0.567 | 0.6585 | 0.801 | 0.8957 | 0.9976 | 0.9719 |
| 026_8252_00276570 | Esophagus | 8252 | OACp4C | 456 | 1.678468 | 0.101 | 0.3 | 0.567 | 0.6503 | 0.7826 | 0.861 | 0.8531 | 0.9243 | 0.9446 |
| 026_496_00276530 | Esophagus | 496 | KYSE-140 | 456 | 2.209734 | 0.522 | 0.516 | 0.476 | 0.5824 | 0.6741 | 0.815 | 0.8515 | 0.806 | 0.8896 |
| 026_8233_00278570 | Esophagus | 8233 | ESO26 | 456 | 2.595405 | 0.493 | 0.568 | 0.679 | 0.7293 | 0.7791 | 0.852 | 0.8801 | 1.0449 | 0.8251 |
| 026_8184_00282680 | Esophagus | 8184 | TE-6 | 456 | 2.946928 | 1.152 | 0.677 | 0.704 | 0.6755 | 0.7901 | 0.89 | 1.1989 | 1.0724 | 0.9825 |
| 026_8277_00276670 | Esophagus | 8277 | TE-4 | 456 | 3.072573 | 0.518 | 0.605 | 0.768 | 0.8018 | 0.8549 | 0.883 | 0.9093 | 0.8952 | 0.9579 |
| 026_506_00277170 | Esophagus | 506 | OE19 | 456 | 3.143883 | 0.544 | 0.752 | 0.743 | 0.8799 | 1.0437 | 0.937 | 1.0332 | 1.0004 | 1.0701 |
| 026_8179_00276220 | Esophagus | 8179 | TE-12 | 456 | 3.163617 | 0.183 | 0.742 | 0.633 | 0.6476 | 0.7356 | 0.839 | 0.775 | 0.681 | 0.8318 |
| 026_8185_00276250 | Esophagus | 8185 | TE-8 | 456 | 3.50176 | 0.201 | 0.606 | 0.658 | 0.7374 | 0.6587 | 0.744 | 0.7964 | 0.863 | 0.9258 |
| 026_8184_00293680 | Esophagus | 8184 | TE-6 | 456 | 3.545508 | 0.552 | 0.767 | 0.935 | 0.8745 | 0.8626 | 0.742 | 1.0239 | 0.9777 | 0.9232 |
| 026_8178_00280260 | Esophagus | 8178 | TE-10 | 456 | 3.804003 | 0.664 | 0.735 | 0.78 | 0.9124 | 0.8781 | 1.01 | 1.0331 | 1.0386 | 1.0127 |
| 026_499_00276630 | Esophagus | 499 | KYSE-270 | 456 | 4.027681 | 0.678 | 0.727 | 0.767 | 0.7928 | 0.8774 | 0.984 | 0.9911 | 0.9777 | 1.0007 |
| 026_509_00276620 | Esophagus | 509 | KYSE-220 | 456 | 4.075564 | 0.637 | 0.656 | 0.682 | 0.7368 | 0.7969 | 0.844 | 0.873 | 0.9181 | 0.9229 |
| 026_8235_00276520 | Esophagus | 8235 | FLO-1 | 456 | 4.100409 | 0.604 | 0.732 | 0.778 | 0.7882 | 0.8071 | 0.864 | 0.8729 | 0.8842 | 0.9483 |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_8251_00276640 | Esophagus | 8251 | OACM5-1 | 456 | 4.18038 | 0.673 | 0.784 | 0.878 | 0.8883 | 0.9366 | 0.926 | 0.9214 | 0.9309 | 0.9714 |
| 026_8186_00282690 | Esophagus | 8186 | TE-9 | 456 | 4.291684 | 0.689 | 0.795 | 0.742 | 0.8146 | 0.856 | 0.846 | 1.0123 | 0.8588 | 1.0654 |
| 026_495_00274190 | Esophagus | 495 | COLO-680N | 456 | 4.332573 | 0.742 | 0.818 | 0.865 | 0.9122 | 0.97 | 0.96 | 1.1262 | 0.9684 | 1.0444 |
| 026_510_00273560 | Esophagus | 510 | KYSE-50 | 456 | 4.431288 | 0.658 | 0.743 | 0.781 | 0.8044 | 0.8395 | 0.815 | 0.8665 | 0.9009 | 1.0802 |
| 026_8186_00292740 | Esophagus | 8186 | TE-9 | 456 | 4.438695 | 0.739 | 0.769 | 0.893 | 0.8667 | 0.8573 | 0.944 | 1.0623 | 1.0025 | 1.1458 |
| 026_503_00274070 | Esophagus | 503 | KYSE-510 | 456 | 4.484808 | 0.731 | 0.796 | 0.816 | 0.8942 | 0.9487 | 0.912 | 0.9785 | 1.0104 | 1.0221 |
| 026_504_00276560 | Esophagus | 504 | KYSE-520 | 456 | 4.773857 | 0.716 | 0.731 | 0.748 | 0.7768 | 0.8124 | 0.867 | 0.9459 | 0.995 | 0.9576 |
| 026_8208_00276600 | Esophagus | 8208 | HCE-4 | 456 | 4.88732 | 0.748 | 0.785 | 0.808 | 0.8645 | 0.9033 | 0.954 | 0.9197 | 0.9231 | 0.9878 |
| 026_512_00274080 | Esophagus | 512 | T.T | 456 | 4.943912 | 0.781 | 0.839 | 0.89 | 0.9002 | 0.9769 | 0.929 | 0.9845 | 0.9744 | 1.0152 |
| 026_8268_00276650 | Esophagus | 8268 | SK-GT-4 | 456 | 5.079273 | 0.835 | 0.788 | 0.758 | 0.735 | 0.7503 | 0.833 | 0.9063 | 0.9163 | 0.972 |
| 026_505_00274210 | Esophagus | 505 | KYSE-70 | 456 | 5.137973 | 0.794 | 0.857 | 0.892 | 0.8943 | 0.9411 | 0.957 | 0.9493 | 0.9907 | 1.0431 |
| 026_508_00278520 | Esophagus | 508 | OE33 | 456 | 5.424479 | 0.701 | 0.81 | 0.783 | 0.7873 | 0.7763 | 0.833 | 0.8596 | 0.903 | 0.9287 |
| 026_498_00276540 | Esophagus | 498 | KYSE-180 | 456 | 5.533652 | 0.84 | 0.853 | 0.898 | 0.9109 | 0.9353 | 0.924 | 0.9336 | 0.9199 | 0.942 |
| 026_8202_00276660 | Esophagus | 8202 | TE-11 | 456 | 5.740526 | 0.822 | 0.845 | 0.848 | 0.8684 | 0.8821 | 0.913 | 0.9297 | 0.9627 | 1.0605 |
| 026_8039_00276580 | Esophagus | 8039 | EC-GI-10 | 456 | 5.844841 | 0.878 | 0.905 | 0.892 | 0.951 | 0.9277 | 0.926 | 0.9555 | 1.04 | 1.0068 |
| 026_501_00274060 | Esophagus | 501 | KYSE-410 | 456 | 6.135532 | 0.762 | 0.836 | 0.846 | 0.8398 | 0.8691 | 0.887 | 0.9278 | 0.9729 | 0.9854 |
| 026_8246_00276610 | Esophagus | 8246 | KYAE-1 | 456 | 6.1525 | 0.887 | 0.93 | 0.92 | 0.9326 | 0.9185 | 0.978 | 0.97 | 0.9663 | 0.9315 |
| 026_507_00278510 | Esophagus | 507 | OE21 | 456 | 6.23551 | 0.922 | 0.838 | 0.875 | 0.7771 | 0.8079 | 0.985 | 0.9753 | 0.9667 | 0.9919 |
| 026_8183_00276240 | Esophagus | 8183 | TE-5 | 456 | 6.777236 | 0.111 | 1.028 | 0.936 | 1.0341 | 0.9858 | 0.876 | 0.8843 | 0.9699 | 0.8561 |
| 026_8177_00282670 | Esophagus | 8177 | TE-1 | 456 | 7.848711 | 1.022 | 1.1 | 0.912 | 1.0973 | 1.0898 | 1.065 | 1.0874 | 1.0775 | 1.0749 |
| 026_545_00260020 | Head & Neck | 545 | DOK | 456 | -0.22061 | 0.308 | 0.451 | 0.33 | 0.4014 | 0.4436 | 0.534 | 0.6634 | 0.7589 | 0.8693 |
| 026_1217_00255750 | Head & Neck | 1217 | H3118 | 456 | 0.314816 | 0.254 | 0.413 | 0.453 | 0.4692 | 0.5199 | 0.565 | 0.691 | 0.6788 | 0.7738 |
| 026_526_00308740 | Head & Neck | 526 | PCI-4B | 456 | 1.887412 | 0.418 | 0.409 | 0.489 | 0.7595 | 0.7429 | 0.873 | 0.9067 | 0.918 | 1.0403 |
| 026_530_00260620 | Head & Neck | 530 | PCI-30 | 456 | 1.98819 | 0.142 | 0.356 | 0.628 | 0.7119 | 0.7851 | 0.825 | 0.9139 | 0.8747 | 0.8098 |
| 026_552_00252890 | Head & Neck | 552 | SAT | 456 | 2.534279 | 0.382 | 0.613 | 0.727 | 0.8554 | 0.7778 | 0.977 | 0.8474 | 0.7957 | 0.9605 |
| 026_550_00258980 | Head & Neck | 550 | SCC-4 | 456 | 2.544916 | 0.464 | 0.564 | 0.904 | 0.7519 | 0.7827 | 0.709 | 0.7715 | 0.8596 | 0.9574 |
| 026_1224_00256200 | Head & Neck | 1224 | SCC-9 | 456 | 2.68588 | 0.466 | 0.633 | 0.641 | 0.6635 | 0.6231 | 0.758 | 0.8287 | 0.8854 | 0.9263 |
| 026_1223_00259190 | Head & Neck | 1223 | SCC-25 | 456 | 2.934793 | 0.193 | 0.664 | 0.718 | 0.8957 | 0.937 | 0.932 | 1.0111 | 0.988 | 1.0055 |
| 026_548_00261030 | Head & Neck | 548 | RPMI 2650 | 456 | 3.095229 | 0.489 | 0.696 | 0.761 | 0.8664 | 0.8685 | 0.911 | 0.9177 | 0.9218 | 0.9624 |
| 026_517_00255800 | Head & Neck | 517 | JHU-011 | 456 | 3.112112 | 0.536 | 0.616 | 0.696 | 0.7845 | 0.8433 | 0.813 | 0.9157 | 0.9495 | 1.0827 |
| 026_8011_00257080 | Head & Neck | 8011 | BB30-HNC | 456 | 3.217966 | 0.541 | 0.677 | 0.734 | 0.7445 | 0.7909 | 0.917 | 0.9622 | 0.9832 | 1.1203 |
| 026_553_00259140 | Head & Neck | 553 | OSC-20 | 456 | 3.378306 | 0.587 | 0.751 | 0.792 | 0.8761 | 0.9722 | 0.983 | 1.0097 | 0.974 | 0.999 |
| 026_556_00257220 | Head & Neck | 556 | SKN-3 | 456 | 3.392608 | 0.207 | 0.626 | 0.805 | 0.7174 | 0.6353 | 0.718 | 0.757 | 0.8593 | 0.8383 |
| 026_536_00256080 | Head & Neck | 536 | BHY | 456 | 3.443799 | 0.593 | 0.821 | 0.877 | 0.8931 | 0.9405 | 1.049 | 1.0289 | 0.9991 | 1.0281 |
| 026_561_00257110 | Head & Neck | 561 | Ca9-22 | 456 | 3.710495 | 0.634 | 0.867 | 0.849 | 0.916 | 0.9493 | 0.99 | 1.0155 | 1.0225 | 1.0222 |
| 026_532_00308750 | Head & Neck | 532 | PCI-6A | 456 | 3.742916 | 0.628 | 0.684 | 0.811 | 0.8452 | 0.8862 | 0.945 | 0.9298 | 0.9056 | 0.9974 |
| 026_8012_00266550 | Head & Neck | 8012 | BB49-HNC | 456 | 3.77782 | 0.46 | 0.775 | 0.9 | 0.8967 | 0.924 | 0.968 | 0.9717 | 1.0116 | 0.9946 |
| 026_8100_00255030 | Head & Neck | 8100 | LB771-HNC | 456 | 3.926882 | 0.701 | 0.899 | 0.929 | 0.9987 | 0.9867 | 0.989 | 1.0145 | 0.9621 | 0.9588 |
| 026_1222_00253030 | Head & Neck | 1222 | SCC-15 | 456 | 4.189701 | 0.411 | 0.772 | 0.855 | 0.8291 | 0.7747 | 1.02 | 0.8664 | 0.932 | 0.9717 |
| 026_533_00260900 | Head & Neck | 533 | PCI-15A | 456 | 4.236361 | 1.325 | 1.15 | 0.832 | 0.7174 | 0.8188 | 0.863 | 0.9549 | 1.0427 | 1.0471 |
| 026_547_00314270 | Head & Neck | 547 | KOSC-2 cl3-43 | 456 | 4.563275 | 0.708 | 0.872 | 0.897 | 0.9 | 0.7378 | 0.941 | 0.9549 | 0.9825 | 1.0471 |
| 026_544_00256140 | Head & Neck | 544 | Detroit 562 | 456 | 4.601961 | 0.746 | 0.964 | 0.951 | 0.9801 | 0.9656 | 0.961 | 0.9765 | 0.9793 | 0.9061 |
| 026_543_00256100 | Head & Neck | 543 | BICR 78 | 456 | 4.851894 | 0.728 | 0.818 | 0.868 | 0.8349 | 0.9283 | 0.925 | 0.9696 | 0.966 | 0.9649 |
| 026_537_00256120 | Head & Neck | 537 | CAL-33 | 456 | 5.580216 | 0.834 | 0.892 | 0.921 | 0.9097 | 0.9511 | 0.935 | 0.9977 | 1.0062 | 0.9837 |
| 026_549_00256220 | Head & Neck | 549 | HO-1-N-1 | 456 | 5.63511 | 0.866 | 0.873 | 0.883 | 0.8726 | 0.8907 | 0.97 | 0.987 | 0.9898 | 1.0714 |
| 026_557_00259180 | Head & Neck | 557 | SAS | 456 | 6.035072 | 0.85 | 0.97 | 0.967 | 0.9738 | 0.925 | 1.043 | 1.0896 | 1.0407 | 1.0277 |
| 026_534_00256110 | Head & Neck | 534 | CAL 27 | 456 | 6.045151 | 0.85 | 0.904 | 0.912 | 0.9312 | 0.977 | 0.939 | 0.9758 | 0.9901 | 0.9927 |
| 026_542_00269190 | Head & Neck | 542 | BICR 31 | 456 | 6.045414 | 0.903 | 0.908 | 0.952 | 0.9408 | 0.977 | 0.97 | 0.9966 | 1.0002 | 1.0269 |

TABLE 22-continued

| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_530_00262500 | Head & Neck | 530 | PCI-30 | 456 | 6.119674 | 0.884 | 0.955 | 1.145 | 0.9682 | 1.009 | 0.988 | 0.9261 | 1.0121 | 0.9861 |
| 026_540_00258490 | Head & Neck | 540 | BICR 10 | 456 | 6.128463 | 0.839 | 1.048 | 1.049 | 1.0556 | 1.0464 | 1.041 | 1.0301 | 0.974 | 0.9953 |
| 026_541_00256090 | Head & Neck | 541 | BICR 22 | 456 | 6.156446 | 0.828 | 1.076 | 1.058 | 0.9602 | 1.0898 | 1.064 | 1.0874 | 0.9689 | 1.0462 |
| 026_8003_00263440 | Head & Neck | 8003 | A253 | 456 | 6.291179 | 0.877 | 0.857 | 0.859 | 0.8594 | 0.9753 | 0.982 | 0.9985 | 0.9367 | 0.969 |
| 026_535_00256160 | Head & Neck | 535 | FaDu | 456 | 6.303565 | 0.841 | 1.063 | 1.091 | 1.0795 | 1.0793 | 1.034 | 1.0404 | 1.0191 | 1.0095 |
| 026_554_00257210 | Head & Neck | 554 | OSC-19 | 456 | 6.322489 | 0.938 | 0.942 | 0.914 | 0.9247 | 0.9682 | 1.004 | 1.0285 | 1.0504 | 1.0506 |
| 026_559_00256250 | Head & Neck | 559 | HSC-3 | 456 | 6.797258 | 0.909 | 1.024 | 1.057 | 1.0632 | 1.0572 | 1.029 | 1.0059 | 0.9701 | 0.9782 |
| 026_8071_00256760 | Head & Neck | 8071 | HCE-T | 456 | 6.917353 | 0.576 | 1.146 | 1.274 | 1.3514 | 1.1688 | 1.173 | 1.0336 | 1.1999 | 0.8849 |
| 026_521_00257180 | Head & Neck | 521 | JHU-022 | 456 | 7.049785 | 0.896 | 0.846 | 0.901 | 0.8757 | 0.9278 | 0.886 | 0.9103 | 0.9436 | 0.9699 |
| 026_555_00256270 | Head & Neck | 555 | KON | 456 | 7.114386 | 0.946 | 0.982 | 0.977 | 0.9826 | 0.9957 | 0.96 | 0.9991 | 0.961 | 0.9207 |
| 026_538_00258510 | Head & Neck | 538 | HN | 456 | 7.118392 | 0.947 | 1.007 | 0.984 | 1.0014 | 1.0052 | 0.998 | 1.0105 | 0.9648 | 0.9952 |
| 026_546_00259150 | Head & Neck | 546 | PE/CA-PJ15 | 456 | 7.26219 | 0.96 | 0.963 | 0.931 | 0.9179 | 0.9698 | 0.969 | 0.9884 | 1.006 | 0.9974 |
| 026_560_00256260 | Head & Neck | 560 | HSC-4 | 456 | 7.41962 | 1.005 | 0.994 | 1.003 | 0.9486 | 1.2114 | 0.897 | 0.9756 | 0.9433 | 0.9255 |
| 026_551_00259130 | Head & Neck | 551 | HO-1-u-1 | 456 | 7.903602 | 0.999 | 1.037 | 1.039 | 1.0722 | 1.0616 | 1.067 | 1.0655 | 1.0038 | 0.9405 |
| 026_558_00256240 | Head & Neck | 558 | HSC-2 | 456 | 8.185707 | 1.148 | 1.077 | 0.985 | 1.1269 | 1.0034 | 1.093 | 0.9608 | 0.9252 | 0.9888 |
| 026_531_00258970 | Head & Neck | 531 | PCI-38 | 456 | 8.493869 | 1.046 | 1.067 | 1.063 | 1.0751 | 1.0712 | 0.965 | 1.0236 | 1.0421 | 0.9848 |
| 026_570_00293670 | Intestine | 570 | SK-CO-1 | 456 | -0.30187 | 0.268 | 0.258 | 0.267 | 0.2555 | 0.3743 | 0.418 | 0.7306 | 0.9824 | 0.9276 |
| 026_8153_00295901 | Intestine | 8153 | RKO | 456 | 0.044041 | 0.222 | 0.197 | 0.246 | 0.3161 | 0.4612 | 0.693 | 0.7818 | 0.9061 | 1.1131 |
| 18 | Intestine | 586 | COLO 205 | 456 | 0.350012 | 0.083 | 0.182 | 0.196 | 0.3978 | 0.5206 | 0.706 | 0.8518 | 0.9472 | 0.9745 |
| 026_582_00295550 | Intestine | 582 | LoVo | 456 | 0.399717 | 0.325 | 0.396 | 0.385 | 0.4168 | 0.4097 | 0.533 | 0.75 | 0.8239 | 0.9276 |
| 026_8108_00298530 | Intestine | 8108 | LS-513 | 456 | 0.423432 | 0.094 | 0.146 | 0.195 | 0.2527 | 0.5673 | 0.876 | 1.1755 | 1.0179 | 1.1926 |
| 026_8274_00258540 | Intestine | 8274 | SNU-61 | 456 | 0.467862 | 0.432 | 0.599 | 0.539 | 0.5369 | 0.5735 | 0.603 | 0.7283 | 0.7462 | 0.9243 |
| 026_8136_00260060 | Intestine | 8136 | NCI-H747 | 456 | 0.578701 | 0.356 | 0.465 | 0.488 | 0.5338 | 0.5471 | 0.613 | 0.7238 | 0.8107 | 0.9473 |
| 026_574_00298390 | Intestine | 574 | CL-11 | 456 | 0.894127 | 0.381 | 0.401 | 0.395 | 0.4593 | 0.6002 | 0.69 | 0.749 | 0.8474 | 0.9789 |
| 026_589_00295371 | Intestine | 589 | HCT 116 | 456 | 0.931657 | 0.336 | 0.381 | 0.435 | 0.4732 | 0.5791 | 0.862 | 1.1049 | 1.0627 | 1.1072 |
| 026_608_00293620 | Intestine | 608 | CCK-81 | 456 | 1.046144 | 0.242 | 0.394 | 0.399 | 0.4912 | 0.6325 | 0.738 | 0.9653 | 0.9069 | 0.9123 |
| 026_610_00293660 | Intestine | 610 | RCM-1 | 456 | 1.475794 | 0.45 | 0.416 | 0.414 | 0.6252 | 0.6775 | 0.804 | 0.981 | 1.0277 | 1.0565 |
| 026_569_00295390 | Intestine | 569 | HT-29 | 456 | 1.526342 | 0.48 | 0.464 | 0.5 | 0.5547 | 0.5893 | 0.74 | 0.9536 | 0.9048 | 0.9241 |
| 026_8271_00314300 | Intestine | 8271 | SNU-175 | 456 | 1.739925 | 0.382 | 0.522 | 0.535 | 0.5651 | 0.6481 | 0.701 | 0.7957 | 0.9458 | 0.9851 |
| 026_8108_00296610 | Intestine | 8108 | LS-513 | 456 | 1.815428 | 0.37 | 0.448 | 0.511 | 0.6156 | 0.8074 | 0.933 | 0.9905 | 0.9579 | 0.9991 |
| 026_592_00295380 | Intestine | 592 | HT115 | 456 | 1.869689 | 0.377 | 0.436 | 0.5 | 0.6258 | 0.8213 | 1.101 | 1.0858 | 1.0169 | 1.1148 |
| 026_606_00293630 | Intestine | 606 | HCC-56 | 456 | 1.929923 | 0.646 | 0.599 | 0.536 | 0.5915 | 0.6327 | 0.867 | 0.8829 | 0.9131 | 0.9417 |
| 026_8107_00296450 | Intestine | 8107 | LS-411N | 456 | 2.297731 | 0.497 | 0.55 | 0.585 | 0.5585 | 0.6884 | 0.755 | 0.8626 | 0.8921 | 0.9253 |
| 026_595_00295420 | Intestine | 595 | LS180 | 456 | 2.32965 | 0.453 | 0.515 | 0.551 | 0.6999 | 0.8666 | 0.91 | 1.0102 | 0.9178 | 1.1155 |
| 026_8169_00295910 | Intestine | 8169 | SNU-C2B | 456 | 2.617884 | 0.503 | 0.566 | 0.598 | 0.7373 | 0.671 | 0.774 | 0.9066 | 0.8796 | 0.9886 |
| 026_564_00292860 | Intestine | 564 | NCI-H630 | 456 | 2.627492 | 0.496 | 0.556 | 0.55 | 0.4912 | 1.0007 | 0.964 | 0.9563 | 0.8783 | 0.9169 |
| 026_603_00292731 | Intestine | 603 | SW837 | 456 | 2.797981 | 0.525 | 0.597 | 0.586 | 0.7713 | 0.7763 | 1.002 | 1.023 | 1.0218 | 1.0696 |
| 026_588_00302650 | Intestine | 588 | GP5d | 456 | 2.925873 | 0.521 | 0.65 | 0.67 | 0.679 | 0.8325 | 0.964 | 1.0479 | 1.1013 | 0.1678 |
| 026_598_00295360 | Intestine | 598 | SW 1417 | 456 | 3.077195 | 0.616 | 0.696 | 0.742 | 0.6531 | 1.034 | 1.029 | 1.0798 | 0.8321 | 1.2207 |
| 026_8276_00296000 | Intestine | 8276 | SNU-C5 | 456 | 3.153347 | 0.603 | 0.592 | 0.612 | 0.6327 | 0.7283 | 0.812 | 0.8824 | 0.9411 | 0.9768 |
| 026_593_00295530 | Intestine | 593 | HT55 | 456 | 3.164186 | 0.589 | 0.646 | 0.61 | 0.7857 | 0.7974 | 1.03 | 1.1134 | 1.0941 | 1.1175 |
| 026_8106_00264670 | Intestine | 8106 | LS-123 | 456 | 3.191118 | 0.547 | 0.687 | 0.783 | 0.7554 | 0.8823 | 0.879 | 0.9202 | 0.965 | 0.9375 |
| 026_599_00296340 | Intestine | 599 | SW 1463 | 456 | 3.237942 | 0.572 | 0.642 | 0.631 | 0.6255 | 0.6275 | 0.757 | 0.9237 | 0.9401 | 0.9681 |
| 026_8086_00296431 | Intestine | 8086 | KM12 | 456 | 3.240654 | 0.564 | 0.657 | 0.65 | 0.6739 | 0.8062 | 0.903 | 0.8847 | 0.9825 | 0.9793 |
| 026_587_00302320 | Intestine | 587 | COLO 741 | 456 | 3.269221 | 0.615 | 0.622 | 0.694 | 0.6624 | 0.7236 | 0.816 | 1.1047 | 1.0995 | 1.0783 |
| 026_8273_00295970 | Intestine | 8273 | SNU-407 | 456 | 3.390403 | 0.577 | 0.622 | 0.663 | 0.7325 | 0.7399 | 0.745 | 0.8059 | 0.8644 | 1.0342 |
| 026_8270_00304630 | Intestine | 8270 | SNU-1040 | 456 | 3.643993 | 0.604 | 0.78 | 0.799 | 0.8256 | 0.8028 | 0.92 | 0.9246 | 0.9919 | 1.2066 |
| 026_8168_00295990 | Intestine | 8168 | SNU-C1 | 456 | 3.717495 | 0.645 | 0.673 | 0.685 | 0.6875 | 0.8368 | 0.739 | 0.8513 | 1.1115 | 1.0883 |

TABLE 22-continued

| Barcode | Organ | Cell ID | Cell Line | Compound No | Fitted MGH_IC50 | Viability ratio | | | | | | | | |
|---|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_8275_00256210 | Intestine | 8275 | SNU-81 | 456 | 3.903109 | 0.338 | 0.659 | 0.68 | 0.6942 | 0.7065 | 0.761 | 0.7749 | 0.8653 | 0.9224 |
| 026_583_00295921 | Intestine | 583 | SW-948 | 456 | 3.908038 | 0.735 | 0.672 | 0.851 | 0.9918 | 1.0392 | 0.979 | 0.9178 | 0.9736 | 0.9758 |
| 026_8274_00295980 | Intestine | 8274 | SNU-61 | 456 | 4.14154 | 0.663 | 0.72 | 0.672 | 0.6639 | 0.7521 | 0.794 | 0.8775 | 0.8761 | 0.9371 |
| 026_8105_00296440 | Intestine | 8105 | LS-1034 | 456 | 4.222062 | 0.732 | 0.754 | 0.781 | 0.8085 | 0.8857 | 1.006 | 1.1032 | 1.0973 | 1.0698 |
| 026_580_00295930 | Intestine | 580 | COLO-678 | 456 | 4.449849 | 0.891 | 0.793 | 0.767 | 0.8394 | 0.8741 | 0.917 | 1.0326 | 0.9344 | 1.0884 |
| 026_580_00266560 | Intestine | 580 | COLO-678 | 456 | 4.550688 | 0.724 | 0.686 | 0.785 | 0.8147 | 0.8701 | 0.885 | 0.9546 | 0.9558 | 0.9803 |
| 026_581_00295830 | Intestine | 581 | HCT-15 | 456 | 4.608693 | 0.811 | 0.75 | 0.973 | 0.9405 | 1.0972 | 0.98 | 1.098 | 1.0722 | 1.1405 |
| 026_573_00296370 | Intestine | 573 | SW620 | 456 | 4.816766 | 0.775 | 0.787 | 0.797 | 0.8519 | 0.8683 | 0.915 | 0.9626 | 1.0901 | 1.097 |
| 026_8021_00296390 | Intestine | 8021 | COLO-320-HSR | 456 | 4.87923 | 0.817 | 0.861 | 0.828 | 1.0219 | 0.8974 | 1.103 | 1.0927 | 0.9967 | 1.1145 |
| 026_8106_00298521 | Intestine | 8106 | LS-123 | 456 | 4.895207 | 0.706 | 0.749 | 0.852 | 0.7598 | 0.7605 | 0.923 | 0.8934 | 0.9319 | 1.0175 |
| 026_600_00296361 | Intestine | 600 | SW 48 | 456 | 4.951306 | 0.706 | 0.776 | 0.775 | 0.7937 | 0.8445 | 0.857 | 0.9382 | 0.915 | 0.9609 |
| 026_8070_00296411 | Intestine | 8070 | HCC2998 | 456 | 4.984157 | 0.701 | 0.788 | 0.743 | 0.7463 | 0.8151 | 0.891 | 0.9115 | 0.9572 | 0.9432 |
| 026_8135_00295950 | Intestine | 8135 | NCI-H716 | 456 | 4.988916 | 0.813 | 0.864 | 0.948 | 0.9832 | 0.9658 | 0.94 | 0.9372 | 0.9633 | 1.1237 |
| 026_8136_00295961 | Intestine | 8136 | NCI-H747 | 456 | 5.220086 | 0.699 | 0.693 | 0.763 | 0.7315 | 0.7863 | 0.815 | 0.8715 | 0.8842 | 1.1461 |
| 026_574_00263900 | Intestine | 574 | CL-11 | 456 | 5.294016 | 0.826 | 0.812 | 0.761 | 0.7543 | 0.8087 | 0.891 | 0.9784 | 0.9577 | 0.9649 |
| 026_8026_00300671 | Intestine | 8026 | CW-2 | 456 | 5.403672 | 0.827 | 0.955 | 0.974 | 0.9551 | 0.9288 | 0.954 | 0.9824 | 0.9866 | 1.0636 |
| 026_607_00293610 | Intestine | 607 | CaR-1 | 456 | 5.551737 | 0.834 | 0.873 | 0.912 | 0.8795 | 0.9318 | 0.939 | 0.9636 | 0.9483 | 0.9415 |
| 026_8074_00296420 | Intestine | 8074 | HUTU-80 | 456 | 5.701754 | 0.841 | 0.852 | 0.876 | 0.9027 | 0.8952 | 1.007 | 1.0026 | 0.966 | 0.9322 |
| 026_563_00316540 | Intestine | 563 | C2BBe1 | 456 | 5.783056 | 0.853 | 0.949 | 0.926 | 0.9333 | 0.9253 | 0.879 | 0.9164 | 1.0369 | 1.0733 |
| 026_596_00296280 | Intestine | 596 | MDST8 | 456 | 6.402689 | 0.885 | 0.885 | 0.874 | 0.8768 | 0.9374 | 0.931 | 0.9758 | 0.9779 | 1.0734 |
| 026_597_00300651 | Intestine | 597 | SW 1116 | 456 | 6.447765 | 0.647 | 1.058 | 0.925 | 1.031 | 0.9839 | 0.997 | 1.0631 | 1.0277 | 0.905 |
| 026_601_00296480 | Intestine | 601 | T84 | 456 | 7.233631 | 0.973 | 0.939 | 0.93 | 0.9736 | 0.9545 | 0.891 | 0.964 | 0.9372 | 1.0259 |
| 026_622_00288160 | Intestine | 622 | G-401 | 456 | 1.158385 | 0.363 | 0.358 | 0.433 | 0.5045 | 0.6202 | 0.865 | 0.8778 | 1.0261 | 1.0061 |
| 026_626_00298790 | Kidney | 626 | BFTC-909 | 456 | 1.589633 | 0.292 | 0.387 | 0.526 | 0.5522 | 0.8154 | 0.895 | 0.9347 | 1.005 | 1.054 |
| 026_623_00288201 | Kidney | 623 | SK-NEP-1 | 456 | 1.837955 | 0.412 | 0.444 | 0.507 | 0.7421 | 0.8141 | 0.813 | 0.9099 | 0.9209 | 0.981 |
| 026_8264_00290630 | Kidney | 8264 | RCC-JF | 456 | 2.377362 | 0.452 | 0.535 | 0.585 | 0.6574 | 0.9675 | 0.851 | 0.9828 | 1.0591 | 1.0712 |
| 026_619_00290290 | Kidney | 619 | 769-P | 456 | 2.463867 | 0.439 | 0.58 | 0.576 | 0.7655 | 0.8898 | 0.994 | 1.0776 | 1.0508 | 1.1513 |
| 026_627_00291130 | Kidney | 627 | CAL-54 | 456 | 2.931844 | 0.586 | 0.588 | 0.649 | 0.6813 | 0.7826 | 0.858 | 0.9811 | 0.9726 | 1.0003 |
| 026_617_00290310 | Kidney | 617 | ACHN | 456 | 2.983353 | 0.545 | 0.592 | 0.627 | 0.7345 | 0.7447 | 0.733 | 0.7712 | 0.919 | 1.1152 |
| 026_8263_00290620 | Kidney | 8263 | RCC-FG2 | 456 | 3.111338 | 0.517 | 0.756 | 0.691 | 0.7857 | 0.7896 | 0.884 | 0.8746 | 0.9754 | 1.0284 |
| 026_8190_00290280 | Kidney | 8190 | TK10 | 456 | 3.318654 | 0.638 | 0.654 | 0.671 | 0.7606 | 0.892 | 0.932 | 1.0085 | 1.0009 | 0.9983 |
| 026_638_00288220 | Kidney | 638 | VMRC-RCZ | 456 | 3.36569 | 0.14 | 0.709 | 0.838 | 0.9211 | 0.92 | 0.981 | 0.9922 | 0.9588 | 0.989 |
| 026_8261_00308760 | Kidney | 8261 | RCC-AB | 456 | 3.394556 | 0.566 | 0.724 | 0.758 | 0.85 | 0.8258 | 0.948 | 0.9492 | 0.9471 | 0.9351 |
| 026_628_00288210 | Kidney | 628 | SW 13 | 456 | 3.41636 | 0.454 | 0.733 | 0.735 | 0.7572 | 0.8068 | 0.826 | 0.8584 | 0.9361 | 1.0195 |
| 026_8262_00290610 | Kidney | 8262 | RCC-ER | 456 | 3.745967 | 0.583 | 0.783 | 0.794 | 0.8415 | 0.9082 | 0.87 | 0.8861 | 0.9471 | 0.9855 |
| 026_8265_00302360 | Kidney | 8265 | RCC-JW | 456 | 3.749626 | 0.686 | 0.758 | 0.874 | 0.9595 | 1.0107 | 1.003 | 1.0135 | 1.0068 | 1.0345 |
| 026_8261_00311200 | Kidney | 8261 | RCC-AB | 456 | 3.919417 | 0.288 | 0.72 | 0.73 | 0.765 | 0.8515 | 0.878 | 0.9287 | 0.8965 | 0.9174 |
| 026_618_00290300 | Kidney | 618 | 786-O | 456 | 3.967789 | 0.657 | 0.756 | 0.822 | 0.8016 | 0.8829 | 0.898 | 0.9012 | 0.917 | 1.0472 |
| 026_625_00290670 | Kidney | 625 | UO-31 | 456 | 3.998088 | 0.662 | 0.719 | 0.767 | 0.9002 | 0.8304 | 0.876 | 0.9235 | 1.0588 | 1.1507 |
| 026_8096_00290860 | Kidney | 8096 | LB2241-RCC | 456 | 3.99857 | 0.643 | 0.686 | 0.74 | 0.8137 | 0.8533 | 0.902 | 0.903 | 0.9107 | 0.9322 |
| 026_614_00291210 | Kidney | 614 | SW 156 | 456 | 4.137243 | 0.651 | 0.665 | 0.71 | 0.7683 | 0.8365 | 0.896 | 0.9933 | 0.9074 | 0.9013 |
| 026_8249_00295560 | Kidney | 8249 | NCC021 | 456 | 4.201277 | 0.701 | 0.897 | 0.903 | 0.9199 | 0.9735 | 0.942 | 1.027 | 1.0276 | 1.0113 |
| 026_633_00290250 | Kidney | 633 | KMRC-20 | 456 | 4.24311 | 0.713 | 0.872 | 0.83 | 0.9644 | 0.8737 | 1.135 | 1.0474 | 1.0923 | 1.0373 |
| 026_8068_00290231 | Kidney | 8068 | HA7-RCC | 456 | 4.403879 | 0.761 | 0.764 | 0.7 | 0.8322 | 0.7944 | 0.89 | 1.0739 | 1.1224 | 1.0563 |
| 026_8095_00290260 | Kidney | 8095 | LB1047-RCC | 456 | 4.460236 | 0.772 | 0.824 | 0.914 | 1.0356 | 1.0154 | 1.004 | 1.0217 | 1.1192 | 1.1745 |
| 026_618_00290300 | Kidney | 618 | BFTC-909 | 456 | 4.464205 | 0.741 | 0.932 | 1.057 | 1.0395 | 1.0888 | 1.03 | 1.0718 | 1.0625 | 1.0049 |
| 026_626_00258890 | Kidney | 626 | OS-RC-2 | 456 | 4.480976 | 0.767 | 0.794 | 0.799 | 0.8302 | 0.9419 | 1.023 | 0.9509 | 1.0847 | 1.1694 |
| 026_8147_00290270 | Kidney | 8147 | BB65-RCC | 456 | 4.50555 | 0.714 | 0.769 | 0.765 | 0.8909 | 0.8509 | 0.865 | | 1.0096 | 0.903 |

TABLE 22-continued

| | | | | | | Viability ratio | | | | | | | |
|---|---|---|---|---|---|---|---|---|---|---|---|---|---|
| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
| 026_8006_00293300 | Kidney | 8006 | A704 | 456 | 4.630889 | 0.755 | 0.917 | 0.918 | 0.9328 | 0.9788 | 1.112 | 0.981 | 0.9813 | 1.0413 |
| 026_637_00290240 | Kidney | 637 | KMRC-1 | 456 | 4.786417 | 0.748 | 0.889 | 0.97 | 0.9322 | 0.836 | 1.012 | 1.0239 | 0.9503 | 1.088 |
| 026_624_00290320 | Kidney | 624 | Caki-1 | 456 | 4.808296 | 0.821 | 0.803 | 0.908 | 0.9738 | 0.9722 | 1.083 | 1.1676 | 1.1464 | 1.1228 |
| 026_8266_00290640 | Kidney | 8266 | RCC-MF | 456 | 4.811179 | 0.754 | 0.903 | 0.819 | 0.8455 | 0.8764 | 0.999 | 0.9885 | 0.935 | 1.1762 |
| 026_620_00288170 | Kidney | 620 | G-402 | 456 | 4.865533 | 0.694 | 0.721 | 0.686 | 0.7919 | 0.7766 | 0.804 | 0.8404 | 0.885 | 0.9093 |
| 026_8152_00293381 | Kidney | 8152 | RCC10RGB | 456 | 5.110675 | 0.821 | 0.719 | 0.793 | 0.9032 | 0.8829 | 0.858 | 0.8991 | 0.9287 | 1.0343 |
| 026_640_00291220 | Kidney | 640 | VMRC-RCW | 456 | 5.287926 | 0.73 | 0.737 | 0.783 | 0.8088 | 0.8744 | 0.905 | 0.9003 | 0.9127 | 0.9163 |
| 026_8102_00293360 | Kidney | 8102 | LB996-RCC | 456 | 5.484542 | 0.855 | 0.901 | 0.954 | 0.9116 | 0.9754 | 0.98 | 0.958 | 0.9786 | 0.9921 |
| 026_1119_00290901 | Kidney | 1119 | SN-12C | 456 | 5.586587 | 0.818 | 0.749 | 0.747 | 0.783 | 0.8058 | 0.856 | 0.9038 | 0.9508 | 0.9573 |
| 026_626_00290810 | Kidney | 626 | BFTC-909 | 456 | 5.753321 | 0.799 | 0.854 | 0.903 | 0.9293 | 0.9289 | 0.92 | 0.9333 | 0.9322 | 0.9535 |
| 026_8005_00266530 | Kidney | 8005 | A498 | 456 | 5.843211 | 0.594 | 0.917 | 1.009 | 1.0079 | 0.9307 | 0.996 | 1.0002 | 1.0033 | 0.9941 |
| 026_8157_00296471 | Kidney | 8157 | RXF393 | 456 | 6.166218 | 0.853 | 0.878 | 0.91 | 0.8924 | 0.9071 | 0.932 | 0.9081 | 0.9505 | 0.9889 |
| 026_8102_00253000 | Kidney | 8102 | LB996-RCC | 456 | 6.306723 | 0.959 | 0.873 | 0.878 | 0.9741 | 0.9596 | 1.025 | 0.9525 | 0.9849 | 0.9931 |
| 026_8006_00263880 | Kidney | 8006 | A704 | 456 | 6.969306 | 1.351 | 0.929 | 1.157 | 0.9881 | 1.0206 | 0.957 | 1.0009 | 0.9583 | 0.9931 |
| 026_8152_00256190 | Kidney | 8152 | RCC10RGB | 456 | 7.15535 | 1.178 | 0.835 | 1.76 | 0.846 | 0.8683 | 1.123 | 1.1733 | 1.1056 | 1.0876 |
| 026_8005_00296380 | Kidney | 8005 | A498 | 456 | 8.190783 | 1.022 | 1.025 | 1.024 | 1.0158 | 1.03 | 1.032 | 1.0128 | 1.0239 | 1.0104 |
| 026_233_00277420 | Leukemia | 233 | SIG-M5 | 456 | −5.883853 | 0.228 | 0.243 | 0.233 | 0.2401 | 0.2362 | 0.247 | 0.2641 | 0.2732 | 0.4405 |
| 026_217_00277380 | Leukemia | 217 | OCI-AML2 | 456 | −1.42786 | 0.09 | 0.102 | 0.106 | 0.1256 | 0.1044 | 0.132 | 0.3277 | 0.8333 | 0.8618 |
| 026_179_00314500 | Leukemia | 179 | KMOE-2 | 456 | −0.249088 | 0.13 | 0.135 | 0.138 | 0.1591 | 0.3658 | 0.608 | 0.865 | 0.8967 | 1.0615 |
| 026_214_00285590 | Leukemia | 214 | NB-4 | 456 | −0.011745 | 0.18 | 0.323 | 0.315 | 0.3611 | 0.4215 | 0.592 | 0.8144 | 0.8865 | 0.9464 |
| 026_168_00280410 | Leukemia | 168 | JURL-MK1 | 456 | 0.181843 | 0.145 | 0.179 | 0.186 | 0.2526 | 0.4638 | 0.727 | 0.9379 | 0.904 | 0.9907 |
| 026_194_00280680 | Leukemia | 194 | ML-2 | 456 | 0.294246 | 0.418 | 0.395 | 0.379 | 0.4439 | 0.4739 | 0.633 | 0.7874 | 0.8519 | 1.0223 |
| 026_186_00280670 | Leukemia | 186 | LAMA-84 | 456 | 0.295979 | 0.152 | 0.15 | 0.191 | 0.3623 | 0.6147 | 0.774 | 0.777 | 0.8716 | 0.8816 |
| 026_234_00314650 | Leukemia | 234 | SKM-1 | 456 | 0.349518 | 0.37 | 0.347 | 0.369 | 0.4439 | 0.4995 | 0.57 | 0.729 | 0.9566 | 1.2103 |
| 026_221_00280300 | Leukemia | 221 | OCI-M1 | 456 | 0.656393 | 0.183 | 0.235 | 0.344 | 0.5052 | 0.5942 | 0.759 | 0.8267 | 0.8418 | 1.1212 |
| 026_260_00280430 | Leukemia | 260 | KO52 | 456 | 0.674413 | 0.348 | 0.376 | 0.357 | 0.3446 | 0.4195 | 0.753 | 0.7217 | 0.7637 | 1.0996 |
| 026_45_00274530 | Leukemia | 45 | HL-60 | 456 | 0.756274 | 0.344 | 0.389 | 0.403 | 0.4669 | 0.6154 | 0.78 | 0.9211 | 0.9579 | 1.0107 |
| 026_218_00279140 | Leukemia | 218 | OCI-AML3 | 456 | 0.868641 | 0.368 | 0.38 | 0.401 | 0.4571 | 0.5459 | 0.76 | 0.8359 | 0.9311 | 0.9403 |
| 026_219_00280290 | Leukemia | 219 | OCI-AML5 | 456 | 0.879404 | 0.245 | 0.404 | 0.427 | 0.4943 | 0.686 | 0.712 | 0.8112 | 0.9498 | 0.9021 |
| 026_199_00314510 | Leukemia | 199 | MOLT-13 | 456 | 0.892109 | 0.227 | 0.339 | 0.454 | 0.5097 | 0.5774 | 0.766 | 0.8101 | 0.9633 | 1.1416 |
| 026_226_00280310 | Leukemia | 226 | PL-21 | 456 | 0.938066 | 0.406 | 0.425 | 0.463 | 0.4834 | 0.537 | 0.657 | 0.7338 | 0.7978 | 0.8482 |
| 026_8141_00274380 | Leukemia | 8141 | NOMO-1 | 456 | 1.040856 | 0.375 | 0.445 | 0.435 | 0.4798 | 0.5465 | 0.636 | 0.9597 | 0.9214 | 0.9288 |
| 026_8069_00279180 | Leukemia | 8069 | HAL-01 | 456 | 1.147185 | 0.349 | 0.345 | 0.454 | 0.634 | 0.6764 | 1.103 | 0.7322 | 0.8261 | 1.0097 |
| 026_68_00274440 | Leukemia | 68 | MV-4-11 | 456 | 1.155322 | 0.061 | 0.517 | 0.444 | 0.5488 | 0.6586 | 0.777 | 0.8697 | 0.9167 | 1.045 |
| 026_175_00282940 | Leukemia | 175 | KARPAS-620 | 456 | 1.190853 | 0.562 | 0.376 | 0.59 | 0.6051 | 0.7411 | 0.916 | 0.9551 | 1.1003 | 1.0193 |
| 026_89_00278880 | Leukemia | 89 | MEG-01 | 456 | 1.211836 | 0.223 | 0.454 | 0.433 | 0.6062 | 0.6931 | 0.86 | 0.9075 | 0.9993 | 1.0376 |
| 026_8017_00279150 | Leukemia | 8017 | BV-173 | 456 | 1.464827 | 0.147 | 0.403 | 0.57 | 0.8503 | 0.5534 | 0.638 | 0.7679 | 0.8629 | 1.0089 |
| 026_225_00277400 | Leukemia | 225 | PF-382 | 456 | 1.646942 | 0.317 | 0.339 | 0.525 | 0.6985 | 0.7396 | 0.932 | 0.9611 | 0.9018 | 1.0833 |
| 026_285_00282960 | Leukemia | 285 | KY821A3 | 456 | 1.656661 | 0.422 | 0.426 | 0.445 | 0.6672 | 0.7787 | 0.935 | 1.0015 | 1.0293 | 1.0583 |
| 026_8008_00280620 | Leukemia | 8008 | ALL-PO | 456 | 1.659142 | 0.406 | 0.425 | 0.463 | 0.6225 | 0.537 | 0.725 | 0.845 | 0.8482 | 1.019 |
| 026_177_00278860 | Leukemia | 177 | KE-37 | 456 | 1.711407 | 0.143 | 0.451 | 0.523 | 0.6745 | 0.6911 | 0.897 | 0.9087 | 0.9169 | 1.0477 |
| 026_126_00280270 | Leukemia | 126 | GDM-1 | 456 | 1.723253 | 0.195 | 0.444 | 0.595 | 0.682 | 0.9068 | 0.786 | 0.9053 | 0.9081 | 0.8666 |
| 026_261_00274440 | Leukemia | 261 | MY-M12 | 456 | 1.811821 | 0.297 | 0.471 | 0.59 | 0.6443 | 0.7944 | 0.832 | 0.8778 | 1.0023 | 1.0569 |
| 026_201_00277390 | Leukemia | 201 | MOLT-16 | 456 | 1.821177 | 0.395 | 0.43 | 0.578 | 0.7394 | 0.7461 | 0.857 | 0.9379 | 1.0322 | 0.9678 |
| 026_148_00277330 | Leukemia | 148 | CMK | 456 | 1.894859 | 0.276 | 0.484 | 0.637 | 0.6101 | 0.7801 | 0.771 | 0.9002 | 0.8949 | 1.0376 |
| 026_28_00280320 | Leukemia | 28 | SUP-B15 | 456 | 1.921651 | 0.275 | 0.506 | 0.579 | 0.7214 | 0.744 | 0.82 | 0.908 | 0.9679 | 0.9913 |
| 026_190_00287920 | Leukemia | 190 | ME-1 | 456 | 1.924633 | 0.261 | 0.596 | 0.587 | 0.5806 | 0.7165 | 0.684 | 0.7906 | 0.8581 | 0.9106 |
| 026_8150_00273700 | Leukemia | 8150 | QIMR-WIL | 456 | 1.928333 | 0.441 | 0.546 | 0.595 | 0.6574 | 0.7011 | 0.771 | 0.852 | 0.962 | 0.9148 |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_8156_00273710 | Leukemia | 8156 | RPMI-8866 | 456 | 1.939976 | 0.339 | 0.474 | 0.598 | 0.694 | 0.7428 | 0.867 | 0.9518 | 0.9936 | 0.9682 |
| 026_161_00277350 | Leukemia | 161 | HC-1 | 456 | 1.948766 | 0.447 | 0.517 | 0.568 | 0.6165 | 0.6342 | 0.768 | 0.7642 | 0.9074 | 1.0155 |
| 026_195_00279120 | Leukemia | 195 | MOLM-13 | 456 | 1.961596 | 0.394 | 0.455 | 0.518 | 0.6868 | 0.817 | 0.872 | 0.9157 | 0.983 | 1.0345 |
| 026_209_00279130 | Leukemia | 209 | NALM-6 | 456 | 2.000316 | 0.14 | 0.471 | 0.592 | 0.6915 | 0.7587 | 0.808 | 0.8658 | 0.9205 | 0.9768 |
| 026_127_00278810 | Leukemia | 127 | CESS | 456 | 2.000616 | 0.342 | 0.505 | 0.625 | 0.6869 | 0.7679 | 0.843 | 0.9355 | 0.9565 | 0.9827 |
| 026_8196_00278790 | Leukemia | 8196 | 697 | 456 | 2.032634 | 0.337 | 0.476 | 0.617 | 0.7249 | 0.8167 | 0.885 | 0.885 | 1.0695 | 1.0723 |
| 026_223_00276841 | Leukemia | 223 | P12-ICHIKAWA | 456 | 2.094412 | 0.266 | 0.472 | 0.62 | 1.0139 | 0.9551 | 0.864 | 0.9219 | 1.0481 | 0.907 |
| 026_157_00279291 | Leukemia | 157 | DND-41 | 456 | 2.109279 | 0.354 | 0.498 | 0.624 | 0.7174 | 0.8189 | 0.89 | 0.9495 | 0.9928 | 1.0144 |
| 026_174_00276850 | Leukemia | 174 | KARPAS-45 | 456 | 2.156973 | 0.368 | 0.541 | 0.63 | 0.778 | 0.8566 | 0.998 | 0.0142 | 0.9561 | 0.9985 |
| 026_223_00277461 | Leukemia | 223 | P12-ICHIKAWA | 456 | 2.170641 | 0.274 | 0.465 | 0.567 | 0.909 | 0.9914 | 1.041 | 1.0272 | 0.9908 | 1.0038 |
| 026_231_00277410 | Leukemia | 231 | RPMI-8402 | 456 | 2.171412 | 0.292 | 0.525 | 0.673 | 0.8379 | 0.894 | 0.956 | 1.0525 | 1.0069 | 1.0163 |
| 026_176_00278840 | Leukemia | 176 | KCL-22 | 456 | 2.178418 | 0.342 | 0.551 | 0.66 | 0.7185 | 0.7521 | 0.822 | 0.8942 | 1.034 | 0.9817 |
| 026_198_00279320 | Leukemia | 198 | MOLP-8 | 456 | 2.182175 | 0.422 | 0.613 | 0.604 | 0.6789 | 0.7123 | 0.753 | 0.8469 | 0.8678 | 0.9555 |
| 026_35_00274541 | Leukemia | 35 | MOLT-4 | 456 | 2.185513 | 0.368 | 0.518 | 0.657 | 0.7557 | 0.8266 | 0.893 | 0.9057 | 1.0649 | 1.0505 |
| 026_256_00273800 | Leukemia | 256 | U266B1 | 456 | 2.191112 | 0.423 | 0.53 | 0.596 | 0.6351 | 0.7316 | 0.782 | 0.8701 | 0.9616 | 0.9089 |
| 026_41_00278850 | Leukemia | 41 | KG-1 | 456 | 2.260524 | 0.445 | 0.507 | 0.569 | 0.7321 | 0.8443 | 0.89 | 0.9006 | 0.9237 | 0.9648 |
| 026_38_00278900 | Leukemia | 38 | THP-1 | 456 | 2.296961 | 0.389 | 0.568 | 0.692 | 0.7667 | 0.7899 | 0.895 | 0.9332 | 0.9649 | 0.9902 |
| 026_153_00277340 | Leukemia | 153 | CTV-1 | 456 | 2.301756 | 0.308 | 0.563 | 0.682 | 0.7882 | 0.8949 | 0.972 | 1.0362 | 1.0213 | 1.0568 |
| 026_284_00273770 | Leukemia | 284 | KY821 | 456 | 2.31293 | 0.459 | 0.524 | 0.599 | 0.642 | 0.7677 | 0.831 | 0.9119 | 0.9596 | 0.9938 |
| 26_256_00304780 | Leukemia | 256 | U266B1 | 456 | 2.374209 | 0.453 | 0.543 | 0.608 | 0.6629 | 0.7604 | 0.806 | 0.9117 | 0.9547 | 0.9487 |
| 026_8033_00279160 | Leukemia | 8033 | DEL | 456 | 2.390133 | 0.433 | 0.595 | 0.647 | 0.7617 | 0.7648 | 0.851 | 0.9096 | 0.9116 | 0.9641 |
| 026_227_00314640 | Leukemia | 227 | RCH-ACV | 456 | 2.405281 | 0.39 | 0.571 | 0.742 | 0.8517 | 0.9043 | 0.946 | 0.9917 | 1.0175 | 1.1197 |
| 026_33_00274521 | Leukemia | 33 | CCRF-CEM | 456 | 2.408403 | 0.354 | 0.606 | 0.685 | 0.7594 | 0.8191 | 0.904 | 0.9597 | 0.9629 | 1.0269 |
| 026_141_00276820 | Leukemia | 141 | K-562 | 456 | 2.457405 | 0.51 | 0.504 | 0.624 | 0.8081 | 0.8379 | 1.163 | 0.9404 | 1.0057 | 1.0193 |
| 026_8137_00273680 | Leukemia | 8137 | NKM-1 | 456 | 2.543263 | 0.464 | 0.601 | 0.622 | 0.6486 | 0.7425 | 0.801 | 0.8993 | 0.9038 | 0.9449 |
| 026_36_00274550 | Leukemia | 36 | Reh | 456 | 2.569808 | 0.418 | 0.628 | 0.742 | 0.8367 | 0.88 | 0.896 | 0.9262 | 0.8979 | 0.9849 |
| 026_8042_00285400 | Leukemia | 8042 | EoL-1-cell | 456 | 2.64235 | 0.232 | 0.569 | 0.651 | 0.7409 | 0.7743 | 0.894 | 0.8333 | 0.905 | 0.9094 |
| 026_281_00273690 | Leukemia | 281 | P30/OHK | 456 | 2.804566 | 0.473 | 0.654 | 0.769 | 0.9121 | 0.8865 | 1.022 | 1.0746 | 1.0233 | 1.0407 |
| 026_59_00278820 | Leukemia | 59 | JRT3-T3.5 | 456 | 2.830428 | 0.457 | 0.659 | 0.795 | 0.8429 | 0.9259 | 1.002 | 1.0587 | 0.9873 | 1.1396 |
| 026_164_00277360 | Leukemia | 164 | HEL | 456 | 2.835925 | 0.426 | 0.745 | 0.939 | 0.9081 | 1.0194 | 0.987 | 1.0611 | 1.0159 | 0.9841 |
| 026_183_00277370 | Leukemia | 183 | L-363 | 456 | 2.864138 | 0.468 | 0.685 | 0.82 | 0.9025 | 0.9548 | 1.046 | 1.0249 | 0.9812 | 1.02 |
| 026_90_00278840 | Leukemia | 90 | KU812 | 456 | 2.874545 | 0.446 | 0.74 | 0.806 | 0.917 | 0.9589 | 0.978 | 0.9646 | 1.0111 | 1.0409 |
| 026_27_00278890 | Leukemia | 27 | RS4;11 | 456 | 2.914096 | 0.47 | 0.684 | 0.809 | 0.8895 | 0.9144 | 0.975 | 0.9547 | 0.9619 | 1.0194 |
| 026_167_00314490 | Leukemia | 167 | JURKAT | 456 | 2.954834 | 0.503 | 0.713 | 0.842 | 0.9399 | 0.9544 | 0.985 | 0.9987 | 1.034 | 1.0702 |
| 026_181_00278860 | Leukemia | 181 | KOPN-8 | 456 | 2.957727 | 0.484 | 0.669 | 0.731 | 0.7843 | 0.8662 | 0.92 | 0.9473 | 0.9339 | 0.9555 |
| 026_8155_00309110 | Leukemia | 277 | RPMI 8226 | 456 | 2.959542 | 0.648 | 0.63 | 0.689 | 0.8376 | 0.888 | 0.99 | 0.9938 | 0.9182 | 1.0157 |
| 026_8041_00280640 | Leukemia | 8041 | EM-2 | 456 | 3.022652 | 0.557 | 0.687 | 0.614 | 0.634 | 0.706 | 0.679 | 0.8613 | 0.8617 | 1.9538 |
| 026_142_00279280 | Leukemia | 142 | ALL-SIL | 456 | 3.085854 | 0.187 | 0.624 | 0.769 | 0.7092 | 0.7975 | 0.937 | 0.9525 | 0.9717 | 0.8276 |
| 026_277_00280420 | Leukemia | 277 | RPMI 8226 | 456 | 3.102844 | 0.659 | 0.636 | 0.566 | 0.6117 | 0.6594 | 0.722 | 0.8693 | 0.9508 | 0.9057 |
| 026_180_00279310 | Leukemia | 180 | KMS-12-BM | 456 | 3.125028 | 0.512 | 0.704 | 0.788 | 0.8503 | 0.8703 | 0.949 | 0.905 | 0.9806 | 0.9931 |
| 026_8066_00279170 | Leukemia | 8066 | GR-ST | 456 | 3.192114 | 0.532 | 0.681 | 0.762 | 0.8318 | 0.8448 | 0.865 | 1.0258 | 0.9609 | 0.9989 |
| 26_283_00273780 | Leukemia | 283 | LC4-1 | 456 | 3.243599 | 0.592 | 0.732 | 0.916 | 0.9522 | 1.0268 | 1.078 | 0.9517 | 1.0295 | 1.0135 |
| 026_114_00273650 | Leukemia | 114 | SUP-T1 | 456 | 3.397019 | 0.637 | 0.807 | 0.908 | 1.0154 | 0.984 | 1.031 | 0.99 | 0.9877 | 1.0134 |
| 026_138_00287901 | Leukemia | 138 | Loucy | 456 | 3.501279 | 0.289 | 0.749 | 0.772 | 0.942 | 0.9225 | 0.948 | 0.9678 | 0.9653 | 1.0654 |
| 026_8014_00282911 | Leukemia | 8014 | BE-13 | 456 | 3.615529 | 0.68 | 0.757 | 0.965 | 1.1246 | 1.0528 | 1.075 | 1.0884 | 1.0694 | 1.1037 |
| 26_274_00273860 | Leukemia | 274 | BALL-1 | 456 | 3.704228 | 0.65 | 0.709 | 0.777 | 0.8768 | 0.9725 | 0.983 | 0.9819 | 0.9839 | 0.9978 |
| 026_222_00280480 | Leukemia | 222 | OPM-2 | 456 | 3.757754 | 0.681 | 0.619 | 0.771 | 0.9443 | 0.8789 | 1.073 | 0.9014 | 0.9191 | 0.9051 |
| 026_8164_00283540 | Leukemia | 8164 | SK-MM-2 | 456 | 3.790344 | 0.669 | 0.788 | 0.861 | 0.8903 | 0.938 | 0.941 | 1.0087 | 0.9277 | 0.9972 |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_166_00278830 | Leukemia | 166 | JJN-3 | 456 | 3.901981 | 0.636 | 0.791 | 0.85 | 0.8566 | 0.8711 | 0.916 | 0.9455 | 0.9892 | 1.057 |
| 026_230_00282970 | Leukemia | 230 | ROS-50 | 456 | 4.130585 | 0.714 | 0.775 | 0.805 | 0.9413 | 0.9813 | 1.11 | 1.1334 | 1.0559 | 0.999 |
| 026_159_00314480 | Leukemia | 159 | EJM | 456 | 4.251735 | 0.765 | 0.845 | 0.899 | 0.9099 | 1.0285 | 0.923 | 1.0677 | 1.0768 | 1.0543 |
| 026_278_00304730 | Leukemia | 278 | KMS-12-PE | 456 | 4.269602 | 0.73 | 0.814 | 0.84 | 1.0641 | 0.988 | 1.023 | 1.045 | 1.0284 | 0.0665 |
| 026_8219_00282850 | Leukemia | 8219 | Mo-T | 456 | 4.313664 | 0.705 | 0.825 | 0.804 | 0.9425 | 0.9233 | 1.033 | 0.8454 | 1.1551 | 1.0561 |
| 026_279_00274450 | Leukemia | 279 | P31/FUJ | 456 | 4.386897 | 0.703 | 0.805 | 0.799 | 0.819 | 0.8632 | 1.043 | 1.0364 | 0.9822 | 1.0363 |
| 026_171_00285190 | Leukemia | 171 | KARPAS-231 | 456 | 4.404825 | 0.698 | 0.9 | 0.906 | 0.9339 | 0.9295 | 0.904 | 0.9725 | 0.9496 | 0.9164 |
| 026_244_00273660 | Leukemia | 244 | TALL-1 | 456 | 4.411016 | 0.665 | 0.758 | 0.785 | 0.8345 | 0.8593 | 0.861 | 1.0445 | 1.0026 | 1.0194 |
| 026_158_00291340 | Leukemia | 158 | EHEB | 456 | 4.509743 | 0.781 | 0.745 | 0.765 | 0.7841 | 0.8282 | 0.839 | 0.92 | 0.9348 | 1.0344 |
| 026_134_00278800 | Leukemia | 134 | ARH-77 | 456 | 4.545002 | 0.856 | 0.856 | 0.96 | 0.848 | 1.0568 | 1.029 | 1.0104 | 1.0156 | 1.0086 |
| 026_246_00273670 | Leukemia | 246 | U-698-M | 456 | 4.580953 | 0.754 | 0.891 | 0.936 | 0.9419 | 0.9607 | 0.937 | 1.032 | 0.9352 | 1.0229 |
| 026_8113_00280440 | Leukemia | 8113 | MHH-CALL-2 | 456 | 4.648418 | 0.771 | 0.883 | 0.929 | 0.9704 | 0.9337 | 0.987 | 1.0345 | 1.0223 | 1.0471 |
| 026_159_00311690 | Leukemia | 159 | EJM | 456 | 4.699945 | 0.746 | 0.894 | 0.921 | 0.9275 | 0.9393 | 0.941 | 0.9575 | 0.9338 | 0.9675 |
| 026_159_00282920 | Leukemia | 159 | EJM | 456 | 4.832393 | 0.746 | 0.976 | 1.016 | 0.9859 | 1.0015 | 1.002 | 1.1587 | 1.1041 | 1.0548 |
| 026_8115_00280450 | Leukemia | 8115 | MN-60 | 456 | 4.861437 | 0.826 | 0.804 | 0.822 | 1.0586 | 0.9555 | 0.947 | 1.0471 | 1.128 | 1.0314 |
| 026_204_00280460 | Leukemia | 204 | MONO-MAC-6 | 456 | 4.946039 | 0.736 | 0.802 | 0.771 | 0.8409 | 0.8712 | 0.833 | 0.8634 | 1.0677 | 0.855 |
| 026_8117_00280470 | Leukemia | 8117 | MUTZ-1 | 456 | 5.304526 | 0.823 | 0.984 | 1.063 | 1.051 | 1.0142 | 1.007 | 0.9986 | 0.9654 | 0.9525 |
| 026_188_00282930 | Leukemia | 188 | LP-1 | 456 | 5.373997 | 0.831 | 0.887 | 0.972 | 0.8808 | 0.9105 | 0.886 | 0.9533 | 0.9576 | 1.138 |
| 026_8081_00285580 | Leukemia | 8081 | JVM-3 | 456 | 5.581328 | 0.884 | 0.904 | 0.95 | 0.9131 | 1.01 | 1.097 | 1.0593 | 0.9629 | 1.0333 |
| 026_159_00309070 | Leukemia | 159 | EJM | 456 | 5.810283 | 0.882 | 0.986 | 0.998 | 1.0992 | 1.0048 | 1.045 | 1.0126 | 1.024 | 1.0649 |
| 026_8080_00280660 | Leukemia | 8080 | JVM-2 | 456 | 5.982881 | 0.867 | 0.876 | 0.901 | 0.8865 | 0.9235 | 0.909 | 0.9782 | 0.8964 | 0.9789 |
| 026_278_00280630 | Leukemia | 278 | KMS-12-PE | 456 | 6.629507 | 0.92 | 0.92 | 0.95 | 0.9554 | 0.9046 | 0.905 | 0.9657 | 1.0243 | 0.9236 |
| 026_8010_00280630 | Leukemia | 8010 | ATN-1 | 456 | 7.14863 | 1.03 | 0.958 | 0.835 | 0.8896 | 0.8651 | 0.907 | 0.9392 | 0.8582 | 0.9763 |
| 26_262_00273790 | Leukemia | 262 | MLMA | 456 | 7.68552 | 0.485 | 1.033 | 1.077 | 1.0216 | 1.0341 | 0.962 | 1.0378 | 0.9821 | 1.0245 |
| 026_278_00282950 | Leukemia | 278 | KMS-12-PE | 456 | 7.74945 | 0.958 | 1.101 | 1.04 | 1.1177 | 1.0046 | 1.029 | 1.0272 | 1.0311 | 1.0037 |
| 026_649_00264910 | Liver | 649 | Hep 3B2.1-7 | 456 | -0.30042 | 0.134 | 0.098 | 0.087 | 0.1121 | 0.2203 | 0.601 | 0.8432 | 0.8926 | 0.9089 |
| 026_658_00262810 | Liver | 658 | JHH-1 | 456 | -0.185127 | 0.054 | 0.329 | 0.515 | 0.3993 | 0.5194 | 0.524 | 0.6608 | 0.6499 | 0.6863 |
| 026_649_00266180 | Liver | 649 | Hep 3B2.1-7 | 456 | -0.037335 | 0.073 | 0.105 | 0.093 | 0.0908 | 0.1037 | 0.202 | 0.8123 | 0.9207 | 1.007 |
| 026_667_00273550 | Liver | 667 | HuH-7 | 456 | 1.289162 | 0.279 | 0.565 | 0.539 | 0.5535 | 0.7134 | 0.77 | 0.8626 | 0.9675 | 0.9662 |
| 026_659_00275780 | Liver | 659 | JHH-2 | 456 | 1.758427 | 0.283 | 0.473 | 0.657 | 0.7149 | 0.551 | 0.819 | 0.8858 | 0.8891 | 1.0202 |
| 026_643_00266460 | Liver | 643 | SNU-398 | 456 | 2.578054 | 0.415 | 0.687 | 0.643 | 0.6854 | 0.6879 | 0.717 | 0.7896 | 0.8076 | 0.9193 |
| 026_667_00269210 | Liver | 667 | HuH-7 | 456 | 2.760591 | 0.501 | 0.59 | 0.665 | 0.6852 | 0.6886 | 0.781 | 0.95 | 1.0287 | 1.0142 |
| 026_647_00269110 | Liver | 647 | SNU-387 | 456 | 2.930627 | 0.494 | 0.772 | 0.829 | 0.9402 | 0.9686 | 1.046 | 1.0372 | 1.0223 | 1.2144 |
| 026_661_00252500 | Liver | 661 | JHH-7 | 456 | 3.286573 | 0.539 | 0.889 | 0.794 | 0.8777 | 1.0776 | 0.953 | 0.9918 | 1.037 | 0.9476 |
| 026_643_00263980 | Liver | 643 | SNU-398 | 456 | 3.293137 | 0.487 | 0.768 | 0.854 | 0.8235 | 0.8763 | 0.883 | 0.9616 | 1.068 | 1.0718 |
| 026_642_00308440 | Liver | 642 | C3A | 456 | 3.554832 | 0.587 | 0.68 | 0.706 | 0.7687 | 0.817 | 0.878 | 0.8123 | 0.9574 | 0.9245 |
| 026_648_00258350 | Liver | 648 | SNU-423 | 456 | 3.576003 | 0.139 | 0.699 | 0.902 | 0.9157 | 0.9485 | 0.909 | 0.8626 | 0.9469 | 1.0028 |
| 026_656_00275490 | Liver | 656 | JHH-4 | 456 | 3.61979 | 0.701 | 0.653 | 0.631 | 0.8187 | 0.7968 | 0.977 | 0.8858 | 0.9897 | 0.9288 |
| 026_660_00269200 | Liver | 660 | JHH-6 | 456 | 3.831185 | 0.696 | 0.88 | 1.034 | 0.9294 | 0.9465 | 1.04 | 0.9417 | 1.0528 | 0.952 |
| 026_644_00252750 | Liver | 644 | SNU-449 | 456 | 4.40481 | 0.664 | 0.733 | 0.764 | 0.7954 | 0.8597 | 0.896 | 0.9485 | 0.9457 | 0.9162 |
| 026_644_00306170 | Liver | 644 | SNU-449 | 456 | 6.450644 | 0.96 | 0.961 | 0.745 | 1.0716 | 1.0197 | 1.08 | 0.991 | 0.9007 | 0.9369 |
| 26_646_00314060 | Liver | 654 | SNU-475 | 456 | 6.501654 | 0.181 | 0.97 | 0.971 | 0.9863 | 1.0061 | 1.007 | 1.0271 | 1.0202 | 0.057 |
| 026_654_00255800 | Liver | 654 | SK-HEP-1 | 456 | 6.515068 | 0.927 | 1.006 | 1.087 | 0.9827 | 0.9589 | 0.98 | 0.9783 | 0.9726 | 0.9998 |
| 026_668_00252690 | Liver | 668 | HLE | 456 | 7.25378 | 0.434 | 1.006 | 1.072 | 0.9897 | 1.1103 | 0.964 | 1.006 | 1.068 | 0.9541 |
| 026_662_00252460 | Liver | 662 | huH-1 | 456 | 7.722693 | 0.466 | 1.165 | 1.063 | 1.0401 | 1.0408 | 1.136 | 1.015 | 0.9574 | 0.9778 |
| 026_645_00306160 | Liver | 645 | JHH-6 | 456 | 7.852049 | 1.105 | 1.061 | 1.007 | 1.0055 | 1.0268 | 1.053 | 1.0365 | 1.123 | 1.0842 |
| 026_642_00252670 | Liver | 642 | C3A | 456 | 7.864415 | 0.386 | 1.1 | 1.108 | 0.3049 | 0.9463 | 1.051 | 0.9803 | 1.029 | 0.9218 |
| 026_830_00304760 | Lung | 830 | NCI-H2135 | 456 | -0.374655 | 0.298 | 0.262 | 0.246 | 0.3692 | 0.528 | 0.7269 | 0.8905 | 0.977 | |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_698_00300170 | Lung | 698 | NCI-H524 | 456 | 2.279246 | 0.443 | 0.506 | 0.63 | 0.8741 | 0.9302 | 1.005 | 1.0131 | 1.0304 | 1.0567 |
| 026_672_00314460 | Lung | 672 | NCI-H510A | 456 | 2.367223 | 0.323 | 0.585 | 0.763 | 0.783 | 0.8906 | 0.969 | 0.9972 | 1.1809 | 1.0131 |
| 026_761_00300410 | Lung | 761 | COR-L279 | 456 | 3.131703 | 0.559 | 0.745 | 0.868 | 0.9821 | 1.0079 | 1.06 | 1.0144 | 1.0182 | 1.0709 |
| 026_726_00304770 | Lung | 726 | NCI-H2171 | 456 | 3.185965 | 0.524 | 0.729 | 0.842 | 0.8655 | 0.9088 | 0.871 | 1.0252 | 0.9207 | 1.129 |
| 026_740_00302760 | Lung | 740 | NCI-H82 | 456 | 3.210581 | 0.542 | 0.755 | 0.865 | 0.9592 | 1.0522 | 0.888 | 0.9137 | 1.004 | 1.0151 |
| 026_787_00302910 | Lung | 787 | SBC-3 | 456 | 3.410219 | 0.582 | 0.655 | 0.694 | 0.802 | 0.8502 | 0.902 | 0.9485 | 0.9451 | 0.9885 |
| 026_695_00300150 | Lung | 695 | NCI-H211 | 456 | 3.515811 | 0.644 | 0.645 | 0.719 | 0.8327 | 0.8177 | 0.933 | 0.9519 | 0.9812 | 1.0305 |
| 026_721_00302860 | Lung | 721 | NCI-H2029 | 456 | 3.591515 | 0.606 | 0.8 | 0.891 | 0.9011 | 0.8579 | 0.931 | 0.9429 | 1.0032 | 1.0011 |
| 026_776_00303250 | Lung | 776 | MS-1-L | 456 | 3.614256 | 0.642 | 0.767 | 0.855 | 0.8458 | 1.1115 | 0.929 | 1.0414 | 1.0285 | 1.162 |
| 026_8197_00304741 | Lung | 8197 | LU-139 | 456 | 3.667637 | 0.66 | 0.84 | 0.901 | 1.0158 | 0.9097 | 0.912 | 1.0844 | 1.1048 | 1.0641 |
| 026_702_00302900 | Lung | 702 | NCI-H847 | 456 | 3.686524 | 0.818 | 0.707 | 0.668 | 0.6815 | 0.7184 | 0.743 | 0.7999 | 0.9145 | 0.9524 |
| 026_8203_00309050 | Lung | 8203 | IST-SL1 | 456 | 3.697133 | 0.635 | 0.801 | 0.87 | 0.931 | 0.9112 | 1 | 1.0127 | 0.9507 | 1.0704 |
| 026_724_00300140 | Lung | 724 | NCI-H2081 | 456 | 3.857634 | 0.623 | 0.866 | 0.895 | 0.9027 | 0.9349 | 0.948 | 0.969 | 0.9681 | 1.0072 |
| 026_765_00300050 | Lung | 765 | DMS 273 | 456 | 3.890251 | 0.702 | 0.844 | 0.904 | 0.9648 | 1.028 | 0.968 | 1.0795 | 1.0165 | 1.0825 |
| 026_829_00305160 | Lung | 829 | NCI-H2110 | 456 | 3.972695 | 0.67 | 0.694 | 0.776 | 0.8765 | 0.8765 | 0.946 | 1.0573 | 0.91 | 0.9398 |
| 026_742_00303230 | Lung | 742 | DMS 53 | 456 | 3.990104 | 0.711 | 0.802 | 0.867 | 0.9734 | 1.0075 | 1.037 | 1.0307 | 1.0204 | 1.0405 |
| 026_710_00316710 | Lung | 710 | NCI-H1341 | 456 | 4.024081 | 0.591 | 0.852 | 0.7 | 0.7407 | 0.8259 | 0.789 | 0.8069 | 0.8386 | 0.865 |
| 026_738_00302800 | Lung | 738 | NCI-H446 | 456 | 4.043153 | 0.692 | 0.871 | 0.917 | 1.0421 | 0.9341 | 0.915 | 1.0657 | 0.9649 | 1.0382 |
| 026_751_00308570 | Lung | 751 | NCI-H209 | 456 | 4.061511 | 0.657 | 0.848 | 0.89 | 0.9403 | 0.8939 | 0.91 | 0.9316 | 0.9524 | 0.9513 |
| 026_716_00298900 | Lung | 716 | NCI-H1876 | 456 | 4.083964 | 0.744 | 0.866 | 0.936 | 0.9448 | 0.9881 | 0.979 | 0.9782 | 0.9994 | 1.0261 |
| 026_725_00303280 | Lung | 725 | NCI-H2141 | 456 | 4.09696 | 0.711 | 0.842 | 0.928 | 0.9702 | 0.9155 | 0.924 | 1.044 | 1.0101 | 0.9559 |
| 026_688_00302810 | Lung | 688 | SW 1271 | 456 | 4.124557 | 0.602 | 0.761 | 0.79 | 0.8093 | 0.807 | 0.823 | 0.896 | 0.8782 | 0.9341 |
| 026_720_00302380 | Lung | 720 | NCI-H1994 | 456 | 4.130367 | 0.696 | 0.694 | 0.73 | 0.8114 | 0.9245 | 0.935 | 0.9484 | 0.9393 | 0.9738 |
| 026_811_00311720 | Lung | 811 | NCI-H1435 | 456 | 4.138326 | 0.635 | 0.803 | 0.855 | 0.8503 | 0.8571 | 0.89 | 0.8912 | 0.955 | 0.9956 |
| 026_704_00300250 | Lung | 704 | NCI-H1048 | 456 | 4.178908 | 0.166 | 0.762 | 0.867 | 0.8914 | 0.9318 | 0.923 | 0.9201 | 1.0122 | 0.9635 |
| 026_746_00302780 | Lung | 746 | SHP-77 | 456 | 4.20487 | 0.79 | 0.843 | 0.955 | 1.029 | 0.9896 | 1.021 | 1.0111 | 0.9931 | 1.0025 |
| 026_829_00311740 | Lung | 829 | NCI-H2110 | 456 | 4.22315 | 0.739 | 0.83 | 0.914 | 0.9675 | 0.9597 | 0.983 | 0.9791 | 1.032 | 0.9995 |
| 026_736_00300181 | Lung | 736 | NCI-H69 | 456 | 4.26966 | 0.798 | 0.87 | 0.945 | 1.0535 | 1.0472 | 1.143 | 1.0521 | 1.0846 | 1.1743 |
| 026_724_00303270 | Lung | 724 | NCI-H2081 | 456 | 4.274134 | 0.708 | 0.95 | 1.023 | 0.9666 | 1.0134 | 0.99 | 1.0037 | 1.0388 | 1.0531 |
| 026_714_00300260 | Lung | 714 | NCI-H1694 | 456 | 4.276996 | 0.701 | 0.831 | 0.843 | 0.8708 | 0.9426 | 0.93 | 0.9095 | 1.1071 | 1.0848 |
| 026_715_00298890 | Lung | 715 | NCI-H1836 | 456 | 4.291554 | 0.755 | 0.833 | 0.997 | 0.9315 | 0.9434 | 0.955 | 0.9291 | 0.9423 | 1 |
| 026_757_00302870 | Lung | 757 | CPC-N | 456 | 4.345126 | 0.73 | 0.869 | 0.906 | 0.9009 | 0.9283 | 0.901 | 1.003 | 0.9238 | 1.0153 |
| 026_8229_00304990 | Lung | 8229 | COR-L303 | 456 | 4.468573 | 0.718 | 0.819 | 0.887 | 1.02 | 0.9158 | 1.082 | 0.9997 | 0.9139 | 0.9772 |
| 026_691_00308560 | Lung | 691 | NCI-H526 | 456 | 4.602758 | 0.685 | 0.828 | 0.788 | 1.0672 | 0.9906 | 1.099 | 1.0035 | 1.0955 | 1.0007 |
| 026_8099_00316740 | Lung | 8099 | LB647-SCLC | 456 | 4.613258 | 0.748 | 0.932 | 0.944 | 0.9468 | 0.9744 | 0.94 | 0.9635 | 1.1259 | 0.9506 |
| 026_725_00302750 | Lung | 725 | NCI-H2141 | 456 | 4.618451 | 0.755 | 0.954 | 0.998 | 0.9372 | 0.957 | 1.041 | 1.0171 | 1.0378 | 1.1424 |
| 026_705_00314520 | Lung | 705 | NCI-H1092 | 456 | 4.678169 | 0.747 | 0.869 | 0.906 | 1.0426 | 0.9283 | 0.955 | 1.003 | 0.9238 | 0.961 |
| 026_684_00300160 | Lung | 684 | NCI-H1688 | 456 | 4.865947 | 0.77 | 0.861 | 0.911 | 0.9503 | 0.9158 | 0.901 | 0.9997 | 1.0378 | 1.0698 |
| 026_725_00300160 | Lung | 725 | NCI-H2141 | 456 | 4.894458 | 0.832 | 0.831 | 0.988 | 1.0426 | 0.9906 | 1.082 | 1.0391 | 1.0477 | 0.9963 |
| 026_8281_00300930 | Lung | 8281 | COR-L311 | 456 | 5.024667 | 0.785 | 0.908 | 0.936 | 1.0148 | 0.9974 | 0.94 | 0.9635 | 1.0989 | 1.045 |
| 026_757_00300940 | Lung | 757 | CPC-N | 456 | 5.046784 | 0.792 | 0.892 | 0.947 | 0.9155 | 0.9117 | 0.871 | 1.0268 | 0.9063 | 1.0167 |
| 026_701_00309060 | Lung | 701 | NCI-H841 | 456 | 5.157768 | 0.796 | 0.904 | 0.984 | 1.0041 | 1.0137 | 0.919 | 0.905 | 1.0474 | 1.0933 |
| 026_814_00304750 | Lung | 814 | NCI-H1568 | 456 | 5.159278 | 0.826 | 0.808 | 0.939 | 0.891 | 0.8811 | 0.919 | 0.9514 | 0.9 | 0.9817 |
| 026_741_00305010 | Lung | 741 | NCI-H345 | 456 | 5.184481 | 0.784 | 0.726 | 0.739 | 0.745 | 0.7127 | 0.774 | 0.9411 | 0.9853 | 1.083 |
| 026_705_00311700 | Lung | 705 | NCI-H1092 | 456 | 5.191642 | 0.801 | 0.818 | 0.835 | 0.9503 | 0.9116 | 0.894 | 0.8849 | 0.9158 | 1.0581 |
| 026_786_00300950 | Lung | 786 | SBC-5 | 456 | 5.281883 | 0.849 | 0.892 | 0.945 | 1.0426 | 0.9184 | 0.981 | 1.0366 | 0.9158 | 1.0015 |
| 026_723_00316720 | Lung | 723 | NCI-H2066 | 456 | 5.313778 | 0.841 | 1.002 | 0.991 | 1.0148 | 0.9974 | 0.998 | 1.0298 | 1.0075 | 0.9757 |
| 026_705_00309080 | Lung | 705 | NCI-H1092 | 456 | 5.329516 | 0.793 | 0.815 | 0.866 | 0.86 | 0.9117 | 0.892 | 0.9084 | 0.923 | 1.0506 |
| | | | | | | 0.829 | 0.941 | 0.999 | 0.9672 | 0.8963 | 0.935 | 0.9991 | 0.9888 | |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_709_00305000 | Lung | 709 | NCI-H304 | 456 | 5.330039 | 0.838 | 0.882 | 0.906 | 0.8939 | 0.9384 | 0.978 | 1.0127 | 1.0322 | 1.0575 |
| 026_739_00314630 | Lung | 739 | NCI-H146 | 456 | 5.38813 | 0.858 | 0.893 | 0.978 | 1.0115 | 1.0583 | 0.937 | 0.9685 | 1.0018 | 1.0831 |
| 026_8110_00314450 | Lung | 8110 | LU-165 | 456 | 5.539798 | 0.87 | 0.909 | 0.986 | 0.9964 | 0.9809 | 1.094 | 0.9305 | 0.9513 | 1.1416 |
| 026_811_00305140 | Lung | 811 | NCI-H1435 | 456 | 5.586661 | 0.886 | 0.953 | 0.978 | 0.9914 | 1.0102 | 0.994 | 0.9871 | 0.9783 | 0.9731 |
| 026_711_00311710 | Lung | 711 | NCI-H1417 | 456 | 5.606717 | 0.875 | 0.91 | 0.911 | 0.9612 | 1.0374 | 0.917 | 1.267 | 1.0195 | 0.9447 |
| 026_712_00309090 | Lung | 712 | NCI-H1436 | 456 | 5.636542 | 0.85 | 0.918 | 0.976 | 0.9527 | 0.9331 | 0.932 | 0.9583 | 0.9477 | 1.0343 |
| 026_711_00305130 | Lung | 711 | NCI-H1417 | 456 | 5.804325 | 0.849 | 0.976 | 0.916 | 0.9247 | 0.9771 | 0.939 | 0.9326 | 1.0168 | 1.0143 |
| 026_728_00311760 | Lung | 728 | NCI-H2196 | 456 | 5.845371 | 0.89 | 1.022 | 0.918 | 0.9801 | 0.875 | 1.033 | 0.9519 | 0.931 | 1.0431 |
| 026_831_00311750 | Lung | 831 | NCI-H2172 | 456 | 5.851811 | 0.879 | 0.908 | 1.002 | 0.9709 | 0.9562 | 0.984 | 0.9781 | 1.0144 | 0.974 |
| 026_1216_00300060 | Lung | 1216 | H292 | 456 | 5.909493 | 0.869 | 0.986 | 1.008 | 0.8192 | 0.8429 | 0.864 | 0.9245 | 0.9789 | 1.0777 |
| 026_8109_00314440 | Lung | 8109 | LU-134-A | 456 | 5.930349 | 0.868 | 0.823 | 0.808 | 0.9375 | 0.9332 | 0.959 | 0.9516 | 1.1207 | 1.1025 |
| 026_831_00305170 | Lung | 831 | NCI-H2172 | 456 | 6.053261 | 0.837 | 0.95 | 0.972 | 0.8908 | 0.9397 | 0.905 | 0.9677 | 0.9512 | 0.9839 |
| 026_728_00305180 | Lung | 728 | NCI-H2196 | 456 | 6.171009 | 0.9 | 0.856 | 0.908 | 0.9979 | 0.9199 | 0.928 | 0.9453 | 0.9369 | 0.941 |
| 026_689_00300910 | Lung | 689 | NCI-H187 | 456 | 6.191556 | 0.887 | 0.903 | 0.976 | 0.9979 | 0.9535 | 1.047 | 1.021 | 1.0846 | 0.959 |
| 026_785_00302770 | Lung | 785 | SBC-1 | 456 | 6.234067 | 0.875 | 1.009 | 0.976 | 0.9779 | 0.9535 | 0.937 | 1.021 | 1.0039 | 1.1602 |
| 026_8280_00306910 | Lung | 8280 | COR-L321 | 456 | 6.254083 | 0.965 | 1.037 | 1.061 | 0.9376 | 1.0385 | 1.048 | 0.9403 | 1.0039 | 0.9586 |
| 026_706_00318720 | Lung | 706 | NCI-H1105 | 456 | 6.355 | 0.897 | 0.937 | 1.019 | 0.8492 | 0.948 | 1.037 | 1.0366 | 1.0761 | 0.9589 |
| 026_712_00305150 | Lung | 712 | NCI-H1436 | 456 | 6.498513 | 0.959 | 0.965 | 1.009 | 0.9821 | 0.9646 | 0.922 | 0.9974 | 0.9667 | 0.9263 |
| 026_8079_00306720 | Lung | 8079 | IST-SL2 | 456 | 6.56418 | 0.947 | 0.818 | 0.938 | 1.1033 | 0.9924 | 0.966 | 1.0128 | 1.0035 | 1.006 |
| 026_743_00303220 | Lung | 743 | DMS 114 | 456 | 6.614771 | 0.862 | 0.972 | 0.935 | 0.9658 | 0.9445 | 0.937 | 0.9554 | 1.0191 | 1.0374 |
| 026_8022_00306711 | Lung | 8022 | COLO-668 | 456 | 6.912523 | 0.97 | 0.853 | 0.785 | 0.7831 | 0.861 | 0.851 | 0.8815 | 0.9129 | 0.9308 |
| 026_8109_00308510 | Lung | 8109 | LU-134-A | 456 | 6.98132 | 0.897 | 0.968 | 0.956 | 1 | 0.9608 | 0.917 | 1.0093 | 0.9217 | 0.9606 |
| 026_758_00303240 | Lung | 758 | HCC-33 | 456 | 7.022636 | 0.924 | 1.012 | 1.105 | 0.9946 | 0.9684 | 1.081 | 0.9878 | 0.9397 | 1.1932 |
| 026_771_00306940 | Lung | 771 | Lu-135 | 456 | 7.040802 | 0.931 | 1.056 | 1.002 | 1.0822 | 0.9924 | 1.011 | 1.0128 | 1.1612 | 1.1932 |
| 026_694_00302790 | Lung | 694 | NCI-H196 | 456 | 7.041262 | 0.988 | 0.969 | 0.972 | 1.0271 | 1.0508 | 1.006 | 1.0081 | 1.1612 | 1.0235 |
| 026_764_00308550 | Lung | 764 | COR-L95 | 456 | 7.251052 | 0.976 | 0.954 | 0.975 | 0.9548 | 0.9989 | 1.047 | 0.993 | 1.0649 | 1.019 |
| 026_763_00300900 | Lung | 763 | COR-L88 | 456 | 7.365052 | 0.978 | 1.021 | 0.944 | 1.002 | 0.9357 | 0.922 | 0.9564 | 0.9433 | 0.903 |
| 026_8134_00306730 | Lung | 8134 | NCI-H64 | 456 | 7.782872 | 0.96 | 1.168 | 1.105 | 1.1434 | 1.0708 | 0.947 | 0.9637 | 0.9383 | 0.9838 |
| 026_712_00311730 | Lung | 712 | NCI-H1436 | 456 | 7.804947 | 1.026 | 1.003 | 0.891 | 1.0025 | 1.1503 | 1.011 | 1.0066 | 1.1636 | 1.052 |
| 026_8018_00304801 | Lung: NSCLC | 8018 | Calu-6 | 456 | -0.899538 | 1.019 | 1.049 | 0.976 | 0.9403 | 0.951 | 0.976 | 0.9338 | 0.8997 | 1.0076 |
| 026_1246_00304570 | Lung: NSCLC | 1246 | NCI-H1770 | 456 | -0.072444 | 0.106 | 0.165 | 0.183 | 0.2075 | 0.9104 | 1.047 | 0.9349 | 0.9472 | 0.9659 |
| 026_847_00304580 | Lung: NSCLC | 847 | NCI-H2087 | 456 | 1.048994 | 0.109 | 0.175 | 0.267 | 0.3543 | 0.2699 | 0.931 | 0.8182 | 0.9121 | 0.9531 |
| 026_680_00298830 | Lung: NSCLC | 680 | NCI-H727 | 456 | 1.334143 | 0.368 | 0.402 | 0.458 | 0.4756 | 0.4184 | 0.394 | 0.6475 | 1.0183 | 0.9838 |
| 026_748_00304590 | Lung: NSCLC | 748 | NCI-H226 | 456 | 1.690128 | 0.329 | 0.434 | 0.475 | 0.4492 | 0.5065 | 0.552 | 0.7888 | 0.9774 | 0.9846 |
| 026_851_00304600 | Lung: NSCLC | 851 | CAL-12T | 456 | 1.708943 | 0.342 | 0.457 | 0.514 | 0.5901 | 0.5064 | 0.683 | 0.8522 | 0.9134 | 0.98 |
| 026_861_00300230 | Lung: NSCLC | 861 | LCLC-97TM1 | 456 | 2.249036 | 0.452 | 0.449 | 0.49 | 0.5839 | 0.7687 | 0.604 | 0.7854 | 1.0039 | 0.932 |
| 026_1245_00304550 | Lung: NSCLC | 1245 | NCI-H1648 | 456 | 2.511131 | 0.424 | 0.573 | 0.622 | 0.7209 | 0.7337 | 0.757 | 0.9205 | 0.9724 | 0.9948 |
| 026_1180_00308140 | Lung: NSCLC | 1180 | NCI-H3122 | 456 | 2.550953 | 0.507 | 0.571 | 0.662 | 0.5623 | 0.7074 | 0.842 | 1.0412 | 1.0483 | 0.974 |
| 026_802_00298451 | Lung: NSCLC | 802 | NCI-H358 | 456 | 2.662533 | 0.534 | 0.517 | 0.616 | 0.6044 | 0.7611 | 0.873 | 1.0696 | 1.0483 | 1.4204 |
| 026_815_00311140 | Lung: NSCLC | 815 | NCI-H1623 | 456 | 2.802368 | 0.509 | 0.53 | 0.626 | 0.7229 | 0.7162 | 0.961 | 0.9512 | 0.9659 | 0.9657 |
| 026_1180_00302350 | Lung: NSCLC | 1180 | NCI-H3122 | 456 | 2.945291 | 0.523 | 0.592 | 0.685 | 0.6168 | 0.8072 | 0.883 | 0.8743 | 0.9218 | 0.9534 |
| 026_8040_00304501 | Lung: NSCLC | 8040 | EKVX | 456 | 3.134434 | 0.724 | 0.649 | 0.605 | 0.6264 | 0.7455 | 0.806 | 0.7888 | 0.8493 | 1.0805 |
| 026_865_00308451 | Lung: NSCLC | 865 | COR-L23 | 456 | 3.225036 | 0.532 | 0.642 | 0.782 | 0.75 | 0.7074 | 0.746 | 0.872 | 1.0538 | 1.1763 |
| 026_1243_00304541 | Lung: NSCLC | 1243 | NCI-H1395 | 456 | 3.23207 | 0.58 | 0.657 | 0.735 | 0.752 | 0.9489 | 0.913 | 0.9083 | 1.0521 | 1.0032 |
| 026_884_00308160 | Lung: NSCLC | 884 | RERF-LC-MS | 456 | 3.239905 | 0.553 | 0.739 | 0.944 | 0.83 | 0.9289 | 0.804 | 0.9087 | 1.0355 | 1.0002 |
| 026_796_00295871 | Lung: NSCLC | 796 | NCI-H2009 | 456 | 3.244878 | 0.585 | 0.663 | 0.662 | 0.948 | 0.7423 | 0.935 | 1.0144 | 1.0441 | 1.1113 |
| 026_799_00295880 | Lung: NSCLC | 799 | NCI-H661 | 456 | 3.295179 | 0.582 | 0.62 | 0.631 | 0.6574 | 0.7036 | 0.926 | 0.9919 | 0.9621 | 0.9957 |
| 026_822_00311150 | Lung: NSCLC | 822 | NCI-H1869 | 456 | 3.570833 | 0.667 | 0.587 | 0.685 | 0.635 | 0.7423 | 0.886 | 0.9636 | 0.9443 | 0.9943 |
| | | | | | | 0.153 | 0.716 | 0.736 | 0.7399 | 0.8095 | 0.819 | 1.026 | 0.9674 | 1.0055 |

TABLE 22-continued

| Barcode | Organ | Cell Line | Cell ID | Compound No | Fitted MGH_IC50 | Viability ratio | | | | | | | | |
|---|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_756_00302670 | Lung: NSCLC | BEN | 756 | 456 | 3.65632 | 0.639 | 0.833 | 0.942 | 0.9322 | 0.9128 | 0.965 | 0.9486 | 1.0116 | 1.0192 |
| 026_876_00299781 | Lung: NSCLC | LU65 | 876 | 456 | 3.69068 | 0.635 | 0.695 | 0.704 | 0.7208 | 0.8211 | 0.878 | 0.9851 | 1.0211 | 1.0551 |
| 026_805_00304531 | Lung: NSCLC | NCI-H1155 | 805 | 456 | 3.716538 | 0.61 | 0.788 | 0.787 | 0.8467 | 0.9573 | 0.91 | 0.953 | 1.0683 | 1.0508 |
| 026_834_00304610 | Lung: NSCLC | NCI-H2347 | 834 | 456 | 3.72347 | 0.653 | 0.736 | 0.756 | 0.8026 | 0.8524 | 0.984 | 0.9516 | 1.2251 | 1.0554 |
| 026_822_00304840 | Lung: NSCLC | NCI-H1869 | 822 | 456 | 3.749478 | 0.594 | 0.659 | 0.791 | 0.7802 | 0.8592 | 0.824 | 0.8872 | 0.9703 | 1.0592 |
| 026_835_00302390 | Lung: NSCLC | NCI-H2405 | 835 | 456 | 3.789193 | 0.693 | 0.659 | 0.651 | 0.6574 | 0.7337 | 0.768 | 0.8849 | 0.9046 | 1.0375 |
| 026_678_00304981 | Lung: NSCLC | UMC-11 | 678 | 456 | 3.815948 | 0.655 | 0.751 | 0.848 | 0.8851 | 0.9411 | 1.013 | 0.9806 | 1.0842 | 1.1132 |
| 026_807_00314280 | Lung: NSCLC | NCI-H650 | 807 | 456 | 3.884087 | 0.604 | 0.778 | 0.772 | 0.8577 | 0.8346 | 0.815 | 1.0068 | 0.831 | 0.9772 |
| 026_871_00299771 | Lung: NSCLC | LK-2 | 871 | 456 | 3.898613 | 0.684 | 0.806 | 0.903 | 0.9071 | 0.958 | 1.018 | 0.9981 | 1.0604 | 1.0786 |
| 026_1249_00308150 | Lung: NSCLC | NCI-H720 | 1249 | 456 | 3.907633 | 0.632 | 0.829 | 0.932 | 1.0847 | 1.526 | 0.799 | 0.8751 | 1.1242 | 1.1215 |
| 026_8231_00304510 | Lung: NSCLC | EMC-BAC-1 | 8231 | 456 | 3.943946 | 0.675 | 0.713 | 0.751 | 0.8781 | 0.831 | 0.886 | 0.976 | 1.0569 | 1.0459 |
| 026_820_00304560 | Lung: NSCLC | NCI-H1755 | 820 | 456 | 3.964037 | 0.658 | 0.769 | 0.785 | 0.8744 | 0.8799 | 0.931 | 0.9563 | 1.1261 | 1.0206 |
| 026_815_00304830 | Lung: NSCLC | NCI-H1623 | 815 | 456 | 3.981628 | 0.646 | 0.709 | 0.712 | 0.7108 | 0.8124 | 0.879 | 0.7844 | 1.0245 | 1.0786 |
| 026_839_00302410 | Lung: NSCLC | SW 900 | 839 | 456 | 3.982367 | 0.65 | 0.725 | 0.782 | 0.8242 | 0.8576 | 0.897 | 0.9535 | 1.0086 | 0.9978 |
| 026_804_00308480 | Lung: NSCLC | NCI-H810 | 804 | 456 | 4.03318 | 0.731 | 0.763 | 0.91 | 0.9442 | 0.9087 | 1.003 | 0.9482 | 0.9716 | 1.0139 |
| 026_678_00309011 | Lung: NSCLC | UMC-11 | 678 | 456 | 4.0744 | 0.514 | 0.846 | 0.86 | 0.931 | 0.9037 | 0.925 | 0.9312 | 0.9354 | 1.0786 |
| 026_842_00299540 | Lung: NSCLC | NCI-H520 | 842 | 456 | 4.082969 | 0.729 | 0.811 | 0.916 | 1.0516 | 1.0142 | 1.002 | 1.0457 | 1.0025 | 0.9761 |
| 026_824_00314260 | Lung: NSCLC | NCI-H1944 | 824 | 456 | 4.107799 | 0.695 | 0.731 | 0.691 | 0.7704 | 0.893 | 0.886 | 0.905 | 0.9791 | 1.0866 |
| 026_888_00298370 | Lung: NSCLC | ABC-1 | 888 | 456 | 4.123019 | 0.64 | 0.676 | 0.751 | 0.7343 | 0.8328 | 0.84 | 0.8774 | 0.9195 | 0.9448 |
| 026_823_00298430 | Lung: NSCLC | NCI-H1915 | 823 | 456 | 4.260241 | 0.691 | 0.707 | 0.702 | 0.7393 | 0.7957 | 0.834 | 0.9053 | 0.9612 | 0.9902 |
| 026_8232_00304520 | Lung: NSCLC | EMC-BAC-2 | 8232 | 456 | 4.327709 | 0.712 | 0.795 | 0.825 | 0.8558 | 0.8815 | 0.959 | 0.9014 | 1.1842 | 1.0135 |
| 026_755_00300611 | Lung: NSCLC | NCI-H1975 | 755 | 456 | 4.450033 | 0.666 | 0.968 | 0.963 | 0.9052 | 0.9346 | 0.928 | 0.9969 | 0.9681 | 0.973 |
| 026_868_00295440 | Lung: NSCLC | PC-14 | 868 | 456 | 4.458594 | 0.726 | 0.893 | 0.842 | 0.8971 | 0.9361 | 1.057 | 0.9146 | 1.1281 | 1.0139 |
| 026_872_00299750 | Lung: NSCLC | HARA | 872 | 456 | 4.480998 | 0.731 | 0.742 | 0.798 | 0.8152 | 0.8972 | 0.941 | 0.9735 | 1.0074 | 1.0301 |
| 026_800_00298441 | Lung: NSCLC | NCI-H23 | 800 | 456 | 4.511394 | 0.702 | 0.698 | 0.786 | 0.7938 | 0.8549 | 0.889 | 0.9216 | 0.9447 | 1.013 |
| 026_836_00304620 | Lung: NSCLC | NCI-H2444 | 836 | 456 | 4.530511 | 0.684 | 0.798 | 0.819 | 0.8507 | 0.863 | 0.86 | 0.9116 | 1.0106 | 1.0518 |
| 026_865_00296401 | Lung: NSCLC | COR-L23 | 865 | 456 | 4.577187 | 0.791 | 0.78 | 0.815 | 0.8605 | 0.9148 | 0.924 | 1.1179 | 1.1287 | 1.1293 |
| 026_858_00300591 | Lung: NSCLC | HCC-78 | 858 | 456 | 4.583505 | 0.703 | 0.983 | 0.936 | 1.06 | 0.9813 | 0.96 | 1.0028 | 0.9854 | 1.0584 |
| 026_854_00300681 | Lung: NSCLC | EPLC-272H | 854 | 456 | 4.590654 | 0.736 | 0.914 | 0.943 | 1.0019 | 1.0017 | 0.864 | 0.8937 | 0.9686 | 1.0373 |
| 026_837_00311160 | Lung: NSCLC | NCI-H2122 | 837 | 456 | 4.595192 | 0.771 | 0.917 | 0.969 | 0.9878 | 0.9667 | 1.017 | 1.0165 | 1.0062 | 1.0324 |
| 026_8111_00308110 | Lung: NSCLC | LXF-289 | 8111 | 456 | 4.689278 | 0.711 | 0.796 | 0.884 | 0.8648 | 0.868 | 0.89 | 0.9108 | 0.8979 | 0.9642 |
| 026_1136_00308471 | Lung: NSCLC | NCI-H1993 | 1136 | 456 | 4.705234 | 0.725 | 0.768 | 0.682 | 0.7469 | 0.7866 | 0.883 | 0.9296 | 0.914 | 0.9652 |
| 026_827_00308860 | Lung: NSCLC | NCI-H2085 | 827 | 456 | 4.711775 | 0.79 | 0.823 | 0.87 | 0.9311 | 0.924 | 1.007 | 0.967 | 1.0124 | 1.1093 |
| 026_859_00311090 | Lung: NSCLC | HCC-827 | 859 | 456 | 4.735253 | 0.737 | 0.86 | 0.852 | 0.7863 | 0.8298 | 0.853 | 1.0366 | 1.1949 | 0.9783 |
| 026_886_00296261 | Lung: NSCLC | EBC-1 | 886 | 456 | 4.744821 | 0.761 | 0.848 | 0.884 | 0.9053 | 0.9307 | 0.969 | 0.9903 | 0.9432 | 1.0947 |
| 026_8132_00308130 | Lung: NSCLC | NCI-H2126 | 8132 | 456 | 4.781635 | 0.749 | 0.796 | 0.839 | 0.8331 | 0.8916 | 0.939 | 0.9049 | 0.9661 | 0.9286 |
| 026_793_00299711 | Lung: NSCLC | NCI-H1781 | 793 | 456 | 4.904802 | 0.775 | 0.801 | 0.686 | 0.7429 | 0.7804 | 0.897 | 0.9136 | 0.9608 | 1.0112 |
| 026_1247_00314271 | Lung: NSCLC | NCI-H2291 | 1247 | 456 | 4.945975 | 0.773 | 0.893 | 0.836 | 0.831 | 0.851 | 1.029 | 1.0615 | 0.9828 | 1.0493 |
| 026_860_00304400 | Lung: NSCLC | LCLC-103H | 860 | 456 | 4.97209 | 0.751 | 0.819 | 0.803 | 0.8985 | 0.8725 | 0.898 | 0.9606 | 0.9519 | 1.061 |
| 026_806_00300270 | Lung: NSCLC | NCI-H647 | 806 | 456 | 5.044917 | 0.792 | 0.845 | 0.882 | 0.8698 | 0.8856 | 0.881 | 1.0769 | 0.9333 | 1.0648 |
| 026_877_00300630 | Lung: NSCLC | PC-3 [JPC-3] | 877 | 456 | 5.056812 | 0.847 | 0.832 | 0.968 | 0.9943 | 1.0985 | 1.01 | 1.0152 | 1.0063 | 1.1608 |
| 026_753_00298460 | Lung: NSCLC | NCI-H460 | 753 | 456 | 5.061076 | 0.839 | 0.888 | 0.945 | 0.9015 | 1.041 | 1.039 | 1.021 | 0.9905 | 1.0126 |
| 026_844_00295461 | Lung: NSCLC | SW 1573 | 844 | 456 | 5.077077 | 0.798 | 0.834 | 0.833 | 0.8824 | 0.8946 | 0.971 | 1.0223 | 0.9943 | 1.0074 |
| 026_8088_00314320 | Lung: NSCLC | KNS-62 | 8088 | 456 | 5.130485 | 0.86 | 0.847 | 0.879 | 0.9874 | 0.9738 | 1.047 | 1.0602 | 1.0303 | 0.9876 |
| 026_848_00300641 | Lung: NSCLC | SK-LU-1 | 848 | 456 | 5.2771 | 0.811 | 0.91 | 0.946 | 0.9174 | 0.9429 | 0.922 | 0.9544 | 1.0372 | 1.0115 |
| 026_864_00304961 | Lung: NSCLC | COR-L 105 | 864 | 456 | 5.319498 | 0.718 | 0.78 | 0.762 | 0.8018 | 0.7683 | 0.837 | 0.9721 | 0.8644 | 0.9527 |
| 026_677_00298361 | Lung: NSCLC | A549 | 677 | 456 | 5.414187 | 0.763 | 0.799 | 0.843 | 0.8595 | 0.9001 | 0.919 | 0.9405 | 0.9783 | 0.996 |
| 026_8207_00304810 | Lung: NSCLC | LC-1F | 8207 | 456 | 5.423228 | 0.825 | 0.794 | 0.845 | 0.8457 | 0.8483 | 0.976 | 0.8421 | 0.8626 | 0.9602 |

TABLE 22-continued

| Barcode | Organ | Cell Line | Cell ID | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| | | | | | | | | | Viability ratio | | | | | |
| 026_833_00299790 | Lung: NSCLC | NCI-H2342 | 833 | 456 | 5.548934 | 0.856 | 0.888 | 0.917 | 0.9241 | 0.9293 | 1.015 | 0.9449 | 1.0616 | 0.9624 |
| 026_870_00299801 | Lung: NSCLC | RERF-LC-KJ | 870 | 456 | 5.685511 | 0.892 | 0.96 | 0.999 | 0.9623 | 1.0469 | 1.054 | 1.0305 | 1.0128 | 1.0476 |
| 026_845_00311341 | Lung: NSCLC | NCI-H1838 | 845 | 456 | 5.711103 | 0.847 | 0.867 | 0.909 | 0.9088 | 0.9208 | 0.932 | 0.9775 | 0.9857 | 0.9755 |
| 026_8103_00306210 | Lung: NSCLC | LC-2-ad | 8103 | 456 | 5.718708 | 0.836 | 0.96 | 1.004 | 0.9427 | 1.0257 | 1.064 | 1.0682 | 0.9834 | 1.007 |
| 026_794_00300601 | Lung: NSCLC | NCI-H1792 | 794 | 456 | 5.721238 | 0.339 | 0.904 | 0.992 | 0.9248 | 0.9615 | 1.005 | 0.9405 | 0.9595 | 1.0225 |
| 026_890_00300220 | Lung: NSCLC | H3255 | 890 | 456 | 5.722728 | 0.903 | 0.862 | 0.844 | 0.9926 | 1.005 | 0.998 | 1.1503 | 1.1306 | 1.1501 |
| 026_862_00304820 | Lung: NSCLC | LOU-NH91 | 862 | 456 | 5.738178 | 0.886 | 0.864 | 0.837 | 0.9386 | 0.9258 | 0.887 | 0.948 | 1.1306 | 1.1752 |
| 026_812_00298410 | Lung: NSCLC | NCI-H1437 | 812 | 456 | 5.791603 | 0.894 | 0.946 | 0.993 | 0.9231 | 0.9704 | 1.003 | 1.0591 | 1.0561 | 1.0361 |
| 026_862_00316560 | Lung: NSCLC | LOU-NH91 | 862 | 456 | 5.867157 | 0.871 | 0.905 | 0.923 | 0.9415 | 0.9143 | 0.955 | 0.9491 | 1.0305 | 0.9923 |
| 026_857_00296270 | Lung: NSCLC | HCC-44 | 857 | 456 | 5.930045 | 0.904 | 0.868 | 0.893 | 0.9249 | 0.9348 | 0.956 | 1.0259 | 0.9721 | 1.0027 |
| 026_679_00296240 | Lung: NSCLC | ChaGo-K-1 | 679 | 456 | 5.965866 | 0.878 | 0.915 | 0.949 | 0.8968 | 0.942 | 0.953 | 0.9732 | 0.9727 | 1.0338 |
| 026_791_00298421 | Lung: NSCLC | NCI-H1650 | 791 | 456 | 5.971987 | 0.888 | 0.896 | 0.979 | 0.9429 | 0.9543 | 0.921 | 0.9516 | 0.9711 | 0.9966 |
| 026_864_00311551 | Lung: NSCLC | COR-L 105 | 864 | 456 | 5.975297 | 0.765 | 0.838 | 0.843 | 0.8384 | 0.8225 | 0.848 | 0.8917 | 0.9551 | 0.9811 |
| 026_846_00300620 | Lung: NSCLC | NCI-H2030 | 846 | 456 | 6.014339 | 0.886 | 0.979 | 0.985 | 0.9316 | 1.0238 | 0.925 | 0.9778 | 0.8749 | 0.9904 |
| 026_841_00296291 | Lung: NSCLC | NCI-H2170 | 841 | 456 | 6.01763 | 0.897 | 0.938 | 0.928 | 0.9356 | 0.9557 | 0.955 | 1.0968 | 1.056 | 1.0963 |
| 026_813_00308231 | Lung: NSCLC | NCI-H1563 | 813 | 456 | 6.06364 | 0.856 | 0.979 | 0.977 | 0.9369 | 0.9242 | 0.912 | 0.8859 | 0.9059 | 0.8856 |
| 026_816_00295860 | Lung: NSCLC | NCI-H1651 | 816 | 456 | 6.160326 | 0.864 | 1.039 | 1.026 | 1.008 | 1.0776 | 0.871 | 1.0553 | 1.0199 | 0.9978 |
| 026_818_00308241 | Lung: NSCLC | NCI-H1703 | 818 | 456 | 6.172519 | 0.946 | 0.829 | 0.858 | 0.9042 | 0.9197 | 0.887 | 0.9097 | 0.9729 | 0.9634 |
| 026_808_00296300 | Lung: NSCLC | NCI-H1838 | 808 | 456 | 6.172929 | 0.922 | 0.941 | 0.955 | 1.022 | 0.964 | 1.043 | 1.0358 | 1.0134 | 1.0658 |
| 026_855_00302330 | Lung: NSCLC | HCC-15 | 855 | 456 | 6.195295 | 0.868 | 0.911 | 0.901 | 0.8895 | 0.9071 | 0.95 | 0.9608 | 1.0091 | 1.0383 |
| 026_803_00298470 | Lung: NSCLC | NCI-H522 | 803 | 456 | 6.200929 | 0.878 | 0.933 | 0.953 | 0.8695 | 0.9015 | 0.833 | 0.8882 | 0.8789 | 1.1066 |
| 026_832_00303110 | Lung: NSCLC | NCI-H2228 | 832 | 456 | 6.240586 | 0.908 | 0.872 | 0.907 | 0.9005 | 0.9724 | 0.974 | 0.9776 | 0.9706 | 0.968 |
| 026_874_00308171 | Lung: NSCLC | RERF-LC-Sq1 | 874 | 456 | 6.282697 | 1.064 | 0.854 | 0.829 | 0.8009 | 0.8914 | 0.925 | 0.8612 | 0.9931 | 0.9393 |
| 026_879_00308101 | Lung: NSCLC | LU99A | 879 | 456 | 6.327465 | 0.881 | 0.987 | 0.995 | 1.0199 | 0.9725 | 0.948 | 0.9588 | 0.9756 | 0.9692 |
| 026_856_00299760 | Lung: NSCLC | HCC-366 | 856 | 456 | 6.328052 | 0.936 | 0.943 | 0.959 | 1.0286 | 0.9991 | 1.002 | 1.0072 | 1.0077 | 1.0015 |
| 026_798_00304790 | Lung: NSCLC | Calu-3 | 798 | 456 | 6.338698 | 0.926 | 0.986 | 0.869 | 0.9635 | 1.0683 | 1.166 | 1.1053 | 1.1123 | 1.1003 |
| 026_825_00308250 | Lung: NSCLC | NCI-H2023 | 825 | 456 | 6.435057 | 0.938 | 0.885 | 0.929 | 0.961 | 0.9166 | 0.959 | 0.9502 | 0.9835 | 0.9846 |
| 026_8072_00306200 | Lung: NSCLC | HOP-62 | 8072 | 456 | 6.481774 | 0.973 | 0.958 | 0.931 | 0.9405 | 0.9799 | 0.901 | 1.0374 | 0.9717 | 1.1512 |
| 026_843_00296331 | Lung: NSCLC | SK-MES-1 | 843 | 456 | 6.499026 | 0.91 | 0.99 | 0.934 | 0.9509 | 0.9694 | 1.003 | 0.9804 | 0.9674 | 1.0295 |
| 026_1251_00318710 | Lung: NSCLC | NCI-H835 | 1251 | 456 | 6.684349 | 0.964 | 1.054 | 0.854 | 0.9853 | 0.77 | 0.963 | 0.8714 | 0.9637 | 1.1416 |
| 026_816_00302370 | Lung: NSCLC | NCI-H1651 | 816 | 456 | 6.769433 | 0.903 | 1.072 | 1.021 | 1.002 | 1.0583 | 0.94 | 1.0664 | 1.0462 | 1.0774 |
| 026_801_00295941 | Lung: NSCLC | NCI-H1299 | 801 | 456 | 6.808075 | 1.036 | 0.898 | 0.912 | 0.9194 | 0.9832 | 0.955 | 1.0252 | 0.9946 | 1.085 |
| 026_850_00311050 | Lung: NSCLC | 201T | 850 | 456 | 6.874432 | 0.942 | 0.957 | 0.988 | 0.989 | 0.9596 | 0.985 | 0.9759 | 0.9839 | 0.9726 |
| 026_818_00309001 | Lung: NSCLC | NCI-H1703 | 818 | 456 | 7.192409 | 0.889 | 0.857 | 0.855 | 0.8355 | 0.8207 | 0.856 | 0.8191 | 0.9124 | 0.9468 |
| 026_1247_00304851 | Lung: NSCLC | NCI-H2291 | 1247 | 456 | 7.252153 | 1.162 | 1.047 | 0.877 | 1.034 | 0.8759 | 0.6949 | 1.2149 | 1.0391 | 1.1021 |
| 026_819_00306250 | Lung: NSCLC | NCI-H1734 | 819 | 456 | 7.342705 | 1.046 | 1.007 | 1.012 | 1.018 | 0.9902 | 0.945 | 0.9742 | 0.9718 | 1.0221 |
| 026_821_00306261 | Lung: NSCLC | NCI-H1793 | 821 | 456 | 7.345651 | 1.015 | 1.1 | 1.058 | 1.0171 | 1.0121 | 1.065 | 10.342 | 1.0776 | 1.0468 |
| 026_798_00308080 | Lung: NSCLC | Calu-3 | 798 | 456 | 7.389624 | 1.032 | 1.058 | 0.914 | 0.9927 | 1.0342 | 1.004 | 1.0095 | 0.9327 | 0.938 |
| 026_678_00308181 | Lung: NSCLC | UMC-11 | 678 | 456 | 7.458364 | 1.03 | 1.076 | 1.054 | 1.0958 | 1.0021 | 1.03 | 1.0784 | 1.0779 | 1.0688 |
| 026_797_00308730 | Lung: NSCLC | NCI-H596 | 797 | 456 | 7.556662 | 1.124 | 1 | 0.92 | 0.9992 | 0.9285 | 0.936 | 0.911 | 1.0276 | 0.8862 |
| 026_790_00306231 | Lung: NSCLC | NCI-H1573 | 790 | 456 | 7.606756 | 1.049 | 1.064 | 1.054 | 1.0146 | 1.0291 | 0.99 | 1.0304 | 1.0221 | 1.0512 |
| 026_752_00306191 | Lung: NSCLC | A-427 | 752 | 456 | 7.608444 | 1.109 | 0.988 | 1.054 | 1.0224 | 0.9429 | 1.084 | 1.0956 | 1.0273 | 1.0528 |
| 026_845_00306271 | Lung: NSCLC | NCI-H1838 | 845 | 456 | 7.666847 | 1.074 | 1.08 | 1.064 | 1.0779 | 1.0805 | 1.046 | 1.0674 | 0.9941 | 1.02 |
| 026_8133_00306280 | Lung: NSCLC | NCI-H322M | 8133 | 456 | 7.713112 | 1.158 | 1.06 | 1.135 | 1.1499 | 1.1305 | 1.103 | 1.1464 | 1.1475 | 1.0913 |
| 026_8130_00306220 | Lung: NSCLC | NCI-H1355 | 8130 | 456 | 7.765888 | 1.12 | 1.188 | 1.002 | 0.9001 | 0.8103 | 1.095 | 0.9608 | 0.9714 | 0.9997 |
| 026_683_00306241 | Lung: NSCLC | NCI-H1581 | 683 | 456 | 7.774034 | 1.163 | 1.024 | 0.949 | 1.0959 | 1.0605 | 1.114 | 1.0118 | 0.9537 | 0.9212 |
| 026_792_00306140 | Lung: NSCLC | NCI-H1666 | 792 | 456 | 7.825548 | 1.136 | 1.069 | 1.132 | 1.0901 | 1.0688 | 1.097 | 1.0684 | 1.0463 | 1.1115 |
| 026_840_00306151 | Lung: NSCLC | NCI-H441 | 840 | 456 | 7.946249 | 1.088 | 1.059 | 1.052 | 1.0622 | 1.0476 | 1.049 | 1.0439 | 1.045 | 1.0714 |

TABLE 22-continued

| Barcode | Organ | Cell ID | Cell Line | Compound No | Fitted MGH_IC50 | Viability ratio | | | | | | | | |
|---|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_8075_00306131 | Lung: NSCLC | 8075 | IA-LM | 456 | 7.984543 | 1.046 | 1.042 | 1.043 | 1.0424 | 1.0323 | 1.048 | 1.0441 | 1.0279 | 1.0694 |
| 026_61_00285570 | Lymphoma | 61 | JSC-1 | 456 | 0.316646 | 0.313 | 0.329 | 0.341 | 0.3908 | 0.5654 | 0.63 | 0.724 | 0.8346 | 0.8527 |
| 026_8222_00291350 | Lymphoma | 8222 | H9 | 456 | 0.402947 | 0.102 | 0.284 | 0.272 | 0.3996 | 0.5762 | 0.732 | 0.8412 | 0.8346 | 0.8529 |
| 026_140_00291320 | Lymphoma | 140 | A3/KAW | 456 | 0.717935 | 0.185 | 0.296 | 0.408 | 0.4762 | 0.5561 | 0.736 | 0.8297 | 0.8761 | 0.8425 |
| 026_237_00291380 | Lymphoma | 237 | SU-DHL-16 | 456 | 0.982467 | 0.155 | 0.278 | 0.405 | 0.5737 | 0.6759 | 0.816 | 0.9129 | 0.9363 | 0.9318 |
| 026_220_00288720 | Lymphoma | 220 | OCI-LY-19 | 456 | 1.28484 | 0.324 | 0.393 | 0.455 | 0.5338 | 0.6443 | 0.826 | 0.9343 | 0.9969 | 0.9969 |
| 026_257_00285640 | Lymphoma | 257 | WIL2 NS | 456 | 1.523653 | 0.32 | 0.456 | 0.509 | 0.6199 | 0.6926 | 0.771 | 0.8518 | 0.9524 | 1.073 |
| 026_239_00288750 | Lymphoma | 239 | SU-DHL-5 | 456 | 1.616577 | 0.174 | 0.577 | 0.461 | 0.7856 | 0.7368 | 0.845 | 0.9512 | 0.9535 | 0.934 |
| 026_124_00287850 | Lymphoma | 124 | BC-1 | 456 | 1.816766 | 0.239 | 0.53 | 0.6 | 0.6778 | 0.8612 | 0.946 | 0.9754 | 0.9846 | 1.2005 |
| 026_104_00287960 | Lymphoma | 104 | TUR | 456 | 2.217781 | 0.396 | 0.51 | 0.597 | 0.7468 | 0.9062 | 0.94 | 0.9822 | 0.9761 | 1.0038 |
| 026_8199_00291330 | Lymphoma | 8199 | CTB-1 | 456 | 2.341488 | 0.445 | 0.509 | 0.654 | 0.6993 | 0.7792 | 0.767 | 0.8214 | 0.8543 | 1.0165 |
| 026_69_00283480 | Lymphoma | 69 | CA46 | 456 | 2.43077 | 0.358 | 0.6 | 0.775 | 0.78 | 0.8817 | 0.896 | 0.9912 | 0.9446 | 0.9676 |
| 026_112_00285620 | Lymphoma | 112 | SR | 456 | 2.466522 | 0.224 | 0.573 | 0.653 | 0.7668 | 0.8482 | 0.866 | 0.9087 | 0.9409 | 0.9358 |
| 026_241_00288760 | Lymphoma | 241 | SU-DHL-8 | 456 | 2.509783 | 0.398 | 0.583 | 0.743 | 0.8249 | 0.935 | 0.956 | 1.0439 | 0.9903 | 0.9255 |
| 026_255_00285610 | Lymphoma | 255 | Sci-1 | 456 | 2.705483 | 0.445 | 0.61 | 0.788 | 0.9473 | 0.9153 | 1.003 | 0.9035 | 0.8642 | 1.0527 |
| 026_62_00293930 | Lymphoma | 62 | IM-9 | 456 | 2.809638 | 0.572 | 0.562 | 0.594 | 0.6839 | 0.7773 | 1.18 | 0.876 | 1.0089 | 0.8757 |
| 026_93_00287880 | Lymphoma | 93 | HH | 456 | 2.828886 | 0.523 | 0.575 | 0.731 | 0.804 | 0.9283 | 0.948 | 0.9965 | 0.999 | 1.0329 |
| 026_216_00290710 | Lymphoma | 216 | NU-DUL-1 | 456 | 2.880782 | 0.459 | 0.664 | 0.767 | 0.8093 | 0.7784 | 0.884 | 0.9338 | 0.9363 | 1.0069 |
| 026_123_00287860 | Lymphoma | 123 | BC-3 | 456 | 2.893681 | 0.495 | 0.678 | 0.776 | 0.9051 | 1.0108 | 1.003 | 1.0056 | 0.9841 | 0.9519 |
| 026_113_00288520 | Lymphoma | 113 | DB | 456 | 2.901204 | 0.479 | 0.705 | 0.868 | 0.9097 | 0.9559 | 0.984 | 1.0104 | 0.992 | 0.9941 |
| 026_8035_00303290 | Lymphoma | 8035 | DOHH-2 | 456 | 2.927461 | 0.508 | 0.78 | 0.831 | 0.8009 | 0.9998 | 0.997 | 1.0295 | 0.9393 | 1.0316 |
| 026_240_00300290 | Lymphoma | 240 | SU-DHL-6 | 456 | 2.933827 | 0.208 | 0.663 | 0.733 | 0.7473 | 0.7814 | 0.839 | 0.8554 | 0.9327 | 1.0203 |
| 026_248_00285630 | Lymphoma | 248 | VAL | 456 | 2.964017 | 0.528 | 0.639 | 0.739 | 0.9112 | 0.9265 | 0.96 | 1.0023 | 0.9827 | 1.029 |
| 026_162_00290790 | Lymphoma | 162 | HDLM-2 | 456 | 2.980685 | 0.56 | 0.811 | 0.678 | 0.7341 | 0.7627 | 0.782 | 0.7915 | 0.9638 | 0.9859 |
| 026_105_00287940 | Lymphoma | 105 | RPMI 6666 | 456 | 3.064381 | 0.516 | 0.701 | 0.691 | 0.7257 | 0.8234 | 0.904 | 0.9883 | 1.0013 | 0.7387 |
| 026_240_00302920 | Lymphoma | 240 | SU-DHL-6 | 456 | 3.114948 | 0.326 | 0.629 | 0.741 | 0.7802 | 0.8119 | 0.831 | 0.9347 | 0.921 | 1.033 |
| 026_163_00287730 | Lymphoma | 163 | HD-MY-Z | 456 | 3.123344 | 0.582 | 0.606 | 0.654 | 0.6825 | 0.785 | 0.896 | 0.9395 | 0.98 | 0.9838 |
| 026_139_00283530 | Lymphoma | 139 | MC116 | 456 | 3.12577 | 0.085 | 0.686 | 0.917 | 0.9565 | 0.9611 | 0.99 | 0.9875 | 0.9789 | 1.0207 |
| 026_133_00293941 | Lymphoma | 133 | NK-92MI | 456 | 3.297366 | 0.637 | 0.637 | 0.757 | 0.8911 | 0.8633 | 1.136 | 1.0548 | 0.89 | 0.9559 |
| 026_282_00287750 | Lymphoma | 282 | P32/ISH | 456 | 3.328203 | 0.416 | 0.744 | 0.875 | 0.8947 | 0.8754 | 0.907 | 0.9959 | 0.9144 | 0.9001 |
| 026_80_00287950 | Lymphoma | 80 | ST486 | 456 | 3.520498 | 0.263 | 0.688 | 0.699 | 0.7969 | 0.8071 | 0.904 | 0.8902 | 0.9142 | 0.9277 |
| 026_73_00283500 | Lymphoma | 73 | EB-3 | 456 | 3.528971 | 0.566 | 0.739 | 0.806 | 0.8214 | 0.8547 | 1.09 | 0.8321 | 0.8619 | 1.017 |
| 026_60_00287891 | Lymphoma | 60 | JM1 | 456 | 3.618767 | 0.577 | 0.678 | 0.734 | 0.7932 | 0.8209 | 0.833 | 0.8444 | 0.8567 | 0.8548 |
| 026_185_00288820 | Lymphoma | 185 | L-540 | 456 | 3.666174 | 0.626 | 0.88 | 0.936 | 1.0302 | 1.0245 | 1.037 | 1.0524 | 1.0175 | 0.902 |
| 026_70_00283490 | Lymphoma | 70 | Daudi | 456 | 3.687192 | 0.603 | 0.789 | 0.925 | 0.8867 | 0.9929 | 0.987 | 0.8586 | 0.9555 | 1.0525 |
| 026_228_00291370 | Lymphoma | 228 | RC-K8 | 456 | 3.710403 | 0.605 | 0.678 | 0.732 | 0.7776 | 0.8387 | 0.943 | 0.9437 | 0.9368 | 0.8243 |
| 026_74_00285600 | Lymphoma | 74 | Raji | 456 | 3.736373 | 0.639 | 0.768 | 0.89 | 0.8258 | 0.9671 | 0.97 | 0.9444 | 0.9665 | 0.9149 |
| 026_173_00288920 | Lymphoma | 173 | KARPAS-422 | 456 | 3.812903 | 0.638 | 0.787 | 0.876 | 0.8937 | 0.8652 | 0.959 | 0.9976 | 0.9896 | 1.046 |
| 026_125_00287910 | Lymphoma | 125 | MC/CAR | 456 | 3.860302 | 0.687 | 0.792 | 0.873 | 0.8871 | 1.009 | 1.011 | 0.9976 | 0.987 | 1.005 |
| 026_280_00285420 | Lymphoma | 280 | SCC-3 | 456 | 3.903427 | 0.648 | 0.86 | 0.895 | 0.9301 | 0.9335 | 0.934 | 1.0707 | 0.9 | 1.0162 |
| 026_242_00288770 | Lymphoma | 242 | SUP-HD1 | 456 | 4.023177 | 0.671 | 0.815 | 0.875 | 0.8573 | 0.8914 | 0.965 | 1.0137 | 0.9754 | 0.9445 |
| 026_160_00285410 | Lymphoma | 160 | GRANTA-519 | 456 | 4.112789 | 0.631 | 0.706 | 0.761 | 0.7798 | 0.7991 | 0.771 | 0.9167 | 0.9366 | 1.1043 |
| 026_144_00287710 | Lymphoma | 144 | BL-41 | 456 | 4.441898 | 0.536 | 1.076 | 0.941 | 0.9045 | 0.8922 | 0.893 | 0.9542 | 0.9696 | 0.9971 |
| 026_184_00290800 | Lymphoma | 184 | L-428 | 456 | 4.489131 | 0.614 | 0.705 | 0.723 | 0.7315 | 0.7351 | 0.721 | 1.0011 | 0.7501 | 1.0289 |
| 026_128_00290690 | Lymphoma | 128 | Farage | 456 | 4.585156 | 0.766 | 0.834 | 0.861 | 0.8151 | 0.9324 | 0.908 | 1.3723 | 1.1697 | 0.8687 |
| 026_250_00285660 | Lymphoma | 250 | WSU-NHL | 456 | 4.693667 | 0.719 | 0.765 | 0.866 | 0.8242 | 0.9178 | 0.947 | 0.9725 | 0.9585 | 1.2229 |
| 026_182_00290700 | Lymphoma | 182 | L-1236 | 456 | 4.714251 | 0.76 | 0.859 | 0.875 | 0.8522 | 0.9702 | 0.962 | 1.0483 | 0.9432 | 0.9714 |
| 026_95_00283510 | Lymphoma | 95 | HT | 456 | 4.721481 | 0.719 | 0.842 | 0.88 | 0.8266 | 0.8534 | 0.902 | 1.0348 | 0.9564 | 1.3018 |
| | | | | | | | | | | | | | | 0.966 |

TABLE 22-continued

| Barcode | Organ | Cell ID | Cell Line | Compound No | Fitted MGH_IC50 | Viability ratio | | | | | | | | |
|---|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_264_00288840 | Lymphoma | 264 | TK | 456 | 4.750226 | 0.794 | 0.966 | 0.936 | 0.9709 | 1.0212 | 1.024 | 1.0348 | 1.0318 | 1.0681 |
| 026_266_00287760 | Lymphoma | 266 | SLVL | 456 | 4.90866 | 0.731 | 0.786 | 0.794 | 0.8012 | 0.8742 | 0.873 | 0.9435 | 0.9199 | 0.977 |
| 026_75_00282830 | Lymphoma | 75 | Jiyoye | 456 | 4.937844 | 0.801 | 0.99 | 0.974 | 1.0523 | 1.196 | 1.107 | 1.0641 | 1.1044 | 1.0749 |
| 026_111_00291360 | Lymphoma | 111 | Hs 445 | 456 | 5.022248 | 0.704 | 0.734 | 0.703 | 0.794 | 0.7451 | 0.779 | 0.8243 | 0.8675 | 0.946 |
| 026_8151_00288540 | Lymphoma | 8151 | Ramos-2G6-4C10 | 456 | 5.147746 | 0.242 | 0.868 | 0.954 | 0.9827 | 1.022 | 0.974 | 0.9967 | 0.9674 | 1.0529 |
| 026_156_00287720 | Lymphoma | 156 | DG-75 | 456 | 5.222394 | 0.834 | 1.001 | 1.03 | 1.0349 | 0.9848 | 0.996 | 1.012 | 0.9965 | 0.9857 |
| 026_243_00296620 | Lymphoma | 243 | SUP-M2 | 456 | 5.25553 | 0.648 | 0.88 | 0.96 | 0.9351 | 0.9518 | 0.968 | 0.9742 | 0.9627 | 0.9659 |
| 026_86_00287870 | Lymphoma | 86 | EB2 | 456 | 5.287284 | 0.86 | 1.017 | 1.01 | 1.0356 | 1.0217 | 1.05 | 1.0267 | 1.0118 | 1.0227 |
| 026_162_00288790 | Lymphoma | 162 | HDLM-2 | 456 | 5.425219 | 0.877 | 0.903 | 0.797 | 0.9228 | 1.0293 | 1.043 | 1.0157 | 1.0517 | 1.0837 |
| 026_172_00287740 | Lymphoma | 172 | KARPAS-299 | 456 | 5.433687 | 0.832 | 0.891 | 0.95 | 0.9494 | 0.955 | 0.954 | 0.9499 | 0.9633 | 0.9487 |
| 026_235_00285430 | Lymphoma | 235 | SU-DHL-1 | 456 | 6.401484 | 0.885 | 0.997 | 0.987 | 0.9424 | 0.9387 | 0.884 | 0.8642 | 0.9464 | 0.9439 |
| 026_143_00288690 | Lymphoma | 143 | AMO-1 | 456 | 6.692908 | 0.924 | 1.025 | 1.129 | 1.034 | 1.1112 | 1.034 | 1.0278 | 1.0136 | 1.0255 |
| 026_193_00288830 | Lymphoma | 193 | MHH-PREB-1 | 456 | 6.799634 | 0.622 | 0.958 | 1.012 | 1.0149 | 1.0368 | 1.025 | 1.0064 | 0.9803 | 0.989 |
| 026_236_00285650 | Lymphoma | 236 | SU-DHL-10 | 456 | 6.99662 | 0.175 | 0.993 | 1.05 | 1.0763 | 1.0476 | 1.029 | 1.0509 | 1.0397 | 1.0494 |
| 026_238_00288740 | Lymphoma | 238 | GA-10 | 456 | 7.031749 | 0.608 | 1.003 | 1.009 | 1.1142 | 1.0869 | 1.071 | 0.9837 | 1.0247 | 1.0207 |
| 026_81_00288530 | Lymphoma | 81 | YT | 456 | 7.411746 | 0.64 | 0.986 | 1.008 | 1.1031 | 1.0252 | 1.029 | 1.0113 | 1.018 | 1.0848 |
| 026_251_00287840 | Lymphoma | 251 | KM-H2 | 456 | 7.739504 | 1.008 | 1.009 | 0.976 | 1.0201 | 1.0204 | 1.021 | 1.0236 | 1.0077 | 1.0079 |
| 026_178_00287840 | Lymphoma | 178 | WSU-DLCL2 | 456 | 8.212885 | 1.047 | 0.617 | 0.642 | 1.0197 | 1.0404 | 1.022 | 1.0267 | 0.9848 | 1.1375 |
| 026_249_00285650 | Lymphoma | 249 | SU-DHL-4 | 456 | 8.647656 | 1.061 | 1.226 | 0.719 | 0.6508 | 1.0869 | 1.036 | 1.0412 | 1.0156 | 1.0276 |
| 026_131_00287930 | Lymphoma | 131 | RL | 456 | 8.679308 | 1.124 | 1.077 | 1.045 | 0.7459 | 1.0384 | 1.071 | 0.9837 | 1.0247 | 1.0224 |
| 026_915_00269070 | Miscellaneous | 915 | Hs 633T | 456 | 1.797943 | 0.344 | 1.094 | 1.048 | 1.0257 | 1.0252 | 1.029 | 1.0236 | 1.018 | 1.0204 |
| 026_911_00269060 | Miscellaneous | 911 | GCT | 456 | 2.424125 | 0.433 | 0.532 | 0.607 | 1.024 | 1.1204 | 1.012 | 1.0293 | 0.9824 | 1.0061 |
| 026_8172_00269460 | Miscellaneous | 8172 | SW872 | 456 | 3.196746 | 0.511 | 0.617 | 0.642 | 0.6061 | 0.6357 | 0.736 | 0.8936 | 0.9346 | 1.1375 |
| 026_913_00271970 | Miscellaneous | 913 | JAR | 456 | 3.876744 | 0.685 | 0.716 | 0.719 | 0.6508 | 0.655 | 0.804 | 0.7763 | 0.9066 | 0.9967 |
| 026_8194_00271980 | Miscellaneous | 8194 | JEG-3 | 456 | 3.901223 | 0.623 | 0.695 | 0.794 | 0.7459 | 0.8264 | 0.881 | 0.9107 | 0.9313 | 1.0224 |
| 026_8171_00274180 | Miscellaneous | 8171 | SW684 | 456 | 3.978538 | 0.693 | 0.808 | 0.876 | 0.851 | 0.9936 | 1.011 | 0.9013 | 1.0881 | 1.0491 |
| 026_8112_00269450 | Miscellaneous | 8112 | MFH-ino | 456 | 4.013788 | 0.691 | 0.91 | 0.98 | 0.9097 | 0.9037 | 0.874 | 0.9014 | 0.943 | 1.1354 |
| 026_916_00271320 | Miscellaneous | 916 | HT 1080 | 456 | 4.254215 | 0.695 | 0.674 | 0.795 | 1.1114 | 1.0275 | 1.032 | 0.9881 | 0.9218 | 1.0725 |
| 026_8004_00271280 | Miscellaneous | 8004 | A388 | 456 | 4.494172 | 0.743 | 0.804 | 0.766 | 0.8068 | 0.8378 | 0.91 | 0.9824 | 1.0389 | 1.0625 |
| 026_8112_00271340 | Miscellaneous | 8112 | MFH-ino | 456 | 4.624376 | 0.721 | 0.793 | 0.841 | 0.7943 | 0.8276 | 0.873 | 1.1135 | 1.1006 | 1.1093 |
| 026_8004_00269400 | Miscellaneous | 8004 | A388 | 456 | 4.778414 | 0.747 | 0.732 | 0.741 | 0.8441 | 0.8899 | 0.888 | 1.1408 | 0.925 | 1.1327 |
| 026_8192_00269470 | Miscellaneous | 8192 | VA-ES-BJ | 456 | 4.956405 | 0.78 | 0.764 | 0.776 | 0.7501 | 0.7753 | 0.799 | 1.017 | 0.9044 | 1.0866 |
| 026_8194_00269440 | Miscellaneous | 8194 | JEG-3 | 456 | 5.058221 | 0.786 | 0.867 | 0.874 | 0.8164 | 0.8628 | 0.861 | 0.9217 | 0.8924 | 1.0697 |
| 026_913_00269430 | Miscellaneous | 913 | JAR | 456 | 5.170211 | 0.816 | 0.87 | 1.048 | 0.984 | 0.9192 | 0.889 | 0.9737 | 1.0227 | 1.0186 |
| 026_916_00269420 | Miscellaneous | 916 | HT 1080 | 456 | 5.302771 | 0.831 | 0.891 | 0.849 | 0.908 | 0.8876 | 0.984 | 0.8804 | 1.0294 | 1.0609 |
| 026_8175_00269140 | Miscellaneous | 8175 | SW982 | 456 | 5.586364 | 0.832 | 0.904 | 0.904 | 0.8709 | 0.8661 | 0.88 | 1.0502 | 1.0585 | 1.0591 |
| 026_1225_00269660 | Muscle | 1225 | RD | 456 | 2.694207 | 0.612 | 0.968 | 0.988 | 0.9053 | 0.9327 | 0.978 | 0.9465 | 1.1023 | 1.1108 |
| 26_135_00271680 | Muscle | 135 | SJCRH30 | 456 | 2.740947 | 0.247 | 0.595 | 0.602 | 1.1946 | 1.0638 | 1.017 | 1.0728 | 1.1006 | 1.2781 |
| 026_924_00269640 | Muscle | 924 | A673 | 456 | 2.779569 | 0.563 | 0.61 | 0.713 | 0.575 | 0.6051 | 0.678 | 0.8404 | 0.9183 | 0.947 |
| 26_562_00271660 | Muscle | 562 | KYM-1 | 456 | 2.818237 | 0.433 | 0.554 | 0.607 | 0.8654 | 0.8633 | 0.854 | 0.9433 | 0.9991 | 1.105 |
| 026_135_00271410 | Muscle | 135 | SJCRH30 | 456 | 3.059385 | 0.345 | 0.665 | 0.727 | 0.6884 | 0.7085 | 0.808 | 0.8122 | 0.8796 | 0.9437 |
| 026_923_00269680 | Muscle | 923 | RH-41 | 456 | 3.133389 | 0.309 | 0.672 | 0.79 | 0.7663 | 0.7943 | 0.835 | 0.9132 | 0.9948 | 0.9596 |
| 026_562_00270060 | Muscle | 562 | KYM-1 | 456 | 3.396905 | 0.586 | 0.65 | 0.731 | 0.8395 | 0.8741 | 0.957 | 0.9768 | 1.032 | 1.1796 |
| 026_920_00270070 | Muscle | 920 | RH-1 | 456 | 3.433085 | 0.581 | 0.748 | 0.78 | 0.7895 | 0.6971 | 0.795 | 0.7303 | 0.9458 | 0.9325 |
| 026_135_00270070 | Muscle | 135 | SJCRH30 | 456 | 3.759361 | 0.326 | 0.772 | 0.846 | 0.8707 | 0.8698 | 0.955 | 1.0372 | 1.0323 | 1.0217 |
| 026_919_00269630 | Muscle | 919 | A-204 | 456 | 5.25605 | 0.778 | 0.727 | 0.825 | 0.9032 | 0.9238 | 0.951 | 0.9496 | 0.9615 | 0.9852 |
| 026_921_00285151 | Muscle | 921 | RH-18 | 456 | 5.863422 | 0.84 | 0.798 | 0.868 | 0.8737 | 0.9084 | 0.931 | 0.9701 | 0.9946 | 0.9435 |
| 026_8182_00293791 | Muscle | 8182 | TE-441-T | 456 | 6.133177 | 0.848 | 0.987 | 0.961 | 0.8744 | 0.861 | 0.89 | 0.9735 | 0.9392 | 0.9765 |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_369_00258500 | Nervous System | 369 | CHP-212 | 456 | -4.151196 | 0.165 | 0.184 | 0.183 | 0.1873 | 0.1985 | 0.219 | 0.2948 | 0.3285 | 0.4946 |
| 026_390_00262920 | Nervous System | 390 | NB69 | 456 | -1.3827 | 0.056 | 0.074 | 0.068 | 0.0948 | 0.096 | 0.163 | 0.4343 | 0.6938 | 0.8833 |
| 026_629_00316570 | Nervous System | 629 | NB(TU)1-10 | 456 | -0.654294 | 0.322 | 0.361 | 0.388 | 0.398 | 0.4347 | 0.594 | 0.7533 | 0.6321 | 0.6782 |
| 026_366_00257090 | Nervous System | 366 | BE(2)-M17 | 456 | -0.258429 | 0.204 | 0.352 | 0.333 | 0.3872 | 0.4128 | 0.547 | 0.6415 | 0.7687 | 0.9298 |
| 026_384_00314240 | Nervous System | 384 | MHH-NB-11 | 456 | 1.316182 | 0.368 | 0.42 | 0.48 | 0.6318 | 0.5903 | 0.783 | 0.7802 | 0.9243 | 0.5317 |
| 026_385_00314290 | Nervous System | 385 | SIMA | 456 | 1.359572 | 0.402 | 0.496 | 0.488 | 0.5135 | 0.6006 | 0.629 | 0.8787 | 0.8808 | 1.0864 |
| 026_630_00264810 | Nervous System | 630 | NH-12 | 456 | 1.516245 | 0.143 | 0.443 | 0.537 | 0.5763 | 0.6816 | 0.684 | 0.7263 | 0.9504 | 0.791 |
| 026_8124_00308720 | Nervous System | 8124 | NB14 | 456 | 1.784337 | 0.802 | 0.401 | 0.6 | 0.6379 | 0.6871 | 0.943 | 0.8827 | 0.8247 | 0.9343 |
| 026_639_00271120 | Nervous System | 639 | GOTO | 456 | 1.784838 | 0.174 | 0.52 | 0.54 | 0.6353 | 0.6485 | 0.726 | 0.9341 | 0.8908 | 1.1295 |
| 026_8094_00314230 | Nervous System | 8094 | LAN-6 | 456 | 1.824343 | 0.55 | 0.565 | 0.476 | 0.5734 | 0.6862 | 0.656 | 0.7893 | 0.9264 | 0.7016 |
| 026_8076_00260401 | Nervous System | 8076 | IMR-5 | 456 | 1.864038 | 0.346 | 0.489 | 0.575 | 1.2246 | 0.8619 | 0.823 | 1.0781 | 0.7607 | 0.8894 |
| 026_8127_00258950 | Nervous System | 8127 | NB5 | 456 | 2.106125 | 0.202 | 0.628 | 0.611 | 0.6823 | 0.725 | 0.845 | 0.9541 | 0.9703 | 1.0012 |
| 026_8124_00311130 | Nervous System | 8124 | NB14 | 456 | 2.216808 | 0.544 | 0.563 | 0.516 | 0.5711 | 0.5857 | 0.776 | 0.9014 | 0.9091 | 1.0395 |
| 026_8126_00264800 | Nervous System | 8126 | NB17 | 456 | 2.289546 | 0.347 | 0.54 | 0.684 | 0.7567 | 0.8851 | 0.929 | 0.8729 | 0.9752 | 0.9196 |
| 026_641_00308180 | Nervous System | 641 | TGW | 456 | 2.326645 | 0.456 | 0.502 | 0.593 | 0.7234 | 0.8006 | 0.88 | 0.9296 | 0.9651 | 0.9821 |
| 026_8121_00256290 | Nervous System | 8121 | NB10 | 456 | 2.356578 | 0.646 | 0.568 | 0.562 | 0.5835 | 0.6642 | 0.613 | 0.5487 | 0.6035 | 1.0005 |
| 026_8220_00308810 | Nervous System | 8220 | KP-N-YN | 456 | 2.470465 | 0.366 | 0.619 | 0.752 | 0.7815 | 0.7642 | 0.87 | 0.8457 | 0.8335 | 0.8942 |
| 026_8090_00263920 | Nervous System | 8090 | KP-N-YS | 456 | 2.547617 | 0.267 | 0.583 | 0.69 | 0.9135 | 0.905 | 0.924 | 0.9505 | 0.9232 | 1.012 |
| 026_363_00311110 | Nervous System | 363 | SK-N-FI | 456 | 2.667265 | 0.519 | 0.583 | 0.574 | 0.6332 | 0.5059 | 0.571 | 0.7766 | 0.6898 | 0.9188 |
| 026_382_00311110 | Nervous System | 382 | KELLY | 456 | 3.39659 | 0.518 | 0.757 | 0.767 | 0.7123 | 0.7538 | 0.883 | 0.8718 | 0.8733 | 0.9755 |
| 026_8064_00259120 | Nervous System | 8064 | GI-ME-N | 456 | 3.426922 | 0.582 | 0.763 | 0.78 | 0.8295 | 0.8371 | 0.955 | 1.0539 | 1.0652 | 1.104 |
| 026_8195_00318640 | Nervous System | 8195 | CHP-134 | 456 | 3.519288 | 0.6 | 0.8 | 0.86 | 0.909 | 0.9931 | 0.919 | 0.9533 | 0.941 | 1.0273 |
| 026_382_00308720 | Nervous System | 382 | KELLY | 456 | 3.678148 | 0.59 | 0.706 | 0.666 | 0.7413 | 0.8277 | 0.814 | 0.8335 | 0.8742 | 0.9843 |
| 026_8129_00256290 | Nervous System | 8129 | NB7 | 456 | 3.824042 | 0.644 | 0.861 | 0.945 | 0.972 | 0.9655 | 0.998 | 1.0941 | 1.0771 | 1.0471 |
| 026_8126_00280241 | Nervous System | 8126 | NB17 | 456 | 3.845261 | 0.611 | 0.771 | 0.746 | 1.0569 | 0.8567 | 0.864 | 0.9408 | 0.9041 | 0.972 |
| 026_8007_00252850 | Nervous System | 8007 | ACN | 456 | 3.989797 | 0.411 | 0.72 | 0.821 | 0.7359 | 0.7717 | 0.797 | 0.8528 | 0.9564 | 0.9564 |
| 026_8122_00273460 | Nervous System | 8122 | NB12 | 456 | 4.358880 | 0.15 | 0.809 | 0.911 | 0.9912 | 0.9113 | 1.021 | 0.9055 | 0.8723 | 1.0083 |
| 026_8226_00252530 | Nervous System | 8226 | NBsusSR | 456 | 4.365592 | 1.14 | 0.81 | 0.878 | 0.6567 | 0.6737 | 0.94 | 0.7615 | 0.8399 | 1.1136 |
| 026_8064_00256670 | Nervous System | 8064 | GI-ME-N | 456 | 4.809816 | 0.398 | 0.871 | 0.839 | 0.9402 | 0.8757 | 0.96 | 0.9284 | 0.9838 | 1.0451 |
| 026_8128_00257200 | Nervous System | 8128 | NB6 | 456 | 4.886145 | 0.836 | 0.93 | 0.956 | 1.0121 | 0.9926 | 1.008 | 0.9893 | 0.9944 | 0.9472 |
| 026_8123_00256300 | Nervous System | 8123 | NB13 | 456 | 5.775254 | 0.837 | 1.028 | 1.034 | 0.9756 | 1.0272 | 0.974 | 0.9893 | 0.9781 | 0.9486 |
| 026_396_00261020 | Nervous System | 396 | NB-1 | 456 | 5.873385 | 0.813 | 1.039 | 0.892 | 0.8527 | 0.9085 | 0.934 | 0.9583 | 0.9709 | 1.0441 |
| 026_370_00252740 | Nervous System | 370 | SK-N-SH | 456 | 6.176056 | 0.926 | 0.811 | 0.891 | 1.0803 | 2.0427 | 1.01 | 0.892 | 0.9269 | 0.9864 |
| 026_364_00252720 | Nervous System | 364 | SK-N-DZ | 456 | 6.251974 | 0.895 | 1.012 | 0.958 | 0.1963 | 0.9642 | 0.976 | 1.0005 | 0.9787 | 0.9774 |
| 026_370_00258530 | Nervous System | 370 | SK-N-SH | 456 | 6.266144 | 0.36 | 0.933 | 1.052 | 1.0961 | 1.0754 | 0.948 | 0.9798 | 1.0134 | 0.9668 |
| 026_362_00252710 | Nervous System | 362 | SK-N-AS | 456 | 6.874316 | 0.911 | 1.075 | 0.916 | 1.0354 | 0.9179 | 0.939 | 1.178 | 0.9451 | 0.9362 |
| 026_368_00257200 | Nervous System | 368 | MC-IXC | 456 | 6.982443 | 0.494 | 0.616 | 1.087 | 1.1559 | 1.0678 | 1.11 | 1.0784 | 0.9917 | 0.9902 |
| 026_8122_00262490 | Nervous System | 8122 | NB12 | 456 | 7.149853 | 0.084 | 0.93 | 1.019 | 1.3067 | 1.0528 | 0.999 | 1.4063 | 0.9955 | 0.9632 |
| 026_934_00287430 | Ovary | 934 | A2780 | 456 | -0.227264 | 0.063 | 0.3 | 0.342 | 0.3503 | 0.3758 | 0.467 | 0.7239 | 0.7489 | 0.9268 |
| 026_1126_00293760 | Ovary | 1126 | OV-90 | 456 | 0.856076 | 0.302 | 0.361 | 0.384 | 0.4703 | 0.5785 | 0.701 | 0.8275 | 0.885 | 0.873 |
| 026_1129_00290660 | Ovary | 1129 | TOV-112D | 456 | 2.270257 | 0.323 | 0.481 | 0.592 | 0.7498 | 0.7692 | 0.925 | 0.9217 | 0.9942 | 1.1258 |
| 026_1220_00291150 | Ovary | 1220 | ES-2 | 456 | 2.397868 | 0.47 | 0.504 | 0.584 | 0.5655 | 0.9851 | 0.957 | 1.1602 | 1.1706 | 1.0966 |
| 026_949_00290350 | Ovary | 949 | TYK-nu | 456 | 2.489488 | 0.584 | 0.577 | 0.587 | 0.5768 | 0.6153 | 0.686 | 0.7718 | 1.0687 | 1.0378 |
| 026_925_00290850 | Ovary | 925 | IGROV-1 | 456 | 2.753994 | 0.511 | 0.608 | 0.578 | 0.7594 | 0.7462 | 0.857 | 0.9169 | 0.8966 | 0.8943 |
| 026_8244_00314220 | Ovary | 8244 | JHOS-4 | 456 | 2.779507 | 0.494 | 0.601 | 0.597 | 0.6381 | 0.7711 | 0.88 | 0.955 | 0.9128 | 0.9028 |
| 026_8279_00293400 | Ovary | 8279 | UWB1.289 | 456 | 2.893774 | 0.63 | 0.625 | 0.723 | 0.7182 | 0.783 | 1.079 | 0.9597 | 1.044 | 1.0467 |
| 026_940_00290340 | Ovary | 940 | RMG-I | 456 | 3.11591 | 0.764 | 0.604 | 0.66 | 0.6995 | 0.6871 | 0.846 | 0.8531 | 0.9424 | 1.0257 |
| 26_8238_00304370 | Ovary | 8238 | IOSE-364- | 456 | 3.149354 | 0.587 | 0.763 | 0.761 | 0.7451 | 0.8102 | 0.848 | 1.0558 | 1.0226 | 1.0295 |

TABLE 22-continued

Viability ratio

| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| 026_8237_00295840 | Ovary | 8237 | Hey | 456 | 3.317969 | 0.551 | 0.783 | 0.688 | 0.776 | 0.8484 | 0.917 | 1.1038 | 1.0681 | 1.1892 |
| 026_8260_00292720 | Ovary | 8260 | PEO1 | 456 | 3.508406 | 0.648 | 0.61 | 0.642 | 0.7269 | 0.6891 | 0.74 | 1.0027 | 0.9408 | 0.9148 |
| 026_8230_00303100 | Ovary | 8230 | DOV13 | 456 | 3.68994 | 0.636 | 0.73 | 0.886 | 0.851 | 0.9406 | 0.961 | 0.9388 | 0.9681 | 1.0998 |
| 026_8230_00292650 | Ovary | 8230 | DOV13 | 456 | 3.809459 | 0.641 | 0.685 | 0.768 | 0.9488 | 0.8764 | 0.863 | 0.9076 | 0.9226 | 1.0565 |
| 026_8092_00295850 | Ovary | 8092 | KURAMOCHI | 456 | 3.819916 | 0.757 | 0.729 | 0.642 | 0.6589 | 0.9868 | 0.914 | 0.9211 | 1.0035 | 1.0531 |
| 026_8240_00291160 | Ovary | 8240 | IOSE-523- | 456 | 3.834885 | 0.676 | 0.747 | 0.827 | 0.9249 | 0.9868 | 1 | 0.9181 | 0.9742 | 1.0197 |
| 026_932_00291140 | Ovary | 932 | EFO-27 | 456 | 3.943589 | 0.65 | 0.668 | 0.65 | 0.7216 | 0.7753 | 0.887 | 0.9104 | 0.9136 | 0.9152 |
| 026_8084_00292670 | Ovary | 8084 | KGN | 456 | 4.00968 | 0.776 | 0.686 | 0.68 | 0.804 | 0.816 | 0.93 | 0.911 | 0.9826 | 0.9092 |
| 026_1125_00290571 | Ovary | 1125 | Caov-3 | 456 | 4.050855 | 0.676 | 0.787 | 0.855 | 0.951 | 0.9041 | 1.029 | 0.9092 | 0.8992 | 1.0107 |
| 026_8256_00292920 | Ovary | 8256 | OV-7 | 456 | 4.064163 | 0.666 | 0.844 | 0.821 | 0.9099 | 0.9293 | 0.961 | 1.0098 | 0.9638 | 0.9379 |
| 026_8241_00292900 | Ovary | 8241 | IOSE-75-16SV40 | 456 | 4.094216 | 0.698 | 0.804 | 0.834 | 0.8672 | 0.894 | 1.02 | 1.0443 | 1.0711 | 1.107 |
| 026_938_00287450 | Ovary | 938 | OAW42 | 456 | 4.158942 | 0.689 | 0.707 | 0.728 | 0.8613 | 0.7453 | 0.912 | 0.7815 | 1.0258 | 1.0515 |
| 026_1235_00298501 | Ovary | 1235 | Caov-4 | 456 | 4.19878 | 0.673 | 0.815 | 0.851 | 0.7794 | 0.8482 | 0.895 | 1.0046 | 1.0048 | 0.9449 |
| 026_1221_00293780 | Ovary | 1221 | SW 626 | 456 | 4.261643 | 0.636 | 0.704 | 0.69 | 0.6894 | 0.7014 | 0.755 | 0.8172 | 0.8859 | 1.0281 |
| 026_933_00295510 | Ovary | 933 | FU-OV-1 | 456 | 4.35795 | 0.921 | 0.786 | 0.66 | 0.785 | 0.7855 | 0.932 | 1.0797 | 1.0643 | 1.0563 |
| 026_8259_00292710 | Ovary | 8259 | OVK-18 | 456 | 4.419332 | 0.714 | 0.849 | 0.926 | 0.7816 | 0.8328 | 1.11 | 1.0158 | 0.9241 | 1.1619 |
| 026_8242_00295400 | Ovary | 8242 | JHOS-2 | 456 | 4.46038 | 0.744 | 0.845 | 0.843 | 0.8069 | 0.9687 | 1.09 | 0.9491 | 1.0683 | 1.0333 |
| 026_1128_00292620 | Ovary | 1128 | PA-1 | 456 | 4.524728 | 0.741 | 0.875 | 0.809 | 0.8925 | 0.9409 | 1.005 | 1.0033 | 1.0111 | 1.0682 |
| 026_938_00290330 | Ovary | 938 | OAW42 | 456 | 4.600882 | 0.772 | 0.772 | 0.843 | 0.9103 | 0.8456 | 1.001 | 1.0305 | 1.0314 | 1.0721 |
| 026_8148_00292700 | Ovary | 8148 | OVCAR-4 | 456 | 4.649732 | 0.715 | 0.824 | 0.723 | 0.6704 | 0.8391 | 0.855 | 0.9034 | 1.0922 | 1.0169 |
| 026_8243_00295410 | Ovary | 8243 | JHOS-3 | 456 | 4.699022 | 0.801 | 0.758 | 0.691 | 0.7427 | 0.8184 | 0.86 | 1.0104 | 0.9653 | 1.0478 |
| 026_1130_00308501 | Ovary | 1130 | TOV-21G | 456 | 4.743414 | 0.744 | 0.838 | 0.882 | 0.8952 | 0.9369 | 0.922 | 0.9212 | 0.9456 | 0.9683 |
| 026_931_00252940 | Ovary | 931 | FU-OV-1 | 456 | 4.786052 | 0.749 | 0.962 | 0.957 | 1.0202 | 1.0143 | 0.983 | 0.9976 | 0.9688 | 0.9523 |
| 026_931_00290820 | Ovary | 931 | EFO-21 | 456 | 4.852802 | 0.791 | 0.924 | 0.954 | 0.9827 | 1.0247 | 0.961 | 0.9353 | 0.9274 | 0.9237 |
| 026_932_00288450 | Ovary | 932 | EFO-21 | 456 | 4.890908 | 0.759 | 0.729 | 0.783 | 0.7813 | 0.828 | 0.851 | 0.9362 | 1.0032 | 1.0515 |
| 026_8258_00291180 | Ovary | 8258 | EFO-27 | 456 | 4.901177 | 0.703 | 0.713 | 0.753 | 0.7366 | 0.79 | 0.864 | 0.9468 | 0.9244 | 0.9669 |
| 026_928_00290870 | Ovary | 928 | OVCAR433 | 456 | 4.903025 | 0.791 | 0.718 | 0.699 | 0.6913 | 0.7147 | 0.8 | 0.831 | 0.8925 | 0.9149 |
| 026_8257_00293650 | Ovary | 8257 | OVCAR-5 | 456 | 4.98883 | 0.716 | 0.738 | 0.79 | 0.8055 | 0.8238 | 0.819 | 0.8677 | 0.8812 | 1.0222 |
| 026_8257_00292690 | Ovary | 8257 | OVCA420 | 456 | 5.050268 | 0.789 | 0.822 | 0.798 | 0.9932 | 0.8382 | 0.876 | 0.928 | 0.9213 | 1.1024 |
| 026_8239_00292890 | Ovary | 8239 | OVCA420 | 456 | 5.092878 | 0.842 | 0.8 | 0.866 | 0.8796 | 0.8926 | 0.921 | 1.2015 | 0.9976 | 1.2125 |
| 026_8255_00293640 | Ovary | 8255 | IOSE-397 | 456 | 5.095259 | 0.874 | 0.883 | 0.798 | 0.796 | 0.8682 | 0.983 | 1.195 | 1.0697 | 1.0119 |
| 026_941_00288490 | Ovary | 941 | OV-56 | 456 | 5.147098 | 0.777 | 0.805 | 0.822 | 0.8457 | 0.8675 | 0.961 | 0.9211 | 0.9687 | 1.0047 |
| 026_929_00290880 | Ovary | 929 | RKN | 456 | 5.38803 | 0.763 | 0.99 | 0.986 | 1.0451 | 1.0092 | 0.888 | 1.0495 | 0.9963 | 1.0021 |
| 026_8215_00287660 | Ovary | 8215 | OVCAR-8 | 456 | 5.430154 | 0.869 | 0.848 | 0.834 | 0.8094 | 0.8719 | 1.01 | 0.9424 | 0.903 | 1.1026 |
| 026_939_00287460 | Ovary | 939 | OC-314 | 456 | 5.797932 | 0.806 | 0.737 | 0.748 | 0.7949 | 0.7921 | 0.891 | 0.8857 | 0.9368 | 0.9866 |
| 026_945_00288480 | Ovary | 945 | SK-OV-3 | 456 | 5.89738 | 0.75 | 0.912 | 0.942 | 0.9614 | 0.938 | 0.844 | 0.9025 | 0.9329 | 0.9575 |
| 026_948_00291230 | Ovary | 948 | OVMIU | 456 | 5.989644 | 0.829 | 0.894 | 0.904 | 0.9225 | 0.9189 | 0.909 | 0.9267 | 0.9453 | 0.9277 |
| 026_8255_00293640 | Ovary | 8255 | OVTOKO | 456 | 6.027686 | 0.874 | 0.878 | 1.001 | 0.9358 | 0.7724 | 0.911 | 1.0447 | 0.8649 | 1.0363 |
| 026_937_00288460 | Ovary | 937 | OV-56 | 456 | 6.109694 | 0.859 | 0.95 | 0.992 | 0.9785 | 0.8788 | 0.814 | 0.9619 | 1.0732 | 0.8745 |
| 026_1127_00296460 | Ovary | 1127 | OAW28 | 456 | 6.266319 | 0.886 | 0.823 | 0.875 | 0.8874 | 0.9093 | 0.986 | 0.9175 | 0.9563 | 0.9507 |
| 026_947_00263500 | Ovary | 947 | NIH: OVCAR-3 | 456 | 6.299032 | 0.819 | 0.963 | 0.958 | 0.9614 | 0.9778 | 1.041 | 1.0213 | 0.9899 | 1.0087 |
| 026_938_00292910 | Ovary | 938 | OVKATE | 456 | 6.360298 | 0.918 | 0.987 | 1.001 | 0.9225 | 0.8452 | 0.776 | 0.8273 | 0.9233 | 1.0102 |
| 026_945_00256180 | Ovary | 945 | OAW42 | 456 | 6.600815 | 0.891 | 0.737 | 0.737 | 0.7358 | 0.7593 | 0.759 | 0.8539 | 0.8664 | 0.8624 |
| 026_946_00291190 | Ovary | 946 | OVMIU | 456 | 6.877329 | 0.805 | 0.739 | 0.974 | 1.0282 | 1.0077 | 1.015 | 1.0376 | 0.9484 | 1.0604 |
| 026_8254_00295890 | Ovary | 8254 | OVISE | 456 | 0.866739 | 0.913 | 1.041 | 0.362 | 0.4721 | 0.5603 | 0.814 | 1.0984 | 0.8938 | 1.1407 |
| 026_973_00295540 | Pancreas | 973 | OV-17R | 456 | 1.197889 | 0.321 | 0.315 | 0.382 | 0.581 | 0.6565 | 0.942 | 0.9937 | 1.019 | 0.8745 |
| 026_983_00295450 | Pancreas | 983 | HUP-T4 | 456 | 1.430625 | 0.397 | 0.339 | 0.492 | 0.5682 | 0.6307 | 0.8 | 0.8372 | 0.9601 | 1.1926 |
| 026_982_00292940 | Pancreas | 982 | SUIT-2 | 456 | 1.48113 | 0.538 | 0.437 | 0.382 | 0.5335 | 0.6471 | 0.8 | 0.8372 | 1.008 | 1.0476 |
| 026_8118_00295430 | Pancreas | 8118 | QGP-1 | 456 | 1.48113 | 0.363 | 0.489 | 0.495 | 0.5335 | 0.6471 | 0.671 | 0.9118 | 1.008 | 0.9838 |

TABLE 22-continued

| Barcode | Organ | Cell ID | Cell Line | Compound No | Fitted MGH_IC50 | Viability ratio | | | | | | | | |
|---|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_8149_00293771 | Pancreas | 8149 | PSN1 | 456 | 1.829333 | 0.531 | 0.553 | 0.5 | 0.5231 | 0.6104 | 0.71 | 0.8375 | 0.909 | 0.9509 |
| 026_953_00295470 | Pancreas | 953 | AsPC-1 | 456 | 1.847893 | 0.476 | 0.515 | 0.508 | 0.4987 | 0.5741 | 0.746 | 0.8281 | 1.0377 | 1.0843 |
| 026_1256_00260300 | Pancreas | 1256 | 950-MPS | 456 | 1.902786 | 0.332 | 0.473 | 0.515 | 0.7193 | 0.8035 | 0.916 | 0.9125 | 1.0441 | 0.9009 |
| 026_976_00298480 | Pancreas | 976 | Panc 04.03 | 456 | 2.685969 | 0.592 | 0.594 | 0.57 | 0.562 | 0.6645 | 0.706 | 0.8319 | 0.9296 | 1.0176 |
| 026_954_00292870 | Pancreas | 954 | BxPC-3 | 456 | 2.90077 | 0.574 | 0.607 | 0.558 | 0.6572 | 0.7404 | 0.813 | 1.0541 | 1.0916 | 0.9092 |
| 026_967_00292570 | Pancreas | 967 | Capan-1 | 456 | 3.140577 | 0.522 | 0.69 | 0.758 | 0.8527 | 0.6713 | 0.874 | 0.9506 | 0.894 | 0.958 |
| 026_975_00295591 | Pancreas | 975 | YAPC | 456 | 3.507979 | 0.613 | 0.705 | 0.797 | 0.9196 | 0.8833 | 0.921 | 1.0616 | 1.0323 | 1.0675 |
| 026_1135_00292930 | Pancreas | 1135 | PL18 | 456 | 3.513426 | 0.636 | 0.623 | 0.694 | 0.6978 | 0.7917 | 0.832 | 0.9096 | 0.9334 | 0.9721 |
| 026_977_00308210 | Pancreas | 977 | KP-1N | 456 | 3.657778 | 0.607 | 0.764 | 0.684 | 0.7525 | 0.7655 | 0.908 | 0.9944 | 0.9837 | 0.9553 |
| 026_969_00295580 | Pancreas | 969 | PA-TU-8988T | 456 | 3.657963 | 0.664 | 0.653 | 0.725 | 0.7145 | 0.7879 | 0.992 | 1.0299 | 1.0048 | 1.0863 |
| 026_1491_00273490 | Pancreas | 1491 | SNU-324 | 456 | 3.732679 | 0.387 | 0.683 | 0.791 | 0.7879 | 0.8486 | 0.832 | 0.9455 | 0.9813 | 0.9695 |
| 026_961_00295570 | Pancreas | 961 | Panc 02.03 | 456 | 4.088522 | 0.702 | 0.699 | 0.633 | 0.701 | 0.7003 | 0.795 | 0.8748 | 0.9019 | 1.1113 |
| 026_974_00292601 | Pancreas | 974 | HUP-T3 | 456 | 4.280085 | 0.684 | 0.754 | 0.793 | 0.909 | 0.7596 | 0.88 | 0.9895 | 0.9696 | 1.0099 |
| 026_963_00293710 | Pancreas | 963 | Hs 766T | 456 | 4.34359 | 0.709 | 0.746 | 0.833 | 0.7623 | 0.8169 | 1.052 | 0.9605 | 0.9551 | 1.0544 |
| 026_959_00292630 | Pancreas | 959 | Panc 03.27 | 456 | 4.482408 | 0.701 | 0.682 | 0.805 | 0.8272 | 0.7565 | 0.838 | 0.9087 | 0.9434 | 1.0258 |
| 026_981_00293750 | Pancreas | 981 | KP-4 | 456 | 4.755774 | 0.733 | 0.9 | 0.784 | 0.9218 | 0.8875 | 1.007 | 0.9325 | 1.0003 | 0.8788 |
| 026_968_00293580 | Pancreas | 968 | CFPAC-1 | 456 | 4.814885 | 0.772 | 0.822 | 0.87 | 0.9195 | 0.9082 | 0.935 | 0.8889 | 1.0106 | 1.1286 |
| 026_1134_00300280 | Pancreas | 1134 | PL4 | 456 | 4.852316 | 0.738 | 0.739 | 0.727 | 0.7443 | 0.7816 | 0.797 | 0.9521 | 0.9663 | 1.0376 |
| 026_979_00293740 | Pancreas | 979 | KP-3 | 456 | 4.900084 | 0.956 | 0.777 | 0.839 | 0.8825 | 0.8836 | 0.909 | 0.9593 | 0.9092 | 0.9686 |
| 026_956_00292591 | Pancreas | 956 | HPAF-II | 456 | 5.005523 | 0.734 | 0.786 | 0.762 | 0.6523 | 0.7269 | 0.755 | 0.9185 | 0.979 | 1.0195 |
| 026_953_00257150 | Pancreas | 953 | AsPC-1 | 456 | 5.141432 | 0.761 | 0.708 | 0.731 | 0.7295 | 0.7369 | 0.79 | 0.8534 | 0.8911 | 0.9577 |
| 26_968_03043450 | Pancreas | 968 | CFPAC-1 | 456 | 5.151366 | 0.817 | 0.828 | 0.864 | 0.8724 | 0.8715 | 1.008 | 1.007 | 0.9779 | 1.001 |
| 026_957_00296350 | Pancreas | 957 | SW 1990 | 456 | 5.575766 | 0.849 | 0.911 | 0.906 | 0.8954 | 0.9494 | 0.957 | 0.977 | 0.9769 | 1.1173 |
| 026_960_00296311 | Pancreas | 960 | Panc 08.13 | 456 | 5.65459 | 0.875 | 0.894 | 0.924 | 0.9669 | 0.9243 | 0.96 | 1.1005 | 1.065 | 1.0309 |
| 026_951_00256230 | Pancreas | 951 | HPAC | 456 | 5.736336 | 0.862 | 1.024 | 0.931 | 0.8532 | 0.9386 | 1.035 | 1.0328 | 1.0507 | 1.0612 |
| 026_964_00295480 | Pancreas | 964 | Capan-2 | 456 | 5.74256 | 0.877 | 0.928 | 0.759 | 0.8346 | 0.9905 | 0.925 | 1.0364 | 1.027 | 0.9499 |
| 026_1134_00298560 | Pancreas | 1134 | PL4 | 456 | 5.771259 | 0.844 | 0.812 | 0.91 | 0.8479 | 0.7738 | 0.977 | 0.9068 | 1.059 | 0.9774 |
| 026_970_00293370 | Pancreas | 970 | PA-TU-8902 | 456 | 5.772043 | 0.841 | 0.97 | 0.919 | 0.8896 | 0.9177 | 0.966 | 0.9181 | 1.322 | 0.9871 |
| 026_952_00292610 | Pancreas | 952 | MIA PaCa-2 | 456 | 5.946631 | 0.923 | 0.885 | 0.718 | 0.8919 | 0.8505 | 1.058 | 1.0586 | 0.8995 | 1.1403 |
| 026_972_00295250 | Pancreas | 972 | DAN-G | 456 | 5.955955 | 0.897 | 0.924 | 0.945 | 0.9646 | 0.9703 | 0.978 | 1.0074 | 1.032 | 1.0585 |
| 026_951_00295520 | Pancreas | 951 | HPAC | 456 | 5.962773 | 0.923 | 0.889 | 0.787 | 0.9719 | 0.9562 | 1.118 | 0.986 | 0.9708 | 1.1145 |
| 026_975_00257910 | Pancreas | 975 | YAPC | 456 | 5.989883 | 1.015 | 0.914 | 0.897 | 0.8713 | 0.8903 | 1.037 | 0.9777 | 1.1409 | 0.981 |
| 026_963_00252950 | Pancreas | 963 | Hs 766T | 456 | 6.264463 | 0.496 | 0.974 | 0.953 | 1.0445 | 0.9118 | 1.028 | 0.9324 | 1.0245 | 1.0186 |
| 026_958_00296320 | Pancreas | 958 | Panc 10.05 | 456 | 6.318194 | 0.851 | 0.835 | 0.851 | 0.824 | 0.8929 | 0.879 | 0.9003 | 1.0065 | 1.0291 |
| 026_955_00292640 | Pancreas | 955 | SU.86.86 | 456 | 6.593699 | 1.017 | 0.82 | 0.986 | 0.9378 | 1.1258 | 1.072 | 1.0873 | 1.0381 | 0.9789 |
| 026_759_00300240 | Pleura | 759 | MSTO-211H | 456 | 3.066599 | 0.666 | 0.637 | 0.664 | 0.6954 | 0.8026 | 0.901 | 1.0485 | 1.0165 | 1.0436 |
| 026_1213_00303050 | Pleura | 1213 | H2818 | 456 | 3.157415 | 0.577 | 0.674 | 0.728 | 0.8558 | 0.9032 | 0.962 | 0.9285 | 1.0744 | 1.1008 |
| 026_8116_00303080 | Pleura | 8116 | MPP-89 | 456 | 3.723631 | 0.416 | 0.808 | 0.823 | 0.9733 | 0.9887 | 0.968 | 1.0012 | 0.9912 | 1.0294 |
| 026_1206_00302600 | Pleura | 1206 | H2722 | 456 | 3.764667 | 0.604 | 0.768 | 0.801 | 0.8049 | 0.8692 | 0.937 | 0.9073 | 0.9842 | 0.9698 |
| 026_1210_00302610 | Pleura | 1210 | H2803 | 456 | 4.117283 | 0.686 | 0.723 | 0.669 | 0.7081 | 0.719 | 0.892 | 0.9533 | 1.0129 | 0.9547 |
| 026_1215_00311260 | Pleura | 1215 | H290 | 456 | 4.122283 | 0.629 | 0.753 | 0.69 | 0.7652 | 0.7781 | 0.737 | 0.8199 | 0.9853 | 0.9812 |
| 026_1206_00308200 | Pleura | 1206 | H2722 | 456 | 4.184817 | 0.699 | 0.769 | 0.85 | 0.8838 | 0.889 | 0.906 | 1.0135 | 0.9948 | 1.0129 |
| 026_1212_00300580 | Pleura | 1212 | H2810 | 456 | 4.445211 | 0.69 | 0.929 | 0.942 | 0.9243 | 0.9927 | 0.884 | 0.9289 | 0.9051 | 0.9626 |
| 026_682_00304600 | Pleura | 682 | NCI-H2452 | 456 | 4.452468 | 0.722 | 0.847 | 0.891 | 0.906 | 0.9407 | 0.899 | 0.9567 | 1.0786 | 1.1287 |
| 026_1200_00300690 | Pleura | 1200 | H2373 | 456 | 4.612295 | 0.695 | 0.911 | 0.887 | 0.9257 | 0.9258 | 0.849 | 0.9218 | 0.9772 | 0.9399 |
| 026_1214_00308460 | Pleura | 1214 | H2869 | 456 | 4.934927 | 0.775 | 0.881 | 0.878 | 0.926 | 0.9241 | 0.914 | 0.9475 | 0.9536 | 1.0138 |
| 026_1214_00308790 | Pleura | 1214 | H2869 | 456 | 4.961713 | 0.802 | 0.879 | 0.908 | 0.9132 | 0.9528 | 0.991 | 0.9959 | 1.0132 | 1.0202 |
| 026_1202_00303040 | Pleura | 1202 | H2591 | 456 | 5.067997 | 0.82 | 0.918 | 0.945 | 1.0327 | 0.9338 | 0.983 | 0.9541 | 1.0755 | 1.1707 |

TABLE 22-continued

| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
|---|---|---|---|---|---|---|---|---|---|---|---|---|---|---|
| | | | | | | | | | | Viability ratio | | | | |
| 026_1209_00300210 | Pleura | 1209 | H28 | 456 | 5.341766 | 0.817 | 0.821 | 0.827 | 0.8331 | 0.8999 | 0.927 | 0.9491 | 1.0072 | 0.9857 |
| 026_8078_00303060 | Pleura | 8078 | IST-MES1 | 456 | 5.358253 | 0.782 | 0.897 | 0.859 | 0.8822 | 0.8445 | 0.907 | 0.9752 | 0.926 | 1.0513 |
| 026_1199_00300560 | Pleura | 1199 | H2369 | 456 | 5.439636 | 0.82 | 0.91 | 0.99 | 0.8596 | 0.9181 | 0.984 | 0.9172 | 0.9896 | 1.1394 |
| 026_8078_00304970 | Pleura | 8078 | IST-MES1 | 456 | 5.505825 | 0.847 | 0.88 | 0.853 | 0.8587 | 0.8938 | 0.89 | 0.9416 | 0.9423 | 1.0968 |
| 026_1207_00298510 | Pleura | 1207 | H2731 | 456 | 5.56988 | 0.819 | 1.018 | 1.003 | 0.8986 | 0.9778 | 0.921 | 0.9543 | 0.9856 | 0.9695 |
| 026_1198_00302580 | Pleura | 1198 | H2052 | 456 | 5.579483 | 0.859 | 0.966 | 0.995 | 0.9551 | 0.9651 | 1.01 | 1.0265 | 1.0233 | 1.0095 |
| 026_1201_00302590 | Pleura | 1201 | H2461 | 456 | 5.654117 | 0.856 | 0.868 | 0.914 | 0.904 | 0.8852 | 0.908 | 0.9343 | 1.0239 | 1.1079 |
| 026_1213_00300720 | Pleura | 1213 | H2818 | 456 | 5.828097 | 0.843 | 0.946 | 0.86 | 0.9682 | 0.9236 | 0.942 | 0.9493 | 0.9688 | 0.9576 |
| 026_1211_00300570 | Pleura | 1211 | H2804 | 456 | 5.890027 | 0.881 | 0.886 | 0.907 | 0.8753 | 0.9153 | 0.955 | 0.969 | 0.9857 | 1.0448 |
| 026_1218_00300730 | Pleura | 1218 | H513 | 456 | 5.953268 | 0.9 | 0.905 | 0.905 | 1.0722 | 1.0284 | 0.976 | 0.9507 | 1.0341 | 1.2023 |
| 026_1208_00300710 | Pleura | 1208 | H2795 | 456 | 6.063798 | 0.3 | 0.943 | 0.961 | 0.8752 | 0.9823 | 0.905 | 0.9466 | 0.9643 | 0.975 |
| 026_1203_00300850 | Pleura | 1203 | H2595 | 456 | 6.184806 | 0.92 | 0.909 | 0.899 | 1.0357 | 1.0632 | 0.905 | 0.974 | 1.018 | 0.9037 |
| 026_8245_00282710 | pleural effusion | 8245 | KMS-11 | 456 | 0.702427 | 0.356 | 0.381 | 0.404 | 0.4804 | 0.491 | 0.652 | 0.7128 | 1.0645 | 1.1048 |
| 026_996_00298490 | Prostate | 996 | 22RV1 | 456 | 2.346887 | 0.542 | 0.521 | 0.592 | 0.6235 | 0.6635 | 0.707 | 0.7764 | 0.8517 | 0.9168 |
| 026_985_00303070 | Prostate | 985 | LNCaP clone FGC | 456 | 4.018762 | 0.727 | 0.863 | 0.923 | 1.1164 | 1.0922 | 0.984 | 1.0179 | 1.1749 | 1.0533 |
| 026_987_00298550 | Prostate | 987 | PC-3 | 456 | 4.097696 | 0.698 | 0.761 | 0.871 | 0.9338 | 0.9109 | 0.914 | 0.9938 | 1.2109 | 0.991 |
| 026_1001_00300200 | Prostate | 1001 | DU 145 | 456 | 5.044916 | 0.768 | 0.832 | 0.867 | 0.8699 | 0.8879 | 0.906 | 0.9933 | 0.9168 | 1.1136 |
| 026_988_00308270 | Prostate | 988 | PWR-1E | 456 | 5.228199 | 0.804 | 0.854 | 0.877 | 0.8566 | 0.8621 | 0.923 | 0.9727 | 0.9516 | 0.9806 |
| 026_997_00300660 | Prostate | 997 | BPH-1 | 456 | 5.448713 | 0.479 | 0.868 | 1.201 | 1.1209 | 1.1016 | 0.674 | 0.9562 | 1.1603 | 0.8983 |
| 026_1000_00300740 | Prostate | 1000 | VCaP | 456 | 5.968581 | 0.692 | 1.071 | 1.005 | 1.0988 | 0.9203 | 0.91 | 0.9225 | 0.9154 | 1.1301 |
| 026_1009_00264700 | Skin | 1009 | WM35 | 456 | -2.372512 | 0.112 | 0.201 | 0.203 | 0.2168 | 0.2138 | 0.242 | 0.3676 | 0.463 | 0.7025 |
| 026_8212_00264590 | Skin | 8212 | CP50-MEL-B | 456 | -1.651863 | 0.151 | 0.398 | 0.392 | 0.3817 | 0.3556 | 0.35 | 0.4631 | 0.5633 | 0.8209 |
| 026_1039_00265170 | Skin | 1039 | SK-MEL-30 | 456 | -1.476493 | 0.263 | 0.352 | 0.317 | 0.3236 | 0.3515 | 0.424 | 0.5534 | 0.8565 | 0.8549 |
| 026_1023_00269690 | Skin | 1023 | SK-MEL-2 | 456 | -1.357658 | 0.147 | 0.207 | 0.235 | 0.2621 | 0.2935 | 0.343 | 0.5053 | 0.6866 | 0.8939 |
| 026_1034_00264680 | Skin | 1034 | MEL-HO | 456 | -0.964561 | 0.144 | 0.372 | 0.375 | 0.3139 | 0.3537 | 0.327 | 0.4189 | 0.6188 | 0.8613 |
| 026_8073_00264800 | Skin | 8073 | HT-144 | 456 | -0.641233 | 0.154 | 0.241 | 0.236 | 0.3036 | 0.3695 | 0.397 | 0.6432 | 0.7444 | 0.9033 |
| 026_8114_00259970 | Skin | 8114 | MMAC-SF | 456 | -0.613008 | 0.211 | 0.399 | 0.492 | 0.3813 | 0.4238 | 0.662 | 0.5683 | 0.6942 | 1.0563 |
| 026_8209_00266540 | Skin | 8209 | A4-Fuk | 456 | -0.557176 | 0.179 | 0.476 | 0.467 | 0.4234 | 0.4176 | 0.498 | 0.6644 | 0.7338 | 0.7609 |
| 026_1046_00263470 | Skin | 1046 | HMVII | 456 | -0.454742 | 0.389 | 0.419 | 0.403 | 0.3903 | 0.4097 | 0.503 | 0.6117 | 0.8285 | 1.0625 |
| 026_8120_00262840 | Skin | 8120 | MZ7-mel | 456 | -0.254795 | 0.073 | 0.323 | 0.41 | 0.4001 | 0.4106 | 0.468 | 0.6687 | 0.6311 | 0.8761 |
| 026_8191_00260580 | Skin | 8191 | UACC-257 | 456 | -0.10266 | 0.456 | 0.468 | 0.426 | 0.404 | 0.4006 | 0.534 | 0.6654 | 0.7954 | 0.894 |
| 026_1176_00266430 | Skin | 1176 | 451Lu | 456 | -0.00066 | 0.26 | 0.428 | 0.38 | 0.386 | 0.4254 | 0.499 | 0.6795 | 0.8423 | 0.9729 |
| 026_1149_00263460 | Skin | 1149 | G-MEL | 456 | 0.018696 | 0.065 | 0.23 | 0.181 | 0.1928 | 0.2465 | 0.404 | 0.7707 | 0.8991 | 0.9576 |
| 026_1147_00263750 | Skin | 1147 | SK-MEL-28 | 456 | 0.142676 | 0.187 | 0.48 | 0.376 | 0.4566 | 0.4611 | 0.565 | 0.6083 | 0.8116 | 0.9418 |
| 026_1037_00260080 | Skin | 1037 | SK-MEL-1 | 456 | 0.168848 | 0.176 | 0.417 | 0.368 | 0.3716 | 0.3919 | 0.613 | 0.6978 | 0.9091 | 0.966 |
| 026_1190_00266570 | Skin | 1190 | Hs 939.T | 456 | 0.185332 | 0.283 | 0.631 | 0.615 | 0.5802 | 0.5603 | 0.559 | 0.5576 | 0.7187 | 0.8082 |
| 026_1024_00265150 | Skin | 1024 | M-14 | 456 | 0.192152 | 0.418 | 0.433 | 0.383 | 0.391 | 0.4651 | 0.618 | 0.742 | 0.7678 | 0.9177 |
| 026_1025_00264710 | Skin | 1025 | COLO-679 | 456 | 0.228168 | 0.267 | 0.288 | 0.296 | 0.3664 | 0.4611 | 0.681 | 0.8141 | 0.9334 | 1.1196 |
| 026_8161_00263740 | Skin | 8161 | SH-4 | 456 | 0.433257 | 0.203 | 0.383 | 0.33 | 0.3147 | 0.3323 | 0.488 | 0.7539 | 0.8959 | 0.983 |
| 026_8097_00262820 | Skin | 8097 | LB2518-MEL | 456 | 0.437866 | 0.076 | 0.501 | 0.37 | 0.3813 | 0.4237 | 0.706 | 0.7414 | 0.8914 | 0.9396 |
| 026_8120_00260550 | Skin | 8120 | MZ7-mel | 456 | 0.447706 | 0.299 | 0.428 | 0.435 | 0.4782 | 0.4839 | 0.498 | 0.6521 | 0.7326 | 0.8788 |
| 026_1033_00262470 | Skin | 1033 | IPC-298 | 456 | 0.460127 | 0.363 | 0.36 | 0.404 | 0.4297 | 0.5245 | 0.562 | 0.7868 | 0.9191 | 0.8529 |
| 026_1031_00264030 | Skin | 1031 | IGR-37 | 456 | 0.57267 | 0.159 | 0.498 | 0.512 | 0.4794 | 0.5367 | 0.602 | 0.8381 | 0.9754 | 1.0032 |
| 026_1006_00260110 | Skin | 1006 | WM-115 | 456 | 0.616077 | 0.079 | 0.437 | 0.583 | 0.4912 | 0.4928 | 0.627 | 0.6176 | 0.6485 | 0.9586 |
| 026_8023_00265291 | Skin | 8023 | COLO-829 | 456 | 0.740747 | 0.164 | 0.659 | 0.533 | 0.5534 | 0.5976 | 0.709 | 0.8699 | 0.9148 | 0.9877 |
| 026_1036_00264690 | Skin | 1036 | RVH-421 | 456 | 0.784255 | 0.099 | 0.511 | 0.489 | 0.5329 | 0.5785 | 0.531 | 0.5954 | 0.5867 | 0.7408 |
| 026_1011_00269770 | Skin | 1011 | WM278 | 456 | 0.944573 | 0.289 | 0.463 | 0.457 | 0.4545 | 0.4605 | 0.568 | 0.7513 | 0.8836 | 0.9597 |
| 026_1003_00269650 | Skin | 1003 | G-361 | 456 | 0.948854 | 0.099 | 0.326 | 0.434 | 0.5233 | 0.6155 | 0.705 | 0.83 | 0.8998 | 1.0756 |

TABLE 22-continued

| | | | | | | | Viability ratio | | | | | | |
|---|---|---|---|---|---|---|---|---|---|---|---|---|---|
| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
| 026_8002_00263700 | Skin | 8002 | A101D | 456 | 0.960267 | 0.088 | 0.468 | 0.524 | 0.5105 | 0.5276 | 0.55 | 0.5835 | 0.7643 | 0.8791 |
| 026_8104_00260540 | Skin | 8104 | LOXIMVI | 456 | 1.072404 | 0.278 | 0.403 | 0.39 | 0.4769 | 0.6158 | 0.839 | 0.877 | 0.864 | 0.9209 |
| 026_1005_00268780 | Skin | 1005 | A-375 | 456 | 1.191442 | 0.45 | 0.499 | 0.485 | 0.4604 | 0.5149 | 0.506 | 0.6624 | 0.892 | 0.928 |
| 026_1004_00260870 | Skin | 1004 | C32 | 456 | 1.195832 | 0.288 | 0.331 | 0.256 | 0.265 | 0.3055 | 0.504 | 0.8497 | 0.9278 | 0.9753 |
| 026_1030_00264020 | Skin | 1030 | IGR-1 | 456 | 1.307792 | 0.075 | 0.388 | 0.556 | 0.5173 | 0.6922 | 0.688 | 0.8911 | 0.7819 | 0.8658 |
| 026_1035_00265160 | Skin | 1035 | MEL-JUSO | 456 | 1.414781 | 0.305 | 0.481 | 0.494 | 0.5153 | 0.7013 | 0.739 | 0.9127 | 0.9597 | 1.0093 |
| 026_8119_00259980 | Skin | 8119 | MZ2-MEL | 456 | 1.446447 | 0.402 | 0.467 | 0.438 | 0.4246 | 0.4152 | 0.679 | 0.7345 | 0.8985 | 0.9484 |
| 026_8097_00260530 | Skin | 8097 | LB2518-MEL | 456 | 1.447504 | 0.439 | 0.438 | 0.44 | 0.3578 | 0.3688 | 0.635 | 0.8111 | 0.8622 | 0.8731 |
| 026_8225_00260640 | Skin | 8225 | SK-MEL-5 | 456 | 1.574212 | 0.07 | 0.432 | 0.581 | 0.5597 | 0.6534 | 0.603 | 0.7648 | 0.9285 | 1.0194 |
| 026_8104_00262830 | Skin | 8104 | LOXIMVI | 456 | 1.676415 | 0.172 | 0.565 | 0.594 | 0.5546 | 0.7085 | 0.865 | 1.2098 | 1.0454 | 1.1061 |
| 026_1042_00274340 | Skin | 1042 | COLO 792 | 456 | 1.75025 | 0.329 | 0.514 | 0.573 | 0.6166 | 0.6518 | 0.787 | 0.8993 | 0.9066 | 0.9485 |
| 026_1026_00269720 | Skin | 1026 | COLO-783 | 456 | 1.791757 | 0.479 | 0.599 | 0.603 | 0.6144 | 0.5728 | 0.634 | 0.6979 | 0.8575 | 0.9077 |
| 026_1010_00263450 | Skin | 1010 | WM1552C | 456 | 2.109919 | 0.364 | 0.794 | 0.685 | 0.6806 | 0.6737 | 0.881 | 0.8586 | 0.9992 | 0.9359 |
| 026_1041_00263450 | Skin | 1041 | A431 | 456 | 2.481335 | 0.436 | 0.563 | 0.633 | 0.821 | 0.8517 | 0.858 | 1.0792 | 0.8962 | 0.9346 |
| 026_8098_00269090 | Skin | 8098 | LB373-MEL-D | 456 | 2.623655 | 0.496 | 0.615 | 0.627 | 0.6225 | 0.6708 | 0.815 | 0.8109 | 0.9711 | 1.0201 |
| 026_1022_00262940 | Skin | 1022 | RPMI-7951 | 456 | 2.647594 | 0.249 | 0.552 | 0.678 | 0.6664 | 0.7181 | 0.824 | 0.8966 | 0.8605 | 0.908 |
| 026_1181_00269080 | Skin | 1181 | Hs 944.T | 456 | 2.824283 | 0.206 | 0.612 | 0.779 | 0.8499 | 0.8608 | 0.892 | 0.9924 | 1.1546 | 1.1214 |
| 026_1008_00262540 | Skin | 1008 | WM793B | 456 | 2.933974 | 0.371 | 0.744 | 0.693 | 0.6962 | 0.7393 | 0.731 | 0.8508 | 0.9586 | 0.8942 |
| 026_1027_00265280 | Skin | 1027 | COLO-800 | 456 | 3.132083 | 0.537 | 0.717 | 0.804 | 0.8959 | 0.9417 | 0.926 | 0.9678 | 0.954 | 0.9346 |
| 026_8034_00265300 | Skin | 8034 | DJM-1 | 456 | 3.234358 | 0.249 | 0.552 | 0.806 | 0.9452 | 0.9331 | 1.005 | 0.9966 | 1.0061 | 1.0084 |
| 026_1181_00264620 | Skin | 1181 | Hs 944.T | 456 | 3.491747 | 0.094 | 0.698 | 0.822 | 0.9152 | 0.8448 | 0.9 | 0.9921 | 0.9743 | 0.9841 |
| 026_8225_00263510 | Skin | 8225 | SK-MEL-5 | 456 | 3.505326 | 0.234 | 0.653 | 0.694 | 0.7331 | 0.7681 | 0.79 | 0.9216 | 0.9437 | 0.9528 |
| 026_1145_00263720 | Skin | 1145 | CHL-1 | 456 | 3.811805 | 0.609 | 0.895 | 0.833 | 0.8778 | 0.9025 | 0.855 | 0.9286 | 0.9316 | 1.0458 |
| 026_8060_00265311 | Skin | 8060 | GAK | 456 | 4.2621 | 0.37 | 0.758 | 0.827 | 0.7891 | 0.8733 | 0.894 | 0.9899 | 0.9692 | 0.9911 |
| 026_1047_00265320 | Skin | 1047 | MEWO | 456 | 4.342961 | 0.779 | 0.931 | 0.98 | 0.9757 | 0.9449 | 0.991 | 1.0008 | 0.9996 | 1 |
| 026_1022_00260910 | Skin | 1022 | RPMI-7951 | 456 | 4.58823 | 0.257 | 0.748 | 0.801 | 0.8703 | 0.8751 | 0.884 | 0.9495 | 0.9173 | 0.9542 |
| 026_1038_00260090 | Skin | 1038 | SK-MEL-3 | 456 | 4.834702 | 0.151 | 0.731 | 0.777 | 0.7955 | 0.7955 | 0.827 | 0.8793 | 0.913 | 0.9361 |
| 026_1002_00260861 | Skin | 1002 | A2058 | 456 | 5.928358 | 0.795 | 0.897 | 0.85 | 0.894 | 0.8474 | 0.885 | 1.0053 | 0.8902 | 0.984 |
| 026_8025_00306491 | Skin | 8025 | CP66-MEL | 456 | 6.278644 | 0.914 | 0.888 | 1.059 | 0.9053 | 1.0334 | 0.961 | 0.8798 | 1.0258 | 0.9475 |
| 026_1120_00264061 | Skin | 1120 | UACC-62 | 456 | 6.317961 | 0.417 | 0.99 | 0.941 | 0.9531 | 0.9635 | 1.005 | 1.0535 | 1.0033 | 0.9903 |
| 026_1049_00269761 | Skin | 1049 | VMRC-MELG | 456 | 6.363031 | 0.904 | 0.991 | 0.949 | 0.974 | 0.9849 | 1.004 | 1.032 | 1.0282 | 1.0264 |
| 026_8077_00311281 | Skin | 8077 | IST-MEL1 | 456 | 6.486215 | 0.817 | 0.849 | 0.783 | 0.8212 | 0.8361 | 0.894 | 0.8282 | 0.9342 | 0.9134 |
| 026_1002_00262871 | Skin | 1002 | A2058 | 456 | 6.768535 | 0.494 | 1.023 | 0.918 | 0.9957 | 0.9334 | 0.899 | 0.9223 | 0.931 | 0.9502 |
| 026_1191_00266580 | Skin | 1191 | Hs 940.T | 456 | 7.017835 | 0.562 | 0.98 | 1.123 | 1.1931 | 0.9727 | 1.159 | 1.1334 | 1.0446 | 1.0643 |
| 026_8211_00306531 | Skin | 8211 | SK-MEL-24 | 456 | 7.240348 | 0.995 | 1.062 | 1.047 | 0.9379 | 1.0364 | 1.075 | 1.0521 | 1.0504 | 1.0137 |
| 026_1004_00262880 | Skin | 1004 | C32 | 456 | 7.407136 | 1.327 | 0.196 | 1.169 | 1.1356 | 1.1547 | 0.213 | 1.1935 | 0.7281 | 1.1468 |
| 026_8077_00263490 | Skin | 8077 | IST-MEL1 | 456 | 8.189893 | 1.25 | 1.21 | 1.184 | 1.1565 | 0.9453 | 0.931 | 1.1642 | 1.0861 | 1.0387 |
| 026_1076_00260350 | Stomach | 1076 | OCUM-1 | 456 | -1.975727 | 0.138 | 0.299 | 0.203 | 0.1441 | 0.1472 | 0.137 | 0.1598 | 0.2644 | 0.5747 |
| 026_1050_00262790 | Stomach | 1050 | AGS | 456 | 0.402284 | 0.198 | 0.304 | 0.337 | 0.4411 | 0.6201 | 0.452 | 0.6355 | 0.7729 | 1.0239 |
| 026_1070_00258920 | Stomach | 1070 | HSC-39 | 456 | 1.218484 | 0.163 | 0.38 | 0.469 | 0.5806 | 0.7048 | 0.892 | 1.16 | 0.922 | 1.1787 |
| 026_8193_00311240 | Stomach | 8193 | ECC10 | 456 | 1.328742 | 0.306 | 0.42 | 0.445 | 0.5445 | 0.7218 | 0.758 | 0.8813 | 0.9883 | 0.9993 |
| 026_1052_00255810 | Stomach | 1052 | SNU-1 | 456 | 1.425654 | 0.369 | 0.469 | 0.497 | 0.5342 | 0.5814 | 0.77 | 0.7984 | 0.8285 | 0.947 |
| 026_1056_00316590 | Stomach | 1056 | KATO III | 456 | 1.949149 | 0.309 | 0.531 | 0.622 | 0.6777 | 0.7504 | 0.912 | 0.9052 | 1.0407 | 1.0158 |
| 026_1060_00256830 | Stomach | 1060 | MKN45 | 456 | 2.285447 | 0.504 | 0.586 | 0.532 | 0.5224 | 0.5043 | 0.577 | 0.7757 | 0.8156 | 0.9028 |
| 026_1072_00258880 | Stomach | 1072 | 23132/87 | 456 | 2.907608 | 0.473 | 0.717 | 0.911 | 0.8748 | 1.0846 | 1.055 | 1.07 | 0.981 | 1.001 |
| 026_1060_00263910 | Stomach | 1060 | MKN45 | 456 | 2.913103 | 0.498 | 0.498 | 0.474 | 0.9422 | 0.5296 | 0.623 | 1.0575 | 0.9958 | 0.8867 |
| 026_1078_00263960 | Stomach | 1078 | IM-95 | 456 | 3.209661 | 0.348 | 0.625 | 0.723 | 1.042 | 0.7453 | 0.866 | 0.8746 | 0.9835 | 0.9734 |
| 026_1054_00308870 | Stomach | 1054 | SNU-16 | 456 | 3.34225 | 0.574 | 0.78 | 0.883 | 0.9578 | 0.9599 | 0.973 | 0.9861 | 1.0293 | 1.027 |

TABLE 22-continued

| | | | | | | | Viability ratio | | | | | | | |
|---|---|---|---|---|---|---|---|---|---|---|---|---|---|---|
| Barcode | Organ | Cell ID | Cell Line | Compound No | Fitted MGH_IC50 | 20 uM | 10 uM | 5 uM | 2.5 uM | 1.25 uM | 0.625 uM | 0.3125 uM | 0.15625 uM | 0.078125 uM |
| 026_1064_00258960 | Stomach | 1064 | NUGC-3 | 456 | 3.516892 | 0.253 | 0.754 | 0.947 | 0.9636 | 0.9596 | 1.019 | 1.0426 | 1.0278 | 1.0027 |
| 026_1075_00308260 | Stomach | 1075 | NUGC-4 | 456 | 3.652276 | 0.617 | 0.827 | 0.703 | 0.9984 | 1.0102 | 1.068 | 1.1379 | 0.9929 | 1.1512 |
| 026_1065_00273570 | Stomach | 1065 | MKN7 | 456 | 3.792655 | 0.621 | 0.777 | 0.872 | 0.891 | 0.9122 | 0.904 | 0.9197 | 0.9359 | 0.9547 |
| 026_1067_00311560 | Stomach | 1067 | RERF-GC-1B | 456 | 4.166168 | 0.732 | 0.677 | 0.761 | 0.8438 | 0.781 | 0.877 | 0.8716 | 0.958 | 1.0772 |
| 26_1067_00314080 | Stomach | 1067 | RERF-GC-1B | 456 | 4.402339 | 0.708 | 0.833 | 0.831 | 0.8383 | 0.8843 | 0.854 | 0.9212 | 0.9276 | 1.1227 |
| 026_1068_0028930 | Stomach | 1068 | MKN28 | 456 | 4.480011 | 0.554 | 0.885 | 0.897 | 0.9579 | 0.9774 | 1.009 | 1.0156 | 1.0042 | 1.0326 |
| 026_1057_00271310 | Stomach | 1057 | Hs 746T | 456 | 4.481195 | 0.745 | 0.743 | 0.677 | 0.6977 | 0.6882 | 0.86 | 0.875 | 0.9503 | 1.0984 |
| 026_1060_00260890 | Stomach | 1060 | MKN45 | 456 | 4.604315 | 0.753 | 0.738 | 0.731 | 0.6895 | 0.6891 | 0.836 | 1.0727 | 1.0008 | 0.9928 |
| 026_1051_00269200 | Stomach | 1051 | FU97 | 456 | 4.755599 | 0.738 | 0.851 | 0.914 | 0.8985 | 0.8947 | 0.955 | 0.9241 | 0.9866 | 1.0457 |
| 026_8187_00316461 | Stomach | 8187 | TGBC11TKB | 456 | 4.931222 | 0.775 | 0.953 | 0.925 | 0.9227 | 0.9488 | 0.988 | 0.9649 | 0.9982 | 0.9763 |
| 026_1058_00263730 | Stomach | 1058 | NCI-N87 | 456 | 5.400356 | 0.754 | 0.824 | 0.808 | 0.8382 | 0.8486 | 0.868 | 0.9105 | 0.9132 | 0.9828 |
| 026_1064_00264040 | Stomach | 1064 | NUGC-3 | 456 | 6.53754 | 0.915 | 1.021 | 1.007 | 1.0316 | 0.9966 | 1.014 | 1.0431 | 0.9819 | 1.0068 |
| 026_1077_00264820 | Stomach | 1077 | SCH | 456 | 6.77844 | 0.466 | 1.271 | 1.195 | 1.2103 | 1.1255 | 0.977 | 0.9179 | 1.1315 | 1.1153 |
| 026_1051_00265140 | Stomach | 1051 | FU97 | 456 | 6.812551 | 0.149 | 0.752 | 0.783 | 0.8562 | 0.833 | 0.758 | 0.8748 | 0.8287 | 0.8438 |
| 026_8067_00258320 | Stomach | 8067 | GT3TKB | 456 | 7.007727 | 0.623 | 0.977 | 1.004 | 1.0575 | 1.0443 | 1.026 | 1.0598 | 1.0143 | 1.0267 |
| 026_1053_00258360 | Stomach | 1053 | SNU-5 | 456 | 7.265878 | 1 | 0.967 | 0.868 | 0.95 | 0.958 | 1.018 | 1.0763 | 1.0284 | 1.0105 |
| 026_1073_00258910 | Stomach | 1073 | HGC-27 | 456 | 7.474785 | 0.055 | 1.003 | 1.012 | 1.0288 | 1.0225 | 1.013 | 1.0331 | 0.9845 | 0.9972 |
| 026_8062_00266170 | Stomach | 8062 | GCIY | 456 | 7.70033 | 1.076 | 1.218 | 0.962 | 1.0422 | 0.9155 | 1.202 | 0.9466 | 0.9302 | 1.1001 |
| 026_1059_00256820 | Stomach | 1059 | MKN1 | 456 | 7.84127 | 1.023 | 1.223 | 1.097 | 1.1806 | 1.0334 | 0.924 | 1.0209 | 0.9691 | 0.9885 |
| 026_8216_00258330 | Stomach | 8216 | RF-48 | 456 | 8.041101 | 0.627 | 1.056 | 1.075 | 1.0873 | 1.0084 | 1.031 | 1.0144 | 1.008 | 0.9914 |
| 026_8143_00302630 | Testes | 8143 | NTERA-S-cl-D1 | 456 | 4.238289 | 0.709 | 0.74 | 0.781 | 0.8439 | 0.8942 | 0.971 | 0.9553 | 0.9264 | 1.0878 |
| 026_1081_00299690 | Testes | 1081 | NCC-IT-A3 | 456 | 4.69755 | 0.834 | 0.925 | 0.99 | 1.0022 | 1.0753 | 0.959 | 1.0664 | 0.9907 | 0.9674 |
| 026_1082_00300430 | Testes | 1082 | NEC8 | 456 | 5.794775 | 0.518 | 0.919 | 1.026 | 1.1263 | 1.0267 | 0.882 | 1.2293 | 0.8206 | 0.9481 |
| 026_1087_00311210 | Thyroid | 1087 | BHT-101 | 456 | 0.094631 | 0.409 | 0.442 | 0.405 | 0.4025 | 0.4677 | 0.606 | 0.749 | 0.9156 | 0.9734 |
| 026_1098_00252970 | Thyroid | 1098 | IHH-4 | 456 | 0.734299 | 0.193 | 0.418 | 0.365 | 0.5027 | 0.4309 | 0.608 | 0.6796 | 0.9903 | 0.9333 |
| 026_1093_00253040 | Thyroid | 1093 | TT2609-C02 | 456 | 1.438563 | 0.33 | 0.462 | 0.489 | 0.4674 | 0.6027 | 0.719 | 0.8623 | 0.9552 | 1.0031 |
| 026_1100_00252990 | Thyroid | 1100 | KMH-2 | 456 | 1.898194 | 0.142 | 0.5 | 0.577 | 0.6566 | 0.6074 | 0.682 | 0.7694 | 0.8888 | 0.9822 |
| 026_1085_00252920 | Thyroid | 1085 | 8505C | 456 | 2.3348 | 0.536 | 0.498 | 0.605 | 0.5369 | 0.584 | 0.788 | 0.7985 | 1.0523 | 0.937 |
| 026_1088_00252930 | Thyroid | 1088 | CAL-62 | 456 | 2.495611 | 0.451 | 0.785 | 0.606 | 0.8114 | 0.6653 | 0.836 | 1.0285 | 1.0053 | 0.944 |
| 026_1089_00261010 | Thyroid | 1089 | HTC-C3 | 456 | 2.538171 | 0.577 | 0.55 | 0.623 | 0.7757 | 0.5886 | 0.616 | 0.7161 | 0.7476 | 0.9625 |
| 026_1090_00311330 | Thyroid | 1090 | ML-1 | 456 | 2.64388 | 0.368 | 0.64 | 0.793 | 0.8005 | 0.8127 | 0.931 | 0.9783 | 0.9389 | 1.0355 |
| 026_1090_00253010 | Thyroid | 1090 | ML-1 | 456 | 3.121258 | 0.165 | 0.778 | 0.787 | 0.6376 | 0.6432 | 0.975 | 1.0524 | 0.7737 | 1.0765 |
| 026_1087_00308850 | Thyroid | 1087 | BHT-101 | 456 | 3.18393 | 0.308 | 0.673 | 0.724 | 0.8112 | 0.8338 | 0.925 | 0.9016 | 0.8988 | 1.0407 |
| 026_1098_00255730 | Thyroid | 1098 | IHH-4 | 456 | 3.682081 | 0.171 | 0.695 | 0.763 | 0.7585 | 0.7239 | 0.856 | 0.9452 | 0.9473 | 1.0079 |
| 026_1086_00314210 | Thyroid | 1086 | B-CPAP | 456 | 4.407018 | 0.694 | 0.874 | 0.871 | 0.8186 | 0.9478 | 0.965 | 0.9497 | 1.0206 | 1.0176 |
| 026_8020_00266520 | Thyroid | 8020 | CGTH-W-1 | 456 | 4.442179 | 0.592 | 0.739 | 0.746 | 0.7517 | 0.73 | 0.793 | 0.8273 | 0.8894 | 0.8901 |
| 026_1084_00259200 | Thyroid | 1084 | 8305C | 456 | 4.648028 | 0.769 | 0.966 | 0.965 | 0.9831 | 0.9968 | 0.984 | 0.9765 | 0.9632 | 0.942 |
| 026_8213_00252980 | Thyroid | 8213 | TT | 456 | 6.262224 | 0.27 | 0.935 | 0.007 | 0.9319 | 0.951 | 0.93 | 0.997 | 0.9506 | 0.9691 |
| 026_8082_00306470 | Thyroid | 8082 | K5 | 456 | 6.573461 | 0.912 | 0.905 | 0.964 | 0.9293 | 0.932 | 0.965 | 0.9777 | 0.9947 | 1.0629 |
| 026_1099_00306470 | Thyroid | 1099 | ASH-3 | 456 | 6.767861 | 0.084 | 0.958 | 0.978 | 1.0951 | 1.0879 | 1.057 | 1.063 | 1.0254 | 0.8654 |
| 026_1094_00253110 | Thyroid | 1094 | FTC-133 | 456 | 7.698514 | 0.271 | 0.973 | 0.988 | 1.0669 | 1.039 | 1.047 | 1.018 | 1.0563 | 1.0542 |
| 026_1092_00252540 | Thyroid | 1092 | S-117 | 456 | 1.200178 | 0.685 | 1.079 | 1.053 | 1.0554 | 1.0411 | 1.049 | 1.0682 | 1.0349 | 1.0563 |
| 026_1097_00259160 | Thyroid | 1097 | RO82-W-1 | 456 | 2.281802 | 0.377 | 0.348 | 0.397 | 0.5545 | 0.7402 | 0.871 | 0.9778 | 0.9884 | 1.0288 |
| 026_8036_00304360 | Thyroid | 8036 | DSH1 | 456 | 2.448355 | 0.504 | 0.543 | 0.577 | 0.6272 | 0.7473 | 0.889 | 1.0564 | 1.0628 | 1.0768 |
| 26_24_00299840 | UrinaryTrack | 24 | RT4 | 456 | 2.668527 | 0.479 | 0.581 | 0.587 | 0.6728 | 0.7768 | 0.797 | 0.8705 | 1.106 | 1.03 |
| 026_18_00299720 | UrinaryTrack | 18 | RT-112 | 456 | 2.668527 | 0.216 | 0.59 | 0.634 | 0.6994 | 0.7144 | 0.855 | 0.9368 | 0.9696 | 1.0194 |
| 026_24_00257170 | UrinaryTrack | 24 | RT4 | 456 | 2.728478 | 0.679 | 0.605 | 0.639 | 0.6941 | 0.7355 | 0.829 | 0.9411 | 1.0033 | 1.0113 |
| 026_8036_00304360 | UrinaryTrack | 8036 | DSH1 | 456 | 2.896276 | 0.523 | 0.587 | 0.676 | 0.7538 | 0.7859 | 0.866 | 0.9594 | 0.9717 | 1.0348 |
| 026_9_00298850 | UrinaryTrack | 9 | SW 780 | 456 | | | | | | | | | | |

TABLE 22-continued

| Barcode | Organ | Cell ID | Cell Line | Compound No | Fitted MGH_IC50 | Viability ratio | | | | | | | |
|---|---|---|---|---|---|---|---|---|---|---|---|---|---|
| | | | | | | 20 uM | 10 uM | 5 uM | 2.5 uM | 1.25 uM | 0.625 uM | 0.3125 uM | 0.15625 uM | 0.078125 uM |
| 026_15_00316530 | UrinaryTrack | 15 | BFTC-905 | 456 | 3.218144 | 0.607 | 0.59 | 0.688 | 0.6971 | 0.8338 | 0.848 | 0.8978 | 1.0448 | 1.0799 |
| 026_8_00298880 | UrinaryTrack | 8 | UM-UC-3 | 456 | 3.221517 | 0.557 | 0.72 | 0.789 | 0.8471 | 0.8599 | 0.995 | 1.0484 | 1.045 | 1.0264 |
| 026_6_00303090 | UrinaryTrack | 6 | 5637 | 456 | 3.348554 | 0.726 | 0.725 | 0.744 | 0.7649 | 0.9313 | 0.918 | 0.9221 | 0.9563 | 1.0354 |
| 026_6_00256650 | UrinaryTrack | 6 | 5637 | 456 | 3.837233 | 0.504 | 0.703 | 0.715 | 0.7187 | 0.7189 | 0.755 | 0.9193 | 0.965 | 1.0004 |
| 026_8101_00256280 | UrinaryTrack | 8101 | LB831-BLC | 456 | 3.939929 | 0.697 | 0.835 | 0.952 | 1.0143 | 1.0014 | 1.01 | 0.9848 | 0.9739 | 0.9713 |
| 026_11_00298870 | UrinaryTrack | 11 | T24 | 456 | 4.120815 | 0.697 | 0.744 | 0.763 | 0.8533 | 0.8788 | 0.941 | 0.9969 | 1.0222 | 1.1105 |
| 026_19_00298860 | UrinaryTrack | 19 | SW-1710 | 456 | 4.713264 | 0.758 | 0.847 | 0.828 | 0.7824 | 0.8943 | 0.979 | 0.9968 | 1.0264 | 1.0955 |
| 026_7_00302400 | UrinaryTrack | 7 | SCaBER | 456 | 4.780909 | 0.779 | 0.775 | 0.708 | 0.9235 | 0.8163 | 0.882 | 1.0463 | 0.9494 | 1.0621 |
| 026_8101_00302620 | UrinaryTrack | 8101 | LB831-BLC | 456 | 4.856105 | 0.76 | 0.882 | 0.929 | 0.8692 | 0.9393 | 0.926 | 0.9386 | 0.9281 | 1.0507 |
| 026_22_00298810 | UrinaryTrack | 22 | HT 1376 | 456 | 4.888331 | 0.823 | 0.879 | 1.047 | 1.0283 | 0.988 | 1.0731 | 1.1432 | 1.097 |
| 026_20_00299740 | UrinaryTrack | 20 | VM-CUB1 | 456 | 4.987745 | 0.751 | 0.753 | 0.758 | 0.8989 | 0.8726 | 0.877 | 0.9581 | 0.9471 | 0.9762 |
| 026_14_00298780 | UrinaryTrack | 14 | 647-V | 456 | 5.049696 | 0.854 | 0.851 | 0.873 | 0.8859 | 0.9584 | 1.097 | 1.1389 | 1.2074 | 1.0083 |
| 026_12_00299730 | UrinaryTrack | 12 | TCCSUP | 456 | 5.306108 | 0.821 | 0.876 | 0.897 | 0.9178 | 0.9315 | 0.962 | 0.9176 | 1.0469 | 1.0217 |
| 026_13_00298770 | UrinaryTrack | 13 | 639-V | 456 | 5.658711 | 0.867 | 0.933 | 0.849 | 0.9317 | 0.8466 | 1.046 | 0.1223 | 1.1266 | 1.2765 |
| 026_16_00298800 | UrinaryTrack | 16 | CAL-29 | 456 | 5.956916 | 0.811 | 0.834 | 0.909 | 0.8884 | 0.9073 | 0.924 | 0.956 | 0.9709 | 0.9841 |
| 026_3_00308800 | UrinaryTrack | 3 | HT-1197 | 456 | 6.060787 | 0.877 | 0.935 | 0.984 | 0.8762 | 0.9541 | 0.87 | 1.0393 | 1.0266 | 1.0429 |
| 026_17_00300420 | UrinaryTrack | 17 | KU-19-19 | 456 | 6.388593 | 0.216 | 0.953 | 0.975 | 0.9996 | 0.9834 | 0.744 | 0.9959 | 0.9777 | 1.0473 |
| 026_10_00298820 | UrinaryTrack | 10 | J82 | 456 | 6.755266 | 0.951 | 0.965 | 0.925 | 0.9536 | 1.0393 | 1.06 | 1.0882 | 1.0657 | 1.037 |
| 026_8154_00262510 | Uterus | 8154 | RL95-2 | 456 | 0.033885 | 0.116 | 0.241 | 0.307 | 0.315 | 0.5516 | 0.413 | 0.6863 | 0.814 | 0.8778 |
| 026_1116_00268860 | Uterus | 1116 | SNG-M | 456 | 2.236003 | 0.377 | 0.605 | 0.635 | 0.4653 | 0.7155 | 0.805 | 0.9708 | 1.0702 | 1.1724 |
| 026_8154_00280250 | Uterus | 8154 | RL95-2 | 456 | 2.655708 | 0.475 | 0.611 | 0.69 | 0.5902 | 0.6865 | 0.677 | 0.826 | 0.8426 | 0.9723 |
| 026_8166_00269750 | Uterus | 8166 | SK-UT-1 | 456 | 2.769805 | 0.399 | 0.642 | 0.861 | 0.9305 | 0.8691 | 0.946 | 0.8217 | 0.867 | 0.9308 |
| 026_1115_00298850 | Uterus | 1115 | SKN | 456 | 3.232484 | 0.402 | 0.724 | 0.819 | 0.8345 | 0.9291 | 0.941 | 1.0001 | 0.9878 | 0.9814 |
| 026_1112_00268820 | Uterus | 1112 | Ishikawa (Heraldio) 02 ER- | 456 | 3.572844 | 0.62 | 0.659 | 0.62 | 0.6814 | 0.702 | 0.72 | 0.9036 | 0.8807 | 1.0744 |
| 026_1107_00311310 | Uterus | 1107 | MFE-296 | 456 | 3.590101 | 0.601 | 0.697 | 0.647 | 0.7074 | 0.7773 | 0.802 | 0.8186 | 0.9166 | 1.0105 |
| 026_1108_00308840 | Uterus | 1108 | MFE-319 | 456 | 3.953038 | 0.7 | 0.723 | 0.698 | 0.8033 | 0.8993 | 0.819 | 0.9773 | 1.1189 | 1.0369 |
| 026_1109_00269701 | Uterus | 1109 | COLO 684 | 456 | 4.059524 | 0.645 | 0.818 | 0.925 | 0.873 | 0.8541 | 0.934 | 0.9505 | 0.9782 | 1.0023 |
| 026_1102_00268790 | Uterus | 1102 | AN3CA | 456 | 4.238238 | 0.395 | 0.808 | 0.815 | 0.8203 | 0.9291 | 0.817 | 0.9786 | 0.9815 | 0.9877 |
| 026_1108_00314330 | Uterus | 1108 | MFE-319 | 456 | 4.375739 | 0.745 | 0.784 | 0.794 | 0.8526 | 0.9259 | 0.907 | 1.0498 | 1.0643 | 1.1339 |
| 026_1113_00268840 | Uterus | 1113 | MES-SA | 456 | 4.83984 | 0.832 | 0.962 | 1.003 | 0.9833 | 0.9906 | 0.984 | 0.9981 | 1.0121 | 0.9684 |
| 026_1117_00268810 | Uterus | 1117 | HEC-1 | 456 | 5.215029 | 0.824 | 0.904 | 0.885 | 0.8856 | 0.9834 | 0.972 | 0.9217 | 1.0697 | 1.0963 |
| 026_1113_00318661 | Uterus | 1113 | MES-SA | 456 | 5.307659 | 0.807 | 0.995 | 0.947 | 0.9632 | 1.0122 | 1.033 | 1.0384 | 1.0103 | 0.9636 |
| 026_8206_00264270 | Uterus | 8206 | KLE | 456 | 5.888467 | 0.885 | 1 | 1.029 | 1.0338 | 1.0454 | 1.029 | 0.9964 | 1.0291 | 0.9684 |
| 026_1105_00308190 | Uterus | 1105 | ESS-1 | 456 | 6.082924 | 0.887 | 0.915 | 0.911 | 0.9349 | 0.8927 | 0.94 | 0.9007 | 0.9407 | 0.9198 |
| 026_1104_00306500 | Uterus | 1104 | EN | 456 | 7.302741 | 1.047 | 0.983 | 0.999 | 0.9204 | 1.0053 | 1.011 | 1.0162 | 1.0749 | 1.0308 |
| 026_1106_00306510 | Uterus | 1106 | MFE-280 | 456 | 7.686964 | 1.124 | 0.983 | 1 | 0.9683 | 1.0601 | 1.156 | 1.0799 | 1.0206 | 0.9018 |
| 026_8163_00302640 | Vulva | 8163 | SK-LMS-1 | 456 | 2.4327011 | 0.479 | 0.526 | 0.621 | 0.7198 | 0.8786 | 0.991 | 1.0278 | 1.0369 | 1.1613 |
| 026_8173_00302660 | Vulva | 8173 | SW954 | 456 | 2.875791 | 0.539 | 0.622 | 0.644 | 0.6956 | 0.8294 | 0.866 | 1.072 | 1.0089 | 1.087 |
| 26_8174_00304380 | Vulva | 8174 | SW962 | 456 | 4.641057 | 0.756 | 0.704 | 0.824 | 0.7868 | 0.8056 | 0.875 | 0.851 | 0.96 | 1.0607 |
| 026_481_00302570 | Vulva | 481 | CAL-39 | 456 | 5.164144 | 0.803 | 0.856 | 0.841 | 0.8864 | 0.9389 | 0.924 | 0.983 | 0.9909 | 1.1127 |
| 026_8174_00306540 | Vulva | 8174 | SW962 | 456 | 6.896884 | 0.97 | 0.963 | 1.002 | 0.9267 | 1.0771 | 0.973 | 1.0027 | 1.0435 | 1.0588 |

Example 12

BVD-523 Demonstrates In Vivo Antitumor Activity in BRAF$^{V600E}$-Mutant Cancer Cell Line Xenograft Models Based on our in vitro findings that BVD-523 reduced proliferation and induced apoptosis in a concentration-dependent manner, BVD-523 was administered by oral gavage to demonstrate its in vivo anti-tumor activity in models with MAPK/ERK-pathway dependency. Xenograft models of melanoma (cell line A375), and colorectal cancer (cell line Colo205), were utilized, both of which harbor a BRAF$^{V600E}$ mutation.

Figure 31A:
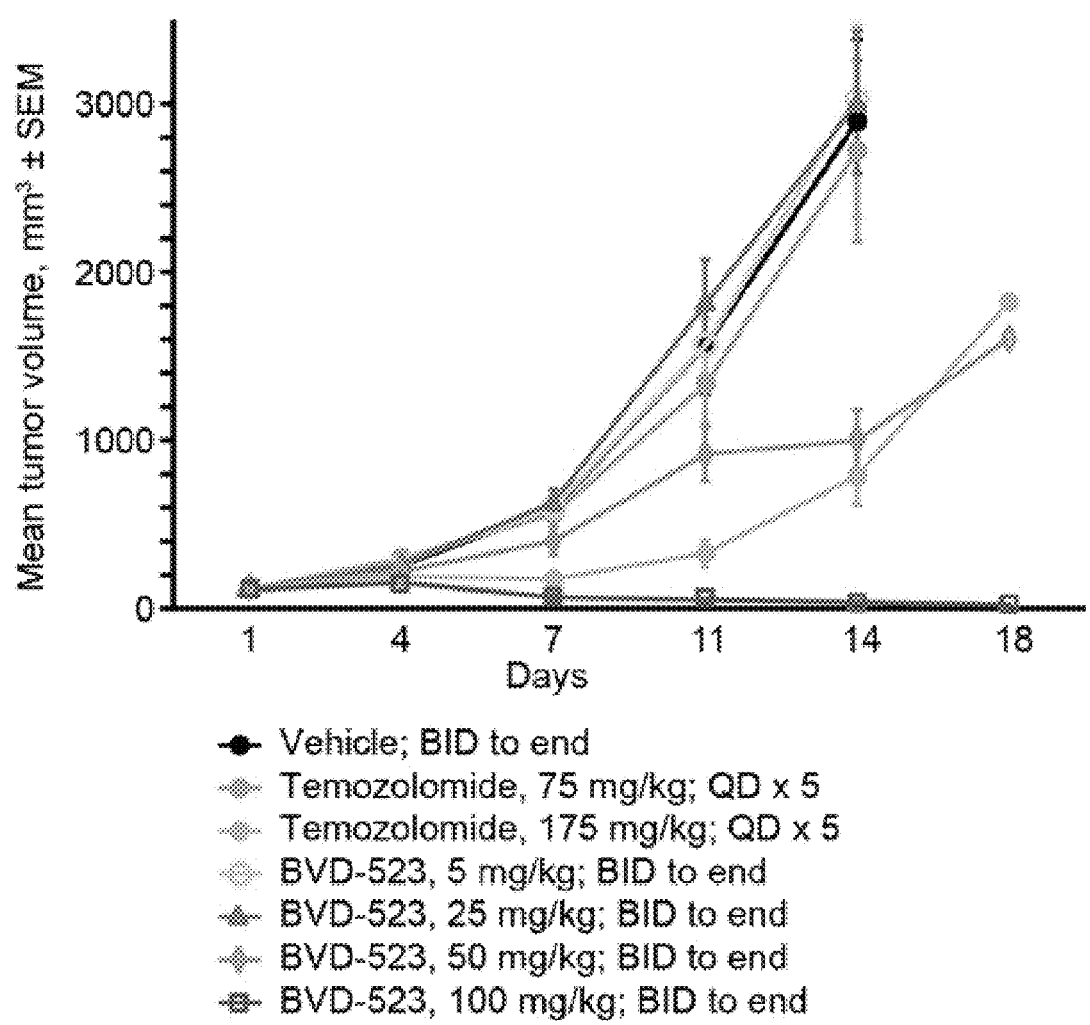
FIG. 31A-FIG. 31C show in vivo BVD-523 anti-tumor activity. BVD-523 monotherapy inhibits tumor growth in (FIG. 31A) A375 and (FIG. 31B) Colo205 cell line xenograft models ($^{a}P<0.0001$, compared with vehicle control; CPT-11 dosed on Day 14 and Day 18 only). Abbreviations: BID, twice daily; CMC, carboxymethylcellulose; QD, every day; Q4D, every 4 days.

In A375 cell line xenografts, BVD-523 efficacy was compared with the control cytotoxic alkylating agent temozolomide following 14 days of treatment. BVD-523 demonstrated significant dose-dependent antitumor activity starting at 50 mg/kg twice daily (BID) (FIG. 31A). Doses of 50 and 100 mg/kg BID significantly attenuated tumor growth, with tumor growth inhibition (TGI) of 71% (P=0.004) and 99% (P<0.001), respectively. Seven partial regressions (PRs) were noted in the 100 mg/kg BID group; no regression responses were noted in any other group. The efficacy observed compared favorably with that of temozolomide, which when administered at 75 and 175 mg/kg resulted in modest dose-dependent TGI of 34% (P>0.05) and 78% (P=0.005), respectively.

Figure 31B:
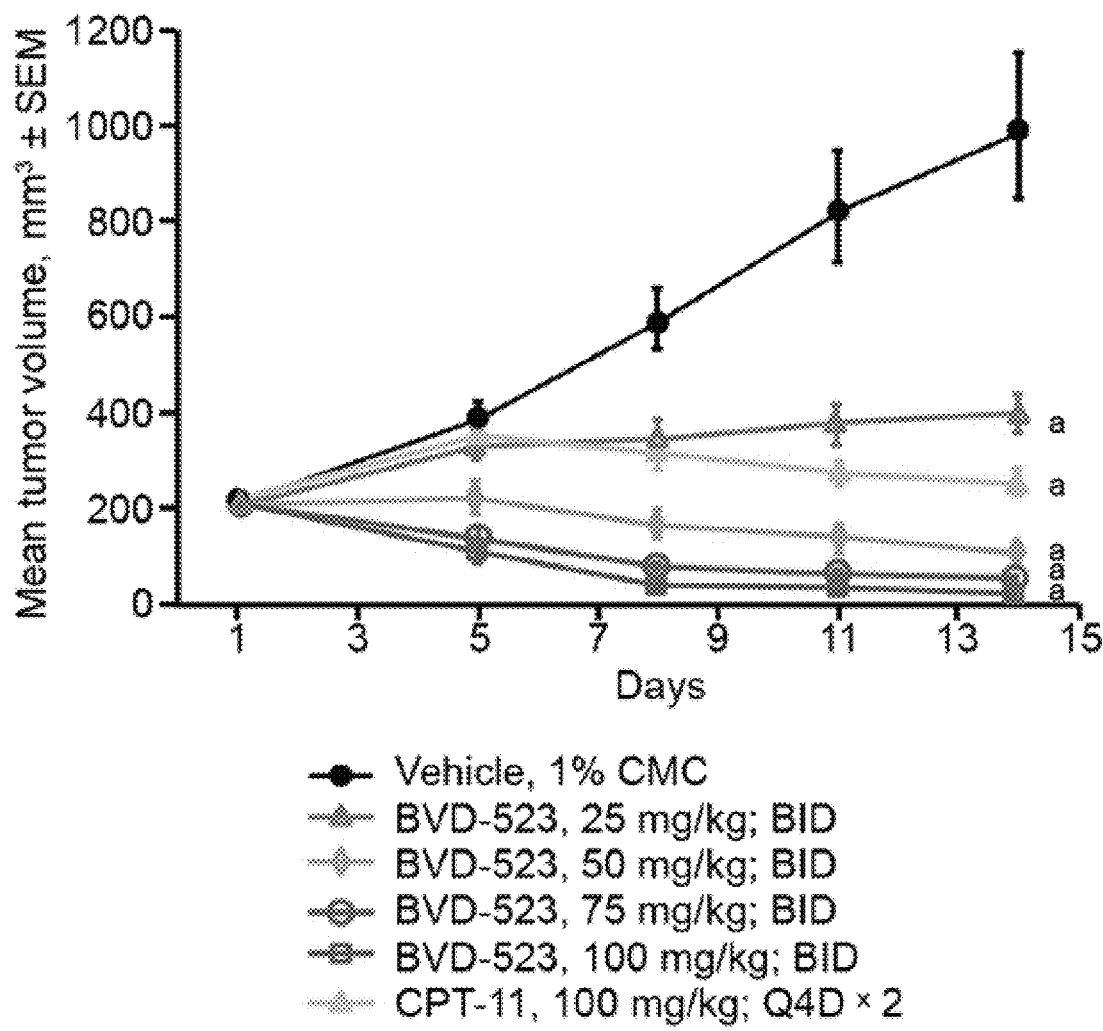

Additionally, BVD-523 demonstrated antitumor efficacy in a Colo205 human colorectal cancer cell line xenograft model (FIG. 31B). BVD-523 again showed significant dose-dependent tumor regressions at doses of 50, 75, and 100 mg/kg BID, yielding mean tumor regressions $T/T_i$ ($T$=End of treatment, $T_i$=Treatment initiation) of −48.2%, −77.2%, and −92.3%, respectively (all P<0.0001). Regression was not observed at the lowest dose of BVD-523 (25 mg/kg BID); however, significant tumor growth inhibition, with a T/C (T=Treatment, C=Control) of 25.2% (P<0.0001), was observed. Although not well tolerated, the positive control chemotherapeutic agent irinotecan (CPT-11) showed significant antitumor activity, inhibiting Colo205 tumor growth with a T/C of 6.4% (P<0.0001). However, even at its maximum tolerated dose in mice, CPT-11 was not as effective as BVD-523 at doses of 50, 75, or 100 mg/kg BID.

Figure 31C:
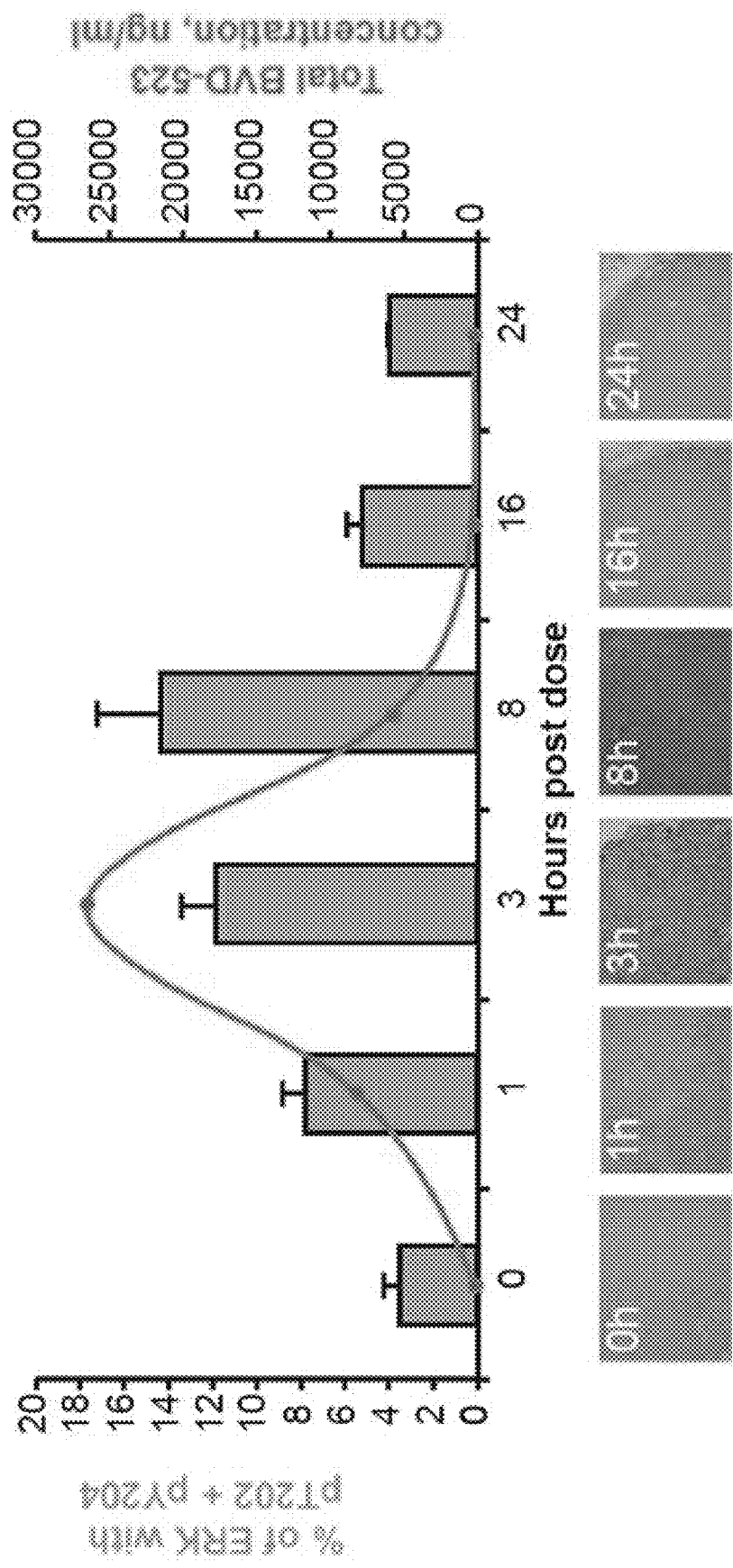

To establish the relationship between pharmacokinetics and pharmacodynamics, BVD-523 plasma concentrations were compared with pERK1/2 levels measured in the tumor by immunohistochemistry and isotope-tagged internal standard mass spectrometry over a 24-hour period following a single 100 mg/kg oral dose of BVD-523 (FIG. 31C). Phosphorylation of ERK1/2 was low in untreated tumors (0 hours). Following treatment with BVD-523, ERK1/2 phosphorylation steadily increased from 1 hour post-dose to maximal levels at 8 hours post-dose, then returned to pre-dose levels by 24 hours. This increase in pERK1/2 correlated with BVD-523 drug plasma concentrations. The in vivo observation of increased pERK1/2 with BVD-523 treatment is consistent with earlier in vitro findings (FIG. 30D).

Example 13

Figure 32A:
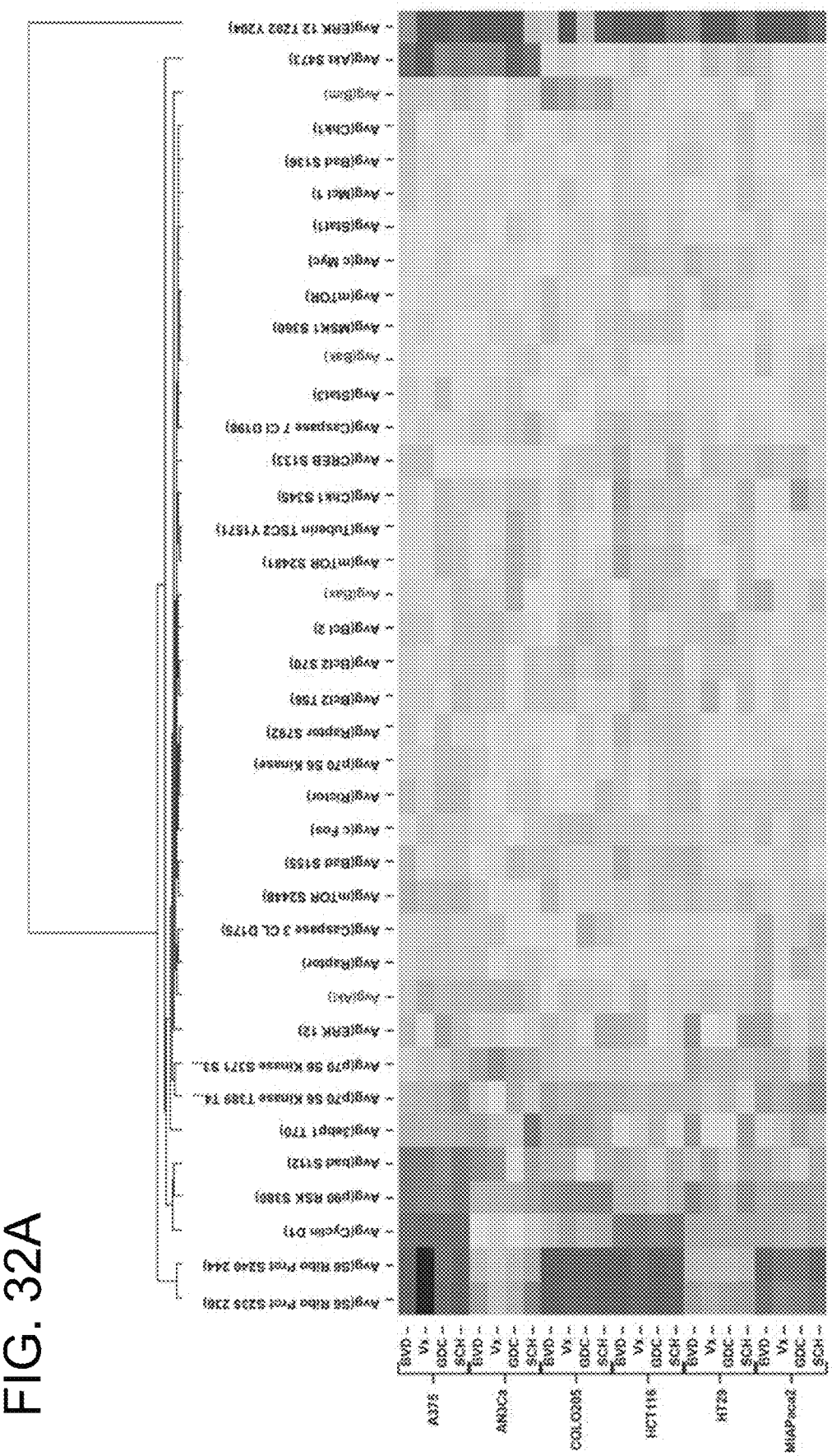
FIG. 32A shows signaling effects of ERK1/2 inhibitors. Using RPPA, effects on proteins are measured in cell lines (A375, AN3Ca, Colo205, HCT116, HT29 and MIAPaca2) following treatment with ERK1/2 inhibitors BVD-523 (BVD), Vx11e (Vx), GDC-0994 (GDC), or SCH722984 (SCH).
Figure 32B:
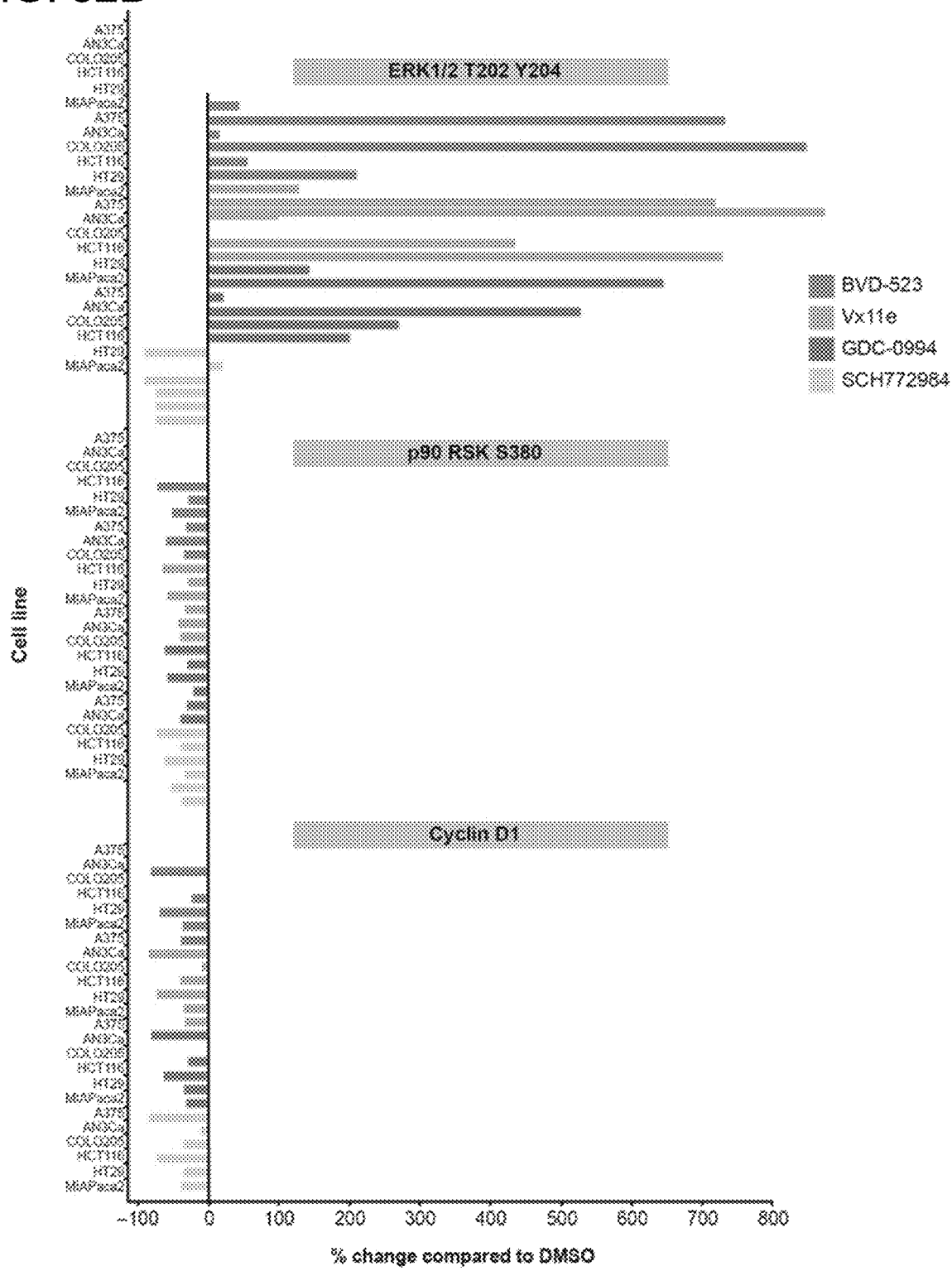
FIG. 32B shows that the ERK inhibitors BVD-523, GDC-0994, and Vx11e have differential effects on phospho-ERK (ERK 1/2 T202 Y204) compared with SCH722984; phospho-RSK (p90 RSK 380) and Cyclin D1 are inhibited by the ERK inhibitors tested. Abbreviations: BRAFi, BRAF inhibitors; MEKi, MEK inhibitors.

BVD-523 Results in ERK1/2 Substrate Inhibition Despite Increased ERK1/2 Phosphorylation To examine the effects of BVD-523 on signaling relative to other known ERK1/2 inhibitors (SCH772984, GDC-0994, and Vx-11e) (Morris et al. 2013 and Liu et al. 2015), a large-scale reverse phase protein array (RPPA) of approximately 40 proteins was employed in a variety of cell lines with sensitivity to ERK inhibition. Cell lines with common alterations in BRAF and RAS were assayed: BRAF$^{V600E}$ mutant lines A375, Colo205, and HT29; KRAS$^{G12C}$-mutant cell line MIAPACa-2; KRAS$^{G13D}$-mutant cell line HCT116; and AN3Ca with atypical HRAS$^{F82L}$ mutation. Changes in protein levels are shown as a percentage change from dimethyl sulfoxide (DMSO)-treated parental control (FIG. 32A and Table 23). All ERK inhibitors elicited qualitatively similar protein effects, with the exception of phosphorylation of ERK1/2 (pERK1/2 [ERK1/2-T202, -Y204]); SCH7722984 inhibited pERK1/2 in all cell lines, while BVD-523, GDC-0994, and Vx-11e markedly increased pERK1/2. Phospho-p90 RSK (pRSK1) and cyclin D1, which are proximal and distal targets of pERK1/2, respectively, were similarly inhibited by all inhibitors tested regardless of the degree of ERK1/2 phosphorylation (FIG. 32B). These independent findings for BVD-523 are consistent with studies showing that phosphorylation of ERK1/2 substrates RSK1/2 remained inhibited despite dramatically elevated pERK1/2 by Western blots in A375 cells (FIG. 32D), in addition to protein-binding studies demonstrating BVD-523 binding and stabilization of pERK1/2 and inactive ERK1/2 (FIG. 29E and FIG. 29F). Therefore, measuring increased pERK1/2 levels could be considered as a clinical pharmacodynamic biomarker for BVD-523, while quantifying inhibition of ERK1/2 targets such as pRSK1 and DUSP6 as well could serve a similar purpose.

Figure 33:
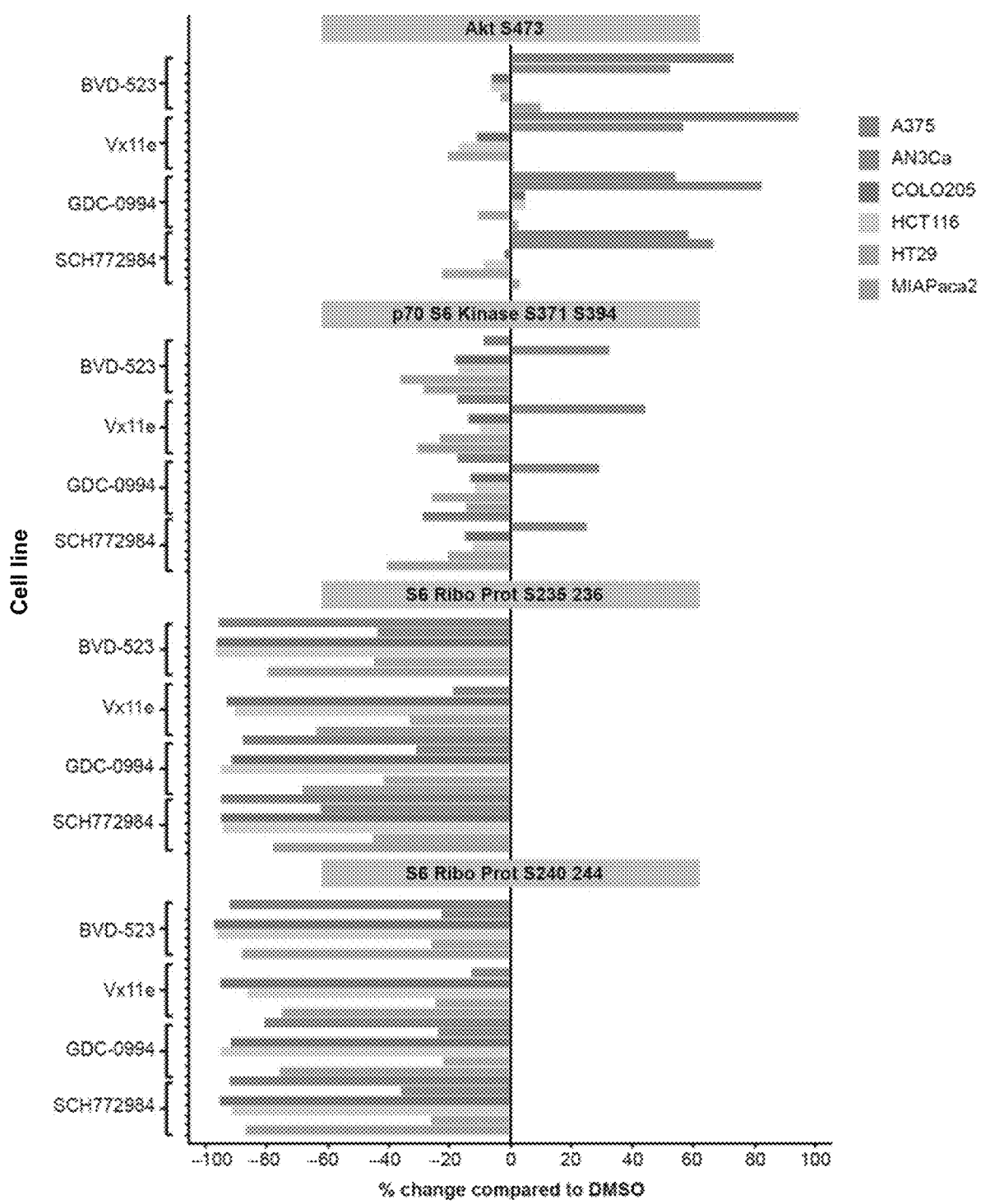
FIG. 33 shows that the ERK inhibitors BVD-523, Vx11, GDC-0994, and SCH772984 (SCH) demonstrate cell line-dependent changes in phospho-ATK levels. Abbreviation: DMSO, dimethyl sulfoxide.

Additional protein changes are of note in this RPPA dataset (FIG. 32A). Decreased pS6-ribosomal protein appears to be another pharmacodynamic marker of ERK1/2 inhibition, as evidenced in all cell lines with all compounds (FIG. 32B). Furthermore, prominent induction of pAKT appears to be a cell line-dependent observation, where each ERK1/2 inhibitor induced pAKT in cell lines A375 and AN3CA cells (FIG. 33). Interestingly, the degree of inhibition of survival marker pBAD appears to differ between compounds, with only modest inhibition of pBAD by GDC-0994 compared with the other ERK1/2 inhibitors tested (FIG. 32A).

Figure 32C:
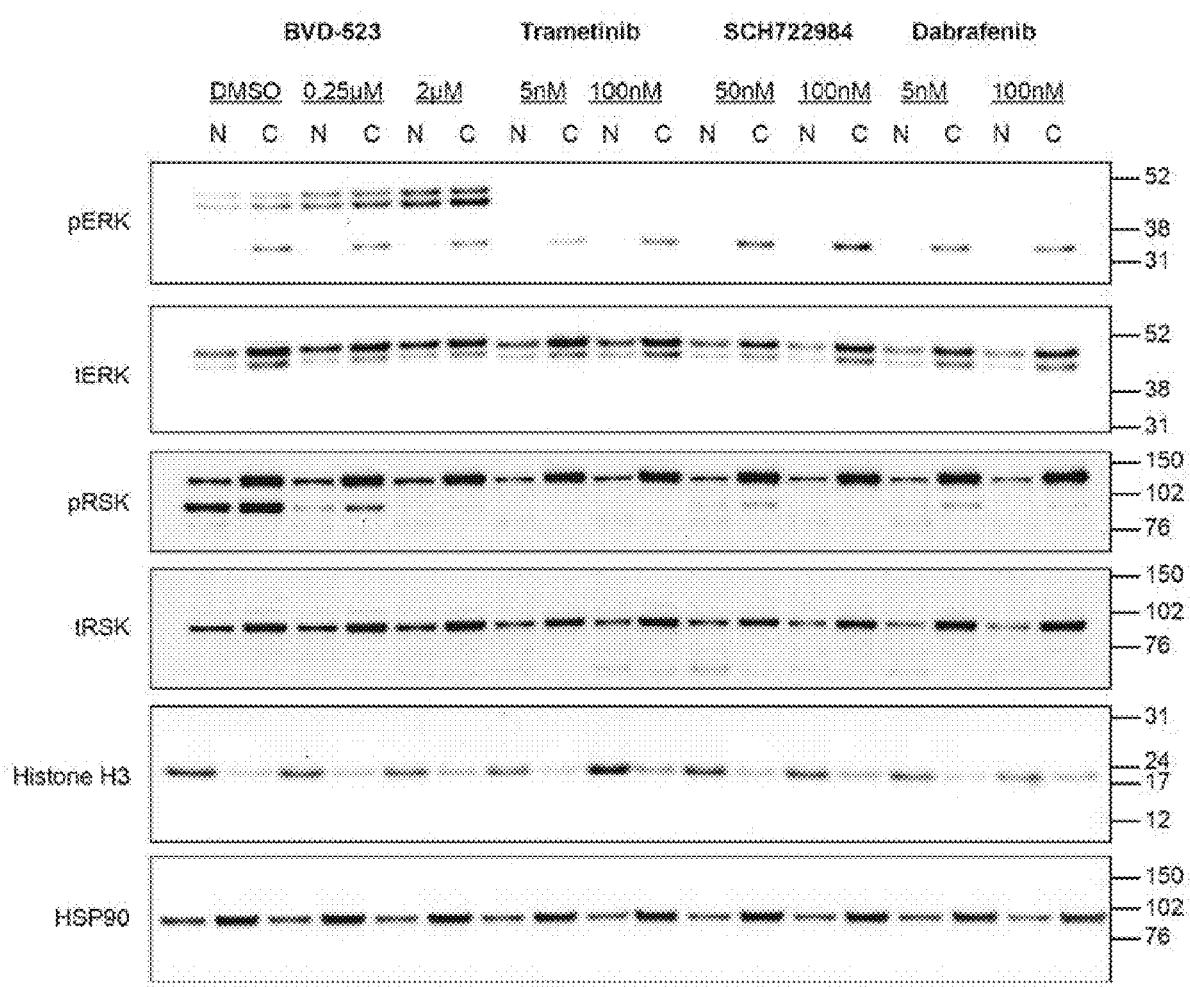
FIG. 32C shows a western blot assay of cellular and nuclear fractions from a RKO cell line following treatment with BVD-523, trametinib, SCH722984, or dabrafenib. Histone H3 (nuclear localized protein) and HSP90 (cytoplasmically localized protein) were included as positive controls to confirm that the nuclear and cytoplasmic fractions were properly enriched; nuclear fractions have high H3 and cytoplasmic fractions have higher HSP90.

Next, how BVD-523 affects cellular localization of ERK1/2 and downstream target pRSK in a BRAF$^{V600E}$-mutant RKO colorectal cell line (FIG. 32C) was investigated. In resting cells, ERK1/2 localizes to the cytoplasm, and once stimulated pERK1/2 migrates to target organelles, particularly the nucleus where transcriptional targets are activated (Weinstein et al. 2016). In DMSO-treated control cells, pERK1/2 is evident in both nuclear and cytoplasmic fractions, which is likely reflective of MAPK pathway activity due to the presence of BRAF$^{V600E}$ in this cell line. Treatment with BVD-523 resulted in elevated pERK1/2 in the nucleus and cytoplasm as well as a modest increase in nuclear total ERK1/2 compared with DMSO-treated cells, suggesting that compound-induced stabilization of pERK1/2 stimulates some nuclear translocation. Despite increased pERK1/2 in both compartments, pRSK levels are lower in the cytoplasmic and nuclear compartments compared with DMSO control. Comparator MAPK signaling inhibitors (i.e., trametinib, SCH7722984, dabrafenib) inhibited phosphorylation of ERK1/2 and RSK, as reflected by lower levels in the nuclear and cytoplasmic compartments. These data again suggest that BVD-523-associated increases in pERK1/2 are evident in both the cytoplasm and nucleus; however, this does not translate to activation of target substrates. This is consistent with data presented in FIG. 30D and FIG. 32A.

TABLE 23

| | | % change from DMSO (matched cell line) | | | | | |
|---|---|---|---|---|---|---|---|
| Cell Line | Treatment | Avg(S6 Ribo Prot S235 236) | Avg(S6 Ribo Prot S240 244) | Avg(Cyclin D1) | Avg(p90 RSK S380) | Avg(bad S112) | Avg(4ebp1 T70) |
| A375 | BVD | −95.3 | −91.98 | −81.45 | −71 | −72.37 | −31.82 |
| A375 | Vx | (Empty) | (Empty) | −85.46 | −65.25 | −69.29 | 23.33 |
| A375 | GDC | −87.61 | −80.3 | −81.65 | −60.74 | −55.32 | −29.47 |
| A375 | SCH | −94.71 | −91.78 | −84.05 | −72.44 | −71.44 | −31.75 |
| AN3Ca | BVD | −43.41 | −22.2 | −0.69 | −28.11 | −54.1 | 32.17 |
| AN3Ca | Vx | −18.54 | −12.55 | −9.59 | −28.41 | −45.63 | 16.67 |
| AN3Ca | GDC | −30.74 | −23.47 | 0.34 | −29.44 | 2.53 | 11.28 |
| AN3Ca | SCH | −61.99 | −35.88 | −11.33 | −40.26 | −39.14 | 61.57 |
| COLO205 | BVD | −96.15 | −97.33 | −23.65 | −50.84 | −31.51 | −36.35 |
| COLO205 | Vx | −93.04 | −94.89 | −39.79 | −58.6 | −30.28 | −43.71 |
| COLO205 | GDC | −91.19 | −91.59 | −28.02 | −57.5 | −6.12 | −36.69 |
| COLO205 | SCH | −94.67 | −95.09 | −36.7 | −62.31 | −29.4 | −27.51 |
| HCT116 | BVD | −96.31 | −96.26 | −69.62 | −31.81 | −34.27 | 4.03 |
| HCT116 | Vx | −90.03 | −86.06 | −72.72 | −33.05 | −23.88 | 10.35 |
| HCT116 | GDC | −94.82 | −95.1 | −63.59 | −22.25 | −12.36 | 20.5 |
| HCT116 | SCH | −93.86 | −91.07 | −73.21 | −33.7 | −31.29 | 5.6 |
| HT29 | BVD | −44.68 | −25.67 | −37.21 | −60.5 | −20.66 | −41.47 |
| HT29 | Vx | −32.8 | −24.35 | −35.2 | −43.41 | −35.62 | −2.89 |
| HT29 | GDC | −41.45 | −21.74 | −35.69 | −30.59 | −12.98 | 1.95 |
| HT29 | SCH | −44.9 | −25.73 | −36.66 | −53.88 | −33.9 | −40.58 |
| MIAPaca2 | BVD | −79.46 | −88.03 | −37.9 | −35 | −30.29 | −9.42 |
| MIAPaca2 | Vx | −63.36 | −74.82 | −33.96 | −39.91 | −20.85 | −15.72 |
| MIAPaca2 | GDC | −67.9 | −75.59 | −31.92 | −39.09 | −10.08 | −34.01 |
| MIAPaca2 | SCH | −77.57 | −86.61 | −39.88 | −38.58 | −33.07 | 19.27 |

| | | % change from DMSO (matched cell line) | | | | | |
|---|---|---|---|---|---|---|---|
| Cell Line | Treatment | Avg(p70 S6 Kinase T389 T412) | Avg(p70 S6 Kinase S371 S394) | Avg(ERK 1 2) | Avg(Akt) | Avg(Raptor) | Avg(Caspase 3 CL D175) |
| A375 | BVD | −23.79 | −8.58 | −22.91 | −14.03 | −7.77 | −8.06 |
| A375 | Vx | −25.54 | −17.32 | −5.39 | −30.34 | −12.7 | −9.27 |
| A375 | GDC | −31.9 | −17.34 | 31.55 | −20.7 | −14.32 | −16.74 |
| A375 | SCH | −42.73 | −28.72 | −21.65 | −23.26 | −11.66 | −9.87 |
| AN3Ca | BVD | −14.78 | 32.26 | −9.05 | −22.43 | −13.82 | −10.8 |
| AN3Ca | Vx | 0.56 | 44.04 | −11.27 | −24.62 | −2.47 | −12.7 |
| AN3Ca | GDC | 26.01 | 29.09 | −2.87 | −26.04 | −8.05 | 1.55 |
| AN3Ca | SCH | −16.63 | 24.56 | −9.27 | −16.35 | −11.09 | 1.25 |
| COLO205 | BVD | −36.4 | −18.11 | −18.83 | −3.85 | −7.14 | −3.18 |
| COLO205 | Vx | −28 | −13.64 | −12.32 | −12.51 | −0.05 | −2.67 |
| COLO205 | GDC | −32.2 | −13.02 | −3.33 | −11.83 | −5.48 | 23.06 |
| COLO205 | SCH | −30.4 | −14.59 | −31.87 | −10.31 | −2.2 | 14.08 |
| HCT116 | BVD | −28.11 | −16.9 | −29.42 | 4.41 | −7.06 | −10.11 |
| HCT116 | Vx | −20.99 | −9.89 | −24.01 | −18.15 | −4.32 | −5.19 |
| HCT116 | GDC | −24.73 | −11.47 | −1.9 | −6.13 | −6.2 | −8.36 |
| HCT116 | SCH | −24.63 | −12.3 | −10.22 | −9.86 | −9.66 | −4.63 |
| HT29 | BVD | −24.58 | −35.94 | −44.3 | −13.41 | −8.53 | −7.03 |
| HT29 | Vx | −12.31 | −22.86 | 0.24 | −17.84 | −6.53 | −2.86 |
| HT29 | GDC | −20.86 | −25.73 | 4.66 | −10.01 | −6.85 | −3.44 |
| HT29 | SCH | −9.55 | −20.52 | −37 | −16.93 | −12.18 | −7.9 |
| MIAPaca2 | BVD | −39.23 | −28.27 | −40.33 | 23.63 | 21.15 | 22.35 |
| MIAPaca2 | Vx | −30.66 | −30.35 | −14.85 | −0.15 | 5.4 | 6.17 |
| MIAPaca2 | GDC | −40.99 | −14.4 | −6.88 | 4.33 | 22.43 | 10.47 |
| MIAPaca2 | SCH | −50.97 | −40.47 | −23.09 | 13.47 | 17.66 | 21.05 |

| | | % change from DMSO (matched cell line) | | | | | |
|---|---|---|---|---|---|---|---|
| Cell Line | Treatment | Avg(mTOR S2448) | Avg(Bad S155) | Avg(c Fos) | Avg(Rictor) | Avg(p70 S6 Kinase) | Avg(Raptor S792) | Avg(Bcl 2 T56) |
| A375 | BVD | −27.87 | −21.9 | 4.39 | −20.11 | −7.6 | −10.33 | −8.54 |
| A375 | Vx | −21.66 | −6.3 | −13.65 | −8.16 | −6.42 | −0.86 | −7.53 |
| A375 | GDC | −23.61 | −13.31 | −12.46 | −23.29 | −18.11 | −15.93 | −4.1 |
| A375 | SCH | −26.17 | −13.86 | −12.51 | −22.13 | −17.66 | −6.89 | −19.55 |
| AN3Ca | BVD | −10.79 | 0.66 | −5.15 | −4.52 | −10.27 | −8.47 | −12.85 |
| AN3Ca | Vx | −2.37 | 4.59 | −5.52 | 0.02 | −2.33 | 0.37 | −11.73 |
| AN3Ca | GDC | −2.96 | 17.31 | −0.63 | −9.21 | −3.67 | 4.85 | 1.23 |
| AN3Ca | SCH | −4.84 | 12.92 | −9.18 | −10.89 | −7.71 | −4.03 | −10.73 |

TABLE 23-continued

| Cell Line | Treatment | | | | | | |
|---|---|---|---|---|---|---|---|
| COLO205 | BVD | −23.51 | −18.18 | −12.25 | −5.21 | 0.14 | 0.41 | −11.84 |
| COLO205 | Vx | −8.52 | −9.72 | −19.34 | 1.65 | −3.42 | 0.2 | −12.02 |
| COLO205 | GDC | −7.36 | −9.11 | −21.33 | −5.04 | 5.83 | −9.04 | −4.6 |
| COLO205 | SCH | −9.44 | −10.96 | −15.17 | −19.07 | −2.85 | −4.17 | −6.73 |
| HCT116 | BVD | −12.78 | −30.72 | −14.08 | −13.05 | −12.86 | −22.04 | −8.36 |
| HCT116 | Vx | −10.12 | −15.59 | −13.89 | 1.78 | −4.45 | −11.21 | −25 |
| HCT116 | GDC | −19.33 | −19.71 | −10.36 | −10.98 | −9.9 | −15.77 | −11.96 |
| HCT116 | SCH | −16.05 | −22.96 | −15.27 | −18.5 | −14.12 | −18.18 | −15.89 |
| HT29 | BVD | −20.68 | −25.9 | −13.48 | −18.76 | −10.64 | −10.48 | −8.18 |
| HT29 | Vx | −13.94 | −11.26 | −8.23 | −2.6 | −1.72 | −2.13 | −25.01 |
| HT29 | GDC | −11.44 | −6.7 | −12.92 | −10.62 | −2.83 | −1.75 | 1.61 |
| HT29 | SCH | −22.65 | −7.98 | −9.26 | −13.03 | −2.36 | −6.38 | −17.9 |
| MIAPaca2 | BVD | −11.73 | −5.65 | −18.44 | −11.11 | −3.59 | 5.95 | −1.78 |
| MIAPaca2 | Vx | −5.38 | 7.38 | −4.43 | −13.24 | −9.27 | −3.74 | −9.86 |
| MIAPaca2 | GDC | 11.84 | 8.18 | −16.12 | −11.25 | −3.25 | 2.18 | −2.12 |
| MIAPaca2 | SCH | −11.48 | −1.71 | −8.99 | −15.15 | −7.51 | 4.43 | −1.98 |

| | | % change from DMSO (matched cell line) | | | | | | |
|---|---|---|---|---|---|---|---|
| Cell Line | Treatment | Avg(Bcl2 S70) | Avg(Bcl 2) | Avg(Bax) | Avg(mTOR S2481) | Avg(Tuberin TSC2 Y1571) | Avg(Chk1 S345) | Avg(CREB S133) |
| A375 | BVD | −7.91 | −12.55 | −6.98 | −3.36 | −6.32 | −7.43 | −12.65 |
| A375 | Vx | −4.02 | −9.93 | −5.05 | −2.9 | −3.55 | 0.56 | −15.8 |
| A375 | GDC | 6.3 | −3.13 | 3.97 | −19.37 | −16.74 | −18.35 | −1.18 |
| A375 | SCH | −12.91 | −18.53 | −17.32 | −15.82 | −13.7 | −10.59 | −1.55 |
| AN3Ca | BVD | −14.81 | −16.83 | −10.47 | 2.75 | 2.86 | −13.34 | 1.03 |
| AN3Ca | Vx | −14.39 | −18.77 | −7.89 | 7.22 | 3.8 | −9.54 | 0.16 |
| AN3Ca | GDC | −0.65 | 7.8 | 23.83 | 25.42 | 25.18 | 15.46 | 5.03 |
| AN3Ca | SCH | −12.42 | −5.14 | 0.15 | 11.24 | 13.44 | 14.56 | 3.64 |
| COLO205 | BVD | −10.2 | −0.13 | 0.28 | −1.33 | −3.48 | −4.63 | −2.67 |
| COLO205 | Vx | −20.82 | −14.09 | −9.16 | −9.43 | −9.45 | 13.12 | −10.64 |
| COLO205 | GDC | −9 | 17.95 | 8.2 | 0.96 | 0.66 | 6.08 | −11.85 |
| COLO205 | SCH | −18.52 | −14.56 | −6.44 | −6.68 | −1.38 | 1 | −14.56 |
| HCT116 | BVD | −8.23 | −3.59 | −0.8 | −34.09 | −29.89 | −39.65 | −30.64 |
| HCT116 | Vx | −17.79 | −17.3 | −20.46 | −17.82 | −16.51 | −16.49 | −9.17 |
| HCT116 | GDC | −12.53 | −4.56 | −20.11 | −18.34 | −9.4 | −18.77 | −8.56 |
| HCT116 | SCH | −18.34 | −10.58 | −13.86 | −22.53 | −16.17 | −18.51 | −24.18 |
| HT29 | BVD | 2.83 | 10.68 | 8.39 | −8.64 | 0.66 | −13.48 | −3.46 |
| HT29 | Vx | −12.55 | −16.73 | −18.47 | 0.52 | 2.85 | 6.44 | 14.16 |
| HT29 | GDC | 10.59 | 18.16 | 1.1 | 3.23 | 11.86 | 6.88 | 9.54 |
| HT29 | SCH | −11.45 | −10.01 | −20.59 | 13.93 | 13.25 | 19.05 | 9.87 |
| MIAPaca2 | BVD | 0.89 | 5.86 | 23.44 | −0.24 | 1.7 | 1.2 | −19.26 |
| MIAPaca2 | Vx | −7.83 | −2.3 | 4.33 | −3.12 | −0.01 | 2.09 | −13.28 |
| MIAPaca2 | GDC | −6.78 | −7.8 | 3.48 | 3.65 | 5.71 | 32.96 | −21.37 |
| MIAPaca2 | SCH | −4.23 | 4.96 | 15.67 | 2.43 | 8.86 | 13.39 | −6.63 |

| | | % change from DMSO (matched cell line) | | | | | | |
|---|---|---|---|---|---|---|---|
| Cell Line | Treatment | Avg(Caspase 7 Cl D198) | Avg(Stat3) | Avg(Bak) | Avg(MAK1 S360) | Avg(mTOR) | Avg(c Myc) | Avg(Stat1) | Avg(Mcl1) |
| A375 | BVD | 3.18 | 6.02 | −3.26 | 3.35 | 0.2 | 2.56 | 1.32 | 10.67 |
| A375 | Vx | −7.62 | 1.71 | 0.65 | −7.63 | −3.31 | −0.97 | 0.23 | 1.6 |
| A375 | GDC | −5.53 | 14.24 | 2.76 | −5.21 | −6.2 | −9.11 | −5.67 | −9.09 |
| A375 | SCH | −6 | −1.42 | −2.37 | 0.97 | −5.18 | 1.86 | −6.01 | 2.11 |
| AN3Ca | BVD | −12.35 | −4.97 | 3.38 | 0.49 | 5.58 | −0.58 | −5.65 | −4.9 |
| AN3Ca | Vx | −8.09 | −7.67 | −1.6 | 6.83 | −6.27 | −5.47 | −0.83 | −4.24 |
| AN3Ca | GDC | −15.56 | −13.05 | 7.33 | 6.84 | −2.85 | 3.99 | 9.15 | −4.16 |
| AN3Ca | SCH | −24.17 | −6.01 | 9.73 | −5.02 | −5.33 | 0.88 | 5.52 | −7.15 |
| COLO205 | BVD | 6.76 | −2.58 | 3.79 | 14.69 | 12.77 | −1.11 | 0.53 | −2.7 |
| COLO205 | Vx | 0.03 | −7.96 | −2.79 | 6.22 | 3.62 | −7.42 | −6.1 | −10.64 |
| COLO205 | GDC | 1.37 | −0.86 | 6.58 | 0.82 | 3.39 | −6.22 | 7.26 | 2.5 |
| COLO205 | SCH | 12.36 | −6.1 | 4.59 | 7.54 | −5.62 | −0.64 | −4.31 | −0.14 |
| HCT116 | BVD | −21.09 | −5.52 | −13.16 | −13.45 | −11.96 | −11.15 | −13.76 | −8.72 |
| HCT116 | Vx | −11.41 | −7.76 | −3.07 | −13.73 | −0.59 | −18.56 | −14.06 | −7.79 |
| HCT116 | GDC | −13.99 | −0.25 | −1.74 | −12.93 | −4.85 | −12.03 | −6.32 | −4.77 |
| HCT116 | SCH | −16.35 | −7.67 | −4.66 | −15.32 | −12.56 | −12.86 | −10.74 | −6.55 |
| HT29 | BVD | −6.93 | −6.46 | −1.42 | 1.49 | 5.02 | 17.85 | 4.74 | −2.83 |
| HT29 | Vx | 8.28 | −4.28 | 2.69 | 5.64 | 16.94 | 10.71 | 4.29 | 1.36 |
| HT29 | GDC | −0.88 | −3.69 | 3.56 | −0.04 | 10.45 | 7.56 | 2.58 | 3.71 |
| HT29 | SCH | 7.02 | −2.15 | 2.78 | 1.25 | 9.31 | 13.55 | 5.79 | 14.05 |
| MIAPaca2 | BVD | −6.44 | −1.23 | −15.15 | −10.72 | −3.27 | −8.77 | 8.62 | −7.27 |
| MIAPaca2 | Vx | −0.32 | 0.61 | −1.93 | −0.87 | −1.58 | −5.94 | −1.64 | −6.58 |
| MIAPaca2 | GDC | −4.92 | −9.44 | −8.11 | −5.25 | −9.8 | −7.84 | 7.4 | −1.79 |
| MIAPaca2 | SCH | 8.35 | −9.19 | −10.88 | 2.74 | 1.64 | 2.11 | 7.17 | −1.88 |

TABLE 23-continued

| | | % change from DMSO (matched cell line) | | | | |
|---|---|---|---|---|---|---|
| Cell Line | Treatment | Avg(Bad S136) | Avg(Chk1) | Avg(Bim) | Avg(Akt S473) | Avg(ERK 1 2 T202 Y204) |
| A375 | BVD | 12.31 | 16.94 | 14.57 | 73.07 | 43.34 |
| A375 | Vx | 5.06 | −0.86 | 12.32 | 93.85 | 128.93 |
| A375 | GDC | −6.21 | −7.72 | 9.8 | 53.66 | 142.37 |
| A375 | SCH | 5.32 | 2.83 | 17.52 | 58.13 | −90.63 |
| AN3Ca | BVD | −1.02 | −8.45 | −12.57 | 52.11 | 733.27 |
| AN3Ca | Vx | −3.81 | −0.46 | −1.46 | 56.17 | 718.94 |
| AN3Ca | GDC | 0.71 | 9.43 | −11.63 | 82.37 | 645.51 |
| AN3Ca | SCH | 5.26 | 1.35 | −14.09 | 66.17 | 19.75 |
| COLO205 | BVD | 5.05 | −2.86 | 41.73 | −5.78 | 14.39 |
| COLO205 | Vx | −1.01 | −9.16 | 34.1 | −10.96 | 98.48 |
| COLO205 | GDC | 4 | 5.06 | 20.59 | 4.45 | 20.01 |
| COLO205 | SCH | 1.88 | 7.49 | 29.22 | −1.74 | −91.43 |
| HCT116 | BVD | −11.49 | −11.26 | 12.44 | −6.14 | 849.12 |
| HCT116 | Vx | −5.39 | −8.63 | 4.82 | −16.94 | 873.33 |
| HCT116 | GDC | −1.24 | 2.28 | 6.2 | 4.69 | 526.64 |
| HCT116 | SCH | −10.55 | −5.58 | 1.95 | −8.76 | −75.21 |
| HT29 | BVD | 10.73 | 7.4 | 2.81 | −3.06 | 54.82 |
| HT29 | Vx | 5.53 | 4.68 | 3.12 | −20.5 | 435.68 |
| HT29 | GDC | 2 | 5.68 | 7.74 | −10.5 | 268.99 |
| HT29 | SCH | 9.67 | 14.64 | 0.69 | −22.14 | −74.84 |
| MIAPaca2 | BVD | −4.12 | −3.51 | −12.51 | 9.9 | 209.14 |
| MIAPaca2 | Vx | 0.36 | −1.8 | 2.1 | 0.48 | 729.27 |
| MIAPaca2 | GDC | 2.25 | 6.56 | 5.07 | 2.24 | 199.59 |
| MIAPaca2 | SCH | 8.62 | 12.07 | 2.08 | 2.84 | −76.71 |

Example 14

Figure 34A:
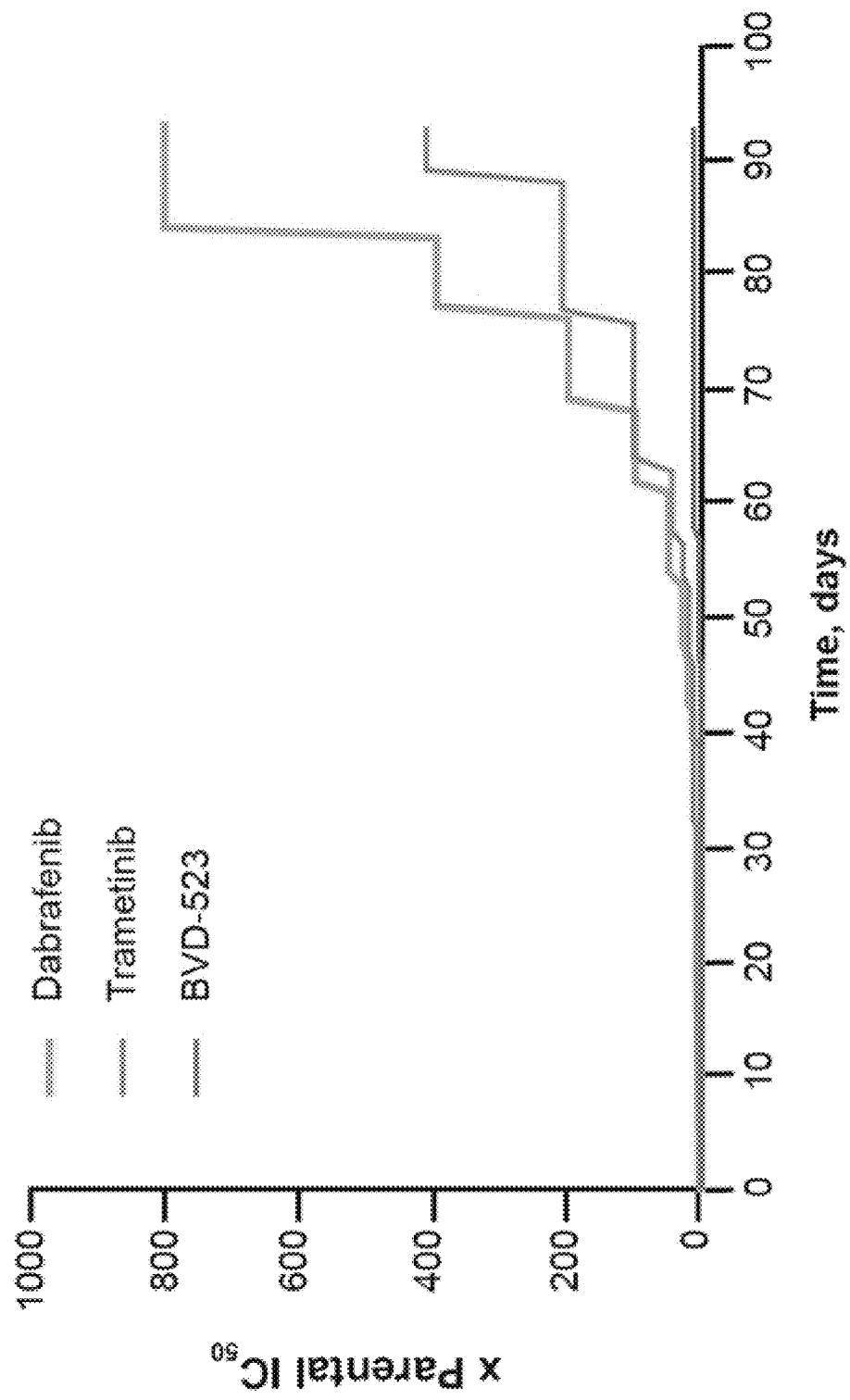

BVD-523 Exhibited Activity in In Vitro Models of BRAF and MEK Inhibitor Resistance Emergence of resistance to BRAF and MEK inhibitors limits their clinical efficacy. Here, the experiments sought to model and compare the development of resistance to BRAF (dabrafenib), MEK (trametinib), and ERK1/2 (BVD-523) inhibition in vitro. Over several months, BRAF$^{V600E}$-mutant A375 cells were cultured in progressively increasing concentrations of each inhibitor. Drug-resistant A375 cell lines were readily obtained following growth in high concentrations of trametinib or dabrafenib, while developing cell lines with resistance to BVD-523 proved challenging (FIG. 34A). Overall, these in vitro data suggest that at concentrations yielding similar target inhibition, resistance to BVD-523 is delayed compared with dabrafenib or trametinib, and may translate to durable responses in the clinic.

Reactivation and dependence on ERK1/2 signaling is a common feature of acquired resistance to BRAF/MEK inhibition (Morris et al. 2013 and Hatzivassiliou et al. 2012); therefore, the activity of BVD-523 in in vitro models of acquired resistance was evaluated. First, a dabrafenib and trametinib combination-resistant A375 population was obtained using the increased concentration method described. The $IC_{50}$ and $IC_{50}$-fold change from parental A375 for dabrafenib, trametinib, and BVD-523 in the BRAF/MEK combination-resistant population is shown in Table 24. BVD-523 $IC_{50}$ was modestly shifted (2.5-fold), while dabrafenib and trametinib were more significantly shifted (8.5-fold and 13.5-fold, respectively) (Table 24). The cytotoxic agent paclitaxel was tested as a control with only a modest shift in potency observed. These data support the investigation of BVD-523 in the setting of BRAF/MEK therapy resistance, although the mechanism of resistance in this cell population remains to be characterized.

TABLE 24

BVD-523 activity in models of BRAF/MEK inhibition

| Cell Line | Dabrafenib | Trametinib | BVD-523 | Paclitaxel |
|---|---|---|---|---|
| Parental ($IC_{50}$nM) | 2.1 | 0.2 | 129 | 1.9 |
| BRAFi- + MEKi-resistant ($IC_{50}$nM) | 17.9 | 2.7 | 323 | 3.5 |
| Fold Change | +8.5 | +13.5 | +2.5 | +1.8 |

Figure 34B:
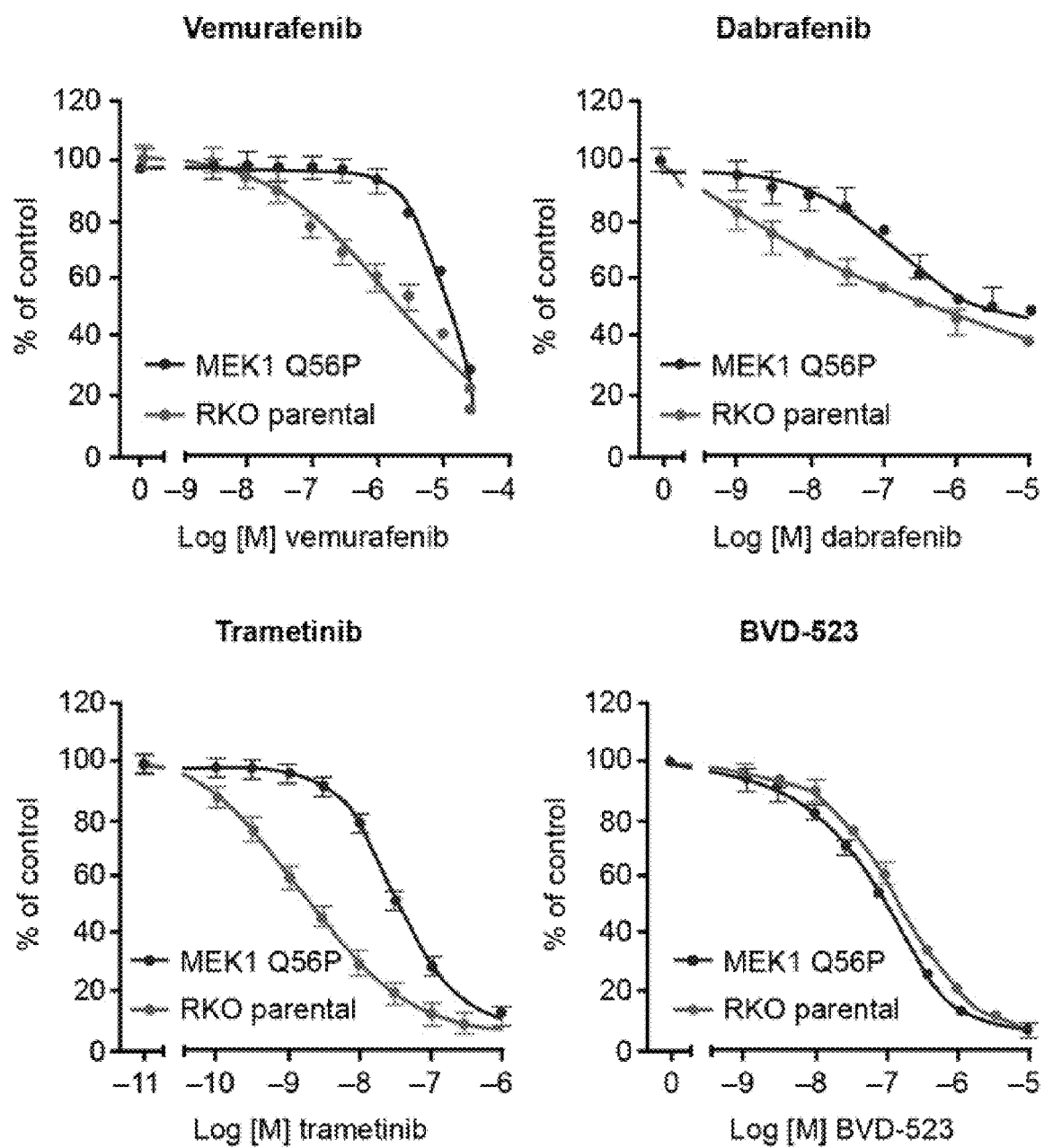

To further investigate the tractability of ERK1/2 inhibition in a model with a known mechanism of BRAF inhibitor resistance, AAV-mediated gene targeting was used to generate a pair of RKO BRAF$^{V600E}$-mutant cell lines isogenic for the presence or absence of an engineered heterozygous knock-in of MEK1$^{Q56P}$-activating mutation (Trunzer et al. 2013 and Emery et al. 2009). MEK1/2 mutations, including MEK1$^{Q56P}$, have been implicated in both single-agent BRAF and combination BRAF/MEK therapy-acquired resistance in patients (Wagle et al. 2011, Wagle et al. 2014, Emery et al. 2009 and Johnson et al. 2015). Single-agent assays demonstrated that relative to the parental BRAF$^{V600E}$::MEK1$^{wt}$ cells, the double-mutant BRAF$^{V600E}$::MEK1$^{Q56P}$ cells displayed a markedly reduced sensitivity to the BRAF inhibitors vemurafenib and dabrafenib and the MEK inhibitor trametinib (FIG. 34B). In contrast, response to BVD-523 was essentially identical in both the parental and MEK$^{Q56P}$-mutant cells, indicating that BVD-523 is not susceptible to this mechanism of acquired resistance. These results were confirmed in 2 independently derived double-mutant BRAF$^{V600E}$::MEK1$^{Q56P}$ cell line clones, thus validating that results were specifically related to the presence of the MEK1$^{Q56P}$ mutation rather than an unrelated clonal artifact (data not shown). Similar results were also observed with a second mechanistically distinct ERK1/2 inhibitor (SCH772984), supporting the expectation that these observations are specifically related to mechanistic inhibition of ERK1/2 and not due to an off-target compound effect.

To further characterize the mechanistic effects of BVD-523 on MAPK pathway signaling in BRAF$^{V600E}$::MEK1$^{Q56P}$ cell lines, protein levels were assessed by Western blot (FIG. 34C). In the parental BRAF$^{V600E}$ RKO cells, a reduced level of pRSK1/2 was observed following 4-hour treatment with BRAF (vemurafenib), MEK (trametinib), or ERK1/2 (BVD-523) inhibitors at pharmacologically active concentrations. In contrast, isogenic double-mutant BRAF$^{V600E}$::MEK1$^{Q56P}$ cells did not exhibit reduced RSK phosphorylation following BRAF or MEK inhibitor treatment, while BVD-523 remained effective in inhibiting pRSK1/2 to a level comparable to parental RKO. Similarly, pRB is reduced, indicating G0/G1 arrest, by 24 hours of BVD-523 treatment in both parental RKO and BRAF$^{V600E}$::MEK1$^{Q56P}$.

Figure 34D:
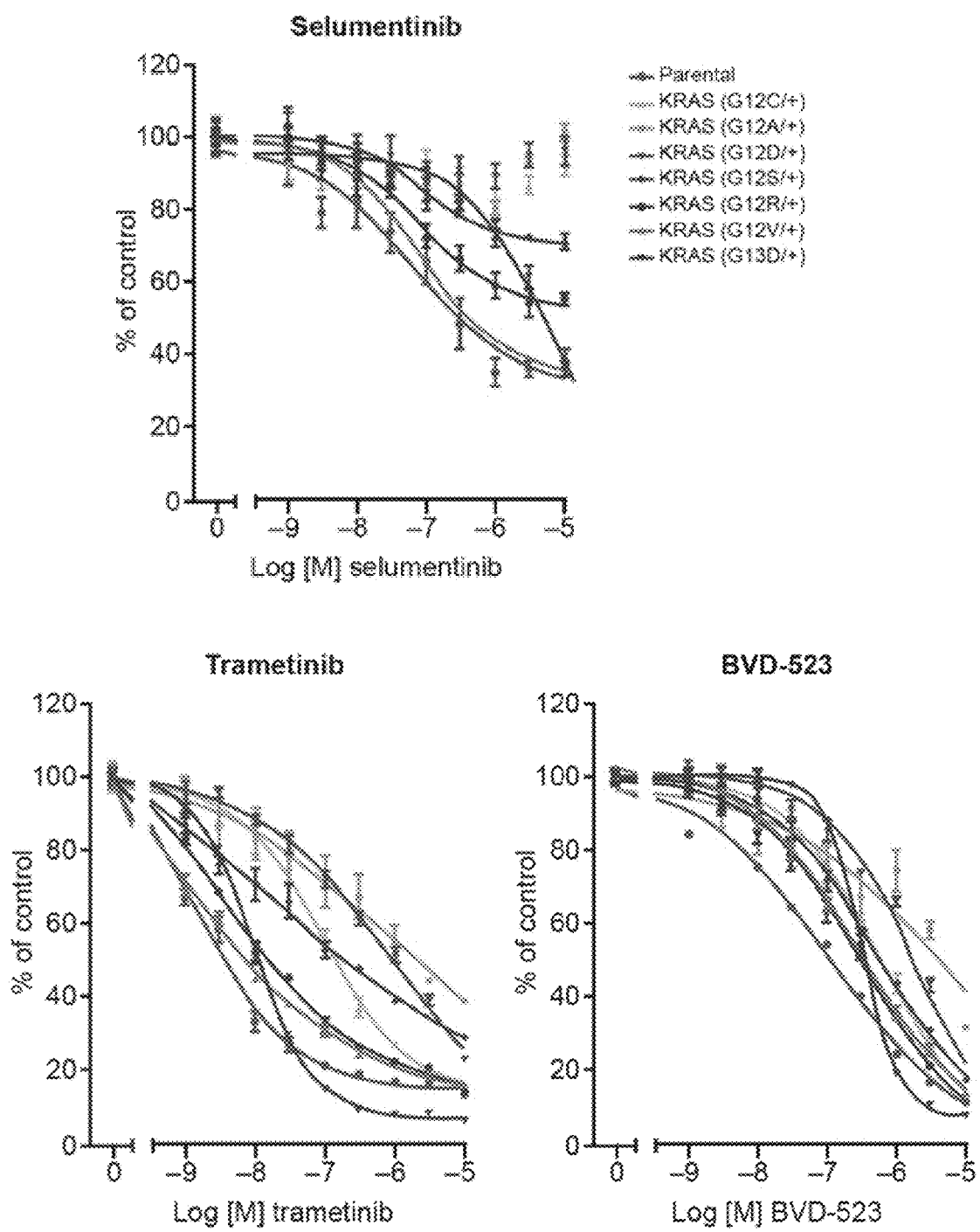
Figure 37A:
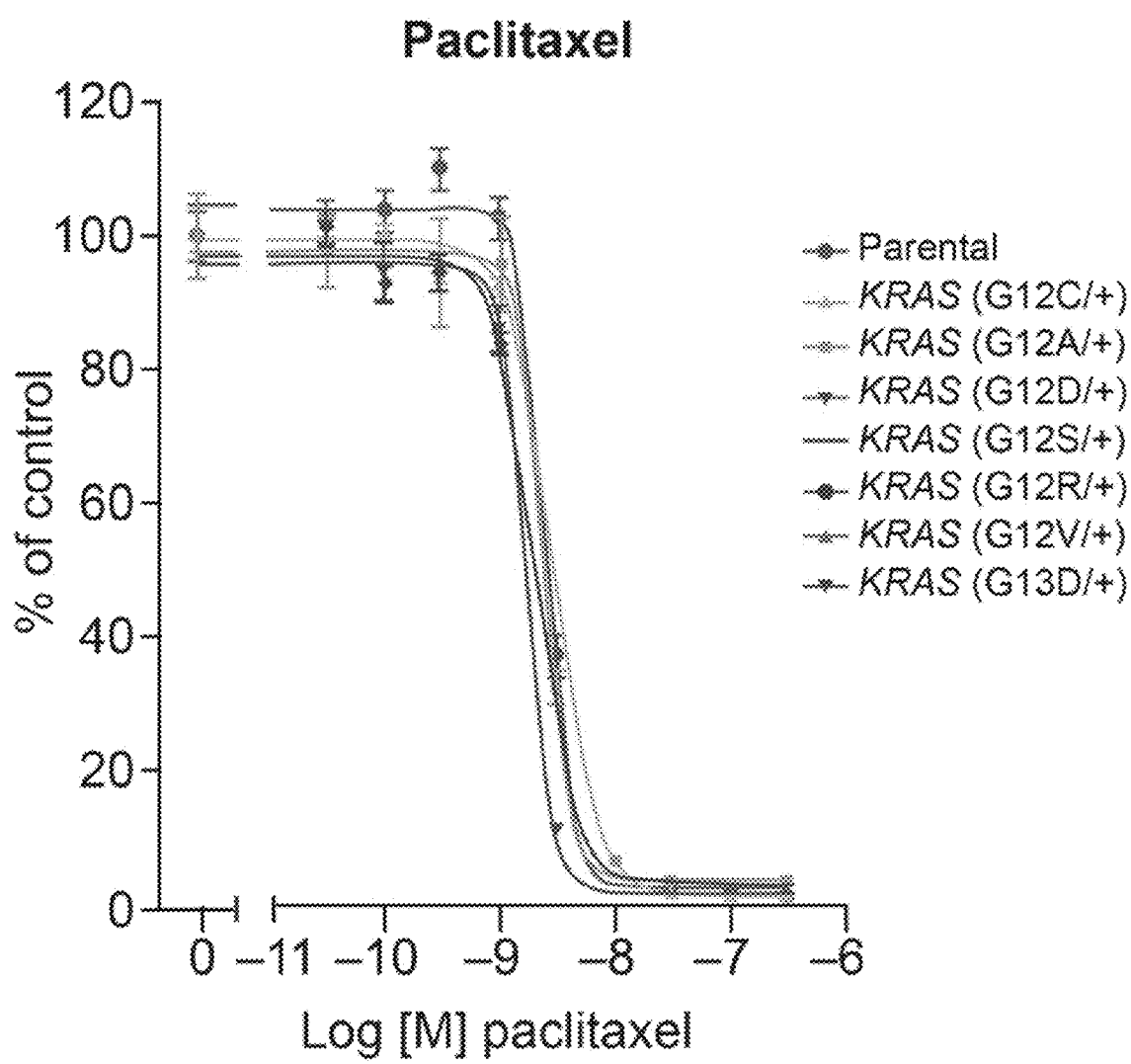
FIG. 37A shows that, in SW48 colorectal cells engineered with KRAS alleles, response to paclitaxel was unaltered compared to control.

Acquired KRAS mutations are also known drivers of resistance to MAPK pathway inhibitors. To understand the susceptibility of BVD-523 to this mechanism of resistance, an isogenic panel of clinically relevant KRAS mutations in colorectal cell line SW48 was used. Sensitivity to BVD-523 was compared with MEK inhibitors selumetinib and trametinib (FIG. 34D). Sensitivity to paclitaxel was unaltered (FIG. 37A). While several mutant KRAS alleles conferred robust to intermediate levels of resistance to MEK inhibition, sensitivity to BVD-523 was unaltered by the majority of alleles, and where a shift in sensitivity was observed, it was not to the extent observed with trametinib or selumetinib. Overall, these data suggest that BVD-523 is more efficacious in this context than MEK inhibitors.

Example 15

Figure 35A:
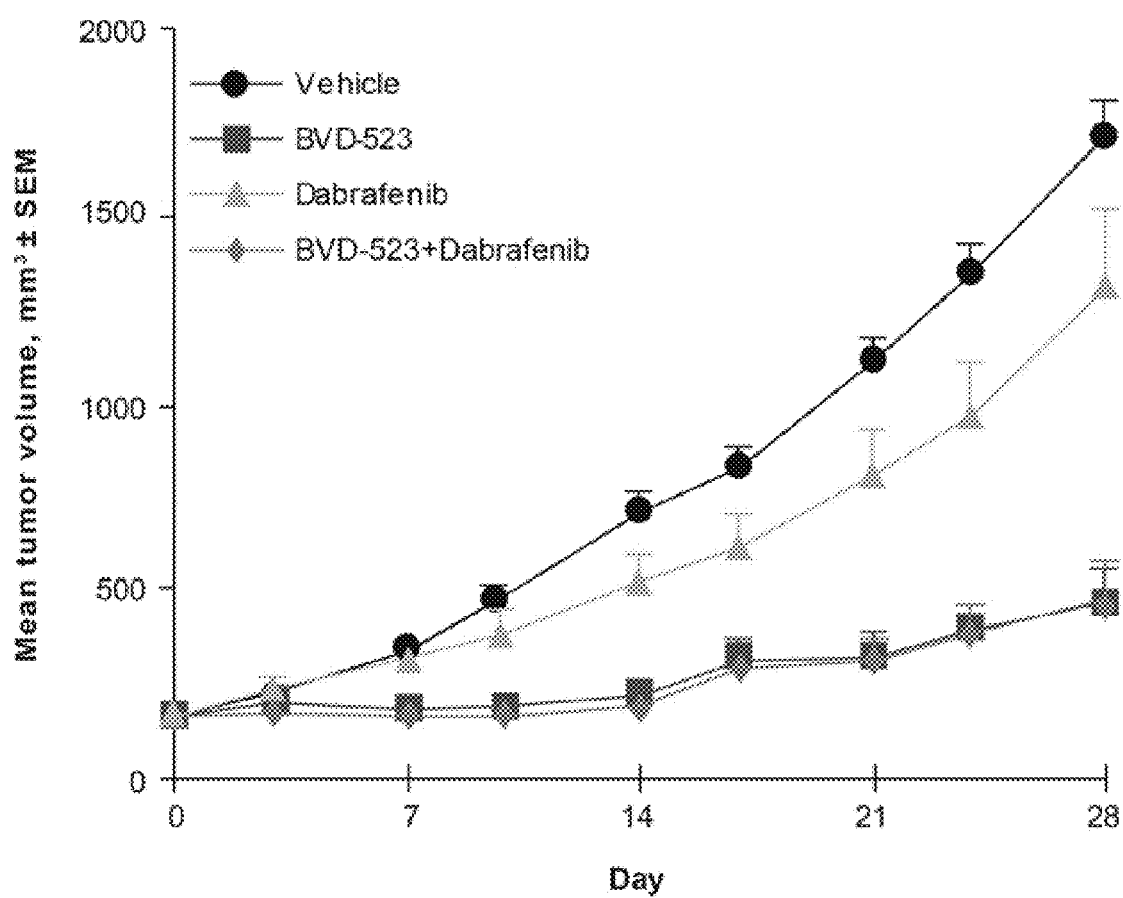
FIG. 35A shows BVD-523 in vivo activity in xenografts derived from a vemurafenib-relapsed patient. Mean tumor volume (±SEM) is shown for BVD-523 100 mg/kg BID alone, dabrafenib 50 mg/kg BID alone, and BVD-523 100 mg/kg BID plus dabrafenib 50 mg/kg BID. Abbreviations: BID, twice daily; SEM, standard error of mean.

BVD-523 Demonstrates In Vivo Activity in a BRAF Inhibitor-Resistant Patient-Derived Melanoma Xenograft Model To confirm and extend the antitumor effects of BVD-523 observed in in vitro models of BRAF-/MEK-acquired resistance, a BRAF-resistant xenograft model derived from a patient with resistance to vemurafenib was utilized. BVD-523 was dosed by oral gavage at 100 mg/kg BID for 28 days, both alone and in combination with dabrafenib at 50 mg/kg BID (FIG. 35). As expected, minimal antitumor activity was demonstrated for single-agent dabrafenib (22% TGI). BVD-523 activity was significant compared with vehicle control (P≤0.05), with a TGI of 78%. In this model, combining BVD-523 with dabrafenib resulted in a TGI of 76% (P≤0.05); therefore, further benefit was not gained for the combination compared with single-agent BVD-523 in this model of BRAF-acquired resistance.

Example 16

Figure 37B:
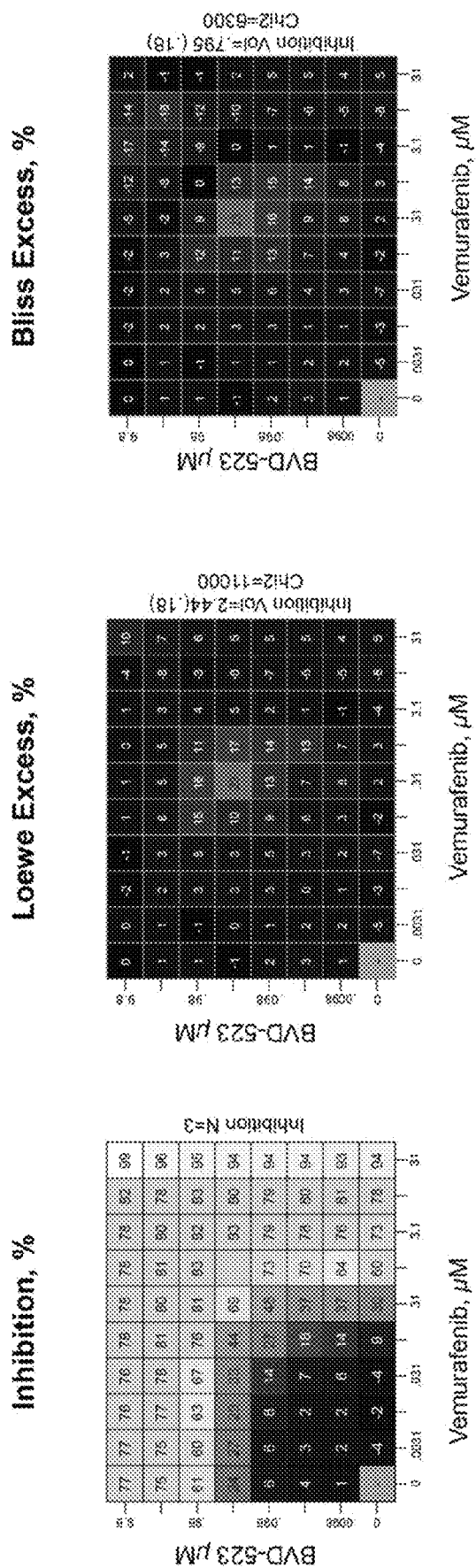
FIG. 37B shows combination interactions between BVD-523 and vemurafenib, which were assessed using an 8×10 matrix of concentrations using the Loewe Additivity and Bliss Independence Models, and analyzed with Horizon's Chalice, Bioinformatics Software. Chalice enables potential synergistic interactions to be identified by displaying the calculated excess inhibition over that predicted as being additive across the dose matrix as a heat map, and by reporting a quantitative "Synergy Score" based on the Loewe model. The results suggest that interactions between BVD-523 and vemurafenib are at least additive, and in some cases synergistic in melanoma cell lines carrying a BRAF$^{V600E}$ mutation.
Figure 37C:
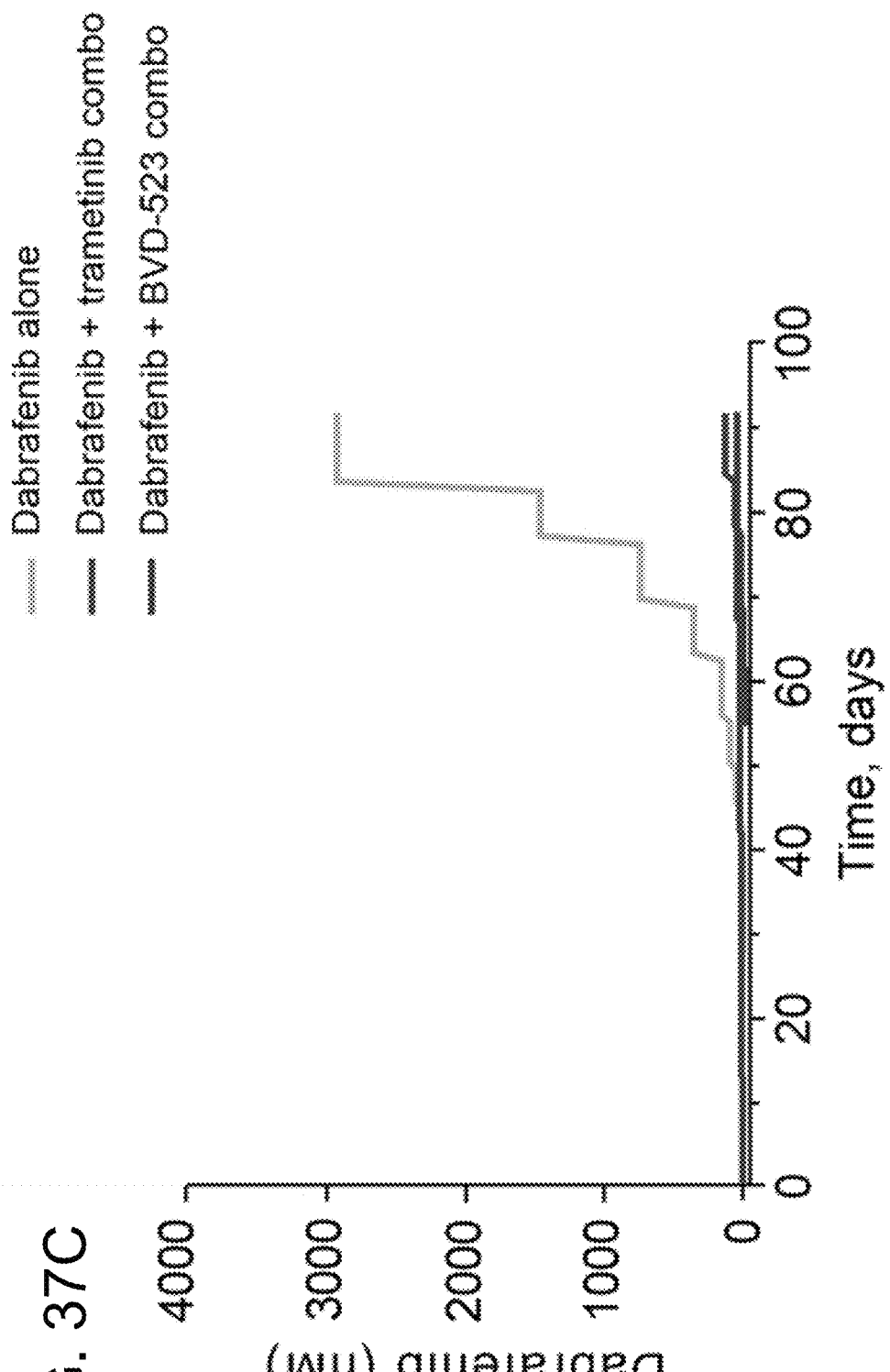
FIG. 37C shows that BVD-523 in combination with dabrafenib markedly delays the onset of acquired resistance in A375 BRAF$^{V600E}$ melanoma cells. The temporal acquisition of resistance in response to escalating concentrations of dabrafenib alone or in combination with BVD-523 or trametinib was assessed. Strict criteria were applied as to when the dose could be increased to ensure that the kinetics of adaptation was comparable between treatments. See, Example 1.

Combination Therapy with BVD-523 and a BRAF Inhibitor Provides Promising Antitumor Activity Patients with BRAF-mutant cancer may acquire resistance to combined BRAF/MEK therapy (Wagle et al. 2014), warranting consideration of other combination approaches within the MAPK pathway. The anti-proliferative effects of combining BVD-523 with the BRAF inhibitor vemurafenib was assessed in the BRAF$^{V600E}$-mutant melanoma cell line G-361. As anticipated, single agents BVD-523 and vemurafenib were both active, and modest synergy was observed when combined (FIG. 37B). This indicates that BVD-523 combined with BRAF inhibitors are at least additive and potentially synergistic in melanoma cell lines carrying a BRAF$^{V600E}$ mutation. Furthermore, generating acquired resistance in vitro following continuous culturing of BRAF$^{V600E}$ mutant cell line (A375) in BRAF inhibitor plus BVD-523 was challenging. In contrast generating resistance to dabrafenib alone occurred relatively rapidly (FIG. 37C). Even resistance to combined dabrafenib and trametinib emerged before dabrafenib plus trametinib.

Figure 36A:
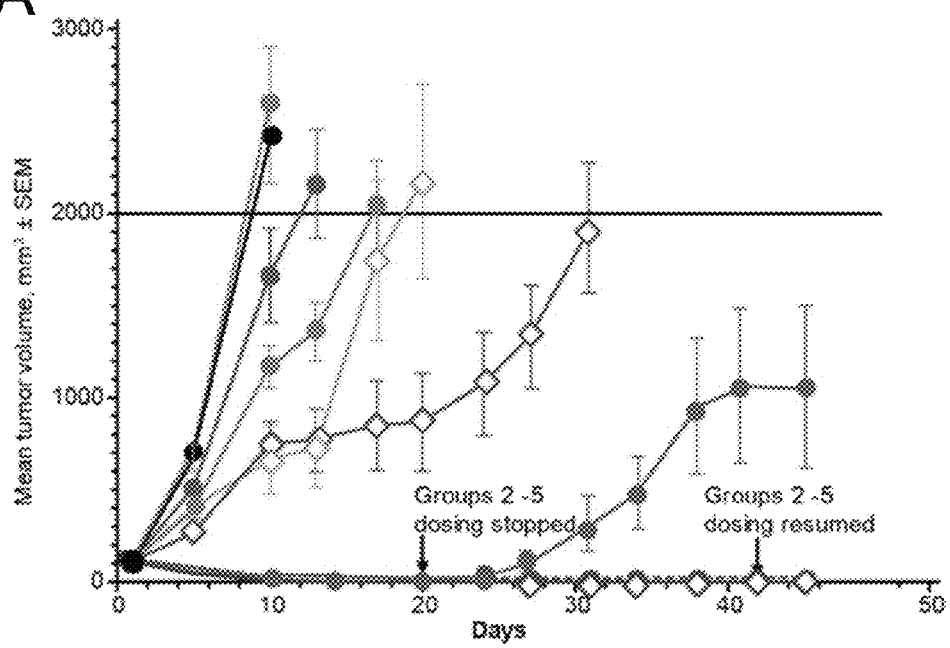
FIG. 36A-FIG. 36D show the benefit of combined BVD-523 and BRAF inhibition.
Figure 36B:
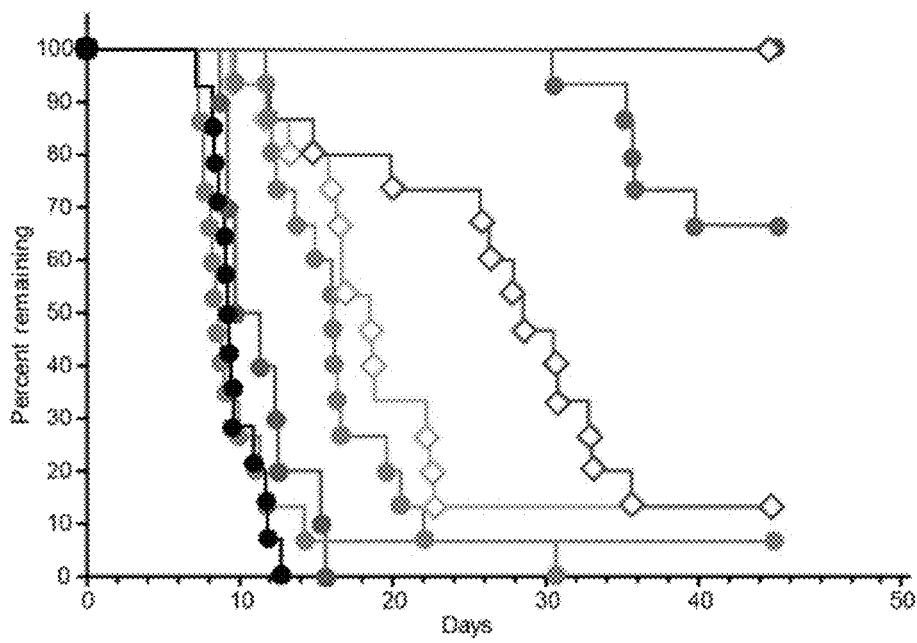

The benefit of combined BRAF and ERK inhibition may not be fully realized in in vitro combination studies where concentrations are not limited by tolerability. To understand the benefit of the combination, efficacy was assessed in vivo utilizing xenografts of the BRAF$^{V600E}$-mutant human melanoma cell line A375. Due to the noteworthy response to combination treatment, dosing in the combination groups was stopped on Day 20 to monitor for tumor regrowth, and was reinitiated on Day 42 (FIG. 36A). Tumors were measured twice weekly until the study was terminated on Day 45. The median time to endpoint (TTE) for controls was 9.2 days, and the maximum possible tumor growth delay (TGD) of 35.8 days was defined as 100%. Temozolomide treatment resulted in a TGD of 1.3 days (4%) and no regressions. The 50- and 100-mg/kg dabrafenib monotherapies produced TGDs of 6.9 days (19%) and 19.3 days (54%), respectively, a significant survival benefit (P<0.001), and 1 PR in the 100-mg/kg group. The 100-mg/kg BVD-523 monotherapy resulted in a TGD of 9.3 days (26%), a significant survival benefit (P<0.001), and 2 durable complete responses. The combinations of dabrafenib with BVD-523 each produced the maximum possible 100% TGD with noteworthy regression responses, and statistically superior overall survival compared with their corresponding monotherapies (P<0.001). The lowest dose combination produced a noteworthy 7/15 tumor-free survivors (TFS), and the 3 higher-dosage combinations produced a total of 43/44 TFS, consistent with curative or near-curative activity (FIG. 36B). In summary, the combination of dabrafenib with BVD-523 produced a greater number of TFS and superior efficacy to either single agent.

Figure 36C:
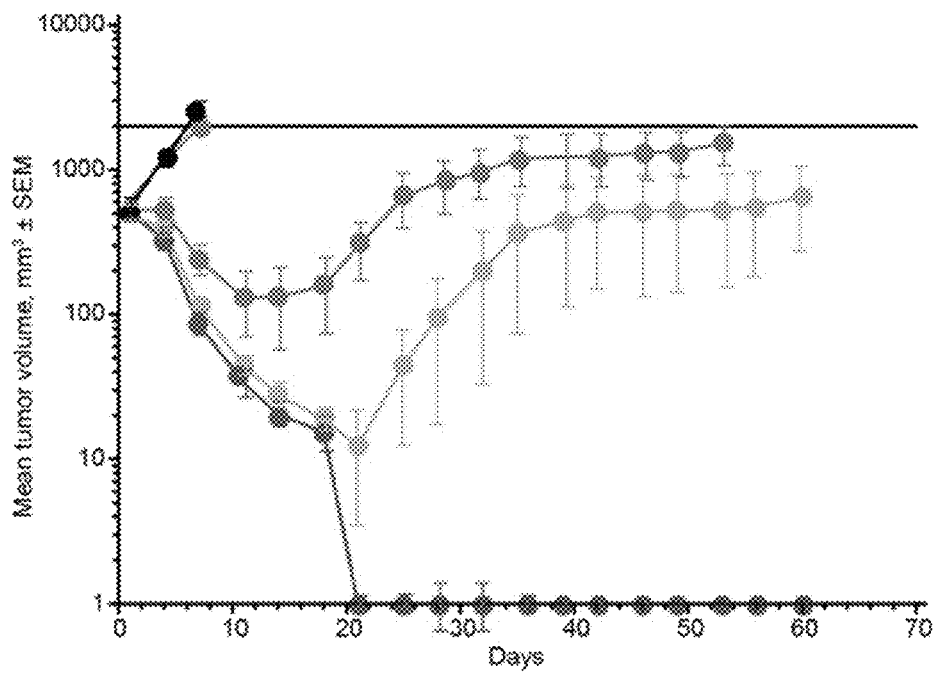
Figure 36D:
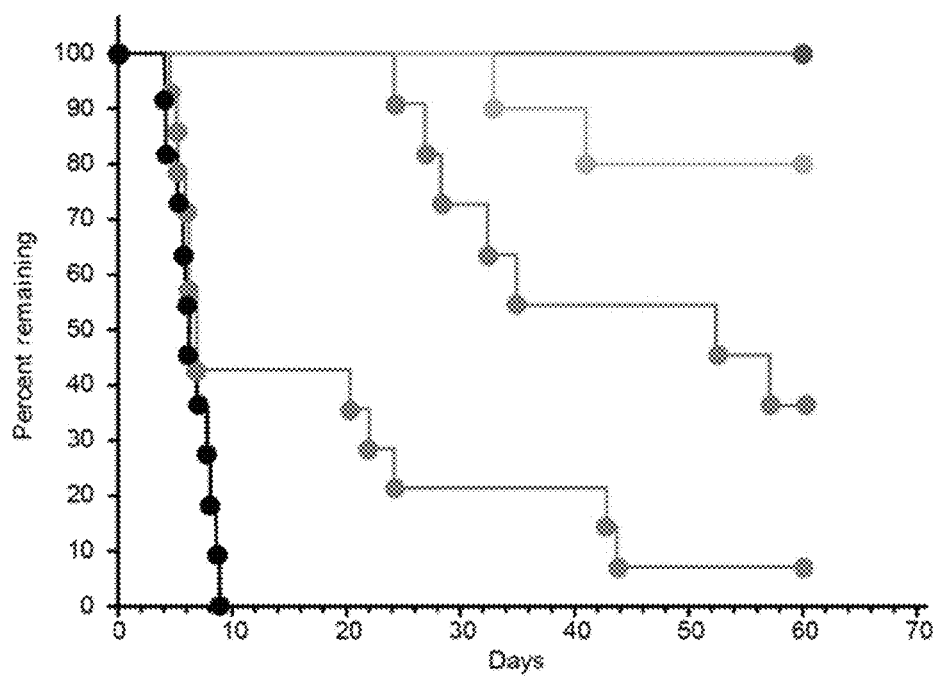

Based on the activity of BVD-523 plus dabrafenib in A375 xenograft models with a starting tumor volume of approximately 75-144 mm$^3$, a follow-up experiment was conducted to determine the efficacy of combination therapy in "upstaged" A375 xenografts (average tumor start volume, 700-800 mm$^3$) (FIG. 36C). The median TTE for controls was 6.2 days, establishing a maximum possible TGD of 53.8 days, which was defined as 100% TGD for the 60-day study. BVD-523 100-mg/kg monotherapy produced a negligible TGD (0.7 day, 1%) and no significant survival difference from controls (P>0.05). The distribution of TTEs and 2 PRs suggested there may have been a subset of responders to treatment with BVD-523 alone. Dabrafenib 50-mg/kg monotherapy was efficacious, yielding a TGD of 46.2 days (86%) and a significant survival benefit compared with controls (P<0.001). This group had 5 PRs and 5 CRs, including 3 TFS, among the 11 evaluable mice (FIG. 36D). Both combinations of dabrafenib with BVD-523 produced the maximum 100% TGD and a significant survival benefit compared with controls (P<0.001). Each combination produced 100% regression responses among evaluable mice, though there were distinctions in regression activity. The 25-mg/kg dabrafenib and 50-mg/kg BVD-523 combination had 2 PRs and 8 CRs, with 6/10 TFS, whereas the 50-mg/kg dabrafenib and 100-mg/kg BVD-523 combination had 11/11 TFS on Day 60 (FIG. 36D). Overall, these data support the rationale for frontline combination of BVD-523 with BRAF-targeted therapy in BRAF$^{V600E}$-mutant melanoma, and this is likely to extend to other tumor types harboring this alteration.

Discussion

BVD-523 is a potent, highly selective, reversible, small molecule ATP-competitive inhibitor of ERK1/2 with activity in in vivo and in vitro cancer models. In vitro, BVD-523 demonstrated potent inhibition against several human tumor cell lines, particularly those harboring activating mutations in the MAPK signaling pathway, consistent with its mechanism of action. BVD-523 elicited changes in downstream target and effector proteins, including inhibition of direct substrate of ERK1/2, pRSK, and total DUSP6 protein levels. These findings are in line with those of previous studies of other ERK1/2 inhibitors, which demonstrated effective suppression of pRSK with ERK1/2 inhibition (Morris et al. 2013 and Hatzivassiliou et al. 2012). Interestingly, BVD-523 treatment resulted in a marked increase in ERK1/2 phosphorylation in vitro and in vivo. Similar to our findings, an increase in pERK1/2 has been reported with the ERK1/2 inhibitor Vx11e; conversely, pERK1/2 inhibition occurs with SCH772984 (Morris et al. 2013). Although differences in pERK1/2 levels were observed among the various ERK1/2 inhibitors tested, downstream effectors (i.e., pRSK1 and total DUSP6) were similarly inhibited. These findings suggest quantifying ERK1/2 target substrates, such as pRSK1, may serve as reliable pharmacodynamic biomarkers for BVD-523-mediated inhibition of ERK1/2 activity.

While BRAF (dabrafenib, vemurafenib) and MEK (trametinib, cobimetinib) inhibitors validate the MAPK pathway as a therapeutic target, particularly in patients with BRAF$^{V600}$ mutations, the antitumor response is limited by the emergence of acquired resistance and subsequent disease progression. Resistance has been attributed to the upregulation and activation of compensatory signaling molecules (Nazarian et al. 2010, Villanueva et al. 2010, Johannessen et al. 2010 and Wang et al. 2011), amplification of the target genes (Corcoran et al. 2010), and activating mutations of pathway components (e.g., RAS, MEK) (Wagle et al. 2011, Emery et al. 2009 and Wang et al. 2011). Reactivation of the ERK1/2 pathway is one common consequence of acquired resistance mechanism. When introduced into the BRAF$^{V600E}$-mutant melanoma cell line A375, MEK$^{Q56P}$ conferred resistance to MEK and BRAF inhibition (Wagle et al. 2011). By contrast, BVD-523 retained its potent inhibitory activity in the engineered MEK$^{Q56P}$ cell line, indicating that ERK1/2 inhibition is effective in the setting of upstream activating alterations which can arise in response to BRAF/MEK treatment. As further evidence of a role for BVD-523 in the context of acquired resistance, efficacy of BVD-523 was evident in a xenograft model derived from a tumor sample from a patient whose disease progressed on vemurafenib; the BRAF inhibitor dabrafenib was not effective in this model. These data support a role for targeting ERK1/2 in the setting of BRAF/MEK resistance, and complement previously published findings (Morris et al. 2013 and Hatzivassiliou et al. 2012). To further characterize resistance to inhibitors of the MAPK pathway, the emergence of resistance to BVD-523 itself was investigated. It was found that single-agent treatment of cancer cells with BVD-523 was durable and more challenging to develop resistance compared with other agents targeting upstream MAPK signaling components (i.e., dabrafenib, trametinib). This may suggest that acquiring resistance to ERK1/2-targeting agents is harder to achieve than acquiring resistance to BRAF or MEK therapy, potentially due to the fact that BVD-523 preferentially targets the more conserved active confirmation of the ATP binding site. However, in vitro studies with other ERK1/2 inhibitors have identified specific mutants in ERK1/2 that drive resistance (Jha et al. 2016 and Goetz et al. 2014); these specific mutations have yet to be identified in clinical samples from ERK1/2 inhibitor-relapsed patients.

The potential clinical benefit of ERK1/2 inhibition with BVD-523 extends beyond the setting of BRAF/MEK therapy-resistant patients. As ERK1/2 is a downstream master node within this MAPK pathway, its inhibition is attractive in numerous cancer settings where tumor growth depends on MAPK signaling. Approximately 30% of all cancers harbor RAS mutations; therefore, targeting downstream ERK1/2 with BVD-523 is a rational treatment approach for these cancers. Furthermore, results from a study by Hayes et al. indicate that prolonged ERK1/2 inhibition in KRAS-mutant pancreatic cancer is associated with senescent-like growth suppression (Hayes et al. 2016). However, a combination approach may be required for maximal and durable attenuation of MAPK signaling in the setting of RAS mutations. For example, MEK inhibition in KRAS-mutant colorectal cancer cell results in an adaptive response of ErbB family activation, which dampens the response to MEK inhibition (Sun et al. 2014). Similar context-specific adaptive responses may occur following ERK1/2 inhibition with BVD-523. The optimal treatment combinations for various genetic profiles and cancer histologies are the subject of ongoing research. In addition to BRAF$^{V600}$ and RAS mutations, other alterations which drive MAPK are emerging. For example, novel RAF fusions and atypical non-V600 BRAF mutations which promote RAF dimerization activate the MAPK pathway (Yao et al. 2015). BRAF inhibitors such as vemurafenib and dabrafenib which inhibit BRAF$^{V600E}$-mutant monomer proteins have been shown to be inactive in atypical RAF alterations which drive MAPK signaling in a dimerization-dependent manner (Yao et al. 2015). However, treatment with BVD-523 to target downstream ERK1/2 in these tumors may be a novel approach to addressing this unmet medical need.

In the setting of BRAF$^{V600E}$-mutant melanoma tumors, combined BRAF and MEK inhibition exemplifies how agents targeting different nodes of the same pathway can improve treatment response and duration. Our combination studies in BRAF$^{V600E}$-mutant xenografts of human melanoma cell line A375 provides support for combination therapy with BVD-523 and BRAF inhibitors. The combination demonstrated superior benefit relative to single-agent treatments, including results consistent with curative responses. The clinical efficacy and tolerability of combined BRAF/BVD-523 therapy remains to be determined. It would not be unreasonable to expect that a BRAF/ERK1/2 combination will at least be comparable in efficacy to a targeted BRAF/MEK combination. Furthermore, the in vitro observation that acquired resistance to BVD-523 is more challenging to achieve compared with other MAPK pathway inhibitors suggests that the BRAF/BVD-523 inhibitor combination has the potential to provide a more durable response.

Significant progress has also been made using immunotherapy for melanoma. The US FDA has approved various immune checkpoint inhibitors for the treatment of advanced melanoma, including the cytotoxic T-lymphocyte antigen-4 targeted agent ipilimumab and the programmed death −1 inhibitors pembrolizumab and nivolumab. Combining BVD-523 with such immunotherapies is an attractive therapeutic option; further investigation is warranted to explore dosing schedules and to assess whether synergistic response can be achieved.

Based on the preclinical data, BVD-523 may hold promise for treatment of patients with malignancies dependent on MAPK signaling, including those whose tumors have acquired resistance to other treatments. The clinical development of BVD-523 is described below. See, Examples 17-24

Example 17

Phase I Dose-Escalation Study of the First-in-Class Novel Oral ERK1/2 Kinase Inhibitor BVD-523 (ulixertinib) in Patients With Advanced Solid Tumors The present invention describes the first-in-human dose escalation study of an ERK1/2 inhibitor for the treatment of patients with advanced solid tumors. BVD-523 has an acceptable safety profile with favorable pharmacokinetics and early evidence of clinical activity.

Mitogen-activated protein kinase (MAPK) signaling via the RAS-RAF-MEK-ERK cascade plays a critical role in oncogenesis; thus attracting significant interest as a therapeutic target. This ubiquitous pathway is composed of RAS upstream of a cascade of the protein kinases RAF, MEK1/2, and ERK1/2. RAS is activated by GTP binding, which in turn results in activation of each protein kinase sequentially. Although they appear to be the only physiologic substrates for MEK1/2, ERK1/2 have many targets in the cytoplasm and nucleus, including the transcription factors Elk1, c-Fos, p53, Ets1/2, and c-Jun (Shaul et al. 2007). ERK1/2 activation and kinase activity influences cellular proliferation, differentiation, and survival through a variety of mechanisms (Rasola et al. 2010), including activation of the ribosomal S6 kinase (RSK) family members (Romeo et al. 2012).

Constitutive, aberrant activation of the RAS-RAF-MEK1/2-ERK1/2 signaling pathway has been identified and implicated in the development or maintenance of many cancers (Schubbert et al. 2007 and Gollob et al. 2006). Mutations in RAS family genes, such as KRAS, NRAS, and HRAS are the most common, with activating RAS mutations occurring in ≈30% of human cancers (Schubbert et al. 2007). KRAS mutations are prevalent in pancreatic (>90%) (Kanda et al. 2012), biliary tract (3%-50%) (Hezel et al. 2014), colorectal (30%-50%) (Arrington et al. 2012), lung (27%) (Pennycuick et al. 2012), ovarian (15%-39%) (Dobrzycka et al. 2009), and endometrioid endometrial (18%) (O'Hara and Bell 2012) cancers; NRAS mutations are prevalent in melanoma (20%) (Khattak et al. 2013) and myeloid leukemia (8%-13%) (Yohe 2015); and HRAS mutations are prevalent in bladder (12%) cancer (Fernandez-Medarde and Santos 2011). Mutations in RAF family genes, most notably BRAF, are frequent, particularly in melanoma. BRAF mutations have been identified in 66% of malignant melanomas and in ~7% of a wide range of other cancers (Davies et al. 2002), while MEK mutations are rarer, occurring at an overall frequency of 8% in melanomas (Nikolaev et al. 2012). In contrast, ERK mutations resulting in tumorigenesis have been reported only rarely to date (Deschenes-Simard et al. 2014).

The US Food and Drug Administration (FDA) has approved two selective BRAF inhibitors, vemurafenib and dabrafenib, as monotherapies for patients with $BRAF^{V600}$-mutant metastatic melanoma (Taflinar [package insert] and Zelboraf [package insert]). Though response rates for these targeted therapies can be as high as 50% in in patients with $BRAF^{V600}$ mutations, duration of response is often measured in months, not years (Hauschild et al. 2012 and McArthur et al. 2014). The MEK1/2 inhibitor trametinib is also approved as a monotherapy in this setting (Mekinist [package insert]), but is more commonly used in combination with the BRAF inhibitor dabrafenib. First-line use of trametinib administered in combination with dabrafenib offers an even greater improvement in overall survival compared with vemurafenib monotherapy without increased overall toxicity (Robert et al. 2015), highlighting the potential utility of simultaneously targeting multiple proteins of this MAPK signaling pathway. This therapeutic combination was also associated with a lower incidence of MEK inhibitor-associated rash and BRAF inhibitor-induced hyperproliferative skin lesions compared with each single agent alone (Flaherty et al. 2012). Recently, a phase III trial also demonstrated significant improvements in overall survival (25.1 vs. 18.7 months, hazard ratio [HR] 0.71, P=0.0107), progression-free survival (PFS) (11.0 vs. 8.8 months, HR 0.67, P=0.0004), and overall response (69% vs. 53%; P=0.0014) with dabrafenib plus trametinib versus dabrafenib alone in patients with $BRAF^{V600E/K}$ mutation-positive melanoma (Long et al. 2015). Similarly, significant improvements in PFS (9.9 vs. 6.2 months, HR 0.51, P<0.001) and the rate of complete response (CR) or partial response (PR) (68% vs. 45%; P<0.001) have been demonstrated with the combination of cobimetinib plus vemurafenib compared with vemurafenib alone (Larkin et al. 2014). To this end, FDA approval was recently granted for the combination of vemurafenib and cobemetinib for $BRAF^{V600E/K}$-mutated melanoma. Based on these and related findings, the combination of a BRAF inhibitor plus a MEK inhibitor has become a standard targeted treatment option for patients with metastatic melanoma containing $BRAF^{V600E/K}$ mutations.

Though BRAF/MEK-targeted combination therapy has been demonstrated to provide significant additional benefit beyond single-agent options, most patients eventually develop resistance and disease progression after ~12 months (Robert et al. 2015, Flaherty et al. 2012 and Long et al. 2015). Several mechanisms of acquired resistance following either single-agent or combination therapies have been identified, including the generation of BRAF splicing variants, BRAF amplification, development of NRAS or MEK mutations, and upregulation of bypass pathways (Poulikakos et al. 2011, Corcoran et al. 2010, Nazarian et al. 2010, Shi et al. 2014, Johannessen et al. 2010, Wagle et al. 2011, Wagle et al. 2014 and Ahronian et al. 2015). Central to many of these mechanisms of resistance is the reactivation of ERK signaling, which enables the rapid recovery of MAPK pathway signaling and escape of tumor cells from single-agent BRAF or combination BRAF/MEK inhibitor therapies (Paraiso et al. 2010). ERK inhibition may provide the opportunity to avoid or overcome resistance from upstream mechanisms, as it is the most distal master kinase of this MAPK signaling pathway. This is supported by preclinical evidence that inhibition of ERK by small molecule inhibitors acted to both inhibit the emergence of resistance and overcome acquired resistance to BRAF and MEK inhibitors (Morris et al. 2013 and Hatzivassiliou et al. 2012).

BVD-523 is a highly potent, selective, reversible, ATP-competitive ERK1/2 inhibitor which has been shown to reduce tumor growth and induce tumor regression in BRAF and RAS mutant xenograft models. Furthermore, single-agent BVD-523 inhibited human xenograft models that were cross-resistant to both BRAF and MEK inhibitors. See, Examples 9-16. Therefore, an open-label, first-in-human study (Clinicaltrials.gov identifier, NCT01781429) of oral BVD-523 to identify both the maximum tolerated dose and the recommended dose for further study was undertaken. The present study also aimed to assess pharmacokinetic and pharmacodynamic properties as well as preliminary efficacy in patients with advanced cancers.

Example 18

Patient Characteristics

A total of 27 patients were enrolled and received at least one dose of study drug from Apr. 4, 2013 to Dec. 1, 2015. Baseline demographics and disease characteristics are shown in Table 25. The median patient age was 61 years (range, 33-86 years). Fifty-two percent (14/27) of patients were male and 63% (17/27) had an Eastern Cooperative Oncology Group (ECOG) performance status of 1. Melanoma was the most common cancer (30%; BRAF mutation present in 7/8 of these patients). The remaining patients had colorectal (19%; 5/27), papillary thyroid (15%; 4/27), or non-small cell lung cancer (NSCLC) (7%; 2/27), and 8 (30%) were classified as having other cancers (2 pancreatic, 1 appendiceal, 1 nonseminomatous germ cell, 1 ovarian and 3 with unknown primary). The majority of patients had received 2 or more prior lines of systemic therapy, with 41% (11/27) receiving 2 to 3 and 48% (13/27) receiving >3 prior lines of systemic therapy.

TABLE 25

Baseline demographics and clinical characteristics of patients

| Parameter | N = 27 |
|---|---|
| Median age, years (range) | 61 (33-86) |
| Sex, n (%) | |
| Female | 13 (48) |
| Male | 14 (52) |
| Ethnicity, n (%) | |
| Not Hispanic/Latino | 27 (100) |
| ECOG performance status | |
| 0 | 10 (37) |
| 1 | 17 (63) |
| Cancer type, n (%) | |
| Melanoma[a] | 8 (30) |
| Colorectal | 5 (19) |
| Papillary thyroid | 4 (15) |
| Non-small cell lung | 2 (7) |
| Other[b] | 8 (30) |
| Molecular abnormalities, n (%)[c] | |
| BRAF mutant | 13 (48) |
| KRAS mutant | 6 (22) |
| NRAS mutant | 2 (7) |
| Other[d] | 7 (26) |
| Unknown | 4 (15) |
| Number of prior systemic anticancer regimens, n (%) | |
| 0 | 1 (4) |
| 1 | 2 (7) |
| 2-3 | 11 (41) |
| >3 | 13 (48) |
| Prior BRAF/MEK-targeted therapy[e], n (%) | 11 (41) |
| BRAF | 5 (19) |
| MEK | 6 (22) |
| BRAF/MEK | 2 (7) |

[a]Seven were BRAF mutant and 1 was unknown.
[b]Two pancreatic, 1 appendiceal, 1 non-seminomatous germ cell, 1 ovarian, 3 unknown primary.
[c]Patients may have more than 1 molecular abnormality.
[d]Other molecular abnormalities included ERCC1, RRM1, thymidylate synthetase, GNAS, MEK1, TP53, CREBBP, ROS1, PTEN, AKT3, and PIK3CA.
[e]Some patients were treated with more than one BRAF inhibitor.
Abbreviation:
ECOG, Eastern Cooperative Oncology Group.

Example 19

Ex Vivo Effects of BVD-523 on RSK1/2 Phosphorylation

Figure 38:
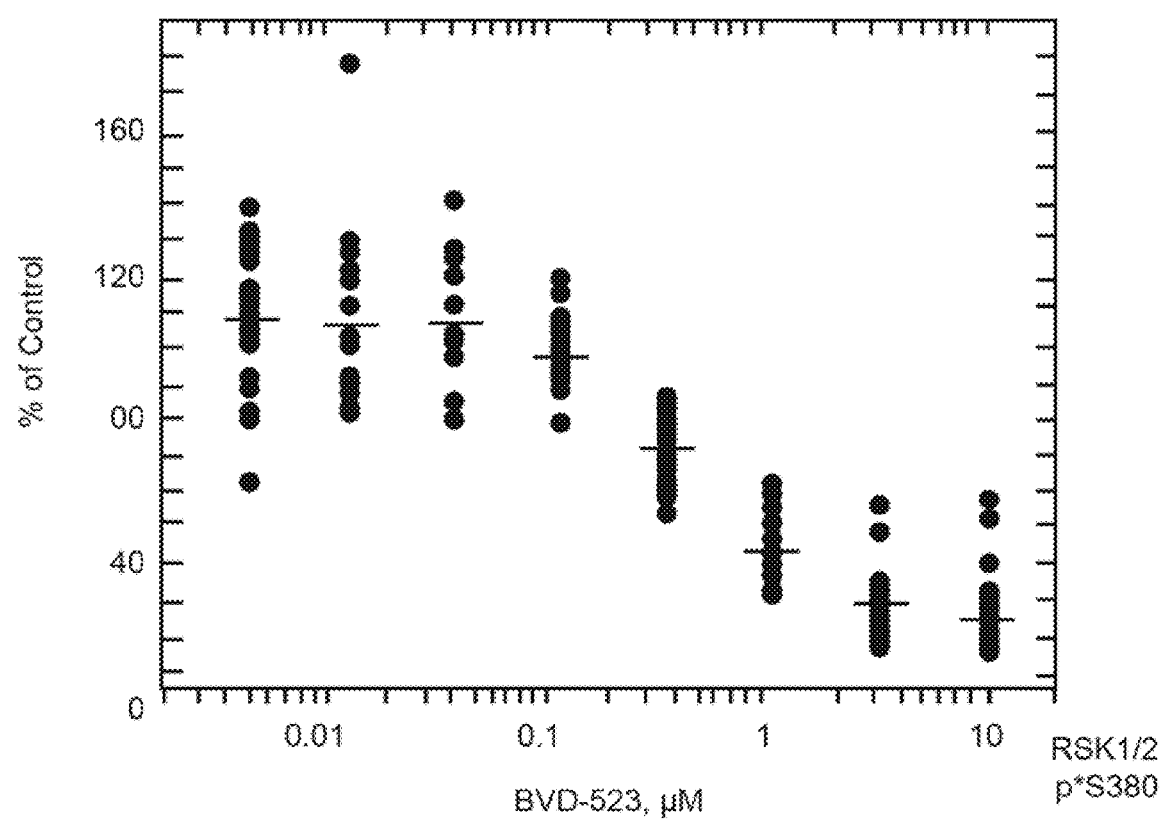
FIG. 38 shows that BVD-523 inhibits ex vivo PMA-stimulated RSK1/2 phosphorylation in human whole blood. Averages of BVD-523 concentration data set are indicated by (-). n=20 for each concentration of BVD-523. Abbreviations: PBMC, peripheral blood mononuclear cells; RSK, ribosomal S6 kinase.

An ex vivo biomarker assay that could be used to support clinical studies was developed to demonstrate the inhibitory effects of BVD-523 on ERK activity. The assay extends preclinical cellular data where inhibitors of MAPK signaling, such as BVD-523, dabrafenib, trametinib, and vemurafenib, have been shown to inhibit RSK phosphorylation as a function of inhibitor concentration in BRAF mutant cancer cell lines. See, Examples 9-16. Specifically, ERK inhibitor-dependent inhibition of phorbol 12-myristate 13-acetate (PMA)-stimulated phosphorylation of the ERK substrate RSK1 in whole blood was used as a target marker. When BVD-523 was added directly to whole blood from healthy volunteers, PMA-stimulated RSK phosphorylation decreased with increasing concentrations of BVD-523 (FIG. 38). The mean $IC_{50}$ for the cumulative data was 461±20 nM for BVD-523, with a maximum inhibition of 75.8±2.7% at 10 μM BVD-523. Maximum inhibition was defined as the RSK phosphorylation measured in the presence of 10 μM BVD-523. Patient-derived whole blood samples, collected just prior to dosing or at defined timepoints following dosing with BVD-523, were similarly treated and RSK phosphorylation levels quantitated.

Example 20

Dose Escalation, Dose-Limiting Toxicities (DLTs), Maximum Tolerated Dose (MTD), and Recommended Phase II Dose (RP2D)

As per protocol, 5 single-patient cohorts (from 10 to 150 mg twice-daily [BID]) proceeded without evidence of a DLT. The 300-mg BID cohort was expanded to more fully characterize BVD-523 exposures. One of 6 patients given 600 mg BID experienced a DLT of Grade 3 rash. The 900-mg BID dose exceeded the MTD, with one patient experiencing Grade 3 pruritus and elevated aspartate aminotransferase (AST) and another patient experiencing Grade 3 diarrhea, vomiting, dehydration, and elevated creatinine (Table 26). The subsequent intermediate dose of 750 mg BID also exceeded the MTD, with DLTs of Grade 3 rash and Grade 2 diarrhea in 1 patient and Grade 2 hypotension, elevated creatinine, and anemia in another patient. Therefore, the MTD and RP2D were determined to be 600 mg BID.

TABLE 26

Dose-limiting toxicities in Cycle 1 (21 days)

| Dose, mg (BID) | DLT Frequency | DLT Description |
|---|---|---|
| 10 | 0/1 | N/A |
| 20 | 0/1 | N/A |
| 40 | 0/1 | N/A |
| 75 | 0/1 | N/A |
| 150 | 0/1 | N/A |
| 300 | 0/4 | N/A |
| 600 | 1/8 | Rash (Grade 3) |
| 750[a] | 2/4 | Rash (Grade 3), diarrhea (Grade 2) Hypotension (Grade 2), elevated creatinine (Grade 2), anemia (Grade 2), delay to cycle 2 dosing |
| 900 | 2/7 | Pruritus (Grade 3), elevated AST (Grade 3) Diarrhea (Grade 3), vomiting (Grade 3), dehydration (Grade 3), elevated creatinine (Grade 3) |

[a]Intermediate dose.
Abbreviations:
AST, aspartate transaminase,
BID, twice daily;
DLT, dose-limiting toxicity;
N/A, not applicable.

Example 21

Adverse Events (AEs)

Investigator-assessed treatment-related AEs of any grade were noted in 26 of 27 patients (96%). The most common treatment-related AEs (>30%) were rash (predominately acneiform) (70%), fatigue (59%), diarrhea (52%), and nausea (52%) (Table 27). No patients experienced a Grade 4 or 5 treatment-related AE or discontinued treatment due to a treatment-related AE. Most events were Grade 1 to 2, with treatment-related Grade 3 events noted in 13 of 27 patients (48%). The only Grade 3 treatment-related events present in ≥10% of patients were diarrhea (15%) and increased liver function tests (11%), all of which occurred above the 600-mg BID dose.

TABLE 27

Adverse events possibly/definitely related to BVD-523 in ≥10% of patients

| | N = 27 | | |
|---|---|---|---|
| Event | Any grade, n (%) | Grade 1 or 2, n (%) | Grade 3[a], n (%) |
| Rash | 20 (74) | 18 (67) | 2[b] (7) |
| Fatigue | 17 (63) | 16 (59) | 1 (4) |
| Diarrhea | 16 (59) | 12 (44) | 4 (15) |
| Nausea | 14 (52) | 14 (52) | 0 |
| Vomiting | 8 (30) | 7 (26) | 1 (4) |
| Anorexia | 6 (22) | 6 (22) | 0 |
| Pruritus | 6 (22) | 6 (22) | 0 |
| Anemia | 5 (19) | 3 (11) | 2 (7) |
| Increased creatinine | 5 (19) | 4 (15) | 1 (4) |
| Dehydration | 5 (19) | 3 (11) | 2 (7) |
| Peripheral edema | 4 (15) | 4 (15) | 0 |
| Increased LFTs (ALT and AST) | 4 (14) | 1 (4) | 3 (11) |
| Blurry/dimmed vision[c] | 3 (11) | 3 (11) | 0 |
| Constipation | 3 (11) | 3 (11) | 0 |
| Fever | 3 (11) | 3 (11) | 0 |

[a]No patients experienced Grade 4 or 5 AEs that were possibly or definitely related to BVD-523 treatment.
[b]Acneiform and maculo-papular rash.
[c]One Grade 1 event of related central serous retinopathy.
Analysis cut-off date: Dec. 1, 2015.
Abbreviations:
AEs, adverse events;
ALT, alanine transaminase;
AST, aspartate transaminase;
LFTs, liver function tests.

Fourteen patients experienced a total of 28 serious AEs (SAEs). Nine of these were considered to be related or possibly related to BVD-523 by the investigator, which included dehydration, diarrhea, or elevated creatinine (2 patients each), vomiting, nausea, and fever (1 patient each). All other SAEs were considered to be unrelated to treatment with BVD-523. Dose reductions resulting from AEs occurred in 3 patients during the study: 1 patient reduced from 600 mg BID to 300 mg BID and 2 patients reduced from 900 mg BID to 600 mg BID.

Example 22

Pharmacokinetics

Figure 39A:
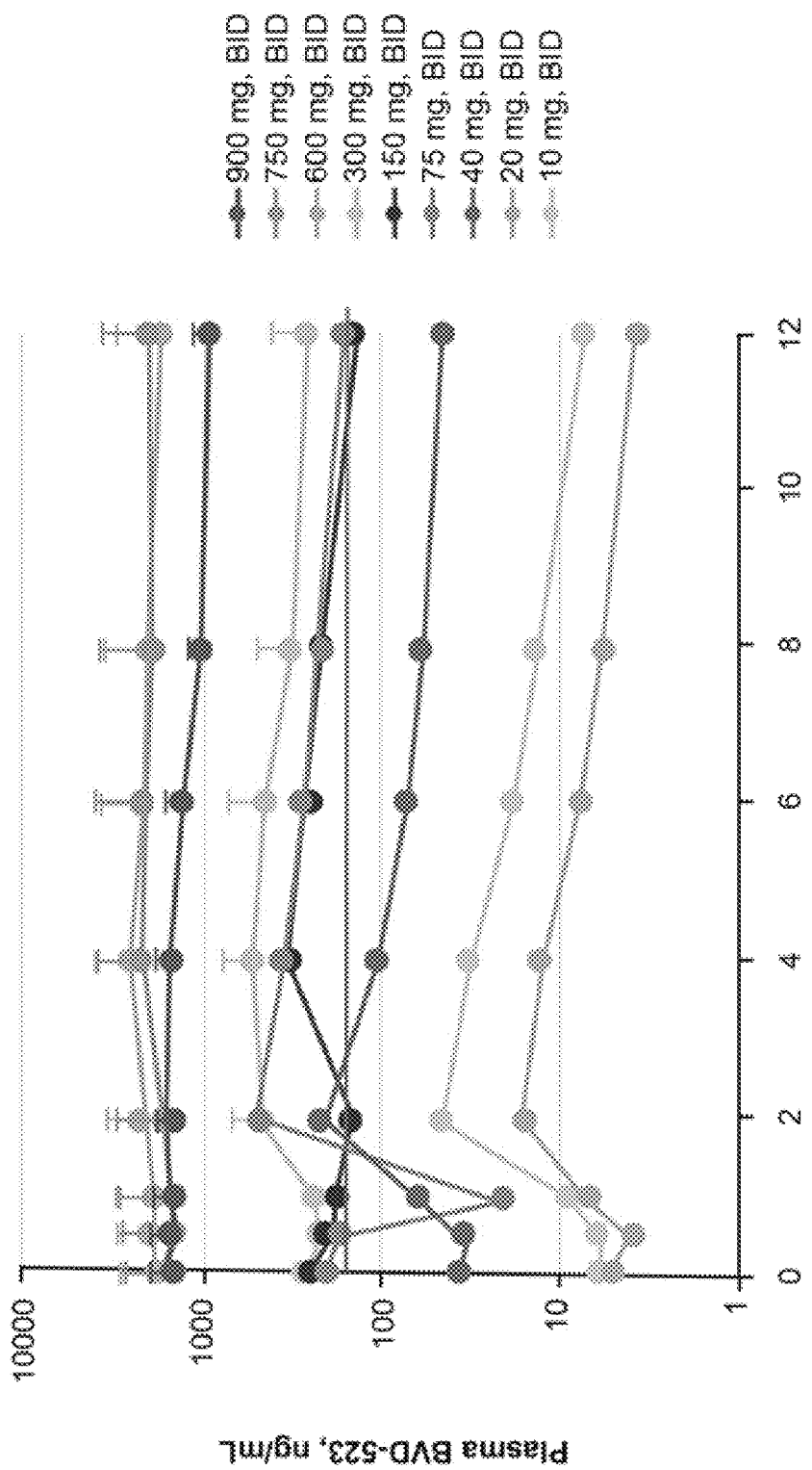
FIG. 39A shows steady-state BVD-523 pharmacokinetics (Cycle 1, Day 15). The dashed red line indicates an EC$_{50}$ 200 ng/mL HWB. Abbreviations: AUC, area under the curve; BID, twice daily; C$_{max}$, maximum concentration; EC$_{50}$, 50% maximum effective concentration; HWB, human whole blood; SD, standard deviation.

Single-dose and steady-state pharmacokinetics of BVD-523 are summarized in FIG. 39A and Table 28. Generally, orally administered BVD-523 was slowly absorbed in patients with advanced malignancies. After reaching the maximum concentration ($C_{max}$), plasma BVD-523 levels remained sustained for approximately 2 to 4 hours. Subsequently, plasma drug concentrations slowly declined. Since plasma drug concentrations were measured only up to 12 hours after the morning dose, it was not possible to calculate an effective or terminal phase elimination rate. BVD-523 pharmacokinetics were linear and dose proportional in terms of both C. and area under the curve (AUC) when administered up to 600 mg BID. A further increase in exposure was not observed as the dose increased from 600 to 900 mg BID. The $C_{max}$ reached the level of the $EC_{50}$ based on the ex vivo whole blood assay (200 ng/mL) for all doses above 20 mg BID. Additionally, steady-state exposures remained at or above the target $EC_{50}$ for dose levels of 150 mg BID throughout the dosing period. Minimal plasma accumulation of BVD-523 and its metabolites were observed on Day 15 at the lower (<75 mg BID) dose levels, whereas accumulation ranged from approximately 1.3- to 4.0-fold for the higher dose levels. Predose concentrations on Day 22 were generally similar to those on Day 15, indicating that steady state had already been attained by Day 15 (data not shown). The degree of interpatient variability in plasma exposure to BVD-523 and its metabolites was considered moderate and not problematic.

TABLE 28

Steady-state BVD-523 pharmacokinetics (Cycle 1, Day 15)

| Dose, mg[a] | n∞ | $C_{max}$, ng/mL ± SD Day 1 | Day 15 | $AUC_{0-22}$, ng · hr/mL ± SD Day 1 | Day 15 |
|---|---|---|---|---|---|
| 10 | 1 | 48.2 | 45.7 | 220 | 234 |
| 20 | 1 | 14.9 | 15.8 | 91.7 | 98.7 |
| 40 | 1 | 100 | 191 | 614 | 999 |
| 150 | 1 | 133 | 326 | 817 | 2770 |
| 300 | 4[b] | 765 ± 234 | 586 ± 257 | 4110 ± 1140 | 4460 ± 2460 |
| 600[c] | 7[d] | 1110 ± 589 | 2750 ± 1740 | 2750 ± 1740 | 24400 ± 16200 |
| 750 | 4[b] | 1450 ± 539 | 2290 ± 1790[f] | 10700 ± 1120[g] | 23300 ± 19800[f] |
| 900 | 7[e] | 1430 ± 1010 | 1720 ± 328 | 10800 ± 6320[h] | 15900 ± 1300[g] |

[a]Dose level administered twice daily;
[b]N = 3 on Day 15;
[c]Number of subjects for Day 15 at the 600 mg dose level includes two subjects who started Day 1 dosing at 900 mg and were later reduced to 600 mg;
[d]n = 8 on Day 15;
[e]n = 4 on Day 15;
[f]One subject started on Day 1 dosing at 750 mg and was later reduced to 450 mg. Day 15 parameters for this subject reflect at least 10 consecutive doses at 450 mg/dose. Individual Day 15 parameters were 1300 ng/ml, for $C_{max}$ and 10700 ng · hr/mL for $AU_{0-22}$;
[g]n = 3;
[h]n = 5.

The urinary excretion after first dose and at steady state of BVD-523 was negligible (<0.2% of the dose) at all dose levels within 12 hours postdose, and not dose-related within this very low percentage range. Renal clearance appeared to be dose-independent. Individual renal clearance values ranged from 0.128 to 0.0895 L/hr (where n=1 per dose level) and mean values ranged from 0.0149 to 0.0300 L/hr (where n 3).

Example 23

Pharmacodynamic Confirmation of Target Inhibition by BVD-523

Figure 39B:
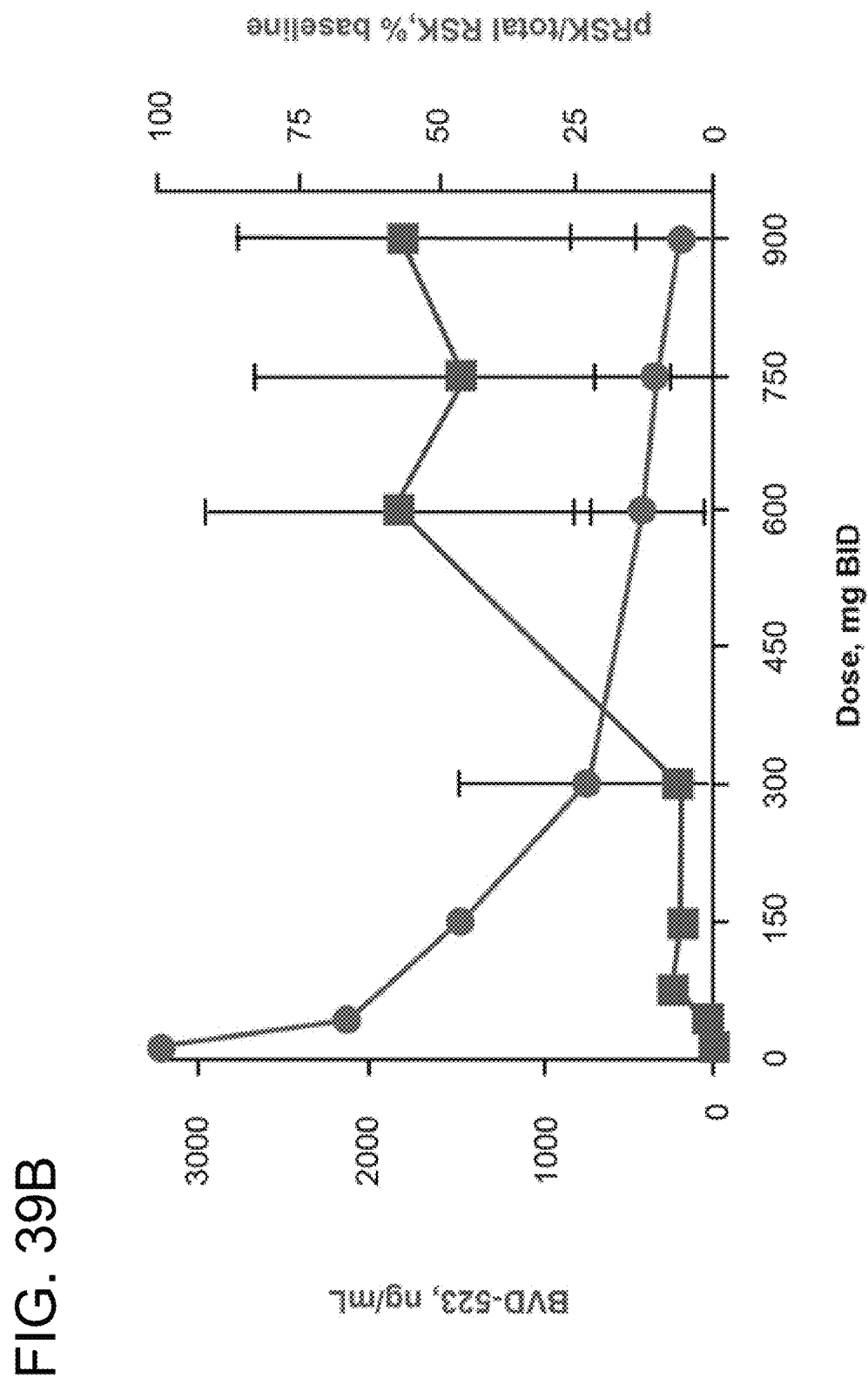
FIG. 39B shows pharmacodynamic inhibition of ERK phosphorylation by BVD-523 in human whole blood. Abbreviations: BID, twice daily; pRSK, phospho-RSK; RSK, ribosomal S6 kinase.

To confirm on-target and pathway inhibition by BVD-523, RSK-1 phosphorylation was examined as a target biomarker in human whole blood samples from patients with solid tumors who received BVD-523. Steady state whole blood samples collected just prior to Day 15 dosing from BVD-523-treated patients displayed concentration-dependent inhibition of PMA stimulated ERK activity (FIG. 39B), ranging from 0% ERK inhibition with BVD-523 dosing at 10 mg BID to 93±8% ERK inhibition with dosing at 900 mg BID. The plasma concentrations of BVD-523 that yielded 50% inhibition of ERK phosphorylation were similar whether BVD-523 was spiked directly into healthy volunteer plasma or was present following oral dosing of patients.

Example 24

Antitumor Effects

Figure 40A:
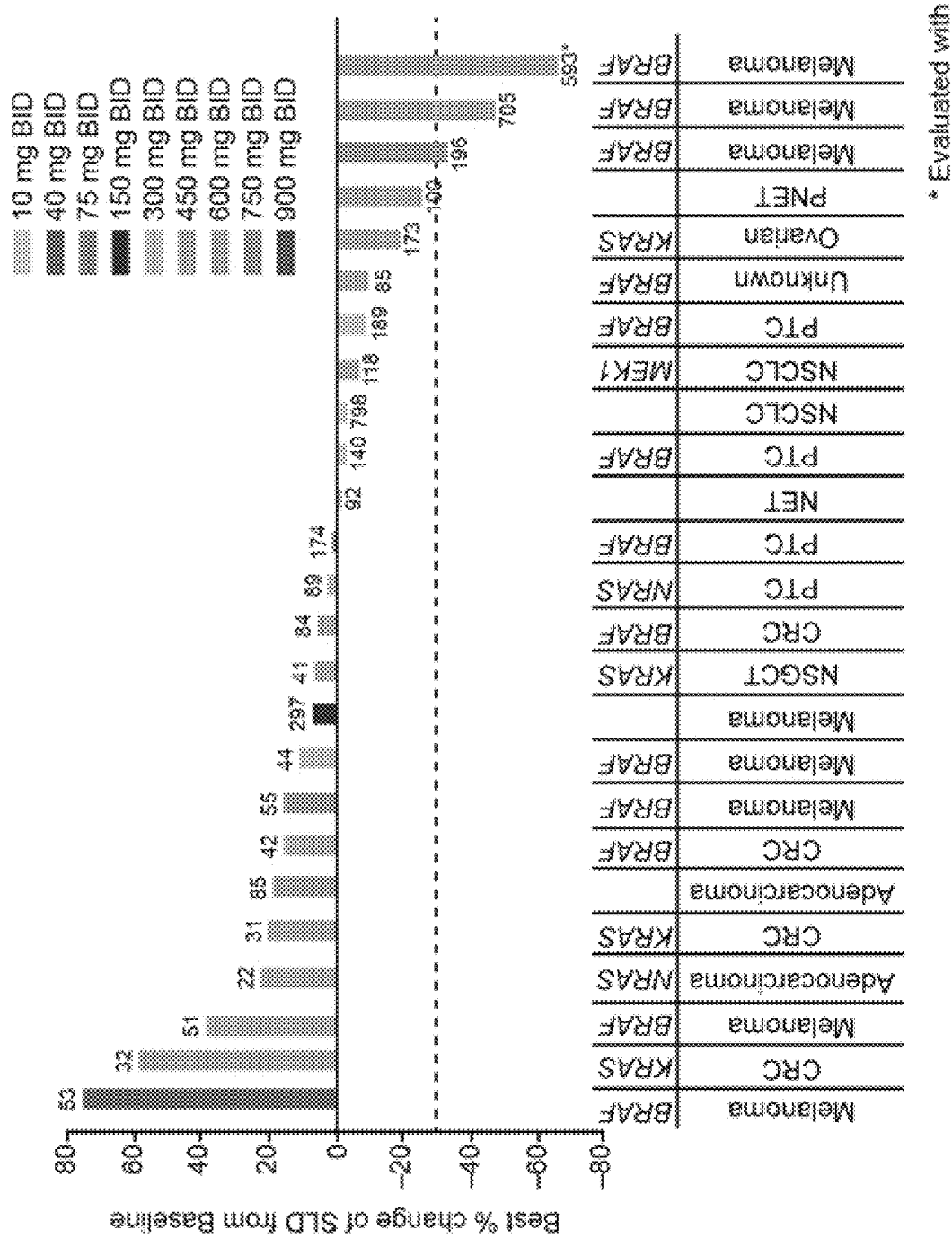
FIG. 40A shows the best radiographic response in patients treated with BVD-523. Included are all patients with disease measured by RECIST v1.1 who received ≥1 dose of study treatment and had >1 on-treatment tumor assessment (25/27; 2 did not receive both scans of target lesions). Response was measured as the change from baseline in the sum of the longest diameter of each target lesion. Dose shown is that which the patient was receiving at the time of response. The dashed line indicates the threshold for a partial response according to RECIST v1.1. Abbreviations: CRC, colorectal cancer; NET, neuroendocrine tumors; NSCLC, non-small cell lung cancer; NSGCT, nonseminomatous germ cell tumors; PNET, pancreatic NET; PTC, papillary thyroid cancer; RECIST v1.1, Response Evaluation Criteria in Solid Tumors version 1.1; SLD, sum of the largest diameter.

Tumor response to BVD-523 was assessed in 25 evaluable patients using Response Evaluation Criteria in Solid Tumors version 1.1 (RECIST v1.1); 2 patients did not receive both scans of target lesions and were thus not evaluated using RECIST v1.1. No patients achieved a complete response, but 3 patients (all patients with melanoma with $BRAF^{V600}$ mutations) achieved a partial response (129 days [BRAF/MEK-inhibitor naïve], 294 days ongoing at [refractory to prior BRAF/MEK inhibitors], 313 days ongoing by the data cutoff date [intolerant to other BRAF/MEK inhibitors]) (FIG. 40A). Interestingly, all 3 partial responders had BRAF-mutant melanoma. One partial responder, who was receiving BVD-523 at a dose of 450 mg BID, had an approximate 70% reduction in the sum of target lesions from baseline, while the other partial responders showed reductions of 47.0% and 33.6%. Stable disease was demonstrated in 18 patients, with 6 having stable disease for more than 6 months, and 6 additional patients having stable disease for more than 3 months. In this study, 4 patients displayed progressive disease at first evaluation.

Figure 40B:
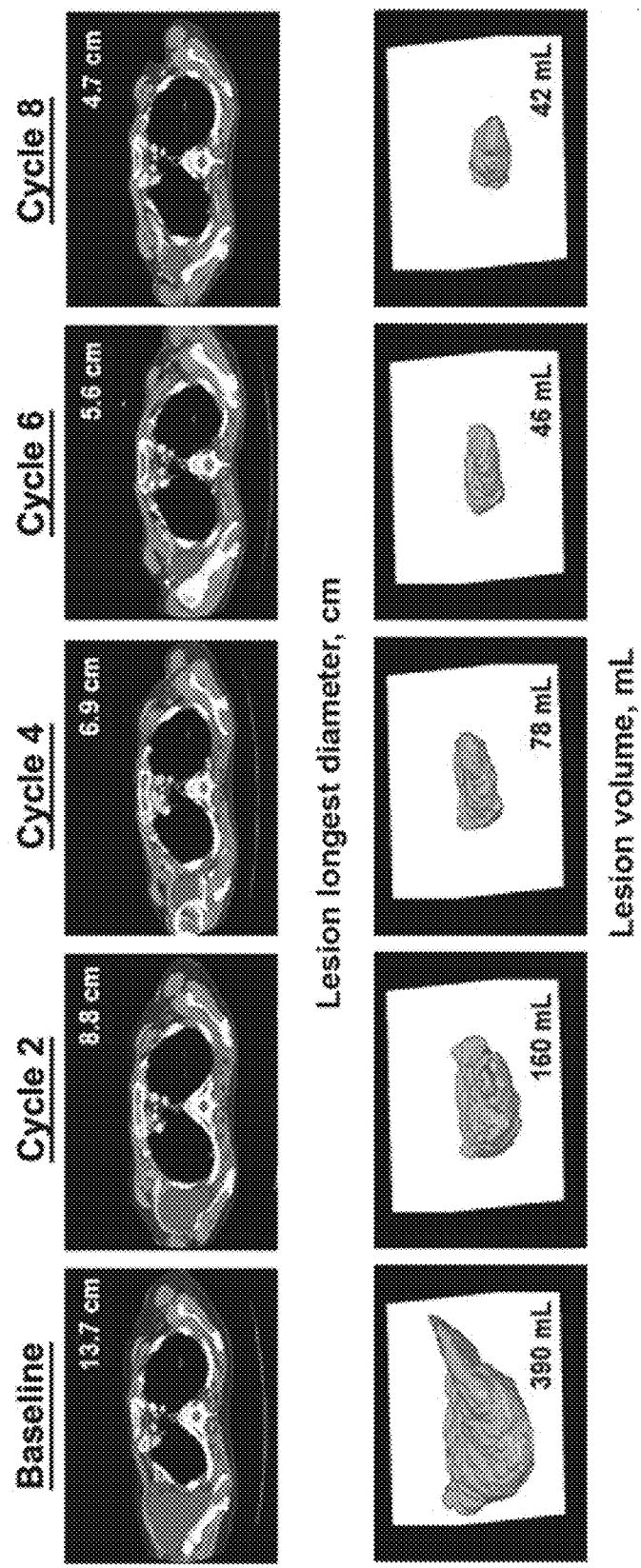
FIG. 40B shows a computerized tomography scan of a confirmed partial response in a 61-year-old patient with a BRAF-mutant melanoma treated with BVD-523.

FIG. 40B shows computed tomography (CT) scans of 1 of the 3 partial responders (RECIST v1.1) who had progressed on prior vemurafenib and subsequent dabrafenib/trametinib treatment; a durable partial response was observed following dosing of BVD-523 600 mg BID for >300 days. BVD-523 was associated with a metabolic response using fluorodeoxyglucose-positive emission tomography ($^{18}$F-FDG-PET) in 5 of 16 evaluable patients.

Figure 41:
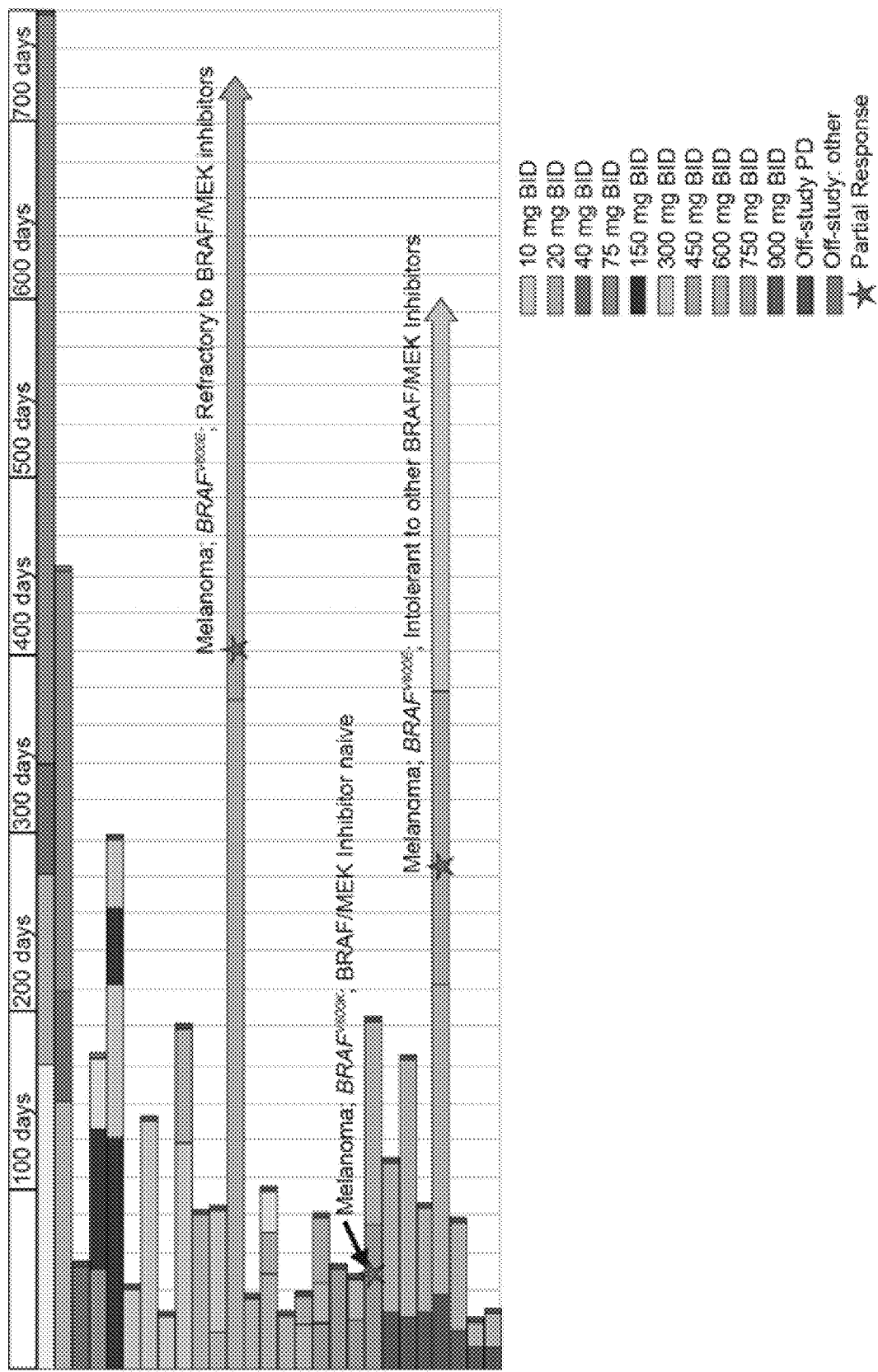
FIG. 41 shows tumor response and tumor progression. Shown is a swimmer plot of tumor response, tumor progression, and duration of treatment in response-evaluable patients treated with BVD-523. Origin of the vertical axis corresponds to randomization date or reference start date. Analysis cut-off date: Dec. 1, 2015. Abbreviation: BID, twice daily.

FIG. 41 depicts the time to response and the duration of response in the study population. The two patients who demonstrated responses to BVD-523 remained on study and continued with BVD-523 treatment as of the study cutoff date (>500 days); additionally, one patient with bronchoalveolar NSCLC (not enough tissue for molecular profiling) had been on treatment for >700 days with stable disease. Twenty-four of 27 patients (90%) discontinued treatment due to progressive disease (22/27, 82%) or other reasons (2/27, 7%). The mean duration of BVD-523 treatment before discontinuation was 4.7 months.

Discussion

The present invention presents results from a first-in-human study evaluating the safety, pharmacokinetics, pharmacodynamics, and preliminary efficacy of BVD-523 in 27 patients with advanced solid tumors. In this dose-escalation study, oral treatment with BVD-523 resulted in both radiographic responses by RECIST v1.1 (3 partial responses) and prolonged disease stabilization in some patients, the majority of whom had been treated with prior systemic therapies. Evidence of BVD-523-dependent inhibition of metabolic response in tumors was established in a subset of patients by imaging tumor uptake of $^{18}$F-glucose. Drug exposures increased linearly with increasing doses up to 600 mg BID, with exposures at 600 mg BID providing near complete 24/7 inhibition of ERK-dependent substrate (RSK-1) phosphorylation in an ex vivo whole blood assay. Furthermore, tolerability to BVD-523 was manageable when administered up to its MTD and RP2D, determined to be 600 mg BID.

BVD-523 was generally well tolerated, with manageable and reversible toxicity. The most common AEs were rash (usually acneiform), fatigue, and gastrointestinal side effects, including nausea, vomiting, and diarrhea. The safety profile of BVD-523 is consistent with its selective inhibition of the MAPK pathway; the AE profile shows considerable overlap with MEK inhibitor experience. However, toxicities associated with any targeted therapy may include dependence on both the specific mechanism and the degree of target inhibition as well as any off-target effects (Zelboraf [package insert] and Hauschild et al. 2012). Ongoing and future investigations will extend both the efficacy and safety profile demonstrated in this dose-escalation study, and will guide how the unique profile of the ERK inhibitor BVD-523 might be used as a single agent or in combination with other agents.

Durable responses by RAF and MEK inhibitors are often limited by intrinsic and eventual acquired resistance, with a common feature often involving reactivation of the ERK pathway (Poulikakos et al. 2011, Corcoran et al. 2010, Nazarian et al. 2010, Shi et al. 2014, Johannessen et al. 2010, Wagle et al. 2011, Wagle et al. 2014, Ahronian et al. 2015 and Paraiso et al. 2010). Thus, ERK inhibition with BVD-523 alone or in combination with other MAPK signaling pathway inhibitors may have the potential to delay the development of resistance to existing therapies and to benefit a broader patient population. That ERK inhibitors, including BVD-523, retain their potency in BRAF- and MEK-resistant cell lines provide preclinical evidence for the use of ERK inhibitors in patients with acquired resistance to standard of care (BRAF/MEK combination therapy) See, e.g., Examples 9-16. Importantly, in this study, a patient whose cancer had progressed after experiencing stable disease when treated initially with a BRAF inhibitor (vemurafenib) and subsequently with a combination of BRAF and MEK inhibitors (dabrafenib/trametinib) had a partial response when receiving single-agent BVD-523. This patient has remained on-study for a total of 708 days, as of the cutoff date of the study reported herein. Based in part on the antitumor effects observed in this patient, the FDA has designated as a Fast Track development program the investigation of BVD-523 for the treatment of patients with unresectable or metastatic $BRAF^{v600}$ mutation-positive melanoma that is refractory to or has progressed following treatment with a BRAF and/or MEK inhibitor(s). Precise definition of exactly how BVD-523 might best support patient care (eg, as a single agent or in various combinations) requires additional clinical studies.

In summary, the present examples present data from an initial data from the dose escalation portion of a phase I study evaluating BVD-523, a novel first-in-class ERK inhibitor, as a treatment for patients with advanced cancers. Continuous, twice-daily oral treatment with BVD-523 resulted in antitumor effects in several patients, including patients either naïve to or having progressed on available MAPK pathway-targeted therapies. BVD-523 was generally well tolerated in this advanced cancer patient population and toxicities were manageable; the MTD and RP2D were 600 mg BID. BVD-523 exposures increased linearly up to the RP2D and robust pharmacodynamics effects were evident at this dose level. An expansion of this phase I clinical study is currently underway to confirm and extend the observations made in the dose-escalation phase. Specifically, patients are being enrolled into molecularly classified expansion cohorts (e.g., NRAS, BRAF, MEK or ERK alterations) across various tumor histologies. Furthermore, expansion cohorts are evaluating the use of BVD-523 in patients with cancer who are either naïve to available MAPK pathway therapies or those whose disease has progressed on such treatments.

DOCUMENTS

ABSALAN, Farnaz, Mostafa Ronaghi (2008). Molecular Inversion Probe Assay. Methods in Molecular Biology 396. Humana Press. pp. 315-330.

AHRONIAN L G, Sennott E M, Van Allen E M, Wagle N, Kwak E L, Faris J E, et al. Clinical acquired resistance to RAF inhibitor combinations in BRAF-mutant colorectal cancer through MAPK pathway alterations. Cancer Discov 2015; 5:358-67.

ARCILA M E, Drilon A, Sylvester B E, Lovly C M, Borsu L, Reva B, et al. MAP2K1 (MEK1) mutations define a distinct subset of lung adenocarcinoma associated with smoking. Clin Cancer Res 2015; 21:1935-43.

ARONOV A M, Baker C, Bemis G W, Cao J, Chen G, Ford P J, et al. Flipped out: structure-guided design of selective pyrazolylpyrrole ERK inhibitors. J Med Chem 2007; 50:1280-7.

ARONOV A M, Tang Q, Martinez-Botella G, Bemis G W, Cao J, Chen G, et al. Structure-guided design of potent and selective pyrimidylpyrrole inhibitors of extracellular signal-regulated kinase (ERK) using conformational control. J Med Chem 2009; 52:6362-8.

ARRINGTON A K, Heinrich E L, Lee W, Duldulao M, Patel S, Sanchez J, et al. Prognostic and predictive roles of KRAS mutation in colorectal cancer. Int J Mol Sci 2012; 13:12153-68.

CARGNELLO M, Roux P P. Activation and function of the MAPKs and their substrates, the MAPK-activated protein kinases. Microbiol Mol Biol Rev 2011; 75:50-83.

CARLINO M S, Fung C, Shahheydari H, Todd J R, Boyd S C, Irvine M, et al. Preexisting MEK1P124 mutations diminish response to BRAF inhibitors in metastatic melanoma patients. Clin Cancer Res 2015; 21:98-105.

CHAPMAN P B, Hauschild A, Robert C, Haanen J B, Ascierto P, Larkin J, et al. Improved survival with vemurafenib in melanoma with BRAF V600E mutation. N Engl J Med 2011; 364:2507-16.

CORCORAN, R. B., et al. BRAF gene amplification can promote acquired resistance to MEK inhibitors in cancer cells harboring the BRAF V600E mutation. Sci Signal (2010); 3(149): ra84.

DAI, B., et al. STAT3 mediates resistance to MEK inhibitor through microRNA miR-17. Cancer Res (2011); 71:3658-3668.

DAVIES H, Bignell G R, Cox C, Stephens P, Edkins S, Clegg S, et al. Mutations of the BRAF gene in human cancer. Nature 2002; 417:949-54.

DESCHENES-SIMARD X, Kottakis F, Meloche S, Ferbeyre G. ERKs in cancer: friends or foes? Cancer Res 2014; 74:412-9.

DOBRZYCKA B, Terlikowski S J, Kowalczuk O, Niklinska W, Chyczewski L, Kulikowski M. Mutations in the KRAS gene in ovarian tumors. Folia Histochem Cytobiol 2009; 47:221-4.

EMERY, C. M., et al. MEK1 mutations confer resistance to MEK and B-RAF inhibition. PNAS (2009); 106(48): 20411-6.

FEDOROV O, Niesen F H, Knapp S. Kinase inhibitor selectivity profiling using differential scanning fluorimetry. Methods Mol Biol 2012; 795:109-18.

FERNÁNDEZ-MEDARDE A, Santos E. Ras in cancer and developmental diseases. Genes Cancer 2011; 2:344-58.

FLAHERTY K T, Infante J R, Daud A, Gonzalez R, Kefford R F, Sosman J, et al. Combined BRAF and MEK inhibition in melanoma with BRAF V600 mutations. N Engl J Med 2012; 367:1694-703.

GOETZ E M, Ghandi M, Treacy D J, Wagle N, Garraway L A. ERK mutations confer resistance to mitogen-activated protein kinase pathway inhibitors. Cancer Res 2014; 74:7079-89.

GOLLOB J A, Wilhelm S, Carter C, Kelley S L. Role of Raf kinase in cancer: therapeutic potential of targeting the Raf/MEK/ERK signal transduction pathway. Semin Oncol 2006; 33:392-406.

GREGER, James G., et al. "Combinations of BRAF, MEK, and PI3K/mTOR inhibitors overcome acquired resistance to the BRAF inhibitor GSK2118436 dabrafenib, mediated by NRAS or MEK mutations." Molecular cancer therapeutics 11.4 (2012): 909-920.

GROENENDIJK F H, Bernards R. Drug resistance to targeted therapies: deja vu all over again. Mol Oncol 2014; 8:1067-83.

HALL R D, Kudchadkar R R. BRAF mutations: signaling, epidemiology, and clinical experience in multiple malignancies. Cancer Control 2014; 21:221-30.

HARDENBOL, P., et al. Multiplexed genotyping with sequence-tagged molecular inversion probes. Nat. Biotechnol. 2003, no. 21, p. 673-678.

HATZIVASSILIOU, Georgia, et al. "RAF inhibitors prime wild-type RAF to activate the MAPK pathway and enhance growth." Nature 464.7287 (2010): 431-435.

HATZIVASSILIOU G, Liu B, O'Brien C, Spoerke J M, Hoeflich K P, Haverty P M, et al. ERK inhibition overcomes acquired resistance to MEK inhibitors. Mol Cancer Ther 2012; 11:1143-54.

HAUSCHILD A, Grob J-J, Demidov L V, Jouary T, Gutzmer R, Millward M, et al. Dabrafenib in BRAF-mutated metastatic melanoma: a multicentre, open-label, phase 3 randomised controlled trial. Lancet 2012; 380:358-65.

HAYES T K, Neel N F, Hu C, Gautam P, Chenard M, Long B, et al. Long-Term ERK Inhibition in KRAS-Mutant Pancreatic Cancer Is Associated with MYC Degradation and Senescence-like Growth Suppression. Cancer Cell 2016; 29:75-89.

HEZEL A F, Noel M S, Allen J N, Abrams T A, Yurgelun M, Faris J E, et al. Phase II study of gemcitabine, oxaliplatin in combination with panitumumab in KRAS wild-type unresectable or metastatic biliary tract and gallbladder cancer. Br J Cancer 2014; 111:430-6.

JHA S, Morris E J, Hruza A, Mansueto M S, Schroeder G, Arbanas J, et al. Dissecting therapeutic resistance to ERK inhibition. Mol Cancer Ther 2016; 15:548-59.

JOHANNESSEN, C. M., et al. COT/MAP3K8 drives resistance to RAF inhibition through MAP kinase pathway reactivation. Nature (2010); 468(7326):968-972.

JOHNSON D B, Menzies A M, Zimmer L, Eroglu Z, Ye F, Zhao S, et al. Acquired BRAF inhibitor resistance: A multicenter meta-analysis of the spectrum and frequencies, clinical behaviour, and phenotypic associations of resistance mechanisms. Eur J Cancer 2015; 51:2792-9.

KANDA M, Matthaei H, Wu J, Hong S M, Yu J, Borges M, et al. Presence of somatic Mutations in most early-stage pancreatic intraepithelial neoplasia. Gastroenterology 2012; 142:730-733.

KHATTAK M, Fisher R, Turajlic S, Larkin J. Targeted therapy and immunotherapy in advanced melanoma: an evolving paradigm. Ther Adv Med Oncol 2013; 5:105-18.

KING, Alastair J., et al. "Dabrafenib; preclinical characterization, increased efficacy when combined with trametinib, while BRAF/MEK tool combination reduced skin lesions." PloS one 8.7 (2013): e67583.

LARKIN J, Ascierto P A, Dreno B, Atkinson V, Liszkay G, Maio M, et al. Combined vemurafenib and cobimetinib in BRAF-mutated melanoma. N Engl J Med 2014; 371:1867-76.

LITTLE, A. S., et al., Amplification of the Driving Oncogene, KRAS or BRAF, Underpins Acquired Resistance to MEK1/2 Inhibitors in Colorectal Cancer Cells. Sci. Signal. 4, ra17 (2011).

LIU, Dingxie, et al. "BRAF V600E maintains proliferation, transformation, and tumorigenicity of BRAF-mutant papillary thyroid cancer cells." Journal of Clinical Endocrinology & Metabolism 92.6 (2007): 2264-2271.

LIU B, Fu L, Zhang C, Zhang L, Zhang Y, Ouyang L, et al. Computational design, chemical synthesis, and biological evaluation of a novel ERK inhibitor (BL-EI001) with apoptosis-inducing mechanisms in breast cancer. Oncotarget 2015; 6:6762-75.

LONG G V, Fung C, Menzies A M, Pupo G M, Carlino M S, Hyman J, et al. Increased MAPK reactivation in early resistance to dabrafenib/trametinib combination therapy of BRAF-mutant metastatic melanoma. Nat Commun 2014; 5:5694.

LONG G V, Stroyakovskiy D, Gogas H, Levchenko E, de Braud F, Larkin J, et al. Dabrafenib and trametinib versus dabrafenib and placebo for Val600 BRAF-mutant melanoma: a multicentre, double-blind, phase 3 randomised controlled trial. Lancet 2015; 386:444-51.

MANANDHAR S P, Hildebrandt E R, Schmidt W K. Small-molecule inhibitors of the Rce1p CaaX protease. J Biomol Screen. 2007; 12(7):983-993.

MASSEY P R, Prasad V, Figg W D, Fojo T. Multiplying therapies and reducing toxicity in metastatic melanoma. Cancer Biol Ther 2015; 16:1014-8.

MAURER, T, Garrenton, L S, Oh, A, Pitts, K, Anderson, D J, Skelton, N J, Fauber, B P, Pan, B, Malek, S, Stokoe, D, Ludlam, M J C, Bowman, K K, Wu, J, Giannetti, A M, Starovasnik, M A, Mailman, I, Jackson, P K, Rudolph, J, Wang, W, Fang, G. Small-molecule ligands bind to a distinct pocket in Ras and inhibit SOS-mediated nucleotide exchange activity. PNAS. 2012; 109(14):5299-304.

MCARTHUR G A, Chapman P B, Robert C, Larkin J, Haanen J B, Dummer R, et al. Safety and efficacy of vemurafenib in $BRAF^{V600E}$ and $BRAF^{V600K}$ mutation-positive melanoma (BRIM-3): extended follow-up of a phase 3, randomised, open-label study. Lancet Oncol 2014; 15:323-32.

MEKINIST [package insert]. Research Triangle Park, N C: GlaxoSmithKline; 2014.

METZKER, Emerging technologies in DNA sequencing Genome Res. 2005. 15: 1767-1776.

MITTAL, Rohit et al. "The acetyltransferase activity of the bacterial toxin YopJ of Yersinia is activated by eukaryotic host cell inositol hexakisphosphate." Journal of Biological Chemistry 285.26 (2010): 19927-19934.

MORRIS E J, Jha S, Restaino C R, Dayananth P, Zhu H, Cooper A, et al. Discovery of a novel ERK inhibitor with activity in models of acquired resistance to BRAF and MEK inhibitors. Cancer Discov 2013; 3:742-50.

NAZARIAN, R., et al. Melanomas acquire resistance to B-RAF (V600E) inhibition by RTK or N-RAS upregulation. Nature. 2010; 468(7326):973-977.

NIKOLAEV S I, Rimoldi D, Iseli C, Valsesia A, Robyr D, Gehrig C, et al. Exome sequencing identifies recurrent somatic MAP2K1 and MAP2K2 mutations in melanoma. Nat Genet 2012; 44:133-9.

NILSSON, M., et al. Padlock probes: circularizing oligonucleotides for localized DNA detection. Science. 1994, no. 265, p. 2085-2088.

O'HARA A J, Bell D W. The genomics and genetics of endometrial cancer. Adv Genomics Genet 2012; 2012:33-47.

OJESINA A I, Lichtenstein L, Freeman S S, Pedamallu C S, Imaz-Rosshandler I, Pugh T J, et al. Landscape of genomic alterations in cervical carcinomas. Nature 2014; 506:371-5.

OTA et al., Single nucleotide polymorphism detection by polymerase chain reaction-restriction fragment length polymorphism. Nat Protoc. 2007; 2(11):2857-64.

PARAISO K H T, Fedorenko I V, Cantini L P, Munko A C, Hall M, Sondak V K, et al. Recovery of phospho-ERK activity allows melanoma cells to escape from BRAF inhibitor therapy. Br J Cancer 2010; 102:1724-30.

PATGIRI A, Yadav, K K, Arora, P S, Bar-Sagi, D. An orthosteric inhibitor of the Ras-Sos interaction. Nat Chem Biol. 2011; 7:585-587.

PENNYCUICK A, Simpson T, Crawley D, Lal R, Santis G, Cane P, et al. Routine EGFR and KRAS mutation analysis using COLD-PCR in non-small cell lung cancer. Int J Clin Pract 2012; 66:748-52.

PORTER S B, Hildebrandt E R, Breevoort S R, Mokry D Z, Dore™, Schmidt W K. Inhibition of the CaaX proteases Rce1p and Ste24p by peptidyl (acyloxy)methyl ketones. Biochim Biophys Acta. 2007; 1773(6):853-862.

POULIKAKOS P I, Persaud Y, Janakiraman M, Kong X, Ng C, Moriceau G, et al. RAF inhibitor resistance is mediated by dimerization of aberrantly spliced BRAF(V600E). Nature 2011; 480:387-90.

QUEIROLO P, Picasso V, Spagnolo F. Combined BRAF and MEK inhibition for the treatment of BRAF-mutated metastatic melanoma. Cancer Treat Rev 2015; 41:519-26.

RASOLA A, Sciacovelli M, Chiara F, Pantic B, Brusilow W S, Bernardi P. Activation of mitochondrial ERK protects cancer cells from death through inhibition of the permeability transition. Proc Natl Acad Sci USA 2010; 107: 726-31.

RIZOS H, Menzies A M, Pupo G M, Carlino M S, Fung C, Hyman J, et al. BRAF inhibitor resistance mechanisms in metastatic melanoma: spectrum and clinical impact. Clin Cancer Res 2014; 20:1965-77.

ROBERT C, Karaszewska B, Schachter J, Rutkowski P, Mackiewicz A, Stroiakovski D, et al. Improved overall survival in melanoma with combined dabrafenib and trametinib. N Engl J Med 2015; 372:30-9.

ROMEO Y, Zhang X, Roux P P. Regulation and function of the RSK family of protein kinases. Biochem J 2012; 441:553-69.

RUDOLPH J, Xiao Y, Pardi A, Ahn N G. Slow inhibition and conformation selective properties of extracellular signal-regulated kinase 1 and 2 inhibitors. Biochemistry 2015; 54:22-31.

SHAUL Y D, Seger R. The MEK/ERK cascade: from signaling specificity to diverse functions. Biochim Biophys Acta 2007; 1773:1213-26.

SHI H, Hugo W, Kong X, Hong A, Koya R C, Moriceau G, et al. Acquired resistance and clonal evolution in melanoma during BRAF inhibitor therapy. Cancer Discov 2014; 4:80-93.

SHIMA, F, Yoshikawa, Y, Ye, M, Araki, M, Matsumoto, S, Liao, J, Hu, L, Sugimoto, T, Ijiri, Y, Takeda, A, Nishiyama, Y, Sato, C, Muraoka, S, Tamura, A, Osoda, T, Tsuda, K-I, Miyakawa, T, Fukunishi, H, Shimada, J, Kumasaka, Yamamoto, M, Kataoka, T. In silico discovery of small-molecule Ras inhibitors that display antitumor activity by blocking the Ras-effector interaction. PNAS. 2013; 110(20):8182-7.

SCHUBBERT S, Shannon K, Bollag G. Hyperactive Ras in developmental disorders and cancer. Nat Rev Cancer 2007; 7:295-308.

SUN C, Hobor S, Bertotti A, Zecchin D, Huang S, Galimi F, et al. Intrinsic resistance to MEK inhibition in KRAS mutant lung and colon cancer through transcriptional induction of ERBB3. Cell Rep 2014; 7:86-93.

TAFLINAR [package insert]. Research Triangle Park, N C: GlaxoSmithKline; 2015.

TRUNZER K, Pavlick A C, Schuchter L, Gonzalez R, McArthur G A, Hutson T E, et al. Pharmacodynamic effects and mechanisms of resistance to vemurafenib in patients with metastatic melanoma. J Clin Oncol 2013; 31:1767-74.

VILLANUEVA, J., et al. Acquired resistance to BRAF inhibitors mediated by a RAF kinase switch in melanoma can be overcome by cotargeting MEK and IGF-1R/PI3K. Cancer Cell. 2010; 18:683-695.

WAGLE, N., et al. Dissecting therapeutic resistance to RAF inhibition in melanoma by tumor genomic profiling. Journal of Clinical Oncology 2011; 29(22):3085-3096.

WAGLE N, Van Allen E M, Treacy D J, Frederick D T, Cooper Z A, Taylor-Weiner A, et al. MAP kinase pathway alterations in BRAF-mutant melanoma patients with acquired resistance to combined RAF/MEK inhibition. Cancer Discov 2014; 4:61-8.

Wainstein E, Seger R. The dynamic subcellular localization of ERK: mechanisms of translocation and role in various organelles. Curr Opin Cell Biol 2016; 39:15-20.

WANG, H., et al. Identification of the MEK1(F129L) activating mutation as a potential mechanism of acquired resistance to MEK inhibition in human cancers carrying the B-RAF V600E mutation. Cancer Res (2011); 71(16): 5535-45.

YANG W, Soares J, Greninger P, Edelman E J, Lightfoot H, Forbes S, et al. Genomics of Drug Sensitivity in Cancer (GDSC): a resource for therapeutic biomarker discovery in cancer cells. Nucleic Acids Res 2013; 41: D955-D961.

YAO Z, Torres N M, Tao A, Gao Y, Luo L, Li Q, et al. BRAF Mutants Evade ERK-Dependent Feedback by Different Mechanisms that Determine Their Sensitivity to Pharmacologic Inhibition. Cancer Cell 2015; 28:370-83.

YOHE S. Molecular genetic markers in acute myeloid leukemia. J Clin Med 2015; 4:460-78.

ZELBORAF [package insert]. South San Francisco, Calif.: Genentech USA, Inc.; 2015.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for treating or ameliorating the effects of a cancer in a subject comprising:
   (a) identifying a subject with cancer that has become refractory or resistant to BRAF inhibitor therapy, MEK inhibitor therapy, or BRAF and MEK inhibitor therapy, comprising:
      (1) obtaining a biological sample from the subject; and
      (2) screening the sample to determine whether the subject has become resistant to an inhibitor therapy selected from the group consisting of BRAF inhibitor therapy, MEK inhibitor therapy, and combinations thereof,
         wherein the screening for a cancer that is refractory or resistant to BRAF inhibitor therapy comprises identifying (i) a switch between RAF isoforms, (ii) upregulation of RTK signaling, (iii) reactivation of mitogen activated protein kinase (MAPK) signaling, (iv) the presence of a MEK activating mutation, and combinations thereof; and
   (b) administering to the subject with said refractory or resistant cancer an effective amount of an ERK inhibitor, which is BVD-523 or a pharmaceutically acceptable salt thereof.

2. The method according to claim 1, wherein the subject is a mammal.

3. The method according to claim 2, wherein the mammal is selected from the group consisting of humans, primates, farm animals, and domestic animals.

4. The method according to claim 2, wherein the mammal is a human.

5. The method according to claim 1, wherein the cancer has MAPK activity.

6. The method according to claim 5, wherein the cancer is a solid tumor cancer or a hematologic cancer.

7. The method according to claim 5, wherein the cancer is selected from the group consisting of a cancer of the large intestine, breast cancer, pancreatic cancer, skin cancer, and endometrial cancers.

8. The method according to claim 5, wherein the cancer is melanoma.

9. The method according to claim 1, wherein the screening for a cancer that is refractory or resistant to MEK inhibitor therapy comprises identifying (i) amplification of mutant BRAF, (ii) STAT3 upregulation, (iii) mutations in the allosteric pocket of MEK that directly block binding of inhibitors to MEK or lead to constitutive MEK activity, and combinations thereof.

10. The method according to claim 1 further comprising administering at least one additional therapeutic agent selected from the group consisting of an antibody or fragment thereof, a cytotoxic agent, a toxin, a radionuclide, an immunomodulator, a photoactive therapeutic agent, a radiosensitizing agent, a hormone, an anti-angiogenesis agent, and combinations thereof.

11. The method according to claim 10, wherein the additional therapeutic agent is an inhibitor of the PI3K/Akt pathway.

12. The method according to claim 11, wherein the inhibitor of the PI3K/Akt pathway is selected from the group consisting of A-674563 (CAS #552325-73-2), AGL 2263, AMG-319 (Amgen, Thousand Oaks, Calif.), AS-041164 (5-benzo[1,3]dioxol-5-ylmethylene-thiazolidine-2,4-dione), AS-604850 (542,2-Difluoro-benzo[1,3]dioxol-5-ylmethyleneythiazolidine-2,4-dione), AS-605240 (5-quinoxilin-6-methylene-1,3-thiazolidine-2,4-dione), AT7867 (CAS #857531-00-1), benzimidazole series, Genentech (Roche Holdings Inc., South San Francisco, Calif.), BML-257 (CAS #32387-96-5), CAL-120 (Gilead Sciences, Foster City, Calif.), CAL-129 (Gilead Sciences), CAL-130 (Gilead Sciences), CAL-253 (Gilead Sciences), CAL-263 (Gilead Sciences), CAS #612847-09-3, CAS #681281-88-9, CAS #75747-14-7, CAS #925681-41-0, CAS #98510-80-6, CCT128930 (CAS #885499-61-6), CH5132799 (CAS #1007207-67-1), CHR-4432 (Chroma Therapeutics, Ltd., Abingdon, UK), FPA 124 (CAS #902779-59-3), GS-1101 (CAL-101) (Gilead Sciences), GSK 690693 (CAS #937174-76-0), H-89 (CAS #127243-85-0), Honokiol, IC87114 (Gilead Science), IPI-145 (Intellikine Inc.), KAR-4139 (Karus Therapeutics, Chilworth, UK), KAR-4141 (Karus Therapeutics), KIN-1 (Karus Therapeutics), KT 5720 (CAS #108068-98-0), Miltefosine, MK-2206 dihydrochloride (CAS #1032350-13-2), ML-9 (CAS #105637-50-1), Naltrindole Hydrochloride, OXY-111A (NormOxys Inc., Brighton, Mass.), perifosine, PHT-427 (CAS #1191951-57-1), PI3 kinase delta inhibitor, Merck KGaA (Merck & Co., Whitehouse Station, N.J.), PI3 kinase delta inhibitors, Genentech (Roche Holdings Inc.), PI3 kinase delta inhibitors, Incozen (Incozen Therapeutics, Pvt. Ltd., Hydrabad, India), PI3 kinase delta inhibitors-2, Incozen (Incozen 217 Therapeutics), PI3 kinase inhibitor, Roche-4 (Roche Holdings Inc.), PI3 kinase inhibitors, Roche (Roche Holdings Inc.), PI3 kinase inhibitors, Roche-5 (Roche Holdings Inc.), PI3-alpha/delta inhibitors, Pathway Therapeutics (Pathway Therapeutics Ltd., South San Francisco, Calif.), PI3-delta inhibitors, Cellzome (Cellzome AG, Heidelberg, Germany), PI3-delta inhibitors, Intellikine (Intellikine Inc., La Jolla, Calif.), PI3-delta inhibitors, Pathway Therapeutics-1 (Pathway Therapeutics Ltd.), PI3-delta inhibitors, Pathway Therapeutics-2 (Pathway Therapeutics Ltd.), PI3-delta/gamma inhibitors, Cellzome (Cellzome AG), PI3-delta/gamma inhibitors, Cellzome (Cellzome AG), PI3-delta/gamma inhibitors, Intellikine (Intellikine Inc.), PI3-delta/gamma inhibitors, Intellikine (Intellikine Inc.), PI3-delta/gamma inhibitors, Pathway Therapeutics (Pathway Therapeutics Ltd.), PI3-delta/gamma inhibitors, Pathway Therapeutics (Pathway Therapeutics Ltd.), PI3-gamma inhibitor Evotec (Evotec), PI3-gamma inhibitor, Cellzome (Cellzome AG), PI3-gamma inhibitors, Pathway Therapeutics (Pathway Therapeutics Ltd.), PI3K delta/gamma inhibitors, Intellikine-1 (Intellikine Inc.), PI3K delta/gamma inhibitors, Intellikine-1 (Intellikine Inc.), pictilisib (Roche Holdings Inc.), PIK-90 (CAS #677338-12-4), SC-103980 (Pfizer, New York, N.Y.), SF-1126 (Semafore Pharmaceuticals, Indianapolis, Ind.), SH-5, SH-6, Tetrahydro Curcumin, TG100-1 15 (Targegen Inc., San Diego, Calif.), Triciribine, X-339 (Xcovery, West Palm Beach, Fla.), XL-499 (Evotech, Hamburg, Germany), pharmaceutically acceptable salts thereof, and combinations thereof.

\* \* \* \* \*

SEQUENCE LISTING

<160> NUMBER OF SEQ ID NOS: 82

<210> SEQ ID NO 1
<211> LENGTH: 2949
<212> TYPE: DNA
<213> ORGANISM: Homo sapiens

<400> SEQUENCE: 1 cgcctcccctt cccctcccc gcccgacagc ggccgctcgg gccccggctc tcggttataa    60

```
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgattttc tgtttctagc tctgcatcaa tggataccgt     420
tacatcttct tcctcttcta gcctttcagt gctaccttca tctctttcag ttttcaaaa    480
tcccacagat gtggcacgga gcaacccca gtcaccacaa aaacctatcg ttagagtctt     540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
accacaggaa gaggcgtcct tagcagagac tgccctaaca tctggatcat cccttccgc   1020
acccgcctcg gactctattg ggccccaaat tctcaccagt ccgtctcctt caaaatccat   1080
tccaattcca cagcccttcc gaccagcaga tgaagatcat cgaaatcaat ttgggcaacg   1140
agaccgatcc tcatcagctc ccaatgtgca tataaacaca atagaacctg tcaatattga   1200
tgacttgatt agagaccaag gatttcgtgg tgatggagga tcaaccacag gtttgtctgc   1260
tacccccct gcctcattac ctggctcact aactaacgtg aaagccttac agaaatctcc   1320
aggacctcag cgagaaagga agtcatcttc atcctcagaa gacaggaatc gaatgaaaac   1380
acttggtaga cgggactcga gtgatgattg ggagattcct gatgggcaga ttacagtggg   1440
acaaagaatt ggatctggat catttggaac agtctacaag ggaaagtggc atggtgatgt   1500
ggcagtgaaa atgttgaatg tgacagcacc tacacctcag cagttacaag ccttcaaaaa   1560
tgaagtagga gtactcagga aaacacgaca tgtgaatatc ctactcttca tgggctattc   1620
cacaaagcca caactggcta ttgttaccca gtggtgtgag ggctccagct tgtatcacca   1680
tctccatatc attgagacca aatttgagat gatcaaactt atagatattg cacgacagac   1740
tgcacagggc atggattact tacacgccaa gtcaatcatc cacagagacc tcaagagtaa   1800
taatatattt cttcatgaag acctcacagt aaaaataggt gattttggtc tagctacagt   1860
gaaatctcga tggagtgggt cccatcagtt tgaacagttg tctggatcca ttttgtggat   1920
ggcaccagaa gtcatcagaa tgcaagataa aaatccatac agctttcagt cagatgtata   1980
tgcatttgga attgttctgt atgaattgat gactggacag ttaccttatt caaacatcaa   2040
caacagggac cagataattt ttatggtggg acgaggatac ctgtctccag atctcagtaa   2100
ggtacggagt aactgtccaa aagccatgaa gagattaatg gcagagtgcc tcaaaaagaa   2160
aagagatgag agaccactct tcccccaaat tctcgcctct attgagctgc tggcccgctc   2220
attgccaaaa attcaccgca gtgcatcaga accctccttg aatcgggctg gtttccaaac   2280
agaggatttt agtctatatg cttgtgcttc tccaaaaaca cccatccagg caggggata    2340
tggtgcgttt cctgtccact gaaacaaatg agtgagagag ttcaggagag tagcaacaaa   2400
```

-continued

```
aggaaaataa atgaacatat gtttgcttat atgttaaatt gaataaaata ctctcttttt    2460 tttaaggtg aaccaaagaa cacttgtgtg gttaaagact agatataatt tttccccaaa     2520
ctaaaattta tacttaacat tggatttta acatccaagg gttaaaatac atagacattg     2580
ctaaaaattg gcagagcctc ttctagaggc tttactttct gttccgggtt tgtatcattc    2640
acttggttat tttaagtagt aaacttcagt ttctcatgca acttttgttg ccagctatca    2700
catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaatgtgg atgtctttta tttccttgaa gcaataaact aagtttcttt     2940
ttataaaaa                                                            2949
```

<210> SEQ ID NO 2
<211> LENGTH: 765
<212> TYPE: PRT
<213> ORGANISM: Homo sapiens

<400> SEQUENCE: 2

```
Ala Ala Leu Ser Gly Gly Gly Gly Gly Ala Glu Pro Gly Gln Ala
1               5                   10                  15

Leu Phe Asn Gly Asp Met Glu Pro Glu Ala Gly Ala Gly Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Met Asp Thr Val Thr Ser Ser Ser Ser Ser Ser Leu Ser
        115                 120                 125

Val Leu Pro Ser Ser Leu Ser Val Phe Gln Asn Pro Thr Asp Val Ala
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270
```

```
Thr Glu Val Pro Leu Met Cys Val Asn Tyr Asp Gln Leu Asp Leu Leu
            275                 280                 285

Phe Val Ser Lys Phe Phe Glu His His Pro Ile Pro Gln Glu Glu Ala
        290                 295                 300

Ser Leu Ala Glu Thr Ala Leu Thr Ser Gly Ser Ser Pro Ser Ala Pro
305                 310                 315                 320

Ala Ser Asp Ser Ile Gly Pro Gln Ile Leu Thr Ser Pro Ser Pro Ser
                325                 330                 335

Lys Ser Ile Pro Ile Pro Gln Pro Phe Arg Pro Ala Asp Glu Asp His
                340                 345                 350

Arg Asn Gln Phe Gly Gln Arg Asp Arg Ser Ser Ser Ala Pro Asn Val
            355                 360                 365

His Ile Asn Thr Ile Glu Pro Val Asn Ile Asp Asp Leu Ile Arg Asp
        370                 375                 380

Gly Phe Arg Gly Asp Gly Gly Ser Thr Thr Gly Leu Ser Ala Thr
385                 390                 395                 400

Pro Pro Ala Ser Leu Pro Gly Ser Leu Thr Asn Val Lys Ala Leu Gln
                405                 410                 415

Lys Ser Pro Gly Pro Gln Arg Glu Arg Lys Ser Ser Ser Ser Glu
                420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
        450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
                500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
        530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
        610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
                660                 665                 670

Leu Ser Pro Asp Leu Ser Lys Val Arg Ser Asn Cys Pro Lys Ala Met
            675                 680                 685

Lys Arg Leu Met Ala Glu Cys Leu Lys Lys Lys Arg Asp Glu Arg Pro
```

```
              690                 695                 700
Leu Phe Pro Gln Ile Leu Ala Ser Ile Glu Leu Leu Ala Arg Ser Leu
705                 710                 715                 720

Pro Lys Ile His Arg Ser Ala Ser Glu Pro Ser Leu Asn Arg Ala Gly
            725                 730                 735

Phe Gln Thr Glu Asp Phe Ser Leu Tyr Ala Cys Ala Ser Pro Lys Thr
                740                 745                 750

Pro Ile Gln Ala Gly Gly Tyr Gly Ala Phe Pro Val His
            755                 760                 765

<210> SEQ ID NO 3
<211> LENGTH: 3906
<212> TYPE: DNA
<213> ORGANISM: Rattus norvegicus

<400> SEQUENCE: 3
```

| | | | | | |
|---|---|---|---|---|---|
| atggcggcgc | tgagtggcgg | cggtggcagc | agcagcggtg | gcggtggcgg | cggcggcggc | 60
| ggcggtggtg | gcggcggcgg | cggcggcgcc | gaacagggac | aggctctgtt | caatggcgac | 120
| atggagccgg | aggccggcgc | tggcgccgcg | gcctcttcgg | ccgcggaccc | ggccattcct | 180
| gaagaggtgt | ggaatatcaa | gcaaatgatt | aagttgacac | aggaacatat | agaggcccta | 240
| ttggacaagt | tggtgggga | gcataaccca | ccgtcaatat | acctggaggc | ctatgaagag | 300
| tacaccagca | agctagatgc | ccttcagcag | agagagcagc | agctgttgga | atccctggtt | 360
| tttcaaactc | ccacagatgt | atcacggaac | aaccccaagt | caccacagaa | acctatcgtt | 420
| cgtgtcttcc | tgcccaacaa | acagaggaca | gtggtgcccg | caagatgtgg | tgtaacggtc | 480
| cgagacagtc | taaagaaagc | actaatgatg | aggggtctca | tcccagagtg | ctgtgctgtt | 540
| tacagaattc | aggacggaga | gaagaaacca | attggctggg | acactgacat | ttcctggctt | 600
| actggagagg | agctacatgt | tgaagtacta | gagaatgttc | ctctgacaac | ccacaacttc | 660
| gtacggaaaa | cttttttcac | cttagcattt | tgtgactttt | gccgaaagct | gcttttccag | 720
| ggtttccgct | gtcaaacatg | tggttataag | tttcaccagc | gttgtagtac | agaggttcca | 780
| ctgatgtgtg | ttaattatga | ccaacttgat | ttgctgtttg | tctccaagtt | ctttgagcat | 840
| cacccagtac | acaggagga | ggccttctca | gcagagacta | cccttccatc | tggatgctct | 900
| tccgcacccc | cctcagactc | tattgggccc | caaatcctca | ccagtccatc | tccttcaaaa | 960
| tccattccaa | ttccacagcc | cttccggcca | gcagatgaag | atcatcgcaa | tcagtttggg | 1020
| caacgagacc | gctcctcctc | cgctcccaat | gttcatataa | acacaatcga | acctgtcaat | 1080
| attgatgaaa | aattcccaga | agtggaatta | caggatcaaa | gggatttgat | tagagaccag | 1140
| gggtttcgtg | gggatggagc | ccctttgaac | cagctgatgc | gctgtcttcg | gaaataccaa | 1200
| tcccggactc | ccagcccct | cctccattct | gtccccagtg | aaatagtgtt | tgattttgag | 1260
| cctggcccag | tgttcagagg | gtcaaccaca | ggcttgtcgg | ccaccccacc | tgcctcatta | 1320
| cctggctcac | tcactaacgt | gaaagcctta | cagaaatctc | caggacctca | gcgggaaagg | 1380
| aagtcctcct | cctcctcctc | ctccacggaa | gacagaagtc | ggatgaaaac | acttggtaga | 1440
| agagattcaa | gtgatgattg | ggagattcct | gatggacaga | ttacagtggg | acagagaatt | 1500
| ggatctgggt | cctttggaac | tgtctacaag | ggaaagtggc | atggcgacgt | ggcagtgaaa | 1560
| atgctgaatg | tgacagcacc | cacacctcag | cagttacagg | ccttcaaaaa | cgaagtcgga | 1620
| gtactcagga | aaactcgaca | tgtgaacatc | ctcctttca | tgggctattc | tacaaagcca | 1680
| cagctggcta | ttgttacaca | gtggtgtgaa | ggctccagct | tatatcacca | tctccacatc | 1740

```
attgagacca aatttgagat gatcaaactt atagatattg cacggcagac tgcacagggc    1800
atggattact tacacgccaa gtcaatcatc cacagagacc tcaagagtaa taatatattt    1860
cttcatgaag acctcacggt aaaaataggt gactttggtt tagccacagt gaagtcccga    1920
tggagtgggt cccatcagtt tgaacagttg tctggatcta ttttgtggat ggcacccgaa    1980
gtaatcagaa tgcaagataa aaacccatat agctttcagt cagacgtgta tgcatttggg    2040
attgttctgt atgaactgat gactggtcag ctaccttatt caaacatcaa caacagggat    2100
cagataattt ttatggtggg acgaggatac ctatctccag atctcagtaa ggtacggagt    2160
aactgtccaa aagccatgaa gagattaatg gcagagtgcc tcaaaaagaa aagagacgag    2220
agaccactct ttccccaaat tctcgcctct attgagctgc tggcccgctc attgccaaaa    2280
attcaccgca gtcatcaga accctccttg aatcgggctg gtttccaaac agaagatttt    2340
agtctgtatg cttgtgcttc tccaaaaaca cccatccaag caggggata tggagaattt     2400
gcagccttca agtagccact ccatcatggc agcatctact cttatttct taagtcttgt      2460
gttcatacaa tttgttaaca tcaaaacaca gttctgttcc tcaaattttt tttaaagata    2520
caaaattttc aatgcataag ctcgtgtgga acagaatgga atttcctatt caacaaaaga   2580
gggaagaatg ttttaggaac cagaattctc tgctgcccgt gtttcttctt caacacaaat    2640
atcatgtgca tacaactctg cccattccca agaagaaaga ggagagaccc cgaattctgc    2700
cctttggtg gtcaggcatg atggaaagaa tttgctgctg cagcttggga aaaattgcta     2760
tggaaagtct gccagtcaac tttgcccttc taaccaccag atccatttgt ggctggtcat    2820
ctgatggggc gatttcaatc accaagcatc gttcttgcct gttgtgggat tatgtcgtgg    2880
agcactttcc ctatccacca ccgttaattt ccgagggatg gagtaaatgc agcatacccct   2940
ttgtgtagca cctgtccagt cctcaaccaa tgctatcaca gtgaagctct ttaaatttaa    3000
gtggtgggtg agtgttgagg agagactgcc ttggggcag agaaaagggg atgctgcatc    3060
ttcttcctca cctccagctc tctcacctcg ggttgccttg cacactgggc tccgcctaac    3120
cactcgggct gggcagtgct ggcacacatt gccgccttt tcattgggt ccagcaattg       3180
agcagagggt tggggatttg tttcctccac aatgtagcaa attctcagga aaatacagtc   3240
catatcttcc tctcagctct tccagtcacc aaatacttac gtggctcctt tgtccaggac    3300
ataaaacacc gtgacaaca cctaattaaa agcctacaaa actgcttact gacagttttg     3360
aatgtgagac atttgtgtaa tttaaatgta aggtacaggt cttaatttct tctattaagt    3420
ttcttctatt tttatttaaa cgaagaaaat aattttcagg tttaattgga ataaacgaat    3480
acttcccaaa agactatata ccctgaaaat tatattttg ttaattgtaa acaactttta      3540
aaaaatggtt attatccttt tctctaccta aaattatggg aaatcttagc ataatgacaa    3600
ttatttatac ttttaaata aatggtactt gctggatcca cactaacatc tttgctaaca    3660
ttcccattgt ttcttccaac ttcactccta cactacatcc tccatcctct ttctagtctt     3720
ttatctataa tatgcaacct aaaataaaag tggtggtgtc tccattcatt cttcttcttc    3780
cttttttccc caagcctggt cttcaaaagg ttgggtaatt tagtagctga gttccctagg    3840
tagaaataga actattaggg acattggggt tgtaggaaag cgtgaggcct gtcaccagtt    3900
gttctt                                                               3906
```

<210> SEQ ID NO 4
<211> LENGTH: 804
<212> TYPE: PRT

<213> ORGANISM: Rattus norvegicus

<400> SEQUENCE: 4

```
Met Ala Ala Leu Ser Gly Gly Gly Ser Ser Gly Gly Gly
1               5                   10                  15

Gly Gly Gly Gly Gly Gly Gly Gly Gly Gly Gly Ala Glu Gln
            20                  25                  30

Gly Gln Ala Leu Phe Asn Gly Asp Met Glu Pro Glu Ala Gly Ala Gly
        35                  40                  45

Ala Ala Ala Ser Ser Ala Ala Asp Pro Ala Ile Pro Glu Glu Val Trp
    50                  55                  60

Asn Ile Lys Gln Met Ile Lys Leu Thr Gln Glu His Ile Glu Ala Leu
65                  70                  75                  80

Leu Asp Lys Phe Gly Gly Glu His Asn Pro Pro Ser Ile Tyr Leu Glu
                85                  90                  95

Ala Tyr Glu Glu Tyr Thr Ser Lys Leu Asp Ala Leu Gln Gln Arg Glu
                100                 105                 110

Gln Gln Leu Leu Glu Ser Leu Val Phe Gln Thr Pro Thr Asp Val Ser
            115                 120                 125

Arg Asn Asn Pro Lys Ser Pro Gln Lys Pro Ile Val Arg Val Phe Leu
130                 135                 140

Pro Asn Lys Gln Arg Thr Val Val Pro Ala Arg Cys Gly Val Thr Val
145                 150                 155                 160

Arg Asp Ser Leu Lys Lys Ala Leu Met Met Arg Gly Leu Ile Pro Glu
                165                 170                 175

Cys Cys Ala Val Tyr Arg Ile Gln Asp Gly Glu Lys Lys Pro Ile Gly
                180                 185                 190

Trp Asp Thr Asp Ile Ser Trp Leu Thr Gly Glu Glu Leu His Val Glu
            195                 200                 205

Val Leu Glu Asn Val Pro Leu Thr Thr His Asn Phe Val Arg Lys Thr
210                 215                 220

Phe Phe Thr Leu Ala Phe Cys Asp Phe Cys Arg Lys Leu Leu Phe Gln
225                 230                 235                 240

Gly Phe Arg Cys Gln Thr Cys Gly Tyr Lys Phe His Gln Arg Cys Ser
                245                 250                 255

Thr Glu Val Pro Leu Met Cys Val Asn Tyr Asp Gln Leu Asp Leu Leu
                260                 265                 270

Phe Val Ser Lys Phe Phe Glu His His Pro Val Pro Gln Glu Glu Ala
            275                 280                 285

Phe Ser Ala Glu Thr Thr Leu Pro Ser Gly Cys Ser Ser Ala Pro Pro
290                 295                 300

Ser Asp Ser Ile Gly Pro Gln Ile Leu Thr Ser Pro Ser Pro Ser Lys
305                 310                 315                 320

Ser Ile Pro Ile Pro Gln Pro Phe Arg Pro Ala Asp Glu Asp His Arg
                325                 330                 335

Asn Gln Phe Gly Gln Arg Asp Arg Ser Ser Ser Ala Pro Asn Val His
                340                 345                 350

Ile Asn Thr Ile Glu Pro Val Asn Ile Asp Glu Lys Phe Pro Glu Val
            355                 360                 365

Glu Leu Gln Asp Gln Arg Asp Leu Ile Arg Asp Gln Gly Phe Arg Gly
370                 375                 380

Asp Gly Ala Pro Leu Asn Gln Leu Met Arg Cys Leu Arg Lys Tyr Gln
385                 390                 395                 400
```

```
Ser Arg Thr Pro Ser Pro Leu Leu His Ser Val Pro Ser Glu Ile Val
                405                 410                 415
Phe Asp Phe Glu Pro Gly Pro Val Phe Arg Gly Ser Thr Thr Gly Leu
            420                 425                 430
Ser Ala Thr Pro Pro Ala Ser Leu Pro Gly Ser Leu Thr Asn Val Lys
        435                 440                 445
Ala Leu Gln Lys Ser Pro Gly Pro Gln Arg Glu Arg Lys Ser Ser Ser
450                 455                 460
Ser Ser Ser Ser Thr Glu Asp Arg Ser Arg Met Lys Thr Leu Gly Arg
465                 470                 475                 480
Arg Asp Ser Ser Asp Asp Trp Glu Ile Pro Asp Gly Gln Ile Thr Val
                485                 490                 495
Gly Gln Arg Ile Gly Ser Gly Ser Phe Gly Thr Val Tyr Lys Gly Lys
            500                 505                 510
Trp His Gly Asp Val Ala Val Lys Met Leu Asn Val Thr Ala Pro Thr
        515                 520                 525
Pro Gln Gln Leu Gln Ala Phe Lys Asn Glu Val Gly Val Leu Arg Lys
    530                 535                 540
Thr Arg His Val Asn Ile Leu Leu Phe Met Gly Tyr Ser Thr Lys Pro
545                 550                 555                 560
Gln Leu Ala Ile Val Thr Gln Trp Cys Glu Gly Ser Ser Leu Tyr His
                565                 570                 575
His Leu His Ile Ile Glu Thr Lys Phe Glu Met Ile Lys Leu Ile Asp
            580                 585                 590
Ile Ala Arg Gln Thr Ala Gln Gly Met Asp Tyr Leu His Ala Lys Ser
        595                 600                 605
Ile Ile His Arg Asp Leu Lys Ser Asn Asn Ile Phe Leu His Glu Asp
    610                 615                 620
Leu Thr Val Lys Ile Gly Asp Phe Gly Leu Ala Thr Val Lys Ser Arg
625                 630                 635                 640
Trp Ser Gly Ser His Gln Phe Glu Gln Leu Ser Gly Ser Ile Leu Trp
                645                 650                 655
Met Ala Pro Glu Val Ile Arg Met Gln Asp Lys Asn Pro Tyr Ser Phe
            660                 665                 670
Gln Ser Asp Val Tyr Ala Phe Gly Ile Val Leu Tyr Glu Leu Met Thr
        675                 680                 685
Gly Gln Leu Pro Tyr Ser Asn Ile Asn Asn Arg Asp Gln Ile Ile Phe
    690                 695                 700
Met Val Gly Arg Gly Tyr Leu Ser Pro Asp Leu Ser Lys Val Arg Ser
705                 710                 715                 720
Asn Cys Pro Lys Ala Met Lys Arg Leu Met Ala Glu Cys Leu Lys Lys
                725                 730                 735
Lys Arg Asp Glu Arg Pro Leu Phe Pro Gln Ile Leu Ala Ser Ile Glu
            740                 745                 750
Leu Leu Ala Arg Ser Leu Pro Lys Ile His Arg Ser Ala Ser Glu Pro
        755                 760                 765
Ser Leu Asn Arg Ala Gly Phe Gln Thr Glu Asp Phe Ser Leu Tyr Ala
    770                 775                 780
Cys Ala Ser Pro Lys Thr Pro Ile Gln Ala Gly Gly Tyr Gly Glu Phe
785                 790                 795                 800
Ala Ala Phe Lys

<210> SEQ ID NO 5
```

<211> LENGTH: 9728
<212> TYPE: DNA
<213> ORGANISM: Mus musculus

<400> SEQUENCE: 5

```
ccctcaggct cggctgcgcc ggggccgccg gcgggttcca gaggtggcct ccgccccggc      60
cgctccgccc acgcccccg cgcctccgcg cccgcctccg cccgccctgc gcctcccttc     120
cccctccccg ccccgcggcg gccgctcggc ccggctcgcg cttcgaagat ggcggcgctg    180
agtggcggcg gtggcagcag cagcggtggc ggcggcggcg gtgcggcgg cggtggcggt     240
ggcgacggcg gcggcggcgc cgagcagggc caggctctgt tcaatggcga catggagccg    300
gaggccggcg ctggcgccgc ggcctcttcg gctgcggacc cggccattcc tgaagaggta    360
tggaatatca agcaaatgat taagttgaca caggaacata tagaggccct attggacaaa    420
tttggtggag agcataaccc accatcaata tacctggagg cctatgaaga gtacaccagc    480
aagctagatg cccttcagca agagaacag cagcttttgg aatccctggt ttttcaaact     540
cccacagatg catcacggaa caccccaag tcaccacaga aacctatcgt tagagtcttc     600
ctgcccaaca acagaggac agtggtaccc gcaagatgtg tgttacagt tcgagacagt      660
ctaaagaaag cactgatgat gagaggtctc atcccagaat gctgtgctgt ttacagaatt    720
caggatggag agaagaaacc aattggctgg gacacggaca tttcctggct tactggagag    780
gagttacatg ttgaagtact ggagaatgtc ccacttacaa cacacaactt tgtacgaaa     840
actttttca ccttagcatt ttgtgacttt tgccgaaagc tgcttttcca gggtttccgt     900
tgtcaaacat gtggttataa atttcaccag cgttgtagta cagaggttcc actgatgtgt    960
gtaaattatg accaacttga tttgctgttt gtctccaagt tctttgagca tcacccagta   1020
ccacaggagg aggcctcctt cccagagact gcccttccat ctggatcctc ttccgcaccc   1080
ccctcagact ctactgggcc ccaaatcctc accagtccat ctccttcaaa atccattcca   1140
attccacagc ccttccgacc agcagatgaa gatcatcgca atcagtttgg gcaacgagac   1200
cggtcctcct cagctcccaa tgttcatata aacacaattg agcctgtgaa tatcgatgaa   1260
aaattcccag aagtggaatt acaggatcaa agggatttga ttagagacca ggggtttcgt   1320
ggtgatggag ccccttgaa ccaactgatg cgctgtcttc ggaaatacca atcccggact    1380
cccagccccc tcctccattc tgtccccagt gaaatagtgt ttgattttga gcctggccca   1440
gtgttcagag ggtcaaccac aggcttgtcc gccaccccgc ctgcctcatt acctggctca   1500
ctcactaacg tgaaagcctt acagaaatct ccaggtcctc agcgggaaag gaagtcatct   1560
tcttcctcat cctcggagga cagaagtcgg atgaaaacac ttggtagaag agattcaagt   1620
gatgactggg agattcctga tggacagatt acagtgggac agagaattgg atctgggtca   1680
tttggaactg tctacaaggg aaagtggcat ggtgatgtgg cagtgaaaat gttgaatgtg   1740
acagcaccca cctcaacaa gctacaggcc ttcaaaaatg aagtaggagt gctcaggaaa   1800
actcgacatg tgaatatcct cctttcatg ggctattcta caaagccaca actggcaatt   1860
gttacacagt ggtgtgaggg ctccagctta tatcaccatc tccacatcat tgagaccaaa   1920
tttgagatga tcaaacttat agatattgct cggcagactg cacagggcat ggattactta   1980
cacgccaagt caatcatcca cagagacctc aagagtaata atatattct tcatgaagac   2040
ctcacggtaa aaataggtga ctttggtcta gccacagtga atctcggtg gagtgggtcc   2100
catcagtttg aacagttgtc tggatctatt ttgtggatgg caccagaagt aatcagaatg   2160
caagataaaa acccgtatag ctttcagtca gacgtgtatg cgtttgggat tgttctgtac   2220
```

```
gaactgatga ccggccagct accttattca aacatcaaca acagggatca gataatttt    2280
atggtgggac gaggatacct atctccagat ctcagtaagg tacggagtaa ctgtccaaaa    2340
gccatgaaga gattaatggc agagtgcctc aaaaagaaaa gagacgagag accactcttt    2400
ccccaaattc tcgcctccat tgagctgctg gcccgctcat tgccaaaaat tcaccgcagt    2460
gcatcagaac cttccttgaa tcgggctggt ttccaaacag aagattttag tctgtatgct    2520
tgtgcttctc cgaaaacacc catccaagca gggggatatg gagaatttgc agccttcaag    2580
tagccagtcc atcatggcag catctactct ttatttctta agtcttgtgt tcatacagtt    2640
tgttaacatc aaaacacagt tctgttcctc aaaaaatttt ttaaagatac aaaattttca    2700
atgcataagt tcatgtggaa cagaatggaa tttcctattc aacaaagag ggaagaatgt     2760
tttaggaacc agaattctct gctgcccgtg tttcttcttc aacataacta tcacgtgcat    2820
acaagtctgc ccattcccaa gaagaaagag gagagaccct gaattctgcc cttttggtgg    2880
tcaggcatga tggaaagaat tgctgctgc agcttgggaa aattgctatg gaaagtctgc    2940
cagtcgactt tgcccttcta accaccagat cagcctgtgg ctggtcatct gatggggcga    3000
tttccatcac caagcatcgt tcttgcctat tctgggatta tgttgtggag cactttccct    3060
gtccagcacc gttcatttct gagggatgga gtaaatgcag cattcccttg tgtagcgcct    3120
gttcagtcct cagcagctgc tgtcacagcg aagcttttta cagttaagtg gtgggggaga    3180
gttgaggaga gcctgcctcg gggcagagaa aaggggggtgc tgcatcttct tcctcacctc   3240
cagctctctc acctcgggtt gccttgctca ctgggctccg cctaaccact caggctgctc    3300
agtgctggca cacattgcct tcttttctca ttgggtccag caattgagga gagggttggg    3360
ggattgtttc ctcctcaatg tagcaaattc tcaggaaaat acagtccata tcttcctctc    3420
agctcttcca gtcaccaaat acttacgtgg ctccttttgtc caggacataa acaccgtgg    3480
acaacaccta attaaaagcc tacaaaactg cttactgaca gttttgaatg tgagacactt    3540
gtgtaattta aatgtaaggt acaggtttta atttctgagt ttcttctatt tttatttaaa    3600
agaagaaaat aattttcagt tttaattgga ataaatgagt acttcccaca agactatata    3660
ccctgaaaat tatattttg ttaattgtaa acaacttta aagaataatt attatccttt      3720
tctctaccta aaaattatgg ggaatcttag cataatgaca attatttata cttttttaaat   3780
aaatggtact tgctggatcc acactaacat cttttgctaac aatcccattg tttcttccaa   3840
cttaactcct acactacatc ctacatcctc tttctagtct tttatctata atatgcaacc    3900
taaaataaac gtggtggcgt ctccattcat tctccctctt cctgtttcc caagcctgg      3960
tcttcaaaag gttgggtaat cggtccctga gctccctagc tggcaatgca actattaggg    4020
acattggagt tgcaggagag caggaagcct gtccccagct gttcttctag aaccctaaat    4080
cttatctttg cacagatcaa agtatcacc tcgtcacagt tctccttagc ctttacttac     4140
aggtaatata aataaaaatc accatagtag taaagaaaac aactggatgg attgatgacc    4200
agtacctctc agagccagga atcttgaatc tccaggattt atacgtgcaa atttaaggag    4260
atgtacttag caacttcaag ccaagaactt ccaaaatact agcgaatcta aaataaaatg    4320
gaattttgag ttatttttaa agttcaaatt ataattgata ccactatgta tttaagccta    4380
ctcacagcaa gttagatgga ttttgctaaa ctcattgcca gactgtggtg gtggtggtgg    4440
tagtgtgcac ctttaatcca agcaactcag caatcagaat gaggtaaatc tctgtgaata    4500
caaggcctgc ctagtctgca gcgctagttc caggatagcc agggctacac acacaaaaac    4560
```

```
cctctctcaa aaaaaacaaa attaattagt tgataataaa aaataactaa agtatcatca    4620
aaggaaggcc tactggaagt tttatatatt cccagtaaat tgaaaaatat tctgaagtta    4680
ttaaccagtt agcaacaatg tgtttttaag tcttacataa acagagcaaa gtcttcaaat    4740
gtttcagagc tgagaagata attgtgcttg atatgaaaaa tagcctctcc atatgatgtg    4800
ccacattgaa aggcgtcatt acccttttaa atacttctta atgtggcttt gttcccttta    4860
cccaggatta gctagaaaga gctaggtagg cttcggccac agttgcacat ttcgggcctg    4920
ctgaagaatg ggagctttga aggctggcct tggtggagga gcccctcagt gctggagggt    4980
ggggcgtgta cgcagcatgg aagtggtcta gacagagtgc aaagggacag acttctttct    5040
cattttagta tagggtgatg tctcacttga aatgagaaag tagagttgat attaaacgaa    5100
gctgtgccca gaaccaggc tcagggtatt gtgagatttt cttttaaat agagaatata    5160 aaagatagaa ataaatattt aaaccttcct tcttattttc tatcaaatag attttttta    5220 tcatttgcaa acaacataaa aaaggtttc ttttgtgggg ttttctttcc ttcttttttt    5280 ttttttttt tttttaagac tgcagataat cttgttgagc tcctcggaaa atacaaggaa    5340
gtccgtgttt gtgcagagcg ctttatgagt aactgtatag acagtgtggc tgcttcactc    5400
atcccagagg gctgcagctg tcggcccatg aagtggctgc agtgcctcgt gagatctgct    5460
ttgttttgtt tggagtgaag tctttgaaag gtttgagtgc aactatatag gactgttttt    5520
aaataagtag tattcctcat gaactttctc attgttaagc tacaggaccc aaactctacc    5580
actaagatat tattaacctc aaaatgtagt ttatagaagg aatttgcaaa tagaatatcc    5640
agttcgtact tatatgcatc ttcaacaaag attctctgtg acttgttgga tttggttcct    5700
gaacagccca tttctgtatt tgaggttagg agggcataat gaggcatcct aaaagacaat    5760
ctgatataaa ctgtatgcta gatgtatgct ggtaggggag aaagcattct gtaaagacat    5820
gatttaagac ttcagctctg tcaaccagaa accttgtaaa tacttcctgt cttggtgcag    5880 ccccgccct tgatcacac gatgttgtct tgtgcttgtc agacactgtc agagctgctg    5940
ttcgtccctc tgcagatctc acctgtcccc actgcacacc cacctcctgc ctcttgcaga    6000
cctcagcatc tagctttagt tggaaacagt tcagggttca ggtgacttct taaaaaaaaa    6060 aaaaaccct acctcctcag aatgaggtaa tgaatagtta tttatttaaa gtatgaagag    6120
tcaggagcgc tcgaacatga aggtgattta agatggttcc tttcgtgtgt attgtagctg    6180
agcacttgtt tttgtcctaa agggcattat acatttaagc agtgattctg tttaaagatg    6240 tttttctta aaggtgtagc tcagagtatc tgttgttgga attggtgcca gagtctgctt    6300
aatagatttc agaatcctaa gcttaagtca gtcgcatgaa gttaagtagt tatggtaaca    6360
ctttgctagc catgatataa ttctactttt taggagtagg tttggcaaaa ctgtatgcct    6420
tcaaagtgag ttggccacag ctttgtcaca tgcacagata ctcatctgaa gagactgccc    6480
agctaagagg gcgaaggat acccttttt cctacgattc gcttctttgt ccacgttggc    6540
attgttagta ctagtttatc agcaccttga ccagcagatg tcaaccaata agctattttt    6600
aaaaccatag ccagagatgg agaggtcact gtgagtagaa acagcaggac gcttacagga    6660
gtgaaatggt gtagggaggc tctagaaaaa tatcttgaca atttgccaaa tgatcttact    6720
gtgccttcat gatgcaataa aaaagctaac attttagcag aaatcagtga tttacgaaga    6780
gagtggccag tctggtttaa ctcagctggg ataatatttt tagagtgcaa tttagactgc    6840
gaagataaat gcactaaaga gtttatagcc aattcacatt tgaaaaataa gaaaatggta    6900
aattttcagt gaaatatttt tttaaagcac ataatcccta gtgtagccag aaatatttac    6960
```

-continued

```
cacatagagc agctaggctg agatacagtc cagtgacatt tctagagaaa cctttctac    7020
tcccacgggc tcctcaaagc atggaaattt tatacaaaat gtttgacatt ttaagatact    7080
gctgtagttt agttttgaaa tagtatgtgc tgagcagcaa tcatgtacta actcagagag    7140
agaaaacaac aacaaattgt gcatctgatt tgttttcaga gaaatgctgc caacttagat    7200
actgagttct cagagcttca agtgtaaact tgcctcccaa gtcctgtttg caaatgaagt    7260
tggctagtgc tactgactgc tccagcacat gatggaaggc aggggctgt tctctgaagtg    7320
tcttctataa agggacaata gaatagtgag agacctggtc agtgtgtgtc agctggacac    7380
tccatgctat gggacttgca tcttctgtcc tcaccatccc caagacattg tgctttcctc    7440
agttgtcctc tagctgtttc actcagacac caagatgaat tactgatgcc agaaggggcc    7500
aaaatggcca gtgtgttttg ggggttgtat cagttgactg gacaataact ttaatagttt    7560
cagatcattt attttttactt ccatttgac agacatttaa atggaaattt agtcctaact    7620
tttgtcattt gaaggaaaa attaacagtt cctataagat acttttgagg tggaatctga    7680
catcctaatt ttttttcttt tcagtgggtt tgcagcgagg gtcttgtatg cactaggcaa    7740
gggttctacc actaagccac atttcccagg aaataaaatg ttaacagtta aaacatacac    7800
acaaatacac aaacacctta ttaccacttt agtaaagtga gagatgtgcg tcctttgtct    7860
cagtctccac gatttcagct gcccccttgta tgaataactc agtctcgcta aactgtttac    7920
ttttatttac ctggtttgac tagttgcagc tatataacca gttgtgcatg aggacaacag    7980
ccagtgtgtt tgtttgttt ttggttttt gtggtacatt ttttgtaaag aattctgtag    8040
attgaagtgc tctttgaaaa cagaactgag atatatttat tcttgttagc atcaaaaaac    8100
attttgtgca aatgatttgc ttttcctggc aggctgagta ccatatccag cgcccacaat    8160
tgcgggttcc catctaccat gtccacaggg gagacagacg ggaagcacat gaggggtgtg    8220
tttacagagt tgtaggagtt atgtagttct cttgttgcct tggaaatcac tgttgttta    8280
agactgttga acccgtgtgt ttggctgggc tgtgagttac atgaagaaac tgcaaactag    8340
catatgcaga caaagctcac agactaggcg taaatggagg aaaatggacc aaaataaggc    8400
agggtgacac ataaaccttg ggcttcggag aaaactaagg gtggagatga actataatca    8460
cctgaataca atgtaagagt gcaataagtg tgcttattct aagctgtgaa cttctttaa    8520
atcattcctt tctaatacat ttatgtatgt tccattgctg actaaaacca gctatgaaa    8580
catatgcctt tttattcatg ttaactacca gtttaagtgg ctaaccttaa tgtcttattt    8640
atcttcattt tgtattagtt tacataccag gtatgtgtgt gtgctgtact cttcttccct    8700
ttatttgaaa acactttca ctgggtcatc tccttggcca ttccacaaca caactttggt    8760
ttggctttca atgtcacctt atttgatggc ctgtgtccca gtagcagaat ttatggtatt    8820
cccattgctg gctgctcttc cgaccctttg cttctacagc acttgtctct cctaagatag    8880
tcagaaacta actgatcagg ggatggactt caccattcat cgtgtctctt caattctatt    8940
aaatagacca ctcttgggct ttagaccagg aaaaaggaga cagctctagc catctaccaa    9000
gcctcaccct aaaaggtcac ccgtacttct tggtctgagg acaagtctcc actccagtaa    9060
gggagagggg aggaaatgct tcctgttga aatgcagtga attcctatgg ctcctgttc    9120
accacccgca cctatggcaa cccatataca ttcctcttgt ctgtaactgc caaaggttgg    9180
gtttatgtca cttcagttcc actcaagcat tgaaaaggtt tcatggagt ctgggtgtg    9240
cccagtgaaa agatggggac ttttcatta tccacagacc tctctatacc tgctttgcaa    9300
```

-continued

```
aaattataat ggagtaacta tttttaaagc ttattttca attcataaga aaaagacatt      9360
tattttcaat caaatggatg atgtctctta tcccttatcc ctcaatgttt gcttgaattt      9420
tgtttgttcc ctatacctac tccctaattc tttagttcct tcctgctcag gtcccttcat      9480
ttgtactttg gagttttct catgtaaatt tgtataatgg aaatattgt tcagtttgga       9540 tagaaagcat ggagaaataa ataaaaaaag atagctgaaa atcaaattga agaaatttat     9600
ttctgtgtaa agttatttaa aaactctgta ttatatttaa agaaaaaagc ccaaccccc       9660 aaaaagtgct atgtaattga tgtgaatatg cgaatactgc tataataaag attgactgca     9720
tggagaaa                                                              9728
```

<210> SEQ ID NO 6
<211> LENGTH: 804
<212> TYPE: PRT
<213> ORGANISM: Mus musculus

<400> SEQUENCE: 6

```
Met Ala Ala Leu Ser Gly Gly Gly Ser Ser Gly Gly Gly Gly
1               5                   10                  15

Gly Gly Gly Gly Gly Gly Gly Gly Asp Gly Gly Gly Ala Glu
            20                  25                  30

Gln Gly Gln Ala Leu Phe Asn Gly Asp Met Glu Pro Glu Ala Gly Ala
        35                  40                  45

Gly Ala Ala Ala Ser Ser Ala Ala Asp Pro Ala Ile Pro Glu Glu Val
    50                  55                  60

Trp Asn Ile Lys Gln Met Ile Lys Leu Thr Gln Glu His Ile Glu Ala
65                  70                  75                  80

Leu Leu Asp Lys Phe Gly Gly Glu His Asn Pro Pro Ser Ile Tyr Leu
                85                  90                  95

Glu Ala Tyr Glu Glu Tyr Thr Ser Lys Leu Asp Ala Leu Gln Gln Arg
            100                 105                 110

Glu Gln Gln Leu Leu Glu Ser Leu Val Phe Gln Thr Pro Thr Asp Ala
        115                 120                 125

Ser Arg Asn Asn Pro Lys Ser Pro Gln Lys Pro Ile Val Arg Val Phe
    130                 135                 140

Leu Pro Asn Lys Gln Arg Thr Val Val Pro Ala Arg Cys Gly Val Thr
145                 150                 155                 160

Val Arg Asp Ser Leu Lys Lys Ala Leu Met Met Arg Gly Leu Ile Pro
                165                 170                 175

Glu Cys Cys Ala Val Tyr Arg Ile Gln Asp Gly Glu Lys Lys Pro Ile
            180                 185                 190

Gly Trp Asp Thr Asp Ile Ser Trp Leu Thr Gly Glu Glu Leu His Val
        195                 200                 205

Glu Val Leu Glu Asn Val Pro Leu Thr Thr His Asn Phe Val Arg Lys
    210                 215                 220

Thr Phe Phe Thr Leu Ala Phe Cys Asp Phe Cys Arg Lys Leu Leu Phe
225                 230                 235                 240

Gln Gly Phe Arg Cys Gln Thr Cys Gly Tyr Lys Phe His Gln Arg Cys
                245                 250                 255

Ser Thr Glu Val Pro Leu Met Cys Val Asn Tyr Asp Gln Leu Asp Leu
            260                 265                 270

Leu Phe Val Ser Lys Phe Phe Glu His His Pro Val Pro Gln Glu Glu
        275                 280                 285

Ala Ser Phe Pro Glu Thr Ala Leu Pro Ser Gly Ser Ser Ser Ala Pro
```

```
              290             295                 300
Pro Ser Asp Ser Thr Gly Pro Gln Ile Leu Thr Ser Pro Ser Pro Ser
305                 310                 315                 320

Lys Ser Ile Pro Ile Pro Gln Pro Phe Arg Pro Ala Asp Glu Asp His
                325                 330                 335

Arg Asn Gln Phe Gly Gln Arg Asp Arg Ser Ser Ser Ala Pro Asn Val
                340                 345                 350

His Ile Asn Thr Ile Glu Pro Val Asn Ile Asp Glu Lys Phe Pro Glu
            355                 360                 365

Val Glu Leu Gln Asp Gln Arg Asp Leu Ile Arg Asp Gln Gly Phe Arg
        370                 375                 380

Gly Asp Gly Ala Pro Leu Asn Gln Leu Met Arg Cys Leu Arg Lys Tyr
385                 390                 395                 400

Gln Ser Arg Thr Pro Ser Pro Leu Leu His Ser Val Pro Ser Glu Ile
                405                 410                 415

Val Phe Asp Phe Glu Pro Gly Pro Val Phe Arg Gly Ser Thr Thr Gly
                420                 425                 430

Leu Ser Ala Thr Pro Pro Ala Ser Leu Pro Gly Ser Leu Thr Asn Val
            435                 440                 445

Lys Ala Leu Gln Lys Ser Pro Gly Pro Gln Arg Glu Arg Lys Ser Ser
        450                 455                 460

Ser Ser Ser Ser Glu Asp Arg Ser Arg Met Lys Thr Leu Gly Arg Arg
465                 470                 475                 480

Arg Asp Ser Ser Asp Asp Trp Glu Ile Pro Asp Gly Gln Ile Thr Val
                485                 490                 495

Gly Gln Arg Ile Gly Ser Gly Ser Phe Gly Thr Val Tyr Lys Gly Lys
                500                 505                 510

Trp His Gly Asp Val Ala Val Lys Met Leu Asn Val Thr Ala Pro Thr
            515                 520                 525

Pro Gln Gln Leu Gln Ala Phe Lys Asn Glu Val Gly Val Leu Arg Lys
        530                 535                 540

Thr Arg His Val Asn Ile Leu Leu Phe Met Gly Tyr Ser Thr Lys Pro
545                 550                 555                 560

Gln Leu Ala Ile Val Thr Gln Trp Cys Glu Gly Ser Ser Leu Tyr His
                565                 570                 575

His Leu His Ile Ile Glu Thr Lys Phe Glu Met Ile Lys Leu Ile Asp
                580                 585                 590

Ile Ala Arg Gln Thr Ala Gln Gly Met Asp Tyr Leu His Ala Lys Ser
            595                 600                 605

Ile Ile His Arg Asp Leu Lys Ser Asn Asn Ile Phe Leu His Glu Asp
610                 615                 620

Leu Thr Val Lys Ile Gly Asp Phe Gly Leu Ala Thr Val Lys Ser Arg
625                 630                 635                 640

Trp Ser Gly Ser His Gln Phe Glu Gln Leu Ser Gly Ser Ile Leu Trp
                645                 650                 655

Met Ala Pro Glu Val Ile Arg Met Gln Asp Lys Asn Pro Tyr Ser Phe
                660                 665                 670

Gln Ser Asp Val Tyr Ala Phe Gly Ile Val Leu Tyr Glu Leu Met Thr
            675                 680                 685

Gly Gln Leu Pro Tyr Ser Asn Ile Asn Asn Arg Asp Gln Ile Ile Phe
        690                 695                 700

Met Val Gly Arg Gly Tyr Leu Ser Pro Asp Leu Ser Lys Val Arg Ser
705                 710                 715                 720
```

```
Asn Cys Pro Lys Ala Met Lys Arg Leu Met Ala Glu Cys Leu Lys Lys
                725                 730                 735

Lys Arg Asp Glu Arg Pro Leu Phe Pro Gln Ile Leu Ala Ser Ile Glu
            740                 745                 750

Leu Leu Ala Arg Ser Leu Pro Lys Ile His Arg Ser Ala Ser Glu Pro
        755                 760                 765

Ser Leu Asn Arg Ala Gly Phe Gln Thr Glu Asp Phe Ser Leu Tyr Ala
    770                 775                 780

Cys Ala Ser Pro Lys Thr Pro Ile Gln Ala Gly Gly Tyr Gly Glu Phe
785                 790                 795                 800

Ala Ala Phe Lys

<210> SEQ ID NO 7
<211> LENGTH: 2232
<212> TYPE: DNA
<213> ORGANISM: Oryctolagus cuniculus

<400> SEQUENCE: 7
```

| | | | | |
|---|---|---|---|---|
| atgggggaatg tgtggaatat caaacaaatg attaagttga cacaggagca tatagaggcc | | | | 60 |
| ctattggaca aatttggtgg ggagcataat ccaccatcaa tatatctgga ggcctacgaa | | | | 120 |
| gaatacacca gcaagctaga tgccctccaa caaagagaac agcagttatt ggaatccta | | | | 180 |
| gttttcaaa atcccacaga tgtgtcacg agcaacccca gtcaccaca aaaacctat | | | | 240 |
| gttagagtct tcctgcccaa caaacagagg acagtggtac ctgcaagatg tggagttacg | | | | 300 |
| gttcgagaca gtctaaagaa agcgctgatg atgagaggtc tgatcccaga atgctgtgct | | | | 360 |
| gtttacagaa ttcaggatgg agagaagaag ccaattggct gggacactga tatttcctgg | | | | 420 |
| ctcactggag aagagctgca tgtggaagtg ttagagaatg tcccactcac cacacataac | | | | 480 |
| tttgtacgga aaactttttt caccttagca ttttgtgact tctgtagaaa gctgcttttc | | | | 540 |
| cagggtttcc gctgtcaaac atgtggctac aaatttcacc agcgttgtag tacgaagtt | | | | 600 |
| ccactgatgt gtgttaatta tgaccaactt gatttgctgt ttgtctccaa gttctttgaa | | | | 660 |
| caccacccag taccaagga gaggcctcc ttagcagaga ctgccctcac atctgggtca | | | | 720 |
| tcgccttccg cacctccctc agactctatt gggcaccaaa ttctcaccag tccgtccct | | | | 780 |
| tcaaaatcca ttccgattcc acagtccttc cgaccagcag atgaagatca tcgaaatcag | | | | 840 |
| tttgggcaac gagaccggtc ttcatcagcg cctaatgttc acattaacac aatagaaacct | | | | 900 |
| gtcaatattg atgaaaaatt cccagaagtg gaattacagg atcaaaggga cttgattaga | | | | 960 |
| gaccaagggt tcgtggtga tggagcccct ttgaaccagc tgatgcgctg tcttcggaaa | | | | 1020 |
| taccaatccc ggactccag tcccctccta ccttctgtcc ccagtgacat agtgtttgat | | | | 1080 |
| tttgagcctg gcccagtgtt cagaggatcg accacgggtt tgtctgccac tcccctgcc | | | | 1140 |
| tcattacctg gctcactcac tagtgtgaaa gctgtacaga atccccagg acctcagcga | | | | 1200 |
| gagaggaagt cgtcttctc ctcagaagac aggaatcgaa tgaaaactct tggtagacgg | | | | 1260 |
| gattcaagtg atgattggga gattcctgat gggcagatca ccgtgggaca gagaattgga | | | | 1320 |
| tctggatcat ttggaaccgt ctacaaggga aaatggcacg tgatgtggc agtaaaaatg | | | | 1380 |
| ttgaatgtga cagcacctac acctcagcag ttacaggcct tcaaaaatga agtaggagta | | | | 1440 |
| ctcaggaaaa cacgacatgt gaatatccta cttttcatgg gctattccac aaagccacag | | | | 1500 |
| ctggctattg ttacccagtg gtgtgagggc tccagtttat atcaccatct ccacatcatt | | | | 1560 |
| gagaccaaat tcgagatgat caaacttata gatattgcac ggcagactgc acagggcatg | | | | 1620 |

-continued

```
gattacttac acgccaagtc aatcatccac agagacctca agagtaataa tatatttctt    1680
catgaagacc tcacagtaaa aataggtgat tttggtctag ccacagtgaa atctcgatgg    1740
agtgggtccc atcagtttga acaattgtct ggatccattt tgtggatggc accagaagta    1800
atcagaatgc aagacaaaaa cccatatagc tttcagtcag atgtatatgc atttgggatt    1860
gttctgtatg aattgatgac tgggcagtta ccttactcaa acatcaacaa cagggaccag    1920 atcatttta tggtgggacg tggctacctg tctccagacc tcagtaaggt acggagtaac     1980
tgtccgaaag ccatgaagag attaatggca gagtgcctca aaaagaaaag agatgagaga    2040
ccactctttc cccaaattct cgcctccatt gagctgctgg cccgctcatt gccaaaaatc    2100
caccgcagtg catcagaacc ctccttgaat cgggctggtt tccagacaga ggatttagt     2160 ctatatgctt gtgcttctcc aaaaacaccc atccaggcag ggggatatgg agaatttgca    2220
gccttcaagt ag                                                       2232
```

<210> SEQ ID NO 8
<211> LENGTH: 743
<212> TYPE: PRT
<213> ORGANISM: Oryctolagus cuniculus

<400> SEQUENCE: 8

```
Met Gly Asn Val Trp Asn Ile Lys Gln Met Ile Lys Leu Thr Gln Glu
1               5                   10                  15

His Ile Glu Ala Leu Leu Asp Lys Phe Gly Gly Glu His Asn Pro Pro
            20                  25                  30

Ser Ile Tyr Leu Glu Ala Tyr Glu Tyr Thr Ser Lys Leu Asp Ala
        35                  40                  45

Leu Gln Gln Arg Glu Gln Gln Leu Leu Glu Ser Leu Val Phe Gln Asn
    50                  55                  60

Pro Thr Asp Val Ser Arg Ser Asn Pro Lys Ser Pro Gln Lys Pro Ile
65                  70                  75                  80

Val Arg Val Phe Leu Pro Asn Lys Gln Arg Thr Val Val Pro Ala Arg
                85                  90                  95

Cys Gly Val Thr Val Arg Asp Ser Leu Lys Lys Ala Leu Met Met Arg
            100                 105                 110

Gly Leu Ile Pro Glu Cys Cys Ala Val Tyr Arg Ile Gln Asp Gly Glu
        115                 120                 125

Lys Lys Pro Ile Gly Trp Asp Thr Asp Ile Ser Trp Leu Thr Gly Glu
    130                 135                 140

Glu Leu His Val Glu Val Leu Glu Asn Val Pro Leu Thr Thr His Asn
145                 150                 155                 160

Phe Val Arg Lys Thr Phe Phe Thr Leu Ala Phe Cys Asp Phe Cys Arg
                165                 170                 175

Lys Leu Leu Phe Gln Gly Phe Arg Cys Gln Thr Cys Gly Tyr Lys Phe
            180                 185                 190

His Gln Arg Cys Ser Thr Glu Val Pro Leu Met Cys Val Asn Tyr Asp
        195                 200                 205

Gln Leu Asp Leu Leu Phe Val Ser Lys Phe Phe Glu His His Pro Val
    210                 215                 220

Pro Gln Glu Glu Ala Ser Leu Ala Glu Thr Ala Leu Thr Ser Gly Ser
225                 230                 235                 240

Ser Pro Ser Ala Pro Ser Asp Ser Ile Gly His Gln Ile Leu Thr
                245                 250                 255
```

```
Ser Pro Ser Pro Ser Lys Ser Ile Pro Ile Pro Gln Ser Phe Arg Pro
            260                 265                 270

Ala Asp Glu Asp His Arg Asn Gln Phe Gly Gln Arg Asp Arg Ser Ser
            275                 280                 285

Ser Ala Pro Asn Val His Ile Asn Thr Ile Glu Pro Val Asn Ile Asp
        290                 295                 300

Glu Lys Phe Pro Glu Val Glu Leu Gln Asp Gln Arg Asp Leu Ile Arg
305                 310                 315                 320

Asp Gln Gly Phe Arg Gly Asp Gly Ala Pro Leu Asn Gln Leu Met Arg
                325                 330                 335

Cys Leu Arg Lys Tyr Gln Ser Arg Thr Pro Ser Pro Leu Leu Pro Ser
            340                 345                 350

Val Pro Ser Asp Ile Val Phe Asp Phe Glu Pro Gly Pro Val Phe Arg
            355                 360                 365

Gly Ser Thr Thr Gly Leu Ser Ala Thr Pro Ala Ser Leu Pro Gly
        370                 375                 380

Ser Leu Thr Ser Val Lys Ala Val Gln Arg Ser Pro Gly Pro Gln Arg
385                 390                 395                 400

Glu Arg Lys Ser Ser Ser Ser Glu Asp Arg Asn Arg Met Lys Thr
            405                 410                 415

Leu Gly Arg Arg Asp Ser Ser Asp Trp Glu Ile Pro Asp Gly Gln
            420                 425                 430

Ile Thr Val Gly Gln Arg Ile Gly Ser Gly Ser Phe Gly Thr Val Tyr
            435                 440                 445

Lys Gly Lys Trp His Gly Asp Val Ala Val Lys Met Leu Asn Val Thr
    450                 455                 460

Ala Pro Thr Pro Gln Gln Leu Gln Ala Phe Lys Asn Glu Val Gly Val
465                 470                 475                 480

Leu Arg Lys Thr Arg His Val Asn Ile Leu Leu Phe Met Gly Tyr Ser
            485                 490                 495

Thr Lys Pro Gln Leu Ala Ile Val Thr Gln Trp Cys Glu Gly Ser Ser
            500                 505                 510

Leu Tyr His His Leu His Ile Ile Glu Thr Lys Phe Glu Met Ile Lys
            515                 520                 525

Leu Ile Asp Ile Ala Arg Gln Thr Ala Gln Gly Met Asp Tyr Leu His
530                 535                 540

Ala Lys Ser Ile Ile His Arg Asp Leu Lys Ser Asn Asn Ile Phe Leu
545                 550                 555                 560

His Glu Asp Leu Thr Val Lys Ile Gly Asp Phe Gly Leu Ala Thr Val
            565                 570                 575

Lys Ser Arg Trp Ser Gly Ser His Gln Phe Glu Gln Leu Ser Gly Ser
            580                 585                 590

Ile Leu Trp Met Ala Pro Glu Val Ile Arg Met Gln Asp Lys Asn Pro
            595                 600                 605

Tyr Ser Phe Gln Ser Asp Val Tyr Ala Phe Gly Ile Val Leu Tyr Glu
            610                 615                 620

Leu Met Thr Gly Gln Leu Pro Tyr Ser Asn Ile Asn Asn Arg Asp Gln
625                 630                 635                 640

Ile Ile Phe Met Val Gly Arg Gly Tyr Leu Ser Pro Asp Leu Ser Lys
                645                 650                 655

Val Arg Ser Asn Cys Pro Lys Ala Met Lys Arg Leu Met Ala Glu Cys
            660                 665                 670

Leu Lys Lys Lys Arg Asp Glu Arg Pro Leu Phe Pro Gln Ile Leu Ala
```

```
               675                 680                 685
Ser Ile Glu Leu Leu Ala Arg Ser Leu Pro Lys Ile His Arg Ser Ala
        690                 695                 700

Ser Glu Pro Ser Leu Asn Arg Ala Gly Phe Gln Thr Glu Asp Phe Ser
705                 710                 715                 720

Leu Tyr Ala Cys Ala Ser Pro Lys Thr Pro Ile Gln Ala Gly Gly Tyr
                725                 730                 735

Gly Glu Phe Ala Ala Phe Lys
            740

<210> SEQ ID NO 9
<211> LENGTH: 2186
<212> TYPE: DNA
<213> ORGANISM: Cavia porcellus

<400> SEQUENCE: 9
```

| | | | | | |
|---|---|---|---|---|---|
| atggcggcgc | tcagcggcgg | cggtggcgcg | gagcagggcc | aggctctgtt | caacggggac | 60 |
| atggagctcg | aggccggcgc | cggcgccgca | gcctcttcgg | ctgcagaccc | tgccattccc | 120 |
| gaggaggtat | ggaatatcaa | acaaatgatt | aagttgacgc | aggaacacat | agaggcccta | 180 |
| ttggacaaat | ttggtggaga | gcataatcca | ccatcaatat | acctggaggc | ctatgaagaa | 240 |
| tacaccagca | aactagatgc | cctccaacaa | agagaacagc | agttactgga | tccctcgggg | 300 |
| aatggaactg | attttttctgt | ttctagctct | gcatcactgg | acaccgttac | atcttcttct | 360 |
| tcttctagcc | tttcagtact | accttcatct | ctttcagttt | ttcaaaatcc | tacagatgtg | 420 |
| tcacggagca | cccccaaatc | accacaaaaa | cctattgtta | gagtcttcct | gcccaacaaa | 480 |
| cagaggacag | tggtacctgc | aaggtgtgga | gttacagtcc | gagacagtct | gaagaaagca | 540 |
| ctcatgatga | gaggtcttat | cccagagtgc | tgtgctgtgt | acagaattca | ggatggagaa | 600 |
| aagaaaccaa | ttggctggga | cactgacatt | tcctggctta | ctggggaaga | attacatgta | 660 |
| gaagtattgg | agaatgttcc | acttacaaca | cacaattttg | tatgtatctt | tatatttttt | 720 |
| ttgctgtttg | tctccaagtt | cttttgaacac | cacccaatac | acaggagga | ggcttcctta | 780 |
| gcagagacca | cccttacatc | tggatcatcc | ccttctgcac | cccccctcaga | gtccattggg | 840 |
| cccccaattc | tcaccagccc | atctccttca | aaatccattc | caattccaca | gccttttccgg | 900 |
| ccaggagagg | aagatcatcg | aaatcaattt | gggcagcgag | accggtcctc | atctgctccc | 960 |
| aatgtgcata | taaacacaat | agaacctgtc | aatattgatg | atttgattag | agaccaaggg | 1020 |
| tttcgtagtg | atggaggatc | aactacaggt | ttgtctgcca | ccccacctgc | ctcattacct | 1080 |
| ggctcactca | ctaatgtgaa | agccttacag | aaatctccag | gacctcagcg | agaaaggaag | 1140 |
| tcatcttcat | cctcagaaga | cagaaatcga | atgaaaacgc | ttggtagacg | ggactcaagt | 1200 |
| gatgattggg | agattcctga | tgggcagatt | acagtgggac | aaagaattgg | atctgggtca | 1260 |
| tttggaacag | tctacaaggg | gaagtggcat | ggtgacgtgg | cagtgaaaat | gttgaatgtg | 1320 |
| acagcaccca | cacctcaaca | gttacaggcc | ttcaaaaatg | aagtaggagt | actcaggaaa | 1380 |
| acacgacatg | tgaatatcct | actcttcatg | ggctattcca | caaagccaca | gctagctatt | 1440 |
| gttacccagt | ggtgtgaggg | ctccagctta | taccaccatc | tccacatcat | cgagaccaaa | 1500 |
| tttgagatga | tcaaacttat | agatattgca | cgacagactg | cccagggcat | ggattactta | 1560 |
| cacgccaagt | caatcatcca | cagagacctc | aagagtaata | tatatttct | tcacgaagac | 1620 |
| ctcacggtta | aataggtga | ttttggtcta | gccacagtga | aatctcgatg | gagtgggtcc | 1680 |
| catcagtttg | aacagttgtc | tggatccatt | ttgtggatgg | caccagaagt | aatcagaatg | 1740 |

```
cgagataaaa acccatacag ttttcagtcc gatgtatatg catttgggat tgttctatat      1800
gaattgatga ctgggcagtt accctattca aatatcaaca acagggacca gataatttt       1860 atggtgggac gaggatatct atctccagat ctcagcaagg tacggagtaa ctgtccaaaa      1920
gccatgaaga ggttaatggc ggagtgcctc aaaaagaaaa gagatgagag accactcttt      1980
ccccaaattc tcgcctctat tgagctgctg gcccgctcat tgccaaaaat tcaccgcagt      2040
gcatcagaac cctccttgaa tcgggctggt ttccaaacag aggattttag tctctatgct      2100
tgtgcttctc caaaaacacc catccaggca gggggatatg gtgcgtttcc tgtccactga      2160
tgcaaattaa atgagtgaga aataaa                                           2186
```

<210> SEQ ID NO 10
<211> LENGTH: 719
<212> TYPE: PRT
<213> ORGANISM: Cavia porcellus

<400> SEQUENCE: 10

```
Met Ala Ala Leu Ser Gly Gly Gly Ala Glu Gln Gly Gln Ala Leu
1               5                   10                  15

Phe Asn Gly Asp Met Glu Leu Glu Ala Gly Ala Gly Ala Ala Ala Ser
            20                  25                  30

Ser Ala Ala Asp Pro Ala Ile Pro Glu Glu Val Trp Asn Ile Lys Gln
        35                  40                  45

Met Ile Lys Leu Thr Gln Glu His Ile Glu Ala Leu Leu Asp Lys Phe
    50                  55                  60

Gly Gly Glu His Asn Pro Pro Ser Ile Tyr Leu Glu Ala Tyr Glu Glu
65                  70                  75                  80

Tyr Thr Ser Lys Leu Asp Ala Leu Gln Gln Arg Glu Gln Gln Leu Leu
                85                  90                  95

Glu Ser Leu Gly Asn Gly Thr Asp Phe Ser Val Ser Ser Ser Ala Ser
            100                 105                 110

Leu Asp Thr Val Thr Ser Ser Ser Ser Ser Leu Ser Val Leu Pro
        115                 120                 125

Ser Ser Leu Ser Val Phe Gln Asn Pro Thr Asp Val Ser Arg Ser Asn
    130                 135                 140

Pro Lys Ser Pro Gln Lys Pro Ile Val Arg Val Phe Leu Pro Asn Lys
145                 150                 155                 160

Gln Arg Thr Val Val Pro Ala Arg Cys Gly Val Thr Val Arg Asp Ser
                165                 170                 175

Leu Lys Lys Ala Leu Met Met Arg Gly Leu Ile Pro Glu Cys Cys Ala
            180                 185                 190

Val Tyr Arg Ile Gln Asp Gly Glu Lys Lys Pro Ile Gly Trp Asp Thr
        195                 200                 205

Asp Ile Ser Trp Leu Thr Gly Glu Glu Leu His Val Glu Val Leu Glu
    210                 215                 220

Asn Val Pro Leu Thr Thr His Asn Phe Val Cys Ile Phe Ile Phe Phe
225                 230                 235                 240

Leu Leu Phe Val Ser Lys Phe Phe Glu His His Pro Ile Pro Gln Glu
                245                 250                 255

Glu Ala Ser Leu Ala Glu Thr Thr Leu Thr Ser Gly Ser Ser Pro Ser
            260                 265                 270

Ala Pro Pro Ser Glu Ser Ile Gly Pro Pro Ile Leu Thr Ser Pro Ser
        275                 280                 285
```

-continued

```
Pro Ser Lys Ser Ile Pro Ile Pro Gln Pro Phe Arg Pro Gly Glu Glu
    290                 295                 300

Asp His Arg Asn Gln Phe Gly Gln Arg Asp Arg Ser Ser Ser Ala Pro
305                 310                 315                 320

Asn Val His Ile Asn Thr Ile Glu Pro Val Asn Ile Asp Asp Leu Ile
                    325                 330                 335

Arg Asp Gln Gly Phe Arg Ser Asp Gly Ser Thr Thr Gly Leu Ser
                340                 345                 350

Ala Thr Pro Pro Ala Ser Leu Pro Gly Ser Leu Thr Asn Val Lys Ala
            355                 360                 365

Leu Gln Lys Ser Pro Gly Pro Gln Arg Glu Arg Lys Ser Ser Ser
    370                 375                 380

Ser Glu Asp Arg Asn Arg Met Lys Thr Leu Gly Arg Arg Asp Ser Ser
385                 390                 395                 400

Asp Asp Trp Glu Ile Pro Asp Gly Gln Ile Thr Val Gly Gln Arg Ile
                405                 410                 415

Gly Ser Gly Ser Phe Gly Thr Val Tyr Lys Gly Lys Trp His Gly Asp
            420                 425                 430

Val Ala Val Lys Met Leu Asn Val Thr Ala Pro Thr Pro Gln Gln Leu
            435                 440                 445

Gln Ala Phe Lys Asn Glu Val Gly Val Leu Arg Lys Thr Arg His Val
    450                 455                 460

Asn Ile Leu Leu Phe Met Gly Tyr Ser Thr Lys Pro Gln Leu Ala Ile
465                 470                 475                 480

Val Thr Gln Trp Cys Glu Gly Ser Ser Leu Tyr His His Leu His Ile
                485                 490                 495

Ile Glu Thr Lys Phe Glu Met Ile Lys Leu Ile Asp Ile Ala Arg Gln
                500                 505                 510

Thr Ala Gln Gly Met Asp Tyr Leu His Ala Lys Ser Ile Ile His Arg
            515                 520                 525

Asp Leu Lys Ser Asn Asn Ile Phe Leu His Glu Asp Leu Thr Val Lys
    530                 535                 540

Ile Gly Asp Phe Gly Leu Ala Thr Val Lys Ser Arg Trp Ser Gly Ser
545                 550                 555                 560

His Gln Phe Glu Gln Leu Ser Gly Ser Ile Leu Trp Met Ala Pro Glu
                565                 570                 575

Val Ile Arg Met Arg Asp Lys Asn Pro Tyr Ser Phe Gln Ser Asp Val
            580                 585                 590

Tyr Ala Phe Gly Ile Val Leu Tyr Glu Leu Met Thr Gly Gln Leu Pro
    595                 600                 605

Tyr Ser Asn Ile Asn Asn Arg Asp Gln Ile Ile Phe Met Val Gly Arg
610                 615                 620

Gly Tyr Leu Ser Pro Asp Leu Ser Lys Val Arg Ser Asn Cys Pro Lys
625                 630                 635                 640

Ala Met Lys Arg Leu Met Ala Glu Cys Leu Lys Lys Lys Arg Asp Glu
                645                 650                 655

Arg Pro Leu Phe Pro Gln Ile Leu Ala Ser Ile Glu Leu Leu Ala Arg
                660                 665                 670

Ser Leu Pro Lys Ile His Arg Ser Ala Ser Glu Pro Ser Leu Asn Arg
            675                 680                 685

Ala Gly Phe Gln Thr Glu Asp Phe Ser Leu Tyr Ala Cys Ala Ser Pro
    690                 695                 700

Lys Thr Pro Ile Gln Ala Gly Gly Tyr Gly Ala Phe Pro Val His
```

<210> SEQ ID NO 11
<211> LENGTH: 3229
<212> TYPE: DNA
<213> ORGANISM: Canis familiaris

<400> SEQUENCE: 11

```
gtaatgctgg attttcatgg aataagtttg acctgtgctg cagtggcctc cagcaaggta      60
cccgcaagat gtggagttac agtccgggac agtctaaaga aagctctgat gatgagaggt     120
ctaatcccag agtgctgtgc tgtttacaga attcaggatg agagaagaa accgattggc      180
tgggacactg atatttcctg gctcactgga gaggaattgc atgtagaagt gttggaaaat     240
gttccgctta ccacacacaa ctttgtacgg aaaacttttt tcaccttagc attttgtgac    300
ttttgtcgaa agctgctttt ccagggtttt cgctgtcaaa catgtggtta taaatttcac    360
cagcgttgta gtacagaggt tccactgatg tgtgttaatt atgaccaact tgatttgctg    420
tttgtctcca agttctttga acaccaccca ataccacagg aggaggcctc catagcagag    480
actgcccttaa cgtctggatc atcccttct gctccccct ccgattctcc tgggccccca    540
attctgacca gtccgtctcc ttcaaaatcc attccaattc cacagccttt ccgaccagca    600
gatgaagatc atcgaaatca gtttggacaa cgagaccggt cctcatcagc tccaaatgtg    660
catataaaca caatagaacc cgtcaacatt gatgacttga ttagagacca agggtttcgt    720
agtgatggag atcaaccac aggtttgtct gccacccccc ctgcctcatt gcctggctca    780
ctcactaatg taaaagcatt acagaaatct ccaggacctc agcgggaaag aaaatcatct    840
tcatcctcag aagataggaa tcgaatgaaa acacttggta gacgggattc aagtgatgat    900
tgggagatac ctgatgggca gatcacagtg ggacagagaa ttggatccgg gtcatttggg    960
acagtctaca agggaaagtg gcatggtgac gtggcagtga aatgttgaa tgtgacagca   1020
cccacacctc agcagttaca ggccttcaaa aatgaagtag agtactcag gaaaactcga   1080
catgtgaata tcctactctt tatgggctat tcaacaaagc cccaactggc tattgttacc   1140
cagtggtgtg agggctccag cttatatcac catctccaca tcattgagac caaatttgag   1200
atgataaagc ttatagatat tgcacggcag actgcacagg gcatggatta cttacacgcc   1260
aagtcaatca tccacagaga cctcaagagt aataatattt tctcttcatga agacctcaca  1320
gtaaaaatag gtgattttgg tctagccaca gtgaaatctc gatggagtgg gtcccatcag   1380
tttgaacagt tgtctggatc cattttgtgg atggcaccag aagtgatccg aatgcaagac   1440
aaaaacccat atagcttcca gtcagatgta tacgcatttg ggattgttct atatgaattg   1500
atgacagggc agttaccta ttcaaacatc aacaacaggg accagataat ttttatggtg   1560
ggacgaggat atctttctcc agatctcagt aaggtacgga gtaactgtcc aaaagccatg   1620
aagagattga tggcagagtg cctaaaaaag aaaagagatg agaggccact ctttccccaa   1680
attctcgcct ctattgagct gctggcccgc tcattgccaa aaattcaccg cagtgcatca   1740
gaaccctcct tgaatcgggc tggcttccaa acagaggatt ttagtctcta tgcttgcgct   1800
tctccaaaaa cacccatcca ggcagggga tacgagaat ttgcagcctt caagtagcca   1860
caccatcatg gcaacaacta ctcttatttc ttaagtcttg tgttcgtaca atttgttaac   1920
atcaaaacac agttctgttc ctcaaatctt ttttaaaga tacagaattt tcaatgcata   1980
agctggtgtg gaacagaatg gaatttccca tccaacaaaa gagggaagaa tgttttagga   2040
accagaattc tctgctgcca gtgtttcttc ttcaacacaa ataccacgtg catacaagtc   2100
```

```
tgcccactcc caggaaggaa gaggagagcc tgagttctga cctttgatg gtcaggcatg    2160 atggaaagaa actgctgcta cagcttggga gattggctgt ggagagcctg cccgtcagct    2220
ctgcccttct aaccgccaga tgagtgtgtg gctggtcacc tgacagggca gctgcaatcg    2280
ccaagcatcg ttctctttcc tgtcctggga ttttgtcgtg gagctctttc ccctagtca    2340 ccaccggttc atttctgagg gatggaacaa aaatgcagca tggcctttct gtgtggtgca    2400
tgtccggtct ttgacaaatt tttatcaagt gaagctcttg tatttaaatg gagaatgaga    2460
ggcgaggggg ggggatcacg ttttggtgta gggcaaagg gaatgctgca tcttttttcct    2520 gacccactgg gtttctggcc tttgtttcct tgctcactga gggtgtctgc ctataaccac    2580
gcaggctgga aagtgctggc acacattgcc ttctcttctc actgggtcca gcaatgaaga    2640
caagtgttgg ggatttttt ttttgccctc cacaatgtag caagttctca ggaaaataca    2700
gttaatatct tcctcctaag ctcttccagt catcaagtac ttatgtggct actttgtcca    2760
gggcacaaaa tgccatggcg gtatccaatt aaaagcctac aaaactgctt gataacagtt    2820
ttgaatgtgt gagacattta tgtaatttaa atgtaaggta caagttttaa tttctgagtt    2880
tctctattat attttatta aaagaaaat aattttcaga tttaattgaa ttggaataaa    2940
ataatacttc ccaccagaat tatatatcct ggaaaattgt attttttgtta tataaacaac    3000 ttttaaagaa agatcattat ccttttctct acctaaatat ggggagtctt agcataatga    3060
cagatattta taatttttaa attaatggta cttgctggat ccacactaac atctttgcta    3120
atatctcatg ttttcctcca acttactcct cacactacatc ctccatcctc tttccagtct    3180
tttatctaga atatgcaacc taaaataaaa atggtggtgt ctccattca                3229
```

<210> SEQ ID NO 12
<211> LENGTH: 617
<212> TYPE: PRT
<213> ORGANISM: Canis familiaris

<400> SEQUENCE: 12

```
Met Leu Asp Phe His Gly Ile Ser Leu Thr Cys Ala Ala Val Ala Ser
1               5                   10                  15

Ser Lys Val Pro Ala Arg Cys Gly Val Thr Val Arg Asp Ser Leu Lys
                20                  25                  30

Lys Ala Leu Met Met Arg Gly Leu Ile Pro Glu Cys Cys Ala Val Tyr
            35                  40                  45

Arg Ile Gln Asp Gly Glu Lys Lys Pro Ile Gly Trp Asp Thr Asp Ile
        50                  55                  60

Ser Trp Leu Thr Gly Glu Glu Leu His Val Glu Val Leu Glu Asn Val
65                  70                  75                  80

Pro Leu Thr Thr His Asn Phe Val Arg Lys Thr Phe Phe Thr Leu Ala
                85                  90                  95

Phe Cys Asp Phe Cys Arg Lys Leu Leu Phe Gln Gly Phe Arg Cys Gln
            100                 105                 110

Thr Cys Gly Tyr Lys Phe His Gln Arg Cys Ser Thr Glu Val Pro Leu
        115                 120                 125

Met Cys Val Asn Tyr Asp Gln Leu Asp Leu Leu Phe Val Ser Lys Phe
    130                 135                 140

Phe Glu His His Pro Ile Pro Gln Glu Glu Ala Ser Ile Ala Glu Thr
145                 150                 155                 160

Ala Leu Thr Ser Gly Ser Ser Pro Ser Ala Pro Pro Ser Asp Ser Pro
                165                 170                 175
```

```
Gly Pro Pro Ile Leu Thr Ser Pro Ser Lys Ser Ile Pro Ile
            180                 185                 190

Pro Gln Pro Phe Arg Pro Ala Asp Glu Asp His Arg Asn Gln Phe Gly
        195                 200                 205

Gln Arg Asp Arg Ser Ser Ala Pro Asn Val His Ile Asn Thr Ile
210                 215                 220

Glu Pro Val Asn Ile Asp Asp Leu Ile Arg Asp Gln Gly Phe Arg Ser
225                 230                 235                 240

Asp Gly Gly Ser Thr Thr Gly Leu Ser Ala Thr Pro Pro Ala Ser Leu
                245                 250                 255

Pro Gly Ser Leu Thr Asn Val Lys Ala Leu Gln Lys Ser Pro Gly Pro
                260                 265                 270

Gln Arg Glu Arg Lys Ser Ser Ser Ser Glu Asp Arg Asn Arg Met
        275                 280                 285

Lys Thr Leu Gly Arg Arg Asp Ser Ser Asp Asp Trp Glu Ile Pro Asp
290                 295                 300

Gly Gln Ile Thr Val Gly Gln Arg Ile Gly Ser Gly Ser Phe Gly Thr
305                 310                 315                 320

Val Tyr Lys Gly Lys Trp His Gly Asp Val Ala Val Lys Met Leu Asn
                325                 330                 335

Val Thr Ala Pro Thr Pro Gln Gln Leu Gln Ala Phe Lys Asn Glu Val
                340                 345                 350

Gly Val Leu Arg Lys Thr Arg His Val Asn Ile Leu Leu Phe Met Gly
                355                 360                 365

Tyr Ser Thr Lys Pro Gln Leu Ala Ile Val Thr Gln Trp Cys Glu Gly
        370                 375                 380

Ser Ser Leu Tyr His His Leu His Ile Ile Glu Thr Lys Phe Glu Met
385                 390                 395                 400

Ile Lys Leu Ile Asp Ile Ala Arg Gln Thr Ala Gln Gly Met Asp Tyr
                405                 410                 415

Leu His Ala Lys Ser Ile Ile His Arg Asp Leu Lys Ser Asn Asn Ile
                420                 425                 430

Phe Leu His Glu Asp Leu Thr Val Lys Ile Gly Asp Phe Gly Leu Ala
        435                 440                 445

Thr Val Lys Ser Arg Trp Ser Gly Ser His Gln Phe Glu Gln Leu Ser
        450                 455                 460

Gly Ser Ile Leu Trp Met Ala Pro Glu Val Ile Arg Met Gln Asp Lys
465                 470                 475                 480

Asn Pro Tyr Ser Phe Gln Ser Asp Val Tyr Ala Phe Gly Ile Val Leu
                485                 490                 495

Tyr Glu Leu Met Thr Gly Gln Leu Pro Tyr Ser Asn Ile Asn Asn Arg
                500                 505                 510

Asp Gln Ile Ile Phe Met Val Gly Arg Gly Tyr Leu Ser Pro Asp Leu
        515                 520                 525

Ser Lys Val Arg Ser Asn Cys Pro Lys Ala Met Lys Arg Leu Met Ala
        530                 535                 540

Glu Cys Leu Lys Lys Lys Arg Asp Glu Arg Pro Leu Phe Pro Gln Ile
545                 550                 555                 560

Leu Ala Ser Ile Glu Leu Leu Ala Arg Ser Leu Pro Lys Ile His Arg
                565                 570                 575

Ser Ala Ser Glu Pro Ser Leu Asn Arg Ala Gly Phe Gln Thr Glu Asp
                580                 585                 590
```

```
Phe Ser Leu Tyr Ala Cys Ala Ser Pro Lys Thr Pro Ile Gln Ala Gly
            595                 600                 605
Gly Tyr Gly Glu Phe Ala Ala Phe Lys
    610                 615

<210> SEQ ID NO 13
<211> LENGTH: 1889
<212> TYPE: DNA
<213> ORGANISM: Canis familiaris

<400> SEQUENCE: 13
ggaatatcaa acaaatgatt aagttgacac aggaacatat agaagcccta ttggacaagt      60
ttggtgggga gcataatcca ccatcaatat atctggaggc ctatgaagaa tacaccagca     120
aactagatgc cctccaacag cgagaacaac agttattgga atccctgggg aatggaactg     180
atttttctgt ttctagctct gcatcaacgg acaccgttac atcttcttcc tcttctagcc     240
tttcagtgct accttcatct ctttcagttt ttcaaaatcc cacagatata tcacggagca     300
atcccaagtc accacaaaaa cctatcgtta gagtcttcct gcccaataaa cagaggacgg     360
tggtacccgc aagatgtgga gttacagtcc gggacagtct aaagaaagct ctgatgatga     420
gaggtctaat cccagagtgc tgtgctgttt acagaattca ggatggagag aagaaaccga     480
ttggctggga cactgatatt tcctggctca ctggagagga attgcatgta gaagtgttgg     540
aaaatgttcc gcttaccaca cacaactttg tacgaaaaac ttttttcacc ttagcatttt     600
gtgacttttg tcgaaagctg cttttccagg gttttcgctg tcaaacatgt ggttataaat     660
ttcaccagcg ttgtagtaca gaggttccac tgatgtgtgt taattatgac caacttgatt     720
tgctgtttgt ctccaagttc tttgaacacc acccaatacc acaggaggag gcctccatag     780
cagagactgc ccttacgtct ggatcatccc cttctgctcc cccctccgat tctcctgggc     840
ccccaattct gaccagtccg tctccttcaa aatccattcc aattccacag cctttccgac     900
cagcagatga agatcatcga aatcagtttg gacaacgaga ccggtcctca tcagctccaa     960
atgtgcatat aaacacaata gaacccgtca cattgatga cttgattaga gaccaagggt    1020
ttcgtagtga tggaggatca accacaggtt tgtctgccac ccccccctgcc tcattgcctg    1080
gctcactcac taatgtaaaa gcattacaga atctccagg acctcagcgg gaaagaaaat    1140
catcttcatc ctcagaagat aggaatcgaa tgaaaacact tggtagacgg gattcaagtg    1200
atgattggga gatacctgat gggcagatca cagtgggaca gagaattgga tccgggtcat    1260
ttgggacagt ctacaaggga aagtggcatg gtgacgtggc agtgaaaatg ttgaatgtga    1320
cagcacccac acctcagcag ttacaggcct tcaaaaatga gtaggagta ctcaggaaaa    1380
ctcgacatgt gaatatccta ctctttatgg gctattcaac aaagccccaa ctggctattg    1440
ttacccagtg gtgtgagggc tccagcttat atcaccatct ccacatcatt gagaccaaat    1500
ttgagatgat aaagcttata gatattgcac ggcagactgc acagggcatg gattacttac    1560
acgccaagtc aatcatccac agagacctca agagtaataa tattttttctt catgaagacc    1620
tcacagtaaa aataggtgat tttggtctag ccacagtgaa atctcgatgg agtgggtccc    1680
atcagtttga acagttgtct ggatccattt tgtggatggc accagaagtg atccgaatgc    1740
aagacaaaaa cccatatagc ttccagtcag atgtatacgc atttgggatt gttctatatg    1800
aattgatgac agggcagtta ccttattcaa acatcaacaa cagggaccag ctcagatcat    1860
gatcacggtg tcatgagatc aagccccac                                    1889
```

```
<210> SEQ ID NO 14
<211> LENGTH: 615
<212> TYPE: PRT
<213> ORGANISM: Canis familiaris

<400> SEQUENCE: 14
```

| | | | | | | | | | | | | | | |
|---|---|---|---|---|---|---|---|---|---|---|---|---|---|---|
| Met | Ile | Lys | Leu | Thr | Gln | Glu | His | Ile | Glu | Ala | Leu | Leu | Asp | Lys | Phe |
| 1 | | | | 5 | | | | | 10 | | | | | 15 | |
| Gly | Gly | Glu | His | Asn | Pro | Pro | Ser | Ile | Tyr | Leu | Glu | Ala | Tyr | Glu | Glu |
| | | | 20 | | | | | 25 | | | | | 30 | | |
| Tyr | Thr | Ser | Lys | Leu | Asp | Ala | Leu | Gln | Gln | Arg | Glu | Gln | Gln | Leu | Leu |
| | | 35 | | | | | 40 | | | | | 45 | | | |
| Glu | Ser | Leu | Gly | Asn | Gly | Thr | Asp | Phe | Ser | Val | Ser | Ser | Ala | Ser |
| 50 | | | | | 55 | | | | | 60 | | | | |
| Thr | Asp | Thr | Val | Thr | Ser | Ser | Ser | Ser | Ser | Leu | Ser | Val | Leu | Pro |
| 65 | | | | | 70 | | | | | 75 | | | | | 80 |
| Ser | Ser | Leu | Ser | Val | Phe | Gln | Asn | Pro | Thr | Asp | Ile | Ser | Arg | Ser | Asn |
| | | | | 85 | | | | | 90 | | | | | 95 | |
| Pro | Lys | Ser | Pro | Gln | Lys | Pro | Ile | Val | Arg | Val | Phe | Leu | Pro | Asn | Lys |
| | | | 100 | | | | | 105 | | | | | 110 | | |
| Gln | Arg | Thr | Val | Val | Pro | Ala | Arg | Cys | Gly | Val | Thr | Val | Arg | Asp | Ser |
| | | 115 | | | | | 120 | | | | | 125 | | | |
| Leu | Lys | Lys | Ala | Leu | Met | Met | Arg | Gly | Leu | Ile | Pro | Glu | Cys | Cys | Ala |
| 130 | | | | | 135 | | | | | 140 | | | | | |
| Val | Tyr | Arg | Ile | Gln | Asp | Gly | Glu | Lys | Lys | Pro | Ile | Gly | Trp | Asp | Thr |
| 145 | | | | | 150 | | | | | 155 | | | | | 160 |
| Asp | Ile | Ser | Trp | Leu | Thr | Gly | Glu | Glu | Leu | His | Val | Glu | Val | Leu | Glu |
| | | | | 165 | | | | | 170 | | | | | 175 | |
| Asn | Val | Pro | Leu | Thr | Thr | His | Asn | Phe | Val | Arg | Lys | Thr | Phe | Phe | Thr |
| | | | 180 | | | | | 185 | | | | | 190 | | |
| Leu | Ala | Phe | Cys | Asp | Phe | Cys | Arg | Lys | Leu | Leu | Phe | Gln | Gly | Phe | Arg |
| | | 195 | | | | | 200 | | | | | 205 | | | |
| Cys | Gln | Thr | Cys | Gly | Tyr | Lys | Phe | His | Gln | Arg | Cys | Ser | Thr | Glu | Val |
| 210 | | | | | 215 | | | | | 220 | | | | | |
| Pro | Leu | Met | Cys | Val | Asn | Tyr | Asp | Gln | Leu | Asp | Leu | Leu | Phe | Val | Ser |
| 225 | | | | | 230 | | | | | 235 | | | | | 240 |
| Lys | Phe | Phe | Glu | His | His | Pro | Ile | Pro | Gln | Glu | Glu | Ala | Ser | Ile | Ala |
| | | | | 245 | | | | | 250 | | | | | 255 | |
| Glu | Thr | Ala | Leu | Thr | Ser | Gly | Ser | Ser | Pro | Ser | Ala | Pro | Pro | Ser | Asp |
| | | | 260 | | | | | 265 | | | | | 270 | | |
| Ser | Pro | Gly | Pro | Pro | Ile | Leu | Thr | Ser | Pro | Ser | Pro | Ser | Lys | Ser | Ile |
| | | 275 | | | | | 280 | | | | | 285 | | | |
| Pro | Ile | Pro | Gln | Pro | Phe | Arg | Pro | Ala | Asp | Glu | Asp | His | Arg | Asn | Gln |
| 290 | | | | | 295 | | | | | 300 | | | | | |
| Phe | Gly | Gln | Arg | Asp | Arg | Ser | Ser | Ser | Ala | Pro | Asn | Val | His | Ile | Asn |
| 305 | | | | | 310 | | | | | 315 | | | | | 320 |
| Thr | Ile | Glu | Pro | Val | Asn | Ile | Asp | Asp | Leu | Ile | Arg | Asp | Gln | Gly | Phe |
| | | | | 325 | | | | | 330 | | | | | 335 | |
| Arg | Ser | Asp | Gly | Gly | Ser | Thr | Thr | Gly | Leu | Ser | Ala | Thr | Pro | Pro | Ala |
| | | | 340 | | | | | 345 | | | | | 350 | | |
| Ser | Leu | Pro | Gly | Ser | Leu | Thr | Asn | Val | Lys | Ala | Leu | Gln | Lys | Ser | Pro |
| | | 355 | | | | | 360 | | | | | 365 | | | |
| Gly | Pro | Gln | Arg | Glu | Arg | Lys | Ser | Ser | Ser | Ser | Ser | Glu | Asp | Arg | Asn |
| 370 | | | | | 375 | | | | | 380 | | | | | |

Arg Met Lys Thr Leu Gly Arg Arg Asp Ser Ser Asp Asp Trp Glu Ile
385                 390                 395                 400

Pro Asp Gly Gln Ile Thr Val Gly Gln Arg Ile Gly Ser Gly Ser Phe
            405                 410                 415

Gly Thr Val Tyr Lys Gly Lys Trp His Gly Asp Val Ala Val Lys Met
            420                 425                 430

Leu Asn Val Thr Ala Pro Thr Pro Gln Gln Leu Gln Ala Phe Lys Asn
            435                 440                 445

Glu Val Gly Val Leu Arg Lys Thr Arg His Val Asn Ile Leu Leu Phe
    450                 455                 460

Met Gly Tyr Ser Thr Lys Pro Gln Leu Ala Ile Val Thr Gln Trp Cys
465                 470                 475                 480

Glu Gly Ser Ser Leu Tyr His His Leu His Ile Ile Glu Thr Lys Phe
            485                 490                 495

Glu Met Ile Lys Leu Ile Asp Ile Ala Arg Gln Thr Ala Gln Gly Met
            500                 505                 510

Asp Tyr Leu His Ala Lys Ser Ile Ile His Arg Asp Leu Lys Ser Asn
            515                 520                 525

Asn Ile Phe Leu His Glu Asp Leu Thr Val Lys Ile Gly Asp Phe Gly
    530                 535                 540

Leu Ala Thr Val Lys Ser Arg Trp Ser Gly Ser His Gln Phe Glu Gln
545                 550                 555                 560

Leu Ser Gly Ser Ile Leu Trp Met Ala Pro Glu Val Ile Arg Met Gln
            565                 570                 575

Asp Lys Asn Pro Tyr Ser Phe Gln Ser Asp Val Tyr Ala Phe Gly Ile
            580                 585                 590

Val Leu Tyr Glu Leu Met Thr Gly Gln Leu Pro Tyr Ser Asn Ile Asn
            595                 600                 605

Asn Arg Asp Gln Leu Arg Ser
610                 615

<210> SEQ ID NO 15
<211> LENGTH: 3521
<212> TYPE: DNA
<213> ORGANISM: Felis catus
<220> FEATURE:
<221> NAME/KEY: misc_feature
<222> LOCATION: (630)..(649)
<223> OTHER INFORMATION: n is a, c, g, or t

<400> SEQUENCE: 15
atgcctaacc tcagtctctg ccaccacggc caatttgctc atgtgcccac tgtgtcggca      60
ctgggatatt ttgtgatttg ccttggccat tgtccactgt ccttgacatt gcctgaagga     120
gaaccactga tgctaatgtt gaaggtgacc tttgcaggct ctccactact cataccaaag     180
atgcggcccc tgataatcc cagagccact gtctgcacat gggcaaaaca ggctacattc     240
tgtgcagact ggggagaaag gttccaagaa cacagtgcca tagttttggg cagagagttt     300
caacacagca tagtgtctat ggcagtatct ggatttggcc gggggaagtg cccaagagga     360
gacagtcagg ctgtgtccta cggccaagga cctgcactta ttttgcatg cagtggttta     420
gcacagggaa gagaacgaag taggaaatcg gagccatgga acggcagag cggaggaaac     480
gtgcacgcgc gagggtgggc acgaaaggaa agaaccctcc ccagaagact gcgcgagggc     540
gctcctagga ttacgtcacg cacccccgcga aaactgaaat gtactgtgtg tggtcttta     600
attgaactat cttccttatg tgcacttaan nnnnnnnnn nnnnnnnnng cggcggcggc     660

```
ggtggcgcgg agcagggcca ggctctgttc aacggggaca tggagcccga agccggcgcc      720
gcggcctctt cggctgcgga ccctgccatt cccgaggagg tgtggaatat caaacaaatg      780
attaagttga cacaggaaca tatagaggcc ctattggaca aatttggtgg ggagcataat      840
ccaccatcaa tatatctaga ggcctatgaa gaatacacca gcaagctaga tgccctccaa      900
cagagagaac aacagttatt ggaatccctg gggaatggaa ctgattttc tgtttctagc       960
tctgcatcaa cagacaccgt tacatcttcc tcctcttcta gcctttcagt gctaccttca     1020
tctctttcag ttttcaaaa ccccacagat gtgtcacgga gcaatcccaa gtcaccacag      1080
aaacctatcg ttagagtctt cctgcctaat aaacagagga cagtggtacc tgcaagatgt     1140
ggagttacag tccgggacag tctaaagaaa gctctgatga tgagaggtct aatccctgag     1200
tgctgtgctg tttacagaat tcaggatgga gagaagaaac caattggctg ggacactgat     1260
atctcctggc tcaccggaga ggaattgcat gtagaagtgt tggaaaatgt tccacttaca     1320
actcacaact ttgtatgtac ggaaaacgtt ttcaccttag cattttgtga cttttgtcga     1380
aagctgcttt tccaaggttt tcgctgtcaa acgtgtggtt ataaatttca ccagcgttgt     1440
agtacagagg ttccactgat gtgtgttaat tatgaccaac ttgatttgct gtttgtctcc     1500
aagttctttg aacaccaccc aataccacag gaggaggcct ccatagcaga gactgcccta     1560
acgtctggat cgtcccttc tgcccccccc tccgattcta ctgggcccca aattctcacc     1620
agtccgtctc cttcaaaatc cattccaatt ccacagcctt tccgaccagc agatgaagat     1680
catcgaaatc aatttggaca gcgagaccgg tcctcatcag ctccaaatgt gcatataaat     1740
acaatagaac ctgtcaatat tgatgacttg attagagacc aggggtttcg tagtgatgga     1800
ggatcaacca caggcttgtc tgccaccccc cctgcctcat gccgggctc tctcactaat      1860
gtaaaagcat tacagaaatc tccagggcct cagcgggaaa ggaaatcttc ttcatcctca     1920
gaagatagga atcgaatgaa aacacttggt agaagggatt caagtgatga ttgggagatt     1980
cctgatgggc agatcacagt gggacagaga attggatccg ggtcatttgg acagtctac     2040
aagggaaagt ggcatggtga tgtggcagtg aaaatgttga atgtgacagc acccacacct     2100
cagcagttac aggccttcaa aaatgaagta ggagtactca ggaaaactcg gcatgtgaac     2160
atcctgctct tcatgggcta ttcaacaaag ccccagctgg ctattgtcac ccagtggtgt     2220
gagggctcca gcttatacca ccatctccac atcatcgaga ccaaattcga gatgatcaag     2280
ctgatagata ttgctcggca gactgcgcag gcatggatt acttacacgc caagtcaatc     2340
atccacagag acctcaagag taataatatt tttcttcacg aagacctcac agtaaaaata     2400
ggtgattttg gtctagccac agtgaaatct cgatggagtg ggtcccatca gtttgaacag     2460
ttgtctggat ccattttgtg gatggcacca gaagtaattc gaatgcaaga taaaacccca     2520
tatagctttc agtcagatgt atatgcattt gggattgttc tatatgaatt gatgactgga     2580
cagttacctt attcaaacat caacaacagg gaccagataa ttttatggt gggacgagga     2640
tatctttctc cagatctcag taaggtacga agtaactgtc caaaagccat gaagagattg     2700
atggcagagt gcctaaaaaa gaaaagagat gagaggccac tgtttcccca aattcttgcc     2760
tctattgagc tgctggcccg ctcattgcca aaaattcacc gcagtgcatc agaaccctcc     2820
ttgaatcggg ctggcttcca gacagaggat tttagtctct atgcttgtgc ttctccaaaa     2880
acacccatcc aggcagggg atatggtgcg tttcccgtcc actgagataa gttagatgag     2940
tgcgcgagtg caggggccg gggccaagga ggtggaaatg tgcgtgcttc tgtactaagt     3000
tggatagcat cttctttttt aaaaaagat gaaccaaaga atgtgtatgt ttttaaagac     3060
```

-continued

```
tagatataat tatttcctga tctaaaatgt atacttagct ttggattttc aatatccaag    3120
ggttttcaaa atgcacagac attgctgaac atttgcagta cctcttctgg aggctttact    3180
tcctgttaca aattggtttt gtttactggc ttatcctaat tattaaactt caattaaact    3240
tttctcctgc accttttgtt atgagctatc acatgtccct tagggactcg caagagcagt    3300
actgcccccg tgtacgggct tgcaggtaga aaggggatga cgggttttaa cacctgtgtg    3360
aggcaaggca gtccgaacag atctcattta ggaagccacg agagttgaat aagttatttt    3420
tattcttagt attttttctg taactacttt ttattataac ttggaaaata tggatgtcct    3480
ttatacacct tagcaataga ctgaatttct ttttataaat t                        3521
```

<210> SEQ ID NO 16
<211> LENGTH: 974
<212> TYPE: PRT
<213> ORGANISM: Felis catus
<220> FEATURE:
<221> NAME/KEY: misc_feature
<222> LOCATION: (210)..(217)
<223> OTHER INFORMATION: Xaa can be any naturally occurring amino acid

<400> SEQUENCE: 16

```
Met Pro Asn Leu Ser Leu Cys His His Gly Gln Phe Ala His Val Pro
1               5                   10                  15

Thr Val Ser Ala Leu Gly Tyr Phe Val Ile Cys Leu Gly His Cys Pro
            20                  25                  30

Leu Ser Leu Thr Leu Pro Glu Gly Glu Pro Leu Met Leu Met Leu Lys
        35                  40                  45

Val Thr Phe Ala Gly Ser Pro Leu Leu Ile Pro Lys Met Arg Pro Pro
    50                  55                  60

Asp Asn Pro Arg Ala Thr Val Cys Thr Trp Ala Lys Gln Ala Thr Phe
65                  70                  75                  80

Cys Ala Asp Trp Gly Glu Arg Phe Gln Glu His Ser Ala Ile Val Leu
                85                  90                  95

Gly Arg Glu Phe Gln His Ser Ile Val Ser Met Ala Val Ser Gly Phe
            100                 105                 110

Gly Arg Gly Lys Cys Pro Arg Gly Asp Ser Gln Ala Val Ser Tyr Gly
        115                 120                 125

Gln Gly Pro Ala Leu Ile Phe Ala Cys Ser Gly Leu Ala Gln Gly Arg
    130                 135                 140

Glu Arg Ser Arg Lys Ser Glu Pro Trp Lys Arg Gln Ser Gly Gly Asn
145                 150                 155                 160

Val His Ala Arg Gly Trp Ala Arg Lys Glu Arg Thr Leu Pro Arg Arg
                165                 170                 175

Leu Arg Glu Gly Ala Pro Arg Ile Thr Ser Arg Thr Pro Arg Lys Leu
            180                 185                 190

Lys Cys Thr Val Cys Gly Leu Leu Ile Glu Leu Ser Ser Leu Cys Ala
        195                 200                 205

Leu Xaa Xaa Xaa Xaa Xaa Xaa Xaa Gly Gly Gly Gly Ala Glu
    210                 215                 220

Gln Gly Gln Ala Leu Phe Asn Gly Asp Met Glu Pro Glu Ala Gly Ala
225                 230                 235                 240

Ala Ala Ser Ser Ala Ala Asp Pro Ala Ile Pro Glu Glu Val Trp Asn
                245                 250                 255

Ile Lys Gln Met Ile Lys Leu Thr Gln Glu His Ile Glu Ala Leu Leu
            260                 265                 270
```

-continued

```
Asp Lys Phe Gly Gly Glu His Asn Pro Pro Ser Ile Tyr Leu Glu Ala
        275                 280                 285
Tyr Glu Glu Tyr Thr Ser Lys Leu Asp Ala Leu Gln Gln Arg Glu Gln
    290                 295                 300
Gln Leu Leu Glu Ser Leu Gly Asn Gly Thr Asp Phe Ser Val Ser Ser
305                 310                 315                 320
Ser Ala Ser Thr Asp Thr Val Thr Ser Ser Ser Ser Ser Ser Leu Ser
                325                 330                 335
Val Leu Pro Ser Ser Leu Ser Val Phe Gln Asn Pro Thr Asp Val Ser
            340                 345                 350
Arg Ser Asn Pro Lys Ser Pro Gln Lys Pro Ile Val Arg Val Phe Leu
        355                 360                 365
Pro Asn Lys Gln Arg Thr Val Val Pro Ala Arg Cys Gly Val Thr Val
    370                 375                 380
Arg Asp Ser Leu Lys Lys Ala Leu Met Met Arg Gly Leu Ile Pro Glu
385                 390                 395                 400
Cys Cys Ala Val Tyr Arg Ile Gln Asp Gly Glu Lys Lys Pro Ile Gly
                405                 410                 415
Trp Asp Thr Asp Ile Ser Trp Leu Thr Gly Glu Glu Leu His Val Glu
            420                 425                 430
Val Leu Glu Asn Val Pro Leu Thr Thr His Asn Phe Val Cys Thr Glu
        435                 440                 445
Asn Val Phe Thr Leu Ala Phe Cys Asp Phe Cys Arg Lys Leu Leu Phe
    450                 455                 460
Gln Gly Phe Arg Cys Gln Thr Cys Gly Tyr Lys Phe His Gln Arg Cys
465                 470                 475                 480
Ser Thr Glu Val Pro Leu Met Cys Val Asn Tyr Asp Gln Leu Asp Leu
                485                 490                 495
Leu Phe Val Ser Lys Phe Phe Glu His His Pro Ile Pro Gln Glu Glu
            500                 505                 510
Ala Ser Ile Ala Glu Thr Ala Leu Thr Ser Gly Ser Ser Pro Ser Ala
        515                 520                 525
Pro Pro Ser Asp Ser Thr Gly Pro Gln Ile Leu Thr Ser Pro Ser Pro
    530                 535                 540
Ser Lys Ser Ile Pro Ile Pro Gln Pro Phe Arg Pro Ala Asp Glu Asp
545                 550                 555                 560
His Arg Asn Gln Phe Gly Gln Arg Asp Arg Ser Ser Ser Ala Pro Asn
                565                 570                 575
Val His Ile Asn Thr Ile Glu Pro Val Asn Ile Asp Asp Leu Ile Arg
            580                 585                 590
Asp Gln Gly Phe Arg Ser Asp Gly Gly Ser Thr Thr Gly Leu Ser Ala
        595                 600                 605
Thr Pro Pro Ala Ser Leu Pro Gly Ser Leu Thr Asn Val Lys Ala Leu
    610                 615                 620
Gln Lys Ser Pro Gly Pro Gln Arg Glu Arg Lys Ser Ser Ser Ser Ser
625                 630                 635                 640
Glu Asp Arg Asn Arg Met Lys Thr Leu Gly Arg Arg Asp Ser Ser Asp
                645                 650                 655
Asp Trp Glu Ile Pro Asp Gly Gln Ile Thr Val Gly Gln Arg Ile Gly
            660                 665                 670
Ser Gly Ser Phe Gly Thr Val Tyr Lys Gly Lys Trp His Gly Asp Val
        675                 680                 685
```

```
Ala Val Lys Met Leu Asn Val Thr Ala Pro Thr Pro Gln Gln Leu Gln
            690                 695                 700

Ala Phe Lys Asn Glu Val Gly Val Leu Arg Lys Thr Arg His Val Asn
705                 710                 715                 720

Ile Leu Leu Phe Met Gly Tyr Ser Thr Lys Pro Gln Leu Ala Ile Val
                725                 730                 735

Thr Gln Trp Cys Glu Gly Ser Ser Leu Tyr His His Leu His Ile Ile
                740                 745                 750

Glu Thr Lys Phe Glu Met Ile Lys Leu Ile Asp Ile Ala Arg Gln Thr
                755                 760                 765

Ala Gln Gly Met Asp Tyr Leu His Ala Lys Ser Ile Ile His Arg Asp
770                 775                 780

Leu Lys Ser Asn Asn Ile Phe Leu His Glu Asp Leu Thr Val Lys Ile
785                 790                 795                 800

Gly Asp Phe Gly Leu Ala Thr Val Lys Ser Arg Trp Ser Gly Ser His
                805                 810                 815

Gln Phe Glu Gln Leu Ser Gly Ser Ile Leu Trp Met Ala Pro Glu Val
                820                 825                 830

Ile Arg Met Gln Asp Lys Asn Pro Tyr Ser Phe Gln Ser Asp Val Tyr
                835                 840                 845

Ala Phe Gly Ile Val Leu Tyr Glu Leu Met Thr Gly Gln Leu Pro Tyr
850                 855                 860

Ser Asn Ile Asn Asn Arg Asp Gln Ile Ile Phe Met Val Gly Arg Gly
865                 870                 875                 880

Tyr Leu Ser Pro Asp Leu Ser Lys Val Arg Ser Asn Cys Pro Lys Ala
                885                 890                 895

Met Lys Arg Leu Met Ala Glu Cys Leu Lys Lys Lys Arg Asp Glu Arg
                900                 905                 910

Pro Leu Phe Pro Gln Ile Leu Ala Ser Ile Glu Leu Leu Ala Arg Ser
                915                 920                 925

Leu Pro Lys Ile His Arg Ser Ala Ser Glu Pro Ser Leu Asn Arg Ala
                930                 935                 940

Gly Phe Gln Thr Glu Asp Phe Ser Leu Tyr Ala Cys Ala Ser Pro Lys
945                 950                 955                 960

Thr Pro Ile Gln Ala Gly Gly Tyr Gly Ala Phe Pro Val His
                965                 970
```

<210> SEQ ID NO 17
<211> LENGTH: 3853
<212> TYPE: DNA
<213> ORGANISM: Bos taurus

<400> SEQUENCE: 17

| | | | | |
|---|---|---|---|---|
| ctcagctgcg | ccgggtctca | aagacggtt | cccgaggtgg | cccaggcgcc | gtcccaccgc | 60 |
| cgacgccgcc | cgggccgccc | gggccgtccc | tccccgctgc | ccccgtcct | ccgcctccgc | 120 |
| ctcccccgc | cctcagcctc | ccttccccct | ccccgcccag | cagcggtcgc | tcgggcccgg | 180 |
| ctctcggtta | taagatggcg | gcgctgagtg | gcggcggcgg | cggcggcggc | ggtggcgcgg | 240 |
| agcagggcca | ggctctgttc | aacggggaca | tggagcccga | ggccggcgcc | gcggcctctt | 300 |
| cggctgcgga | ccccgccatt | cccgaggagg | tgtggaatat | caaacaaatg | attaagttga | 360 |
| cacaggagca | tatagaggcc | ctattggaca | aatttggtgg | ggagcataat | ccaccatcaa | 420 |
| tatatctgga | ggcctatgaa | gaatacacca | gcaagctaga | tgccctccaa | caaagagaac | 480 |
| aacagttatt | ggaatccctg | gggaatggaa | ctgatttttc | tgtttctagc | tctgcatcaa | 540 |

```
cggacaccgt tacatcttct tcctcttcta gcctttcagt gctgcctcca tctcttcag      600 ttttcaaaa tcccacagat gtgtcacgga gcaaccccaa gtcaccacaa aaacctatcg      660
ttagagtctt cctgcccaat aaacagagga cagtggtacc tgcacggtgt ggagtcacag      720
tccgggacag cctgaagaag gcactgatga tgagaggtct aatcccagag tgctgtgctg      780
tttacagaat tcaggatggg gagaagaaac caattggctg gacactgat atttcctggc      840 ttactggaga ggagttgcat gtagaagtgt tggagaatgt tccacttaca acacacaact      900
ttgtacggaa aactttttc accttagcat tttgtgactt ctgtagaaag ctgcttttcc      960
agggattccg ctgtcaaaca tgtggttata aatttcacca gcgttgtagt acagaggttc     1020
cactgatgtg tgttaattat gaccaactag atttgctgtt tgtctccaag ttctttgaac     1080
accacccaat accacaggag gaggcctcct tagcagagac tacccttcca tgtggctcat     1140
ccccttctgc accccctcc gattctattg gcccccaat tctcaccagt ccatctcctt       1200
caaaatccat tccaattcca cagccttcc gaccagcaga tgaagatcat cgaaatcagt      1260
ttggacaacg agaccggtcc tcatcagctc caaatgtgca tataaacaca atagaacccg     1320
tcaatattga tgacttgatt agagaccaag ggtttcgtag tgatggagga tcaaccacag     1380
gtttatccgc cacacccct gcctcattac ctggctcact ctctaatgtg aaagcattgc      1440
agaaatctcc aggacctcag cgagaaagaa agtcctcttc atcctcagaa gacaggaatc     1500
gaatgaaaac gcttggtaga cgggattcaa gtgacgattg ggagattcct gatggacaga     1560
tcacagtggg acaaagaatt ggatcagggt catttgggac agtctacaag ggaaagtggc     1620
atggtgatgt ggcagtgaaa atgttgaatg tgacagcacc cacacctcag cagttacagg     1680
ccttcaaaaa tgaagtagga gtactcagga aaacgcgaca tgtgaatatc ctcctcttca     1740
tgggttattc aacaaagcca caactggcta ttgttaccca gtggtgtgag ggctccagtt     1800
tatatcatca tctccacatc attgagacca aattcgagat gatcaaactt atagatattg     1860
cacggcagac tgcacagggc atggattact tacacgccaa gtcaatcatc cacagagacc     1920
tcaagagtaa taatatttt cttcatgaag acctcacagt aaaaataggt gattttggtc      1980
tagccacagt gaaatctcga tggagtgggt cccatcagtt tgaacagttg tctggatcca     2040
ttttgtggat ggcaccagaa gtaatcagaa tgcaagataa aaacccatat agctttcagt     2100
cagatgtata tgcatttggg attgttctgt atgaattgat gaccggacag ttaccttatt     2160
caaatatcaa caacagggac cagataattt ttatggtggg acgaggatat ctgtctccag     2220
atctcagtaa ggtacggagt aactgtccaa aagccatgaa gagattaatg gcagagtgcc     2280
taaaaaagaa aagagatgaa agaccactct ttcccaaaat tctcgcctct attgagctgc     2340
tggcccgctc attgccaaaa attcaccgca gtgcatcaga ccctccttg aatcgggctg      2400 gcttccaaac agaggatttt agtctatatg cttgtgcttc tccaaaaaca cccattcagg     2460 caggggata tggtacgttt cctgttcact gaaacaaacc gagtgagtga cagcatgtag      2520
gagggtaggg acaaaagaaa gtgaacaaat gtttgcttat atatttgtta aattgaatag     2580
gatttctttt ttctttaaag gtgaacaaga gaacatgtgt gttttttaaag tttggatata    2640 gttttcttcc cagtctaaaa cccatagtta gcattacatt ttcaacatcg aattttttt     2700 taattcatag acattgctga aaatttataa tacctttcc agaggcttta cttcccattc      2760
caagtttgtt tgtttacttt ggttagtcta atcattaaac tttaaacttt ccccacctac     2820
cttttgctgt tagctatccc gcatccatta ggggctccaa gaacagcact gtctgcgtgt    2880
```

-continued

```
gtgtgttggc aggtgggaag ctgatggtaa gttaggctgt gttagtgaag gtaaactgac    2940
caggtctaat taggagtcac tagaattgaa taagcttatt tttattaata ttttttctta    3000
taactatttc ttttgtaat aatttagaaa atataattgt tctttattcc cttacagcag     3060
tataaattat tggtgcaggt aaccaaagat attactgagg agtggcatgt ttgacatgag    3120
tgacatggtt taactttgga ttttagtta atatttcttt atatattaag gatgtcttac     3180
acattataga agtcaaattt actgacaaag gtattgcctc ctcttcctcc ccaaaaacac    3240
agcaaaattc tctgggaact cgtagcattg ttggttttct tttggatgac tatggttgcc    3300
aaacaaccaa gtaattgatt tttttaaat tattattgct ttagattata ctcacctctc     3360
atgatgcctg ttagcaatca cctttatcca tgtgtcttgt aaaatatctt tcctccttat    3420
attctttgcc caacaagagt ctacttgtta tgaatgagta ctattttctt ttttgattc     3480 cccagtataa ttagtatgtt tagtgctttc taggacttcc actttcttat gttaaaaaaa    3540
aaaacaaact aatgtggcag tcagtatatt cttactgtga atcagagtct ttactgggaa    3600
tcaaagtgaa agaagcagct gttctgactt cagagtcagc ctaggaccaa aaaccagcct    3660
cttaaataca ccttcattta ttcagtttgg atttgtgatg attttcatta tagctgacag    3720
ttcaaggtta ttcagtggca cacagatagc atctgcataa atgcctttct tcttgaaaat    3780
aaaggagaaa attgggaaga ctttacacca atagtttagt ctttaagtac cacagataac    3840
acacaccata aat                                                        3853
```

<210> SEQ ID NO 18
<211> LENGTH: 764
<212> TYPE: PRT
<213> ORGANISM: Bos taurus

<400> SEQUENCE: 18

```
Ala Ala Leu Ser Gly Gly Gly Gly Gly Gly Gly Ala Glu Gln
1               5                   10                  15

Gly Gln Ala Leu Phe Asn Gly Asp Met Glu Pro Glu Ala Gly Ala Ala
                20                  25                  30

Ala Ser Ser Ala Ala Asp Pro Ala Ile Pro Glu Glu Val Trp Asn Ile
            35                  40                  45

Lys Gln Met Ile Lys Leu Thr Gln Glu His Ile Glu Ala Leu Leu Asp
        50                  55                  60

Lys Phe Gly Gly Glu His Asn Pro Pro Ser Ile Tyr Leu Glu Ala Tyr
    65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
                100                 105                 110

Ala Ser Thr Asp Thr Val Thr Ser Ser Ser Ser Ser Leu Ser Val
            115                 120                 125

Leu Pro Ser Ser Leu Ser Val Phe Gln Asn Pro Thr Asp Val Ser Arg
        130                 135                 140

Ser Asn Pro Lys Ser Pro Gln Lys Pro Ile Val Arg Val Phe Leu Pro
    145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
            180                 185                 190

Cys Ala Val Tyr Arg Ile Gln Asp Gly Glu Lys Lys Pro Ile Gly Trp
```

```
            195                 200                 205
Asp Thr Asp Ile Ser Trp Leu Thr Gly Glu Glu Leu His Val Glu Val
210                 215                 220

Leu Glu Asn Val Pro Leu Thr Thr His Asn Phe Val Arg Lys Thr Phe
225                 230                 235                 240

Phe Thr Leu Ala Phe Cys Asp Phe Cys Arg Lys Leu Leu Phe Gln Gly
                245                 250                 255

Phe Arg Cys Gln Thr Cys Gly Tyr Lys Phe His Gln Arg Cys Ser Thr
                260                 265                 270

Glu Val Pro Leu Met Cys Val Asn Tyr Asp Gln Leu Asp Leu Leu Phe
                275                 280                 285

Val Ser Lys Phe Phe Glu His His Pro Ile Pro Gln Glu Glu Ala Ser
                290                 295                 300

Leu Ala Glu Thr Thr Leu Pro Cys Gly Ser Ser Pro Ser Ala Pro Pro
305                 310                 315                 320

Ser Asp Ser Ile Gly Pro Pro Ile Leu Thr Ser Pro Ser Pro Ser Lys
                325                 330                 335

Ser Ile Pro Ile Pro Gln Pro Phe Arg Pro Ala Asp Glu Asp His Arg
                340                 345                 350

Asn Gln Phe Gly Gln Arg Asp Arg Ser Ser Ser Ala Pro Asn Val His
                355                 360                 365

Ile Asn Thr Ile Glu Pro Val Asn Ile Asp Asp Leu Ile Arg Asp Gln
370                 375                 380

Gly Phe Arg Ser Asp Gly Gly Ser Thr Thr Gly Leu Ser Ala Thr Pro
385                 390                 395                 400

Pro Ala Ser Leu Pro Gly Ser Leu Ser Asn Val Lys Ala Leu Gln Lys
                405                 410                 415

Ser Pro Gly Pro Gln Arg Glu Arg Lys Ser Ser Ser Ser Ser Glu Asp
                420                 425                 430

Arg Asn Arg Met Lys Thr Leu Gly Arg Arg Asp Ser Ser Asp Asp Trp
                435                 440                 445

Glu Ile Pro Asp Gly Gln Ile Thr Val Gly Gln Arg Ile Gly Ser Gly
450                 455                 460

Ser Phe Gly Thr Val Tyr Lys Gly Lys Trp His Gly Asp Val Ala Val
465                 470                 475                 480

Lys Met Leu Asn Val Thr Ala Pro Thr Pro Gln Gln Leu Gln Ala Phe
                485                 490                 495

Lys Asn Glu Val Gly Val Leu Arg Lys Thr Arg His Val Asn Ile Leu
                500                 505                 510

Leu Phe Met Gly Tyr Ser Thr Lys Pro Gln Leu Ala Ile Val Thr Gln
                515                 520                 525

Trp Cys Glu Gly Ser Ser Leu Tyr His His Leu His Ile Ile Glu Thr
                530                 535                 540

Lys Phe Glu Met Ile Lys Leu Ile Asp Ile Ala Arg Gln Thr Ala Gln
545                 550                 555                 560

Gly Met Asp Tyr Leu His Ala Lys Ser Ile Ile His Arg Asp Leu Lys
                565                 570                 575

Ser Asn Asn Ile Phe Leu His Glu Asp Leu Thr Val Lys Ile Gly Asp
                580                 585                 590

Phe Gly Leu Ala Thr Val Lys Ser Arg Trp Ser Gly Ser His Gln Phe
                595                 600                 605

Glu Gln Leu Ser Gly Ser Ile Leu Trp Met Ala Pro Glu Val Ile Arg
610                 615                 620
```

```
Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Thr Phe Pro Val His
        755                 760

<210> SEQ ID NO 19
<211> LENGTH: 4936
<212> TYPE: DNA
<213> ORGANISM: Bos taurus

<400> SEQUENCE: 19
ctcagctgcg ccgggtctca caagacggtt cccgaggtgg cccaggcgcc gtcccaccgc        60
cgacgccgcc cgggccgccc gggccgtccc tccccgctgc ccccgtcct ccgcctccgc       120 ctcccccgc cctcagcctc ccttcccct cccgcccag cagcggtcgc tcgggccggg        180
ctctcggtta taagatggcg gcgctgagtg gcggcggcgg cggcggcggc ggtggcgcgg       240
agcagggcca ggctctgttc aacggggaca tggagcccga ggccggcgcc gcggcctctt       300
cggctgcgga ccccgccatt cccgaggagg tgtggaatat caaacaaatg attaagttga       360
cacaggagca tatagaggcc ctattggaca aatttggtgg ggagcataat ccaccatcaa       420
tatatctgga ggcctatgaa gaatacacca gcaagctaga tgccctccaa caaagagaac       480
aacagttatt ggaatccctg ggaatggaa ctgattttt tgtttctagc ctgcatcaa       540 cggacaccgt tacatcttct cctcttcta gcctttcagt gctgccttca tctctttcag       600 ttttttcaaaa tcccacagat gtgtcacgga gcaaccccaa gtcaccacaa aaacctatcg       660
ttagagtctt cctgcccaat aaacagagga cagtggtacc tgcacggtgt ggagtcacag       720
tccgggacag cctgaagaag gcactgatga tgagaggtct aatcccagag tgctgtgctg       780
tttacagaat tcaggatggg gagaagaaac caattggctg ggacactgat atttcctggc       840
ttactggaga ggagttgcat gtagaagtgt tggagaatgt tccacttaca acacacaact       900 tgtacggaa aacttttttc accttagcat tttgtgactt ctgtagaaag ctgctttcc       960 agggattccg ctgtcaaaca tgtggttata aatttcacca gcgttgtagt acagaggttc      1020
cactgatgtg tgttaattat gaccaactag atttgctgtt tgtctccaag ttctttgaac      1080
accacccaat accacaggag gaggcctcct tagcagagac tacccttcca tgtggctcat      1140
ccccttctgc accccctcc gattctattg gccccccaat tctcaccagt ccatctcctt      1200
caaaatccat tccaattcca cagcctttcc gaccagcaga tgaagatcat cgaaatcagt      1260
ttggacaacg agaccggtcc tcatcagctc caaatgtgca tataaacaca atagaacccg      1320
```

```
tcaatattga tgacttgatt agagaccaag ggtttcgtag tgatggagga tcaaccacag    1380
gtttatccgc cacaccccct gcctcattac ctggctcact ctctaatgtg aaagcattgc    1440
agaaatctcc aggacctcag cgagaaagaa agtcctcttc atcctcagaa gacaggaatc    1500
gaatgaaaac gcttggtaga cgggattcaa gtgacgattg ggagattcct gatggacaga    1560
tcacagtggg acaaagaatt ggatcagggt catttgggac agtctacaag ggaaagtggc    1620
atggtgatgt ggcagtgaaa atgttgaatg tgacagcacc cacacctcag cagttacagg    1680
ccttcaaaaa tgaagtagga gtactcagga aaacgcgaca tgtgaatatc ctcctcttca    1740
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacagggc atggattact tacacgccaa gtcaatcatc cacagagacc    1920
tcaagagtaa taatattttt cttcatgaag acctcacagt aaaaataggt gattttggtc    1980
tagccacagt gaaatctcga tggagtgggg cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac cagataattt ttatggtggg acgaggatat ctgtctccag    2220
atctcagtaa ggtacggagt aactgtccaa aagccatgaa gagattaatg gcagagtgcc    2280
taaaaaagaa aagagatgaa agaccactct ttccccaagt aggaaagact ctcctaagca    2340
agagacaaaa ttcagaagtt atcagggaaa aagataagca gattctcgcc tctattgagc    2400
tgctggcccg ctcattgcca aaaattcacc gcagtgcatc agaaccctcc ttgaatcggg    2460
ctggcttcca aacagaggat tttagtctat atgcttgtgc ttctccaaaa acacccattc    2520 aggcagggggg atatgaagca gatttggctc ttacatcaaa taaaaataga gtagaagttg    2580
ggatttagag atttcctgac atgcaagaag gaataagcaa gaaaaaaagg tttgttttcc    2640
ccaaatcata tctattgtct tttacttcta tttttttctta aattttttgt gatttcagag    2700
acatgtagag ttttattgat acctaaaacta tgagttcttt tttttttttt ttttcatta    2760 ttttgatttt tttggccaag aggcatatgg gatcttagct tgagaaagca acaattttct    2820
tgatgtcatt ttgggtgagg gcacatattg ctgtgaacag tgtggtgata gccaccaggg    2880
accaaactca caccccgctgc attgaaaggt gaagtcttaa acactggacc agcagagaaa    2940
ttcctactct atgagttctt tttgtcatcc cctccccgca ccctccaccc ccaacctaaa    3000
gtctgatgat gaaatcaaca actattccat tagaagcagt agattctggt agcatgatct    3060
ttagtttgtt agtaagattt tgtgctttgt ggggttgtgt cgttttaagg ctaatattta    3120
agtttgtcaa atagaatgct gttcagattg taaaaatgag taataaacat ctgaagtttt    3180
ttttaagtta tttttaacat ggtatataca gttgagctta gagtttatca ttttctgata    3240
ttctcttact tagtagatga attctagcca tttttttataa agatttctgt taagcaaatc    3300
ctgttttcac atgggcttcc tttaagggat tttagattct gctggatatg gtgactgctc    3360
ataagactgt tgaaaattac ttttaagatg tattagaata cttctgaaaa aaaatagcaa    3420
ccttaaaacc ataagcaaaa gtagtaaggg tgttatataca tttctagagt ccctgtttag    3480
gtaatagcct cctatgattg tactttaaat gttttgctct ccaaggtttt agtaacttgg    3540 cttttttttct aatcagtgcc aaactccccc agttttttta actttaaata tgaggtaata    3600
aatcttttac ccttccttga tcttttgact tataatacct tggtcagttg tttcttaaaa    3660
```

-continued

```
ggaatcctta aatgcaaaga dacaatatca ctgtctgcag ttctgattag tagttttatt    3720
cagaatggaa aaacagatta ttcatttttg aaaattgttc aggggtatgt tcattgttag    3780
gaccttggac tttggagtca gtgcctagct atgcattcca ggtctgccat tttctggctg    3840
tgaaattttg gacaagttac ttaaccactt taaaccccag ctttaagaag taaattaacc    3900
ccagtaaatt aagaagtaat agcagccact tcgtagagtt gttatgaggc tcagatgcag    3960
tgcaaatgtg tataaagtat tcagggagtc acctggtata ctataataga cactagaata    4020
gttgccaata ttatcagcat acaatctgag gattctgtca gccaatcatt agcaatctgt    4080
tgtttgttgg gacatgccag tgttctccag ttgaaatcag tagcaatcta aaaatggata    4140
gattattcct catttaaata gtgtgttcat ataagtgatt gcttggatcc ttatcagaag    4200
ttgctgttac tgaaaaatga taaggctgac taaattgtga tagttgtcag ttactaacca    4260
actcccagaa atgaataaga ggaacctatc tctagttcct agtagaaggt atggacaaaa    4320
tagtaggtga aaaataatgt cttgaacccc caaattaagt aagctttaaa gagtacaata    4380
cctcaaaggg tctttgcggt ttaaaatttg tatgctgaga atgatgttca ttgacatgtg    4440
cctatatgta attttttgat agtttaaaag gtgaaatgaa ctacagatgg gagaggtctg    4500
aattttcttg ccttcagtca aatgtgtaat gtggacatat tatttgacct gtgaatttta    4560
tcttttaaaa aagattaatt cctgcttctt ccttcctaat agttgcatta taataatgaa    4620
aatgagttga taatttgggg ggaaagtatt ctacaaatca accttattat tttaccattg    4680
gtttctgaga aattttgttc atttgaaccg tttatagctt gattagaatc atagcatgta    4740
aaacccaact gagggattat ctgcagactt aatgtagtat tatgtaagtt gtcttctttc    4800
atttcgacct tttttgcttt tgttgttgct agatctgtag tatgtagcta gtcacctttc    4860
agcgaggttt cagcgaggct tttctgtgtc tctaggttat ttgagataac ttttttaaaa    4920
ttagctcttg tcctcc                                                    4936
```

<210> SEQ ID NO 20
<211> LENGTH: 797
<212> TYPE: PRT
<213> ORGANISM: Bos taurus

<400> SEQUENCE: 20

```
Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140
```

-continued

```
Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
            165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
            195                 200                 205

Trp Asp Thr Asp Ile Ser Trp Leu Thr Gly Glu Glu Leu His Val Glu
            210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
            245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
            275                 280                 285

Phe Val Ser Lys Phe Phe Glu His His Pro Ile Pro Gln Glu Glu Ala
            290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
            325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
            355                 360                 365

His Ile Asn Thr Ile Glu Pro Val Asn Ile Asp Asp Leu Ile Arg Asp
            370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
            405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
            450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
            485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
            530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
```

|     |     |     |     |     |     |     | 565 |     |     |     |     | 570 |     |     |     |     | 575 |     |     |
| --- | --- | --- | --- | --- | --- | --- | --- | --- | --- | --- | --- | --- | --- | --- | --- | --- | --- | --- | --- |

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
            610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
                660                 665                 670

Leu Ser Pro Asp Leu Ser Lys Val Arg Ser Asn Cys Pro Lys Ala Met
                675                 680                 685

Lys Arg Leu Met Ala Glu Cys Leu Lys Lys Lys Arg Asp Glu Arg Pro
690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
                725                 730                 735

Leu Ala Arg Ser Leu Pro Lys Ile His Arg Ser Ala Ser Glu Pro Ser
                740                 745                 750

Leu Asn Arg Ala Gly Phe Gln Thr Glu Asp Phe Ser Leu Tyr Ala Cys
                755                 760                 765

Ala Ser Pro Lys Thr Pro Ile Gln Ala Gly Gly Tyr Glu Ala Asp Leu
                770                 775                 780

Ala Leu Thr Ser Asn Lys Asn Arg Val Glu Val Gly Ile
785                 790                 795

<210> SEQ ID NO 21
<211> LENGTH: 4154
<212> TYPE: DNA
<213> ORGANISM: Bos taurus

<400> SEQUENCE: 21

| | | | | |
|---|---|---|---|---|
| ctcagctgcg | ccgggtctca | caagacggtt | cccgaggtgg | cccaggcgcc | gtcccaccgc |  60 |
| cgacgccgcc | cgggccgccc | gggccgtccc | tccccgctgc | ccccgtcctc | ccgcctccgc | 120 |
| ctcccccgc | cctcagcctc | ccttcccccct | ccccgcccag | cagcggtcgc | tcgggccccgg | 180 |
| ctctcggtta | taagatggcg | gcgctgagtg | gcggcggcgg | cggcggcggc | ggtggcgcgg | 240 |
| agcagggcca | ggctctgttc | aacgggggaca | tggagcccga | ggccggcgcc | gcggcctctt | 300 |
| cggctgcgga | ccccgccatt | cccgaggagg | tgtggaatat | caaacaaatg | attaagttga | 360 |
| cacaggagca | tatagaggcc | ctattggaca | aatttggtgg | ggagcataat | ccaccatcaa | 420 |
| tatatctgga | ggcctatgaa | gaatacacca | gcaagctaga | tgccctccaa | caaagagaac | 480 |
| aacagttatt | ggaatccctg | gggaatggaa | ctgatttttc | tgtttctagc | tctgcatcaa | 540 |
| cggacaccgt | tacatcttct | tcctcttcta | gcctttcagt | gctgccttca | tctctttcag | 600 |
| tttttcaaaa | tcccacagat | gtgtcacgga | gcaaccccaa | gtcaccacaa | aaacctatcg | 660 |
| ttagagtctt | cctgcccaat | aaacagagga | cagtggtacc | tgcacggtgt | ggagtcacag | 720 |
| tccgggacag | cctgaagaag | gcactgatga | tgagaggtct | aatcccagag | tgctgtgctg | 780 |
| tttacagaat | tcaggatggg | gagaagaaac | caattggctg | ggacactgat | atttcctggc | 840 |

```
ttactggaga ggagttgcat gtagaagtgt tggagaatgt tccacttaca acacacaact    900
ttgtacggaa aactttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
cccttctgc accccctcc gattctattg ggccccaat tctcaccagt ccatctcctt      1200
caaaatccat tccaattcca cagccttcc gaccagcaga tgaagatcat cgaaatcagt    1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacaccct gcctcattac ctggctcact ctctaatgtg aaagcattgc     1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaaagaatt ggatcagggt catttgggac agtctacaag ggaaagtggc   1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact acacgccaa gtcaatcatc cacagagacc   1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcagaa tgcaagataa aaacccatat agctttcagt   2100
cagatgtata tgcatttggg attgttctgt atgaattgat gaccggacag ttaccttatt   2160
caaatatcaa caacagggac cagataattt ttatggtggg acgaggatat ctgtctccag   2220
atctcagtaa ggtacggagt aactgtccaa aagccatgaa gagattaatg gcagagtgcc   2280
taaaaagaa aagagatgaa agaccactct ttccccaagt aggaaagact ctcctaagca   2340
agagacaaaa ttcagaagtt atcagggaaa aagataagca gattctcgcc tctattgagc   2400
tgctggcccg ctcattgcca aaaattcacc gcagtgcatc agaaccctcc ttgaatcggg   2460
ctggcttcca aacagaggat tttagtctat atgcttgtgc ttctccaaaa acacccattc   2520
aggcaggggg atatgctga gcacattgtc catcacccac aagtggctgg ttctcatcgc   2580
agaatctacg tagggaatcg ggcgtgaaat tcacttaaga gatagagcag aggaagtgtt   2640
ctgtttacag gaatggagat gagagttatg agtaagttgc ttagtcagtt ggctttgttt   2700
tgaaaattat tgtgttatat ttgtgttaac ctacttgtgt tttgacagta tatgtcacat   2760
aggaagaaac ctcagactag cataataaca aagctcagac taggcacaga tgtacacaga   2820
atggaccaaa atgggatggg ggaaggtatg ggaataagtc taggggtagg gaaaaattga   2880
tgtgagggtg ggaaataaac tgtaattacc tgaaataaaa tgtaagagtg caataagtgt   2940
gctttttatt ctaagctgtg aatgggtttt ttaaaaaaag cattccttcc caatgcattt   3000
gcctatgttc catagctgat taaaaccagc tatataaaca tatgcctttt tattcatgtt   3060
aattaccaat ataatggct aaccttacg tcttatttat cttcatgtta tgttagttta    3120
catacaggga tgtgtgtgtg tgtgtatgct ataaattttc cctccttcgt ttaaaaacgc   3180
```

```
gtttgttgga tcctctctgt ttccttaggc catgccacag ctcatagtct cagcttggcc    3240
ttcctgtcac ctgatctgaa ggactatcac agtgacgtag ctcgttcatt ggttgtacac    3300
actctaaccc tttccttgc tcagcaatta ctgtgtcttc taaaacagga gtgtacaacc    3360
atgagattgc aattaattgt ttgacatatg tcccttgaa ttctatttat tagttatgat    3420
tgattgctct ttggtttgga ccaagaaaaa cgaaatccca cctccccacc ttttcactta    3480
tttcttactt tgaggacaat tctgtaagag agaggaaagg gaactccttc atgttttaac    3540
tgcagcaagt taatggccct ggtttacacc aaacattatg gtgattcaca ttcacattcc    3600
tctcctctct tgctgccaga ggtttgggtt ttgttcagtt ctgctcaagc actgaaaaag    3660
ttttcatgga gtctggagag tgcccagtga aaagatggtt tttaattgtc cacagacctt    3720
tctgttcctg ctttgcaaaa attacaaagg agtaactatt tttaaagctt attttttcaat   3780 tcataaaaaa gacatttatt ttcagtcaga tgatgtctcc ttgtcccta atcctcaatg     3840 tttgcttgaa tctttttttt ttttctgatt ttctcccatc cccacttctt gatacttctt    3900
gagttctctt tcctgctcag gtcctttcat ttgtactttg gagttttttc tcatgtaaat    3960
ttgtacaatg gaaatattg ttcagtttgg atagaacgca tggagaatta aataaaaaag    4020
atagctgaaa ttcagattga aatttatttg tgtaaagtta tttaaaaact ctgtactata    4080
taaaaggcaa aaaagttct atgtacttga tgtgaatatg cgaatactgc tataataaag    4140
attgactgca tgga                                                     4154
```

<210> SEQ ID NO 22
<211> LENGTH: 781
<212> TYPE: PRT
<213> ORGANISM: Bos taurus

<400> SEQUENCE: 22

```
Met Ala Ala Leu Ser Gly Gly Gly Gly Gly Gly Gly Gly Ala Glu
 1               5                  10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
```

```
            195                 200                 205
Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
                260                 265                 270

Thr Glu Val Pro Leu Met Cys Val Asn Tyr Asp Gln Leu Asp Leu Leu
                275                 280                 285

Phe Val Ser Lys Phe Phe Glu His His Pro Ile Pro Gln Glu Glu Ala
290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
                340                 345                 350

Arg Asn Gln Phe Gly Gln Arg Asp Arg Ser Ser Ala Pro Asn Val
                355                 360                 365

His Ile Asn Thr Ile Glu Pro Val Asn Ile Asp Asp Leu Ile Arg Asp
370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Glu
                420                 425                 430

Asp Arg Asn Arg Met Lys Thr Leu Gly Arg Arg Asp Ser Ser Asp Asp
                435                 440                 445

Trp Glu Ile Pro Asp Gly Gln Ile Thr Val Gly Gln Arg Ile Gly Ser
450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
                500                 505                 510

Leu Leu Phe Met Gly Tyr Ser Thr Lys Pro Gln Leu Ala Ile Val Thr
                515                 520                 525

Gln Trp Cys Glu Gly Ser Ser Leu Tyr His His Leu His Ile Ile Glu
530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
                580                 585                 590

Asp Phe Gly Leu Ala Thr Val Lys Ser Arg Trp Ser Gly Ser His Gln
                595                 600                 605

Phe Glu Gln Leu Ser Gly Ser Ile Leu Trp Met Ala Pro Glu Val Ile
610                 615                 620
```

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
            645                 650                 655

Asn Ile Asn Asn Arg Asp Gln Ile Ile Phe Met Val Gly Arg Gly Tyr
        660                 665                 670

Leu Ser Pro Asp Leu Ser Lys Val Arg Ser Asn Cys Pro Lys Ala Met
    675                 680                 685

Lys Arg Leu Met Ala Glu Cys Leu Lys Lys Arg Asp Glu Arg Pro
690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Ile Leu Ala Ser Ile Glu Leu
            725                 730                 735

Leu Ala Arg Ser Leu Pro Lys Ile His Arg Ser Ala Ser Glu Pro Ser
        740                 745                 750

Leu Asn Arg Ala Gly Phe Gln Thr Glu Asp Phe Ser Leu Tyr Ala Cys
    755                 760                 765

Ala Ser Pro Lys Thr Pro Ile Gln Ala Gly Gly Tyr Gly
770                 775                 780

```
<210> SEQ ID NO 23
<211> LENGTH: 7914
<212> TYPE: DNA
<213> ORGANISM: Bos taurus

<400> SEQUENCE: 23
ctcagctgcg ccgggtctca caagacggtt cccgaggtgg cccaggcgcc gtcccaccgc      60
cgacgccgcc cgggccgccc gggccgtccc tccccgctgc ccccgtcct ccgcctccgc     120
ctccccccgc cctcagcctc ccttccccct cccgcccag cagcggtcgc tcgggccccgg    180
ctctcggtta taagatggcg cgctgagtg gcggcggcgg cggcggcggc ggtggcgcgg     240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgatttttc tgtttctagc tctgcatcaa    540
cggacaccgt tacatcttct tcctcttcta gcctttcagt gctgccttca tctctttcag    600
tttttcaaaa tcccacagat gtgtcacgga gcaacccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgctttttcc    960
agggattccg ctgtcaaaca tgtggttata aattcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
cccttctgc accccctcc gattctattg gcccccaat tctcaccagt ccatctcctt   1200
```

-continued

```
caaaatccat tccaattcca cagcctttcc gaccagcaga tgaagatcat cgaaatcagt      1260
ttggacaacg agaccggtcc tcatcagctc caaatgtgca tataaacaca atagaacccg      1320
tcaatattga tgacttgatt agagaccaag ggtttcgtag tgatggagga tcaaccacag      1380
gtttatccgc cacacccct gcctcattac ctggctcact ctctaatgtg aaagcattgc       1440
agaaatctcc aggacctcag cgagaaagaa agtcctcttc atcctcagaa gacaggaatc     1500
gaatgaaaac gcttggtaga cgggattcaa gtgacgattg ggagattcct gatggacaga     1560
tcacagtggg acaaagaatt ggatcagggt catttgggac agtctacaag ggaaagtggc     1620
atggtgatgt ggcagtgaaa atgttgaatg tgacagcacc cacacctcag cagttacagg     1680
ccttcaaaaa tgaagtagga gtactcagga aaacgcgaca tgtgaatatc ctcctcttca     1740
tgggttattc aacaaagcca caactggcta ttgttaccca gtggtgtgag ggctccagtt      1800
tatatcatca tctccacatc attgagacca aattcgagat gatcaaactt atagatattg     1860
cacggcagac tgcacagggc atggattact tacacgccaa gtcaatcatc cacagagacc    1920
tcaagagtaa taatattttt cttcatgaag acctcacagt aaaaataggt gattttggtc    1980
tagccacagt gaaatctcga tggagtgggt cccatcagtt tgaacagttg tctggatcca   2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa aacagggac cagataattt ttatggtggg acgaggatat ctgtctccag   2220
atctcagtaa ggtacggagt aactgtccaa aagccatgaa gagattaatg gcagagtgcc  2280
taaaaaagaa aagagatgaa agaccactct ttccccaaat tctcgcctct attgagctgc    2340
tggcccgctc attgccaaaa attcaccgca gtgcatcaga accctccttg aatcgggctg    2400
gcttccaaac agaggatttt agtctatatg cttgtgcttc tccaaaaaca cccattcagg   2460 caggggata tggagaattt gcagccttca agtagccaca ccatcatgac agcatctact    2520
cttatttctt aagtcttgtg ttcgtacaat ttgttaacat caaaacacag ttctgttcct    2580
caactctttt taaagttaaa attttcagt gcataagctg gtgtggaaca aaggaaatt     2640 tcccatccaa caaagaggg aagaatgttt taggaaccag aattctctgc tgccagtgtt    2700
tcttcttcaa cacaaatatc acaagtctgc ccactcccag gaagaaagag gagagaccct   2760
gagttctgac cttttgatgg tcaggcatga tggaaagaaa ctgctgctac agcttgggag   2820
atttgctctg ggaagtctgc cagtcaactt tgcccttcta accaccagat caatatgtgg    2880
ctgatcatct gatggggcag ttgcaatcac caagccttgt tctctttcct gttctgggat   2940
tgtgttgtgg aaccctttc cctagccacc accagttcat ttctgaggga tggaacaaaa    3000
atgcagcatg cccttcctgt gtggtgcatg ttcagtcctt gacaaatttt taccaaaatg    3060
aagctacttt atttaaaagg agggtgagag gtgaggaggt cactttgggt gtggcggaaa   3120
gggaatgctg catctttttc ctgggctgct ggggctctgg ccttggcttg ccagccggaa   3180
gcgctggcac gcatcgcctt ctttttcccat tgggtccagc aatgaagacg agtgtttggg   3240
gttttttttt tctccaccat gtagcaagtt ctcaggaaaa tacaattgat atcttcctcc    3300
taagctcttc caatcagtca ccaagtactt atgtggttac tttgtccagg gcacaaaatg    3360
cctgtatcta attaaaagcc tacaaaactg cttgataaca gttttgaatg tgagacattt    3420 atgtaaattta aatgtaaggt acaagttta atttctgagt ttcttctatt atatttttat    3480 taaaaaaga aaataatttt cagattgaat tggagtaaaa taatattact tcccactaga   3540
attatatatc ctggaaaatt gtattttgt tacataagca gcttttaaag aaagatcatt     3600
```

```
acccttttct ctacataaat atatggggag tcttagccta atgacaaata tttataattt    3660
ttaaattaat ggtacttgct ggatccatac taacatcttt actaataccct cattgtttct    3720 tccaacttac tcctacacta catcctacat cttcttccta gtcttttatc tagaatatgc    3780
aacctcaaat aaaaatggtg gtgtcctcat tcattctcct ccttccttttt ttcccaagcc    3840 tgatcttcaa aaggttggtt aatttggcag ctgagttcct ccccaggcag agaatagacc    3900
aattttaggt gtattgggac tgagggagga tgtgtaaaga ttaacatcag taaagaaccg    3960
ctgtggagta attaagaact ttgttcttta taactggaga atataaccta accctaacat    4020
ccctcagcct ttactaaagt gtggcgtaaa tcacagtagt agcaaagaaa gtgactctgg    4080
atgtgttcct ggccagtacc tcccttatca tgaatgtaga ctctctcatc aagatttagg    4140
aatataaatc aaatcaaatg tgcccagcca agctatgtag taagggactt gaacaatatt    4200
aggcagaacc tataaaataa atcagggaat tagaaattat ttaaagttttt caaattgtaa    4260 attgccccgg tgtctttcag cctactgcca ttatttttgc tacaataccct acatttcaga    4320 ggagggccta ctgaaaattc catgcaagtg gaaaataatc ctcaagttat taatgagttt    4380
gaaaagcaat gagttcttaa gtctttgtga gtagagcaag atcctacaaa attcagaaat    4440
agtaaaaatg gattcatgct gatttgaaga gcatctgtgt gcataatata atgctgcatc    4500
tcttttaaaa gcagtctatt tttcttttta aatttgtccc catagatgct tttgaacatg    4560
aacatgctta tgttaccttt tccgaggttg ggaagagcca ggagctctca ggcagggccc    4620
cctccctcag ctgggcagga gctgctcagg aggagctagt tatagaggaa gcttagcgtt    4680
ggcattttca aaattcaagg tgataacgct ttcttcttcc tttctgttttt agaatagatt    4740 gctgtctgat ttgaaaaagg gaaatagatt tgatctcaaa tgaatctgtg cccagaagcc    4800
aggctcaggg tattcagaga tttgtatagt gccctcaaaa aataacaaaa ttttagcttt    4860
ccttttttct tcttttctcc atcaaattct ttttctcta gtttacaaat gacatggaaa    4920
aggaatttcc cctgagtttt gtatgccttt tttttttttgg cttagactat agataggcgt    4980
gttgagctcc taagaaaata caaggaggaa ctctttgttg tgcagagcac tttatgagta    5040
gtttgtgtgg ataatatgtg actgcttccc tgacgagctt gtgaggctgt acttatgtct    5100
ttcctgtaag gcagcttcag tgccttctgt agtgtatata aggaaagatt acgccttctg    5160
aaaaatctca gagcaaccat aagattattt taaaatatgt agtatgactg atggactttt    5220
tcatcattaa attagtctag catctaaact tttaccactg aaataatatt gaccaaaaag    5280
caatttataa aaggtatttg tgaatagaaa atacaatgtg atcatttgta cttatgtgca    5340
ccttaaaaga ggaattctgt ctagctgtca aattctggtt ccttaacatc cagtccttga    5400
ttgtgattga gatctggtag gacgtgctgg ggcacgctag cagataaaat cccgtatact    5460
ttaggataga tgttacattt atgtcagtgt tggcaaagag cattgtgtag taataaagaa    5520
ttcaagactt cagcaatgtc aacctgaaac tttgtaaata tttcctagat tgttatttga    5580
tgcagtcaca gctctttatc acacaatgtt gtctttccct catcaggcaa ttttagaact    5640
gctgcacacc cctcctcaga tctcacctgc ccctcctgta cattcacctc tccagccttg    5700
tgcacacctc atttagcttt agtttgaaac acattgcagg gttcaggtga cctcttcaaa    5760
aactacctcc tcagaatgag gtaatgaata gttatttatt ttaaaatatg aaaagtcagg    5820
agctctagaa tatgaagatg atctaagatt ttaacttttta tgtatacttg ttgagcactc    5880
tccttttgtc ctaaagggca ttatacattt aagcagtaat actgaaaaat gtagctcaga    5940
```

```
gtaactgaat gttgttgaaa gtggtgccag aatctgtttt aggggtacgt atcagaatct      6000
taatcttaaa tcggttacat gaaattaaat agttaatggt aacacttgac taacagatat      6060
aattttaatt ttcggtaggc ttttagcaag acagtaagta catcttcata atgagttagc      6120
cacagcttca tcacatgcac agattttcct gttgagagac tgcccagtta agagggtaga      6180
atgatgaacc attttttcagg attctcttct ttgtccaaac tggcattgtg agtgctagaa      6240
tatcagcact ttcaaactag tgattccaac tattaggcta ttaaaaagca aaacaaacca      6300
aacaaaccat agccagacat gggaagttta ctatgagtat aaacagcaaa tagcttacag      6360
gtcatacatt gaaatggtgt aggtaaggcg ttagaaaaat accttgacaa tttgccaaat      6420
gatcttactg tgccttcatg atgcaataaa aaaaaaaaaa atttagcata aatcagtgat      6480
ttgtgaagag agcagccacc ctggtctaac tcagctgtgt taatattttt tagcgtgcaa      6540
tttagactgc aaagataaat gcactaaaga gtttatagcc aaaatcacat ttaaaaaatg      6600
agagaaaaca caggtaaatt ttcagtgaac aaaattattt ttttaaagta cataatccct      6660
agtatagtca gatatattta tcacatagag caaataggtt gaaatcacaa ttcagtgaca      6720
tttctagaga aactttttct actcccatag gttcttcaaa gcatggaact tttatataac      6780
agaaatgtgt gacggtcatt ttaaattgct gtagtttggg gctgaagtac tgtgtgctgg      6840
gcagcaatca catgtattaa ctagtgagaa aggagaaatt aagatatagg acagaatttg      6900
attttcttgt tcccagatta ctgctgccaa cctagcacct gagtttccag aggctgaaac      6960
gtaaacttgc agctcagcaa ctgttttgca aagttagtgg gactgtcctg cttatgctgt      7020
tcaaaaatgc tctgagggcc aggtggggcc tccagggggct cctctctgag gggacatcag      7080
actagctaac gacctggcgg gcggatgtga accggacaca ctccatggtg tgcttcttgt      7140
atcggtccct cgccaccctc aagaaaggct tcagcgggtc tctagacgt ctccactaag      7200 gtgtgttact aacagccatg ggttgttgag cacccgagga gtgcaatagc atctctgcat      7260
gattgtatat tggcccgaag agaatgaagt ggccagtgta ctcatgttcc atgttgctag      7320
ctctggtaaa ctgaaaatac tggtaagatt tttgttttat cagtacacta gagagtaagc      7380
tttgttttgt tgttttttaga taatgttttc acttccattt ggaaagacat ttaaattgag      7440
tttcagtcct aaattttgcc agtcatggta attagcagtt tctatcaggt attttttaagg      7500 tagaagagga tagaaacata agttctaaaa gcttaaggta accgtggttt attttaaaat      7560
gtttaggggt ggttagtctc tacctcaaaa aaagtgagtg aatctttat ttcagcattc      7620 acaagttcgg ctgttgtttt tgtaatacat tttttttta accttttgac cccccttttac      7680 ctaagtgtca atgtagtttt attaattact aagtcagttt cattaaaatg tttatttagc      7740
agttttgact aattgcaatg attaatatag ccagttgtgc atgaggacac agccagtgag      7800
tatatctggg ttttttttgt gatgcttttt ttcttaagac ttctgtagat ttatgaagta      7860
ctcattgaaa acaactaaaa tacgtttatt cgtgttaata tggaaaaaaa aaaa           7914
```

<210> SEQ ID NO 24
<211> LENGTH: 766
<212> TYPE: PRT
<213> ORGANISM: Bos taurus

<400> SEQUENCE: 24

Met Ala Ala Leu Ser Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

```
Ala Ala Ser Ser Ala Ala Asp Pro Ala Ile Pro Glu Glu Val Trp Asn
             35                  40                  45

Ile Lys Gln Met Ile Lys Leu Thr Gln Glu His Ile Glu Ala Leu Leu
 50                  55                  60

Asp Lys Phe Gly Gly Glu His Asn Pro Pro Ser Ile Tyr Leu Glu Ala
 65                  70                  75                  80

Tyr Glu Glu Tyr Thr Ser Lys Leu Asp Ala Leu Gln Gln Arg Glu Gln
                 85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
            115                 120                 125

Val Leu Pro Ser Ser Leu Ser Val Phe Gln Asn Pro Thr Asp Val Ser
            130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
            195                 200                 205

Trp Asp Thr Asp Ile Ser Trp Leu Thr Gly Glu Glu Leu His Val Glu
            210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
                260                 265                 270

Thr Glu Val Pro Leu Met Cys Val Asn Tyr Asp Gln Leu Asp Leu Leu
            275                 280                 285

Phe Val Ser Lys Phe Phe Glu His His Pro Ile Pro Gln Glu Glu Ala
            290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Ile Leu Thr Ser Pro Ser Pro Ser
                325                 330                 335

Lys Ser Ile Pro Ile Pro Gln Pro Phe Arg Pro Ala Asp Glu Asp His
                340                 345                 350

Arg Asn Gln Phe Gly Gln Arg Asp Arg Ser Ser Ser Ala Pro Asn Val
            355                 360                 365

His Ile Asn Thr Ile Glu Pro Val Asn Ile Asp Asp Leu Ile Arg Asp
            370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
                420                 425                 430

Asp Arg Asn Arg Met Lys Thr Leu Gly Arg Arg Asp Ser Ser Asp Asp
            435                 440                 445
```

```
Trp Glu Ile Pro Asp Gly Gln Ile Thr Val Gly Gln Arg Ile Gly Ser
    450                 455                 460
Gly Ser Phe Gly Thr Val Tyr Lys Gly Lys Trp His Gly Asp Val Ala
465                 470                 475                 480
Val Lys Met Leu Asn Val Thr Ala Pro Thr Pro Gln Gln Leu Gln Ala
                485                 490                 495
Phe Lys Asn Glu Val Gly Val Leu Arg Lys Thr Arg His Val Asn Ile
            500                 505                 510
Leu Leu Phe Met Gly Tyr Ser Thr Lys Pro Gln Leu Ala Ile Val Thr
        515                 520                 525
Gln Trp Cys Glu Gly Ser Ser Leu Tyr His His Leu His Ile Ile Glu
    530                 535                 540
Thr Lys Phe Glu Met Ile Lys Leu Ile Asp Ile Ala Arg Gln Thr Ala
545                 550                 555                 560
Gln Gly Met Asp Tyr Leu His Ala Lys Ser Ile Ile His Arg Asp Leu
                565                 570                 575
Lys Ser Asn Asn Ile Phe Leu His Glu Asp Leu Thr Val Lys Ile Gly
            580                 585                 590
Asp Phe Gly Leu Ala Thr Val Lys Ser Arg Trp Ser Gly Ser His Gln
        595                 600                 605
Phe Glu Gln Leu Ser Gly Ser Ile Leu Trp Met Ala Pro Glu Val Ile
    610                 615                 620
Arg Met Gln Asp Lys Asn Pro Tyr Ser Phe Gln Ser Asp Val Tyr Ala
625                 630                 635                 640
Phe Gly Ile Val Leu Tyr Glu Leu Met Thr Gly Gln Leu Pro Tyr Ser
                645                 650                 655
Asn Ile Asn Asn Arg Asp Gln Ile Ile Phe Met Val Gly Arg Gly Tyr
            660                 665                 670
Leu Ser Pro Asp Leu Ser Lys Val Arg Ser Asn Cys Pro Lys Ala Met
        675                 680                 685
Lys Arg Leu Met Ala Glu Cys Leu Lys Lys Arg Asp Glu Arg Pro
    690                 695                 700
Leu Phe Pro Gln Ile Leu Ala Ser Ile Glu Leu Leu Ala Arg Ser Leu
705                 710                 715                 720
Pro Lys Ile His Arg Ser Ala Ser Glu Pro Ser Leu Asn Arg Ala Gly
                725                 730                 735
Phe Gln Thr Glu Asp Phe Ser Leu Tyr Ala Cys Ala Ser Pro Lys Thr
            740                 745                 750
Pro Ile Gln Ala Gly Gly Tyr Gly Glu Phe Ala Ala Phe Lys
        755                 760                 765

<210> SEQ ID NO 25
<211> LENGTH: 4670
<212> TYPE: DNA
<213> ORGANISM: Bos taurus

<400> SEQUENCE: 25
ggtgtgtcat agtgcagcag attgaatgca aagagatatga aaattcagat gtcttctgtt      60
aaggtgtgga atatcaaaca atgattaag ttgacacagg agcatataga ggccctattg       120
gacaaatttg gtggggagca taatccacca tcaatatatc tggaggccta tgaagaatac     180
accagcaagc tagatgccct ccaacaaaga gaacaacagt tattggaatc cctggggaat     240
ggaactgatt tttctgtttc tagctctgca tcaacggaca ccgttacatc ttcttcctct     300
tctagccttt cagtgctgcc ttcatctctt tcagttttc aaaatcccac agatgtgtca      360
```

-continued

| | |
|---|---|
| cggagcaacc ccaagtcacc acaaaaacct atcgttagag tcttcctgcc caataaacag | 420 |
| aggacagtgg tacctgcacg gtgtggagtc acagtccggg acagcctgaa gaaggcactg | 480 |
| atgatgagag gtctaatccc agagtgctgt gctgtttaca gaattcagga tggggagaag | 540 |
| aaaccaattg gctgggacac tgatatttcc tggcttactg gagaggagtt gcatgtagaa | 600 |
| gtgttggaga atgttccact tacaacacac aactttgtac ggaaaacttt tttcacctta | 660 |
| gcattttgtg acttctgtag aaagctgctt ttccagggat ccgctgtca aacatgtggt | 720 |
| tataaatttc accagcgttg tagtacagag gttccactga tgtgtgttaa ttatgaccaa | 780 |
| ctagatttgc tgtttgtctc caagttcttt gaacaccacc caataccaca ggaggaggcc | 840 |
| tccttagcag agactaccct tccatgtggc tcatcccctt ctgcaccccc ctccgattct | 900 |
| attgggcccc caattctcac cagtccatct ccttcaaaat ccattccaat tccacagcct | 960 |
| ttccgaccag cagatgaaga tcatcgaaat cagtttggac aacgagaccg gtcctcatca | 1020 |
| gctccaaatg tgcatataaa cacaatagaa cccgtcaata ttgatgactt gattagagac | 1080 |
| caagggtttc gtagtgatgg aggatcaacc acaggtttat ccgccacacc ccctgcctca | 1140 |
| ttacctggct cactctctaa tgtgaaagca ttgcagaaat ctccaggacc tcagcgagaa | 1200 |
| agaaagtcct cttcatcctc agaagacagg aatcgaatga aaacgcttgg tagacgggat | 1260 |
| tcaagtgacg attgggagat tcctgatgga cagatcacag tgggacaaag aattggatca | 1320 |
| gggtcatttg gacagtctta aagggaaagt tggcatggtg atgtggcagt gaaaatgttg | 1380 |
| aatgtgacag cacccacacc tcagcagtta caggccttca aaaatgaagt aggagtactc | 1440 |
| aggaaaacgc gacatgtgaa tatcctcctc ttcatgggtt attcaacaaa gccacaactg | 1500 |
| gctattgtta cccagtggtg tgagggctcc agtttatatc atcatctcca catcattgag | 1560 |
| accaaattcg agatgatcaa acttatagat attgcacggc agactgcaca gggcatggat | 1620 |
| tacttacacg ccaagtcaat catccacaga gacctcaaga gtaataatat ttttcttcat | 1680 |
| gaagacctca cagtaaaaat aggtgatttt ggtctagcca cagtgaaatc tcgatggagt | 1740 |
| gggtcccatc agtttgaaca gttgtctgga tccatttgt ggatggcacc agaagtaatc | 1800 |
| agaatgcaag ataaaaaccc atatagcttt cagtcagatg tatatgcatt tgggattgtt | 1860 |
| ctgtatgaat tgatgaccgg acagttacct tattcaaata tcaacaacag ggaccagata | 1920 |
| atttttatgg tgggacgagg atatctgtct ccagatctca gtaaggtacg gagtaactgt | 1980 |
| ccaaaagcca tgaagagatt aatggcagag tgcctaaaaa agaaaagaga tgaaagacca | 2040 |
| ctctttcccc aagtaggaaa gactctccta agcaagagac aaaattcaga agttatcagg | 2100 |
| gaaaaagata agcagattct cgcctctatt gagctgctgg cccgctcatt gccaaaaatt | 2160 |
| caccgcagtg catcagaacc ctccttgaat cgggctggct tccaaacaga ggattttagt | 2220 |
| ctatatgctt gtgcttctcc aaaaacaccc attcaggcag ggggatatga agcagatttg | 2280 |
| gctcttacat caaataaaaa tagagtagaa gttgggattt agagatttcc tgacatgcaa | 2340 |
| gaaggaataa gcaagaaaaa aaggtttgtt ttccccaaat catatctatt gtctttact | 2400 |
| tctattttt cttaaatttt ttgtgatttc agagacatgt agagttttat tgatacctaa | 2460 |
| actatgagtt ctttttttt tttttttc attattttga ttttttggc caagaggcat | 2520 |
| atgggatctt agcttgagaa agcaacaatt ttcttgatgt cattttgggt gagggcacat | 2580 |
| attgctgtga acagtgtggt gatagccacc agggaccaaa ctcacacccg ctgcattgaa | 2640 |
| aggtgaagtc ttaaacactg gaccagcaga gaaattccta ctctatgagt tcttttttgtc | 2700 |

| | | | | |
|---|---|---|---|---|
| atccctccc | cgcaccctcc | accccaacc | taaagtctga | tgatgaaatc aacaactatt | 2760 |
| ccattagaag | cagtagattc | tggtagcatg | atctttagtt | tgttagtaag attttgtgct | 2820 |
| ttgtggggtt | gtgtcgtttt | aaggctaata | tttaagtttg | tcaaatagaa tgctgttcag | 2880 |
| attgtaaaaa | tgagtaataa | acatctgaag | ttttttttaa | gttattttta acatggtata | 2940 |
| tacagttgag | cttagagttt | atcattttct | gatattctct | tacttagtag atgaattcta | 3000 |
| gccatttttt | ataaagattt | ctgttaagca | atcctgtttt | tcacatgggc ttcctttaag | 3060 |
| ggattttaga | ttctgctgga | tatggtgact | gctcataaga | ctgttgaaaa ttacttttaa | 3120 |
| gatgtattag | aatacttctg | aaaaaaaata | gcaaccttaa | aaccataagc aaaagtagta | 3180 |
| agggtgttta | tacatttcta | gagtccctgt | ttaggtaata | gcctcctatg attgtacttt | 3240 |
| aaatgttttg | ctctccaagg | ttttagtaac | ttggcttttt | ttctaatcag tgccaaactc | 3300 |
| ccccagtttt | tttaacttta | aatatgaggt | aataaatctt | ttaccccttcc ttgatctttt | 3360 |
| gacttataat | accttggtca | gttgtttctt | aaaaggaatc | cttaaatgga aagagacaat | 3420 |
| atcactgtct | gcagttctga | ttagtagttt | tattcagaat | ggaaaacag attattcatt | 3480 |
| tttgaaaatt | gttcaggggt | atgttcattg | ttaggacctt | ggactttgga gtcagtgcct | 3540 |
| agctatgcat | tccaggtctg | ccattttctg | gctgtgaaat | tttggacaag ttacttaacc | 3600 |
| actttaaacc | ccagctttaa | gaagtaaatt | aaccccagta | aattaagaag taatagcagc | 3660 |
| cacttcgtag | agttgttatg | aggctcagat | gcagtgcaaa | tgtgtataaa gtattcaggg | 3720 |
| agtcacctgg | tatactataa | tagacactag | aatagttgcc | aatattatca gcatacaatc | 3780 |
| tgaggattct | gtcagccaat | cattagcaat | ctgttgtttg | ttgggacatg ccagtgttct | 3840 |
| ccagttgaaa | tcagtagcaa | tctaaaaatg | gatagattat | tcctcattta aatagtgtgt | 3900 |
| tcatataagt | gattgcttgg | atccttatca | gaagttgctg | ttactgaaaa atgataaggc | 3960 |
| tgactaaatt | gtgatagttg | tcagttacta | accaactccc | agaaatgaat aagaggaacc | 4020 |
| tatctctagt | tcctagtaga | aggtatggac | aaaatagtag | gtgaaaaata atgtcttgaa | 4080 |
| cccccaaatt | aagtaagctt | taaagagtac | aatacctcaa | agggtctttg cggttttaaaa | 4140 |
| tttgtatgct | gagaatgatg | ttcattgaca | tgtgcctata | tgtaattttt tgatagttta | 4200 |
| aaaggtgaaa | tgaactacag | atgggagagg | tctgaatttt | cttgccttca gtcaaatgtg | 4260 |
| taatgtggac | atattatttg | acctgtgaat | tttatctttt | aaaaaagatt aattcctgct | 4320 |
| tcttccttcc | taatagttgc | attataataa | tgaaaatgag | ttgataattt ggggggaaag | 4380 |
| tattctacaa | atcaacctta | ttattttacc | attggtttct | gagaaatttt gttcatttga | 4440 |
| accgtttata | gcttgattag | aatcatagca | tgtaaaaccc | aactgaggga ttatctgcag | 4500 |
| acttaatgta | gtattatgta | agttgtcttc | tttcatttcg | accttttttg cttttgttgt | 4560 |
| tgctagatct | gtagtatgta | gctagtcacc | tttcagcgag | gtttcagcga ggcttttctg | 4620 |
| tgtctctagg | ttatttgaga | taactttttt | aaaattagct | cttgtcctcc | 4670 |

<210> SEQ ID NO 26
<211> LENGTH: 761
<212> TYPE: PRT
<213> ORGANISM: Bos taurus

<400> SEQUENCE: 26

Met Lys Ile Gln Met Ser Ser Val Lys Val Trp Asn Ile Lys Gln Met
1               5                   10                  15

Ile Lys Leu Thr Gln Glu His Ile Glu Ala Leu Leu Asp Lys Phe Gly
            20                  25                  30

Gly Glu His Asn Pro Pro Ser Ile Tyr Leu Glu Ala Tyr Glu Glu Tyr
         35                  40                  45

Thr Ser Lys Leu Asp Ala Leu Gln Gln Arg Glu Gln Gln Leu Leu Glu
         50                  55                  60

Ser Leu Gly Asn Gly Thr Asp Phe Ser Val Ser Ser Ala Ser Thr
65                  70                  75                  80

Asp Thr Val Thr Ser Ser Ser Ser Ser Leu Ser Val Leu Pro Ser
                    85                  90                  95

Ser Leu Ser Val Phe Gln Asn Pro Thr Asp Val Ser Arg Ser Asn Pro
                100                 105                 110

Lys Ser Pro Gln Lys Pro Ile Val Arg Val Phe Leu Pro Asn Lys Gln
            115                 120                 125

Arg Thr Val Val Pro Ala Arg Cys Gly Val Thr Val Arg Asp Ser Leu
            130                 135                 140

Lys Lys Ala Leu Met Met Arg Gly Leu Ile Pro Glu Cys Cys Ala Val
145                 150                 155                 160

Tyr Arg Ile Gln Asp Gly Glu Lys Lys Pro Ile Gly Trp Asp Thr Asp
                    165                 170                 175

Ile Ser Trp Leu Thr Gly Glu Glu Leu His Val Glu Val Leu Glu Asn
                180                 185                 190

Val Pro Leu Thr Thr His Asn Phe Val Arg Lys Thr Phe Phe Thr Leu
                195                 200                 205

Ala Phe Cys Asp Phe Cys Arg Lys Leu Leu Phe Gln Gly Phe Arg Cys
            210                 215                 220

Gln Thr Cys Gly Tyr Lys Phe His Gln Arg Cys Ser Thr Glu Val Pro
225                 230                 235                 240

Leu Met Cys Val Asn Tyr Asp Gln Leu Asp Leu Leu Phe Val Ser Lys
                    245                 250                 255

Phe Phe Glu His His Pro Ile Pro Gln Glu Glu Ala Ser Leu Ala Glu
                260                 265                 270

Thr Thr Leu Pro Cys Gly Ser Ser Pro Ser Ala Pro Pro Ser Asp Ser
            275                 280                 285

Ile Gly Pro Pro Ile Leu Thr Ser Pro Ser Pro Ser Lys Ser Ile Pro
            290                 295                 300

Ile Pro Gln Pro Phe Arg Pro Ala Asp Glu Asp His Arg Asn Gln Phe
305                 310                 315                 320

Gly Gln Arg Asp Arg Ser Ser Ala Pro Asn Val His Ile Asn Thr
                    325                 330                 335

Ile Glu Pro Val Asn Ile Asp Asp Leu Ile Arg Asp Gln Gly Phe Arg
                340                 345                 350

Ser Asp Gly Gly Ser Thr Thr Gly Leu Ser Ala Thr Pro Pro Ala Ser
            355                 360                 365

Leu Pro Gly Ser Leu Ser Asn Val Lys Ala Leu Gln Lys Ser Pro Gly
            370                 375                 380

Pro Gln Arg Glu Arg Lys Ser Ser Ser Ser Glu Asp Arg Asn Arg
385                 390                 395                 400

Met Lys Thr Leu Gly Arg Arg Asp Ser Ser Asp Asp Trp Glu Ile Pro
                    405                 410                 415

Asp Gly Gln Ile Thr Val Gly Gln Arg Ile Gly Ser Gly Ser Phe Gly
                420                 425                 430

Thr Val Tyr Lys Gly Lys Trp His Gly Asp Val Ala Val Lys Met Leu
            435                 440                 445

Asn Val Thr Ala Pro Thr Pro Gln Gln Leu Gln Ala Phe Lys Asn Glu
     450                 455                 460

Val Gly Val Leu Arg Lys Thr Arg His Val Asn Ile Leu Leu Phe Met
465                 470                 475                 480

Gly Tyr Ser Thr Lys Pro Gln Leu Ala Ile Val Thr Gln Trp Cys Glu
                485                 490                 495

Gly Ser Ser Leu Tyr His His Leu His Ile Ile Glu Thr Lys Phe Glu
                500                 505                 510

Met Ile Lys Leu Ile Asp Ile Ala Arg Gln Thr Ala Gln Gly Met Asp
            515                 520                 525

Tyr Leu His Ala Lys Ser Ile Ile His Arg Asp Leu Lys Ser Asn Asn
530                 535                 540

Ile Phe Leu His Glu Asp Leu Thr Val Lys Ile Gly Asp Phe Gly Leu
545                 550                 555                 560

Ala Thr Val Lys Ser Arg Trp Ser Gly Ser His Gln Phe Glu Gln Leu
                565                 570                 575

Ser Gly Ser Ile Leu Trp Met Ala Pro Glu Val Ile Arg Met Gln Asp
                580                 585                 590

Lys Asn Pro Tyr Ser Phe Gln Ser Asp Val Tyr Ala Phe Gly Ile Val
            595                 600                 605

Leu Tyr Glu Leu Met Thr Gly Gln Leu Pro Tyr Ser Asn Ile Asn Asn
610                 615                 620

Arg Asp Gln Ile Ile Phe Met Val Gly Arg Gly Tyr Leu Ser Pro Asp
625                 630                 635                 640

Leu Ser Lys Val Arg Ser Asn Cys Pro Lys Ala Met Lys Arg Leu Met
                645                 650                 655

Ala Glu Cys Leu Lys Lys Lys Arg Asp Glu Arg Pro Leu Phe Pro Gln
                660                 665                 670

Val Gly Lys Thr Leu Leu Ser Lys Arg Gln Asn Ser Glu Val Ile Arg
            675                 680                 685

Glu Lys Asp Lys Gln Ile Leu Ala Ser Ile Glu Leu Leu Ala Arg Ser
690                 695                 700

Leu Pro Lys Ile His Arg Ser Ala Ser Glu Pro Ser Leu Asn Arg Ala
705                 710                 715                 720

Gly Phe Gln Thr Glu Asp Phe Ser Leu Tyr Ala Cys Ala Ser Pro Lys
                725                 730                 735

Thr Pro Ile Gln Ala Gly Gly Tyr Glu Ala Asp Leu Ala Leu Thr Ser
            740                 745                 750

Asn Lys Asn Arg Val Glu Val Gly Ile
        755                 760

<210> SEQ ID NO 27
<211> LENGTH: 4816
<212> TYPE: DNA
<213> ORGANISM: Bos taurus

<400> SEQUENCE: 27
ctcagctgcg ccgggtctca caagacggtt cccgaggtgg cccaggcgcc gtcccaccgc      60
cgacgccgcc cggccgcc gggccgtccc tccccgctgc ccccgtcct ccgcctccgc       120 ctcccccgc cctcagcctc ccttcccct cccgcccag cagcggtcgc tcgggcccgg       180
ctctcggtta taagatggcg gcgctgagtg gcggcggcgg cggcggcggc ggtggcgcgg      240
agcagggcca ggctctgttc aacgggggaca tggagcccga ggccggcgcc gcggcctctt      300
cggctgcgga ccccgccatt cccgaggagg tgtggaatat caaacaaatg attaagttga      360

```
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgattttc tgtttctagc tctgcatcaa     540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aacttttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag agccccaat tctcaccagt ccatctcctt    1080
caaaatccat tccaattcca cagccttcc gaccagcaga tgaagatcat cgaaatcagt    1140
ttggacaacg agaccggtcc tcatcagctc caaatgtgca tataaacaca atagaacccg   1200
tcaatattga tgacttgatt agagaccaag ggtttcgtag tgatggagga tcaaccacag   1260
gtttatccgc cacacccct gcctcattac ctggctcact ctctaatgtg aaagcattgc    1320
agaaatctcc aggacctcag cgagaaagaa agtcctcttc atcctcagaa gacaggaatc   1380
gaatgaaaac gcttggtaga cgggattcaa gtgacgattg ggagattcct gatggacaga   1440
tcacagtggg acaaagaatt ggatcagggt catttgggac agtctacaag ggaaagtggc   1500
atggtgatgt ggcagtgaaa atgttgaatg tgacagcacc cacacctcag cagttacagg   1560
ccttcaaaaa tgaagtagga gtactcagga aaacgcgaca tgtgaatatc ctcctcttca   1620
tgggttattc aacaaagcca caactggcta ttgttaccca gtggtgtgag ggctccagtt   1680
tatatcatca tctccacatc attgagacca aattcgagat gatcaaactt atagatattg   1740
cacggcagac tgcacagggc atggattact acacgccaa gtcaatcatc cacagagacc    1800
tcaagagtaa taatattttt cttcatgaag acctcacagt aaaaataggt gattttggtc   1860
tagccacagt gaaatctcga tggagtgggt cccatcagtt tgaacagttg tctggatcca   1920
ttttgtggat ggcaccagaa gtaatcagaa tgcaagataa aaaccatat agctttcagt    1980 cagatgtata tgcatttggg attgttctgt atgaattgat gaccggacag ttaccttatt   2040
caaatatcaa caacagggac cagataattt ttatggtggg acgaggatat ctgtctccag   2100
atctcagtaa ggtacggagt aactgtccaa aagccatgaa gagattaatg gcagagtgcc   2160 taaaaagaa aagagatgaa agaccactct ttccccaagt aggaaagact ctcctaagca   2220
agagacaaaa ttcagaagtt atcagggaaa aagataagca gattctcgcc tctattgagc   2280
tgctggcccg ctcattgcca aaaattcacc gcagtgcatc agaaccctcc ttgaatcggg   2340
ctggcttcca aacagaggat tttagtctat atgcttgtgc ttctccaaaa acacccattc   2400
aggcaggggg atatgaagca gatttggctc ttacatcaaa taaaaataga gtagaagttg   2460
ggatttagag atttcctgac atgcaagaag gaataagcaa gaaaaaaagg tttgttttcc    2520
ccaaatcata tctattgtct tttacttcta ttttttctta aattttttgt gatttcagag    2580
acatgtagag ttttattgat acctaaacta tgagttcttt ttttttttt ttttcatta     2640 ttttgatttt tttggccaag aggcatatgg gatcttagct tgagaaagca acaatttct    2700
```

```
tgatgtcatt ttgggtgagg gcacatattg ctgtgaacag tgtggtgata gccaccaggg    2760
accaaactca cacccgctgc attgaaaggt gaagtcttaa acactggacc agcagagaaa    2820
ttcctactct atgagttctt tttgtcatcc cctccccgca ccctccaccc ccaacctaaa    2880
gtctgatgat gaaatcaaca actattccat tagaagcagt agattctggt agcatgatct    2940
ttagtttgtt agtaagattt tgtgctttgt ggggttgtgt cgttttaagg ctaatattta    3000
agtttgtcaa atagaatgct gttcagattg taaaaatgag taataaacat ctgaagtttt    3060
ttttaagtta ttttttaacat ggtatataca gttgagctta gagtttatca ttttctgata   3120
ttctcttact tagtagatga attctagcca tttttttataa agatttctgt taagcaaatc    3180
ctgttttcac atgggcttcc tttaagggat tttagattct gctggatatg gtgactgctc    3240
ataagactgt tgaaaattac ttttaagatg tattagaata cttctgaaaa aaaatagcaa    3300
ccttaaaacc ataagcaaaa gtagtaaggg tgtttataca tttctagagt ccctgtttag    3360
gtaatagcct cctatgattg tactttaaat gttttgctct ccaaggtttt agtaacttgg    3420 cttttttttct aatcagtgcc aaactccccc agttttttta actttaaata tgaggtaata   3480
aatcttttac ccttccttga tcttttgact tataatacct tggtcagttg tttcttaaaa    3540
ggaatcctta aatggaaaga gacaaatatca ctgtctgcag ttctgattag tagttttatt   3600
cagaatggaa aaacagatta ttcattttg aaaattgttc agggtatgt tcattgttag     3660 gaccttggac tttggagtca gtgcctagct atgcattcca ggtctgccat ttctggctg     3720 tgaaattttg gacaagttac ttaaccactt taaaccccag ctttaagaag taaattaacc    3780
ccagtaaatt aagaagtaat agcagccact tcgtagagtt gttatgaggc tcagatgcag    3840
tgcaaatgtg tataaagtat tcagggagtc acctggtata ctataataga cactagaata    3900
gttgccaata ttatcagcat acaatctgag gattctgtca gccaatcatt agcaatctgt    3960
tgtttgttgg gacatgccag tgttctccag ttgaaatcag tagcaatcta aaaatggata    4020
gattattcct catttaaata gtgtgttcat ataagtgatt gcttggatcc ttatcagaag    4080
ttgctgttac tgaaaaatga taaggctgac taaattgtga tagttgtcag ttactaacca    4140
actcccagaa atgaataaga ggaacctatc tctagttcct agtagaaggt atggacaaaa    4200
tagtaggtga aaaataatgt cttgaacccc caaattaagt aagctttaaa gagtacaata    4260
cctcaaaggg tctttgcggt ttaaaatttg tatgctgaga atgatgttca ttgacatgtg    4320
cctatatgta attttttgat agtttaaaag gtgaaatgaa ctacagatgg gagaggtctg    4380
aattttcttg ccttcagtca aatgtgtaat gtggacatat tatttgaccct gtgaattta     4440 tcttttaaaa aagattaatt cctgcttctt ccttcctaat agttgcatta taataatgaa    4500
aatgagttga taatttgggg ggaaagtatt ctacaaatca accttattat tttaccattg    4560
gtttctgaga aattttgttc atttgaaccg tttatagctt gattagaatc atagcatgta    4620
aaacccaact gagggattat ctgcagactt aatgtagtat tatgtaagtt gtcttctttc    4680
atttcgacct ttttttgcttt tgttgttgct agatctgtag tatgtagcta gtcacctttc    4740
agcgaggttt cagcgaggct tttctgtgtc tctaggttat ttgagataac ttttttaaaa    4800
ttagctcttg tcctcc                                                    4816
```

<210> SEQ ID NO 28
<211> LENGTH: 757
<212> TYPE: PRT
<213> ORGANISM: Bos taurus

<400> SEQUENCE: 28

```
Met Ala Ala Leu Ser Gly Gly Gly Gly Gly Gly Ala Glu
1               5                   10              15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
            35                  40                  45

Ile Lys Gln Met Ile Lys Leu Thr Gln Glu His Ile Glu Ala Leu Leu
50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
            115                 120                 125

Val Leu Pro Ser Ser Leu Ser Val Phe Gln Asn Pro Thr Asp Val Ser
    130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
                180                 185                 190

Cys Cys Ala Val Tyr Arg Ile Gln Asp Gly Glu Lys Lys Pro Ile Gly
                195                 200                 205

Trp Asp Thr Asp Ile Ser Trp Leu Thr Gly Glu Glu Leu His Val Glu
                210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
                260                 265                 270

Thr Glu Val Pro Leu Met Cys Val Asn Tyr Asp Gln Leu Glu Pro Pro
                275                 280                 285

Ile Leu Thr Ser Pro Ser Pro Ser Lys Ser Ile Pro Ile Pro Gln Pro
                290                 295                 300

Phe Arg Pro Ala Asp Glu Asp His Arg Asn Gln Phe Gly Gln Arg Asp
305                 310                 315                 320

Arg Ser Ser Ser Ala Pro Asn Val His Ile Asn Thr Ile Glu Pro Val
                325                 330                 335

Asn Ile Asp Asp Leu Ile Arg Asp Gln Gly Phe Arg Ser Asp Gly Gly
                340                 345                 350

Ser Thr Thr Gly Leu Ser Ala Thr Pro Pro Ala Ser Leu Pro Gly Ser
            355                 360                 365

Leu Ser Asn Val Lys Ala Leu Gln Lys Ser Pro Gly Pro Gln Arg Glu
            370                 375                 380

Arg Lys Ser Ser Ser Ser Ser Glu Asp Arg Asn Arg Met Lys Thr Leu
385                 390                 395                 400

Gly Arg Arg Asp Ser Ser Asp Asp Trp Glu Ile Pro Asp Gly Gln Ile
                405                 410                 415
```

Thr Val Gly Gln Arg Ile Gly Ser Gly Ser Phe Gly Thr Val Tyr Lys
            420                 425                 430

Gly Lys Trp His Gly Asp Val Ala Val Lys Met Leu Asn Val Thr Ala
        435                 440                 445

Pro Thr Pro Gln Gln Leu Gln Ala Phe Lys Asn Glu Val Gly Val Leu
450                 455                 460

Arg Lys Thr Arg His Val Asn Ile Leu Leu Phe Met Gly Tyr Ser Thr
465                 470                 475                 480

Lys Pro Gln Leu Ala Ile Val Thr Gln Trp Cys Glu Gly Ser Ser Leu
                485                 490                 495

Tyr His His Leu His Ile Ile Glu Thr Lys Phe Glu Met Ile Lys Leu
                    500                 505                 510

Ile Asp Ile Ala Arg Gln Thr Ala Gln Gly Met Asp Tyr Leu His Ala
515                 520                 525

Lys Ser Ile Ile His Arg Asp Leu Lys Ser Asn Asn Ile Phe Leu His
530                 535                 540

Glu Asp Leu Thr Val Lys Ile Gly Asp Phe Gly Leu Ala Thr Val Lys
545                 550                 555                 560

Ser Arg Trp Ser Gly Ser His Gln Phe Glu Gln Leu Ser Gly Ser Ile
                565                 570                 575

Leu Trp Met Ala Pro Glu Val Ile Arg Met Gln Asp Lys Asn Pro Tyr
            580                 585                 590

Ser Phe Gln Ser Asp Val Tyr Ala Phe Gly Ile Val Leu Tyr Glu Leu
                595                 600                 605

Met Thr Gly Gln Leu Pro Tyr Ser Asn Ile Asn Asn Arg Asp Gln Ile
            610                 615                 620

Ile Phe Met Val Gly Arg Gly Tyr Leu Ser Pro Asp Leu Ser Lys Val
625                 630                 635                 640

Arg Ser Asn Cys Pro Lys Ala Met Lys Arg Leu Met Ala Glu Cys Leu
                645                 650                 655

Lys Lys Lys Arg Asp Glu Arg Pro Leu Phe Pro Gln Val Gly Lys Thr
            660                 665                 670

Leu Leu Ser Lys Arg Gln Asn Ser Glu Val Ile Arg Glu Lys Asp Lys
            675                 680                 685

Gln Ile Leu Ala Ser Ile Glu Leu Leu Ala Arg Ser Leu Pro Lys Ile
        690                 695                 700

His Arg Ser Ala Ser Glu Pro Ser Leu Asn Arg Ala Gly Phe Gln Thr
705                 710                 715                 720

Glu Asp Phe Ser Leu Tyr Ala Cys Ala Ser Pro Lys Thr Pro Ile Gln
                725                 730                 735

Ala Gly Gly Tyr Glu Ala Asp Leu Ala Leu Thr Ser Asn Lys Asn Arg
                740                 745                 750

Val Glu Val Gly Ile
        755

<210> SEQ ID NO 29
<211> LENGTH: 2499
<212> TYPE: DNA
<213> ORGANISM: Bos taurus

<400> SEQUENCE: 29
ctcagctgcg ccgggtctca caagacggtt cccgaggtgg cccaggcgcc gtcccaccgc    60
cgacgccgcc cgggccgccc gggcgtcccc tcccgctgcc cccccgtcct ccgcctccgc   120
ctccccccgc cctcagcctc ccttcccccct ccccgcccag cagcggtcgc tcgggcccgg   180

```
ctctcggtta taagatggcg gcgctgagtg gcggcggcgg cggcggcggc ggtggcgcgg      240
agcagggcca ggctctgttc aacggggaca tggagcccga ggccggcgcc gcggcctctt      300
cggctgcgga ccccgccatt cccgaggagg tgtggaatat caaacaaatg attaagttga      360
cacaggagca tatagaggcc ctattggaca aatttggtgg ggagcataat ccaccatcaa      420
tatatctgga ggcctatgaa gaatacacca gcaagctaga tgccctccaa caaagagaac      480
aacagttatt ggaatccctg gggaatggaa ctgattttc tgtttctagc ctgcatcaa       540 cggacaccgt tacatcttct tcctcttcta gcctttcagt gctgccttca tctctttcag      600 ttttcaaaa tcccacagat gtgtcacgga gcaaccccaa gtcaccacaa aaacctatcg       660
ttagagtctt cctgcccaat aaacagagga cagtggtacc tgcacggtgt ggagtcacag      720
tccgggacag cctgaagaag gcactgatga tgagaggtct aatcccagag tgctgtgctg      780
tttacagaat tcaggatggg gagaagaaac caattggctg gacactgat atttcctggc       840 ttactggaga ggagttgcat gtagaagtgt tggagaatgt tccacttaca acacacaact      900
ttgtacggaa aacttttttc accttagcat tttgtgactt ctgtagaaag ctgcttttcc      960
agggattccg ctgtcaaaca tgtggttata aatttcacca gcgttgtagt acagaggttc     1020
cactgatgtg tgttaattat gaccaactag atttgctgtt tgtctccaag ttctttgaac     1080
accacccaat accacaggag gaggcctcct tagcagagac tacccttcca tgtggctcat     1140
ccccttctgc acccccctcc gattctattg gcccccaat tctcaccagt ccatctcctt      1200
caaaatccat tccaattcca cagccttcc gaccagcaga tgaagatcat cgaaatcagt      1260
ttggacaacg agaccggtcc tcatcagctc caaatgtgca tataaacaca atagaacccg     1320
tcaatattga tgacttgatt agagaccaag ggtttcgtag tgatggagga tcaaccacag     1380
gtttatccgc cacacccct gcctcattac ctggctcact ctctaatgtg aaagcattgc      1440
agaaatctcc aggacctcag cgagaaagaa agtcctcttc atcctcagaa gacaggaatc     1500
gaatgaaaac gcttggtaga cgggattcaa gtgacgattg ggagattcct gatggacaga     1560
tcacagtggg acaaagaatt ggatcagggt catttgggac agtctacaag ggaaagtggc     1620
atggtgatgt ggcagtgaaa atgttgaatg tgacagcacc cacacctcag cagttacagg     1680
ccttcaaaaa tgaagtagga gtactcagga aaacgcgaca tgtgaatatc ctcctcttca     1740
tgggttattc aacaaagcca caactggcta ttgttaccca gtggtgtgag ggctccagtt     1800
tatatcatca tctccacatc attgagacca aattcgagat gatcaaactt atagatattg     1860
cacggcagac tgcacagggc atggattact acacgccaa gtcaatcatc cacagagacc      1920
tcaagagtaa taatatttt cttcatgaag acctcacagt aaaaataggt gattttggtc      1980
tagccacagt gaaatctcga tggagtgggt cccatcagtt tgaacagttg tctggatcca     2040
ttttgtggat ggcaccagaa gtaatcagaa tgcaagataa aaacccatat agctttcagt     2100
cagatgtata tgcatttggg attgttctgt atgaattgat gaccggacag ttaccttatt     2160
caaatatcaa caacagggac cagataattt ttatggtggg acgaggatat ctgtctccag     2220
atctcagtaa ggtacggagt aactgtccaa aagccatgaa gagattaatg gcagagtgcc     2280
taaaaaagaa aagagatgaa agaccactct ttccccaagt aggaaagact ctcctaagca     2340
agagacaaaa ttcagaagtt atcagggaaa aagataagca ggaaaagtat gtttctttag     2400
tacattccag gcatttggga ttacagtaaa aacaatattc tcgcctctat tgagctgctg     2460
gcccgctcat tgccaaaaat tcaccgcagt gcatcagaa                            2499
```

-continued

```
<210> SEQ ID NO 30
<211> LENGTH: 744
<212> TYPE: PRT
<213> ORGANISM: Bos taurus

<400> SEQUENCE: 30

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
 50                 55                  60

Asp Lys Phe Gly Gly Glu His Asn Pro Pro Ser Ile Tyr Leu Glu Ala
 65                 70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Ser Leu Ser
        115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
370                 375                 380
```

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
            405                 410                 415

Lys Ser Pro Gly Pro Gln Arg Glu Arg Lys Ser Ser Ser Ser Ser Glu
        420                 425                 430

Asp Arg Asn Arg Met Lys Thr Leu Gly Arg Arg Asp Ser Ser Asp Asp
                435                 440                 445

Trp Glu Ile Pro Asp Gly Gln Ile Thr Val Gly Gln Arg Ile Gly Ser
        450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
        610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ile Ile Phe Met Val Gly Arg Gly Tyr
            660                 665                 670

Leu Ser Pro Asp Leu Ser Lys Val Arg Ser Asn Cys Pro Lys Ala Met
        675                 680                 685

Lys Arg Leu Met Ala Glu Cys Leu Lys Lys Lys Arg Asp Glu Arg Pro
        690                 695                 700

Leu Phe Pro Gln Val Gly Lys Thr Leu Leu Ser Lys Arg Gln Asn Ser
705                 710                 715                 720

Glu Val Ile Arg Glu Lys Asp Lys Gln Glu Lys Tyr Val Ser Leu Val
                725                 730                 735

His Ser Arg His Leu Gly Leu Gln
            740

<210> SEQ ID NO 31
<211> LENGTH: 2404
<212> TYPE: DNA
<213> ORGANISM: Bos taurus

<400> SEQUENCE: 31
ctcagctgcg ccgggtctca caagacggtt cccgaggtgg cccaggcgcc gtcccaccgc    60

```
cgacgccgcc cgggccgccc gggccgtccc tccccgctgc ccccgtcct ccgcctccgc    120 ctccccccgc cctcagcctc ccttccccct ccccgcccag cagcggtcgc tcgggccgg    180 ctctcggtta taagatggcg gcgctgagtg gcggcggcgg cggcggcggc ggtggcgcgg    240
agcagggcca ggctctgttc aacggggaca tggagcccga ggccggcgcc gcggcctctt    300
cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg ggaatggaa ctgattttc tgtttctagc ctgcatcaa    540 cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgcttttcc    960
agggattccg ctgtcaaaca tgtggttata aatttcacca gcgttgtagt acagaggttc    1020
cactgatgtg tgttaattat gaccaactag atttgctgtt tgtctccaag ttctttgaac    1080
accacccaat accacaggag gaggcctcct tagcagagac tacccttcca tgtggctcat    1140 cccttctgc accccctcc gattctattg gccccccaat tctcaccagt ccatctcctt    1200
caaaatccat tccaattcca cagcctttcc gaccagcaga tgaagatcat cgaaatcagt    1260
ttggacaacg agaccggtcc tcatcagctc caaatgtgca tataaacaca atagaacccg    1320
tcaatattga tgacttgatt agagaccaag ggtttcgtag tgatggagga tcaaccacag    1380
gtttatccgc cacacccct gcctcattac ctggctcact ctctaatgtg aaagcattgc    1440
agaaatctcc aggacctcag cgagaaagaa agtcctcttc atcctcagaa gacaggaatc    1500
gaatgaaaac gcttggtaga cgggattcaa gtgacgattg ggagattcct gatggacaga    1560
tcacagtggg acaaagaatt ggatcagggt catttgggac agtctacaag ggaaagtggc    1620
atggtgatgt ggcagtgaaa atgttgaatg tgacagcacc cacacctcag cagttacagg    1680
ccttcaaaaa tgaagtagga gtactcagga aaacgcgaca tgtgaatatc ctcctcttca    1740
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacaggc atggattact acacgccaa gtcaatcatc cacagagacc    1920
tcaagagtaa taatattttt cttcatgaag acctcacagt aaaaataggt gattttggtc    1980
tagccacagt gaaatctcga tggagtgggt cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac cagataattt ttatggtggg acgaggatat ctgtctccag    2220
atctcagtaa ggtacggagt aactgtccaa aagccatgaa gagattaatg gcagagtgcc    2280 taaaaagaa aagagatgaa agaccactct ttccccaaga tctctcttcc caccatagac    2340
acaaaaattt cagatggcta caggtttaca tgtaaaaaac agaattataa caaatgattt    2400
``` ttat                                                                                  2404

<210> SEQ ID NO 32
<211> LENGTH: 726
<212> TYPE: PRT
<213> ORGANISM: Bos taurus

<400> SEQUENCE: 32

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
    210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
    290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ala Pro Asn Val
        355                 360                 365

His Ile Asn Thr Ile Glu Pro Val Asn Ile Asp Asp Leu Ile Arg Asp
370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
            405                 410                 415

Lys Ser Pro Gly Pro Gln Arg Glu Arg Lys Ser Ser Ser Ser Ser Glu
        420                 425                 430

Asp Arg Asn Arg Met Lys Thr Leu Gly Arg Arg Asp Ser Ser Asp Asp
    435                 440                 445

Trp Glu Ile Pro Asp Gly Gln Ile Thr Val Gly Gln Arg Ile Gly Ser
450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
            485                 490                 495

Phe Lys Asn Glu Val Gly Val Leu Arg Lys Thr Arg His Val Asn Ile
        500                 505                 510

Leu Leu Phe Met Gly Tyr Ser Thr Lys Pro Gln Leu Ala Ile Val Thr
    515                 520                 525

Gln Trp Cys Glu Gly Ser Ser Leu Tyr His His Leu His Ile Ile Glu
530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
            565                 570                 575

Lys Ser Asn Asn Ile Phe Leu His Glu Asp Leu Thr Val Lys Ile Gly
        580                 585                 590

Asp Phe Gly Leu Ala Thr Val Lys Ser Arg Trp Ser Gly Ser His Gln
    595                 600                 605

Phe Glu Gln Leu Ser Gly Ser Ile Leu Trp Met Ala Pro Glu Val Ile
610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
            645                 650                 655

Asn Ile Asn Asn Arg Asp Gln Ile Ile Phe Met Val Gly Arg Gly Tyr
        660                 665                 670

Leu Ser Pro Asp Leu Ser Lys Val Arg Ser Asn Cys Pro Lys Ala Met
    675                 680                 685

Lys Arg Leu Met Ala Glu Cys Leu Lys Lys Arg Asp Glu Arg Pro
690                 695                 700

Leu Phe Pro Gln Asp Leu Ser Ser His His Arg His Lys Asn Phe Arg
705                 710                 715                 720

Trp Leu Gln Val Tyr Met
            725

<210> SEQ ID NO 33
<211> LENGTH: 2331
<212> TYPE: DNA
<213> ORGANISM: Bos taurus

<400> SEQUENCE: 33
ctcagctgcg ccgggtctca caagacggtt cccgaggtgg cccaggcgcc gtcccaccgc    60

```
cgacgccgcc cgggccgccc gggccgtccc tccccgctgc ccccgtcct ccgcctccgc    120 ctcccccgc  cctcagcctc ccttcccct  cccgcccag  cagcggtcgc tcgggcccgg    180
ctctcggtta taagatggcg cgctgagtg  gcggcggcgg cggcggcggc ggtggcgcgg    240
agcagggcca ggctctgttc aacggggaca tggagcccga ggccgcgcc  gcggcctctt    300 cggctgcgga ccccgccatt cccgaggagg tgtggaatat caaacaaatg attaagttga    360
cacaggagca tatagaggcc ctattggaca aatttggtgg ggagcataat ccaccatcaa    420
tatatctgga ggcctatgaa gaatacacca gcaagctaga tgccctccaa caaagagaac    480
aacagttatt ggaatccctg gggaatggaa ctgattttc  tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aacttttttc accttagcat tttgtgactt ctgtagaaag ctgcttttcc    960
agggattccg ctgtcaaaca tgtggttata aatttcacca gcgttgtagt acagaggttc    1020
cactgatgtg tgttaattat gaccaactag atttgctgtt tgtctccaag ttctttgaac    1080 accaccaat  accacaggag gaggcctcct tagcagagac taccccttcca tgtggctcat    1140 ccccttctgc acccccctcc gattctattg gccccccaat tctcaccagt ccatctcctt    1200
caaaatccat tccaattcca cagccttttcc gaccagcaga tgaagatcat cgaaatcagt    1260
ttggacaacg agaccggtcc tcatcagctc caaatgtgca tataaacaca atagaacccg    1320
tcaatattga tgacttgatt agagaccaag ggtttcgtag tgatggagga tcaaccacag    1380
gtttatccgc cacacccctt gcctcattac ctggctcact ctctaatgtg aaagcattgc    1440
agaaatctcc aggacctcag cgagaaagaa agtcctcttc atcctcagaa gacaggaatc    1500
gaatgaaaac gcttggtaga cgggattcaa gtgacgattg ggagattcct gatggacaga    1560
tcacagtggg acaaagaatt ggatcagggt catttgggac agtctacaag ggaaagtggc    1620
atggtgatgt ggcagtgaaa atgttgaatg tgacagcacc cacacctcag cagttacagg    1680
ccttcaaaaa tgaagtagga gtactcagga aaacgcgaca tgtgaatatc ctcctcttca    1740
tgggttattc aacaaagcca caactggcta ttgttaccca gtggtgtgag ggctccagtt    1800
tatatcatca tctccacatc attgagacca aattcgagat gatcaaactt atagatattg    1860
cacggcagac tgcacagggc atggattact acacgccaa  gtcaatcatc cacagagacc    1920
tcaagagtaa taatatttt  cttcatgaag acctcacagt aaaaataggt gattttggtc    1980
tagccacagt gaaatctcga tggagtgggt cccatcagtt tgaacagttg tctggatcca    2040
ttttgtggat ggcaccagaa gtaatcagaa tgcaagataa aaacccatat agctttcagt    2100
cagatgtata tgcatttggg attgttctgt atgaattgat gaccggacag ttaccttatt    2160
caaatatcaa caacagggac caggtgcttt gtcctccatg ggagtgtaat aaatgctgtg    2220
caagggctta cttcccatga gagaagtgag tgaccaacag aaggataatt tttatggtgg    2280
gacgaggata tctgtctcca gatctcagta aggtacggag taactgtcca a              2331
```

<210> SEQ ID NO 34
<211> LENGTH: 681

<212> TYPE: PRT
<213> ORGANISM: Bos taurus

<400> SEQUENCE: 34

Met Ala Ala Leu Ser Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
50                  55                  60

Asp Lys Phe Gly Gly Glu His Asn Pro Pro Ser Ile Tyr Leu Glu Ala
65                  70                  75                  80

Tyr Glu Glu Tyr Thr Ser Lys Leu Asp Ala Leu Gln Gln Arg Glu Gln
                85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
        115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
        195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
        275                 280                 285

Phe Val Ser Lys Phe Phe Glu His His Pro Ile Pro Gln Glu Glu Ala
290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ser Ala Pro Asn Val
        355                 360                 365

His Ile Asn Thr Ile Glu Pro Val Asn Ile Asp Asp Leu Ile Arg Asp
370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
            405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
            450                 455                 460

Gly Ser Phe Gly Thr Val Tyr Lys Gly Lys Trp His Gly Asp Val Ala
465                 470                 475                 480

Val Lys Met Leu Asn Val Thr Ala Pro Thr Pro Gln Gln Leu Gln Ala
            485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
            530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
            565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
            595                 600                 605

Phe Glu Gln Leu Ser Gly Ser Ile Leu Trp Met Ala Pro Glu Val Ile
            610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
            645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
            675                 680

<210> SEQ ID NO 35
<211> LENGTH: 2319
<212> TYPE: DNA
<213> ORGANISM: Bos taurus

<400> SEQUENCE: 35
ctcagctgcg ccgggtctca caagacggtt cccgaggtgg cccaggcgcc gtcccaccgc      60
cgacgccgcc cggccgcccc gggccgtccc tcccgctgcc ccccgtcct ccgcctccgc      120 ctcccccgc cctcagcctc ccttcccct ccccgcccag cagcggtcgc tcgggcccgg      180
ctctcggtta aagatggcg gcgctgagtg gcggcggcgg cggcggcggc ggtggcgcgg      240
agcagggcca ggctctgttc aacggggaca tggagcccga ggccggcgcc gcggcctctt      300
cggctgcgga ccccgccatt cccgaggagg tgtggaatat caaacaaatg attaagttga      360
cacaggagca tatagaggcc ctattggaca aatttggtgg ggagcataat ccaccatcaa      420
tatatctgga ggcctatgaa gaatacacca gcaagctaga tgccctccaa caaagagaac      480

```
aacagttatt ggaatccctg gggaatggaa ctgattttc tgtttctagc tctgcatcaa    540
cggacaccgt tacatcttct tcctcttcta gcctttcagt gctgccttca tctctttcag    600
tttttcaaaa tcccacagat gtgtcacgga gcaaccccaa gtcaccacaa aaacctatcg    660
ttagagtctt cctgcccaat aaacagagga cagtggtacc tgcacggtgt ggagtcacag    720
tccgggacag cctgaagaag gcactgatga tgagaggtct aatcccagag tgctgtgctg    780
tttacagaat tcaggatggg gagaagaaac caattggctg ggacactgat atttcctggc    840
ttactggaga ggagttgcat gtagaagtgt tggagaatgt tccacttaca acacacaact    900
ttgtacggaa aactttttc accttagcat tttgtgactt ctgtagaaag ctgcttttcc    960
agggattccg ctgtcaaaca tgtggttata aatttcacca gcgttgtagt acagaggttc   1020
cactgatgtg tgttaattat gaccaactag atttgctgtt tgtctccaag ttctttgaac   1080
accacccaat accacaggag gaggcctcct tagcagagac tacccttcca tgtggctcat   1140
ccccttctgc accccctcc gattctattg ggccccaat tctcaccagt ccatctcctt    1200
caaaatccat tccaattcca cagcctttcc gaccagcaga tgaagatcat cgaaatcagt   1260
ttggacaacg agaccggtcc tcatcagctc caaatgtgca tataaacaca atagaacccg   1320
tcaatattga tgacttgatt agagaccaag ggtttcgtag tgatggagga tcaaccacag   1380
gtttatccgc cacacccct gcctcattac ctggctcact ctctaatgtg aaagcattgc    1440
agaaatctcc aggacctcag cgagaaagaa agtcctcttc atcctcagaa gacaggaatc   1500
gaatgaaaac gcttggtaga cgggattcaa gtgacgattg ggagattcct gatggacaga   1560
tcacagtggg acaagaatt ggatcagggt catttgggac agtctacaag ggaaagtggc    1620
atggtgatgt ggcagtgaaa atgttgaatg tgacagcacc cacacctcag cagttacagg   1680
ccttcaaaaa tgaagtagga gtactcagga aaacgcgaca tgtgaatatc ctcctcttca   1740
tgggttattc aacaaagcca caactggcta ttgttaccca gtggtgtgag ggctccagtt   1800
tatatcatca tctccacatc attgagacca aattcgagat gatcaaactt atagatattg   1860
cacggcagac tgcacagggc atggattact acacgccaa gtcaatcatc cacagagacc    1920
tcaagagtaa taatattttt cttcatgaag acctcacagt aaaaataggt gattttggtc   1980
tagccacagt gaaatctcga tggagtgggt cccatcagtt tgaacagttg tctggatcca   2040
ttttgtggat ggcaccagaa gtaatcgaaa tgcaagataa aaaccccatat agctttcagt   2100 cagatgtata tgcatttggg attgttctgt atgaattgat gaccggacag ttaccttatt   2160
caaatatcaa caacagggac caggtgcttt gtcctccatg ggagtgtaat aaatgctgtg   2220
caagggctta cttcccatga gagaagtgag tgaccaacag aaggtctgtg caaggaaaag   2280
agacaaagcc acggatcaga agcacatggc cataactga                          2319
```

<210> SEQ ID NO 36
<211> LENGTH: 681
<212> TYPE: PRT
<213> ORGANISM: Bos taurus

<400> SEQUENCE: 36

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
                20                  25                  30

Ala Ala Ser Ser Ala Ala Asp Pro Ala Ile Pro Glu Glu Val Trp Asn
            35                  40                  45

-continued

Ile Lys Gln Met Ile Lys Leu Thr Gln Glu His Ile Glu Ala Leu Leu
 50              55                  60

Asp Lys Phe Gly Gly Glu His Asn Pro Pro Ser Ile Tyr Leu Glu Ala
 65              70                  75                  80

Tyr Glu Glu Tyr Thr Ser Lys Leu Asp Ala Leu Gln Gln Arg Glu Gln
                 85                  90                  95

Gln Leu Leu Glu Ser Leu Gly Asn Gly Thr Asp Phe Ser Val Ser Ser
            100                 105                 110

Ser Ala Ser Thr Asp Thr Val Thr Ser Ser Ser Ser Ser Leu Ser
            115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
            180                 185                 190

Cys Cys Ala Val Tyr Arg Ile Gln Asp Gly Glu Lys Lys Pro Ile Gly
            195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
            260                 265                 270

Thr Glu Val Pro Leu Met Cys Val Asn Tyr Asp Gln Leu Asp Leu Leu
            275                 280                 285

Phe Val Ser Lys Phe Phe Glu His His Pro Ile Pro Gln Glu Glu Ala
290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
            340                 345                 350

Arg Asn Gln Phe Gly Gln Arg Asp Arg Ser Ser Ala Pro Asn Val
            355                 360                 365

His Ile Asn Thr Ile Glu Pro Val Asn Ile Asp Asp Leu Ile Arg Asp
370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
            420                 425                 430

Asp Arg Asn Arg Met Lys Thr Leu Gly Arg Arg Asp Ser Ser Asp Asp
            435                 440                 445

Trp Glu Ile Pro Asp Gly Gln Ile Thr Val Gly Gln Arg Ile Gly Ser
450                 455                 460

Gly Ser Phe Gly Thr Val Tyr Lys Gly Lys Trp His Gly Asp Val Ala

Val Lys Met Leu Asn Val Thr Ala Pro Thr Pro Gln Gln Leu Gln Ala
                485                 490                 495

Phe Lys Asn Glu Val Gly Val Leu Arg Lys Thr Arg His Val Asn Ile
            500                 505                 510

Leu Leu Phe Met Gly Tyr Ser Thr Lys Pro Gln Leu Ala Ile Val Thr
        515                 520                 525

Gln Trp Cys Glu Gly Ser Ser Leu Tyr His His Leu His Ile Ile Glu
    530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Val Leu Cys Pro Pro Trp Glu Cys Asn
            660                 665                 670

Lys Cys Cys Ala Arg Ala Tyr Phe Pro
        675                 680

<210> SEQ ID NO 37
<211> LENGTH: 2661
<212> TYPE: DNA
<213> ORGANISM: Bos taurus

<400> SEQUENCE: 37
tcagctgcgc cgggtctcac aagacggttc ccgaggtggc ccaggcgccg tcccaccgcc     60
gacgccgccc gggccgcccg ggccgtccct ccccgctgcc ccccgtcctc cgcctccgcc    120 tcccccgcc ctcagcctcc cttccccctc ccgcccagc agcggtcgct cgggcccggc      180
tctcggttat aagatggcgg cgctgagtgg cggcggcggc ggcggcggcg gtggcgcgga    240
gcagggccag gctctgttca acggggacat ggagcccgag gccggcgccg cggcctcttc    300
ggctgcggac cccgccattc ccgaggaggt gtggaatatc aaacaaatga ttaagttgac    360
acaggagcat atagaggccc tattggacaa atttggtggg agcataatc caccatcaat     420 atatctggag gcctatgaag aataccacca caagctagat gccctccaac aaagagaaca    480
acagttattg gaatccctgg ggaatggaac tgattttct gtttctagct ctgcatcaac      540
ggacaccgtt acatcttctt cctcttctag cctttcagtg ctgccttcat ctctttcagt    600
ttttcaaaat cccacagatg tgtcacggag caaccccaag tcaccacaaa aacctatcgt    660
tagagtcttc ctgcccaata aacagaggac agtggtacct gcacggtgtg gagtcacagt    720
ccgggacagc ctgaagaagg cactgatgat gagaggtcta atcccagagt gctgtgctgt    780
ttacagaatt caggatgggg agaagaaacc aattggctgg gacactgata tttcctggct    840
tactggagag gagttgcatg tagaagtgtt ggagaatgtt ccacttacaa cacacaactt    900

```
tgtacggaaa actttttca ccttagcatt ttgtgacttc tgtagaaagc tgcttttcca      960
gggattccgc tgtcaaacat gtggttataa atttcaccag cgttgtagta cagaggttcc     1020
actgatgtgt gttaattatg accaactaga tttgctgttt gtctccaagt tctttgaaca     1080
ccacccaata ccacaggagg aggcctcctt agcagagact acccttccat gtggctcatc     1140
cccttctgca ccccctccg attctattgg gcccccaatt ctcaccagtc catctccttc      1200
aaaatccatt ccaattccac agcctttccg accagcagat gaagatcatc gaaatcagtt     1260
tggacaacga gaccggtcct catcagctcc aaatgtgcat ataaacacaa tagaacccgt     1320
caatattgat gacttgatta gagaccaagg gtttcgtagt gatggaggat caaccacagg     1380
tttatccgcc acacccctg cctcattacc tggctcactc tctaatgtga agcattgca       1440
gaaatctcca ggacctcagc gagaaagaaa gtcctcttca tcctcagaag acaggaatcg     1500
aatgaaaacg cttggtagac gggattcaag tgacgattgg gagattcctg atggacagat     1560
cacagtggga caaagaattg gatcagggtc atttgggaca gtctacaagg gaaagtggca     1620
tggtgatgtg gcagtgaaaa tgttgaatgt gacagcaccc acacctcagc agttacaggc     1680
cttcaaaaat gaagtaggag tactcaggaa aacgcgacat gtgaatatcc tcctcttcat     1740
gggttattca acaaagccac aactggctat tgttacccag tggtgtgagg gctccagttt     1800
atatcatcat ctccacatca ttgagaccaa attcgagatg atcaaactta tagatattgc     1860
acggcagact gcacagggca tggattactt acacgccaag tcaatcatcc acagagacct     1920
caagagtaat aatatttttc ttcatgaaga cctcacagta aaaataggtg attttggtct     1980
agccacagtg aaatctcgat ggagtgggtc ccatcagttt gaacagttgt ctggatccat     2040
tttgtggatg gcaccagaag taatcagaat gcaagataaa aacccatata gctttcagtc     2100
agatgtatat gcatttggga ttgttctgta tgaattgatg accggacagt taccttattc     2160
aaatatcaac aacagggacc agtctgtgca aggaaaagag acaaagccac ggatcagaag     2220
cacatggcca taactgaaga ttttgtgaac tctcacaagg aaaaaatttg ctctttgaac     2280
aataagaagg aactcactaa aatgtaactg agaactgttc aacaggttga agctgaaag      2340
atgccattgg aactgacaaa atgttctta aacataaatg atgaaacagt gaaactacat      2400
aatatctcct ctggctgaaa cattcaagaa gtttaaaatg cttaagttaa aaataaaatc     2460
ctagtaaaca atggacttac tgtgcaacat agagaatatc ttacgataac ctgtaatgga    2520
aaagaatctg aaaaagaatg tatataactg aatcactttg ctgtaaacta gaatctgaca    2580
caacactgta aatcactaca cttttctgtt gcatgccaaa gattatttaa taacgtcatt     2640
aaaaaattat tttaataatt a                                             2661

<210> SEQ ID NO 38
<211> LENGTH: 679
<212> TYPE: PRT
<213> ORGANISM: Bos taurus

<400> SEQUENCE: 38

Met Ala Ala Leu Ser Gly Gly Gly Gly Gly Gly Gly Gly Gly Ala Glu
1               5                   10                  15

Gln Gly Gln Ala Leu Phe Asn Gly Asp Met Glu Pro Glu Ala Gly Ala
            20                  25                  30

Ala Ala Ser Ser Ala Ala Asp Pro Ala Ile Pro Glu Glu Val Trp Asn
        35                  40                  45

Ile Lys Gln Met Ile Lys Leu Thr Gln Glu His Ile Glu Ala Leu Leu
    50                  55                  60
```

```
Asp Lys Phe Gly Gly Glu His Asn Pro Pro Ser Ile Tyr Leu Glu Ala
 65                  70                  75                  80

Tyr Glu Glu Tyr Thr Ser Lys Leu Asp Ala Leu Gln Gln Arg Glu Gln
                 85                  90                  95

Gln Leu Leu Glu Ser Leu Gly Asn Gly Thr Asp Phe Ser Val Ser Ser
                100                 105                 110

Ser Ala Ser Thr Asp Thr Val Thr Ser Ser Ser Ser Ser Ser Leu Ser
                115                 120                 125

Val Leu Pro Ser Ser Leu Ser Val Phe Gln Asn Pro Thr Asp Val Ser
130                 135                 140

Arg Ser Asn Pro Lys Ser Pro Gln Lys Pro Ile Val Arg Val Phe Leu
145                 150                 155                 160

Pro Asn Lys Gln Arg Thr Val Val Pro Ala Arg Cys Gly Val Thr Val
                165                 170                 175

Arg Asp Ser Leu Lys Lys Ala Leu Met Met Arg Gly Leu Ile Pro Glu
                180                 185                 190

Cys Cys Ala Val Tyr Arg Ile Gln Asp Gly Glu Lys Lys Pro Ile Gly
                195                 200                 205

Trp Asp Thr Asp Ile Ser Trp Leu Thr Gly Glu Glu Leu His Val Glu
210                 215                 220

Val Leu Glu Asn Val Pro Leu Thr Thr His Asn Phe Val Arg Lys Thr
225                 230                 235                 240

Phe Phe Thr Leu Ala Phe Cys Asp Phe Cys Arg Lys Leu Leu Phe Gln
                245                 250                 255

Gly Phe Arg Cys Gln Thr Cys Gly Tyr Lys Phe His Gln Arg Cys Ser
                260                 265                 270

Thr Glu Val Pro Leu Met Cys Val Asn Tyr Asp Gln Leu Asp Leu Leu
                275                 280                 285

Phe Val Ser Lys Phe Phe Glu His His Pro Ile Pro Gln Glu Glu Ala
                290                 295                 300

Ser Leu Ala Glu Thr Thr Leu Pro Cys Gly Ser Ser Pro Ser Ala Pro
305                 310                 315                 320

Pro Ser Asp Ser Ile Gly Pro Pro Ile Leu Thr Ser Pro Ser Pro Ser
                325                 330                 335

Lys Ser Ile Pro Ile Pro Gln Pro Phe Arg Pro Ala Asp Glu Asp His
                340                 345                 350

Arg Asn Gln Phe Gly Gln Arg Asp Arg Ser Ser Ser Ala Pro Asn Val
                355                 360                 365

His Ile Asn Thr Ile Glu Pro Val Asn Ile Asp Asp Leu Ile Arg Asp
                370                 375                 380

Gln Gly Phe Arg Ser Asp Gly Gly Ser Thr Thr Gly Leu Ser Ala Thr
385                 390                 395                 400

Pro Pro Ala Ser Leu Pro Gly Ser Leu Ser Asn Val Lys Ala Leu Gln
                405                 410                 415

Lys Ser Pro Gly Pro Gln Arg Glu Arg Lys Ser Ser Ser Ser Ser Glu
                420                 425                 430

Asp Arg Asn Arg Met Lys Thr Leu Gly Arg Arg Asp Ser Ser Asp Asp
                435                 440                 445

Trp Glu Ile Pro Asp Gly Gln Ile Thr Val Gly Gln Arg Ile Gly Ser
                450                 455                 460

Gly Ser Phe Gly Thr Val Tyr Lys Gly Lys Trp His Gly Asp Val Ala
465                 470                 475                 480
```

Val Lys Met Leu Asn Val Thr Ala Pro Thr Pro Gln Gln Leu Gln Ala
            485                 490                 495

Phe Lys Asn Glu Val Gly Val Leu Arg Lys Thr Arg His Val Asn Ile
        500                 505                 510

Leu Leu Phe Met Gly Tyr Ser Thr Lys Pro Gln Leu Ala Ile Val Thr
            515                 520                 525

Gln Trp Cys Glu Gly Ser Ser Leu Tyr His His Leu His Ile Ile Glu
        530                 535                 540

Thr Lys Phe Glu Met Ile Lys Leu Ile Asp Ile Ala Arg Gln Thr Ala
545                 550                 555                 560

Gln Gly Met Asp Tyr Leu His Ala Lys Ser Ile Ile His Arg Asp Leu
                565                 570                 575

Lys Ser Asn Asn Ile Phe Leu His Glu Asp Leu Thr Val Lys Ile Gly
            580                 585                 590

Asp Phe Gly Leu Ala Thr Val Lys Ser Arg Trp Ser Gly Ser His Gln
        595                 600                 605

Phe Glu Gln Leu Ser Gly Ser Ile Leu Trp Met Ala Pro Glu Val Ile
    610                 615                 620

Arg Met Gln Asp Lys Asn Pro Tyr Ser Phe Gln Ser Asp Val Tyr Ala
625                 630                 635                 640

Phe Gly Ile Val Leu Tyr Glu Leu Met Thr Gly Gln Leu Pro Tyr Ser
                645                 650                 655

Asn Ile Asn Asn Arg Asp Gln Ser Val Gln Gly Lys Glu Thr Lys Pro
            660                 665                 670

Arg Ile Arg Ser Thr Trp Pro
        675

<210> SEQ ID NO 39
<211> LENGTH: 7434
<212> TYPE: DNA
<213> ORGANISM: Bos taurus

<400> SEQUENCE: 39
acaccgttac atcttcttcc tcttctagcc tttcagtgct gccttcatct ctttcagttt     60
ttcaaaatcc cacagatgtg tcacggagca accccaagtc accacaaaaa cctatcgtta    120
gagtcttcct gcccaataaa cagaggacag tggtacctgc acggtgtgga gtcacagtcc    180
gggacagcct gaagaaggca ctgatgatga gaggtctaat cccagagtgc tgtgctgttt    240
acagaattca ggatggggag aagaaaccaa ttggctggga cactgatatt tcctggctta    300
ctggagagga gttgcatgta gaagtgttgg agaatgttcc acttacaaca cacaactttg    360
tacggaaaac ttttttcacc ttagcatttt gtgacttctg tagaaagctg cttttccagg    420
gattccgctg tcaaacatgt ggttataaat ttcaccagcg ttgtagtaca gaggttccac    480
tgatgtgtgt taattatgac caactagatt tgctgtttgt ctccaagttc tttgaacacc    540
acccaatacc acaggaggag gcctccttag cagagactac ccttccatgt ggctcatccc    600
cttctgcacc cccctccgat tctattgggc cccaattct caccagtcca tctccttcaa    660
aatccattcc aattccacag cctttccgac cagcagatga agatcatcga aatcagtttg    720
gacaacgaga ccggtcctca tcagctccaa atgtgcatat aaacacaata gaacccgtca    780
atattgatga cttgattaga gaccaagggt ttcgtagtga tggaggatca accacaggtt    840
tatccgccac accccctgcc tcattacctg gctcactctc taatgtgaaa gcattgcaga    900
aatctccagg acctcagcga gaaagaaagt cctcttcatc ctcagaagac aggaatcgaa    960

```
tgaaaacgct tggtagacgg gattcaagtg acgattggga gattcctgat ggacagatca    1020
cagtgggaca aagaattgga tcagggtcat ttgggacagt ctacaaggga aagtggcatg    1080
gtgatgtggc agtgaaaatg ttgaatgtga cagcacccac acctcagcag ttacaggcct    1140
tcaaaaatga agtaggagta ctcaggaaaa cgcgacatgt gaatatcctc ctcttcatgg    1200
gttattcaac aaagccacaa ctggctattg ttacccagtg gtgtgagggc tccagtttat    1260
atcatcatct ccacatcatt gagaccaaat tcgagatgat caaacttata gatattgcac    1320
ggcagactgc acagggcatg gattacttac acgccaagtc aatcatccac agagacctca    1380
agagtaataa tatttttctt catgaagacc tcacagtaaa aataggtgat tttggtctag    1440
ccacagtgaa atctcgatgg agtgggtccc atcagtttga acagttgtct ggatccattt    1500
tgtggatggc accagaagta atcagaatgc aagataaaaa cccatatagc tttcagtcag    1560
atgtatatgc atttgggatt gttctgtatg aattgatgac cggacagtta ccttattcaa    1620
atatcaacaa cagggaccag ataattttta tggtgggacg aggatatctg tctccagatc    1680
tcagtaaggt acggagtaac tgtccaaaag ccatgaagag attaatggca gagtgcctaa    1740
aaaagaaaag agatgaaaga ccactctttc cccaagtagg aaagactctc ctaagcaaga    1800
gacaaaattc agaagttatc agggaaaaag ataagcagat tctcgcctct attgagctgc    1860
tggcccgctc attgccaaaa attcaccgca gtgcatcaga accctccttg aatcgggctg    1920
gcttccaaac agaggatttt agtctatatg cttgtgcttc tccaaaaaca cccattcagg    1980 caggggata tggagaattt gcagccttca gtagccaca ccatcatgac agcatctact    2040
cttatttctt aagtcttgtg ttcgtacaat ttgttaacat caaaacacag ttctgttcct    2100
caactctttt taaagttaaa attttcagt gcataagctg gtgtggaaca aaggaaatt    2160 tcccatccaa caaagagggg aagaatgttt taggaaccag aattctctgc tgccagtgtt    2220
tcttcttcaa cacaaatatc acaagtctgc ccactcccag gaagaaagag gagagaccct    2280
gagttctgac cttttgatgg tcaggcatga tggaaagaaa ctgctgctac agcttgggag    2340
atttgctctg ggaagtctgc cagtcaactt tgcccttcta accaccagat caatatgtgg    2400
ctgatcatct gatggggcag ttgcaatcac caagccttgt tctcttttcct gttctgggat    2460 tgtgttgtgg aaccctttc cctagccacc accagttcat ttctgaggga tggaacaaaa    2520
atgcagcatg cccttcctgt gtggtgcatg ttcagtcctt gacaaatttt taccaaaatg    2580
aagctacttt atttaaaagg agggtgagag gtgaggaggt cactttgggt gtggcggaaa    2640
gggaatgctg catcttttc ctgggctgct ggggctctgg ccttggcttg ccagccggaa    2700
gcgctggcac gcatcgcctt cttttcccat tgggtccagc aatgaagacg agtgtttggg    2760
gttttttttt tctccaccat gtagcaagtt ctcaggaaaa tacaattgat atcttcctcc    2820
taagctcttc caatcagtca ccaagtactt atgtggttac tttgtccagg gcacaaaatg    2880
cctgtatcta attaaaagcc tacaaaactg cttgataaca gttttgaatg tgagacattt    2940
atgtaattta aatgtaaggt acaagttta atttctgagt ttcttctatt atattttat    3000 taaaaaaga aataattttt cagattgaat tggagtaaaa taatattact tcccactaga    3060
attatatatc ctggaaaatt gtattttgt tacataagca gcttttaaag aaagatcatt    3120 accctttct ctacataaat atatggggag tcttagccta atgacaaata tttataattt    3180
ttaaattaat ggtacttgct ggatccatac taacatcttt actaatacct cattgtttct    3240
tccaacttac tcctacacta catcctacat cttcttccta gtcttttatc tagaatatgc    3300
aacctcaaat aaaaatggtg gtgtcctcat tcattctcct ccttcctttt ttcccaagcc    3360
```

```
tgatcttcaa aaggttggtt aatttggcag ctgagttcct ccccaggcag agaatagacc    3420
aattttaggt gtattgggac tgagggagga tgtgtaaaga ttaacatcag taaagaaccg    3480
ctgtggagta attaagaact tgttctttta taactggaga atataaccta accctaacat    3540
ccctcagcct ttactaaagt gtggcgtaaa tcacagtagt agcaaagaaa gtgactctgg    3600
atgtgttcct ggccagtacc tcccttatca tgaatgtaga ctctctcatc aagatttagg    3660
aatataaatc aaatcaaatg tgcccagcca agctatgtag taagggactt gaacaatatt    3720
aggcagaacc tataaaataa atcagggaat tagaaattat ttaaagtttt caaattgtaa    3780
attgccccgg tgtctttcag cctactgcca ttattttgc tacaataccct acatttcaga    3840 ggagggccta ctgaaaattc catgcaagtg gaaaataatc ctcaagttat taatgagttt    3900
gaaaagcaat gagttcttaa gtcttttgtga gtagagcaag atcctacaaa attcagaaat    3960
agtaaaaatg gattcatgct gatttgaaga gcatctgtgt gcataatata atgctgcatc    4020
tcttttaaaa gcagtctatt tttcttttta aatttgtccc catagatgct tttgaacatg    4080
aacatgctta tgttaccttt tccgaggttg ggaagagcca ggagctctca ggcagggccc    4140
cctccctcag ctgggcagga gctgctcagg aggagctagt tatagaggaa gcttagcgtt    4200
ggcattttca aaattcaagg tgataacgct ttcttcttcc tttctgtttt agaatagatt    4260
gctgtctgat ttgaaaaagg gaaatagatt tgatctcaaa tgaatctgtg cccgaaagcc    4320
aggctcaggg tattcagaga tttgtatagt gccctcaaaa aataacaaaa ttttagcttt    4380
ccttttttct tcttttctcc atcaaattct tttttctcta gtttacaaat gacatggaaa    4440
aggaatttcc cctgagtttt gtatgccttt ttttttttgg cttagactat agataggcgt    4500
gttgagctcc taagaaaata caaggaggaa ctctttgttg tgcagagcac tttatgagta    4560
gtttgtgtgg ataatatgtg actgcttccc tgacgagctt gtgaggctgt acttatgtct    4620
ttcctgtaag gcagcttcag tgccttctgt agtgtatata aggaaagatt acgccttctg    4680
aaaaatctca gagcaaccat aagattattt taaaatatgt agtatgactg atggactttt    4740
tcatcattaa attagtctag catctaaaact tttaccactg aaataatatt gaccaaaaag    4800
caatttataa aaggtatttg tgaatagaaa atacaatgtg atcatttgta cttatgtgca    4860
ccttaaaaga ggaattctgt ctagctgtca aattctggtt ccttaacatc cagtccttga    4920
ttgtgattga gatctggtag gacgtgctgg ggcacgctag cagataaaat cccgtatact    4980
ttaggataga tgttacattt atgtcagtgt tggcaaagag cattgtgtag taataaagaa    5040
ttcaagactt cagcaatgtc aacctgaaac tttgtaaata tttcctagat tgttatttga    5100
tgcagtcaca gctctttatc acacaatgtt gtctttccct catcaggcaa ttttagaact    5160
gctgcacacc cctcctcaga tctcacctgc ccctcctgta cattcacctc tccagccttg    5220
tgcacacctc atttagcttt agtttgaaac acattgcagg gttcaggtga cctcttcaaa    5280
aactacctcc tcagaatgag gtaatgaata gttatttatt ttaaaatatg aaaagtcagg    5340
agctctagaa tatgaagatg atctaagatt ttaacttta tgtatacttg ttgagcactc    5400
tccttttgtc ctaaagggca ttatacattt aagcagtaat actgaaaaat gtagctcaga    5460
gtaactgaat gttgttgaaa gtggtgccag aatctgtttt aggggtacgt atcagaatct    5520
taatcttaaa tcggttacat gaaattaaat agttaatggt aacacttgac taacagatat    5580
aattttaatt ttcggtaggc ttttagcaag acagtaagta catcttcata atgagttagc    5640
cacagcttca tcacatgcac agatttttcct gttgagagac tgcccagtta agagggtaga    5700
```

-continued

```
atgatgaacc attttttcagg attctcttct ttgtccaaac tggcattgtg agtgctagaa    5760
tatcagcact ttcaaactag tgattccaac tattaggcta ttaaaaagca aaacaaacca    5820
aacaaaccat agccagacat gggaagttta ctatgagtat aaacagcaaa tagcttacag    5880
gtcatacatt gaaatggtgt aggtaaggcg ttagaaaaat accttgacaa tttgccaaat    5940
gatcttactg tgccttcatg atgcaataaa aaaaaaaaaa atttagcata aatcagtgat    6000
ttgtgaagag agcagccacc ctggtctaac tcagctgtgt taatattttt tagcgtgcaa    6060
tttagactgc aaagataaat gcactaaaga gtttatagcc aaaatcacat ttaaaaaatg    6120
agagaaaaca caggtaaatt ttcagtgaac aaaattattt ttttaaagta cataatccct    6180
agtatagtca gatatattta tcacatagag caaataggtt gaaatcacaa ttcagtgaca    6240
tttctagaga aactttttct actcccatag gttcttcaaa gcatggaact tttatataac    6300
agaaatgtgt gacggtcatt ttaaattgct gtagtttggg gctgaagtac tgtgtgctgg    6360
gcagcaatca catgtattaa ctagtgagaa aggagaaatt aagatatagg acagaatttg    6420
attttcttgt tcccagatta ctgctgccaa cctagacact gagtttccag aggctgaaac    6480
gtaaacttgc agctcagcaa ctgttttgca aagttagtgg gactgtcctg cttatgctgt    6540
tcaaaaatgc tctgagggcc aggtgggcc tccagggcc cctctctgag gggacatcag    6600
actagctaac gacctggcgg gcggatgtga accggacaca ctccatggtg tgcttcttgt    6660
atcggtccct cgccaccctc aagaaaggct tcagcgggtt ctctagacgt ctccactaag    6720
gtgtgttact aacagccatg ggttgttgag cacccgagga gtgcaatagc atctctgcat    6780
gattgtatat tggcccgaag agaatgaagt ggccagtgta ctcatgttcc atgttgctag    6840
ctctggtaaa ctgaaaatac tggtaagatt tttgtttttat cagtacacta gagagtaagc    6900
tttgttttgt tgttttttaga taatgttttc acttccatttt ggaaagacat ttaaattgag    6960
tttcagtcct aaattttgcc agtcatggta attagcagtt tctatcaggt atttttaagg    7020
tagaagagga tagaaacata agttctaaaa gcttaaggta accgtggttt attttaaaat    7080
gtttaggggt ggttagtctc tacctcaaaa aaagtgagtg aatctttttat ttcagcattc    7140 acaagttcgg ctgttgtttt tgtaatacat ttttttttta acctttttgac ccccctttac    7200 ctaagtgtca atgtagtttt attaattact aagtcagttt cattaaaatg tttatttagc    7260
agttttgact aattgcaatg attaatatag ccagttgtgc atgaggacac agccagtgag    7320
tatatctggg ttttttttgt gatgcttttt ttcttaagac ttctgtagat ttatgaagta    7380
ctcattgaaa acaactaaaa tacgtttatt cgtgttaata tggaaaaaaa aaaa    7434
```

<210> SEQ ID NO 40
<211> LENGTH: 603
<212> TYPE: PRT
<213> ORGANISM: Bos taurus

<400> SEQUENCE: 40

Met Met Arg Gly Leu Ile Pro Glu Cys Cys Ala Val Tyr Arg Ile Gln
1               5                   10                  15

Asp Gly Glu Lys Lys Pro Ile Gly Trp Asp Thr Asp Ile Ser Trp Leu
            20                  25                  30

Thr Gly Glu Glu Leu His Val Glu Leu Glu Asn Val Pro Leu Thr
        35                  40                  45

Thr His Asn Phe Val Arg Lys Thr Phe Phe Thr Leu Ala Phe Cys Asp
    50                  55                  60

Phe Cys Arg Lys Leu Leu Phe Gln Gly Phe Arg Cys Gln Thr Cys Gly

-continued

```
                65                  70                  75                  80
Tyr Lys Phe His Gln Arg Cys Ser Thr Glu Val Pro Leu Met Cys Val
                    85                  90                  95

Asn Tyr Asp Gln Leu Asp Leu Leu Phe Val Ser Lys Phe Phe Glu His
                100                 105                 110

His Pro Ile Pro Gln Glu Glu Ala Ser Leu Ala Glu Thr Thr Leu Pro
                115                 120                 125

Cys Gly Ser Ser Pro Ser Ala Pro Pro Ser Asp Ser Ile Gly Pro Pro
            130                 135                 140

Ile Leu Thr Ser Pro Ser Pro Ser Lys Ser Ile Pro Ile Pro Gln Pro
145                 150                 155                 160

Phe Arg Pro Ala Asp Glu Asp His Arg Asn Gln Phe Gly Gln Arg Asp
                165                 170                 175

Arg Ser Ser Ser Ala Pro Asn Val His Ile Asn Thr Ile Glu Pro Val
                180                 185                 190

Asn Ile Asp Asp Leu Ile Arg Asp Gln Gly Phe Arg Ser Asp Gly Gly
            195                 200                 205

Ser Thr Thr Gly Leu Ser Ala Thr Pro Pro Ala Ser Leu Pro Gly Ser
    210                 215                 220

Leu Ser Asn Val Lys Ala Leu Gln Lys Ser Pro Gly Pro Gln Arg Glu
225                 230                 235                 240

Arg Lys Ser Ser Ser Ser Glu Asp Arg Asn Arg Met Lys Thr Leu
                245                 250                 255

Gly Arg Arg Asp Ser Ser Asp Asp Trp Glu Ile Pro Asp Gly Gln Ile
            260                 265                 270

Thr Val Gly Gln Arg Ile Gly Ser Gly Ser Phe Gly Thr Val Tyr Lys
        275                 280                 285

Gly Lys Trp His Gly Asp Val Ala Val Lys Met Leu Asn Val Thr Ala
    290                 295                 300

Pro Thr Pro Gln Gln Leu Gln Ala Phe Lys Asn Glu Val Gly Val Leu
305                 310                 315                 320

Arg Lys Thr Arg His Val Asn Ile Leu Leu Phe Met Gly Tyr Ser Thr
                325                 330                 335

Lys Pro Gln Leu Ala Ile Val Thr Gln Trp Cys Glu Gly Ser Ser Leu
            340                 345                 350

Tyr His His Leu His Ile Ile Glu Thr Lys Phe Glu Met Ile Lys Leu
        355                 360                 365

Ile Asp Ile Ala Arg Gln Thr Ala Gln Gly Met Asp Tyr Leu His Ala
    370                 375                 380

Lys Ser Ile Ile His Arg Asp Leu Lys Ser Asn Asn Ile Phe Leu His
385                 390                 395                 400

Glu Asp Leu Thr Val Lys Ile Gly Asp Phe Gly Leu Ala Thr Val Lys
                405                 410                 415

Ser Arg Trp Ser Gly Ser His Gln Phe Glu Gln Leu Ser Gly Ser Ile
            420                 425                 430

Leu Trp Met Ala Pro Glu Val Ile Arg Met Gln Asp Lys Asn Pro Tyr
        435                 440                 445

Ser Phe Gln Ser Asp Val Tyr Ala Phe Gly Ile Val Leu Tyr Glu Leu
    450                 455                 460

Met Thr Gly Gln Leu Pro Tyr Ser Asn Ile Asn Asn Arg Asp Gln Ile
465                 470                 475                 480

Ile Phe Met Val Gly Arg Gly Tyr Leu Ser Pro Asp Leu Ser Lys Val
                485                 490                 495
```

```
Arg Ser Asn Cys Pro Lys Ala Met Lys Arg Leu Met Ala Glu Cys Leu
                500                 505                 510
Lys Lys Lys Arg Asp Glu Arg Pro Leu Phe Pro Gln Val Gly Lys Thr
            515                 520                 525
Leu Leu Ser Lys Arg Gln Asn Ser Glu Val Ile Arg Glu Lys Asp Lys
530                 535                 540
Gln Ile Leu Ala Ser Ile Glu Leu Leu Ala Arg Ser Leu Pro Lys Ile
545                 550                 555                 560
His Arg Ser Ala Ser Glu Pro Ser Leu Asn Arg Ala Gly Phe Gln Thr
                565                 570                 575
Glu Asp Phe Ser Leu Tyr Ala Cys Ala Ser Pro Lys Thr Pro Ile Gln
                580                 585                 590
Ala Gly Gly Tyr Gly Glu Phe Ala Ala Phe Lys
            595                 600
```

<210> SEQ ID NO 41
<211> LENGTH: 2295
<212> TYPE: DNA
<213> ORGANISM: Equus caballus
<220> FEATURE:
<221> NAME/KEY: misc_feature
<222> LOCATION: (79)..(79)
<223> OTHER INFORMATION: n is a, c, g, or t

<400> SEQUENCE: 41

| | | |
|---|---|---|
| atgaagacgc tgagcggcgg cggcggcggc gcggagcagg gccaggctct gttcaacggg | 60 |
| gacatggaac ccgaggcnc cgcgccggcg cccgcggcct cgtcggccgc ggaccctgcc | 120 |
| attcccgagg aggtatggaa tatcaaacaa atgattaaat tgacacagga acatatagag | 180 |
| gccctattgg acaaatttgg tggggagcat aatccaccat caatatatct ggaggcctat | 240 |
| gaagaataca ccagcaagct agatgccctc aacaaagag aacaacagtt attggaatcc | 300 |
| ctggggaatg gaactgattt ttctgtttct agttctgcat caacggacac cgttacatct | 360 |
| tcttcctctt ctagcctttc agtgctacct tcatctcttt cagttttca aaatcccaca | 420 |
| gatgtgtcac ggagcaaccc taagtcacca caaaaaccta cgttagagt cttcctgccc | 480 |
| aacaaacaga ggacagtggt acctgcaagg tgtggcgtta cagtccggga cagtctaaag | 540 |
| aaagcactga tgatgagagg tctaatccca gagtgctgtg ctgtttacag aattcaggat | 600 |
| ggagagaaga accaattggg ctgggacact gatatttcct ggctcactgg agaggaattg | 660 |
| catgtagaag tgttggagaa tgttccactt acaacacaca actttgtacg gaaaactttt | 720 |
| ttcaccttag cattttgtga cttttgtcga agctgctttt ccagggttt ccgctgtcaa | 780 |
| acatgtggtt ataaatttca ccagcgttgt agtacagagg ttccactgat gtgtgttaat | 840 |
| tatgaccaac ttgatttgct gtttgtctcc aagttctttg aacaccaccc agtatcacag | 900 |
| gaggaggcct ccttagcaga gactgcccctt acatctggat catcccttc tgcacccccc | 960 |
| tccgattcca ttgggcccca aattctcacc agtccatctc cttcaaaatc cattccaatt | 1020 |
| ccacagcctt tccgaccagc agatgaagat catcgaaatc agtttggaca acgagaccgg | 1080 |
| tcctcatcag ctccaaatgt acatataaac acaatagaac ctgtcaatat tgatgacttg | 1140 |
| attagagacc aagggtttcg tagtgatgga ggatcaacca caggtttatc tgccaccccc | 1200 |
| cctgcctcat tacctggctc actcactaat gtgaaggcat acagaaatc tccaggacct | 1260 |
| caacgggaaa ggaaatcatc ttcatcctca gaagacagga atcgaatgaa aactcttggt | 1320 |
| agacgggatt caagtgacga ttgggagatt cctgatgggc agatcacagt gggacaaaga | 1380 |

```
attggatctg ggtcatttgg gacagtctac aagggaaagt ggcatggtga tgtggcagtg    1440
aaaatgttga atgtgacagc acccacacct cagcagttac aggccttcaa aaatgaagta    1500
ggagtactca ggaaaactcg acatgtgaat atcctactct tcatgggcta ttcaacaaag    1560
ccacaactgg ctattgttac ccagtggtgt gagggctcca gcttatatca ccatctccac    1620
atcattgaga ccaaatttga gatgatcaaa cttatagata ttgctcggca aactgcacag    1680
ggcatggatt acttacacgc caagtcaatc atccacagag acctcaagag taataatatt    1740
tttcttcatg aagacctcac agtaaaaata ggtgattttg gtctagccac agtgaaatct    1800
cgatggagtg ggtcccatca gtttgaacag ttgtctggat ccatttttgtg gatggcacca    1860 gaagtaatca gaatgcaaga taaaaacccg tatagctttc aatcagatgt atatgccttt    1920
gggattgttc tgtatgaatt gatgactgga cagttacctt attcaaacat caacaacagg    1980
gaccagataa ttttatggt gggaagagga tatctatctc cagatctcag taaggtacgg    2040
agtaactgtc caaaagccat gaagagatta atggcagagt gcctaaaaaa gaaaagagac    2100
gagagaccac tcttccccca aattctcgcc tctattgagc tgctggcccg ctcattgcca    2160
aaaattcacc gcagtgcatc agagccctcc ttgaatcggg ctggcttcca gacagaggat    2220
tttagtctat atgcttgtgc ttctccgaaa acacccatcc aggcagggggg atatggtgcg    2280 tttcctgtcc actga                                                     2295

<210> SEQ ID NO 42
<211> LENGTH: 764
<212> TYPE: PRT
<213> ORGANISM: Equus caballus
<220> FEATURE:
<221> NAME/KEY: misc_feature
<222> LOCATION: (27)..(27)
<223> OTHER INFORMATION: Xaa can be any naturally occurring amino acid

<400> SEQUENCE: 42

Met Lys Thr Leu Ser Gly Gly Gly Gly Ala Glu Gln Gly Gln Ala
1               5                   10                  15

Leu Phe Asn Gly Asp Met Glu Pro Gly Gly Xaa Ala Pro Ala Pro Ala
            20                  25                  30

Ala Ser Ser Ala Ala Asp Pro Ala Ile Pro Glu Glu Val Trp Asn Ile
        35                  40                  45

Lys Gln Met Ile Lys Leu Thr Gln Glu His Ile Glu Ala Leu Leu Asp
    50                  55                  60

Lys Phe Gly Gly Glu His Asn Pro Pro Ser Ile Tyr Leu Glu Ala Tyr
65                  70                  75                  80

Glu Glu Tyr Thr Ser Lys Leu Asp Ala Leu Gln Gln Arg Glu Gln Gln
                85                  90                  95

Leu Leu Glu Ser Leu Gly Asn Gly Thr Asp Phe Ser Val Ser Ser Ser
            100                 105                 110

Ala Ser Thr Asp Thr Val Thr Ser Ser Ser Ser Leu Ser Val
        115                 120                 125

Leu Pro Ser Ser Leu Ser Val Phe Gln Asn Pro Thr Asp Val Ser Arg
    130                 135                 140

Ser Asn Pro Lys Ser Pro Gln Lys Pro Ile Val Arg Val Phe Leu Pro
145                 150                 155                 160

Asn Lys Gln Arg Thr Val Val Pro Ala Arg Cys Gly Val Thr Val Arg
                165                 170                 175

Asp Ser Leu Lys Lys Ala Leu Met Met Arg Gly Leu Ile Pro Glu Cys
```

```
            180                 185                 190
Cys Ala Val Tyr Arg Ile Gln Asp Gly Glu Lys Lys Pro Ile Gly Trp
            195                 200                 205
Asp Thr Asp Ile Ser Trp Leu Thr Gly Glu Glu Leu His Val Glu Val
            210                 215                 220
Leu Glu Asn Val Pro Leu Thr Thr His Asn Phe Val Arg Lys Thr Phe
225                 230                 235                 240
Phe Thr Leu Ala Phe Cys Asp Phe Cys Arg Lys Leu Leu Phe Gln Gly
                245                 250                 255
Phe Arg Cys Gln Thr Cys Gly Tyr Lys Phe His Gln Arg Cys Ser Thr
            260                 265                 270
Glu Val Pro Leu Met Cys Val Asn Tyr Asp Gln Leu Asp Leu Leu Phe
            275                 280                 285
Val Ser Lys Phe Phe Glu His His Pro Val Ser Gln Glu Glu Ala Ser
            290                 295                 300
Leu Ala Glu Thr Ala Leu Thr Ser Gly Ser Ser Pro Ser Ala Pro Pro
305                 310                 315                 320
Ser Asp Ser Ile Gly Pro Gln Ile Leu Thr Ser Pro Ser Pro Ser Lys
                325                 330                 335
Ser Ile Pro Ile Pro Gln Pro Phe Arg Pro Ala Asp Glu Asp His Arg
            340                 345                 350
Asn Gln Phe Gly Gln Arg Asp Arg Ser Ser Ser Ala Pro Asn Val His
            355                 360                 365
Ile Asn Thr Ile Glu Pro Val Asn Ile Asp Asp Leu Ile Arg Asp Gln
            370                 375                 380
Gly Phe Arg Ser Asp Gly Gly Ser Thr Thr Gly Leu Ser Ala Thr Pro
385                 390                 395                 400
Pro Ala Ser Leu Pro Gly Ser Leu Thr Asn Val Lys Ala Leu Gln Lys
                405                 410                 415
Ser Pro Gly Pro Gln Arg Glu Arg Lys Ser Ser Ser Ser Glu Asp
            420                 425                 430
Arg Asn Arg Met Lys Thr Leu Gly Arg Arg Asp Ser Ser Asp Asp Trp
            435                 440                 445
Glu Ile Pro Asp Gly Gln Ile Thr Val Gly Gln Arg Ile Gly Ser Gly
            450                 455                 460
Ser Phe Gly Thr Val Tyr Lys Gly Lys Trp His Gly Asp Val Ala Val
465                 470                 475                 480
Lys Met Leu Asn Val Thr Ala Pro Thr Pro Gln Gln Leu Gln Ala Phe
                485                 490                 495
Lys Asn Glu Val Gly Val Leu Arg Lys Thr Arg His Val Asn Ile Leu
            500                 505                 510
Leu Phe Met Gly Tyr Ser Thr Lys Pro Gln Leu Ala Ile Val Thr Gln
            515                 520                 525
Trp Cys Glu Gly Ser Ser Leu Tyr His His Leu His Ile Ile Glu Thr
            530                 535                 540
Lys Phe Glu Met Ile Lys Leu Ile Asp Ile Ala Arg Gln Thr Ala Gln
545                 550                 555                 560
Gly Met Asp Tyr Leu His Ala Lys Ser Ile Ile His Arg Asp Leu Lys
                565                 570                 575
Ser Asn Asn Ile Phe Leu His Glu Asp Leu Thr Val Lys Ile Gly Asp
            580                 585                 590
Phe Gly Leu Ala Thr Val Lys Ser Arg Trp Ser Gly Ser His Gln Phe
            595                 600                 605
```

```
Glu Gln Leu Ser Gly Ser Ile Leu Trp Met Ala Pro Glu Val Ile Arg
    610                 615                 620

Met Gln Asp Lys Asn Pro Tyr Ser Phe Gln Ser Asp Val Tyr Ala Phe
625                 630                 635                 640

Gly Ile Val Leu Tyr Glu Leu Met Thr Gly Gln Leu Pro Tyr Ser Asn
                645                 650                 655

Ile Asn Asn Arg Asp Gln Ile Ile Phe Met Val Gly Arg Gly Tyr Leu
            660                 665                 670

Ser Pro Asp Leu Ser Lys Val Arg Ser Asn Cys Pro Lys Ala Met Lys
        675                 680                 685

Arg Leu Met Ala Glu Cys Leu Lys Lys Arg Asp Glu Arg Pro Leu
    690                 695                 700

Phe Pro Gln Ile Leu Ala Ser Ile Glu Leu Leu Ala Arg Ser Leu Pro
705                 710                 715                 720

Lys Ile His Arg Ser Ala Ser Glu Pro Ser Leu Asn Arg Ala Gly Phe
                725                 730                 735

Gln Thr Glu Asp Phe Ser Leu Tyr Ala Cys Ala Ser Pro Lys Thr Pro
            740                 745                 750

Ile Gln Ala Gly Gly Tyr Gly Ala Phe Pro Val His
        755                 760
```

<210> SEQ ID NO 43
<211> LENGTH: 2678
<212> TYPE: DNA
<213> ORGANISM: Gallus gallus

<400> SEQUENCE: 43

```
tcccccctccc tcgccccagc gcttcgatcc aagatggcgg cgctgagcag cggcagcagc      60
gccgaggggg cctcgctctt caacggggac atggagcccg agccgccgcc gcccgtgctg     120
ggcgcctgct acgccgggag cggcggcggc gaccccggcca tcccggagga ggtgtggaat     180
atcaaacaga tgattaaatt aacacaagaa catatagaag cgctgttaga caagtttgga     240
ggagagcata acccaccatc aatatattta gaggcctatg aggagtacac cagcaaacta     300
gatgctctac agcagagaga acagcagtta ttggaatcca tgggaaatgg aactgatttc     360
tctgttttcca gttcagcttc aacggacaca gttgcatcat cttcctcctc tagcctctct     420
gtagcacctt catcccttc agtttatcaa atcctactg atatgtcgcg gaataaccct     480
aagtctccac agaagcctat tgttagagtc ttcctgccca caagcaaag gactgtggtt     540
ccggcaagat gtgggtgac agtccgagac agcctgaaga agctctgat gatgagaggt     600
cttattccag aatgctgtgc tgtttacaga atacaggatg gagagaagaa gccaattggc     660
tgggacactg acatttcctg ctaaccgga gaggagttac acgtggaggt cttggagaat     720
gtgccactca caacacacaa ttttgtacga aaaacattct tcacgttagc gttctgcgac     780
ttctgtcgaa agctgctttt ccagggattc gatgccaga catgtggcta caaatttcac     840
cagcgctgta gcacagaagt gccactgatg tgtgttaact acgaccaact cgatttgctg     900
tttgtctcca gttcttgaa acatcacccc atatcgcagg aggagaccac cttaggagag     960
accaccccgg catcgggatc gtacccctca gtgcccccat cagattctgt tggaccacca    1020
attctcccta gtccttctcc ttcaaaatcc attccaatcc cacagccctt ccgaccagca    1080
gatgaagacc atcggaatca gtttgggcaa cgcgaccgat cctcttcagc tcccaatgtt    1140
cacatcaata caattgagcc agtcaatatt gatgacttga ttagagacca gggtgtacga    1200
```

```
ggagagggag cccctttgaa ccagctgatg cgctgtcttc ggaaatacca atcccggact    1260
cccagtcccc tccttcattc tgtcccagt  gaaatagtgt ttgattttga gcctggccca    1320
gtgttcagag gttcaactgc aggtttgtct gcaacacctc ctgcatcttt gcctgggtca    1380
cttaccaatg tgaaagcatt acagaaatca ccaggccccc aacgggaaag gaaatcatcc    1440
tcatcctcag aagacagaaa taggatgaaa acccttggtc gacgagattc aagtgatgat    1500
tgggaaatac cagatgggca gatcacagtt ggacaaagga taggatctgg atcatttgga    1560
acagtctaca aaggaaagtg gcatggtgac gtggcagtga aaatgttgaa tgttacagca    1620
cccacacctc aacagttaca ggctttcaaa aatgaagtag gagtgctcag gaaaacacgg    1680
catgtgaata tcctactttt tatgggttat tcaacaaaac ctcagttggc tattgttaca    1740
cagtggtgtg aggggtccag cttatatcac catctgcaca taattgagac caagtttgaa    1800
atgatcaaac taattgatat tgcacgacag actgcacaag gcatggatta tttgcatgcc    1860
aagtcaatca tccacagaga cctcaagagt aataatattt tcttcatga  agacctcaca    1920 gtaaaaatag gtgacttcgg tctggctaca gtgaaatcac gatggagtgg atctcatcaa    1980
tttgaacagt tatctggatc aattctatgg atggcaccgg aagtgatcag gatgcaagac    2040
aaaaacccat atagctttca gtcagatgtg tatgcattcg ggattgtgct ttatgaactg    2100
atgactggac agttaccata ctcaaacatc aacaacaggg accagataat ttttatggtg    2160
ggacgaggat atctatctcc agacctcagt aaagtaagaa gtaactgtcc aaaagctatg    2220
aagagactaa tggcagaatg cttgaaaaag aaaagagatg agagacctct ttttccacag    2280
attcttgcct ccattgagct tctggcccgg tcgttgccaa aaattcaccg cagtgcatct    2340
gagccgtcac taaaccgggc tggcttccag accgaggatt tcagtctgta tgcttgtgct    2400
tctccaaaaa cgcccatcca agcaggggga tacggtgggt ttccagtaca ctgaaaagaa    2460
atgtgaaagc gtgtgcctgt ttgctcatgt gctggtgtgt tcctgtgtgt gcaacgcata    2520
cgtacgttct cagttcctac cagcgacttt ttaaggttta ctgagggaat gaagactcat    2580
ttcctaacat ggggcattga acgtcctgag cacaagtcag tgctggtaag gaatgtcttg    2640
ggaacagctg gcaagaagaa ttagaaggta cttaaagg                            2678
```

<210> SEQ ID NO 44
<211> LENGTH: 806
<212> TYPE: PRT
<213> ORGANISM: Gallus gallus

<400> SEQUENCE: 44

```
Met Ala Ala Leu Ser Ser Gly Ser Ser Ala Glu Gly Ala Ser Leu Phe
1               5                   10                  15

Asn Gly Asp Met Glu Pro Glu Pro Pro Pro Val Leu Gly Ala Cys
            20                  25                  30

Tyr Ala Gly Ser Gly Gly Gly Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Met Gly Asn Gly Thr Asp Phe Ser Val Ser
            100                 105                 110
```

```
Ser Ser Ala Ser Thr Asp Thr Val Ala Ser Ser Ser Ser Ser Leu
            115                 120                 125

Ser Val Ala Pro Ser Ser Leu Ser Val Tyr Gln Asn Pro Thr Asp Met
130                 135                 140

Ser Arg Asn Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
            195                 200                 205

Gly Trp Asp Thr Asp Ile Ser Trp Leu Thr Gly Glu Glu Leu His Val
            210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
                260                 265                 270

Ser Thr Glu Val Pro Leu Met Cys Val Asn Tyr Asp Gln Leu Asp Leu
            275                 280                 285

Leu Phe Val Ser Lys Phe Phe Glu His His Pro Ile Ser Gln Glu Glu
            290                 295                 300

Thr Thr Leu Gly Glu Thr Thr Pro Ala Ser Gly Ser Tyr Pro Ser Val
305                 310                 315                 320

Pro Pro Ser Asp Ser Val Gly Pro Pro Ile Leu Pro Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ser Ala Pro Asn
            355                 360                 365

Val His Ile Asn Thr Ile Glu Pro Val Asn Ile Asp Asp Leu Ile Arg
            370                 375                 380

Asp Gln Gly Val Arg Gly Glu Gly Ala Pro Leu Asn Gln Leu Met Arg
385                 390                 395                 400

Cys Leu Arg Lys Tyr Gln Ser Arg Thr Pro Ser Pro Leu Leu His Ser
                405                 410                 415

Val Pro Ser Glu Ile Val Phe Asp Phe Glu Pro Gly Pro Val Phe Arg
            420                 425                 430

Gly Ser Thr Ala Gly Leu Ser Ala Thr Pro Pro Ala Ser Leu Pro Gly
            435                 440                 445

Ser Leu Thr Asn Val Lys Ala Leu Gln Lys Ser Pro Gly Pro Gln Arg
            450                 455                 460

Glu Arg Lys Ser Ser Ser Ser Ser Glu Asp Arg Asn Arg Met Lys Thr
465                 470                 475                 480

Leu Gly Arg Arg Asp Ser Ser Asp Asp Trp Glu Ile Pro Asp Gly Gln
                485                 490                 495

Ile Thr Val Gly Gln Arg Ile Gly Ser Gly Ser Phe Gly Thr Val Tyr
            500                 505                 510

Lys Gly Lys Trp His Gly Asp Val Ala Val Lys Met Leu Asn Val Thr
            515                 520                 525

Ala Pro Thr Pro Gln Gln Leu Gln Ala Phe Lys Asn Glu Val Gly Val
```

```
                530                 535                 540
Leu Arg Lys Thr Arg His Val Asn Ile Leu Leu Phe Met Gly Tyr Ser
545                 550                 555                 560

Thr Lys Pro Gln Leu Ala Ile Val Thr Gln Trp Cys Glu Gly Ser Ser
                565                 570                 575

Leu Tyr His His Leu His Ile Ile Glu Thr Lys Phe Glu Met Ile Lys
                580                 585                 590

Leu Ile Asp Ile Ala Arg Gln Thr Ala Gln Gly Met Asp Tyr Leu His
                595                 600                 605

Ala Lys Ser Ile Ile His Arg Asp Leu Lys Ser Asn Asn Ile Phe Leu
                610                 615                 620

His Glu Asp Leu Thr Val Lys Ile Gly Asp Phe Gly Leu Ala Thr Val
625                 630                 635                 640

Lys Ser Arg Trp Ser Gly Ser His Gln Phe Glu Gln Leu Ser Gly Ser
                645                 650                 655

Ile Leu Trp Met Ala Pro Glu Val Ile Arg Met Gln Asp Lys Asn Pro
                660                 665                 670

Tyr Ser Phe Gln Ser Asp Val Tyr Ala Phe Gly Ile Val Leu Tyr Glu
                675                 680                 685

Leu Met Thr Gly Gln Leu Pro Tyr Ser Asn Ile Asn Asn Arg Asp Gln
                690                 695                 700

Ile Ile Phe Met Val Gly Arg Gly Tyr Leu Ser Pro Asp Leu Ser Lys
705                 710                 715                 720

Val Arg Ser Asn Cys Pro Lys Ala Met Lys Arg Leu Met Ala Glu Cys
                725                 730                 735

Leu Lys Lys Lys Arg Asp Glu Arg Pro Leu Phe Pro Gln Ile Leu Ala
                740                 745                 750

Ser Ile Glu Leu Leu Ala Arg Ser Leu Pro Lys Ile His Arg Ser Ala
                755                 760                 765

Ser Glu Pro Ser Leu Asn Arg Ala Gly Phe Gln Thr Glu Asp Phe Ser
                770                 775                 780

Leu Tyr Ala Cys Ala Ser Pro Lys Thr Pro Ile Gln Ala Gly Gly Tyr
785                 790                 795                 800

Gly Gly Phe Pro Val His
                805

<210> SEQ ID NO 45
<211> LENGTH: 4454
<212> TYPE: DNA
<213> ORGANISM: Homo sapiens

<400> SEQUENCE: 45
gaaacgtccc gtgtgggagg ggcgggtctg ggtgcggcct ccgcatgac  tcgtggttcg      60 gaggcccacg tggccggggc ggggactcag gcgcctgggg cgccgactga ttacgtagcg     120
ggcggggccg gaagtgccgc tccttggtgg gggctgttca tggcggttcc ggggtctcca     180
acatttttcc cggctgtggt cctaaatctg tccaaagcag aggcagtgga gcttgaggtt     240
cttgctggtg tgaaatgact gagtacaaac tggtggtggt tggagcaggt ggtgttggga     300
aaagcgcact gacaatccag ctaatccaga accactttgt agatgaatat gatcccacca     360
tagaggattc ttacagaaaa caagtggtta gatggtgaa cctgtttg ttggacatac        420 tggatacagc tggacaagaa gagtacagtg ccatgagaga ccaatacatg aggacaggcg     480
aaggcttcct ctgtgtattt gccatcaata atagcaagtc atttgcggat attaacctct     540
```

```
acagggagca gattaagcga gtaaaagact cggatgatgt acctatggtg ctagtgggaa    600
acaagtgtga tttgccaaca aggacagttg atacaaaaca agcccacgaa ctggccaaga    660
gttacgggat tccattcatt gaaacctcag ccaagaccag acagggtgtt gaagatgctt    720
tttacacact ggtaagagaa atacgccagt accgaatgaa aaaactcaac agcagtgatg    780
atgggactca gggttgtatg ggattgccat gtgtggtgat gtaacaagat acttttaaag    840
ttttgtcaga aaagagccac tttcaagctg cactgacacc ctggtcctga cttccctgga    900
ggagaagtat tcctgttgct gtcttcagtc tcacagagaa gctcctgcta cttccccagc    960
tctcagtagt ttagtacaat aatctctatt tgagaagttc tcagaataac tacctcctca   1020
cttggctgtc tgaccagaga atgcacctct tgttactccc tgttattttt ctgccctggg   1080
ttcttccaca gcacaaacac acctctgcca ccccaggttt ttcatctgaa aagcagttca   1140
tgtctgaaac agagaaccaa accgcaaacg tgaaattcta ttgaaaacag tgtcttgagc   1200
tctaaagtag caactgctgg tgattttttt tttcttttta ctgttgaact tagaactatg   1260
ctaattttg gagaaatgtc ataaattact gttttgccaa gaatatagtt attattgctg   1320
tttggtttgt ttataatgtt atcggctcta ttctctaaac tggcatctgc tctagattca   1380
taaatacaaa aatgaatact gaattttgag tctatcctag tcttcacaac tttgacgtaa   1440
ttaaatccaa cttttcacagt gaagtgcctt tttcctagaa gtggtttgta gacttccttt   1500
ataatatttc agtggaatag atgtctcaaa aatccttatg catgaaatga atgtctgaga   1560
tacgtctgtg acttatctac cattgaagga aagctatatc tatttgagag cagatgccat   1620
tttgtacatg tatgaaattg gttttccaga ggcctgtttt ggggctttcc caggagaaag   1680
atgaaactga aagcacatga ataatttcac ttaataattt ttacctaatc tccactttt   1740
tcataggtta ctacctatac aatgtatgta atttgtttcc cctagcttac tgataaacct   1800
aatattcaat gaacttccat ttgtattcaa atttgtgtca taccagaaag ctctacattt   1860
gcagatgttc aaatattgta aaactttggt gcattgttat ttaatagctg tgatcagtga   1920
ttttcaaacc tcaaatatag tatattaaca aattacattt tcactgtata tcatggtatc   1980
ttaatgatgt atataattgc cttcaatccc cttctcaccc cacccctcta agcttccccc   2040
acagcaatag gggcttgatt atttcagttg agtaaagcat ggtgctaatg gaccagggtc   2100
acagtttcaa aacttgaaca atccagttag catcacagaa aaagaaattc ttctgcatt    2160
gctcattgca ccagtaactc cagctagtaa ttttgctagg tagctgcagt tagccctgca   2220
aggaaagaag aggtcagtta gcacaaaccc tttaccatga ctggaaaact cagtatcacg   2280
tatttaaaca ttttttttc ttttagccat gtagaaactc taaattaagc caatattctc    2340
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgatacct atgaggattt   2520
ggaggcttgg cattttaatt tgcagataat accctggtaa ttctcatgaa aaatagactt   2580
ggataacttt tgataaaaga ctaattccaa aatggccact tgttcctgt ctttaatatc    2640
taaatactta ctgaggtcct ccatcttcta tattatgaat tttcattat taagcaaatg    2700
tcatattacc ttgaaattca gaagagaaga aacatatact gtgtccagag tataatgaac   2760
ctgcagagtt gtgcttctta ctgctaattc tgggagcttt cacagtactg tcatcatttg   2820
taaatggaaa ttctgctttt ctgtttctgc tccttctgga gcagtgctac tctgtaattt   2880
tcctgaggct tatcacctca gtcatttctt ttttaaatgt ctgtgactgg cagtgattct   2940
```

```
ttttcttaaa aatctattaa atttgatgtc aaattaggga gaaagatagt tactcatctt    3000
gggctcttgt gccaatagcc cttgtatgta tgtacttaga gttttccaag tatgttctaa    3060
gcacagaagt ttctaaatgg ggccaaaatt cagacttgag tatgttcttt gaataacctta   3120
agaagttaca attagccggg catggtggcc cgtgcctgta gtcccagcta cttgagaggc    3180
tgaggcagga gaatcacttc aacccaggag gtggaggtta cagtgagcag agatcgtgcc    3240
actgcactcc agcctgggtg acaagagaga cttgtctcca aaaaaaaagt tacacctagg    3300
tgtgaatttt ggcacaaagg agtgacaaac ttatagttaa aagctgaata acttcagtgt    3360
ggtataaaac gtggttttta ggctatgttt gtgattgctg aaaagaattc tagtttacct    3420
caaaatcctt ctctttcccc aaattaagtg cctggccagc tgtcataaat tacatattcc    3480
ttttggtttt tttaaaggtt acatgttcaa gagtgaaaat aagatgttct gtctgaaggc    3540
taccatgccg gatctgtaaa tgaacctgtt aaatgctgta tttgctccaa cggcttacta    3600
tagaatgtta cttaatacaa tatcatactt attacaattt ttactatagg agtgtaatag    3660
gtaaaattaa tctctatttt agtgggccca tgtttagtct ttcaccatcc tttaaactgc    3720
tgtgaatttt tttgtcatga cttgaaagca aggatagaa aacactttag agatatgtgg    3780
ggttttttta ccattccaga gcttgtgagc ataatcatat ttgctttata tttatagtca    3840
tgaactccta agttggcagc tacaaccaag aaccaaaaaa tggtgcgttc tgcttcttgt    3900
aattcatctc tgctaataaa ttataagaag caaggaaaat tagggaaaat attttatttg    3960
gatggtttct ataaacaagg gactataatt cttgtacatt attttttcatc tttgctgttt   4020
ctttgagcag tctaatgtgc cacacaatta tctaaggtat ttgttttcta taagaattgt    4080
tttaaaagta ttccttgttac cagagtagtt gtattatatt tcaaaacgta agatgatttt    4140
taaaagcctg agtactgacc taagatggaa ttgtatgaac tctgctctgg agggagggga   4200
ggatgtccgt ggaagttgta agactttat ttttttgtgc catcaaatat aggtaaaaat     4260
aattgtgcaa ttctgctgtt taaacaggaa ctattggcct ccttggccct aaatggaagg   4320
gccgatattt taagttgatt attttattgt aaattaatcc aacctagttc tttttaatt     4380
ggttgaatgt tttttcttgt taaatgatgt ttaaaaaata aaaactggaa gttcttggct   4440
tagtcataat tctt                                                      4454
```

<210> SEQ ID NO 46
<211> LENGTH: 189
<212> TYPE: PRT
<213> ORGANISM: Homo sapiens

<400> SEQUENCE: 46

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95
```

```
Arg Glu Gln Ile Lys Arg Val Lys Asp Ser Asp Asp Val Pro Met Val
            100                 105                 110
Leu Val Gly Asn Lys Cys Asp Leu Pro Thr Arg Thr Val Asp Thr Lys
        115                 120                 125
Gln Ala His Glu Leu Ala Lys Ser Tyr Gly Ile Pro Phe Ile Glu Thr
    130                 135                 140
Ser Ala Lys Thr Arg Gln Gly Val Glu Asp Ala Phe Tyr Thr Leu Val
145                 150                 155                 160
Arg Glu Ile Arg Gln Tyr Arg Met Lys Lys Leu Asn Ser Ser Asp Asp
                165                 170                 175
Gly Thr Gln Gly Cys Met Gly Leu Pro Cys Val Val Met
            180                 185
```

<210> SEQ ID NO 47
<211> LENGTH: 1326
<212> TYPE: DNA
<213> ORGANISM: Rattus norvegicus

<400> SEQUENCE: 47

| | | | | | |
|---|---|---|---|---|---|
| gccgttcatg | gcggtttcgg | ggtctccaac | agcttctcag | gttgaaatcc | aaaagcctcc | 60 |
| cgaggcgggg | tctgcggagt | ttgagatttt | tgcaggtgtg | aaatgactga | gtacaaactg | 120 |
| gtggtggttg | gagcaggtgg | cgttgggaaa | agtgctttga | caatccagct | aatccagaac | 180 |
| cactttgtgg | atgaatatga | tcccaccata | gaggattctt | accgaaaaca | agtggtgatt | 240 |
| gacggtgaga | cctgtctact | ggacatactg | gacacagctg | gacaagagga | gtacagtgcc | 300 |
| atgagagacc | aatacatgag | gacaggcgaa | gggttcctct | gtgtgtttgc | catcaataat | 360 |
| agcaaatcct | ttgcagatat | taacctctac | agggagcaaa | ttaagcgcgt | gaaagactct | 420 |
| gatgatgtac | ccatggtgct | ggtagggaac | aagtgtgact | tgccaacaag | gacagttgac | 480 |
| acaaagcaag | cccacgagct | ggccaagagt | tatggaattc | cattcattga | aacctcagcc | 540 |
| aagacccgac | agggtgtgga | ggatgccttt | tacacgcttg | taagggagat | acgccagtac | 600 |
| cggatgaaga | agctcaacag | cagtgaggat | ggcactcaag | gctgtatggg | gctgccctgt | 660 |
| gtggtgatgt | agtaagaccc | tttaaaagtt | ctgtcatcag | aaacgagcca | ctttcaagcc | 720 |
| tcactgatgc | cctggttctg | acatccctgg | aggagacgtg | tttctgctgc | tctctgcatc | 780 |
| tcagagaagc | tcctgcttcc | tgcttcccca | acttagttac | tgagcacagc | catctaacct | 840 |
| gagacctctt | cagaataact | acctcctcac | tcggctgtcc | gaccagagaa | atgaacctgt | 900 |
| ttctccccag | tagttctctg | ccctgggttt | ccctagaaa | caaacacacc | tgccagctgg | 960 |
| ctttgtcctc | cgaaaagcag | tttacattga | tgcagagaac | caaactatag | acaagcaatt | 1020 |
| ctgttgtcaa | cagtttctta | agctctaagg | taacaattgc | tggtgatttc | ccccttgcc | 1080 |
| cccaactgtt | gaacttggcc | ttgttagttt | tgggggaaat | gtcaaaaatt | aatctcttcc | 1140 |
| cgagaataga | attagtgttg | ctgattgcct | gatttgcaat | gtgatcagct | atattctata | 1200 |
| agctggcgtc | tgctctgtat | tcataaatgc | aaacatgagt | actgacgtaa | gtgcatccct | 1260 |
| agtcttctca | gctgcatgca | attaaatcca | acgttcacaa | caaaaaaaaa | aaaaaaaaa | 1320 |
| aaaaaa | | | | | | 1326 |

<210> SEQ ID NO 48
<211> LENGTH: 189
<212> TYPE: PRT
<213> ORGANISM: Rattus norvegicus

<400> SEQUENCE: 48

```
Met Thr Glu Tyr Lys Leu Val Val Gly Ala Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Pro Thr Arg Thr Val Asp Thr Lys
                115                 120                 125

Gln Ala His Glu Leu Ala Lys Ser Tyr Gly Ile Pro Phe Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Glu Asp
                165                 170                 175

Gly Thr Gln Gly Cys Met Gly Leu Pro Cys Val Val Met
                180                 185

<210> SEQ ID NO 49
<211> LENGTH: 4470
<212> TYPE: DNA
<213> ORGANISM: Mus musculus

<400> SEQUENCE: 49
gggactgggg cgccttgggc gcctagtgat tacgtagcgg gtggggccgg aagtgccgct      60
ccctggcggg ggctgttcat ggcggtttcg gggtctccaa cagcttctca ggttgaagtc    120
caaaagcctc ccgaggcggg gtctgcggag tttgaggttt ttgctggtgt gaaatgactg    180
agtacaaact ggtggtggtt ggagcaggtg gtgttgggaa aagcgccttg acgatccagc    240
taatccagaa ccactttgtg gatgaatatg atcccaccat agaggattct taccgaaagc    300
aagtggtgat tgatggtgag acctgcctgc tggacatact ggacacagct ggacaagagg    360
agtacagtgc catgagagac cagtacatga ggacaggcga agggttcctc tgtgtatttg    420
ccatcaataa tagcaaatca tttgcagata ttaacctcta cagggagcaa attaagcgtg    480
tgaaagattc tgatgatgtc cccatggtgc tggtaggcaa caagtgtgac ttgccaacaa    540
ggacagttga cacaaagcaa gcccacgaac tggccaagag ttacggaatt ccattcattg    600
agacctcagc caagacccga cagggtgtgg aggatgcctt ttacacactg gtaagggaga    660
tacgccagta ccgaatgaaa aagctcaaca gcagtgacga tggcactcaa ggttgtatgg    720
ggctgccctg tgtgctgatg tagtaagaca ctttgaaagt tctgtcatca gaaaagagcc    780
actttgaagc tgcactgatg ccctggttct gacatccctg gaggagacct gttcctgctg    840
ctctctgcat ctcagagaag ctcctgcttc ctgcttcccc gactcagtta ctgagcacag    900
ccatctaacc tgagacctct tcagaataac tacctcctca ctcggctgtc tgaccagaga    960
aatagacctg tctctcccgg tcgttctctg ccctgggttc ccctagaaac agacacagcc   1020
```

```
tccagctggc tttgtcctct gaaaagcagt ttacattgat gcagagaacc aaactagaca    1080
tgccattctg ttgacaacag tttcttatac tctaaggtaa caactgctgg tgattttccc    1140
ctgcccccaa ctgttgaact tggccttgtt ggtttggggg gaaaatgtca taaattactt    1200
tcttcccaaa atataattag tgttgctgat tgatttgtaa tgtgatcagc tatattccat    1260
aaactggcat ctgctctgta ttcataaatg caaacacgaa tactctcaac tgcatgcaat    1320
taaatccaac attcacaaca aagtgccttt tcctaaaag tgctctgtag gctccattac      1380
agtttgtaat tggaatagat gtgtcaagaa ccattgtata ggaaagtgac tctgagccat    1440
ctacctttga gggaaaggtg tatgtacctg atggcagatg ctttgtgtat gcacatgaag    1500
atagtttccc tgtctgggat tctcccagga gaaagatgga actgaaacaa ttacaagtaa    1560
tttcatttaa ttctagctaa tctttttttt ttttttttt tttttggta gactatcacc       1620 tataaatatt tggaatatct tctagcttac tgataatcta ataattaatg agcttccatt    1680
ataatgaatt ggttcatacc aggaagccct ccatttatag tatagatact gtaaaaattg    1740
gcatgttgtt actttatagc tgtgattaat gattcctcag accttgctga gatatagtta    1800
ttagcagaca ggttatatct ttgctgcata gtttcttcat ggaatatata tctatctgta    1860
tgtggagaga acgtggccct cagttccctt ctcagcatcc ctcatctctc agcctagaga    1920
agttcgagca tcctagaggg gcttgaacag ttatctcggt taaaccatgg tgctaatgga    1980
ccgggtcatg gtttcaaaac ttgaacaagc cagttagcat cacagagaaa cagtccatcc    2040
atatttgctc cctgcctatt attcctgctt acagactttt gcctgatgcc tgctgttagt    2100
gctacaagga taaagcttgt gtggttctca ccaggactgg aagtacctgg tgagctctgg    2160
ggtaagccta gatatcttta cattttcaga cccttattct tagccacgtg gaaactgaag    2220
ccagagtcca tacctccatc tccttccccc cccaaaaaaa ttagattaat gttctttata    2280 tagcttttttt aaagtattta aaacatgtct ataagttagg ctgccaacta acaaaagctg    2340 atgtgttttgt tcaaataaag aggtatcctt cgctactcga gagaagaatg taaaatgcca    2400
ttgattgttg tcacttggag gcttgatgtt tgccctgata attcattagt gggttttgtt    2460
tgtcacatga tacctaagat gtaactcagc tcagtaattc taatgaaaac ataaattgga    2520
taccttaatt gaaaaaagca aacctaattc caaaatggcc attttctctt ctgatcttgt    2580
aatacctaaa attctgaggt ccttgggatt cttttgttta taacaggatc ttgctgtgta    2640
gtcctagctg gcctcaaact cacaatactc ttcctggatc aatctcccaa gtgctgggat    2700
tacaggcaca ttccaccaca cacacctgac tgagctcgtt cctaatgagt tttcattaag    2760
caaattcccc atcaccttga aactaatcag aaggggggaag aaacatttgc tatgctcctg    2820
agtgctaaca ctgggatcat tcacatgggg tttgcattcc taggcaaact aaactgctgc    2880
cttttacaac aaggctcagt catcttcctg aagctgctga gaccagcact tggtcttgtt    2940 ttgtttttaat atgtctatat gactggtggt ggatccctaa atagtttatt aattaaactc    3000
cagttaagga gaaagttact caccttgacc cgtttgacca tatcccgtgt gtgtgtgtgt    3060
gtgtgtgtgt gtgtgtgtgt gtgtgtgtgt gtgcacgcgt atgtacgtac gtatgtatgt    3120
aggtatgtag gtggtttcca gtataaacac agaaacaaat ggagccaatt caggtttcag    3180
atgcccttac taacatatat tcccacgggg tgtgggtttt ggcacaacag tgacaaactt    3240
aaaagccaag taagagccgg gcgtggtggc gcacgccttt aatcccagca cttgggaggc    3300
agaggcaggc ggatttctga gttctaggcc atcctggtct acagtgagtt ccaggacagc    3360
cagtgctaca cagagaaacc ctgtctcgaa aagccaaaaa aaaaaaaaaa aaaaaaaaa      3420
```

```
aaaagccaag taggtccagt tggtatagta tcaaagtgtt tttagagtaa ttagtgaagg      3480
tctgctttac ctcaaagttg cagagcctct cttcctgagt ttaagtgcct ggccggcagt      3540
cacaaattaa catgttgctg taaggcagtt agttgaagct tgttcacac attggagagt       3600 atgaaaataa agtgttctaa gagcgctgat actggatctg tgtaaacctg gtaaatgccg      3660
tttgtccagg acttagcgtg tgtgagttgg tagctcagta cgagtttact agttccgcag      3720
tgtgtacaat ggaggcgggt ttgttttagc tggccacctg tagaatcagc ctttaaactg      3780
ctgtgaactt tgtcatgact tgaatatgaa gatagacaaa aactctgtaa agacaaatgt      3840 ttgtttttccc ccttacagaa cgtgtgagct tggtttttatc ttcctttgta tttagtcata   3900
acctctcaag ctggcagctc cgaccaagga tcagaagctg tgtgcgttcc acctggtgga     3960
attagctcag ctctatatga gaagtggagt taatggaaaa cgtgttgact gggtggtttc     4020
tatttaaaag agtgatgata attcttgaac agtagttttt attttgctat ttctttaagc    4080
tgactgatgt gccacaaaat tattttaagg tatttgtgtt ttaagagtgt tctcatgaga    4140
ttagttgtag atatttttta aaatacaact ggttttttaaa atctgagtat tgctctaagc   4200
aagtgtttag actcttacgg gaaggtgggt ggaagttgtt tggcttccgt atttccatgc    4260
gtgccgtcag acataggtca gaacgccaac tgtgcatcct gctgtttaaa gacctcttgg   4320
cctctgtgac cctcatgaag gggctgatat tttaagttga ctgtttgatt gtaaattaat   4380
cctttctaat ttttaaagac ttgcttgact gttttccttg ttaaataatt ttaaaaaaat  4440
aaaaaactgg aagttctttg cttaactgta                                    4470
```

<210> SEQ ID NO 50
<211> LENGTH: 189
<212> TYPE: PRT
<213> ORGANISM: Mus musculus

<400> SEQUENCE: 50

Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Leu Met

<210> SEQ ID NO 51
<211> LENGTH: 570
<212> TYPE: DNA
<213> ORGANISM: Cavia porcellus

<400> SEQUENCE: 51

```
atgactgagt ataaactggt ggtggttgga gcaggtggtg tcgggaaaag tgcactgacc      60
atccagctaa ttcagaacca ctttgtcgat gaatatgatc ccaccataga ggattcttac     120
cgaaaacagg tggttataga tggtgaaact tgtctgttgg atattctgga tacagctgga     180
caagaggagt acagtgccat gagagaccaa tacatgagga caggcgaagg cttcctctgt     240
gtgtttgcca tcaataatag caaatcattt gcagatatta acctctacag ggagcagatt     300
aaacgagtaa aagactcaga tgatgtacct atggtgctgg tagggaacaa gtgtgatttg     360
ccaacaagga ctgttgacac aaaacaagcc catgaactgg ccaagagtta cgggattcca     420
ttcattgaaa cctcagccaa gaccagacag ggtgttgaag atgcatttta cactctcgta     480
agagaaatac gccagtacag aatgaaaaaa ctcaacagca tgatgatgg gactcaaggt      540
tgtatggggt tgccatgtgt ggtgatgtaa                                      570
```

<210> SEQ ID NO 52
<211> LENGTH: 189
<212> TYPE: PRT
<213> ORGANISM: Cavia porcellus

<400> SEQUENCE: 52

```
Met Thr Glu Tyr Lys Leu Val Val Gly Ala Gly Val Gly Lys
  1               5                  10                  15

Ser Ala Leu Thr Ile Gln Leu Ile Gln Asn His Phe Val Asp Glu Tyr
                 20                  25                  30

Asp Pro Thr Ile Glu Asp Ser Tyr Arg Lys Gln Val Val Ile Asp Gly
             35                  40                  45

Glu Thr Cys Leu Leu Asp Ile Leu Asp Thr Ala Gly Gln Glu Glu Tyr
         50                  55                  60

Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Asn Asp Asp
                165                 170                 175

Gly Thr Gln Gly Cys Met Gly Leu Pro Cys Val Val Met
            180                 185
```

<210> SEQ ID NO 53
<211> LENGTH: 1220
<212> TYPE: DNA
<213> ORGANISM: Cavia porcellus

<400> SEQUENCE: 53

```
gttccggggt cctcaacgtt tctcagggtt gagattctat atccttttga agctggggcg      60
gcagagcttg aggttcttgc tggtgtgaaa tgactgagta taaactggtg gtggttggag     120
caggtggtgt cgggaaaagt gcactgacca tccagctaat tcagaaccac tttgtcgatg     180
aatatgatcc caccatagag gattcttacc gaaaacaggt ggttatagat ggtgaaactt     240
gtctgttgga tattctggat acagctggac aagaggagta cagtgccatg agagaccaat     300
acatgaggac aggcgaaggc ttcctctgtg tgtttgccat caataatagc aaatcatttg     360
cagatattaa cctctacagg gagcagatta acgagtaaa agactcagat gatgtaccta     420
tggtgctggt agggaacaag tgtgatttgc caacaaggac tgttgacaca aaacaagccc     480
atgaactggc caagagttac gggattccat tcattgaaac ctcagccaag accagacagg     540
gtgttgaaga tgcattttac acactcgtaa agaaatacg ccagtacaga atgaaaaaac     600
tcaacagcaa tgatgatggg actcaaggtt gtatggggtt gccatgtgtg gtgatgtaac     660
aagatattta acaaagttct atcagaaaag agccactttc aagctgcact gataccctgg     720
tcctgacttc cctggaggag aagtatccct gttgctctct tcatctcaga gaagctcctg     780
ctgtttgtcc acctctcagt gtatgagcac agtctctgct tgagaacttc tcagaataac     840
tacctcctca cttggttgtc tgaccagaga atgcacctc ttgttaattc cccaataatt     900
ttctgccctg ggctctcccc aacaaaaaac aaacacttct gccatccaaa aagcaacttg     960
gtctgaaaca gaaccaaact gtagattgaa attctcttaa aaagtcttga gctctaaagt    1020
tagcaaccgc tggtgatttt tattttcctt tttatttttg aacttggaac tgacctatgt    1080
tagattttgg agaaatgtca taaagtactg ttgtgccaag aagataatta tgttgctgaa    1140
tggttgattt atagtgttat cagctatatt ttacaaactg gcatctgctc tgtattcata    1200
aatacaaaaa tgaagccagg                                                 1220
```

<210> SEQ ID NO 54
<211> LENGTH: 189
<212> TYPE: PRT
<213> ORGANISM: Cavia porcellus

<400> SEQUENCE: 54

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140
```

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Asn Asp Asp
            165                 170                 175

Gly Thr Gln Gly Cys Met Gly Leu Pro Cys Val Val Met
            180                 185

<210> SEQ ID NO 55
<211> LENGTH: 1307
<212> TYPE: DNA
<213> ORGANISM: Canis familiaris

<400> SEQUENCE: 55

| | | | | | |
|---|---|---|---|---|---|
| tgattacgta | gcgggcgggg | ccggaagtgc | cgctccctag | tgggggctgt | tcatggcggt | 60 |
| tccgggtct | ccaacctttc | tcctagttgt | ggtcctaaat | acgtcggaag | cggaggcggc | 120 |
| gaagcttgag | gttcttgctg | gtgtgaaatg | actgagtaca | aactggtggt | ggttggagca | 180 |
| ggtggtgttg | ggaaaagcgc | actgacaatc | cagctaatcc | agaaccactt | tgtagatgaa | 240 |
| tatgatccca | ccatagagga | ttcttaccga | aaacaggtgg | ttatagacgg | tgaaacctgt | 300 |
| ctgttggata | tactggatac | agctggtcaa | gaagagtaca | gtgccatgag | agaccaatac | 360 |
| atgaggacag | gcgaaggctt | cctctgtgta | tttgccatca | ataatagcaa | atcatttgca | 420 |
| gacattaacc | tctacaggga | acagattaag | cgagtaaaag | attcagatga | tgtacctatg | 480 |
| gtgctagtag | gaaacaagtg | tgatttgcca | acaaggacag | ttgacacaaa | acaagcccat | 540 |
| gaactggcca | agagttatgg | gattccattc | attgaaacct | cagccaagac | cagacagggt | 600 |
| gtcgaggatg | cctttacac | actggtaaga | gaaatacgtc | agtaccgaat | gaagaaactc | 660 |
| aacagcagtg | atgatgggac | tcaaggttgt | atggggttac | catgtgtggt | gatgtaacaa | 720 |
| gacactttta | agttctagc | atcagaaaag | agccactgtc | aagctgcact | gacaccctgg | 780 |
| tcctgacttc | cctggaggag | aagtattcct | gttgctatct | tcagtctcac | aaagaagctc | 840 |
| ctgctacttc | cccaactctc | agtagatcag | tacaatgttc | tctatttgag | aagttctccg | 900 |
| aacaactacc | tcctcacttg | gttgtctgac | cagagaaatg | aacctcttgt | tccttcccgc | 960 |
| tgttttcca | ccctgaattc | tcccccaaca | cacataaaca | aacctctgcc | atcccaggtt | 1020 |
| tttcatctga | aaataattc | atgctctgaa | acagagaaca | aaactgtaga | catgaaattc | 1080 |
| tgtaggaaac | aaggtcttga | gctcaaaagt | agcaactgct | ggtgaccttt | ttttccccc | 1140 |
| tttttactgt | tgaacttgga | actatgttgg | tttttggaga | aatgtcataa | gttactgttt | 1200 |
| tgctgagaat | atagttaagt | tgacatttgg | tttgtttgta | atatcattag | ctattttcta | 1260 |
| taaattggca | tctgctctgc | attcataaat | acacgagtga | attctga | | 1307 |

<210> SEQ ID NO 56
<211> LENGTH: 189
<212> TYPE: PRT
<213> ORGANISM: Canis familiaris

<400> SEQUENCE: 56

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

```
Glu Thr Cys Leu Leu Asp Ile Leu Asp Thr Ala Gly Gln Glu Glu Tyr
 50                  55                  60

Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Val Pro Met Val
                100                 105                 110

Leu Val Gly Asn Lys Cys Asp Leu Pro Thr Arg Thr Val Asp Thr Lys
                115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
                180                 185
```

<210> SEQ ID NO 57
<211> LENGTH: 3104
<212> TYPE: DNA
<213> ORGANISM: Felis catus

<400> SEQUENCE: 57

```
aaaaaataaa taaatttaag aaaccatttt aaaattatgc acagttgcag cctggaaaac      60
ttaaggtggc gccttatagt atcaatctta ggagcttat ttggtgcatt taacgcaact     120
ggtaattgca aaatccactt cgcctgtgta agtgaaaaat atagactgtt atcttgttgg    180
ccctatgaaa ttctgcactt ggtatttagc atatactcta ccttcattac tatctggcaa    240
gatgttctgc cttagcactc agttgcattc ttttcctttt ctttcctgtt cattatgctt    300
taattctgag gaccatatga gggtagaata tattaaaaat tacaaaaatt ataaaaattt    360
gtataggcaa accatttcct taagttgatg gccaaatgtt aaaatgttat ttttcatatc    420
atttataatc ttgtcacagt ccacttaacg aagtttggtt agatttcagt gaaaattatc    480
ttccagagta gttttttttt tttttttcctg ggattaggga gggggtaac tttactgcaa    540
ttagtatgta tggtgcagaa tttcatgcaa atgaggtgtg ccagcagtgt ggtaatttaa    600
tcgtatttaa acaaaaacaa acaaaaaaaa aacgaatgca caaacttgct gctgcttaga    660
tcactgcagc ttctaggacc cagtttcttt tactgatttc aaaacaaaac aaaacaaaaa    720
aataaaaaaa gttgtgcctg aaatgaatct tgttttttt ataagtagcc gcctggttcc    780
tgtgtcctgt gaaatacagg cacttgaccc ttggtgtagc ttctgttcga ctttatatca    840
cgggaatgga ttggtctgat tcttggccc tcatcttgaa ttggccacat ccagggtccc    900
tggccagtgg actgaaggct ttgtctaaga ggacaagggc agctcagggg atgtggggga    960
gggcgctttt atcttccccg ttgtcgtttg aggttttgat cttctctggg taaagaggcc   1020
gtttatcttt gtaaacacaa aacattttttg ctttctccag ttttctgtta atggcgaaag  1080
aatggaagcg aataaagttt tactgatttt tgagactcta gcacctagcg ctttcatttt   1140
tgaaacgtcc tgtgtgggag gggcgggtct gggtgcggcc cgccgcgtga ctcctgagtc   1200
gggggcccac gtggctgggg cggggactcg gacgccccgg gcgccgactg attacgtagc   1260
gggcggggcc ggaagtgccg ctccctagtg ggggctgttc atggcggttc cggggtctcc   1320
```

```
atccttttc ccagttgttc taaatcagtc ggaagcggag gcagcgaagt tgaggttct      1380 cgctggtgtg aaatgactga gtacaaactg gtggtggttg gagcaggtgg tgttgggaaa      1440
agcgcactga caatccagct aatccagaac cactttgtag atgaatatga tcccaccata      1500
gaggattctt accgaaaaca ggtggttata gacggtgaaa cctgtctgtt ggacatactg      1560
gatacagctg gtcaagaaga gtacagtgcc atgagagacc aatacatgag acaggcgaa      1620 ggcttcctct gtgtatttgc catcaacaat agcaaatcat tgcagatat taacctttac      1680 agggaacaga ttaagcgagt aaaagactcc gatgatgtac ctatggtgct agtaggaaac      1740
aagtgtgatt tgccaacaag gaccgtcgac acaaaacaag cccacgaact ggccaagagt      1800
tatgggattc cattcattga aacctcagcc aagaccagac agggtgttga agatgccttt      1860
tacacactgg taagagaaat acgtcagtac cgaatgaaga aactcaacag cagtgatgac      1920
gggactcaag gttgtatggg gttaccgtgt gtggtgatgt aacaagatac tttaaagtt      1980 ctagcatcag aaaagagcca ctgtcaagct gcactgacac cctggtcctg acttccctgg      2040
aggagaagcg ttcctgttgc tattttcagt ttcacaaaga agctcctgct atttccccaa      2100
ctctccgtag atcagtacat tattctctgt ttgagaagtt ctccgaataa ctacctcctc      2160
acttggttgt ctgaccagag aaatgaacct cttgttactc cccactgttt ttccaccctg      2220
gttctccccc agcacatata acaaacctc ccaggttttt catctgaaaa gtaattcatg      2280
ctctgaaaca gagaaccaaa ctgtagacat gaaattctgt aggaaacaat gtcttgagct      2340
ctaaagtagc aactgctggt gactttttt tttttttt ccttttact gttgaacttg      2400 gaactatgtt ggttttgga gaaatgtcgt aagttactgt tttgctgagt atatagttaa      2460
gtttaccatt cggtttgttt gtaatgtcat ggctatact ctgtacctgg catctgctct      2520
gcattcataa atacaaaagt gaattctgac ttttgagtct atcctagtgt tctcaacttc      2580
cacataatta aatctaactt ttgcagcaaa gtgcctttt cctagaagtg gtttgtagat      2640
ttgctttata atactttggt ggaatagatg tctcaaaaac cattatacat gaaaatgaat      2700
gtctgagata cgtctatgat ctgtctacct ttgagggaaa aatataccga cataatagca      2760
gatgccatgt cttacgtgta tgaagttgga ttttccagaga cctgatttgg gtctcttcca      2820
agagaaagat gaaactggaa acaattatga ataacttcac ttaattttta cctaatctct      2880
acttcggggt gggagggcag ggagtaggtt accacttaca aaatatatgc aatttgtttc      2940
ttctagctta ctgataatga acttccattc ttatttaaat ttaggtcata tcctaaagct      3000
ttacatttgc aggtgttcga aattgtaagt ttaatgcagt tttatttaat agctatgatc      3060
aatgattttc aagcctcaga tgtattaacg gacacatttt cact                       3104
```

<210> SEQ ID NO 58
<211> LENGTH: 189
<212> TYPE: PRT
<213> ORGANISM: Felis catus

<400> SEQUENCE: 58

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

```
Ser Ala Met Arg Asp Gln Tyr Met Arg Thr Gly Glu Gly Phe Leu Cys
 65                  70                  75                  80

Val Phe Ala Ile Asn Asn Ser Lys Ser Phe Ala Asp Ile Asn Leu Tyr
                 85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 59
<211> LENGTH: 4283
<212> TYPE: DNA
<213> ORGANISM: Bos taurus

<400> SEQUENCE: 59
ggccgctccc tagtggggggc tgttcatggc ggttccgggg tctcccaaca attttcccgg      60
ttgtggtcgt aatctatccg aagtggaggc agtggagcta gaggttcttg ctggtgtgaa     120
atgactgagt acaaactggt ggtggttgga gcaggtggtg ttgggaaaag tgcactgaca     180
atccagctaa tccagaacca ctttgtagat gaatatgatc ccaccataga ggattcctac     240
cgaaaacagg tggttataga tggtgaaacc tgtctgttgg acatactgga tacagctgga     300
caagaggagt acagtgccat gagagaccaa tacatgagga caggcgaagg cttcctttgt     360
gtgtttgcca tcaataatag caaatcattt gcagatatta acctctacag ggaacagata     420
aagcgtgtaa aggactcgga tgatgtacct atggtgctag taggaaacaa gtgtgatttg     480
ccaacaagga cagttgacac aaaacaagcc catgaactgg ccaaaagtta tgggattcca     540
ttcattgaaa cctcagccaa gaccagacag ggtgttgaag atgccttttta cactggta      600 agagaaatac gtcagtaccg aatgaaaaag ctcaacagca gtgatgatgg cactcaaggc     660
tgtatggggt tgccgtgtgt ggtgatgtaa caagatactt ttaaagttct cacatcagaa     720
aagagccact gtcaagctgc actgacaccc tggtcctgac ttccctggag agaagtatt     780 cctgttgcta tcttcagttt caaaagaag ctcctgctat tccccaact ctcagtagat     840 caatataata ttctctattt gagaagttct caagaataac tacctcctca cttggttgtc     900
tgaccagaga attgaacctc ttgttactcc cagtattttt ccaccctggg ttctcccca     960 gcacacacaa acgcacctct gccacccagg tttttcatct gaaaagcaat taatactctg    1020
aaacagagaa ccaaactgta gaaacatgaa attctgtaga aacaatgtc ttgagctcta    1080 aagtagcaac tgctggtgat tttttttttt tttttttcct ttttattgtt gaacttggaa    1140
ctatgttggt ttgtggagaa atgtcataaa ttactgtttt gctgagaata tagttaatgt    1200
tgctctctgg tttgtttgta atgttatcag ctatattcta taaactggca tctactctgt    1260
atttagaaat acaaaaatga atactgacct tttgagtcta ccctcatctt ctcgactttc    1320
ttgtaattaa atgtaacttt cacgatgaag tgccttttgc ctgggagtga ctcgtagact    1380
```

```
tcctttaaaa tacttcagtg gaatagatgt ctcagaaact gttatacata agaataaatg    1440
tctgagatat gtctatgacc catctagctt tgagggaaag atataccaat atgatagcag    1500
atgccatttc ttacatctat aacgttgatt ttctggagac ctattttggg gctctccgag    1560
agaaagatga gactataaat gattaggaat aatttcactt aattttaca taacctccac     1620 tttttgtttt gtagtttact acctgcaaaa catataattt gattcctttt agcttacaga    1680
taatctaatg ttaaatgaac ttccattcat atttaatt ggatcatatc aggaagtcta     1740
catttgcagg tgttcaaaaa ttgtaaaagt gtgatgcagt tttatttaat agctgtgatc    1800
aatgattttc aagcctcaaa tatgttaata gacacatttt cactgtatat catggtatta    1860
ataattattg atgtatataa ttgtccttgg tccccttctc tgttcatcac ctcatggcaa    1920
tggcttgatt aattatttca gctgagtaaa gcatggtgct aatagaccag ggtcacagtg    1980
tcaaaacttc agtgagccag taagcatcac agagaaagaa attctttcac atttgctcac    2040
cattaactcc agctaatagt tttgccagat gtgtgtggtt agtcctgcaa ggaaaggaga    2100
agtcagttaa tacaaattct taaccaggac tggaaaaact tgttttcctg agaagggtca    2160
gcttagaagt ctttatctgg actctatttt tagccacatg gaaatcaaat taagctgatc    2220
ttttttctca agttttgag agtgaggatg cctcagatca acattttaa aatattcttt     2280 attcttacgt tcttttaagg gttaaaaca acgttgagta attagtctgg gcataccagg    2340
taacaagctg ataagtttgt gctgaacaag aagtagcctt tggattgaaa ttgctgtttt   2400
gagaagggat agaaaatata attaataatt atgagacttg acttttctat ttgcagataa    2460
tatcctgata attctgatga aaatagactt ggataatttt tgataaaaga atcgttccaa    2520
aatggccact tgctgttctt gtcttctaat gtgtaaatac ttactgaggt cctcttctaa    2580
tatgagttgt catttattaa gcaaattcca cattgccttg aaatgaattc ggaagagaag    2640
aaaaagtcat agtatacccca gagaatgaaa atccagaga attgtgctcc ttagtgttaa   2700
ttctgaagcc ttcgtagtcc acacccatag acagaaactc tctgccactt tgcttctgct    2760
cctcttggag cattgcgctg tcatttcctt gaggatagat tgaggcttgt caactcagtt    2820
gtattgtctt cctcctcttc ctcttgtctg tgtgactgac agtgtgactc ttactaatgt    2880
cagatgcggg gatgcgggga ggtggggggg agtagctcat tttaggctct tgcacccttt    2940
accgttgtat gtgtgtgtct tttagtttc tcaagaatgt tctaagcaca gaagtatcta    3000 aatgggggcca aaattcagac ttgaaaatgt tcttttaata gcttcttaaa aagttacact    3060
ttggtgtgaa ttttggcagg atagagtgac aaactcttaa acgctgaata acttcagtta    3120
gtgtgttata gttttttagaa tatgtttgtg attgctgaaa acaattatag tttacctcaa    3180
aatctgaaag tctcttttccc caagttaagt gcctggccag ctgtcaaaga ttacatatta    3240
ctttatgttt gtttgttttt taaaggttgc acattcaaga ttgtgaaaat aaggtgttct    3300
gtctgaaagc taccatgcct gtctgtaaat gaatccactg agtgctgtac ttgttccaac    3360
agcttactac agaatgctac ttggtaatat catactcgtt acagttttca cttcaggagt    3420
gtactaggta gaatgatcct gtgtgtattg tagtgggctc catgtttagt cttttcagca    3480
tcctttaaac tgctgtgaat ttttgtcttg acttgaaagc aaggatagag aaacacttta    3540
aagagatact ttgggttttt ttccattcca gaattggtga gcatagttag attttgcttt    3600
acatttacag tcatgaactc ttaagctggc agctacaacc aagaaccaaa agagggtgca    3660
ttctgcttct tgtaattcat ctttgctaat aaattatgag aagcaaagat aattaattag    3720
agaaactatt ttatttgggt ggtttctata aacaagggac tataattctt aaacattatt    3780
```

-continued

```
tttcattttt gctgtttctt taagaaacct aatgtgccac aacattattt taaggtgttt    3840
cttaaaagaa ttgttttaa aagtgttctc attttcagag taattgtaga tatatttcaa    3900
aatataactg ataattttta aaggcctgag tactgaccta agaagcagtt gtatgaattc    3960
tctgggggga agggaggagc tcagtgaaag ttgtatgact tttatatttc tgtgccatca    4020
aataaaggta aaatgtctt ttgtgcagtt ttgctgttca aacagaaact attggcctcc     4080
ttggccctaa atgaaagggc tggtatttta agttgactat ttattgtaa attaatccat     4140 cttaattttt ttaaatttgg ttgaatgttc tcttgttaaa tgtttaaaaa ataaaaactg    4200
gaagttcttt gcttagtcat aaaaaaaaaa aaaaaaaaaa aaaaaaaaaa aaaaaaaaaa    4260
aaaaaaataa aaaaaaaaaa aaa                                             4283
```

<210> SEQ ID NO 60
<211> LENGTH: 189
<212> TYPE: PRT
<213> ORGANISM: Bos taurus

<400> SEQUENCE: 60

```
Met Thr Glu Tyr Lys Leu Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Ile Asp Gly
            35                  40                  45

Glu Thr Cys Leu Leu Asp Ile Leu Asp Thr Ala Gly Gln Glu Glu Tyr
    50                  55                      60

Ser Ala Met Arg Asp Gln Tyr Met Arg Thr Gly Glu Gly Phe Leu Cys
65              70                      75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
    130                 135                     140

Ser Ala Lys Thr Arg Gln Gly Val Glu Asp Ala Phe Tyr Thr Leu Val
145             150                     155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185
```

<210> SEQ ID NO 61
<211> LENGTH: 4825
<212> TYPE: DNA
<213> ORGANISM: Gallus gallus

<400> SEQUENCE: 61

```
gcgccgggac cggaagccgg aagctttgca gaagggtgtt ccgcgttcgc ggtgcgggag      60
cggtcagccg gggtggcggg gctggggccg gccggggcag gcggctccgc gctccgcact    120
gggccgctgg gagggcgatg actgaataca agctggtggt ggtgggagct ggcggcgtcg    180
ggaagagcgc gttgaccatc cagctcatcc agaaccactt cgtggacgag tacgacccca    240
```

```
ccatcgagga ttcgtacaga aagcaggttg tcatcgatgg agagacgtgc ttgttggaca    300
ttctggacac tgcaggacag gaagaataca gtgctatgcg tgatcagtac atgagaactg    360
gggaaggatt cctttgtgtg tttgccatta acaacagtaa atcattcgct gatattaacc    420
tttacagaga gcaaatcaag agagtgaaag attcagacga tgtgccaatg gtgctggtgg    480
ggaataagtg cgatttgcca acaaggacag tagacaccaa acaggctcaa gagttagcaa    540
aaagctacgg cattcccttc atagagacat cagccaaaac gagacagggt gtggaagatg    600
cgttttacac actggtgagg gagattcggc agtaccggat gaaaaagctc aacagcaacg    660
aagatgggaa tcagggctgt atgggggttgt cctgcattgt gatgtgataa gatgccaggt    720
tcagatgtag ctgctggaca agtctcgatg ctactgtatt gtgtctcatg ctgatgccct    780
gcagtatttt ggtgccagcg accagactct tggtaccagt taattagctc aggatccttt    840
cctgtgctcc atctgaagaa aacatctctg gtatctacct ccttgctcag ctcacagagc    900
agtcatatct cttggtgtac tgggattctt ttctagctgt gttgtctggg tttgttcaag    960
aagaaaacca gtcacaagaa aagtgaatta cagagactaa atgctgtgaa aaagatcaca   1020
ctttacctcc agagtaaaag ctagaagtgg cgtttgaccc cttttgcattg gattcagatt   1080
tgcggtgttg tcagaggagt ggcagaagta attttgccat tacaaaggtt tctgtcacca   1140
gtcggattgg tatctgctgt ctgtgcaccc acacagtgta tctgcaacat ctgcattgtg   1200
ccagaagtat cacttaactg atgaactgat cctttatttt tctgtaataa aaggagata    1260
tctttgctaa cttaagtgcc tgtttgctca gaaggttgga ggttgtatgc tgttcccttg   1320
ggctgaggag aaccccaagg atgaatttct gggtgctca ttgtcttgag caggcaagtt   1380
ttgtgtgggt gatctctttt catggcagga tattaaaatg gaatttgta gtctggaaga   1440
tggagcagct gtttgtgaga ctcttgagtt agggagagaa atgtatacca cgtctgttct   1500
cgatccatca gaatggatcc atccacctct ttgtgtgtgg aactgtgtat agtctgtatt   1560
ggttttctac agcacttgga tctctttgga ccaaattagc gagctgttca ttttaacata   1620
actgccagta tttatagaca atttcttacg gacagataat gaatttagaa actggaggtt   1680
actttgggca gctgttcctc agctctgtct gtaacttgca aattattctg agttattttc   1740
tgcagaacct ccttccttat cacgggagga gcctgggagt tgaggttgac tgtaattggg   1800
tcaatggttg tcacagactt aaggtgtcca ggctgattgg aggaggcact gagccctaac   1860
agagcactga gctgacttct aattgcagca tccttgcaaa atgaggaagg gagttcagtg   1920
atgtctgcac tgaagatgta tgatacactg atagcagttc tgggtatgtt gtaacagctt   1980
caaagtagaa ccgcagtact gcgtgagctg tgtgacttct tcctagaaca cagcactgtc   2040
acccatatg gttgggacgt gcaggtgaga ccaacaccta ccaggttccc tggcgtaccg   2100
tggccttctc agttcttgtg ccagtgatac tgggttctgt tctgtggtgt cagacagcgt   2160
cctgtagcaa agctgaattc ccacttagtc tggtgagaga ataaagagcc atcagccaac   2220
agagggagcg ttcattctgc tggagcagtg cgagctgtaa gcattacgag aggcgtagtt   2280
tcagtttgtt gcagtcaggt tcctatattt tcaaagctga aatcagaaat aagtaaatac   2340
ggagaaaata agctgttgct tttaatgctc tttcctccac taattgtact cttaattttc   2400
ttcttgggag gccgaggatc catctgcata actttagctg tgatgctcca gataagtgtt   2460
tagaattcat tttatctttg actgatggga ctgataagaa gttaacgcac aatatttta   2520
catacaacat cgttttccag tgacctcctg agccggtggga agcattatgg gatagcaccg   2580
gctgtgactc gagttcattt gaaggcgatc tcttgcctgc aggttaaatg ggacggagtc   2640
```

| | |
|---|---:|
| agaatcactg tgagccgtct gtaatcagca acagtctgt gggcttttct tactgtgttc | 2700 |
| tctctgtttg ccttagtttg gtgcaggaag agttccttgt gacagcgtcc tttgaggtgt | 2760 |
| gttgcaggag ctgaccattt gctccttgag ctgtgtgatg aactgttgtc cacttaatgg | 2820 |
| agttacagaa gcagcttctg ggagtcgcat ctggtcgcat acattcagtg ttttgggaag | 2880 |
| ctgtcagtgt ggtgtttgca ctgtgtttga atggtgttca tggtgggtct gttatgctcc | 2940 |
| tggatgattt ggggagatgt ggggctgctt ccgtggcaga caggatcagc tcagggcgct | 3000 |
| gctgcctatg gctgtgggaa acctcacagt tggtgtttga atagtggcca agtatgtcaa | 3060 |
| ttaaaaatac attttgaagg gaggtttgtc atagctctgt actttggcat gctctgctta | 3120 |
| ctgaaaacat actagctgta gctcaaaaaa agttgtgaat cctcagaata atacaggagc | 3180 |
| tggcaattgt ggctgctttc tctttgtgtt ccttttctct tggggttggat gaagctttaa | 3240 |
| aaaggaagga gccctggtga gggttggtca gtgtgcattt cattcttgga accagagagg | 3300 |
| aagttgcatc aactttcagg acgctgcaga gctcacttgc acaggtggtg ctccagtcta | 3360 |
| tgtgattttt ggggtcaaat cttgagatga tcttacaaaa tcagattttg tacccatcat | 3420 |
| gagcatgagg tgagtggttg tgctcggttt ctagctgcat gtatgtatac agacacgtgt | 3480 |
| atgcagacat gtctatgtgt gagtagttcg agtcagtcaa ggttactggc agcacctaaa | 3540 |
| gcgtatgcac cacataatgc atgcaggcaa aagtcctatc ttaggagcca tctcttcatg | 3600 |
| ggtttgggtt tatataggca gtatttttaa acagaatatc cgaagcactt tctggagttc | 3660 |
| tgtggtaatg cagtgacacc tatttggatg aaggaagatg tgtctgagga gcacgtaagc | 3720 |
| agatttgctg ccctaacaga gaggttttgg taaccgtgga aaaggttttc tcctggatct | 3780 |
| gtgtgtgctc ttggtgagct gcaatccatg acagggcaca accagatgag aaggaaaccc | 3840 |
| ggccatccca tgcttgagca cagctctgac tcagtagttc caccagatgt gcccctttcag | 3900 |
| tcaaagtgtt ctgatctctt agagctttct gtagttcaag ttaccactca ctctccagct | 3960 |
| tgctcggtta atgtctgttg gcggcgttga gttggacttg ggaaaggtgt gtgtggtagg | 4020 |
| aacaagcaga gtgtgatgtg cttctgttat caggacttaa gctagagtgg ttggcagata | 4080 |
| ggaaatgcag ctattccttg aaagcaagca gatcatggat ggtcagccaa actgccctgg | 4140 |
| ctttggtggg agctgcactg cagaaggacc aaaccccaac aagatttggc acatttgttt | 4200 |
| agaagataag cacagatggt tttgcacaag gcagctcctc ataatggtgg ctttgtagat | 4260 |
| ttagtccaaa tgttcttatt tagatctagc agcacatcac tgtgtccgtg cccatctaac | 4320 |
| ctcgctatcc taagtagagc agaccccaaa caaccttgtt caaaaactac cagtgcaaat | 4380 |
| aactgaacta aatatttgtt actgctgact gagaacagct gttcgagtgt agcattgtgg | 4440 |
| cttgttaatg tgagtgcccc aactctatgg tcttattaaa gaaacccaaa cattgctcag | 4500 |
| attttgttct tattgtcatc ataagacttg aatagtgatg gtaatgctta cgtagacgtg | 4560 |
| tcttgtgagt gcacttcagt gatttagaaa gaactggatt tcaagcaact ttggacctgt | 4620 |
| ggggggaggg agattaatga aggtttgaat cacattctaa ttctatgtac agtccttcat | 4680 |
| tactccacaa gcctaaatcc tatacagcct ccaggatagc tggaaactgt tgagatctgg | 4740 |
| actttttttt tttaatccaa gggctaactt gttgtaactt ggtataatta tctgctttcg | 4800 |
| gaaatgcatc tctgttggtt tgaaa | 4825 |

<210> SEQ ID NO 62
<211> LENGTH: 189
<212> TYPE: PRT

<213> ORGANISM: Gallus gallus

<400> SEQUENCE: 62

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
        115                 120                 125

Gln Ala Gln Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Asn Glu Asp
                165                 170                 175

Gly Asn Gln Gly Cys Met Gly Leu Ser Cys Ile Val Met
            180                 185
```

```
<210> SEQ ID NO 63
<211> LENGTH: 2603
<212> TYPE: DNA
<213> ORGANISM: Homo sapiens
```

<400> SEQUENCE: 63

```
aggcgaggct tccccttccc cgcccctccc ccggcctcca gtccctccca gggccgcttc      60
gcagagcggc taggagcacg gcggcggcgg cactttcccc ggcaggagct ggagctgggc     120
tctggtgcgc gcgcggctgt gccgcccgag ccggagggac tggttggttg agagagagag     180
aggaagggaa tcccgggctg ccgaaccgca cgttcagccc gctccgctcc tgcagggcag     240
cctttcggct ctctgcgcgc gaagccgagt cccgggcggg tggggcgggg gtccactgag     300
accgctaccg gcccctcggc gctgacggga ccgcgcgggg cgcacccgct gaaggcagcc     360
ccggggcccg cggcccggac ttggtcctgc gcagcgggcg cggggcagcg cagcgggagg     420
aagcgagagg tgctgccctc cccccggagt tggaagcgcg ttacccgggt ccaaaatgcc     480
caagaagaag ccgacgccca tccagctgaa cccggccccc gacggctctg cagttaacgg     540
gaccagctct gcggagacca acttggaggc cttgcagaag aagctggagg agctagagct     600
tgatgagcag cagcgaaagc gccttgaggc cttttcttacc cagaagcaga aggtgggaga     660
actgaaggat gacgactttg agaagatcag tgagctgggg gctggcaatg gcggtgtggt     720
gttcaaggtc tcccacaagc cttctggcct ggtcatggcc agaaagctaa ttcatctgga     780
gatcaaaccc gcaatccgga accagatcat aagggagctg caggttctgc atgagtgcaa     840
ctctccgtac atcgtgggct tctatggtgc gttctacagc gatggcgaga tcagtatctg     900
catggagcac atggatggag ttctctctgga tcaagtcctg aagaaagctg aagaattcc     960
```

-continued

```
tgaacaaatt ttaggaaaag ttagcattgc tgtaataaaa ggcctgacat atctgaggga    1020
gaagcacaag atcatgcaca gagatgtcaa gccctccaac atcctagtca actcccgtgg    1080
ggagatcaag ctctgtgact ttggggtcag cgggcagctc atcgactcca tggccaactc    1140
cttcgtgggc acaaggtcct acatgtcgcc agaaagactc caggggactc attactctgt    1200
gcagtcagac atctggagca tgggactgtc tctggtagag atggcggttg ggaggtatcc    1260
catccctcct ccagatgcca aggagctgga gctgatgttt gggtgccagg tgaaggaga    1320 tgcggctgag accccaccca ggccaaggac ccccgggagg cccc ttagct catacggaat    1380 ggacagccga cctcccatgg caatttttga gttgttggat tacatagtca acgagcctcc    1440
tccaaaactg cccagtggag tgttcagtct ggaatttcaa gattttgtga ataaatgctt    1500
aataaaaaac cccgcagaga gagcagattt gaagcaactc atggttcatg cttttatcaa    1560
gagatctgat gctgaggaag tggattttgc aggttggctc tgctccacca tcggccttaa    1620
ccagcccagc acaccaaccc atgctgctgg cgtctaagtg tttgggaagc aacaaagagc    1680
gagtcccctg cccggtggtt tgccatgtcg cttttgggcc tccttcccat gcctgtctct    1740
gttcagatgt gcatttcacc tgtgacaaag gatgaagaac acagcatgtg ccaagattct    1800
actcttgtca ttttttaatat tactgtcttt attcttatta ctattattgt tccc ctaagt    1860 ggattggctt tgtgcttggg gctatttgtg tgtatgctga tgatcaaaac ctgtgccagg    1920
ctgaattaca gtgaaatttt ggtgaatgtg ggtagtcatt cttacaattg cactgctgtt    1980
cctgctccat gactggctgt ctgcctgtat tttcgggatt cttt gacatt tggtggtact    2040 ttattcttgc tgggcatact ttctctctag gagggagcct tgtgagatcc ttcacaggca    2100
gtgcatgtga agcatgcttt gctgctatga aaatgagcat cagagagtgt acatcatgtt    2160
attttattat tattatttgc ttttcatgta gaactcagca gttgacatcc aaatctagcc    2220 agagccc ttc actgccatga tagctggggc ttcaccagtc tgtctactgt ggtgatctgt    2280
agacttctgg ttgtatttct atatttattt tcagtatact gtgtgggata cttagtggta    2340 tgtctctttta agttttgatt aatgtttctt aaatggaatt attttgaatg tcacaaattg    2400
atcaagatat taaaatgtcg gatttatctt tccccatatc caagtaccaa tgctgttgta    2460
aacaacgtgt atagtgccta aaattgtatg aaaatccttt taaccatttt aacctagatg    2520
tttaacaaat ctaatctctt attctaataa atatactatg aaataaaaaa aaaaggatga    2580
aagctaaaaa aaaaaaaaaa aaa                                           2603
```

<210> SEQ ID NO 64
<211> LENGTH: 393
<212> TYPE: PRT
<213> ORGANISM: Homo sapiens

<400> SEQUENCE: 64

```
Met Pro Lys Lys Lys Pro Thr Pro Ile Gln Leu Asn Pro Ala Pro Asp
 1               5                  10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80
```

```
Val Val Phe Lys Val Ser His Lys Pro Ser Gly Leu Val Met Ala Arg
            85                  90                  95
Lys Leu Ile His Leu Glu Ile Lys Pro Ala Ile Arg Asn Gln Ile Ile
            100                 105                 110
Arg Glu Leu Gln Val Leu His Glu Cys Asn Ser Pro Tyr Ile Val Gly
            115                 120                 125
Phe Tyr Gly Ala Phe Tyr Ser Asp Gly Glu Ile Ser Ile Cys Met Glu
            130                 135                 140
His Met Asp Gly Gly Ser Leu Asp Gln Val Leu Lys Lys Ala Gly Arg
145                 150                 155                 160
Ile Pro Glu Gln Ile Leu Gly Lys Val Ser Ile Ala Val Ile Lys Gly
                165                 170                 175
Leu Thr Tyr Leu Arg Glu Lys His Lys Ile Met His Arg Asp Val Lys
            180                 185                 190
Pro Ser Asn Ile Leu Val Asn Ser Arg Gly Glu Ile Lys Leu Cys Asp
            195                 200                 205
Phe Gly Val Ser Gly Gln Leu Ile Asp Ser Met Ala Asn Ser Phe Val
            210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
                245                 250                 255
Ala Val Gly Arg Tyr Pro Ile Pro Pro Asp Ala Lys Glu Leu Glu
            260                 265                 270
Leu Met Phe Gly Cys Gln Val Glu Gly Asp Ala Ala Glu Thr Pro Pro
            275                 280                 285
Arg Pro Arg Thr Pro Gly Arg Pro Leu Ser Ser Tyr Gly Met Asp Ser
290                 295                 300
Arg Pro Pro Met Ala Ile Phe Glu Leu Leu Asp Tyr Ile Val Asn Glu
305                 310                 315                 320
Pro Pro Pro Lys Leu Pro Ser Gly Val Phe Ser Leu Glu Phe Gln Asp
            325                 330                 335
Phe Val Asn Lys Cys Leu Ile Lys Asn Pro Ala Glu Arg Ala Asp Leu
            340                 345                 350
Lys Gln Leu Met Val His Ala Phe Ile Lys Arg Ser Asp Ala Glu Glu
            355                 360                 365
Val Asp Phe Ala Gly Trp Leu Cys Ser Thr Ile Gly Leu Asn Gln Pro
370                 375                 380
Ser Thr Pro Thr His Ala Ala Gly Val
385                 390

<210> SEQ ID NO 65
<211> LENGTH: 2151
<212> TYPE: DNA
<213> ORGANISM: Rattus norvegicus

<400> SEQUENCE: 65
cggccgcgcg ctccctgctg agttgcaggc tgtttcccgg ctgcaagatg cccaagaaga      60
agccgacgcc catccagctg aacccggccc ccgatggctc cgcggttaac gggaccagct     120
cggccgagac caacctggag gccttgcaga agaagctgga ggagctggag ctggacgagc     180
agcagcggaa gcgccttgag gccttttctga cgcagaagca gaaggtggga gagttgaagg     240
atgatgactt tgagaagatc agtgaactgg gggctggcaa tggtggagtg gtgttcaagg     300
```

| | |
|---|---|
| tctcccacaa gccatctggc ctggttatgg ctaggaagct aattcacctg gagatcaaac | 360 |
| ccgcaatccg gaaccagatc atccgggagc tgcaggtgct gcatgagtgc aactccccgt | 420 |
| acatagtggg cttctacggg gccttctaca gtgacggcga gatcagcatc tgcatggagc | 480 |
| acatggatgt tgggtccttg gatcaagtgc tgaagaaagc tggaagaatt cctgagcaaa | 540 |
| ttttaggaaa agtcagcatc gctgtgataa aaggcctgac atatctacga gagaagcaca | 600 |
| agattatgca cagagatgtc aagccttcca acattctagt gaactcacgt ggggagatca | 660 |
| aactctgcga ttttggggtc agcgggcagc taattgactc catggccaac tccttcgtgg | 720 |
| gaacaaggtc ctacatgtcg cctgagagac tccaggggac tcactactct gtgcagtcgg | 780 |
| acatctggag catgggctc tctctggtgg agatggcagt tggaagatac cccattcctc | 840 |
| ctcctgatgc caaggagctg gagctgctgt ttggatgcca ggtggaagga acgcggccg | 900 |
| aaacgccacc caggccaagg acccctggga ggcccctcag ctcatatgga atggatagcc | 960 |
| gacctcccat ggcaattttt gagttgttgg attacatcgt caatgagcct cctccaaaac | 1020 |
| tgcccagtgg agtattcagt ctggaatttc aggattttgt gaataagtgc ttaataaaga | 1080 |
| accctgcaga gagagcagat ctgaagcagc tcatggtaca tgctttcatc aagagatctg | 1140 |
| atgccgagga ggtagacttc gcaggctggc tctgctccac cattgggctt aaccagccca | 1200 |
| gcacaccaac ccacgctgcc agcatctgag cctttgggaa gcagcagaga ggaatcctct | 1260 |
| gcccagtggc atgccatgtt gctttcaggc ctctcccatg cttgtctatg ttcagatgtg | 1320 |
| catctcatct gtgacaaagg atgaagaaca cagcatgtgc caaatcgtac ttgtgtcatt | 1380 |
| tttaatattg tctttatcgc tatggttact cccctaagtg gattggcttt gtgcttgggg | 1440 |
| ctatttgtct gttcatcaaa tacatgccag gttgaactac agtgaaaccc tggtgacctg | 1500 |
| ggtggtcttc ttactgatgt ttgcgctgct gttcatcgtg actcactagc tggctgcctg | 1560 |
| tattgtcagg attctcggac ccttggtact tcactcttgc tggtgacctc tcagtctgag | 1620 |
| gagagggggc cttctgagac ccttcacagg cagtgcatgc atgaaaagca tgctttgctg | 1680 |
| ctactgaaat gagcaccaga acgtgtacat catggtattt tattttttgct tttggtatag | 1740 |
| aactcagcag ttcccattta aaaaaaaaat ctaaccagag cccatcactg ccatgatagc | 1800 |
| tggggcttca gtctgtctac tgtggtgatt tttagacttc tggttgtatt tctatattta | 1860 |
| tttttaaata tactgtgtgg gatacttagt ggtatatgtc tctgagtttg gattagtgtt | 1920 |
| tctaaattgg tagttatttt gaatgtcaca aatggattaa ggaatcaacg tatcaagagt | 1980 |
| tctatctttc ttccagtcta agtaccaatg ctattgtaaa cgtgtatagt gcctacaaat | 2040 |
| tgtatgaaaa ccctttttaac cactttactc aagatgttta tcaaatctaa tctcttattc | 2100 |
| taataaaaat actatcaagt taaagtaaaa aaaaaaaaa aaaaaaaaaa a | 2151 |

<210> SEQ ID NO 66
<211> LENGTH: 393
<212> TYPE: PRT
<213> ORGANISM: Rattus norvegicus

<400> SEQUENCE: 66

Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

```
Arg Leu Glu Ala Phe Leu Thr Gln Lys Gln Lys Val Gly Glu Leu Lys
 50                  55                  60

Asp Asp Asp Phe Glu Lys Ile Ser Glu Leu Gly Ala Gly Asn Gly Gly
 65                  70                  75                  80

Val Val Phe Lys Val Ser His Lys Pro Ser Gly Leu Val Met Ala Arg
                 85                  90                  95

Lys Leu Ile His Leu Glu Ile Lys Pro Ala Ile Arg Asn Gln Ile Ile
                100                 105                 110

Arg Glu Leu Gln Val Leu His Glu Cys Asn Ser Pro Tyr Ile Val Gly
                115                 120                 125

Phe Tyr Gly Ala Phe Tyr Ser Asp Gly Glu Ile Ser Ile Cys Met Glu
130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
                180                 185                 190

Pro Ser Asn Ile Leu Val Asn Ser Arg Gly Glu Ile Lys Leu Cys Asp
                195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
                260                 265                 270

Leu Leu Phe Gly Cys Gln Val Glu Gly Asp Ala Ala Glu Thr Pro Pro
                275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Ala Glu Glu
                355                 360                 365

Val Asp Phe Ala Gly Trp Leu Cys Ser Thr Ile Gly Leu Asn Gln Pro
370                 375                 380

Ser Thr Pro Thr His Ala Ala Ser Ile
385                 390

<210> SEQ ID NO 67
<211> LENGTH: 2387
<212> TYPE: DNA
<213> ORGANISM: Mus musculus

<400> SEQUENCE: 67
agtccctcac tgggacgtct gtgcgcggcg tctcggagcg ccggagcagc ggtggccgca      60
ctttctccaa gctggggctg tagctgagct gtgggtagtg cgcagggagc cgtccgagcc     120
cgaggaaccg gtgtgctgag gcgagagttc ccggccggcg agcgcgcgca gctggttctc     180
```

-continued

```
cgcgtgggtt gggcggaggg tcccaggagc gcggcgttga tcgagccgcc ccgactctgg      240
gcagagccga gggaggaagc gagaagcggc cgcgcgctcc ctgctgagtt gcaggctctt      300
tcccggctgc aagatgccca agaagaagcc gacgcccatc cagctgaacc cggcccccga      360
tggctcggcg gttaacggga ccagctcggc cgagaccaac ctggaggcct tgcagaagaa      420
gctggaggag ctggagcttg acgagcagca gcggaagcgg ctcgaggcct ttctgacgca      480
gaagcagaag gtgggggaac tgaaggatga tgactttgag aagatcagcg aactgggagc      540
tggcaacggt ggagtggtct tcaaggtctc ccacaagcca tctggcctgg ttatggctag      600
aaagctgatc cacctggaga tcaaacccgc aatccggaac cagatcatcc gggagctgca      660
ggtactgcac gagtgcaact ccccgtacat cgtgggcttc tacggggcct tctacagcga      720
cggcgagatc agcatctgca tggagcacat ggatggtggg tccttggatc aagttctgaa      780
gaaagctgga agaattcctg agcaaatttt aggaaaagtt agcattgctg tgataaaagg      840
cctgacctat cttcgggaga agcacaagat tatgcacaga gatgtcaagc catccaacat      900
tctagtgaac tcacgtgggg agatcaaact ctgtgatttt ggggtcagcg ggcagctaat      960
tgactctatg gccaactcct tcgtgggcac gagatcctac atgtcgcctg agagactcca     1020
ggggactcac tactctgtgc agtcggacat ctggagcatg gggctctctc tggtggagat     1080
ggcagttggg agatacccca ttcctcctcc tgatgccaag gagctggagc tactgtttgg     1140
atgccatgtg gaaggagacg cagccgaaac accacccagg ccaaggaccc tgggaggcc     1200 tctcagctca tatggaatgg acagccgacc tcccatggca attttgagt tgttggatta     1260 cattgtcaat gagcctcctc caaaactgcc cagtggagta ttcagtctgg agtttcagga     1320
ttttgtgaat aaatgcttaa taagaacccc tgcagagaga gcagatctga agcagctcat     1380
ggtacatgct ttcatcaaaa gatctgacgc cgaggaggta gacttcgcag gctggctctg     1440
ctccaccatt gggcttaacc agcccagcac accaacccac gctgccagca tctgagcctt     1500
taggaagcag caaagaggaa ttctctgccc agtggcatgc catgttgctt tcaggcctct     1560
cccatgcttg tctatgttca gacgtgcatc tcatctgtga caaggatgaa gaacacagc     1620 atgtgccaaa ttgtacttgt gtcattttta atatcattgt ctttatcact atggttactc     1680
ccctaagtgg attggctttg tgcttggggc tatttgtctg ttcatcaaac acatgccagg     1740
ctgaactaca gtgaaaccct agtgacctgg gtggtcgttc ttactgatgt ttgcactgct     1800
gttcatcgtg actcactagc tggctgcctg tattgtcagg attctcggac cttggtactt     1860
cactcttgct ggtgacctct cagtctgaga gggagccttg tgagacccctt cacaggcagt     1920 gcatgcatgg aaagcatgct ttgctgctac tgaaatgagc atcagaacgt gtacgtcatg     1980 gtattttat ttttgctttt ggtatagaa ctcagcaatt cccatcaaaa aaacctaagc     2040
agagcccatc actgccatga tagctgggct tcagtctgtc tactgtggtg attttagac     2100 ttctggttgt atttctatat ttattttaa atatacagtg tgggatactt agtggtgtgt     2160
gtctctaagt ttggattagt gtttctaaat tggtggttat tttgaatgtc acaaatggat     2220
taaagcatca atgtatcaag agttctatct ttcttccagt ctaagtacca atgctattgt     2280
aaacaacgtg tatagtgcct acaaattgta tgaaacccct tttaaccact ttaatcaaga     2340
tgtttatcaa atctaatctc ttattctaat aaaaatacta tcaagtt                  2387
```

<210> SEQ ID NO 68
<211> LENGTH: 393
<212> TYPE: PRT

<213> ORGANISM: Mus musculus

<400> SEQUENCE: 68

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Leu Phe Gly Cys His Val Glu Gly Asp Ala Ala Glu Thr Pro Pro
        275                 280                 285

Arg Pro Arg Thr Pro Gly Arg Pro Leu Ser Ser Tyr Gly Met Asp Ser
    290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
    370                 375                 380

Ser Thr Pro Thr His Ala Ala Ser Ile
385                 390
```

<210> SEQ ID NO 69
<211> LENGTH: 1182
<212> TYPE: DNA
<213> ORGANISM: Oryctolagus cuniculus

<400> SEQUENCE: 69

```
atgccaaaga agaagcccac ccccatccag ctgaatcctg cccctgacgg ctcggcggtg      60
aatggtacca gctcggcgga gaccaacctg gaggccttgc agaagaagct ggaggagctg     120
gagcttgacg agcagcagcg gaagcgcctg gaggccttcc tcacccagaa gcagaaagtg     180
ggagagctga aggacgatga cttcgagaag atcagtgagc tgggagccgg caacggcggc     240
gtggtgttca aggtctccca caagcccagt ggcctggtga tggccagaaa gcttattcac     300
ctggagatca aacctgctat ccggaaccag atcataaggg agctgcaggt tctgcacgag     360
tgcaactccc cgtacatcgt gggcttctac ggggcattct acagcgatgg cgagatcagc     420
atctgcatgg agcacatgga cgggggttcc ttggatcaag tcctgaagaa agctggacgg     480
attcccgagc aaattttggg gaaagttagc attgctgtga tcaagggcct gacgtatctg     540
agggagaagc acaagatcat gcacagagat gtgaagccct ccaacatcct ggtcaactcc     600
cgcggggaga tcaagctctg tgacttcggg gtcagtgggc agctcatcga ctccatggcc     660
aactccttcg tgggcaccag gtcttatatg tcgcccgaga gactccaggg gacacactac     720
tctgtgcagt cggacatctg gagcatgggg ctgtccctgg tggagatggc ggtggggcgg     780
taccccatcc cgcccccgga cgccaaggag ctggagctga tgtttgggtg ccaggtggag     840
ggcgatgcgg ccgagactcc gcccaggccc aggaccctg gcggcccct cagctcgtat     900
ggaatggata gccggcctcc catggcgatt tttgagctgc tggattacat cgtcaatgag     960
cctcctccga aactccccag cgcagtcttc agcctggagt ttcaagattt tgtgaataaa    1020
tgcttaataa aaaaccccgc cgagagagca gacttgaagc agctcatggt tcatgctttt    1080
atcaagaggt ctgatgccga ggaggtggat tttgctggtt ggctgtgctc caccatcggc    1140
cttaaccagc ccagcacgcc gacgcacgcg gccggtgtgt ga                        1182
```

<210> SEQ ID NO 70
<211> LENGTH: 393
<212> TYPE: PRT
<213> ORGANISM: Oryctolagus cuniculus

<400> SEQUENCE: 70

```
Met Pro Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125
```

Phe Tyr Gly Ala Phe Tyr Ser Asp Gly Glu Ile Ser Ile Cys Met Glu
        130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Met Phe Gly Cys Gln Val Glu Gly Asp Ala Ala Glu Thr Pro Pro
        275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Ala Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ser Thr Ile Gly Leu Asn Gln Pro
370                 375                 380

Ser Thr Pro Thr His Ala Ala Gly Val
385                 390

<210> SEQ ID NO 71
<211> LENGTH: 1872
<212> TYPE: DNA
<213> ORGANISM: Cavia porcellus

<400> SEQUENCE: 71
cgtgtcttcg tcgggaccgc cctcctcctt gagtcctccc cccaccggga cggccgagtg     60
gagaggccgg acgaaggcgg cggccccggc ggcggctttt cctcggcttc gctgtgcagc    120
gtgcgcggcg aggttgaccg cccgcgagcg cccgtgactg agggaacagg gagagagctc    180
gggcggccga gcgcgcagcc ctccgtgggc attgccgcct ggacctcccg gaaggcaccc    240
cgggccgcgg ccgccacccg tcccgccctc gttcggagct gagacgccgt cgccgcgcaa    300
gatgcccaag aagaagccga cgcccatcca gctgaaccog ccccgacg gctcggcggt    360 gaacgggacc agctcggccg agaccaacct agaggctttg cagaagaagc tggaggagct    420
ggagctggat gagcagcagc ggaagcgcct cgaagctttc ctgacacaga agcagaaggt    480
gggcgagctg aaggacgatg actttgagaa gatcagtgag ctgggtgccg gcaatggcgg    540
tgtggtgttc aaggtctccc acaagccatc tggcctggtc atgccccgaa agcttatcca    600

```
cctggagatc aagccagcca tccgcaatca gatcatccgt gagctgcagg ttctgcacga    660
gtgcaactcg ccctacattg tgggcttcta tggggccttc tacagtgatg gcgagatcag    720
catctgcatg gagcacatgg atggaggttc cttggatcaa gtcctgaaga aagctggaag    780
aattcctgag caaattttag gaaaagttag cattgctgtg atcaaaggcc tgacatacct    840
gagggagaag cacaagatta tgcacagaga tgtcaagccc tccaacatcc tggtcaactc    900
ccgcggggag atcaagctct gtgactttgg ggtcagcggg cagctcatcg attccatggc    960
caactccttc gtgggcaccc ggtcctacat gtcgccagag agactgcagg cacacacta    1020 ctcagtgcag tcggacatct ggagcatggg actgtcactg gtggagatgg cggttgggag    1080
gtaccccatc ccccctccag atgccaagga gctggagctg gtgttcgggt gccaggtgga    1140
aggagatgca gctgagatgc cgcccaggcc caggaccccc ggaagacccc tgagctcata    1200
tggaatggac agccggcctc ccatggcgat tttcgagctg ttggattaca tagtcaacga    1260
gccacctccc aaactgccca gtggagtctt cagtctggaa ttccaggact tgtaaataa    1320 atgcttaata aagaaccctg cggagagagc agacttgaag cagctcatgg ttcatgcctt    1380
catcaagcgc tctgatgctg aggaggtgga cttcgcaggt tggctctgtg ccaccatcgg    1440
ccttaaccag cccagtaccc cgacccacgt ggccagcatc tgagctgcgg cccggcccag    1500
acgtgctctg ccagcagccg ctatgctctg gcctctccct cgcttctctt cagacgtgcg    1560
tttcacctcc gaccagggtg cagacacagc atgtgccaag ctgtatttgt gttccttttc    1620
agtctttatt gccaccgtgt cacccgagtg gatttgcttt gtgcttaggg ctgtttgtgc    1680
tgatgatcac acacacgctg agctgaacag tgacacttgg tgatgtggtt gtcactgttc    1740
tcactccatg tggctggcct gttgcctcca gtgtctccag acttggggat gtctggtggc    1800
acttcccctg ccagggcatc tcctcagcag agagggaggc ctctgggccc ttgtccttgg    1860
cagtgcaagt ga                                                       1872
```

<210> SEQ ID NO 72
<211> LENGTH: 393
<212> TYPE: PRT
<213> ORGANISM: Cavia porcellus

<400> SEQUENCE: 72

```
Met Pro Lys Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140
```

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
            165                 170                 175

Leu Thr Tyr Leu Arg Glu Lys His Lys Ile Met His Arg Asp Val Lys
        180                 185                 190

Pro Ser Asn Ile Leu Val Asn Ser Arg Gly Glu Ile Lys Leu Cys Asp
    195                 200                 205

Phe Gly Val Ser Gly Gln Leu Ile Asp Ser Met Ala Asn Ser Phe Val
210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270

Leu Val Phe Gly Cys Gln Val Glu Gly Asp Ala Ala Glu Met Pro Pro
        275                 280                 285

Arg Pro Arg Thr Pro Gly Arg Pro Leu Ser Ser Tyr Gly Met Asp Ser
290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
            340                 345                 350

Lys Gln Leu Met Val His Ala Phe Ile Lys Arg Ser Asp Ala Glu Glu
        355                 360                 365

Val Asp Phe Ala Gly Trp Leu Cys Ala Thr Ile Gly Leu Asn Gln Pro
370                 375                 380

Ser Thr Pro Thr His Val Ala Ser Ile
385                 390

<210> SEQ ID NO 73
<211> LENGTH: 1257
<212> TYPE: DNA
<213> ORGANISM: Canis familiaris

<400> SEQUENCE: 73
ggagagcgag acacgggccg ctctccgctc ggagccggac gcgccttccc gcgtccaaaa      60
tgcccaagaa gaagccgacg cccatccagc tgaacccggc ccccgacggc tcggcggtga     120 acggaccag ctcggcggag accaacctgg aggccttgca gaagaagctg aggagctgg      180 agcttgatga gcagcagcgg aagcgccttg aggcctttct cacccagaag cagaaggtcg     240
gggaactgaa ggatgacgac ttcgagaaga tcagtgagct gggtgctggc aacggtggcg     300
tggtgttcaa ggtctcccac aagccgtccg gctagtcat ggccagaaag ctaattcacc      360
tggagatcaa acctgcaatc cggaaccaga tcataaggga gctacaggtt ctacatgagt     420
gcaactcccc gtacatcgtg gcttctatg gtgcattcta cagcgatggc gagatcagta      480
tctgcatgga gcacatggat gggggttcct tggatcaagt cctgaagaaa gctggaagaa     540
ttcctgaaca aattctagga aaagttagca tcgctgtaat aaaaggtctg acatacctga     600
gagagaagca caagattatg cacagagatg tcaagccttc caacatcctc gtgaactccc     660

```
gtggggagat caagctctgt gactttgggg tcagcgggca gctcattgac tccatggcca   720
actccttcgt gggcacaagg tcctacatgt cgccagaaag actccagggg actcattact   780
ccgtgcagtc ggacatctgg agcatggggc tctctctggt ggagatggca gttgggaggt   840
atcccatccc tcctccggat gccaaggagc tggagctgat gtttgggtgc caagtggagg   900
gagacgtggc tgagacccca cccagaccaa ggaccccggg aagacccctt agctcttatg   960
gaatggacag ccgaccgccc atggcaattt ttgagctgtt ggattacata gtcaacgagc  1020
cccctccaaa actgcccagt ggagtattca gtctggaatt tcaagatttt gtgaataaat  1080
gcttaataaa aaacccagca gagagagcag atctgaagca actcatggtt catgccttca  1140
tcaagagatc tgacggtgaa gaagtggatt ttgcaggttg gctctgctcc ccccattggc  1200
cttaaccagc ccagcacgcc gacccacgca gctggcgtct aactcgagtc tagagat      1257
```

<210> SEQ ID NO 74
<211> LENGTH: 381
<212> TYPE: PRT
<213> ORGANISM: Canis familiaris

<400> SEQUENCE: 74

```
Met Pro Lys Lys Pro Thr Pro Ile Gln Leu Asn Pro Ala Pro Asp
1               5                   10                  15

Gly Ser Ala Val Asn Gly Thr Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205

Phe Gly Val Ser Gly Gln Leu Ile Asp Ser Met Ala Asn Ser Phe Val
    210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Val Gly Arg Tyr Pro Ile Pro Pro Asp Ala Lys Glu Leu Glu
            260                 265                 270
```

```
Leu Met Phe Gly Cys Gln Val Glu Gly Asp Val Ala Glu Thr Pro Pro
        275                 280                 285

Arg Pro Arg Thr Pro Gly Arg Pro Leu Ser Ser Tyr Gly Met Asp Ser
        290                 295                 300

Arg Pro Pro Met Ala Ile Phe Glu Leu Leu Asp Tyr Ile Val Asn Glu
305                 310                 315                 320

Pro Pro Pro Lys Leu Pro Ser Gly Val Phe Ser Leu Glu Phe Gln Asp
                325                 330                 335

Phe Val Asn Lys Cys Leu Ile Lys Asn Pro Ala Glu Arg Ala Asp Leu
                340                 345                 350

Lys Gln Leu Met Val His Ala Phe Ile Lys Arg Ser Asp Gly Glu Glu
            355                 360                 365

Val Asp Phe Ala Gly Trp Leu Cys Ser Pro His Trp Pro
    370                 375                 380

<210> SEQ ID NO 75
<211> LENGTH: 2095
<212> TYPE: DNA
<213> ORGANISM: Felis catus

<400> SEQUENCE: 75
agccggcaag gagttgagcg tgcggggtgc ataggcgcgg gtcgtgggag atgaagctgg      60
agaggaccaa cctggaggcc ttgcagaaga agctggagga gctggagctc gatgagcagc     120
aacggaagcg cctggaggcc tttcttaccc agaagcagaa ggtcgggaa ttgaaggatg      180 acgacttcga gaagatcagc gagctgggcg ctggcaacgg tggtgtggtg ttcaaggtct     240
cccataagcc gtctggcctg gtcatggcca gaaagctaat tcacctggag atcaaacctg     300
caatccggaa ccagatcata agggagctgc aggttctaca tgagtgcaac tccccataca     360
tcgtgggctt ctatggcgcg ttctacagcg acggcgagat cagtatctgt atggagcaca     420
tggatggggg ttccttggat caagtcctga gaaagctgg aagaattcct gaacaaattt      480
taggaaaagt tagcattgct gtaataaaag gtctgacata cctgagggag aagcacaaga     540
ttatgcacag agatgtcaag ccttccaaca tcctagtgaa ctctcgtggg gagatcaagc     600
tctgtgactt tggggtcagc gggcagctca tcgactccat ggccaactcc ttcgtgggca     660
caaggtccta catgtcgcca gaaagactcc aggggactca ttactccgtg cagtcggaca     720
tctggagcat ggggcatatct ctggttgaga tggcagtcgg gaggtatccc atccctcctc     780
ccgatgccaa ggagctggag ctgatgtttg ggtgccaagt ggagggagat gcggctgaga     840
cgccacccag gccgaggacc cccggaaggc ccctcagctc gtatggaatg dacagccgac     900
ctcccatggc aattttttgag ttgttggatt acatagtcaa cgagcctcct ccaaagctgc     960
ccagtggagt attcagtctg gaatttcaag attttgtgaa taatgcctc ataaaaaacc     1020 cagcagagag agcagatctg aaacaactca tggttcatgc ctttatcaag agatctgatg     1080
gtgaggaagt ggatttttgca ggttggctct gctccaccat cggccttaac cagcccagca    1140
caccgaccca cgcggccggc gtctaagtat ctgggaagca gcaaagagcg agtcccctgc    1200
ccagtggtgt gccattgtcg ctttcaggcc tctttgccat gcctgtctcc gttcagacgt    1260
gcatttcgcc tacgacaaag gatgaagaac acagcatgtg ccaaaattct atttgtgtct    1320
tttttaatat tactgtcatt tattctgtta tttccctaag tggattggct ttgtgcttgg    1380
ggctattttt gtgtatgttg atccaaacat gcgcaacgtt cagttacagt gaaaccttgg    1440
tgactgtggg tagtcattct tactgaaaat tgcactgctc ttcccccacc gtgactggct    1500
```

-continued

```
agctgcctgt agttttggga ttcttttgac acttggtggt actgcattct tgccgggcgc   1560
accttccttc tgttggggta ggagccttgt aagatccttc acaggcactg catgtgaagc   1620
atgctttgct gctatgaaaa agaacatcag aaagtataga tcttgttatt ttattatatt   1680 tttgctttg gtgtagaatg aagcaatttc tgtcaaaatc tagccagagc ccttcactgc   1740
cacgatagct ggggcttcac cagtctgtct actgtgatga tttgtagact tctggttgta   1800
tttctatatt tattttaaaa tatattatgt gggatattta gtggtatgtg tctctttaag   1860
tttgaattag tgtttctaaa atgatggtta ctttgaatgt tacaaatgga tcaaggcatt   1920
aaaatgtatg agattatct ttccccaaat ccaagtaccg atgctattgt aaacaacagt   1980
gtgtatagtg cctaagaatt gtatgaaaat ccttttaacc atttcaaccc agatgtttaa   2040
caaatctaat ctcttattct aataaatata ctatcaagtt aaaaggatga aaaa          2095
```

<210> SEQ ID NO 76
<211> LENGTH: 371
<212> TYPE: PRT
<213> ORGANISM: Felis catus

<400> SEQUENCE: 76

```
Met Lys Leu Glu Arg Thr Asn Leu Glu Ala Leu Gln Lys Lys Leu Glu
 1               5                  10                  15

Glu Leu Glu Leu Asp Glu Gln Gln Arg Lys Arg Leu Glu Ala Phe Leu
            20                  25                  30

Thr Gln Lys Gln Lys Val Gly Glu Leu Lys Asp Asp Phe Glu Lys
         35                  40                  45

Ile Ser Glu Leu Gly Ala Gly Asn Gly Gly Val Val Phe Lys Val Ser
     50                  55                  60

His Lys Pro Ser Gly Leu Val Met Ala Arg Lys Leu Ile His Leu Glu
 65                  70                  75                  80

Ile Lys Pro Ala Ile Arg Asn Gln Ile Ile Arg Glu Leu Gln Val Leu
                 85                  90                  95

His Glu Cys Asn Ser Pro Tyr Ile Val Gly Phe Tyr Gly Ala Phe Tyr
            100                 105                 110

Ser Asp Gly Glu Ile Ser Ile Cys Met Glu His Met Asp Gly Gly Ser
        115                 120                 125

Leu Asp Gln Val Leu Lys Lys Ala Gly Arg Ile Pro Glu Gln Ile Leu
    130                 135                 140

Gly Lys Val Ser Ile Ala Val Ile Lys Gly Leu Thr Tyr Leu Arg Glu
145                 150                 155                 160

Lys His Lys Ile Met His Arg Asp Val Lys Pro Ser Asn Ile Leu Val
                165                 170                 175

Asn Ser Arg Gly Glu Ile Lys Leu Cys Asp Phe Gly Val Ser Gly Gln
            180                 185                 190

Leu Ile Asp Ser Met Ala Asn Ser Phe Val Gly Thr Arg Ser Tyr Met
        195                 200                 205

Ser Pro Glu Arg Leu Gln Gly Thr His Tyr Ser Val Gln Ser Asp Ile
    210                 215                 220

Trp Ser Met Gly Leu Ser Leu Val Glu Met Ala Val Gly Arg Tyr Pro
225                 230                 235                 240

Ile Pro Pro Pro Asp Ala Lys Glu Leu Glu Leu Met Phe Gly Cys Gln
                245                 250                 255

Val Glu Gly Asp Ala Ala Glu Thr Pro Pro Arg Pro Arg Thr Pro Gly
            260                 265                 270
```

```
Arg Pro Leu Ser Ser Tyr Gly Met Asp Ser Arg Pro Met Ala Ile
            275                 280                 285

Phe Glu Leu Leu Asp Tyr Ile Val Asn Glu Pro Pro Lys Leu Pro
        290                 295                 300

Ser Gly Val Phe Ser Leu Glu Phe Gln Asp Phe Val Asn Lys Cys Leu
305                 310                 315                 320

Ile Lys Asn Pro Ala Glu Arg Ala Asp Leu Lys Gln Leu Met Val His
                325                 330                 335

Ala Phe Ile Lys Arg Ser Asp Gly Glu Val Asp Phe Ala Gly Trp
            340                 345                 350

Leu Cys Ser Thr Ile Gly Leu Asn Gln Pro Ser Thr Pro Thr His Ala
        355                 360                 365

Ala Gly Val
    370

<210> SEQ ID NO 77
<211> LENGTH: 2405
<212> TYPE: DNA
<213> ORGANISM: Bos taurus

<400> SEQUENCE: 77
```

| | | | | |
|---|---|---|---|---|
| ccggttgact gagggagagt gggagggaat cccgggctgc cgagctgcgc cggcggggaa | 60 |
| gcccttcggt tccctgtgca ctgagcaagt gggccggggg gttcccccag accgccactg | 120 |
| gccctttggc cctgacggga ccgcgcaggg cgcgcccccc gaaggcagcc ttcgggcttg | 180 |
| cggcccagac ttggccccgc gaggccggcg cggggcagct cagagggagg aagctagagg | 240 |
| ggccgccctc agagttggga gcgcctttcc tgggtccaaa atgcccaaga agaagccgac | 300 |
| gcccatccag ctgaacccgg ccccggacgc ctccgcggtt aacgggacca gctcggcgga | 360 |
| gaccaacctg gaggccttgc agaagaagct ggaggagctg agctcgatg aacagcagcg | 420 |
| gaagcgcctc gaggcctttc tgacccagaa gcagaaggtg ggggaactga aggatgatga | 480 |
| ctttgagaag atcagtgagc tgggtgccgg caatggaggt gtggtgttca aggtctccca | 540 |
| caagccgtcc ggacttgtta tggccagaaa gctaattcac ctggagatca aacctgccat | 600 |
| ccggaaccag atcataaggg agctgcaggt tctccatgag tgcaactcgc cttatatcgt | 660 |
| gggcttctac ggggcgttct acagcgacgg cgagatcagc atctgcatgg agcacatgga | 720 |
| tgggggttcc ttggatcaag ttctgaagaa agctggaaga attcctgaac aaattttagg | 780 |
| aaaagttagc attgctgtaa taaaaggcct gacatacctg agggagaagc acaagattat | 840 |
| gcacagagat gtcaagccgt ccaacatcct agtgaacagc cgtggagaga tcaagctctg | 900 |
| tgactttggg gtcagcgggc agctcatcga ctccatggcc aactccttcg tgggcaccag | 960 |
| gtcctacatg tcgccagagc gactccaggg gacccattac tccgtgcagt cggacatctg | 1020 |
| gagcatgggg ctctctctgg ttgagatggc tgtcgggagg tatcccatcc ctcctccaga | 1080 |
| tgccaaggag ctggagctga tgtttgggtg ccaggtggag ggagatgcgg ctgagacccc | 1140 |
| gcccaggcca aggacccccg ggaggcccct cagctcttat ggaatggaca gccgacctcc | 1200 |
| aatggcaatt tttgagttgt tggattacat agtcaatgag cctcctccaa aactgcccag | 1260 |
| tggagtattc agtctggaat ttcaagattt tgtgaataaa tgcttaataa aaaacccgc | 1320 |
| agagagagca gatttgaagc aactcatggt tcatgctttt atcaagagat ctgatgctga | 1380 |
| ggaagtggat tttgcaggtt ggctctgctc caccatcggc cttaaccaac ccagcacacc | 1440 |
| cacccatgcg gctggcgtct aagtggttgg aagcagcag tccctgccca agggcatgca | 1500 |

```
ctgttgcttc cgggcagcct tcccatgcct gtctctgttc agacgtgcat ttcacctatg    1560
acaaaggatg aagaacacag catgtgccaa aattctattt gtgtcatttt caatattatc    1620
atctttactc ttattactat tgttattccc ctaagtggat tggctttgtg cttggggcta    1680 ttttttgtgta tattgatgat gaagacatgt gcaatgtaga attacagtga aactctggtg    1740
actgtgggta gtcattctta ctgaaaactg cactgctttc ccacaccatg aactggctgg    1800
tcgcctctat tttcgggatt ctttgacact tggtggtact tcattcttgc caggcatacc    1860
ttctaactga gtaggaagga gccttgtaag atccttcaca ggcagtgcat gtgaagcatg    1920
ctttgctgct ataaaatga gcatcagaaa gtgtgtatca tgttatttta ttatgttctt    1980
gcttttggtg tagaattcag caaattttca tcaaaatcta gccagagccc ttcactgcca    2040
tgatagctgg ggcttcacca gtctgtctac tgtgatgatt tgtagacttc tggttgtatt    2100
tctgtattta tttttaaatc taccgtgtgg atatttagtg ctatgtctct ttaagtttgg    2160
attagtgttt ctaaaatggt ggagttgctc tgaatgttac aaatggatca aggcattaaa    2220
atgaatgaga tctaccttc accaagtact gatgctattg taaacaacag tgtgtatagt    2280
gcctaacaac tgtatgaaaa tccttttacc attttaatcc agatgtttaa caagcctaat    2340
ctcttactct aataaatata ctatcaaatt caaaggaaaa aaaaaaaaa aaaaaaaaa    2400 aaaaa                                                                   2405
```

<210> SEQ ID NO 78
<211> LENGTH: 393
<212> TYPE: PRT
<213> ORGANISM: Bos taurus

<400> SEQUENCE: 78

```
Met Pro Lys Lys Pro Thr Pro Ile Gln Leu Asn Pro Ala Pro Asp
1               5                   10                  15

Gly Ser Ala Val Asn Gly Thr Ser Ser Ala Glu Thr Asn Leu Glu Ala
            20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Val Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
145                 150                 155                 160

Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
            180                 185                 190

Pro Ser Asn Ile Leu Val Asn Ser Arg Gly Glu Ile Lys Leu Cys Asp
        195                 200                 205
```

```
Phe Gly Val Ser Gly Gln Leu Ile Asp Ser Met Ala Asn Ser Phe Val
    210                 215                 220
Gly Thr Arg Ser Tyr Met Ser Pro Glu Arg Leu Gln Gly Thr His Tyr
225                 230                 235                 240
Ser Val Gln Ser Asp Ile Trp Ser Met Gly Leu Ser Leu Val Glu Met
                245                 250                 255
Ala Val Gly Arg Tyr Pro Ile Pro Pro Asp Ala Lys Glu Leu Glu
                260                 265                 270
Leu Met Phe Gly Cys Gln Val Glu Gly Asp Ala Ala Glu Thr Pro Pro
            275                 280                 285
Arg Pro Arg Thr Pro Gly Arg Pro Leu Ser Ser Tyr Gly Met Asp Ser
290                 295                 300
Arg Pro Pro Met Ala Ile Phe Glu Leu Leu Asp Tyr Ile Val Asn Glu
305                 310                 315                 320
Pro Pro Pro Lys Leu Pro Ser Gly Val Phe Ser Leu Glu Phe Gln Asp
                325                 330                 335
Phe Val Asn Lys Cys Leu Ile Lys Asn Pro Ala Glu Arg Ala Asp Leu
                340                 345                 350
Lys Gln Leu Met Val His Ala Phe Ile Lys Arg Ser Asp Ala Glu Glu
            355                 360                 365
Val Asp Phe Ala Gly Trp Leu Cys Ser Thr Ile Gly Leu Asn Gln Pro
370                 375                 380
Ser Thr Pro Thr His Ala Ala Gly Val
385                 390

<210> SEQ ID NO 79
<211> LENGTH: 2146
<212> TYPE: DNA
<213> ORGANISM: Equus caballus

<400> SEQUENCE: 79
caagtgggaa agcttgggat gcgtggagga gccagctact agtttagtgt gctgggtgcg    60
tcggtgcagg tcgcaggaga tgaagccgga gaggaccaac ctggaggcct gcagaagaa   120
gctggaggag ctggagctcg atgaacagca gcgaaagcgc cttgaggcct ttcttactca   180
gaagcagaag gttggggaac tgaaggatga tgactttgag aagatcagtg agctgggtgc   240
tggcaatggt ggtgtggtat tcaaggttgc ccacaaaccg tctggtttgg tcatggccag   300
aaagctaatt cacctggaga tcaagcctgc aatccggaac agatcataa gggagctgca    360
ggttctacat gagtgcaact ccccatatat tgtgggcttc tatggcgcat ctacagcga    420
tggtgagatc agcatctgca tggagcacat ggatgggggt tccttggatc aagtcctaaa   480
gaaagctgga agaattcctg agcaaatttt aggaaaagtt agcattgctg taataaaagg   540
cctgacgtat ctgagggaga agcacaagat tatgcacaga gatgtcaagc cctccaacat   600
cctagtgaac tcccgtgggg agatcaagct gtgtgatttt ggggtcagcg ggcagctcat   660
cgactccatg ccaactcct tcgtgggcac aaggtcttac atgtcgccgg aaagactcca    720
ggggactcat tattcagtgc agtcggacat ctggagcatg gggctctctc tggttgagat   780
ggcggtcggg aggtatccca tccctcctcc agatgccaag gagctggagc tgatgtttgg   840
gtgccaagtg gagggagatg cggctgagac tccgcctagg ccaaggaccc ctggaagacc   900
cctcagctct tatggaatgg acagccgacc tcctatggca atttttgagt tactggatta   960
catagtcaac gagcctcctc ccaagctgcc cagtggagta ttcagtctgg aatttcagga  1020
ttttgtgaat aaatgcttaa tcaaaaaccc tgcagagaga gcagatttga agcaactcat  1080
```

```
ggttcacgct ttatcaaga gatctgatgc cgaggaagtg gattttgcag gttggctctg    1140
ctccaccatt ggccttaacc agcccagcac accaacccac gcggctggcg tctaagcgtt    1200
tgggaagcag caaaaagcga gcccctgcc gcgtggtgtg ccatgttgct tcgggcctc     1260 cttcccatgc ctgtctgttc acacgtgcat ttcacctgtg acaaaggatg aagaacacag    1320
catgtgccaa aattctattt gtgtcatttt taatagtact gtctttattc ttattactat    1380
tgttattccc ctaagtggat tggctttgtg cttgggacta ttttgtgtat gttgatgatc    1440
aaaacatgcg caatgttgaa ttaccgtgaa actggtgact gtgggtagtc cttcttattg    1500
aaaattgcac tgctcttccc tccctgtcac tggctggctg cctgtatttc tggggttctt    1560
tgacacttgg tggtacttca ttcttgcagg gcatacctcc tattcgagta ggaaggagcc    1620
tttaagatcc ttcacaggca gtgcatgtga agcatgcttt gctgctatga aaatgagcat    1680
cagaaagtgt atatcatgtt atttattat tattatgttt ttgcttttgg tgtagaattc    1740
agcaatttcc atcaagatct agccagagcc cttcactgcc atgatagctg ggcttcacc     1800 agtctgccta ctgtgatgat ttgtagactt ctggttgtat ttctatattt attttaaat    1860 atactgtgtg ggatatttag tggtatatgt ctctctaagt ttggagtggt gtttctaaaa    1920
tggagttact ttgaatgtta tagatggatc aaggcataaa atgtatgaga tttatttttc    1980
cccaaatcca aatactgatg ctattgtaaa caacaaacag tgtgtatagt gcctaaaaat    2040
tgtatgaaag tcctttaac cattttaatc cagatgttta acaaatctaa tctcttattc    2100
taataaatat actatcaagt taaacggaca aaagatttct actttc                    2146
```

<210> SEQ ID NO 80
<211> LENGTH: 371
<212> TYPE: PRT
<213> ORGANISM: Equus caballus

<400> SEQUENCE: 80

```
Met Lys Pro Glu Arg Thr Asn Leu Glu Ala Leu Gln Lys Lys Leu Glu
1               5                   10                  15

Glu Leu Glu Leu Asp Glu Gln Gln Arg Lys Arg Leu Glu Ala Phe Leu
                20                  25                  30

Thr Gln Lys Gln Lys Val Gly Glu Leu Lys Asp Asp Phe Glu Lys
        35                  40                  45

Ile Ser Glu Leu Gly Ala Gly Asn Gly Gly Val Val Phe Lys Val Ala
    50                  55                  60

His Lys Pro Ser Gly Leu Val Met Ala Arg Lys Leu Ile His Leu Glu
65                  70                  75                  80

Ile Lys Pro Ala Ile Arg Asn Gln Ile Ile Arg Glu Leu Gln Val Leu
                85                  90                  95

His Glu Cys Asn Ser Pro Tyr Ile Val Gly Phe Tyr Gly Ala Phe Tyr
            100                 105                 110

Ser Asp Gly Glu Ile Ser Ile Cys Met Glu His Met Asp Gly Gly Ser
        115                 120                 125

Leu Asp Gln Val Leu Lys Lys Ala Gly Arg Ile Pro Glu Gln Ile Leu
    130                 135                 140

Gly Lys Val Ser Ile Ala Val Ile Lys Gly Leu Thr Tyr Leu Arg Glu
145                 150                 155                 160

Lys His Lys Ile Met His Arg Asp Val Lys Pro Ser Asn Ile Leu Val
                165                 170                 175

Asn Ser Arg Gly Glu Ile Lys Leu Cys Asp Phe Gly Val Ser Gly Gln
```

```
            180                 185                 190
Leu Ile Asp Ser Met Ala Asn Ser Phe Val Gly Thr Arg Ser Tyr Met
        195                 200                 205

Ser Pro Glu Arg Leu Gln Gly Thr His Tyr Ser Val Gln Ser Asp Ile
        210                 215                 220

Trp Ser Met Gly Leu Ser Leu Val Glu Met Ala Val Gly Arg Tyr Pro
225                 230                 235                 240

Ile Pro Pro Asp Ala Lys Glu Leu Glu Leu Met Phe Gly Cys Gln
                245                 250                 255

Val Glu Gly Asp Ala Ala Glu Thr Pro Pro Arg Pro Arg Thr Pro Gly
                260                 265                 270

Arg Pro Leu Ser Ser Tyr Gly Met Asp Ser Arg Pro Met Ala Ile
        275                 280                 285

Phe Glu Leu Leu Asp Tyr Ile Val Asn Glu Pro Pro Lys Leu Pro
        290                 295                 300

Ser Gly Val Phe Ser Leu Glu Phe Gln Asp Phe Val Asn Lys Cys Leu
305                 310                 315                 320

Ile Lys Asn Pro Ala Glu Arg Ala Asp Leu Lys Gln Leu Met Val His
                325                 330                 335

Ala Phe Ile Lys Arg Ser Asp Ala Glu Glu Val Asp Phe Ala Gly Trp
                340                 345                 350

Leu Cys Ser Thr Ile Gly Leu Asn Gln Pro Ser Thr Pro Thr His Ala
        355                 360                 365

Ala Gly Val
    370

<210> SEQ ID NO 81
<211> LENGTH: 2274
<212> TYPE: DNA
<213> ORGANISM: Gallus gallus

<400> SEQUENCE: 81
ctaaccaggc gggagctgtc ggtgcggagc tcggtgtcgc tccgccgggc aggccgggtc      60
gacggccgcg ctgtgccgga gcggcagcgt cgcgggctcg gctccttctc ggggaggcgg     120
ccgcgcgctg ctccggcgct gaggggcggc cccgaagttt gcttcgcgtc gggaagtccg     180
tcggacctgg ccgaagtggg gccgcggccg ctccgtccgt cacgctctgc gctgccgggg     240
gggcaacatg cccaagaaga agccagggcc gatccagctc aaccccgctc cggatggctc     300
cgccgtcaac gggaccagct ctgccgagac aaacttggaa gctcttcaga agaagctgga     360
agagctagag ctggatgaac agcaaaggaa gcgccttgaa gctttcctta cccagaaaca     420
aaaagttggg gagctgaagg atgatgactt cgagaagatc agtgagctgg agcagggaa      480 tggcggggtg gtgttcaaag tatctcacaa gccttctggc ctcatcatgg caagaaaatt     540
gattcatcta gaaatcaagc cagctattcg aaaccagatc atccgtgagc tgcaggttct     600
acatgagtgc aattcaccat acatagtggg cttttatgga gcttttttaca gtgatgggga     660 aatcagcatt tgcatggaac acatggatgg tggctcattg gatcaagtgc tgaaaaaggc     720
tggaagaatt ccagagcaga tactgggcaa agtcagcatt gcagtaataa aaggactcac     780
atatctgaga gaaaagcata aataatgca cagagatgtt aaaccatcta acatcttggt     840
aaactctaga ggtgagatca agctttgtga ttttggtgtc agtggacaac tgatagattc     900
tatggcaaac tcatttgttg gcacgcgctc ctacatgtct ccggaaagac tgcagggaac     960
tcattattca gtgcagtcag atatatggag tatggggctg tctctggtag aaatggccat    1020
```

```
tggcagatac ccgattcctc ctcctgactc taaggagctc gagttgatgt ttggctgccc    1080
ggtagaggga gattctccag tcacagagac ctcacccagg caaagaacac ctggtcgacc    1140
aatgagctcc tatggaccag acagcagacc cccgatggca atctttgaac ttctggatta    1200
catcgtcaat gagccacctc caaaactgcc caatggtgtc tttggttctg aatttcaaga    1260
ttttgttaac aaatgtttaa ttaaaaatcc tgctgagaga gctgatttga agcagctgat    1320
gattcacgct ttcattaaga gatctgaagc agaggaggtg gattttgcag atggctttg     1380 ctcaaccata ggccttaacc aaccgagtac acccacgcat gctgctggag tctgaatgtg    1440
gaagagcaaa tcctgtcccg tacatctgtt aacagcgcta ctttggtcct atttcctaag    1500
cttgtacctg ttcaaacatg tatttcacct cttaaggaag aatgtcttta tagcatgtgc    1560
caaattgttt tcaattttgt catcaactaa ttggtattgt actgggttac atttgtttgc    1620
tgaccaaaat gtaaaatgtt taagttacag tgcttgctga ttttaagtga ttatggaatt    1680
atggatattc tttcttaatg aaaatatcac tgggggggaa tttaccctg gattgtttga    1740 actttatcaa gactctttgt aaactgttgg tacttcagtc atgcttacct aatctcccat    1800
gcaaaaaaag gggtagggat gctccaaaac tgtatctgtt gagcatgctt ttgctgctgc    1860
caaactgtat cttggaagtt aggcctaatg gttccaattt ggtgttgtgt agagatcact    1920 cttttccaggt aaagaaggta agagctctgc attccttggg atggacaggg cagtatccta   1980
cttgtagact tgttcatatt tctatattta tttttaaaat gtatcatcat acttggattt    2040
agtgatatat gtctttccaa ttgattttta aaggttagct ctcagaagcg tcctacagaa    2100
tcatgacaaa gatctgggct ttcttttaac cttaagattc atgacagctg tgtttggtgt    2160
ctaaaatgta tgaagatcct ctattgtttt attctctcag atgtttagca atggtttctc    2220
ttaataaata tattatcaag taaaaaaaaa aaaaaataa aaaaaaaaa aaaa           2274
```

<210> SEQ ID NO 82
<211> LENGTH: 395
<212> TYPE: PRT
<213> ORGANISM: Gallus gallus

<400> SEQUENCE: 82

```
Met Pro Lys Lys Pro Gly Pro Ile Gln Leu Asn Pro Ala Pro Asp
1               5                  10                 15

Gly Ser Ala Val Asn Gly Thr Ser Ser Ala Glu Thr Asn Leu Glu Ala
                20                  25                  30

Leu Gln Lys Lys Leu Glu Glu Leu Glu Leu Asp Glu Gln Gln Arg Lys
        35                  40                  45

Arg Leu Glu Ala Phe Leu Thr Gln Lys Gln Lys Val Gly Glu Leu Lys
    50                  55                  60

Asp Asp Asp Phe Glu Lys Ile Ser Glu Leu Gly Ala Gly Asn Gly Gly
65                  70                  75                  80

Val Val Phe Lys Val Ser His Lys Pro Ser Gly Leu Ile Met Ala Arg
                85                  90                  95

Lys Leu Ile His Leu Glu Ile Lys Pro Ala Ile Arg Asn Gln Ile Ile
            100                 105                 110

Arg Glu Leu Gln Val Leu His Glu Cys Asn Ser Pro Tyr Ile Val Gly
        115                 120                 125

Phe Tyr Gly Ala Phe Tyr Ser Asp Gly Glu Ile Ser Ile Cys Met Glu
    130                 135                 140

His Met Asp Gly Gly Ser Leu Asp Gln Val Leu Lys Lys Ala Gly Arg
```

```
            145                 150                 155                 160
Ile Pro Glu Gln Ile Leu Gly Lys Val Ser Ile Ala Val Ile Lys Gly
                165                 170                 175

Leu Thr Tyr Leu Arg Glu Lys His Lys Ile Met His Arg Asp Val Lys
                180                 185                 190

Pro Ser Asn Ile Leu Val Asn Ser Arg Gly Glu Ile Lys Leu Cys Asp
            195                 200                 205

Phe Gly Val Ser Gly Gln Leu Ile Asp Ser Met Ala Asn Ser Phe Val
            210                 215                 220

Gly Thr Arg Ser Tyr Met Ser Pro Glu Arg Leu Gln Gly Thr His Tyr
225                 230                 235                 240

Ser Val Gln Ser Asp Ile Trp Ser Met Gly Leu Ser Leu Val Glu Met
                245                 250                 255

Ala Ile Gly Arg Tyr Pro Ile Pro Pro Pro Asp Ser Lys Glu Leu Glu
                260                 265                 270

Leu Met Phe Gly Cys Pro Val Glu Gly Asp Ser Pro Val Thr Glu Thr
                275                 280                 285

Ser Pro Arg Gln Arg Thr Pro Gly Arg Pro Met Ser Ser Tyr Gly Pro
            290                 295                 300

Asp Ser Arg Pro Pro Met Ala Ile Phe Glu Leu Leu Asp Tyr Ile Val
305                 310                 315                 320

Asn Glu Pro Pro Pro Lys Leu Pro Asn Gly Val Phe Gly Ser Glu Phe
                325                 330                 335

Gln Asp Phe Val Asn Lys Cys Leu Ile Lys Asn Pro Ala Glu Arg Ala
                340                 345                 350

Asp Leu Lys Gln Leu Met Ile His Ala Phe Ile Lys Arg Ser Glu Ala
            355                 360                 365

Glu Glu Val Asp Phe Ala Gly Trp Leu Cys Ser Thr Ile Gly Leu Asn
            370                 375                 380

Gln Pro Ser Thr Pro Thr His Ala Ala Gly Val
385                 390                 395
```